US008119624B2

(12) United States Patent
Bai et al.

(10) Patent No.: US 8,119,624 B2
(45) Date of Patent: *Feb. 21, 2012

(54) FUSED PHENYL AMIDO HETEROCYCLIC COMPOUNDS

(75) Inventors: Hao Bai, San Diego, CA (US); Simon Bailey, San Diego, CA (US); Dilip Ramakant Bhumralkar, San Diego, CA (US); Feng C. Bi, La Jolla, CA (US); Fengli Guo, San Diego, CA (US); Mingying He, San Diego, CA (US); Paul Stuart Humphries, Groton, CT (US); Anthony Lai Ling, San Diego, CA (US); Jihong Lou, San Diego, CA (US); Seiji Nukui, San Diego, CA (US); Ru Zhou, San Diego, CA (US)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 12/913,059

(22) Filed: Oct. 27, 2010

(65) Prior Publication Data

US 2011/0039821 A1    Feb. 17, 2011

Related U.S. Application Data

(63) Continuation of application No. 11/746,359, filed on May 9, 2007, now Pat. No. 7,842,713, which is a continuation of application No. PCT/IB2007/001035, filed on Apr. 11, 2007.

(60) Provisional application No. 60/793,703, filed on Apr. 20, 2006.

(51) Int. Cl.
| A61K 31/44 | (2006.01) |
| A61K 31/415 | (2006.01) |
| A61K 31/47 | (2006.01) |
| A61K 31/42 | (2006.01) |
| A61K 31/397 | (2006.01) |
| A61K 31/4965 | (2006.01) |
| A61K 31/41 | (2006.01) |
| C07D 215/00 | (2006.01) |
| C07D 401/00 | (2006.01) |
| C07D 413/00 | (2006.01) |
| C07D 405/00 | (2006.01) |
| C07D 403/00 | (2006.01) |
| C07D 231/00 | (2006.01) |

(52) U.S. Cl. ........... 514/210.18; 514/337; 514/407; 514/312; 514/339; 514/338; 514/375; 514/210.2; 514/255.05; 514/359; 546/158; 546/275.4; 546/277.1; 546/271.7; 546/284.1; 548/217; 548/255; 548/364.1; 548/365.7

(58) Field of Classification Search .......... 514/210.18, 514/210.2, 255.05, 312, 337, 338, 339, 359, 514/375, 407; 546/158, 271.7, 275.4, 277.1, 546/284.1; 548/217, 255, 364.1, 365.7
See application file for complete search history.

(56) References Cited

U.S. PATENT DOCUMENTS 5,972,936 A    10/1999    Dyke et al. ............ 514/233.5
(Continued)

FOREIGN PATENT DOCUMENTS

EP    0606489    7/1993
(Continued)

OTHER PUBLICATIONS

English Language Translation (Machine-Generated) of WO 2007/043638, Apr. 19, 2007.
Janusz et al., Journal of Medicinal Chemistry, 1998, p. 3515-3529, vol. 41 American Chemical Society.

*Primary Examiner* — Rebecca Anderson
*Assistant Examiner* — Samantha Shterengarts
(74) *Attorney, Agent, or Firm* — John Wichtowski; A. Dean Olson

(57)    ABSTRACT

The present invention relates to a compound of formula (I):

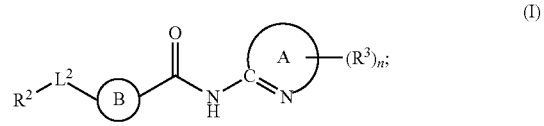

or a pharmaceutically acceptable salt or solvate thereof, wherein:
Ring A is (4-12)-membered heterocyclyl;
Ring B is a fused benzene ring selected from the group consisting of:

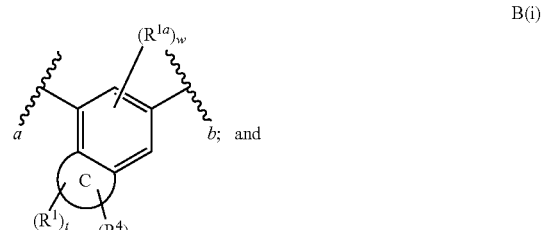

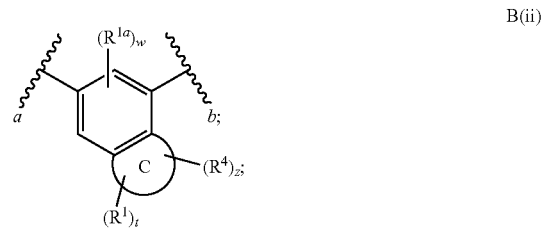

Ring A, ring B, ring C, $R^1$, $R^{1a}$, $R^2$, $R^3$, $R^4$, $L^2$, n, t, w, and z are as defined in the specification. The invention also relates to pharmaceutical compositions comprising the compounds of formula (I) and methods of treating a condition that is mediated by the modulation of glucokinase, the method comprising administering to a mammal an effective amount of a compound of formula (I).

7 Claims, No Drawings

U.S. PATENT DOCUMENTS

| | | | |
|---|---|---|---|
| 6,066,657 A | 5/2000 | Dyke et al. | 514/337 |
| 6,117,874 A | 9/2000 | Dombroski et al. | 514/253.07 |
| 6,121,274 A | 9/2000 | Ulrich et al. | 514/278 |
| 6,133,286 A | 10/2000 | Dombroski et al. | 514/312 |
| 6,211,203 B1 | 4/2001 | Amschier | 514/337 |
| 2004/0013286 A1 | 1/2004 | Viola et al. | 382/118 |
| 2005/0026969 A1 | 2/2005 | Cheng et al. | 514/363 |
| 2006/0058353 A1 | 3/2006 | McKerrecher et al. | 514/337 |
| 2006/0142269 A1 | 6/2006 | Dykes | 514/218 |
| 2006/0148888 A1 | 7/2006 | Krauss et al. | 514/456 |
| 2006/0205751 A1 | 9/2006 | Lee et al. | 514/281 |
| 2006/0287291 A1 | 12/2006 | Johansson et al. | 514/210.19 |

FOREIGN PATENT DOCUMENTS

| | | |
|---|---|---|
| WO | WO 2004046139 | 6/2004 |
| WO | WO 2006030031 | 3/2006 |
| WO | WO 2006106326 | 10/2006 |
| WO | WO 2007043638 | 4/2007 |
| WO | WO 2008079787 | 12/2007 |

FUSED PHENYL AMIDO HETEROCYCLIC COMPOUNDS

This application is a continuation filing of U.S. patent application Ser. No. 11/746,359 filed May 9, 2007, which claims the benefit of International Application No. PCT/IB2007/001035 filed Apr. 11, 2007, which claims the benefit of Provisional Patent Application No. 60/793,703 filed Apr. 20, 2006.

FIELD OF THE INVENTION

The present invention relates to novel fused phenyl amido heterocyclic compounds of formula (I), to pharmaceutical compositions comprising the compounds, as well as to the use of the compounds in the preparation of a medicament for use in the treatment or prevention of a disease or medical condition mediated through glucokinase (GK), leading to a decreased glucose threshold for insulin secretion. In addition the compounds are predicted to lower blood glucose by increasing hepatic glucose uptake. Such compounds may have utility in the treatment of Type 2 diabetes and obesity.

BACKGROUND OF THE INVENTION

In the pancreatic beta cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GK). GK has a high (6-10 mM) Km for glucose and is not inhibited by physiological concentrations of G-6-P. GK expression is limited to a few tissues and cell types, most notably pancreatic beta cells and liver cells (hepatocytes). In these cells GK activity is rate limiting for glucose utilization and therefore regulates the extent of glucose induced insulin secretion and hepatic glycogen synthesis. These processes are critical in the maintenance of whole body glucose homeostasis and both are dysfunctional in diabetes.

The compounds of the present invention are GK agonists, and are therefore believed to be useful in the treatment of diabetes, obesity, glaucoma, osteoporosis, cognitive disorders, immune disorders, depression, hypertension, and metabolic diseases.

SUMMARY OF THE INVENTION

The present invention relates to a compound of formula (I):

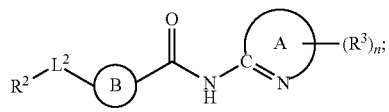

(I)

or a pharmaceutically acceptable salt or solvate thereof, wherein:

Ring A is (4-12)-membered heterocyclyl;

Ring B is a fused benzene ring selected from the group consisting of:

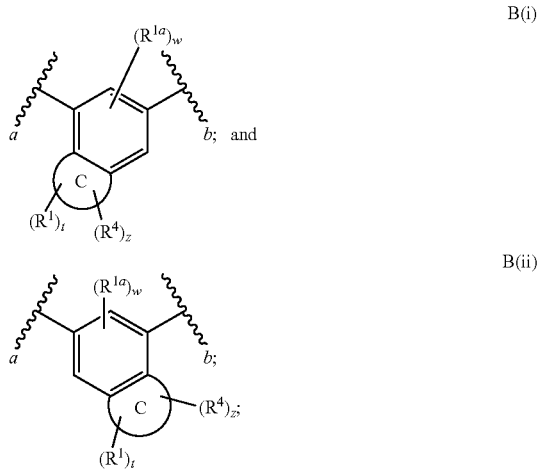

wherein in each of the above formula B(i) and B(ii), bond a is connecting said ring B fused benzene ring to the group $-L^2-R^2$ and bond b is connecting said ring B fused benzene ring to the group $>C=O-NH-$;

Each $R^1$ and $R^4$ can be independently bonded to any carbon atom or nitrogen atom of ring C;

Ring C contains an optional double bond and an optional heteroatom selected from the group consisting of $-O-$, $-NR^5-$, and $-S-$;

each of $R^1$, $R^{1a}$, and $R^4$ are independently selected from H, halo, cyano, nitro, $-CF_3$, $-CHF_2$, $-CH_2F$, trifluoromethoxy, azido, hydroxy, $(C_1-C_6)$alkoxy, $(C_1-C_6)$alkyl, $(C_2-C_6)$alkenyl, $(C_2-C_6)$alkynyl, $-(C=O)-R^5$, $-(C=O)-O-R^5$, $-O-(C=O)-R^5$, $-NR^5(C=O)-R^7$, $-(C=O)-NR^5R^6$, $-NR^5R^6$, $-NR^5OR^6$, $-S(O)_kNR^5R^6$, $-S(O)_l(C_1-C_6)$alkyl, $-O-SO_2-R^5$, $-NR^5-S(O)_k-$, $-(CR^5R^6)_v(3-10)$-membered cycloalkyl, $-(CR^5R^6)_v(C_6-C_{10})$aryl, $-(CR^5R^6)_v(4-10)$-membered heterocyclyl, $-(CR^5R^6)_q(C=O)(CR^5R^6)_v(C_6-C_{10})$aryl, $-(CR^5R^6)_q(C=O)(CR^5R^6)_v(4-10)$-membered heterocyclyl, $-(CR^5R^6)_v O(CR^5R^6)_q(C_6-C_{10})$aryl, $-(CR^5R^6)_v O(CR^5R^6)_q(4-10)$-membered heterocyclyl, $-(CR^5R^6)_q S(O)_j(CR^5R^6)_v(C_6-C_{10})$aryl, and $-(CR^5R^6)_q S(O)_j(CR^5R^6)_v(4-10)$-membered heterocyclyl; or $R^1$ and $R^4$, if they are both attached on one carbon atom of the ring C, together optionally form a (3-10)-membered cycloalkyl or (4-12)-membered heterocyclyl ring;

$L^2$ is $>C=O$, $>C=O-O-$, $-O-C=O-$, $-O-C=O-O-$, $-O-C=O-NR^5-$, $-NR^5-(C=O)-$, $-NR^5-(C=O)-O-$, $-NR^5-(C=O)-NR^6$, $-(C=O)-NR^5-$, $-O-$, $-NR^5-$, $-S(O)_j-$, $-NR^5SO_2-$, $-SO_2NR^5-$, $-(C=O)NR^5SO_2-$, $-SO_2NR^5(C=O)-$, or $-CR^5R^6$;

$R^2$ is H, $(C_1-C_6)$alkyl, $-(CR^5R^6)_v(3-10)$-membered cycloalkyl, $-(CR^5R^6)_v(C_6-C_{10}$aryl), or $-(CR^5R^6)_v(4-12)$-membered heterocyclyl;

$R^3$ is H, halo, cyano, nitro, $-CF_3$, $-CHF_2$, $-CH_2F$, trifluoromethoxy, azido, hydroxy, $(C_1-C_6)$alkoxy, $(C_1-C_6)$alkyl, $(C_2-C_6)$alkenyl, $(C_2-C_6)$alkynyl, $-(C=O)-R^5$, $-(C=O)-O-R^5$, $-O-(C=O)-R^5$, $-NR^5(C=O)-R^7$, $-(C=O)-NR^5R^6$, $-NR^5R^6$, $-NR^5OR^6$, $-S(O)_kNR^5R^6$, $-S(O)_j(C_1-C_6)$alkyl, $-O-SO_2-R^5$, $-NR^5-S(O)_k-$, $-(CR^5R^6)_v(3-10)$-membered cycloalkyl, $-(CR^5R^6)_v$ ($C_6$-$C_{10}$aryl), —($CR^5R^6$)$_v$(4-10)-membered heterocyclyl, —($CR^5R^6$)$_q$(C=O)($CR^5R^6$)$_v$($C_6$-$C_{10}$)aryl, —($CR^5R^6$)$_q$(C=O)($CR^5R^6$)$_v$(4-10)-membered heterocyclyl, —($CR^5R^6$)$_v$O($CR^5R^6$)$_q$($C_6$-$C_{10}$)aryl, —($CR^5R^6$)$_v$O($CR^5R^6$)$_q$(4-10)-membered heterocyclyl, —($CR^5R^6$)$_q$S(O)$_j$($CR^5R^6$)$_v$($C_6$-$C_{10}$)aryl, or —($CR^5R^6$)$_q$S(O)$_j$($CR^5R^6$)$_v$(4-10)-membered heterocyclyl;

each of $R^5$, $R^6$ and $R^7$ are independently selected from H, ($C_1$-$C_6$)alkyl, —($CR^8R^9$)$_v$(3-10)-membered cycloalkyl, —($CR^8R^9$)$_p$($C_6$-$C_{10}$)aryl, and —($CR^8R^9$)$_p$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R^1$, $R^2$, $R^3$, $R^4$, $R^5$, $R^6$ and $R^7$ are independently optionally substituted with 1 to 3 $R^{11}$ substituents each independently selected from halo, cyano, nitro, —$CF_3$, —$CHF_2$, —$CH_2F$, trifluoromethoxy, azido, hydroxy, —O—$R^{12}$, ($C_1$-$C_6$)alkoxy, ($C_1$-$C_6$)alkyl, ($C_2$-$C_6$)alkenyl, ($C_2$-$C_6$)alkynyl, —(C=O)—$R^8$, —(C=O)—$R^{12}$, —(C=O)—O—$R^8$, —(C=O)—O—$R^{12}$, —O—(C=O)—$R^8$, —O—(C=O)—$R^{12}$, —$NR^8$(C=O)—$R^{10}$, —(C=O)—$NR^8R^9$, —(C=O)—$NR^8R^{12}$, —$NR^8R^9$, —$NR^8R^{12}$, —$NR^8OR^9$, —$NR^8OR^{12}$, —S(O)$_k$$NR^8R^9$, —S(O)$_k$$NR^8R^{12}$, —S(O)$_j$($C_1$-$C_6$)alkyl, —S(O)$_j$$R^{12}$, —O—$SO_2$—$R^8$, —O—$SO_2$—$R^{12}$, —$NR^8$—S(O)$_k$, —$NR^{12}$—S(O)$_k$, —($CR^8R^9$)$_v$(3-10)-membered cycloalkyl, —($CR^8R^9$)$_v$($C_6$-$C_{10}$aryl), —($CR^8R^9$)$_v$(4-10)-membered heterocyclyl, —($CR^8R^9$)$_q$(C=O)($CR^8R^9$)$_v$($C_6$-$C_{10}$)aryl, —($CR^8R^9$)$_q$(C=O)($CR^8R^9$)$_v$(4-10)-membered heterocyclyl, —($CR^8R^9$)$_v$O($CR^8R^9$)$_q$($C_6$-$C_{10}$)aryl, —($CR^8R^9$)$_v$O($CR^8R^9$)$_q$(4-10)-membered heterocyclyl, —($CR^8R^9$)$_q$S(O)$_j$($CR^8R^9$)$_v$($C_6$-$C_{10}$)aryl, and —($CR^8R^9$)$_q$S(O)$_j$($CR^8R^9$)$_v$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R^{11}$ are independently optionally substituted with 1 to 3 $R^{13}$ substituents each independently selected from halo, cyano, nitro, —$CF_3$, —$CHF_2$, —$CH_2F$, trifluoromethoxy, azido, ($CH_2$)$_v$OH, ($C_1$-$C_6$)alkoxy, ($C_1$-$C_6$)alkyl, ($C_2$-$C_6$)alkenyl, ($C_2$-$C_6$)alkynyl, —(C=O)—$R^8$, —(C=O)—$R^{12}$, —(C=O)—O—$R^8$, —(C=O)—O—$R^{12}$, —O—(C=O)—$R^8$, —O—(C=O)—$R^{12}$, —$NR^8$(C=O)—$R^{10}$, —(C=O)—$NR^8R^9$, —$NR^8R^9$, and —$NR^8R^{12}$;

any nitrogen atoms of the (4-10)-membered heterocyclyl of the foregoing $R^1$, $R^2$, $R^3$, $R^4$, $R^5$, $R^6$, $R^7$, $R^{11}$ and $R^{12}$ are independently optionally substituted with ($C_1$-$C_6$)alkyl, ($C_2$-$C_6$)alkenyl, ($C_2$-$C_6$)alkynyl, —(C=O)—$R^8$, —(C=O)—O—$R^8$, —(C=O)—$NR^8R^9$, —($CR^8R^9$)$_v$(3-10)-membered cycloalkyl, —($CR^8R^9$)$_v$($C_6$-$C_{10}$aryl), —($CR^8R^9$)$_v$(4-10)-membered heterocyclyl, —($CR^8R^9$)$_q$(C=O)($CR^8R^9$)$_v$($C_6$-$C_{10}$)aryl, or —($CR^8R^9$)$_q$(C=O)($CR^8R^9$)$_v$(4-10)-membered heterocyclyl;

each $R^8$, $R^9$, and $R^{10}$ are independently H or ($C_1$-$C_6$)alkyl;

$R^{12}$ is —($CR^8R^9$)$_v$(3-10)-membered cycloalkyl, —($CR^8R^9$)$_v$($C_6$-$C_{10}$aryl), or —($CR^8R^9$)$_v$(4-10)-membered heterocyclyl;

p, q, and v are each independently 0, 1, 2, 3, 4, or 5;

w, n and j are each independently 0, 1, or 2;

k is 1 or 2; and t and z are each independently 1, 2, 3, or 4;

with the proviso that when compound (I) has the formula:

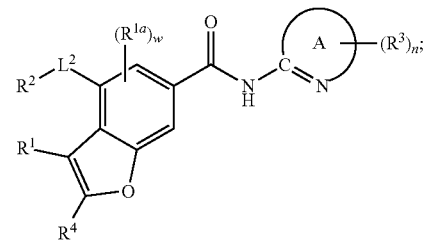

Wherein:

Ring A is pyridin-2-yl or thiazol-2-yl;

$L^2$ is —O—; and $R^2$ is ($C_1$-$C_6$)alkyl, —($CR^8R^8$)$_v$(3-10)-membered cycloalkyl, —($CR^8R^8$)$_v$($C_6$-$C_{10}$aryl), or —($CR^8R^8$)$_v$(4-12)-membered heterocyclyl; then $R^2$ is further substituted by $R^{11}$ substituents each independently selected from —$SO_2$—($C_1$-$C_6$)alkyl, —S(O)$_j$$R^{12}$, —S(O)$_k$$NR^8R^9$, —S(O)$_k$$NR^8R^{12}$, —(C=O)—$R^{12}$, —(C=O)—$NR^8R^9$, and —(C=O)—$NR^8R^{12}$.

The present invention also relates to said compound of formula (I) selected from the group consisting of:

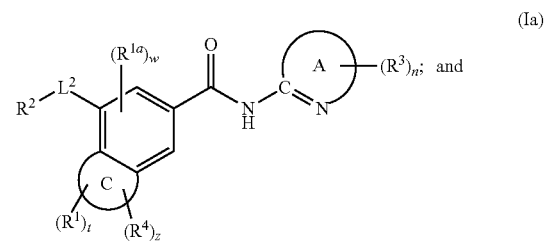

(Ia)

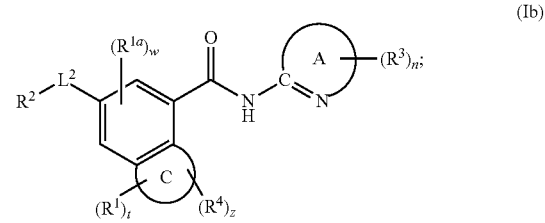

(Ib)

wherein said $L^2$, $R^1$, $R^{1a}$, $R^2$, $R^3$, ring A, t, z, w, and n are as defined above; and wherein ring C is (4-6)-membered heterocyclyl or a (4-10)-membered cycloalkyl.

The present invention also relates to said compound of formula (I) selected from the group consisting of compounds of formula (II) (III), (IV), or (V):

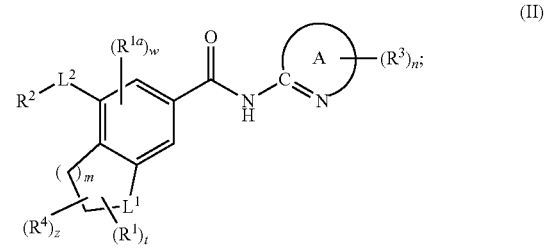

(II)

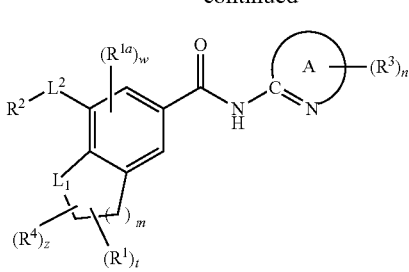

(III)

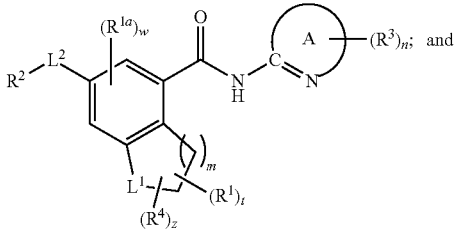

(IV)

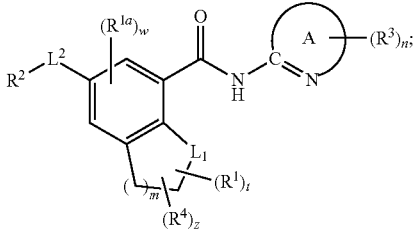

(V)

or a pharmaceutically acceptable salt or solvate thereof, wherein:

Ring A is (4-12)-membered heterocyclyl;

$L^1$ is —O—, —NR$^5$—, —S—, or —CR$^5$R$^6$—;

each of R$^1$, R$^{1a}$, and R$^4$ are independently selected from H, halo, cyano, nitro, —CF$_3$, —CHF$_2$, —CH$_2$F, trifluoromethoxy, azido, hydroxy, (C$_1$-C$_6$)alkoxy, (C$_1$-C$_6$)alkyl, (C$_2$-C$_6$)alkenyl, (C$_2$-C$_6$)alkynyl, —(C=O)—R$^5$, —(C=O)—O—R$^5$, —O—(C=O)—R$^5$, —NR$^5$(C=O)—R$^7$, —(C=O)—NR$^5$R$^6$, —NR$^5$R$^6$, —NR$^5$OR$^6$, —S(O)$_k$NR$^5$R$^6$, —S(O)$_j$(C$_1$-C$_6$)alkyl, —O—SO$_2$—R$^5$, —NR$^5$—S(O)$_k$, —(CR$^5$R$^6$)$_v$(3-10)-membered cycloalkyl, —(CR$^5$R$^6$)$_v$(C$_6$-C$_{10}$aryl), —(CR$^5$R$^6$)$_v$(4-10)-membered heterocyclyl, —(CR$^5$R$^6$)$_q$(C=O)(CR$^5$R$^6$)$_v$(C$_6$-C$_{10}$)aryl, —(CR$^5$R$^6$)$_q$(C=O)(CR$^5$R$^6$)$_v$(4-10)-membered heterocyclyl, —(CR$^5$R$^6$)$_v$O(CR$^5$R$^6$)$_q$(C$_6$-C$_{10}$)aryl, —(CR$^5$R$^6$)$_v$O(CR$^5$R$^6$)$_q$(4-10)-membered heterocyclyl, —(CR$^5$R$^6$)$_q$S(O)$_j$(CR$^5$R$^6$)$_v$(C$_6$-C$_{10}$)aryl, and —(CR$^5$R$^6$)$_q$S(O)$_j$(CR$^5$R$^6$)$_v$(4-10)-membered heterocyclyl; or R$^1$ and R$^4$, if they are both attached on one carbon atom of the ring containing L$^1$, together optionally form a (3-10)-membered cycloalkyl or (4-10)-membered heterocyclyl ring;

The ring containing L$^1$ contains an optional double bond;

L$^2$ is >C=O, >C=O—O—, O—C=O—, —O—C=O—O—, —O—C=O—NR$^5$—, —NR$^5$—(C=O)—, —NR$^5$—(C=O)—O—, —NR$^5$—(C=O)—NR$^6$, —(C=O)—NR$^5$—, —O—, —NR$^5$—, —S(O)$_j$—, —NR$^5$SO$_2$—, —SO$_2$NR$^5$—, —(C=O)NR$^5$SO$_2$—, —SO$_2$NR$^5$(C=O)—, or —CR$^5$R$^6$;

R$^2$ is H, (C$_1$-C$_6$)alkyl, —(CR$^5$R$^6$)$_v$(3-10)-membered cycloalkyl, —(CR$^5$R$^6$)$_v$(C$_6$-C$_{10}$aryl), or —(CR$^5$R$^6$)$_v$(4-12)-membered heterocyclyl;

R$^3$ is H, halo, cyano, nitro, —CF$_3$, —CHF$_2$, —CH$_2$F, trifluoromethoxy, azido, hydroxy, (C$_1$-C$_6$)alkoxy, (C$_1$-C$_6$)alkyl, (C$_2$-C$_6$)alkenyl, (C$_2$-C$_6$)alkynyl, —(C=O)—R$^5$, —(C=O)—O—R$^5$, —O—(C=O)—R$^5$, —NR$^5$(C=O)—R$^7$, —(C=O)—NR$^5$R$^6$, —NR$^5$R$^6$, —NR$^5$OR$^6$, —S(O)$_k$NR$^5$R$^6$, —S(O)$_j$(C$_1$-C$_6$)alkyl, —O—SO$_2$—R$^5$, —NR$^5$—S(O)$_k$, —(CR$^5$R$^6$)$_v$(3-10)-membered cycloalkyl, —(CR$^5$R$^6$)$_v$(C$_6$-C$_{10}$aryl), —(CR$^5$R$^6$)$_v$(4-10)-membered heterocyclyl, —(CR$^5$R$^6$)$_q$(C=O)(CR$^5$R$^6$)$_v$(C$_6$-C$_{10}$)aryl, —(CR$^5$R$^6$)$_q$(C=O)(CR$^5$R$^6$)$_v$(4-10)-membered heterocyclyl, —(CR$^5$R$^6$)$_v$O(CR$^5$R$^6$)$_q$(C$_6$-C$_{10}$)aryl, —(CR$^5$R$^6$)$_v$O(CR$^5$R$^6$)$_q$(4-10)-membered heterocyclyl, —(CR$^5$R$^6$)$_q$S(O)$_j$(CR$^5$R$^6$)$_v$(C$_6$-C$_{10}$)aryl, or —(CR$^5$R$^6$)$_q$S(O)$_j$(CR$^5$R$^6$)$_v$(4-10)-membered heterocyclyl;

each of R$^5$, R$^6$ and R$^7$ are independently selected from H, (C$_1$-C$_6$)alkyl, —(CR$^8$R$^9$)$_v$(3-10)-membered cycloalkyl, —(CR$^8$R$^9$)$_p$(C$_6$-C$_{10}$)aryl, and —(CR$^8$R$^9$)$_p$(4-10)-membered heterocyclyl;

any carbon atoms of the (C$_1$-C$_6$)alkyl, the (3-10)-membered cycloalkyl, the (C$_6$-C$_{10}$)aryl and the (4-10)-membered heterocyclyl of the foregoing R$^1$, R$^2$, R$^3$, R$^4$, R$^5$, R$^6$ and R$^7$ are independently optionally substituted with 1 to 3 R$^{11}$ substituents each independently selected from halo, cyano, nitro, —CF$_3$, —CHF$_2$, —CH$_2$F, trifluoromethoxy, azido, hydroxy, —O—R$^{12}$, (C$_1$-C$_6$)alkoxy, (C$_1$-C$_6$)alkyl, (C$_2$-C$_6$)alkenyl, (C$_2$-C$_6$)alkynyl, —(C=O)—R$^8$, —(C=O)—R$^{12}$, —(C=O)—O—R$^8$, —(C=O)—O—R$^{12}$, —O—(C=O)—R$^8$, —O—(C=O)—R$^{12}$, —NR$^8$(C=O)—R$^{10}$, —(C=O)—NR$^8$R$^9$, —(C=O)—NR$^8$R$^{12}$, —NR$^8$R$^9$, —NR$^8$R$^{12}$, —NR$^8$OR$^9$, —NR$^8$OR$^{12}$, —S(O)$_k$NR$^8$R$^9$, —S(O)$_k$NR$^8$R$^{12}$, —S(O)$_j$(C$_1$-C$_6$)alkyl, —S(O)$_j$R$^{12}$, —O—SO$_2$—R$^8$, —O—SO$_2$—R$^{12}$, —NR$^8$—S(O)$_k$, —NR$^{12}$—S(O)$_k$, —(CR$^8$R$^9$)$_v$(3-10)-membered cycloalkyl, —(CR$^8$R$^9$)$_v$(C$_6$-C$_{10}$aryl), —(CR$^8$R$^9$)$_v$(4-10)-membered heterocyclyl, —(CR$^8$R$^9$)$_q$(C=O)(CR$^8$R$^9$)$_v$(C$_6$-C$_{10}$)aryl, —(CR$^8$R$^9$)$_q$(C=O)$_q$(CR$^8$R$^9$)$_v$(4-10)-membered heterocyclyl, —(CR$^8$R$^9$)$_v$O(CR$^8$R$^9$)$_q$(C$_6$-C$_{10}$)aryl, —(CR$^8$R$^9$)$_v$O(CR$^8$R$^9$)$_q$(4-10)-membered heterocyclyl, —(CR$^8$R$^9$)$_q$S(O)$_j$(CR$^8$R$^9$)$_v$(C$_6$-C$_{10}$)aryl, and —(CR$^8$R$^9$)$_q$S(O)$_j$(CR$^8$R$^9$)$_v$(4-10)-membered heterocyclyl;

any carbon atoms of the (C$_1$-C$_6$)alkyl, the (3-10)-membered cycloalkyl, the (C$_6$-C$_{10}$)aryl and the (4-10)-membered heterocyclyl of the foregoing R$^{11}$ are independently optionally substituted with 1 to 3 R$^{13}$ substituents each independently selected from halo, cyano, nitro, —CF$_3$, —CHF$_2$, —CH$_2$F, trifluoromethoxy, azido, (CH$_2$)$_v$OH, (C$_1$-C$_6$)alkoxy, (C$_1$-C$_6$)alkyl, (C$_2$-C$_6$)alkenyl, (C$_2$-C$_6$)alkynyl, —(C=O)—R$^8$, —(C=O)—R$^{12}$, —(C=O)—O—R$^8$, —(C=O)—O—R$^{12}$, —O—(C=O)—R$^8$, —O—(C=O)—R$^{12}$, —NR$^8$(C=O)—R$^{10}$, —(C=O)—NR$^8$R$^9$, —(C=O)—NR$^8$R$^{12}$, —NR$^8$R$^9$, and —NR$^8$R$^{12}$;

any nitrogen atoms of the (4-10)-membered heterocyclyl of the foregoing R$^1$, R$^2$, R$^3$, R$^4$, R$^5$, R$^6$, R$^7$, R$^{11}$ and R$^{12}$ are independently optionally substituted with (C$_1$-C$_6$)alkyl, (C$_2$-C$_6$)alkenyl, (C$_2$-C$_6$)alkynyl, —(C=O)—R$^8$, —(C=O)—O—R$^8$, —(C=O)—NR$^8$R$^9$, —(CR$^8$R$^9$)$_v$(3-10)-membered cycloalkyl, —(CR$^8$R$^9$)$_v$(C$_6$-C$_{10}$aryl), —(CR$^8$R$^9$)$_v$(4-10)-membered heterocyclyl, —(CR$^8$R$^9$)$_q$(C=O)(CR$^8$R$^9$)$_v$(C$_6$-C$_{10}$)aryl, or —(CR$^8$R$^9$)$_q$(C=O)(CR$^8$R$^9$)$_v$(4-10)-membered heterocyclyl;

each R$^8$, R$^9$, and R$^{10}$ are independently H or (C$_1$-C$_6$)alkyl;

R$^{12}$ is —(CR$^8$R$^9$)$_v$(3-10)-membered cycloalkyl, —(CR$^8$R$^9$)$_v$(C$_6$-C$_{10}$aryl), or —(CR$^8$R$^9$)$_v$(4-10)-membered heterocyclyl;

p, q, and v are each independently 0, 1, 2, 3, 4, or 5;

m is 0, 1, 2, or 3;

w, n and j are each independently 0, 1, or 2;

k is 1 or 2; and t and z are each independently 1, 2, 3, or 4.

Preferably t is 1 or 2.

Preferably z is 1 or 2.

In another embodiment, the invention relates to compounds of the formula (II) selected from the group consisting of

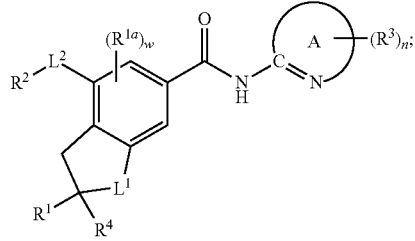

(IIa)

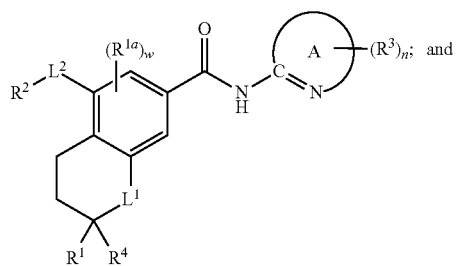

(IIb)

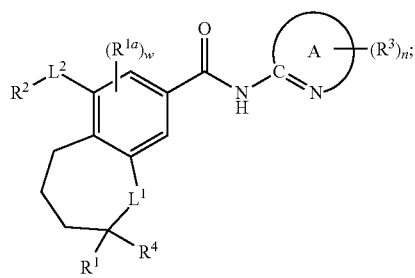

(IIc)

wherein said $L^1$, $L^2$, $R^1$, $R^{1a}$, $R^2$, $R^3$, $R^4$, ring A, w, and n are as defined above.

In another embodiment, the invention relates to compounds of the formula (III) selected from the group consisting of:

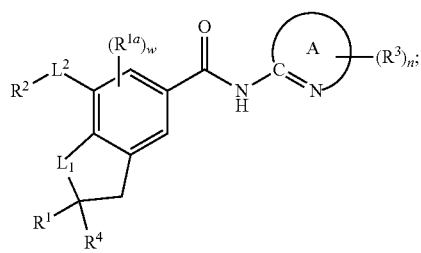

(IIIa)

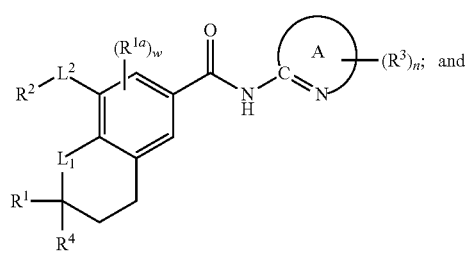

(IIIb)

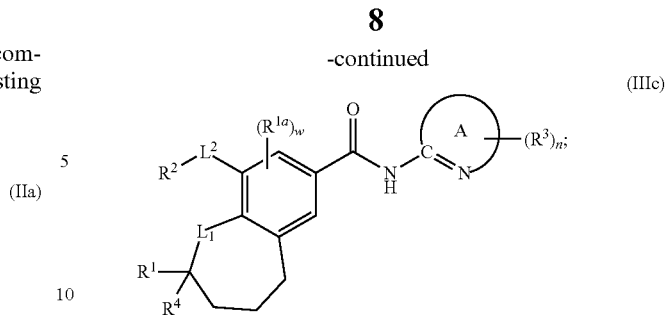

(IIIc)

wherein said $L^1$, $L^2$, $R^1$, $R^{1a}$, $R^2$, $R^3$, $R^4$, ring A, w, and n are as defined above.

In another embodiment, the invention relates to compounds of the formula (IV) selected from the group consisting of:

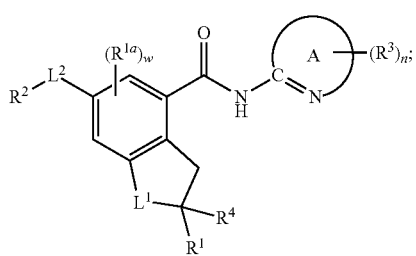

(IVa)

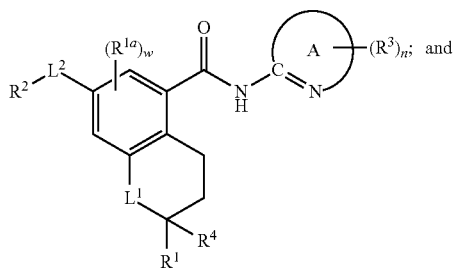

(IVb)

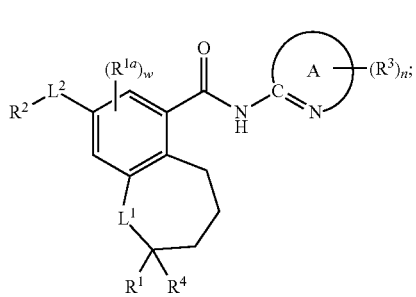

(IVc)

wherein said $L^1$, $L^2$, $R^1$, $R^{1a}$, $R^2$, $R^3$, $R^4$, ring A, w, and n are as defined above.

In another embodiment, the invention relates to compounds of the formula (V) selected from the group consisting of:

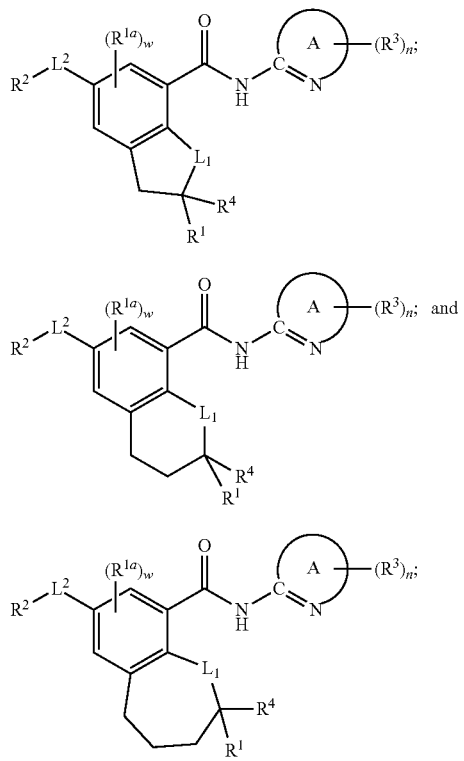

(Va)

(Vb)

(Vc)

wherein said $L^1$, $L^2$, $R^1$, $R^{1a}$, $R^2$, $R^3$, $R^4$, ring A, w, and n are as defined above.

In a preferred embodiment, the invention relates to compounds of the formula (II), wherein said compound of formula (II) has the structure of formula (IIa) as described above.

In another preferred embodiment, the invention relates to compounds of the formula (IV), wherein said compound of formula (IV) has the structure of formula (IVa) as described above.

In another embodiment, the invention relates to compounds of the formula (I) wherein said Ring A is selected from the group consisting of oxadiazolyl, triazolyl, pyrrolyl, oxazolyl, thiazolyl, imidazolyl, imidazolinyl, pyrazolyl, pyrazolinyl, isoxazolyl, isothiazolyl, thiadiazolyl, pyridinyl, pyrimidinyl, pyridazinyl, pyrazinyl, triazinyl, benzimidazolyl, benzothiazolyl, quinolinyl, quinazolinyl, quinoxalinyl, pyridinylcyclohexyl, and naphthyridinyl.

In another embodiment, the invention relates to compounds of the formula (I) wherein said Ring A is a 5-membered heterocyclyl selected from the group consisting of oxadiazolyl, triazolyl, pyrrolyl, oxazolyl, thiazolyl, imidazolyl, imidazolinyl, pyrazolyl, pyrazolinyl, isoxazolyl, isothiazolyl, and thiadiazolyl. Preferably, Ring A is pyrazolyl, pyrazolinyl, isoxazolyl, and triazolyl.

In another embodiment, the invention relates to compounds of the formula (I) wherein said Ring A is a 6-membered heterocyclyl selected from the group consisting of pyridinyl, pyrimidinyl, pyridazinyl, pyrazinyl, and triazinyl. Preferably, Ring A is pyridinyl, pyrimidinyl, and pyrazinyl.

In another embodiment, the invention relates to compounds of the formula (I) wherein said Ring A is a 9-membered or 10-membered heterocyclyl selected from the group consisting of benzimidazolyl, benzothiazolyl, quinolinyl, quinazolinyl, quinoxalinyl, pyridinylcyclohexyl, and naphthyridinyl.

In another embodiment, the invention relates to compounds of the formula (I) selected from the group consisting of (VIa), (VIb), (VIc) and (VId):

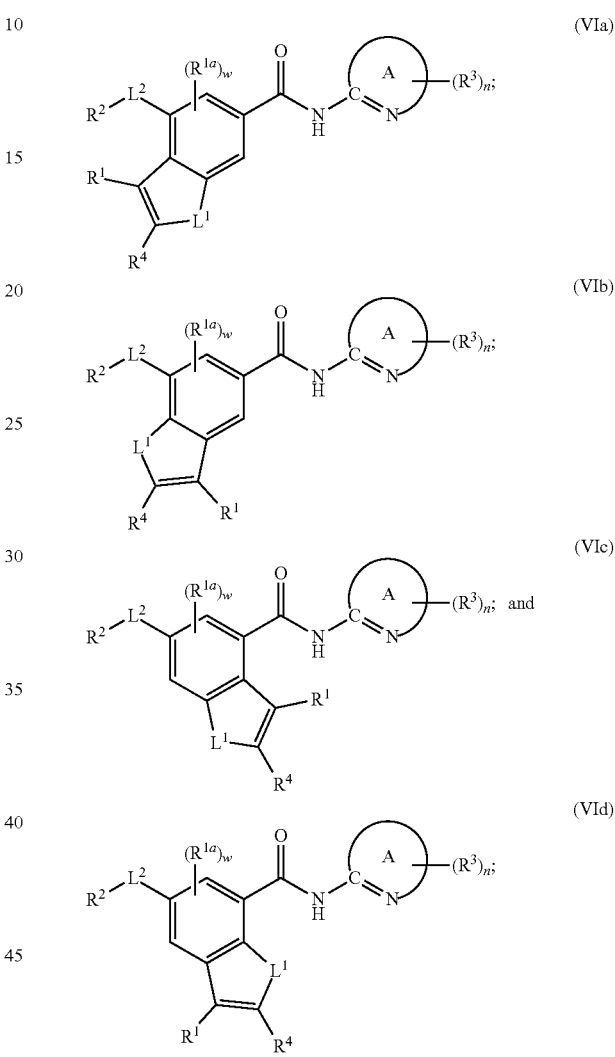

(VIa)

(VIb)

(VIc)

(VId)

wherein $L^2$, $R^1$, $R^2$, $R^3$, $R^4$, ring A, w, and n are as defined above;

$L^1$ is —O—, —NR$^5$—, or —S—;

with the proviso that when in formula (VIa):

Ring A is pyridin-2-yl or thiazol-2-yl;

$L^1$ is —O—;

$L^2$ is —O—; and $R^2$ is $(C_1-C_6)$alkyl, —$(CR^5R^6)_v$(3-10)-membered cycloalkyl, —$(CR^5R^6)_v(C_6-C_{10}$aryl), or —$(CR^5R^6)_v$(4-12)-membered heterocyclyl; then $R^2$ is further substituted by $R^{11}$ substituents each independently selected from —$SO_2$—$(C_1-C_6)$alkyl, —$S(O)_jR^{12}$, —$S(O)_kNR^8R^9$, —$S(O)_kNR^8R^{12}$, —(C=O)—$R^{12}$, —(C=O)—$NR^8R^9$, or —(C=O)—$NR^8R^{12}$. In the compounds of formula (VIa), preferably $R^{11}$ is —$SO_2$—$CH_3$; preferably $R^2$ is phenyl.

In another embodiment, the invention relates to compounds of the formula (I) selected from the group consisting of (VIIa), (VIIb), (VIIc) and (VIId):

(VIIa)
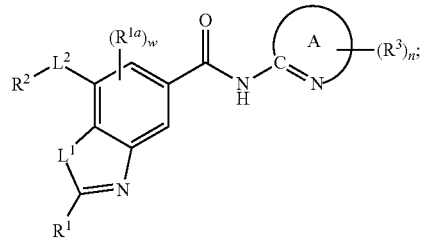

(VIIb)
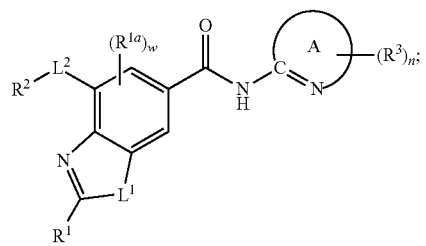

(VIIc)
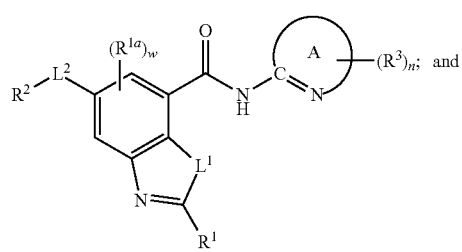

(VIId)
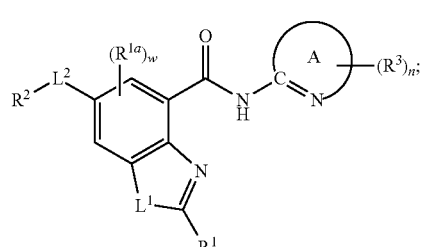

wherein L is —O—, —NR⁵—, or —S—; and wherein $L^2$, $R^1$, $R^2$, $R^3$, ring A, w, and n are as defined above.

In another embodiment, the invention relates to compounds of the formula (I) selected from the group consisting of (VIIIa), (VIIIb), (VIIIc) and (VIIId):

(VIIIa)
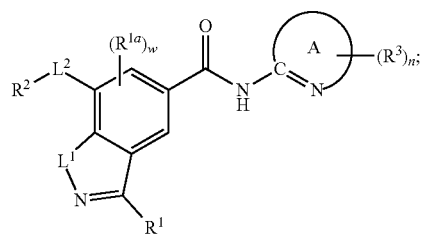

(VIIIb)
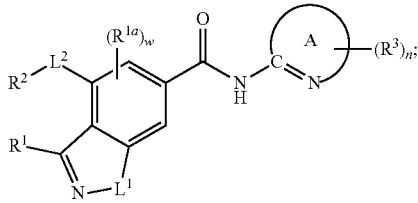

(VIIIc)
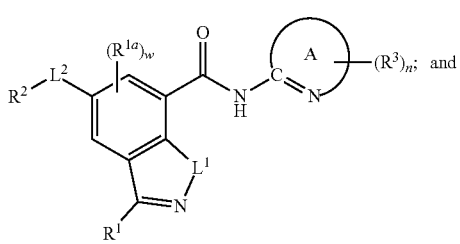

(VIIId)
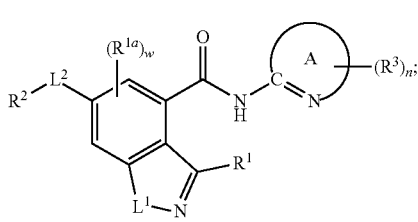

wherein L is wherein $L^1$ is —O—, —NR⁵—, or —S—; and wherein $L^2$, $R^1$, $R^2$, $R^3$, ring A, w, and n are as defined above.

In another embodiment, the invention relates to compounds of the formula (I) selected from the group consisting of (IXa), (IXb), (IXc), and (IXd):

(IXa)
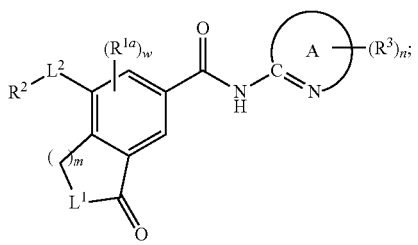

(IXb)
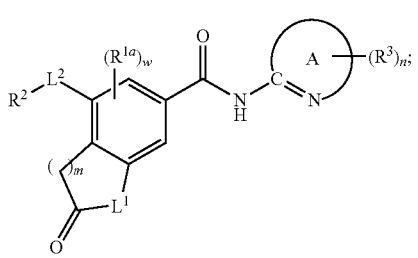

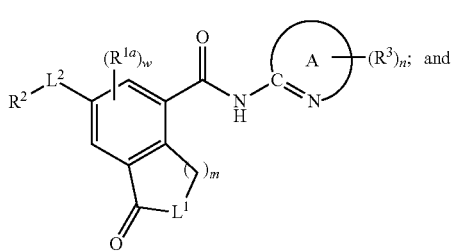

(IXc)

(IXd)

wherein
L is —O—, —NR⁵—, or —CR⁵R⁶;
L², R¹, R², R³, ring A, w, m, and n are as defined above;
and wherein the ring containing L¹ and —C=O— further contains an optional double bond.

In another embodiment, the invention relates to compounds of the formula (I) wherein said Ring C optionally contains a double bond. Specific embodiments within this embodiment include compounds of formula (II), such as formulae (IIb) or (IIc); compounds of formula (III), such as formulae (IIIb) or (IIIc); compounds of formula (IV), such as formulae (IVb) or (IVc); compounds of formula (V), such as formulae (Vb) or (Vc); compounds of formulae (VIa), (VIb), (VIc), (VId); compounds of formulae (VIIa), (VIIb), (VIIc), (VIId); compounds of formulae (VIIIa), (VIIIb), (VIIIc), (VIIId); and compounds of formulae (IXa), (IXb), (IXc), (IXd).

In another embodiment, the invention relates to compounds of the formula (I) wherein R² is (C₁-C₆)alkyl, —(CR⁵R⁶)ᵥ(C₆-C₁₀aryl), or —(CR⁵R⁶)ᵥ(4-12)-membered heterocyclyl.

In another embodiment, the invention relates to compounds of the formula (I) wherein R³ is halo, cyano, CF₃, (C₁-C₆)alkoxy, (C₁-C₆)alkyl, —(C=O)—R⁵, —(C=O)—O—R⁵, —O—(C=O)—R⁵, —NR⁵(C=O)—R⁷, —(C=O)—NR⁵R⁶, —NR⁵R⁶, or —NR⁵OR⁶.

In another embodiment, the invention relates to compounds of the formula (I) wherein each of R⁵, R⁶ and R⁷ are independently selected from H and (C₁-C₆)alkyl.

In another embodiment, the invention relates to compounds of the formula (I) wherein any carbon atoms of the (C₁-C₆)alkyl, the (3-10)-membered cycloalkyl, the (C₆-C₁₀) aryl and the (4-10)-membered heterocyclyl of the foregoing R¹, R², R³, R⁴, R⁵, R⁶ and R⁷ are optionally substituted with 1 to 3 substituents each independently selected from halo, hydroxyl, cyano, —(C=O)—R⁸, (C₁-C₆)alkoxy, and —S(O)ⱼ(C₁-C₆)alkyl.

In another embodiment, the invention relates to compounds of any of the above embodiments, wherein L¹ is —O—.

In another embodiment, the invention relates to compounds of any of the above embodiments, wherein each of R¹ and R⁴ are independently selected from H or (C₁-C₆)alkyl.

In another embodiment, the invention relates to compounds of any of the above embodiments, wherein each of R¹ and R⁴ are independently selected from H, halo, —CHF₂, —CH₂F, (C₁-C₆)alkyl, (C₂-C₆)alkenyl, —(C=O)—R⁵, —(C=O)—NR⁵R⁶, —(CR⁵R⁶)ᵥ(3-10)-membered cycloalkyl, —(CR⁵R⁶)ᵥ(C₆-C₁₀aryl), and —(CR⁵R⁶)ᵥ(4-10)-membered heterocyclyl.

In another embodiment, the invention relates to compounds of any of the above embodiments, wherein R² is H, (C₁-C₆)alkyl, —(CR⁵R⁶)ᵥ(3-10)-membered cycloalkyl, —(CR⁵R⁶)ᵥ(C₆-C₁₀aryl), or —(CR⁵R⁶)ᵥ(4-12)-membered heterocyclyl.

In another embodiment, the invention relates to compounds of any of the above embodiments, wherein m is 1 or 2.

In another embodiment, the invention relates to compounds of any of the above embodiments, wherein R³ is H, cyano, (C₁-C₆)alkoxy, (C₁-C₆)alkyl, —(C=O)—R⁵, —(C=O)—O—R⁵, —O—(C=O)—R⁵, —NR⁵(C=O)—R⁶, —(C=O)—NR⁵R⁶, —NR⁵R⁶, —NR⁵OR⁶, or —(CR⁵R⁶)ᵥ(3-10)-membered cycloalkyl.

In another embodiment, the invention relates to compounds of any of the above embodiments, wherein each of R5, R⁶ and R⁷ are independently selected from H and (C₁-C₆) alkyl.

In another embodiment, the invention relates to compounds of any of the above embodiments, wherein R¹¹ is selected from halo, cyano, —CHF₂, hydroxy, (C₁-C₆)alkoxy, (C₁-C₆)alkyl, —(C=O)—R⁸, —(C=O)—R¹², —O—R¹², —(C=O)—NR⁸R⁹, —(C=O)—NR⁸R¹², —NR⁸R⁹, —NR⁸R¹², —S(O)ⱼ(C₁-C₆)alkyl, —S(O)ⱼR¹², —S(O)ₖNR⁸R⁹, —S(O)ₖNR⁸R¹², —(CR⁸R⁹)ᵥ(3-10)-membered cycloalkyl, —(CR⁸R⁹)ᵥ(C₆-C₁₀aryl), and —(CR⁸R⁹)ᵥ(4-10)-membered heterocyclyl.

Specific Embodiments of Compounds of the Invention are Selected from the Group Consisting of:

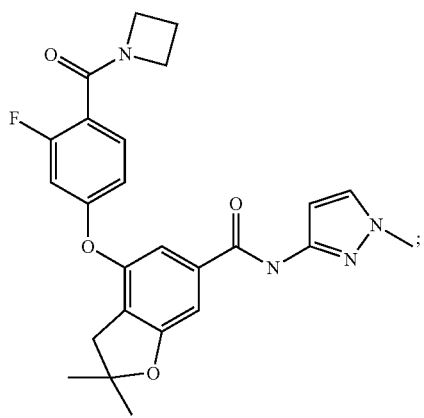

15
-continued
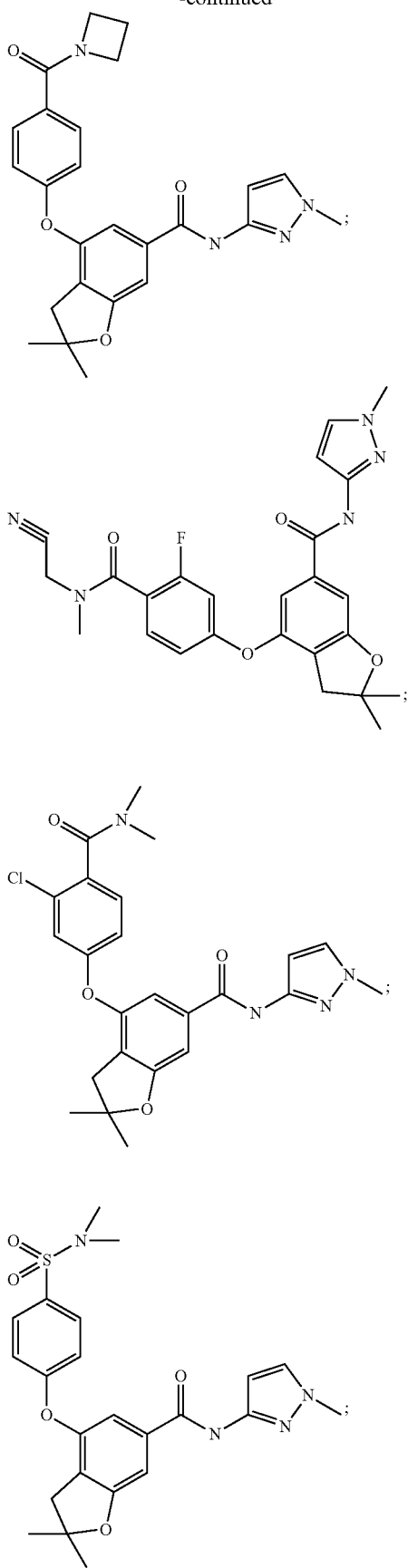
16
-continued
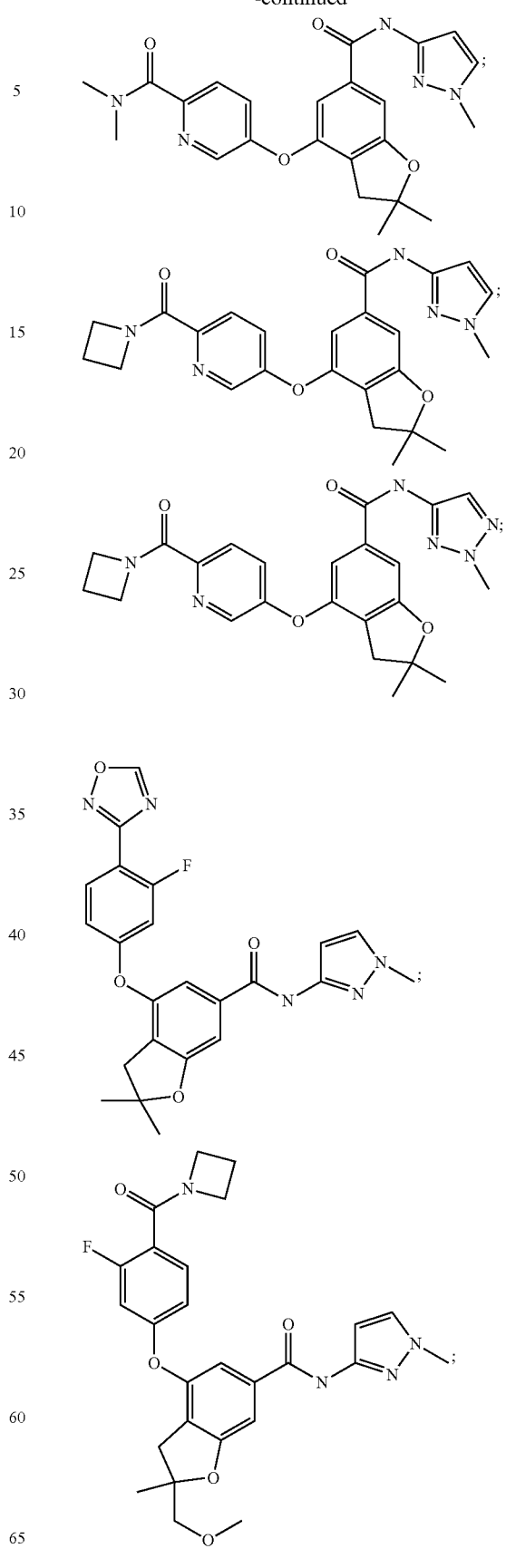

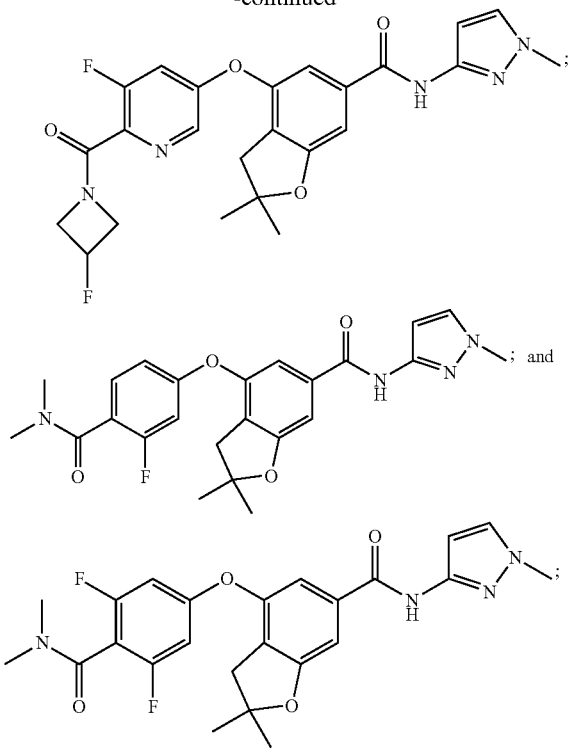

or a pharmaceutically acceptable salt or solvate thereof.

The present invention also relates to pharmaceutical composition comprising an effective amount of a compound of formula formula (I) or a pharmaceutically acceptable salt or solvate thereof, and a pharmaceutically acceptable carrier.

The present invention also relates to a method of treating a condition that is mediated by the modulation of GK, the method comprising administering to a mammal an effective amount of a compound of formula formula (I), or a pharmaceutically acceptable salt or solvate thereof.

The present invention also relates to a method of treating a condition that is mediated by the modulation of GK, the method comprising administering to a mammal an amount of a compound of formula formula (I), or a pharmaceutically acceptable salt or solvate thereof, effective to lower blood glucose levels.

The present invention also relates to a method of treating diabetes, metabolic syndrome, insulin resistance syndrome, obesity, glaucoma, hyperlipidemia, hyperglycemia, hyperinsulinemia, osteoporosis, tuberculosis, atherosclerosis, dementia, depression, virus diseases, inflammatory disorders, ophthalmic diseases, diabetic retinopathy, diabetic macular edema, or diseases in which the liver is a target organ, the method comprising administering to a mammal an effective amount of a compound of formula formula (I), or a pharmaceutically acceptable salt or solvate thereof.

The present invention also relates to a method of treating a condition, the method comprising administering to a mammal an amount effective of a compound of formula formula (I), or a pharmaceutically acceptable salt or solvate thereof, effective to lower blood glucose levels.

DEFINITIONS

For purposes of the present invention, as described and claimed herein, the following terms are defined as follows:

As used herein, the terms "comprising", "including", or "having" are used in their open, non-limiting sense.

The term "halo", as used herein, unless otherwise indicated, means fluoro, chloro, bromo or iodo.

The term "alkyl", as used herein, unless otherwise indicated, includes saturated monovalent hydrocarbon radicals having straight or branched moieties.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes 0-alkyl groups wherein alkyl is as defined above.

The term "Me" means methyl, "Et" means ethyl, and "Ac" means acetyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-10 carbon atoms, such as cyclopropyl, cyclobutyl, cyclopentyl, cyclohexyl, cycloheptyl, and adamantyl. Illustrative examples of cycloalkyl are derived from, but not limited to, the following:

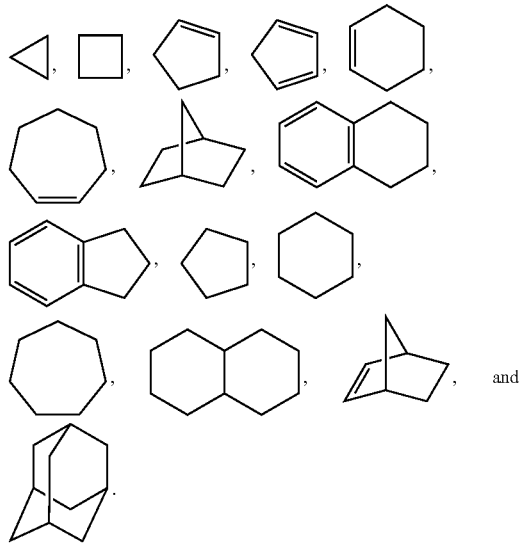

The term "aryl", as used herein, unless otherwise indicated, includes an organic radical derived from an aromatic hydrocarbon by removal of one hydrogen, such as phenyl or naphthyl.

The term "(4-12)-membered heterocyclyl" or "(4-10)-membered heterocyclyl", as used herein, unless otherwise indicated, includes aromatic and non-aromatic heterocyclic groups containing one to four heteroatoms each selected from O, S and N, wherein each heterocyclic group has from 3-7, 6-10, or 4-10 atoms, respectively, in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzofused ring systems. An example of a 3 membered heterocyclic group is aziridine, an example of a 4 membered heterocyclic group is azetidinyl (derived from azetidine). An example of a 5 membered heterocyclic group is thiazolyl, an example of a 7 membered ring is azepinyl, and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4-7 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other Illustrative examples of 4-7 membered heterocyclic are derived from, but not limited to, the following:

Unless otherwise indicated, the term "oxo" refers to =O.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO (dimethylsulfoxide), ethyl acetate, acetic acid, or ethanolamine.

The phrase "pharmaceutically acceptable salt(s)", as used herein, unless otherwise indicated, includes salts of acidic or basic groups which may be present in the compounds of formula (I). The compounds of formula (I) that are basic in nature are capable of forming a wide variety of salts with various inorganic and organic acids. The acids that may be used to prepare pharmaceutically acceptable acid addition salts of such basic compounds of formula (I) are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The term "diseases in which the liver is a target organ", as used herein, unless otherwise indicated means diabetes, hepatitis, liver cancer, liver fibrosis, and malaria.

The term "Metabolic syndrome", as used herein, unless otherwise indicated means psoriasis, diabetes mellitus, wound healing, inflammation, neurodegenerative diseases, galactosemia, maple syrup urine disease, phenylketonuria, hypersarcosinemia, thymine uraciluria, sulfinuria, isovaleric acidemia, saccharopinuria, 4-hydroxybutyric aciduria, glucose-6-phosphate dehydrogenase deficiency, and pyruvate dehydrogenase deficiency.

In the compounds of formula (I), where terms such as $(CR^5R^6)_v$ or $(CR^8R^9)_p$ are used, $R^5$, $R^6$, $R^8$ and $R^9$ may vary with each iteration of v or p. For instance, where v or p is 2 the terms $(CR^5R^6)_v$ or $(CR^8R^9)_p$ may equal —$CH_2CH_2$—, or —CH(CH$_3$)C(CH$_2$CH$_3$)(CH$_2$CH$_2$CH$_3$)—, or any number of similar moieties falling within the scope of the definitions of R$^5$, R$^6$, R$^8$ and R$^9$.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "modulate" or "modulating", as used herein, refers to the ability of a modulator for a member of the steroid/thyroid superfamily to either directly (by binding to the receptor as a ligand) or indirectly (as a precursor for a ligand or an inducer which promotes production of ligand from a precursor) induce expression of gene(s) maintained under hormone expression control, or to repress expression of gene(s) maintained under such control.

The term "obesity" or "obese", as used herein, refers generally to individuals who are at least about 20-30% over the average weight for his/her age, sex and height. Technically, "obese" is defined, for males, as individuals whose body mass index is greater than 27.8 kg/m$^2$, and for females, as individuals whose body mass index is greater than 27.3 kg/m$^2$. Those of skill in the art readily recognize that the invention method is not limited to those who fall within the above criteria. Indeed, the method of the invention can also be advantageously practiced by individuals who fall outside of these traditional criteria, for example, by those who may be prone to obesity.

The term "inflammatory disorders", as used herein, refers to disorders such as rheumatoid arthritis, ankylosing spondylitis, psoriatic arthritis, psoriasis, chondrocalcinosis, gout, inflammatory bowel disease, ulcerative colitis, Crohn's disease, fibromyalgia, and cachexia.

The phrase "therapeutically effective amount", as used herein, refers to that amount of drug or pharmaceutical agent that will elicit the biological or medical response of a tissue, system, animal, or human that is being sought by a researcher, veterinarian, medical doctor or other.

The phrase "amount . . . effective to lower blood glucose levels", as used herein, refers to levels of compound sufficient to provide circulating concentrations high enough to accomplish the desired effect. Such a concentration typically falls in the range of about 10 nM up to 2 μM; with concentrations in the range of about 100 nM up to 500 nM being preferred. As noted previously, since the activity of different compounds which fall within the definition of Formula (I) as set forth above may vary considerably, and since individual subjects may present a wide variation in severity of symptoms, it is up to the practitioner to determine a subject's response to treatment and vary the dosages accordingly.

The phrase "insulin resistance", as used herein, refers to the reduced sensitivity to the actions of insulin in the whole body or individual tissues, such as skeletal muscle tissue, myocardial tissue, fat tissue or liver tissue. Insulin resistance occurs in many individuals with or without diabetes mellitus.

The phrase "insulin resistance syndrome", as used herein, refers to the cluster of manifestations that include insulin resistance, hyperinsulinemia, non insulin dependent diabetes mellitus (NIDDM), arterial hypertension, central (visceral) obesity, and dyslipidemia.

Certain compounds of formula (I) may have asymmetric centers and therefore exist in different enantiomeric forms. All optical isomers and stereoisomers of the compounds of formula (I), and mixtures thereof, are considered to be within the scope of the invention. With respect to the compounds of formula (I), the invention includes the use of a racemate, one or more enantiomeric forms, one or more diastereomeric forms, or mixtures thereof. The compounds of formula (I) may also exist as tautomers. This invention relates to the use of all such tautomers and mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention and pharmaceutically acceptable salts or solvates of said compounds which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula (I) of this invention thereof can generally be prepared by carrying out the procedures disclosed in the Schemes and/or in the Examples below, by substituting a readily available isotopically labelled reagent for a non-isotopically labelled reagent.

Other aspects, advantages, and features of the invention will become apparent from the detailed description below.

DETAILED DESCRIPTION AND EMBODIMENTS OF THE INVENTION

The schemes below describe and depict general routes to prepare specific examples of the present invention of formula (I) wherein the definitions of are given in the summary of the invention.

Scheme A

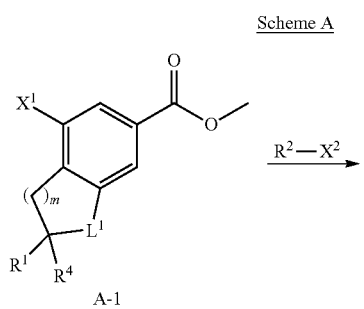
A-1

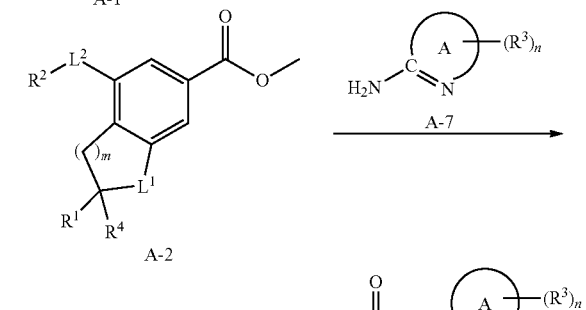
A-2

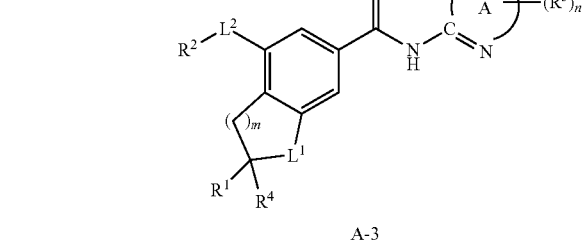
A-3

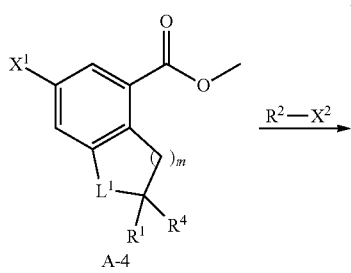
A-4

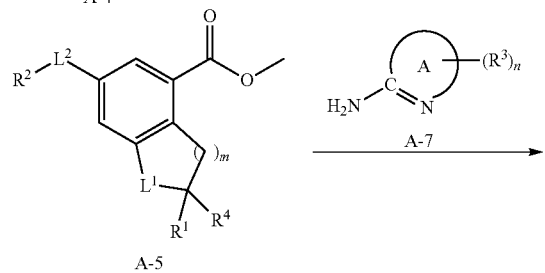
A-5

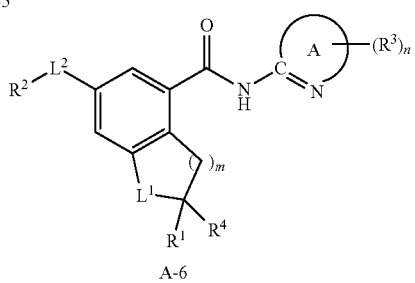
A-6

As depicted in Scheme A, following procedures described elsewhere and known to those skilled in the art, reactions of ester A-1 or A-4 or other ester derivatives thereof with $R^2$-$X^2$, wherein $X^2$ is a leaving group that could be displaced by $X^1$, or $X^1$ is a leaving group that could be displaced by $X^2$, provide ester A-2 or A-5 or other ester derivatives thereof. Reactions of ester A-2 or A-5 or other ester derivatives thereof with heteroaryl amine A-7 and dimethylaluminum chloride in dichloromethane could directly generate corresponding amides A-3 or A-6. A-3 or A-6 could also be obtained by hydrolysis of ester A-2 or A-5 or other ester derivatives thereof to acids and followed by amide formation by procedures known to those skilled in the art.

Scheme B

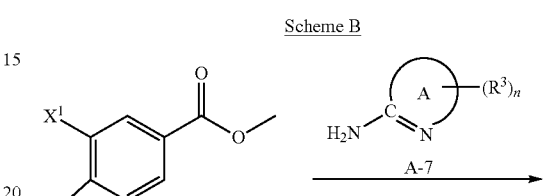
A-1

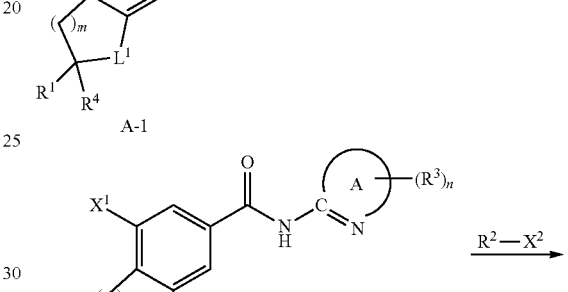
B-1

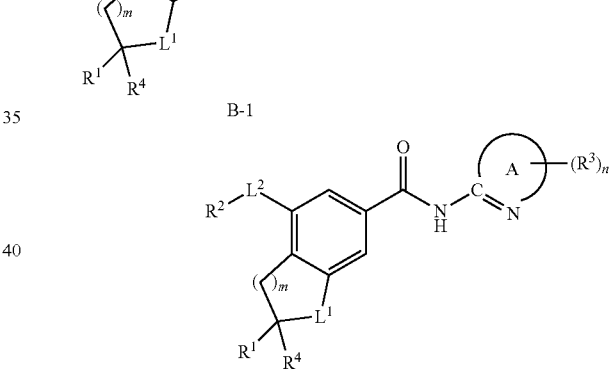
A-3

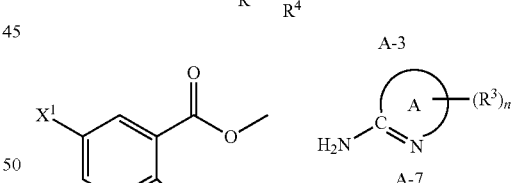
A-4

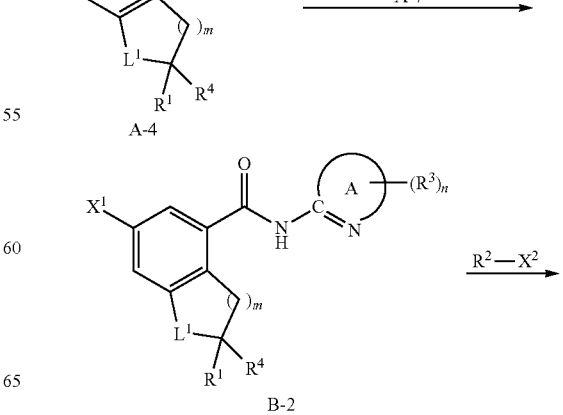
B-2

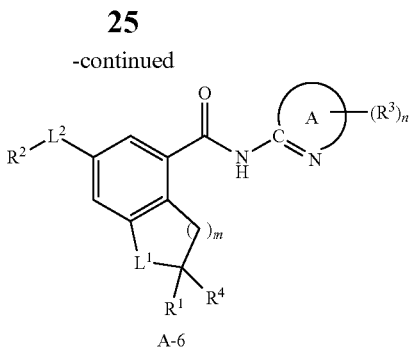

A-6

Alternatively, as depicted in Scheme B, ester A-1 or A-4 or other ester derivatives thereof could be coupled to heteroaryl amine A-7 to generate amides B-1 or B-2. B-1 or B-2 could then be reacted with $R^2$-$X^2$ replacing suitable leaving groups to provide A-3 and A-6, following procedures known to those skilled in the art.

Specific examples of intermediate A-1 and A-4 as described in Schemes A and B above can be prepared using the procedures as described in the following schemes:

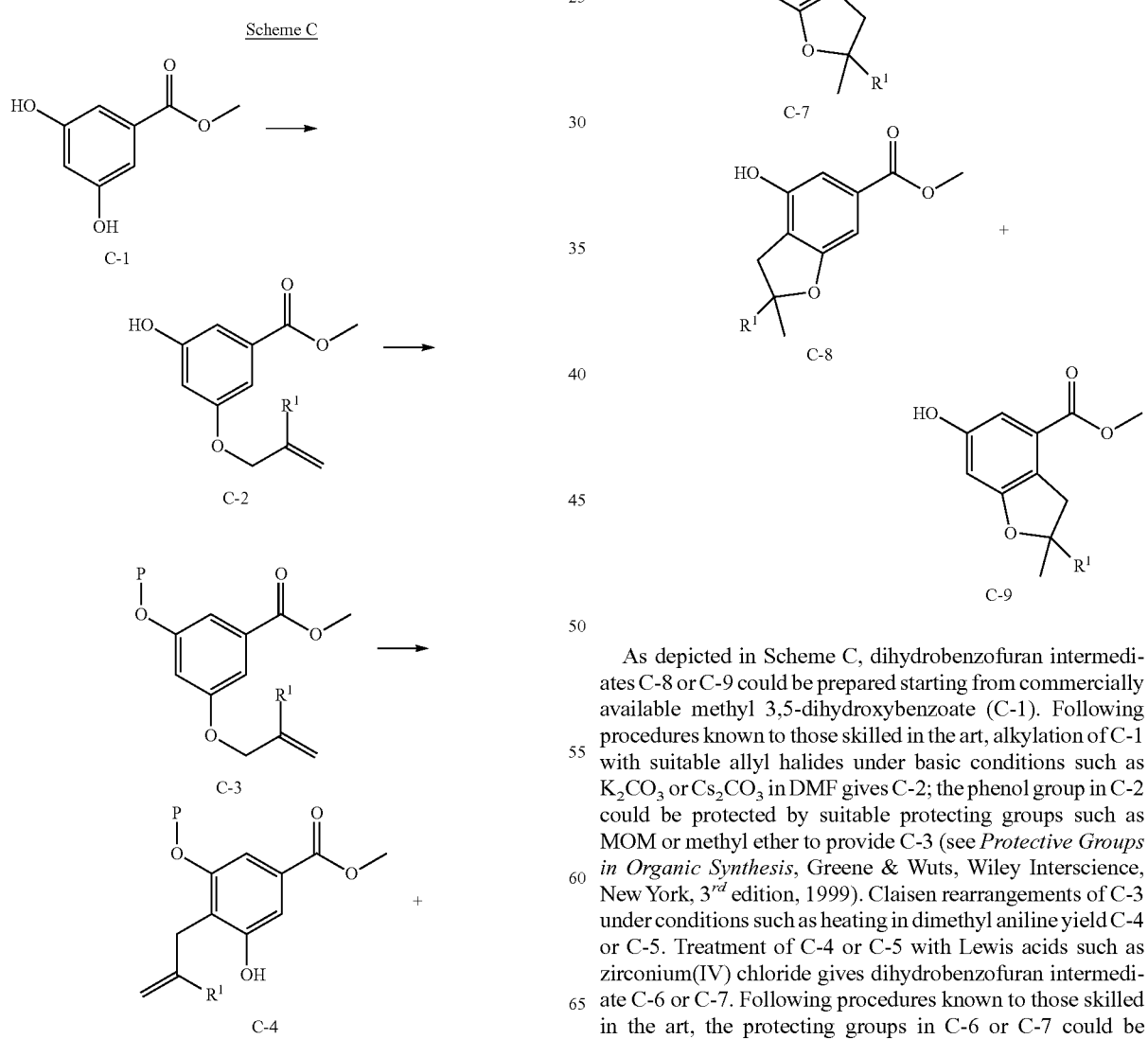

As depicted in Scheme C, dihydrobenzofuran intermediates C-8 or C-9 could be prepared starting from commercially available methyl 3,5-dihydroxybenzoate (C-1). Following procedures known to those skilled in the art, alkylation of C-1 with suitable allyl halides under basic conditions such as $K_2CO_3$ or $Cs_2CO_3$ in DMF gives C-2; the phenol group in C-2 could be protected by suitable protecting groups such as MOM or methyl ether to provide C-3 (see *Protective Groups in Organic Synthesis*, Greene & Wuts, Wiley Interscience, New York, $3^{rd}$ edition, 1999). Claisen rearrangements of C-3 under conditions such as heating in dimethyl aniline yield C-4 or C-5. Treatment of C-4 or C-5 with Lewis acids such as zirconium(IV) chloride gives dihydrobenzofuran intermediate C-6 or C-7. Following procedures known to those skilled in the art, the protecting groups in C-6 or C-7 could be removed to yield phenol intermediate C-8 or C-9.

Scheme D

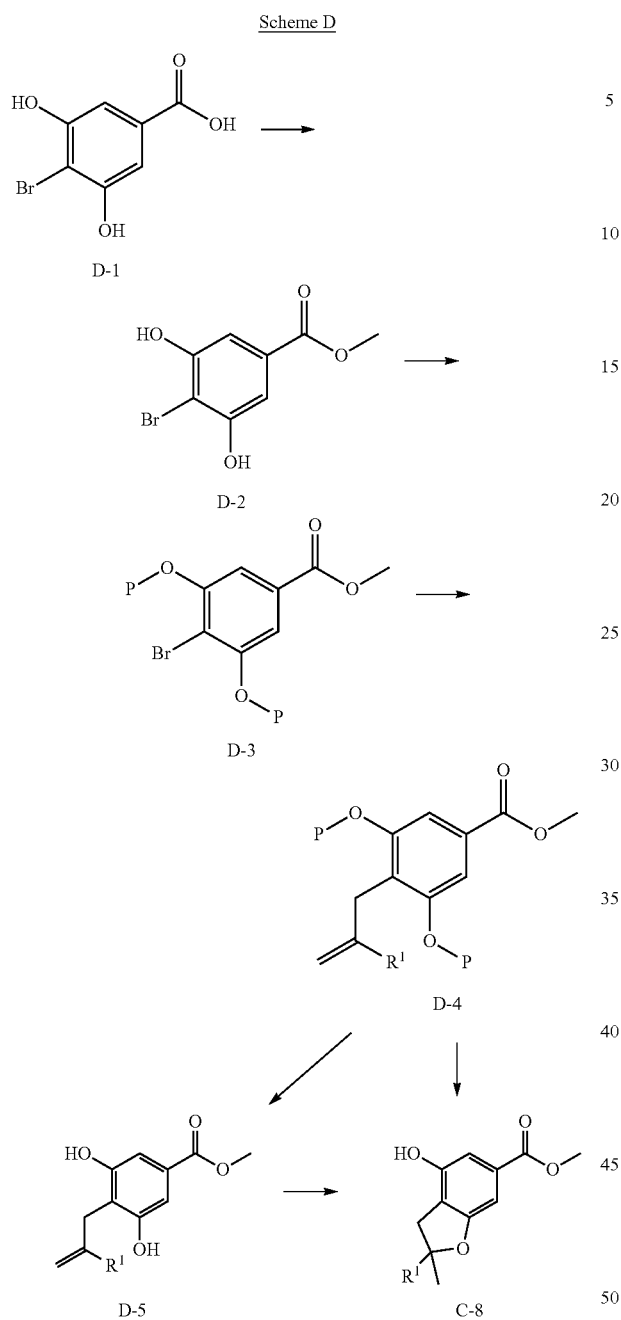

Scheme E

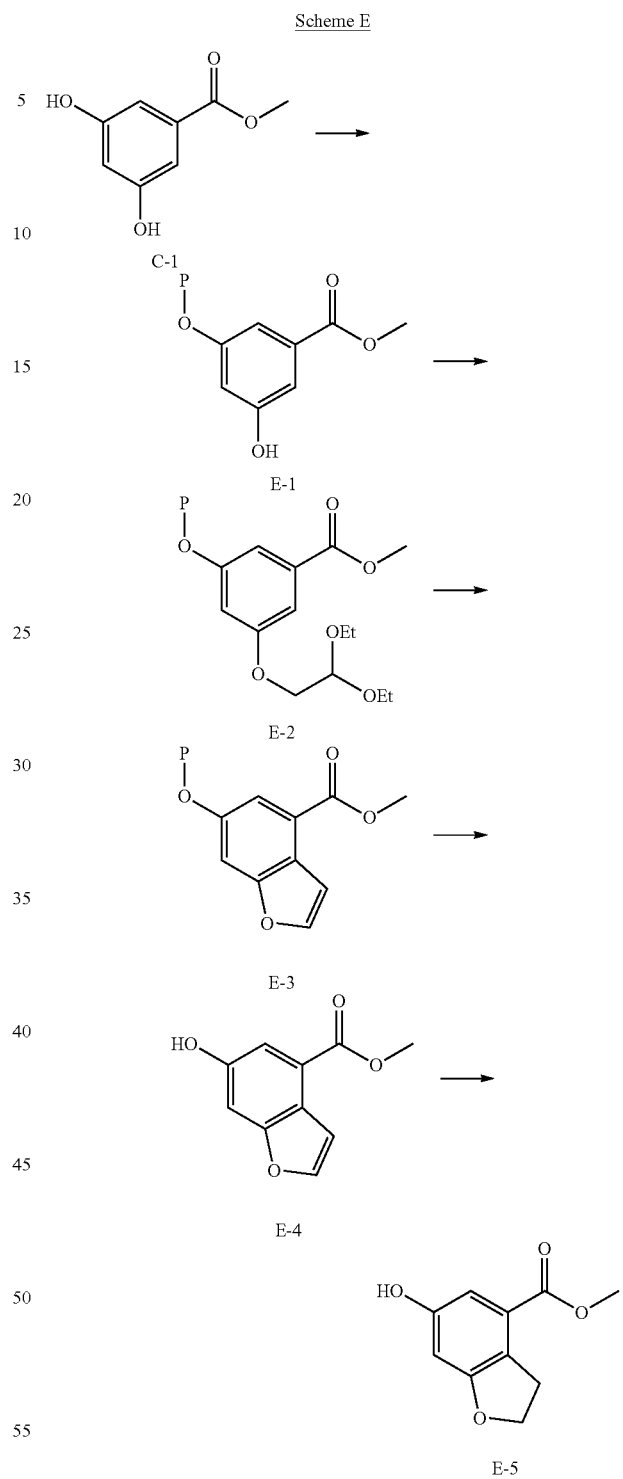

Alternatively, as depicted in Scheme D, dihydrobenzofuran intermediate C-8 could be prepared starting from commercially available 4-bromo-3,5-dihydroxybenzoic acid (D-1). Following procedures known to those skilled in the art, D-1 could be converted to its methyl ester D-2, such as refluxing in methanol with catalytic $H_2SO_4$. The phenol groups in D-2 could be protected by suitable protecting groups such as MOM or methyl ether to provide D-3. D-3 could be coupled to allyltributyltins with suitable catalysts such as $PdCl_2$ with suitable phosphine ligand and CuI to generate D-4. D-4 could be converted directly to C-8 under acidic conditions such as refluxing in MeOH/HCl or could be converted to D-5 through standard protecting group removal procedure followed by ring closure to give C-8.

As depicted in Scheme E, dihydrobenzofuran intermediate E-5 could be prepared starting from commercially available methyl 3,5-dihydroxybenzoate (C-1). Following procedures known to those skilled in the art, one of the phenol groups in C-1 could be protected by suitable protecting groups such as MOM or methyl ether to provide E-1. Alkylation of E-1 with bromoacetaldehyde diethyl acetal under basic conditions such as NaH in DMF gives E-2. Heating E-2 in polyphosphoric acid and benzene generates benzofuran intermediate E-3.

The protecting group in E-3 could be removed under standard conditions known to those skilled in the art to provide E-4. E-4 could be subjected to hydrogenation conditions to provide dihydrobenzofuran E-5.

Scheme F

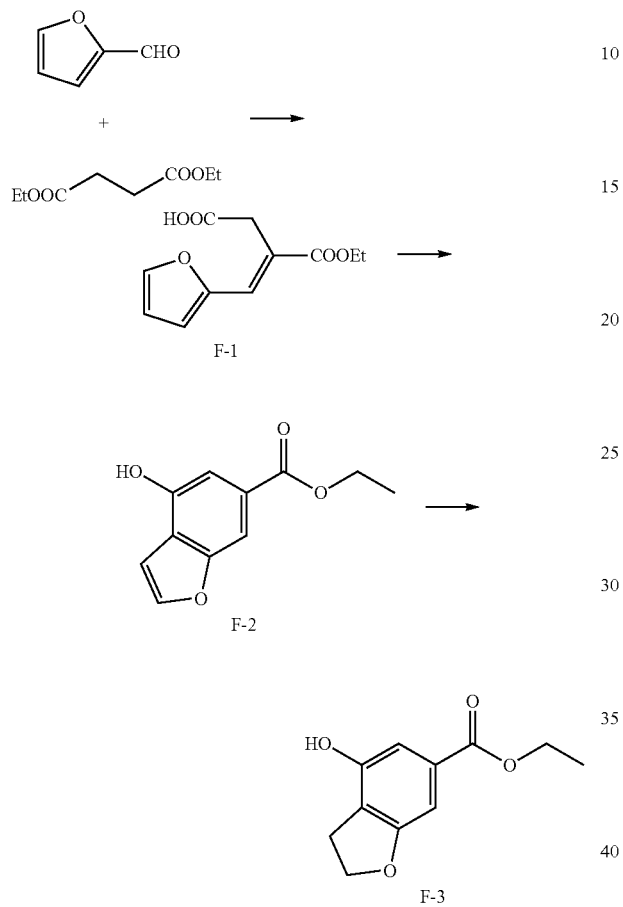

As depicted in Scheme F, dihydrobenzofuran intermediate F-3 could be prepared starting from commercially available 2-furaldehyde and diethyl succinate. Treatment of 2-furaldehyde and diethyl succinate with potassium t-butoxide in refluxing t-butanol gives intermediate F-1. Treatment of F-1 with sodium acetate in refluxing acetic anhydride, followed by aqueous work-up and subsequently refluxing the residue in EtOH in the presence of K₂CO₃, gives benzofuran F-2. F-2 could be subjected to hydrogenation conditions to provide dihydrobenzofuran F-3.

Scheme G

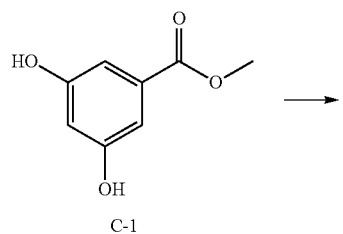

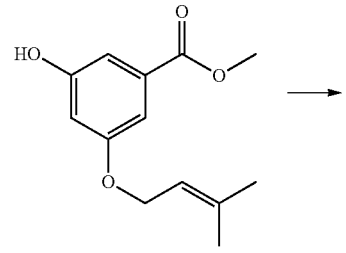

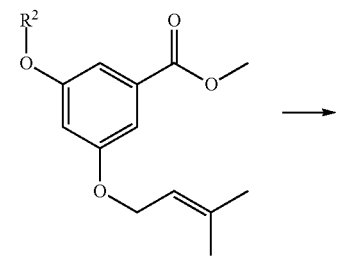

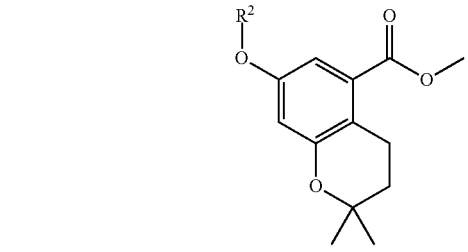

As depicted in Scheme G, tetrahydrobenzopyran intermediate G-3 and G-4 could be prepared starting from commercially available methyl 3,5-dihydroxybenzoate (C-1). Alkylation of C-1 with 1-bromo-3-methyl-but-2-ene under basic conditions such as potassium carbonate in DMF gives G-1. Under conditions known to those skilled in the art, G-1 could be reacted with $R^2$-$X^2$, wherein $X^2$ is a leaving group that could be displaced by phenol in G-1 to give G-2. Treatment of G-2 with Montarillonite K10 yielded tetrahydrobenzopyran intermediates G-3 and G-4.

Scheme H

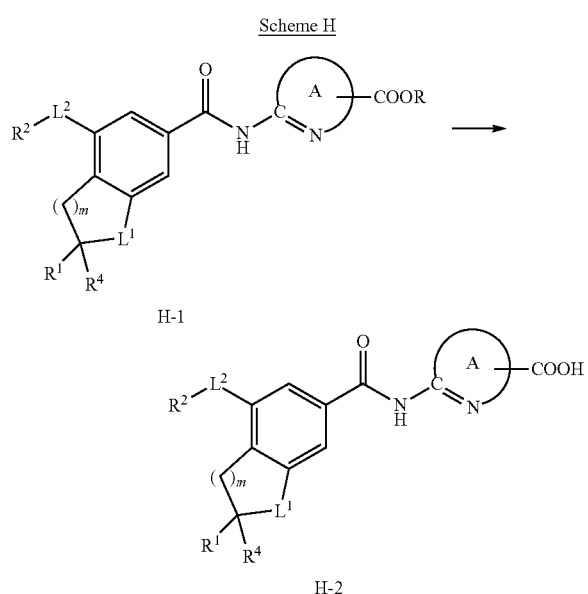

H-1

H-2

When $R_3$ in any specific examples is a carboxylic acid, as depicted in Scheme H, H-2 could be prepared from hydrolysis of the corresponding esters under basic conditions such as treatment of H-1 with aqueous NaOH in THF. H-1 could be prepared following Schemes A-G.

Any of the above compounds described in schemes A-H can be converted into another analogous compound by standard chemical manipulations. These chemical manipulations are known to those skilled in the art and include a) removal of a protecting group by methods outlined in T. W. Greene and P. G. M. Wuts, *Protective Groups in Organic Synthesis*, Second Edition, John Wiley and Sons, New York, 1991; b) displacement of a leaving group (halide, mesylate, tosylate, etc) with a primary or secondary amine, thiol or alcohol to form a secondary or tertiary amine, thioether or ether, respectively; c) treatment of phenyl (or substituted phenyl) carbamates with primary of secondary amines to form the corresponding ureas as in Thavonekham, B., et al., *Synthesis* (1997), 10,189; d) reduction of propargyl or homopropargyl alcohols or N-BOC protected primary amines to the corresponding E-allylic or E-homoallylic derivatives by treatment with sodium bis(2-methoxyethoxy)aluminum hydride (Red-Al) as in Denmark, S. E.; Jones, T. K. J., *Org. Chem.* (1982) 47, 4595-4597 or van Benthem, R. A. T. M.; Michels, J. J.; Speckamp, W. N. Synlett (1994), 368-370; e) reduction of alkynes to the corresponding Z-alkene derivatives by treatment hydrogen gas and a Pd catalyst as in Tomassy, B., et. al., *Synth. Commun.* (1998), 28, 1201 f) treatment of primary and secondary amines with an isocyanate, acid chloride (or other activated carboxylic acid derivative), alkyl/aryl chloroformate or sulfonyl chloride to provide the corresponding urea, amide, carbamate or sulfonamide; g) reductive amination of a primary or secondary amine using $R^1CH(O)$; and h) treatment of alcohols with an isocyanate, acid chloride (or other activated carboxylic acid derivative), alkyl/aryl chloroformate or sulfonyl chloride to provide the corresponding carbamate, ester, carbonate or sulfonic acid ester.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formulas (I) that are basic in nature are capable of forming a wide variety of different salts with various inorganic and organic acids. Although such salts must be pharmaceutically acceptable for administration to animals, it is often desirable in practice to initially isolate the compound of formula (I) from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula (I) that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula (I). Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention may also be useful in the treatment of other metabolic disorders associated with impaired glucose utilization and insulin resistance include major late-stage complications of NIDDM, such as diabetic angiopathy, atherosclerosis, diabetic nephropathy, diabetic neuropathy, and diabetic ocular complications such as retinopathy, cataract formation and glaucoma, and many other conditions linked to NIDDM, including dyslipidemia glucocorticoid induced insulin resistance, dyslipidemia, polycysitic ovarian syndrome, obesity, hyperglycemia, hyperlipidemia, hypercholesteremia, hypertriglyceridemia, hyperinsulinemia, and hypertension. Brief definitions of these conditions are available in any medical dictionary, for instance, *Stedman's Medical Dictionary* (Xth ed.).

Pharmaceutical Compositions/Formulations, Dosaging and Modes of Administration

Methods of preparing various pharmaceutical compositions with a specific amount of active compound are known, or will be apparent, to those skilled in this art. In addition, those of ordinary skill in the art are familiar with formulation and administration techniques. Such topics would be discussed, e.g. in Goodman and Gilman's *The Pharmaceutical Basis of Therapeutics*, current edition, Pergamon Press; and *Remington's Pharmaceutical Sciences*, current edition. Mack Publishing, Co., Easton, Pa. These techniques can be employed in appropriate aspects and embodiments of the methods and compositions described herein. The following examples are provided for illustrative purposes only and are not meant to serve as limitations of the present invention.

The amino heterocyclyl compounds of formula (I) may be provided in suitable topical, oral and parenteral pharmaceutical formulations for use in the treatment of GK mediated diseases. The compounds of the present invention may be administered orally as tablets or capsules, as oily or aqueous suspensions, lozenges, troches, powders, granules, emulsions, syrups or elixirs. The compositions for oral use may include one or more agents for flavoring, sweetening, coloring and preserving in order to produce pharmaceutically elegant and palatable preparations. Tablets may contain pharmaceutically acceptable excipients as an aid in the manufacture of such tablets. As is conventional in the art these tablets may be coated with a pharmaceutically acceptable enteric coating, such as glyceryl monostearate or glyceryl distearate, to delay disintegration and absorption in the gastrointestinal tract to provide a sustained action over a longer period.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain active ingredients in admixture with excipients suitable for the manufacture of an aqueous suspension. Such excipients may be a suspending agent, such as sodium carboxymethyl cellulose, methyl cellulose, hydroxypropylmethyl cellulose, sodium alginate, polyvinylpyrrolidone, gum tragacanth and gum acacia; a dispersing or wetting agent that may be a naturally occurring phosphatide such as lecithin, a condensation product of ethylene oxide and a long chain fatty acid, for example polyoxyethylene stearate, a condensation product of ethylene oxide and a long chain aliphatic alcohol such as heptadecaethylenoxycetanol, a condensation product of ethylene oxide and a partial ester derived from a fatty acid and hexitol such as polyoxyethylene sorbitol monooleate or a fatty acid hexitol anhydrides such as polyoxyethylene sorbitan monooleate.

The pharmaceutical compositions may be in the form of a sterile injectable aqueous or oleagenous suspension. This suspension may be formulated according to know methods using those suitable dispersing or wetting agents and suspending agents that have been mentioned above. The sterile injectable preparation may also be formulated as a suspension in a non toxic perenterally-acceptable diluent or solvent, for example as a solution in 1,3-butanediol. Among the acceptable vehicles and solvents that may be employed are water, Ringers solution and isotonic sodium chloride solution. For this purpose any bland fixed oil may be employed including synthetic mono- or diglycerides. In addition fatty acids such as oleic acid find use in the preparation of injectables.

The amino heterocyclyl compounds of formula (I) may also be administered in the form of suppositories for rectal administration of the drug. These compositions can be prepared by mixing the drug with a suitable non-irritating excipient that is solid at about 25 Celcius but liquid at rectal temperature and will therefore melt in the rectum to release the drug. Such materials include cocoa butter and other glycerides.

For topical use preparations, for example, creams, ointments, jellies solutions, or suspensions, containing the compounds of the present invention are employed.

The amino heterocyclyl compounds of formula (I) may also be administered in the form of liposome delivery systems such as small unilamellar vesicles, large unilamellar vesicles and multimellar vesicles. Liposomes can be formed from a variety of phospholipides, such as cholesterol, stearylamine or phosphatidylcholines.

Dosage levels of the compounds of the present invention are of the order of about 0.5 mg/kg body weight to about 100 mg/kg body weight. A preferred dosage rate is between about 30 mg/kg body weight to about 100 mg/kg body weight. It will be understood, however, that the specific dose level for any particular patient will depend upon a number of factors including the activity of the particular compound being administered, the age, body weight, general health, sex, diet, time of administration, route of administration, rate of excretion, drug combination and the severity of the particular disease undergoing therapy. To enhance the therapeutic activity of the present compounds they may be administered concomitantly with other orally active antidiabetic compounds such as the sulfonylureas, for example, tolbutamide and the like.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The invention will now be described in reference to the following Examples. These Examples are not to be regarded as limiting the scope of the present invention, but shall only serve in an illustrative manner.

EXAMPLES

In the examples described below, unless otherwise indicated, all temperatures are set forth in degrees Celsius and all parts and percentages are by weight. Reagents may be purchased from commercial suppliers, such as Sigma-Aldrich Chemical Company, Acros Organics, or Lancaster Synthesis Ltd. and may be used without further purification unless otherwise indicated. Tetrahydrofuran (THF), methylene chloride ($CH_2Cl_2$), and N,N-dimethylformamide (DMF) may be purchased from Aldrich in Sure-Seal bottles and used as received. All solvents may be purified using standard methods known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glassbacked silica gel 60 F 254 precoated plates (Merck Art 5719) and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.* (1978) 43, 2923) was performed using silica gel 60 (Merck Art 9385) or various MPLC systems, such as Biotage or ISCO purification system.

The compound structures in the examples below were confirmed by one or more of the following methods: proton magnetic resonance spectroscopy, mass spectroscopy, and elemental microanalysis. Proton magnetic resonance ($^1$H NMR) spectra were determined using a Bruker spectrometer operating at a field strength of 300 or 400 megahertz (MHz). Chemical shifts are reported in parts per million (PPM, δ) downfield from an internal tetramethylsilane standard. Alternatively, $^1$H NMR spectra were referenced to signals from residual protons in deuterated solvents as follows: CDCl$_3$=7.25 ppm; DMSO-d$_6$=2.49 ppm; C$_6$D$_6$=7.16 ppm; CD$_3$OD=3.30 ppm. Peak multiplicities are designated as follows: s, singlet; d, doublet; dd, doublet of doublets; t, triplet; dt, doublet of triplets; q, quartet; br, broadened; m, multiplet. Coupling constants are given in Hertz (Hz). Mass spectra (MS) data were obtained using Agilent mass spectrometer with APCI or ESI ionization. Elemental microanalyses were performed by Atlantic Microlab Inc. and gave results for the elements stated within ±0.4% of the theoretical values.

Preferred compounds in accordance with the invention may be prepared in manners analogous to those specifically described below.

The examples and preparations provided below further illustrate and exemplify the compounds of the present invention and methods of preparing such compounds. It is to be understood that the scope of the present invention is not limited in any way by the scope of the following examples and preparations. The skilled artisan will recognize that different acids, amines, alkyl halides, aryl halides, coupling reagents, and heterocycles may be substituted in the following descriptions to suit the preparations of a desired embodiment. The following methods may be scaled upwards or downwards to suit the amount of desired material.

In the examples and specification, "Et" means ethyl, "Ac" means acetyl, "Me" means methyl, "ETOAC" or "EtOAc" means ethyl acetate, "THF" means tetrahydrofuran, and "Bu" means butyl. Et$_2$O refers to diethyl ether. DMF refers to N,N-dimethylformamide. DMSO refers to dimethylsulfoxide. MTBE refers to tert-butyl methylether. Other abbreviations include: CH$_3$OH or MeOH (methanol), EtOH (ethanol), DME (ethylene glycol dimethyl ether), DCM or CH$_2$Cl$_2$ (dichloromethane or methylene chloride), CHCl$_3$ (chloroform), 1,2-DCE (1,2-dichloroethane), Ph (phenyl), TFA (trifluoroacetic acid), DIEA (N,N-diisopropylethylamine), TEA or Et$_3$N (triethylamine), NMM (4-methylmorpholine), HOBt (1-hydroxybenzotriazole hydrate), HATU [O-(7-azabenzotriazol-1-yl)-N,N,N',N'-tetramethyluronium hexafluorophosphate], EDCI [1-(3-dimethylaminopropyl)-3-ethylcarbodiimide hydrochloride], DCC (dicyclohexyl carbodiimide), DMAP (4-dimethylaminopyridine), NaOH (sodium hydroxide), KOH (potassium hydroxide), HCl (hydrogen chloride), MgSO$_4$ (magnesium sulfate), Na$_2$SO$_4$ (sodium sulfate), NH$_4$Cl (ammonium chloride), and NaHCO$_3$ (sodium bicarbonate).

Example 1

6-(4-Methanesulfonyl-phenoxy)-2-methyl-2,3-dihydrobenzofuran-4-carboxylic acid pyridin-2-ylamide

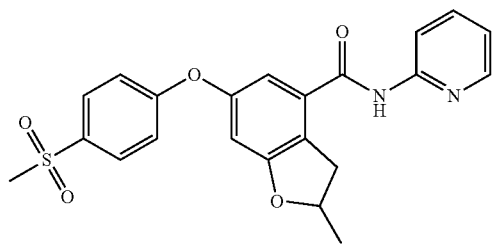

Dimethylaluminum chloride (1.0 M solution in hexanes, 3 mL, 3.0 mmol) was added to a solution of 2-aminopyridine (282 mg, 3.0 mmol) in 1,2-dichloromethane at 0° C. The mixture was stirred at room temperature for 15 min and then 6-(4-methanesulfonyl-phenoxy)-2-methyl-2,3-dihydro-benzofuran-4-carboxylic acid methyl ester (1f) (108 mg, 0.30 mmol) in 1,2-dichloromethane (3 mL) was added. The mixture was stirred at room temperature overnight, and carefully quenched with 20% aqueous potassium sodium tartrate tetrahydrate (5 mL), diluted with H$_2$O (30 mL), extracted with CH$_2$Cl$_2$ (2×50 mL) and concentrated in vacuo. The residue was purified by flash column chromatography eluting with 50% EtOAc in hexane to give a white solid (67 mg, 53% yield). $^1$H NMR (400 MHz, CDCl$_3$) δ 8.39 (br. s., 1 H) 8.21-8.34 (m, 2 H) 7.87-7.96 (m, 2 H) 7.70-7.81 (m, 1 H) 7.04-7.17 (m, 3 H) 6.94 (d, J=2.02 Hz, 1 H) 6.67 (d, J=1.77 Hz, 1 H) 4.97-5.18 (m, 1 H) 3.71 (dd, J=16.67, 8.84 Hz, 1 H) 3.19 (dd, J=16.67, 7.58 Hz, 1 H) 3.07 (s, 3 H) 1.53 (d, J=6.32 Hz, 3 H); LCMS for C$_{22}$H$_{20}$N$_2$O$_5$S m/z 425.10 (M+H)$^+$; Anal. Calcd. for C$_{22}$H$_{20}$N$_2$O$_5$S.0.2 H$_2$O: C, 61.73; H, 4.80; N, 6.54; Found: C, 61.71; H, 4.81; N, 6.41.

Preparation of Intermediate 1a

3-Allyloxy-5-hydroxy-benzoic acid methyl ester

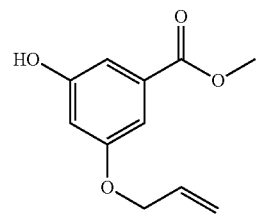

Methyl 3,5-dihydroxybenzoate (20.9 g, 124 mmol) was dissolved in DMF (30 mL). Potassium carbonate (34.4 g, 249 mmol) was added, followed by allyl bromide (10.5 mL, 124 mmol). The resulting suspension was stirred at room temperature overnight under argon atmosphere. The reaction mixture was quenched with H$_2$O, extracted with EtOAc (2×150 mL). The organic layers were washed with H$_2$O (2×200 mL), dried with MgSO$_4$ and concentrated in vacuo to yield a pale yellow oil which was purified by flash column chromatography eluting with 20% EtOAc in hexane to give a pale yellow solid (10.25 g, 40% yield). $^1$H NMR (400 MHz, CDCl$_3$) δ 7.08-7.22 (m, 2 H) 6.65 (t, J=2.40 Hz, 1 H) 5.94-6.21 (m, 1 H) 5.73 (s, 1 H) 5.42 (dd, J=17.18, 1.52 Hz, 1 H) 5.31 (dd, J=10.48, 1.39 Hz, 1 H) 4.55 (d, J=5.05 Hz, 2 H) 3.91 (s, 3 H); LCMS for C$_{14}$H$_{12}$O$_4$ m/z 209.0 (M+H)$^+$.

Preparation of Intermediate 1b

3-Allyloxy-5-methoxy-benzoic acid methyl ester

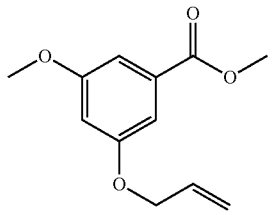

To a solution of 3-allyloxy-5-hydroxy-benzoic acid methyl ester (la) (10.25 g, 49.2 mmol) in DMF (20 mL) was added methyl iodide (3.67 mL, 59.1 mmol) and K$_2$CO$_3$ (13.6 g, 98.5 mmol). The reaction mixture was stirred at 70° C. for 2 hr, cooled to room temperature. The mixture was quenched with H$_2$O (150 mL) and extracted with EtOAc (2×150 mL). The organic layers were washed with H$_2$O (2×150 mL), dried over MgSO$_4$ and concentrated to give a pale yellow oil which was purified by flash column chromatography eluting with 10% EtOAc in hexane to give a colorless oil (9.63 g, 88% yield). $^1$H NMR (400 MHz, CDCl$_3$) δ 7.11-7.24 (m, 2 H) 6.68 (t, J=2.40 Hz, 1 H) 5.91-6.17 (m, 1 H) 5.38-5.51 (m, 1 H) 5.31 (dd, J=10.48, 1.39 Hz, 1 H) 4.52-4.61 (m, 2 H) 3.91 (s, 3 H) 3.83 (s, 3 H); LCMS for C$_{12}$H$_{14}$O$_4$ m/z 223.0 (M+H)$^+$.

Preparation of Intermediate 1c

Mixture of 2-allyl-3-hydroxy-5-methoxy-benzoic acid methyl ester and 4-allyl-3-hydroxy-5-methoxy-benzoic acid methyl ester

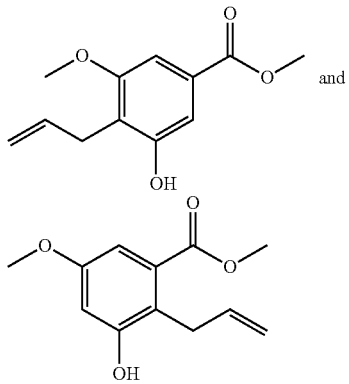

3-Allyloxy-5-methoxy-benzoic acid methyl ester (1b) (8.63 g, 38.8 mmol) was added to dimethyl aniline (20 mL). The mixture was heated to reflux overnight. The mixture was cooled to room temperature, quenched with 1N HCl (200 mL), extracted with EtOAc (2×200 mL), dried over MgSO$_4$ and concentrated. The residue was purified by flash column chromatography eluting with 5-20% EtOAc in hexanes to give a mixture of 2-allyl-3-hydroxy-5-methoxy-benzoic acid methyl ester and 4-allyl-3-hydroxy-5-methoxy-benzoic acid methyl ester as a pale yellow solid (5.1 g, 59% yield) $^1$H NMR (400 MHz, CDCl$_3$) δ 7.21 (s, 1 H) 7.17 (s, 1 H) 6.98 (d, J=2.53 Hz) 6.60 (d, J=2.53 Hz) 5.85-6.13 (m) 5.58 (s) 5.66 (s), 5.11 (s), 5.07-5.09 (m) 3.91 (s) 3.88 (s) 3.86 (s) 3.79 (s) 3.68 (d, J=5.81 Hz) 3.48 (d, J=5.81 Hz). LCMS for C$_{12}$H$_{14}$O$_4$ m/z 223.0 (M+H)$^+$.

Preparation of Intermediate 1d

Mixture of 4-methoxy-2-methyl-2,3-dihydro-benzofuran-6-carboxylic acid methyl ester and 6-methoxy-2-methyl-2,3-dihydro-benzofuran-4-carboxylic acid methyl ester

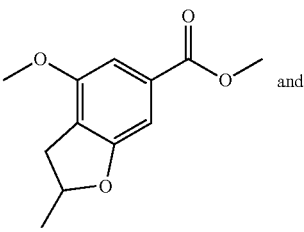

and

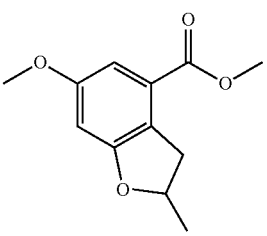

Zirconium(IV) chloride (4.83 g, 20.7 mmol) was added to a mixture of 2-allyl-3-hydroxy-5-methoxy-benzoic acid methyl ester and 4-allyl-3-hydroxy-5-methoxy-benzoic acid methyl ester (1c) (3.84 g, 17.3 mmol) in CH$_2$Cl$_2$ (60 mL) at 0° C. The mixture was stirred at 0° C. and warmed to room temperature overnight, quenched with H$_2$O (100 mL) and extracted with CH$_2$Cl$_2$ (2×100 mL), dried over MgSO$_4$ and concentrated. The residue was purified by flash column chromatography eluting with 5-10% EtOAc in hexanes to give a mixture of methyl 6-methoxyl-2-methyl-2,3-dihydrobenzofuran-4-carboxylate and methyl 4-methoxyl-2-methyl-2,3-dihydrobenzo-furan-6-carboxylate (1:1) as colorless oil (1.91 g, 22% yield). $^1$H NMR (400 MHz, CDCl$_3$) δ 7.11 (d, J=16.17 Hz) 7.03 (d, J=2.53 Hz) 6.54 (d, J=2.27 Hz) 4.92-5.03 (m) 3.86-3.91 (m) 3.81 (s) 3.59 (dd, J=16.93, 8.84 Hz) 3.30 (dd, J=16.29, 8.97 Hz) 3.05 (dd, J=16.80, 7.45 Hz) 2.77 (dd, J=16.17, 7.33 Hz) 1.59 (s) 1.47 (d, J=6.32 Hz).); LCMS for $C_{12}H_{14}O_4$ m/z 223.0 $(M+H)^+$.

Preparation of Intermediate 1e

6-Hydroxy-2-methyl-2,3-dihydro-benzofuran-4-carboxylic acid methyl ester

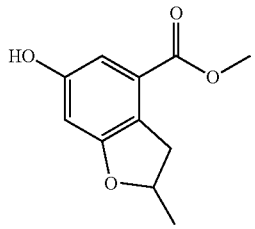

2,6-Lutidine (2.64 mL, 22.7 mmol) and $BBr_3$ (22.7 mL, 22.7 mmol, 1.0 M solution in $CH_2Cl_2$) were added to a mixture of 4-methoxy-2-methyl-2,3-dihydro-benzofuran-6-carboxylic acid methyl ester and 6-methoxy-2-methyl-2,3-dihydro-benzofuran-4-carboxylic acid methyl ester (1d) (1.68 g, 7.58 mmol) in $CH_2Cl_2$ (30 mL) at 0° C. The mixture was stirred at 0° C. and the warmed to room temperature overnight. The mixture was quenched with $H_2O$ (80 mL) and extracted with $CH_2Cl_2$ (2×80 mL). The organic layers were dried over $MgSO_4$ and concentrated. The residue was purified by flash column chromatography eluting with 20-30% EtOAc in hexanes to give a pale brown colored solid (366 mg, 23% yield). $^1$H NMR (400 MHz, $CDCl_3$) δ 6.99 (d, J=2.27 Hz, 1 H) 6.49 (d, J=2.27 Hz, 1 H) 5.46 (s, 1 H) 4.86-5.07 (m, 1 H) 3.89 (s, 3 H) 3.57 (dd, J=16.93, 8.84 Hz, 1H) 3.03 (dd, J=16.93, 7.33 Hz, 1 H) 1.46 (d, J=6.32 Hz, 3 H); LCMS for $C_{11}H_{12}O_4$ m/z 209.0 $(M+H)^+$.

Preparation of Intermediate 1f 6-(4-Methanesulfonyl-phenoxy)-2-methyl-2,3-dihydro-benzofuran-4-carboxylic acid methyl ester

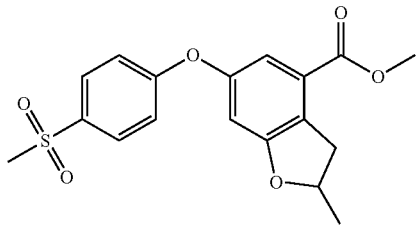

4-Fluorophenyl methyl sulfone (307 mg, 1.76 mmol) and $Cs_2CO_3$ (1.15 g, 3.52 mmol) were added to a solution of 6-hydroxy-2-methyl-2,3-dihydro-benzofuran-4-carboxylic acid methyl ester (1e) (366 mg, 1.76 mmol) in DMF (8 mL). The mixture was heated to 120° C. for 1 hr, cooled to room temperature, quenched with $H_2O$ (50 mL) and extracted with EtOAc (2×50 mL). The organic layers were washed with $H_2O$ (2×80 mL), dried over $MgSO_4$ and concentrated. The residue was purified by flash column chromatography eluting with 40% EtOAc in hexanes to give a pale brown solid (350 mg, 55% yield). $^1$H NMR (400 MHz, $CDCl_3$) δ 7.84-7.93 (m, 2 H) 7.18 (d, J=2.02 Hz, 1 H) 7.04-7.14 (m, 2 H) 6.67 (d, J=2.27 Hz, 1 H) 4.94-5.17 (m, 1 H) 3.89 (s, 3 H) 3.68 (dd, J=17.43, 8.84 Hz, 1 H) 3.13 (dd, J=17.43, 7.58 Hz, 1 H) 3.07 (s, 3H) 1.51 (d, J=6.32 Hz, 3 H);); LCMS for $C_{18}H_{18}O_6S$ m/z 363.0 $(M+H)^+$.

Example 2

6-(4-Methanesulfonyl-phenoxy)-2-methyl-2,3-dihydrobenzofuran-4-carboxylic acid(5-methyl-pyridin-2-yl)-amide

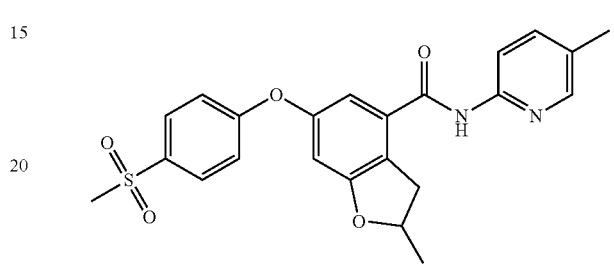

The title compound was prepared in a similar manner as described for Example 1, from 6-(4-methanesulfonyl-phenoxy)-2-methyl-2,3-dihydro-benzofuran-4-carboxylic acid methyl ester (1f) to give a white solid (92 mg, 46% yield). $^1$H NMR (400 MHz, $CDCl_3$) δ 8.33 (br. s., 1 H) 8.20 (d, J=8.34 Hz, 1 H) 8.10 (d, J=2.27 Hz, 1 H) 7.86-7.96 (m, 2 H) 7.57 (dd, J=8.59, 2.27 Hz, 1 H) 7.09-7.14 (m, 2 H) 6.93 (d, J=2.02 Hz, 1 H) 6.66 (d, J=2.02 Hz, 1 H) 4.93-5.19 (m, 1 H) 3.70 (dd, J=16.80, 8.97 Hz, 1 H) 3.18 (dd, J=16.93, 7.58 Hz, 1 H) 3.07 (s, 3 H) 2.32 (s, 3 H) 1.52 (d, J=6.32 Hz, 3 H); LCMS for $C_{23}H_{22}N_2O_5S$ m/z 439.1 $(M+H)^+$; Anal. Calcd. for $C_{23}H_{22}N_2O_5S$: C, 63.09; H, 5.06; N, 6.39; Found: C, 62.90; H, 5.06; N, 6.32.

Example 3

4-(4-Methanesulfonyl-phenoxy)-2,2-dimethyl-2,3-dihydrobenzofuran-6-carboxylic acid(5-methyl-pyridin-2-yl)-amide

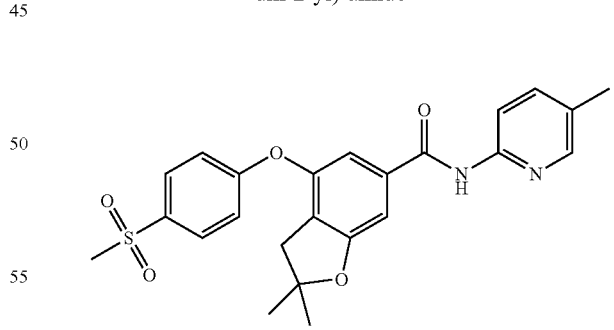

The title compound was prepared in a similar manner as described for Example 1, from 4-(4-methanesulfonyl-phenoxy)-2,2-dimethyl-2,3-dihydro-benzofuran-6-carboxylic acid methyl ester (3f) to give a white solid (71 mg, 65% yield). $^1$H NMR (400 MHz, $CDCl_3$) δ 8.42 (s, 1 H) 8.22 (d, J=8.34 Hz, 1 H) 8.11 (s, 1 H) 7.93 (d, J=8.59 Hz, 2 H) 7.57 (d, J=8.34 Hz, 1 H) 7.13 (d, J=8.84 Hz, 2 H) 7.10 (s, 3H) 2.91 (s, 2 H) 2.32 (s, 3 H) 1.51 (s, 6 H); LCMS for $C_{24}H_{24}N_2O_5S$ m/z 453.10 $(M+H)^+$; Anal. Calcd. for $C_{24}H_{24}N_2O_5S \cdot 0.3\ CH_2Cl_2$: C, 61.06; H, 5.19; N, 5.86; Found: C, 60.97; H, 5.07; N, 5.94.

Preparation for Intermediate 3a

3-Hydroxy-5-(2-methyl-allyloxy)-benzoic acid methyl ester

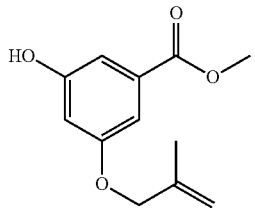

The title compound was prepared in a similar manner as described for Intermediate 1a, from methyl 3,5-dihydroxybenzoate (15.0 g, 89.2 mmol), potassium carbonate (24.7 g, 178.4 mmol) and 3-bromo-2-methyl-propene (9.0 mL, 89.2 mmol). Purification by column chromatography eluting with 15% EtOAc in hexanes gave a pale yellow solid (7.80 g, 39% yield). $^1$H NMR (400 MHz, CDCl$_3$) δ 7.13-7.22 (m, 2 H) 6.66 (t, J=2.27 Hz, 1 H) 5.81 (s, 1 H) 5.06-5.16 (m, 1H) 4.93-5.04 (m, 1H) 4.44 (s, 2 H) 3.91 (s, 3 H) 1.68-1.94 (m, 3 H); LCMS for $C_{12}H_{14}O_4$ m/z 223.10 (M+H)$^+$.

Preparation of Intermediate 3b

3-Methoxy-5-(2-methyl-allyloxy)-benzoic acid methyl ester

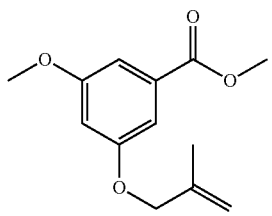

The title compound was prepared in a similar manner as described for Intermediate 1b, from 3-methoxy-5-(2-methyl-allyloxy)-benzoic acid methyl ester (3a) (7.80 g, 35.0 mmol), methyl iodide (2.60 mL, 42.0 mmol) and K$_2$CO$_3$ (9.67 g, 70.0 mmol). Purification by column chromatography eluting with 10% EtOAc in hexanes gave a colorless oil (7.54 g, 91% yield). $^1$H NMR (400 MHz, CDCl$_3$) δ 7.20-7.22 (m, 1 H) 7.18-7.20 (m, 1 H) 6.68 (t, J=2.27 Hz, 1 H) 5.11 (s, 1 H) 5.01 (s, 1 H) 4.46 (s, 2H) 3.91 (s, 3 H) 3.83 (s, 3H) 1.84 (s, 3 H); LCMS for $C_{13}H_{16}O_4$ m/z 237.10 (M+H)$^+$.

Preparation of Intermediate 3c

Mixture of 3-hydroxy-5-methoxy-2-(2-methyl-allyl)-benzoic acid methyl ester and 3-hydroxy-5-methoxy-4-(2-methyl-allyl)-benzoic acid methyl ester

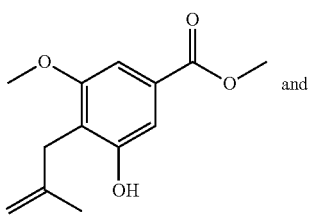

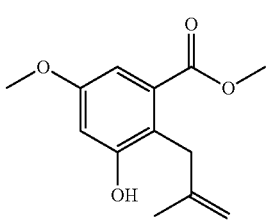

The title compound was prepared in a similar manner as described for Intermediate 1c, from 3-methoxy-5-(2-methyl-allyloxy)-benzoic acid methyl ester (3b) (7.54 g, 32.0 mmol). Purification by column chromatography eluting with 5-20% EtOAc in hexanes gave a mixture of 3-hydroxy-5-methoxy-2-(2-methyl-allyl)-benzoic acid methyl ester and 3-hydroxy-5-methoxy-4-(2-methyl-allyl)-benzoic acid methyl ester as a colorless oil (4.80 g, 64% yield). $^1$H NMR (400 MHz, CDCl$_3$) δ 7.11-7.24 (m) 7.02 (d, J=2.27 Hz) 6.68 (t, J=2.40 Hz) 6.51 (d, J=2.27 Hz) 5.10 (s) 5.00 (s) 3.91 (s) 3.88 (s) 3.83 (s) 3.80 (s) 3.26 (s) 1.83 (s) 1.47 (s); LCMS for $C_{13}H_{16}O_4$ m/z 237.10 (M+H)$^+$.

Preparation of Intermediate 3d

Mixture of 4-methoxy-2,2-dimethyl-2,3-dihydrobenzofuran-6-carboxylic acid methyl ester and 6-methoxy-2,2-dimethyl-2,3-dihydrobenzofuran-4-carboxylic acid methyl ester

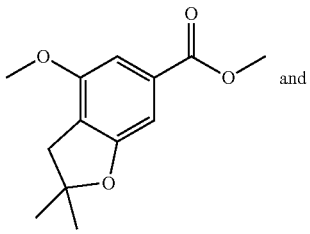

-continued

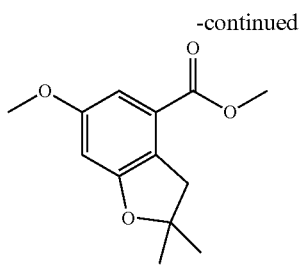

The title compound was prepared in a similar manner as described for Intermediate 1d, from zirconium(IV) chloride (3.03 g, 11.0 mmol) and a mixture of methyl 2-ally-3-hydroxy-5-methoxy-benzoate and methyl 2-ally-3-hydroxy-5-methoxybenzoate (3c) (2.5 g, 13.0 mmol). Purification by column chromatography eluting with 5-10% EtOAc in hexanes gave a mixture of 4-methoxy-2,2-dimethyl-2,3-dihydro-benzofuran-6-carboxylic acid methyl ester and 6-methoxy-2,2-dimethyl-2,3-dihydrobenzofuran-4-carboxylic acid methyl ester (2:1) as a colorless oil (1.74 g, 70% yield). $^1$H NMR (400 MHz, CDCl$_3$) δ 7.12 (s) 7.07 (s) 7.03 (d, J=2.27 Hz) 6.52 (d, J=2.27 Hz) 3.90 (s) 3.87 (s) 3.81 (s) 3.27 (s) 2.97 (s) 1.49 (s) 1.48 (s); LCMS for $C_{13}H_{16}O_4$ m/z 237.10 (M+H)$^+$.

Preparation of Intermediate 3e

4-Hydroxy-2,2-dimethyl-2,3-dihydrobenzofuran-6-carboxy-lic acid methyl ester

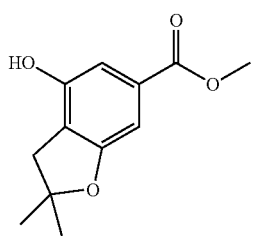

To the mixture of 4-methoxy-2,2-dimethyl-2,3-dihydro-benzofuran-6-carboxylic acid methyl ester and 6-methoxy-2,2-dimethyl-2,3-dihydro-benzofuran-4-carboxylic acid methyl ester (3d) (1.74 g, 7.36 mmol) in CH$_2$Cl$_2$ (10 mL) at 0° C. was added BBr$_3$ (22.0 mL, 22 mmol, 1.0 M solution in CH$_2$Cl$_2$). The reaction mixture was stirred at 0° C. for 6 hr, quenched with H$_2$O (100 mL), extracted with CH$_2$Cl$_2$ (2×100 mL), dried over MgSO$_4$, and concentrated in vacuo. The residue was purified by flash column chromatography eluting with 10% EtOAc in hexanes to give an pale yellow solid (171 mg, 10% yield). $^1$H NMR (400 MHz, CDCl$_3$) δ 7.15 (s, 1 H) 6.99 (s, 1 H) 5.87 (s, 1H) 3.89 (s, 3 H) 3.00 (s, 2 H) 1.50 (s, 6 H); LCMS for $C_{12}H_{14}O_4$ m/z 223.0 (M+H)$^+$.

Preparation of Intermediate 3f 4-(4-Methanesulfonyl-phenoxy)-2,2-dimethyl-2,3-dihydro-benzofuran-6-carboxylic acid methyl ester

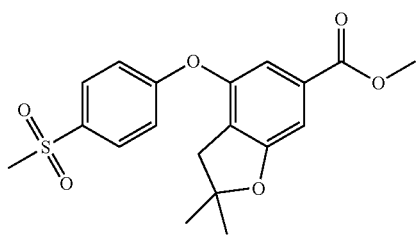

The title compound was prepared in a similar manner as described for Intermediate 1f, from 4-fluorophenyl methyl sulfone (115 mg, 0.77 mmol), Cs$_2$CO$_3$ (507 mg, 1.54 mmol), and methyl 6-hydroxyl-2-methyl-2,3-dihdrovenzofuran-4-carboxylate (3e) (171 mg, 0.77 mmol). Purification by column chromatography eluting with 15-40% EtOAc in hexanes gave a pale brown solid (230 mg, 79% yield). $^1$H NMR (400 MHz, CDCl$_3$) δ 7.88-7.94 (m, 2 H) 7.09 (d, J=2.53 Hz, 1 H) 7.05 (d, J=8.84 Hz, 2 H) 6.66 (d, J=2.53 Hz, 1 H) 3.81 (s, 3 H) 3.07 (s, 3 H) 2.92 (s, 2 H) 1.33 (s, 6 H); LCMS for $C_{19}H_{20}O_6S$ m/z 377.10 (M+H)$^+$.

Alternative method to prepare Intermediate 3e

Preparation of Intermediate 3g

4-Bromo-3,5-dihydroxybenzoic acid methyl ester

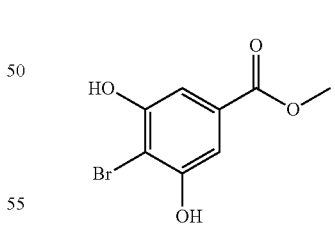

To a solution of 4-bromo-3,5-dihydroxybenzoic acid (13.89 g, 59.6 mmol) in methanol (50 mL) was added H$_2$SO$_4$ (concentrated, 1 mL). The reaction mixture was heated to reflux overnight. The mixture was quenched with H$_2$O (500 mL) and extracted with 10% MeOH in CH$_2$Cl$_2$ (5×500 mL), dried over MgSO$_4$ and concentrated in vacuo to give a white solid (14.8 g, 100% yield). $^1$H NMR (400 MHz, DMSO-d$_6$) δ 10.47 (s, 2 H) 7.00 (s, 2 H) 3.80 (s, 3 H); LCMS for C$_8$H$_7$BrO$_4$ m/z 249.10 (M+H)$^+$.

Preparation of Intermediate 3h

4-Bromo-3,5-bis-methoxymethoxy-benzoic acid methyl ester

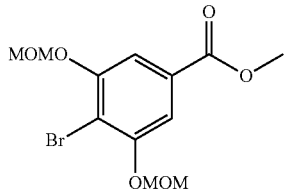

To a solution of 4-bromo-3,5-dihydroxybenzoic acid methyl ester (3g) (3.05 g, 12.3 mmol) in DMF (60 mL) at 0° C. was added NaH (1.47g, 40 mmol, 60% in mineral oil). The mixture was stirred at 0° C. for 30 min, and then chloromethyl methyl ether (2.80 mL, 36.9 mmol) was added. The mixture was stirred at 0° C. and then warmed to room temperature for 3 hr. The mixture was quenched with H$_2$O (100 mL) and extracted with EtOAc (2×100 mL). The organic layers were wash with H$_2$O (2×150 mL), dried over MgSO$_4$ and concentrated. The residue was purified by flash column chromatography eluting with 5% EtOAc in hexanes to give a white solid (2.76 g, 67% yield). $^1$H NMR (400 MHz, CDCl$_3$) δ 7.49 (s, 2 H) 5.32 (s, 4 H) 3.91 (s, 3 H) 3.54 (s, 6 H); LCMS for C$_{12}$H$_{16}$BrO$_6$ m/z 335.0 (M+H)$^+$.

Preparation of Intermediate 3i 3,5-Bis-methoxymethoxy-4-(2-methyl-allyl)-benzoic acid methyl ester

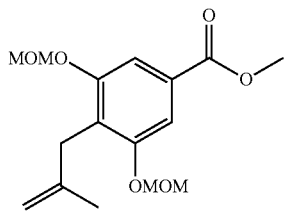

To a solution of 4-bromo-3,5-bis-methoxymethoxy-benzoic acid methyl ester (3 h) (3.10 g, 9.25 mmol) in DMF (20 mL) was added CsF (2.80 g, 18.4 mmol), CuI (200 mg, 1.05 mmol), PdCl$_2$ (200 mg, 1.12 mmol), 2-methylallyltributyltin (3.80, 11.0 mmol) and PtBu$_3$ (220 mg, 1.09 mmol). The reaction mixture was degassed and heated to 45° C. overnight. The mixture was filtered through Celite, quenched with H$_2$O (100 mL), extracted with EtOAc (2×100 mL). The organic layers were dried over MgSO$_4$ and concentrated. The residue was purified by flash column chromatography eluting with 5% EtOAc in hexanes to give the desired product as a brown oil (3.6 g) which contained tin impurities. $^1$H NMR (400 MHz, CDCl$_3$) δ 7.44-7.46 (m, 2 H) 5.22 (s, 4 H) 4.61-4.76 (m, 1 H) 4.38-4.55 (m, 1 H) 3.90 (s, 3 H) 3.47 (s, 6 H) 3.42-3.45 (m, 2 H) 1.80 (s, 3 H); LCMS for C$_{16}$H$_{22}$O$_6$ m/z 311.10 (M+H)$^+$.

Preparation of Intermediate 3e

4-Hydroxy-2,2-dimethyl-2,3-dihydro-benzofuran-6-carboxy-lic acid methyl ester

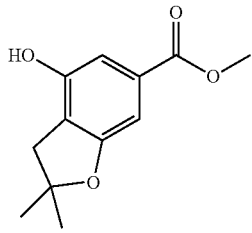

To a solution of 3,5-bis-methoxymethoxy-4-(2-methyl-allyl)-benzoic acid methyl ester (3i) (3.6 g, 9.02 mmol) in methanol (5 mL) was added 1.3 mL concentrated aqueous HCl. The reaction mixture was heated to reflux for 1 hr, quenched with H$_2$O (100 mL), extracted with EtOAc (2×100 mL), dried over MgSO$_4$ and concentrated. The residue was purified by flash column chromatography eluting with 5% EtOAc in hexane to give a pale yellow solid (1.08 g, 54% yield). $^1$H NMR (400 MHz, CDCl$_3$) δ 7.12 (d, J=1.26 Hz, 1 H) 7.00 (d, J=1.01 Hz, 1 H) 5.63 (s, 1 H) 3.89 (s, 3 H) 3.00 (s, 2H) 1.50 (s, 6 H); LCMS for C$_{12}$H$_{14}$O$_4$ m/z 223.10 (M+H)$^+$.

Example 4

5-(4-Methanesulfonyl-phenoxy)-2-methyl-benzofuran-7-carboxylic acid(1-methyl-1H-pyrazol-3-yl)-amide

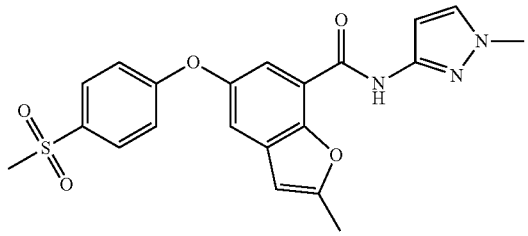

The title compound was prepared in a similar manner as described for Example 1, from 5-(4-methanesulfonyl-phenoxy)-2-methyl-benzofuran-7-carboxylic acid methyl ester (4e). $^1$H NMR (400 MHz, CDCl$_3$) δ 9.63 (s, 1 H) 7.88 (d, J=8.84 Hz, 2 H) 7.81 (d, J=2.53 Hz, 1 H) 7.38 (d, J=2.53 Hz, 1 H) 7.33 (d, J=2.27 Hz, 1 H) 7.08 (d, J=8.84 Hz, 2 H) 6.86 (d, J=2.27 Hz, 1 H) 6.52 (s, 1H) 3.88 (s, 3 H) 3.06 (s, 3 H) 2.62

(s, 3H); LCMS for $C_{21}H_{19}N_3O_5S$ m/z 426.00 (M+H)$^+$; Anal. Calcd. for $C_{21}H_{19}N_3O_5S$: C, 59.28; H, 4.50; N, 9.88; Found: C, 59.11; H, 4.38; N, 9.80.

Preparation of Intermediate 4a

2-Allyloxy-5-methoxy-benzoic acid methyl ester

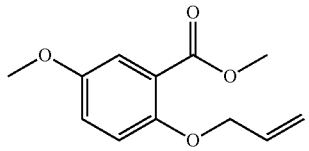

$K_2CO_3$ (4.64 g, 33.6 mmol) and allyl bromide (1.56 mL, 18.5 mmol) were added to a solution of methyl 2-hydroxy-5-methoxybenzoate (2.5 mL, 16.8 mmol) in DMF (10 mL). The reaction mixture was heated to 60° C. for 1 h, and then quenched with $H_2O$ (80 mL) and extracted with EtOAc (2×80 mL). The organic layers were washed with $H_2O$ (150 mL), dried over $MgSO_4$ and concentrated. The residue was purified by flash column chromatograph eluting with 5-10% EtOAc/hexane to give a colorless oil (3.07 g, 82%). $^1$H NMR (400 MHz, CDCl$_3$) δ 7.34 (d, J=3.28 Hz, 1 H) 6.98-7.03 (m, 1H) 6.90-6.94 (m, 1 H) 6.01-6.11 (m, 1 H) 5.44-5.51 (m, 1 H) 5.25-5.31 (m, 1 H) 4.57 (td, J=3.28, 1.52 Hz, 2 H) 3.91 (s, 3 H) 3.80 (s, 3 H).

Preparation of Intermediate 4b

3-Allyl-2-hydroxy-5-methoxy-benzoic acid methyl ester

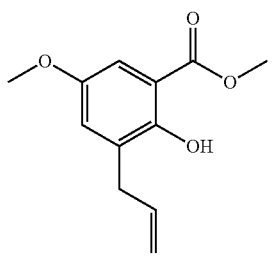

The solution of 2-allyloxy-5-methoxy-benzoic acid methyl ester (4a) (3.07 g, 13.8 mmol) in DMF (1 mL) was heated to 200° C. overnight. The mixture was quenched with $H_2O$ (80 mL) and extracted with EtOAc (2×80 mL). The organic layers were dried over $MgSO_4$ and concentrated. The residue was purified by flash column chromatograph eluting with 10% EtOAc/hexane to give a pale yellow color oil (1.48 g, 48%). $^1$H NMR (400 MHz, CDCl$_3$) δ 7.18 (d, J=3.28 Hz, 1 H) 6.99 (d, J=3.28 Hz, 1 H) 5.95-6.06 (m, 1 H) 5.04-5.16 (m, 2 H) 3.95 (s, 3 H) 3.78 (s, 3 H) 3.38-3.45 (m, 2 H)

Preparation of Intermediate 4c

5-Methoxy-2-methyl-benzofuran-7-carboxylic acid methyl ester

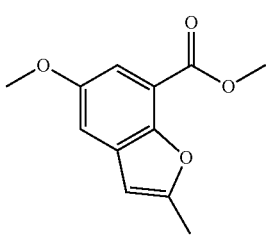

To a solution of 3-allyl-2-hydroxy-5-methoxy-benzoic acid methyl ester (4b) (1.48 g, 6.66 mmol) in DMF (30 mL) was added Cu(OAc)$_2$ (3.63 g, 19.98 mmol), LiCl (847 mg, 19.98 mmol) in $H_2O$ (1 mL) and PdCl$_2$ (24 mg, 0.133 mmol). The reaction mixture was stirred at RT for 3 h, quenched with $H_2O$ (100 mL) and NH$_4$OH (5 mL) and extracted with EtOAc (100 mL). The organic layer was washed with $H_2O$ (100 mL), dried over $MgSO_4$ and concentrated. The residue was purified by flash column chromatograph eluting with 10-15% EtOAc/hexane to give colorless oil (1.48 g, 48%). $^1$H NMR (400 MHz, CDCl$_3$) δ 7.43 (d, J=2.53 Hz, 1 H) 7.17 (d, J=2.53 Hz, 1 H) 6.36 (s, 1 H) 4.00 (s, 3 H) 3.87 (s, 3 H) 2.51 (s, 3 H)

Preparation of Intermediate 4d

5-Hydroxy-2-methyl-benzofuran-7-carboxylic acid methyl ester

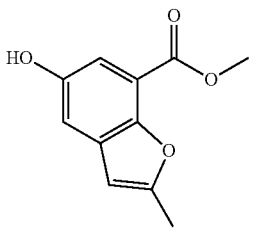

BBr$_3$ (10 mL, 10.08 mmol, 1.0 M in CH$_2$Cl$_2$) was added drop-wise to a solution of 5-methoxy-2-methyl-benzofuran-7-carboxylic acid methyl ester (4c) (951 mg, 4.31 mmol) and 2,6-lutidine (1.17 mL, 10.08 mmol) in CH$_2$Cl$_2$ (20 mL) at 0° C. The mixture was stirred and warmed to RT overnight. The mixture was quenched with $H_2O$ (60 mL) and extracted with CH$_2$Cl$_2$ (2×60 mL). The combined organic layers were dried over $MgSO_4$ and concentrated. The residue was purified by flash column chromatograph eluting with 5% CH$_3$OH/CH$_2$Cl$_2$ to afford a white solid (746 mg, 83%). $^1$H NMR (400

MHz, CDCl₃) δ 7.40 (d, J=2.53 Hz, 1 H) 7.13 (d, J=2.53 Hz, 1 H) 6.33 (d, J=1.01 Hz, 1 H) 5.50 (s, 1H) 4.00 (s, 3 H) 2.49 (d, J=1.01 Hz, 3H).

Preparation of Intermediate 4e 5-(4-Methanesulfonyl-phenoxy)-2-methyl-benzofuran-7-carboxylic acid methyl ester

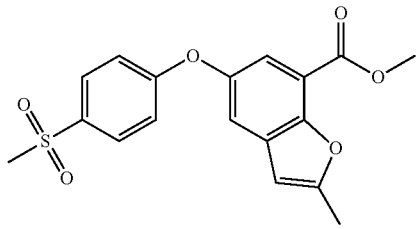

Cs₂CO₃ (2.36 g, 7.24 mmol) and 4-flurophenyl methyl sulfone (631 mg, 3.62 mmol) were added to a solution of 5-hydroxy-2-methyl-benzofuran-7-carboxylic acid methyl ester (4d) (746 mg, 3.62 mmol) in DMF (5 mL). The mixture was heated to 120° C. overnight and then cooled to RT. The mixture was then quenched with H₂O (80 mL) and extracted with EtOAc 92×100 ml). The combined organic layers were dried over MgSO₄ and concentrated. The residue was purified by flash column chromatograph eluting with 4% CH₃OH/CH₂Cl₂ to afford brown color oil (1.2 g, 92%). ¹H NMR (400 MHz, CDCl₃) δ 8.02 (s, 2 H) 7.86-7.90 (m, 1 H) 7.58 (d, J=2.53 Hz, 1 H) 7.38 (d, J=2.53 Hz, 1 H) 7.05 (d, J=8.84 Hz, 1 H) 6.44 (s, 1H) 3.99 (s, 3 H) 3.05 (s, 3 H) 2.56 (s, 3 H); LCMS for C₁₈H₁₆O₆S m/z 361.00 (M+H)⁺.

Example 5

5-(4-Methanesulfonyl-phenoxy)-2-methyl-benzofuran-7-carboxylic acid pyridin-2-ylamide

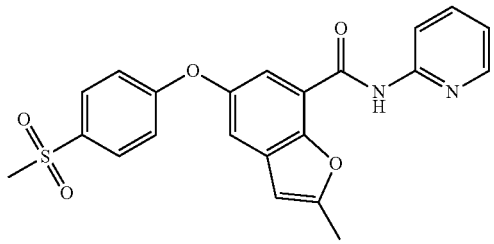

The title compound was prepared in a similar manner as described for Example 1, from 5-(4-methanesulfonyl-phenoxy)-2-methyl-benzofuran-7-carboxylic acid methyl ester (4e). ¹H NMR (400 MHz, CDCl₃) δ 9.85 (s, 1 H) 8.38-8.45 (m, 2 H) 7.87-7.92 (m, 2 H) 7.82 (d, J=2.53 Hz, 1 H) 7.75-7.81 (m, 1H) 7.41 (d, J=2.53 Hz, 1 H) 7.07-7.14 (m, 3 H) 6.54 (d, J=1.01 Hz, 1 H) 3.07 (s, 3 H) 2.66 (s, 3 H); LCMS for C₂₂H₁₈N₂O₅S m/z 423.00 (M+H)⁺; Anal. Calcd. for C₂₂H₁₈N₂O₅S.0.15 H₂O: C, 62.15; H, 4.34; N, 6.59; Found: C, 62.02; H, 4.15; N, 6.69.

Example 6

6-(4-Methanesulfonyl-phenoxy)-2,3-dihydrobenzofuran-4-carboxylic acid(5-methyl-pyridin-2-yl)-amide

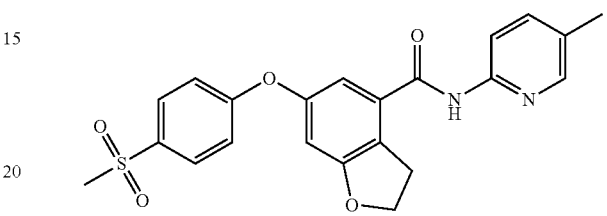

The title compound was prepared in a similar manner as described for Example 1, from a mixture of 6-(4-methanesulfonyl-phenoxy)-2,3-dihydro-benzofuran-4-carboxylic acid methyl ester and 6-(4-methanesulfonyl-phenoxy)-benzofuran-4-carboxylic acid methyl ester (6f) to give a white solid (66 mg, 16% yield). ¹H NMR (400 MHz, CDCl₃) δ 9.05 (s, 1 H) 8.25 (d, J=8.59 Hz, 1 H) 8.06 (d, J=1.52 Hz, 1 H) 7.91 (m, 2 H) 7.60 (dd, J=8.59, 2.27 Hz, 1 H) 7.11-7.17 (m, 2 H) 7.00 (d, J=1.77 Hz, 1 H) 6.69 (d, J=1.77 Hz, 1 H) 4.71 (t, J=8.72 Hz, 2 H) 3.58 (t, J=8.72 Hz, 2 H) 3.06-3.09 (m, 3 H) 2.32 (s, 3 H); LCMS for C₂₂H₂₀N₂O₅S m/z 425.10 (M+H)⁺; Anal. Calcd. for C₂₂H₂₀N₂O₅S.0.65AcOH: C, 60.38; H, 4.91; N, 6.04; Found: C, 60.28; H, 4.90; N, 6.12.

Preparation of Intermediate 6a

3-Hydroxy-5-methoxy-benzoic acid methyl ester

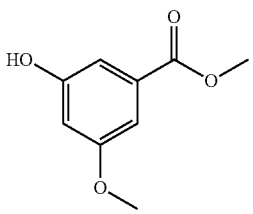

The title compound was prepared in a similar manner as described for Intermediate 1a, from methyl iodide (6.44 mL, 104 mmol), K₂CO₃ (28.8 g, 208.15 mmol), and methyl 3,5-dihydroxybenzoate (17.5 g, 64 mmol). Purification by column chromatography eluting with 15% EtOAc in hexanes gave a pale yellow solid (7.51 g, 40% yield). ¹H NMR (400

MHz, CDCl₃) δ 7.16 (dd, J=4.80, 2.27 Hz, 2 H) 6.63 (t, J=2.27 Hz, 1 H) 5.36 (s, 1H) 3.92 (s, 3 H) 3.83 (s, 3 H).

Preparation of Intermediate 6b 3-(2,2-Diethoxy-ethoxy)-5-methoxy-benzoic acid methyl ester

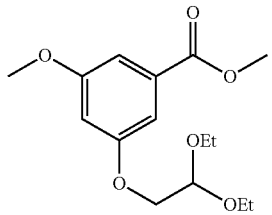

To a suspension of sodium hydride (708 mg, 17.7 mmol, 60% in mineral oil) in anhydrous DMF (10 mL) was added methyl 3-hydroxy-5-methoxy benzoate (6a) (2.15 g, 11.8 mmol) at 0° C. After hydrogen evolution had ceased, bromoacetaldehyde diethyl acetal (2.22 mL, 14.75 mmol) was added. The reaction mixture was heated to 160° C. overnight. The mixture was poured into ice/water, extracted with EtOAc (2×80 mL), dried over MgSO₄, and concentrated. Purification by column chromatography (10% EtOAc in hexanes) afforded pale yellow oil (1.95 g, 55% yield). ¹H NMR (400 MHz, CDCl₃) δ 7.18-7.23 (m, 2 H) 6.66-6.71 (m, 1 H) 4.80-4.86 (m, 1 H) 4.03 (dd, J=5.05, 1.52 Hz, 2 H) 3.91 (s, 3 H) 3.82 (s, 3 H) 3.73-3.80 (m, 2 H) 3.59-3.69 (m, 2 H) 1.21-1.28 (m, 6 H); LCMS for C₁₅H₂₂O₆ m/z 299.10 (M+H)⁺.

Preparation of Intermediate 6c

6-Methoxy-benzofuran-4-carboxylic acid methyl ester

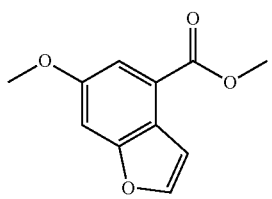

3-(2,2-Diethoxy-ethoxy)-5-methoxy-benzoic acid methyl ester (6b) (1.95 g, 6.53 mmol) was added to a solution of polyphosphoric acid (1.47 g) in benzene (10 mL). The reaction mixture was heated to reflux for 2 hr, filtered and concentrated. The residue was purified by flash column chromatography (5% EtOAc in hexanes) to give a pale yellow solid (840 mg, 62% yield). ¹H NMR (400 MHz, CDCl₃) δ 7.64 (d, J=2.27 Hz, 1 H) 7.61 (d, J=2.27 Hz, 1 H) 7.26 (d, J=2.02 Hz, 1 H) 7.25 (d, J=2.27 Hz, 1 H) 3.99 (s, 3 H) 3.90 (s, 3 H).

Preparation of Intermediate 6d

6-Hydroxy-benzofuran-4-carboxylic acid methyl ester

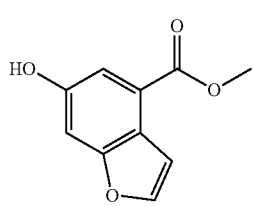

The title compound was prepared in a similar manner as described for Intermediate 1e, from 2,6-lutidine (1.42 mL, 12.2 mmol), BBr₃ (12.2 mL, 12.2 mmol, 1.0 M in CH₂Cl₂) and 6-methoxy-benzofuran-4-carboxylic acid methyl ester (6c) (840 mg, 4.07 mmol). Purification by flash column chromatography (10-15% EtOAc in hexanes) gave a pale yellow solid (350 mg, 45% yield). ¹H NMR (400 MHz, CDCl₃) δ 7.64 (d, J=2.27 Hz, 1 H) 7.61 (d, J=2.02 Hz, 1 H) 7.24 (dd, J=3.28, 2.27 Hz, 2 H) 5.66 (s, 1 H) 4.00 (s, 3 H).

Preparation of Intermediate 6e

6-Hydroxy-2,3-dihydrobenzofuran-4-carboxylic acid methyl ester

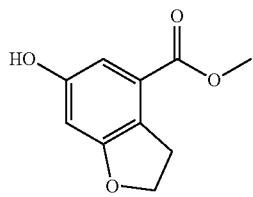

To a solution of 6-hydroxy-benzofuran-4-carboxylic acid methyl ester (6d) (354 mg, 1.82 mmol) in EtOAc was added acetic acid (1 mL) and Pd on carbon (40 mg). The reaction mixture was stirred under hydrogen gas balloon overnight. The mixture was filtered through Celite and concentrated to give a pale yellow solid which was used without further purification. LCMS and NMR showed it was a mixture of 6-hydroxy-benzofuran-4-carboxylic acid methyl ester and 6-hydroxy-2,3-dihydro-benzofuran-4-carboxylic acid methyl ester (2:1). ¹H NMR (400 MHz, CDCl₃) δ 7.02 (d, J=2.27 Hz, 2 H) 6.53 (d, J=2.27 Hz, 1 H) 4.61 (t, J=8.72 Hz, 2 H) 3.90 (s, 3 H) 3.44 (t, J=8.72 Hz, 2 H).

Preparation of Intermediate 6f

Mixture of 6-(4-methanesulfonyl-phenoxy)-2,3-dihydro-benzofuran-4-carboxylic acid methyl ester and 6-(4-methanesulfonyl-phenoxy)-benzo-furan-4-carboxylic acid methyl ester

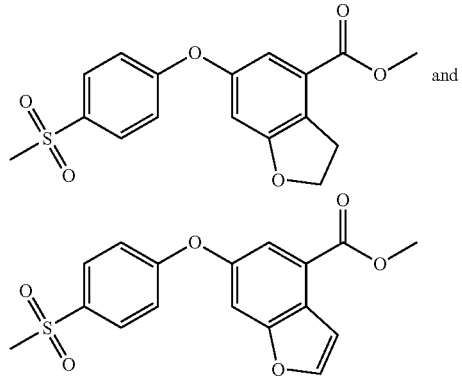

The title compound was prepared in a similar manner as described for Intermediate 1f, from 4-fluorophenyl methyl sulfone (269 mg, 1.55 mmol), $Cs_2CO_3$ (1.01 g, 3.01 mmol), and a mixture of 6-hydroxy-2,3-dihydrobenzofuran-4-carboxylic acid methyl ester (6e) and 6-hydroxy-benzofuran-4-carboxylic acid methyl ester (6d) (2:1 mixture, 300 mg, 1.55 mmol). Purification by column chromatography eluting with 30% EtOAc in hexanes gave a pale yellow solid (230 mg, 79% yield) as a mixture of 6-(4-methanesulfonyl-phenoxy)-2,3-dihydrobenzofuran-4-carboxylic acid methyl ester and 6-(4-methanesulfonyl-phenoxy)-benzofuran-4-carboxylic acid methyl ester (1.4:1). $^1$H NMR (400 MHz, $CDCl_3$) δ 7.87-7.94 (m) 7.76 (dd, J=14.53, 2.15 Hz) 7.44-7.53 (m) 7.39 (d, J=1.52 Hz) 7.18-7.22 (m) 7.07-7.13 (m) 6.67-6.72 (m) 4.69 (t, J=8.84 Hz) 3.95-4.01 (m) 3.87-3.92 (m) 3.56 (t, J=8.84 Hz) 3.05-3.09 (m).

Example 7

6-(4-Methanesulfonyl-phenoxy)-benzofuran-4-carboxylic acid(5-methyl-pyridin-2-yl)-amide

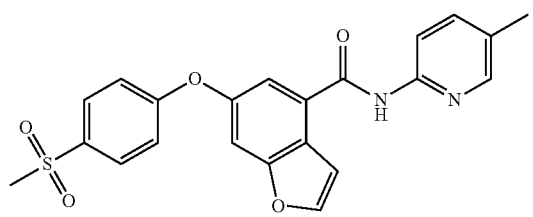

The title compound was prepared in a similar manner as described for Example 1, from a mixtures of 6-(4-methanesulfonyl-phenoxy)-2,3-dihydro-benzofuran-4-carboxylic acid methyl ester and 6-(4-methanesulfonyl-phenoxy)-benzofuran-4-carboxylic acid methyl ester (6f). Purification by reverse phase chromatography gave 6-(4-methanesulfonyl-phenoxy)-benzofuran-4-carboxylic acid(5-methyl-pyridin-2-yl)-amide (21 mg, 6% yield) as a white solid. $^1$H NMR (400 MHz, $CDCl_3$) δ 9.25 (s, 1 H) 8.33 (d, J=8.34 Hz, 1 H) 8.09 (s, 1H) 7.93 (ddd, J=9.22, 2.78, 2.40 Hz, 2 H) 7.80 (d, J=2.27 Hz, 1H) 7.64 (dd, J=8.59, 2.27 Hz, 1 H) 7.57 (d, J=2.02 Hz, 1 H) 7.44-7.47 (m, 1 H) 7.35-7.42 (m, 1 H) 7.12-7.17 (m, 2 H) 3.08 (s, 3 H) 2.34 (s, 3 H); LCMS for $C_{22}H_{18}N_2O_5S$ m/z 423.10 $(M+H)^+$; Anal. Calcd. for $C_{22}H_{18}N_2O_5S \cdot 1.0$ AcOH: C, 59.62; H, 4.54; N, 5.93; Found: C, 59.62; H, 4.54; N, 5.93.

Example 8

4-(4-Methanesulfonyl-phenoxy)-2,3-dihydro-benzofuran-6-carboxylic acid(5-methyl-pyridin-2-yl)-amide

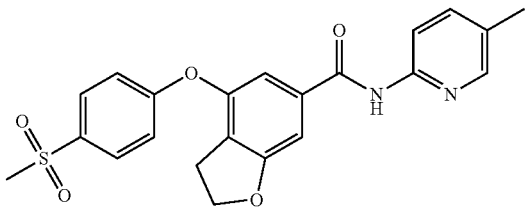

The title compound was prepared in a similar manner as described for Example 1, from 4-(4-methanesulfonyl-phenoxy)-2,3-dihydro-benzo-furan-6-carboxylic acid ethyl ester (8c) (130 mg, 0.36 mmol). Purification by flash column chromatography gave a white solid (105 mg, 69% yield). $^1$H NMR (400 MHz, $CDCl_3$) δ 8.40 (s, 1 H) 8.22 (d, J=8.34 Hz, 1 H) 8.11 (d, J=2.02 Hz, 1 H) 7.91-7.96 (m, 2 H) 7.57 (dd, J=8.46, 2.15 Hz, 1H) 7.19 (d, J=1.26 Hz, 1H) 7.10-7.14 (m, 3 H) 4.70 (t, J=8.84 Hz, 2 H) 3.14 (t, J=8.84 Hz, 2 H) 3.09 (s, 3 H) 2.32 (s, 3 H); LCMS for $C_{22}H_{20}N_2O_5S$ m/z 425.10 $(M+H^+)$; Anal. Calcd. for $C_{22}H_{20}N_2O_5S \cdot 0.10$ $H_2O$: C, 62.09; H, 4.84; N, 6.47; Found: C, 62.02; H, 4.84; N, 6.47.

Preparation of Intermediate 8a

4-Hydroxy-benzofuran-6-carboxylic acid ethyl ester

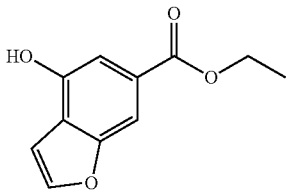

t-Butoxide (1.7 g, 15 mmol) was added to a solution of 2-furaldehyde (2.5 mL, 30.2 mmol) and diethyl succinate (3.2 mL, 19 mmol) in t-butanol (20 mL). The mixture was refluxed for 2 hr, cooled to room temperature and acidified with aqueous HCl (20% v/v) to Ph ~2. The mixture was diluted with 5% HCl (100 mL) and extracted with EtOAc (2×100 mL). The organic layers were then extracted with 10% aqueous solution of $Na_2CO_3$ (2×100 mL). The aqueous solution was washed with EtOAc and then acidified with 20% HCl to Ph ~2. The aqueous layer was finally extracted with EtOAc (3×100 mL), dried over $MgSO_4$ and concentrated to give a brown oil. The crude product was dissolved in $Ac_2O$ (10 mL) and added NaOAc (1.6 g, 19 mmol). The mixture was heated to reflux for 5 hr, cooled to room temperature and concentrated. The residue was taken into ½ saturated Na$_2$CO$_3$, extracted with EtOAc (2×150 mL), dried over MgSO$_4$ and concentrated to give a brown color solid. The solid was then dissolved in EtOH (10 mL). To the solution was added K$_2$CO$_3$ (2.5 g, 18 mmol). The resulting reaction mixture was heated to reflux overnight and the solvent was removed in vacuo. The brown residue was then treated with H$_2$O (50 mL) and acidified with 6N HCl to pH 6. The solution was then extracted with EtOAc (2×50 mL), and combined organic layers were dried over MgSO4 and concentrated. The crude material was purified by flash column chromatography to give a yellow color solid (532 mg, 9% yield). $^1$H NMR (400 MHz, CDCl$_3$) δ 7.83 (s, 1 H) 7.68 (d, J=2.02 Hz, 1 H) 7.51 (s, 1 H) 6.92-7.00 (m, 1 H) 4.42 (q, J=7.24 Hz, 2 H) 1.42 (t, J=7.20 Hz, 3 H).

Preparation of Intermediate 8b

4-Hydroxy-2,3-dihydro-benzofuran-6-carboxylic acid ethyl ester

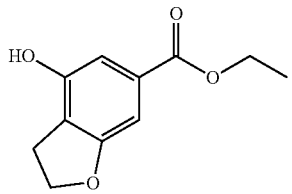

Pd on carbon (100 mg) was added to a solution of 4-hydroxy-benzofuran-6-carboxylic acid ethyl ester (8a) (333 mg, 1.61 mmol) in acetic acid. The mixture was stirred under H$_2$ (50 psi) for 48 hr. The mixture was filtered through Celite and concentrated. The residue was taken into saturated aqueous NaHCO$_3$ and extracted with EtOAc. The organic layers were dried over MgSO$_4$ and concentrated. The residue was purified by flash column chromatography eluting with 15% EtOAc in hexanes to give a pale yellow solid (315 mg, 94% yield). $^1$H NMR (400 MHz, CDCl$_3$) δ 7.16 (d, J=1.26 Hz, 1 H) 7.05 (s, 1 H) 4.65 (t, J=8.72 Hz, 2 H) 4.35 (q, J=7.07 Hz, 2 H) 3.21 (t, J=8.72 Hz, 2 H) 1.38 (t, J=7.07 Hz, 3 H); LCMS for C$_{11}$H$_{12}$O$_4$ m/z 209.10 (M+H)$^+$.

Preparation of Intermediate 8c 4-(4-Methanesulfonyl-phenoxy)-2,3-dihydro-benzofuran-6-carboxylic acid ethyl ester

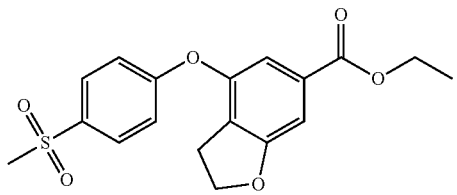

The title compound was prepared in a similar manner as described for Intermediate 1f, from 4-fluorophenyl methyl sulfone (285 mg, 1.64 mmol), Cs$_2$CO$_3$ (997 mg, 3.06 mmol), and 4-hydroxy-2,3-dihydro-benzofuran-6-carboxylic acid ethyl ester (8b) (315 mg, 1.51 mmol). Purification by column chromatography eluting with 10-20% EtOAC in hexanes gave a pale yellow oil (199 mg, 36% yield). $^1$H NMR (400 MHz, CDCl$_3$) δ 7.90-7.97 (m, 2 H) 7.34 (d, J=4.29 Hz, 1 H) 7.24-7.29 (m, 1 H) 7.07-7.13 (m, 2 H) 4.67 (m, 2 H) 4.32-4.39 (m, 2 H) 3.09-3.14 (m, 2 H) 3.06-3.09 (m, 3 H) 1.34-1.42 (m, 3 H); LCMS for C$_{18}$H$_{18}$O$_6$S m/z 385.00 (M+Na)$^+$.

Example 9

4-(4-Methanesulfonyl-phenoxy)-benzofuran-6-carboxylic acid(5-methyl-pyridin-2-yl)-amide

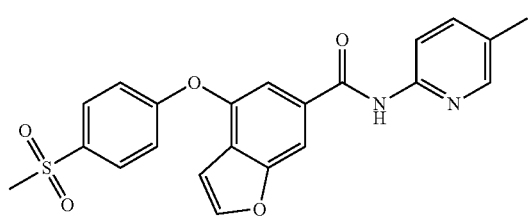

The title compound was prepared in a similar manner as described for Example 1, from 4-(4-methanesulfonyl-phenoxy)-benzofuran-6-carboxylic acid ethyl ester (9a) (153 mg, 0.43 mmol). Purification by flash column chromatography eluting with 15-20% EtOAc in hexanes gave a white solid (100 mg, 50% yield). $^1$H NMR (400 MHz, CDCl$_3$) δ 8.65 (s, 1 H) 8.26 (d, J=8.34 Hz, 1 H) 8.11 (s, 1 H) 7.99 (s, 1 H) 7.94 (d, J=7.58 Hz, 2 H) 7.75 (s, 1 H) 7.59 (d, J=8.34 Hz, 1 H) 7.52 (s, 1 H) 7.16 (d, J=7.33 Hz, 2 H) 6.69 (s, 1 H) 3.09 (s, 3 H) 2.32 (s, 3 H); LCMS for C$_{22}$H$_{18}$N$_2$O$_5$S m/z 423.00 (M+H)$^+$; Anal. Calcd. for C$_{22}$H$_{18}$N$_2$O$_5$S.0.35 EtOAc: C, 62.00; H, 4.63; N, 6.18; Found: C, 61.70; H, 4.56; N, 6.18.

Preparation of Intermediate 9a 4-(4-Methanesulfonyl-phenoxy)-benzofuran-6-carboxylic acid ethyl ester

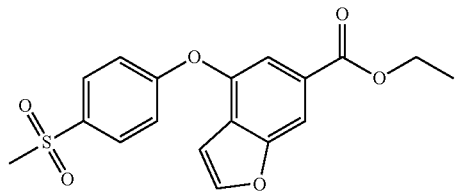

The title compound was prepared in a similar manner as described for Intermediate 1f, from 4-fluorophenyl methyl sulfone (180 mg, 1.03 mmol), Cs$_2$CO$_3$ (630 mg, 1.93 mmol), and 4-hydroxy-benzofuran-6-carboxylic acid ethyl ester (8a) (199 mg, 0.97 mmol). Purification by flash column chromatography eluting with 15% EtOAc in hexanes gave a pale yellow oil (261 mg, 75% yield). $^1$H NMR (400 MHz, CDCl$_3$) δ 8.13 (s, 1 H) 7.91 (s, 2 H) 7.74 (s, 1 H) 7.65 (s, 1 H) 7.13 (s, 2 H) 6.66 (s, 1 H) 4.41 (s, 2 H) 3.08 (s, 3 H) 1.42 (s, 3 H); LCMS for C$_{18}$H$_{16}$O$_6$S m/z 383.00 (M+Na)$^+$.

Example 10

4-(4-Methanesulfonyl-phenoxy)-2-methyl-2,3-dihydro-benzofuran-6-carboxylic acid(5-methyl-pyridin-2-yl)-amide

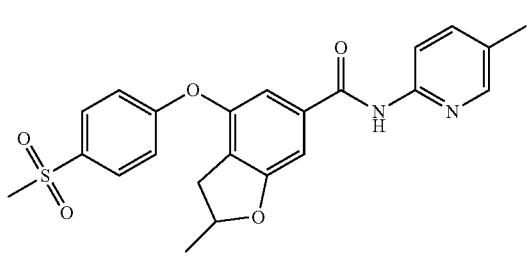

The title compound was prepared in a similar manner as described for Example 1, from 4-(4-methanesulfonyl-phenoxy)-2-methyl-2,3-dihydro-benzofuran-6-carboxylic acid methyl ester (10d) (65 mg, 0.18 mmol). Purification by flash column chromatography eluting with 15-25% EtOAc in hexanes gave a white solid (34 mg, 43% yield). $^1$H NMR (400 MHz, CDCl$_3$) δ 8.36 (s, 1 H) 8.22 (d, J=8.34 Hz, 1 H) 8.12 (s, 1 H) 7.93 (d, J=8.84 Hz, 2 H) 7.57 (dd, J=8.21, 1.64 Hz, 1 H) 7.14 (d, J=10.86 Hz, 2 H) 7.10 (s, 2 H) 5.01-5.10 (m, 1 H) 3.23 (dd, J=16.42, 8.84 Hz, 1 H) 3.09 (s, 3 H) 2.72 (dd, J=16.42, 7.33 Hz, 1 H) 2.32 (s, 3 H) 1.50 (d, J=6.06 Hz, 3 H); LCMS for C$_{23}$H$_{22}$N$_2$O$_5$S m/z 439.10 (M+H$^+$); Anal. Calcd. for C$_{23}$H$_{22}$N$_2$O$_5$S.0.70 H2O: C, 61.24; H, 5.23; N, 6.21; Found: C, 61.21; H, 5.19; N, 6.14.

Preparation of Intermediate 10a

4-Allyl-3,5-bis-methoxymethoxy-benzoic acid methyl ester

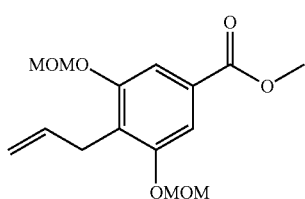

The title compound was prepared in a similar manner as described for Intermediate 3i, from 4-bromo-3,5-bis-methoxymethoxy-benzoic acid methyl ester (3 h) (0.93 g, 2.78 mmol), CsF (0.84 g, 5.53 mmol), CuI (50.0 mg, 0.26 mmol), PdCl$_2$ (50.0 mg, 0.28 mmol), allyltributyltin (1.10 mL, 3.55 mmol) and PtBu$_3$ (65.0 mg, 0.32 mmol). Purification by column chromatography eluting with 15-25% EtOAc in hexanes gave a yellow oil (3.6 g, which contained residue of tin byproduct). $^1$H NMR (400 MHz, CDCl$_3$) δ 7.45 (s, 2 H) 5.74-6.23 (m, 1 H) 5.25 (s, 4 H) 4.94-5.02 (m, 2 H) 3.90 (s, 3 H) 3.49-3.50 (m, 2 H) 3.48 (s, 6 H); LCMS for C$_{15}$H$_{20}$O$_6$ m/z 297.10 (M+H$^+$).

Preparation of Intermediate 10b

4-Allyl-3,5-dihydroxy-benzoic acid methyl ester

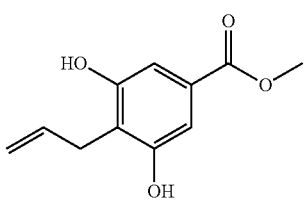

To a solution of 4-allyl-3,5-bis-methoxymethoxy-benzoic acid methyl ester (10a) (513 mg, 1.73 mmol) in MeOH (4 mL) was added 4N HCl (4 mL). The reaction mixture was stirred at room temperature overnight. The mixture was quenched with H$_2$O (80 mL) and extracted with EtOAc (2×80 mL). The organic layers were dried over MgSO$_4$ and concentrated to give yellow oil which was purified by flash column chromatography eluting with 15-25% EtOAc in hexanes to give a pale yellow solid (285 mg, 79% yield). $^1$H NMR (400 MHz, CDCl$_3$) δ 7.20 (s, 2 H) 5.95-6.06 (m, J=5.31, 5.31 Hz, 1 H) 5.76-5.82 (m, 2 H) 5.15-5.20 (m, 1 H) 5.12-5.15 (m, 1 H) 3.90 (s, 3 H) 3.50-3.55 (m, 2 H); LCMS for C$_{11}$H$_{12}$O$_4$S m/z 209.10 (M+H$^+$).

Preparation of Intermediate 10c

4-Hydroxy-2-methyl-2,3-dihydro-benzofuran-6-carboxylic acid methyl ester

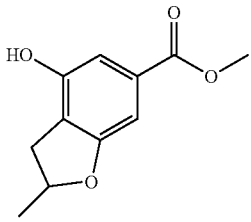

The title compound was prepared in a similar manner as described for Intermediate 1d, from zirconium(IV) chloride and 4-allyl-3,5-dihydroxy-benzoic acid methyl ester (10b) (85 mg, 0.41 mmol). Purification by flash column chromatography eluting with 15-25% EtOAc in hexane gave a pale yellow solid (58 mg, 68% yield). $^1$H NMR (400 MHz, CDCl$_3$)

δ 7.17-7.21 (m, 2 H) 5.76 (s, 1 H) 4.42-4.51 (m, 1H) 3.91 (s, 3 H) 3.11-3.21 (m, 2 H) 1.60 (d, J=6.57 Hz, 3 H).

Preparation of Intermediate 10d 4-(4-Methanesulfonyl-phenoxy)-2-methyl-2,3-dihydro-benzofuran-6-carboxylic acid methyl ester

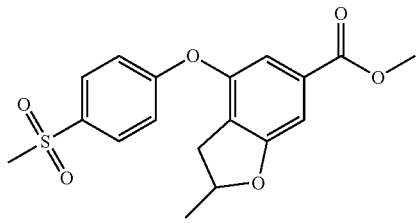

The title compound was prepared in a similar manner as described for Intermediate 1f, from 4-hydroxy-2-methyl-2,3-dihydro-benzofuran-6-carboxylic acid methyl ester (10c) (58 mg, 0.29 mmol). Purification by column chromatography eluting with 15-25% EtOAc in hexanes gave a pale yellow solid (65 mg, 64% yield). $^1$H NMR (400 MHz, CDCl$_3$) δ 7.90-7.93 (m, 2 H) 7.23-7.26 (m, 2 H) 7.10 (s, 1 H) 7.07 (s, 1 H) 4.98-5.07 (m, 1 H) 3.89 (s, 3 H) 3.21 (dd, J=16.67, 8.84 Hz, 1 H) 3.07 (s, 3 H) 2.70 (dd, J=16.55, 7.45 Hz, 1 H) 1.48 (d, J=6.32 Hz, 3 H); LCMS for C$_{18}$H$_{18}$O$_6$S m/z 385.10 (M+Na)$^+$.

Example 11

4-(4-Methanesulfonyl-phenoxy)-2-methyl-2,3-dihydro-benzofuran-6-carboxylic acid(1-methyl-1H-pyrazol-3-yl)-amide

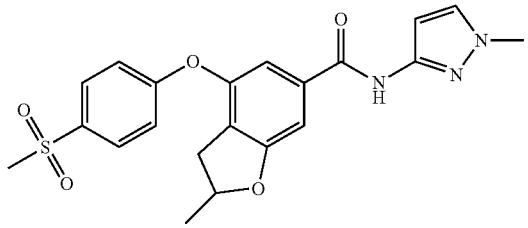

The title compound was prepared in a similar manner as described for Example 1, from 4-(4-methanesulfonyl-phenoxy)-2-methyl-2,3-dihydro-benzofuran-6-carboxylic acid methyl ester (10d). $^1$H NMR (400 MHz, CDCl$_3$) δ 8.29 (s, 1 H) 7.93 (d, J=8.84 Hz, 2 H) 7.29 (d, J=2.27 Hz, 1 H) 7.12 (d, J=8.84 Hz, 2 H) 7.10 (s, 1 H) 7.06 (s, 1 H) 6.78 (d, J=2.27 Hz, 1 H) 5.01-5.09 (m, 1 H) 3.82 (s, 3 H) 3.24 (dd, J=16.42, 8.84 Hz, 1 H) 3.09 (s, 3 H) 2.73 (dd, J=16.29, 7.45 Hz, 1 H) 1.49 (d, J=6.32 Hz, 3 H); LCMS for C$_{21}$H$_{21}$N$_3$O$_5$S m/z 428.10 (M+H)$^+$; Anal. Calcd. for C$_{21}$H$_{21}$N$_3$O$_5$S.0.23 H$_2$O: C, 58.44; H, 5.01; N, 9.74; Found: C, 58.43; H, 4.92; N, 9.68.

Example 12

(−)-4-(4-Methanesulfonyl-phenoxy)-2-methyl-2,3-dihydro-benzofuran-6-carboxylic acid(1-methyl-1H-pyrazol-3-yl)-amide and Example 13

(+)4-(4-Methanesulfonyl-phenoxy)-2-methyl-2,3-dihydro-benzofuran-6-carboxylic acid(1-methyl-1H-pyrazol-3-yl)-amide

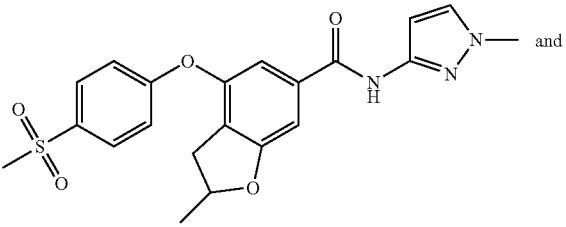

The title compounds were prepared from chiral column chromatography of Example 11.

Example 12: [α]$_D$=−21.49; 100% ee; $^1$H NMR (400 MHz, CDCl$_3$) δ 8.35 (s, 1 H) 7.90-8.01 (m, 2 H) 7.29 (d, J=2.27 Hz, 1 H) 7.11 (d, J=8.59 Hz, 2 H) 7.10 (s, 1 H) 7.06 (s, 1 H) 6.78 (d, J=2.27 Hz, 1 H) 5.00-5.12 (m, 1 H) 3.81 (s, 3 H) 3.24 (dd, J=16.42, 8.84 Hz, 1 H) 3.09 (s, 3 H) 2.73 (dd, J=16.29, 7.45 Hz, 1 H) 1.49 (d, J=6.32 Hz, 3 H); LCMS for C$_{21}$H$_{21}$N$_3$O$_5$S m/z 428.10 (M+H)$^+$; Anal. Calcd. for C$_{21}$ H$_{21}$ N$_3$O$_5$S: C, 59.00; H, 4.95; N, 9.83; Found: C, 58.82; H, 4.96; N, 9.70.

Example 13: [α]$_D$=+19.13; 100% ee; $^1$H NMR (400 MHz, CDCl$_3$) δ 8.38 (s, 1 H) 7.92 (d, J=8.84 Hz, 2 H) 7.29 (d, J=2.02 Hz, 1 H) 7.11 (d, J=8.59 Hz, 2 H) 7.10 (s, 1 H) 7.06 (s, 1 H) 6.78 (d, J=2.02 Hz, 1 H) 5.00-5.12 (m, 1 H) 3.81 (s, 3 H) 3.23 (dd, J=16.42, 8.84 Hz, 1 H) 3.09 (s, 3 H) 2.72 (dd, J=16.42, 7.58 Hz, 1 H) 1.49 (d, J=6.32 Hz, 3 H); LCMS for $C_{21}H_{21}N_3O_5S$ m/z 428.10 (M+H)$^+$; Anal. Calcd. for $C_{21}H_{21}N_3O_5S \cdot 0.23\ H_2O$: C, 58.44; H, 5.01; N, 9.74; Found: C, 58.44; H, 4.99; N, 9.68.

Example 14

6-[(4-Isobutoxy-2,2-dimethyl-2,3-dihydro-benzofuran-6-carbonyl)-amino]-nicotinic acid

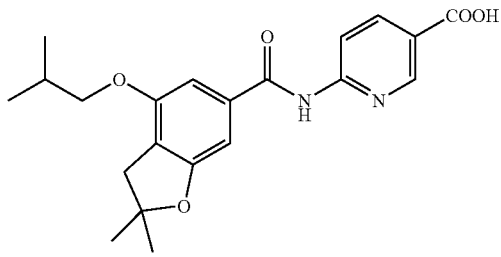

To a solution of 6-[(4-isobutoxy-2,2-dimethyl-2,3-dihydro-benzofuran-6-carbonyl)-amino]-nicotinic acid methyl ester (14b) (125 mg, 0.31 mmol) in THF (4 mL) was added 1 N aqueous NaOH (300 uL, 0.3 mmol). The mixture was stirred at room temperature overnight, diluted with $H_2O$ (15 mL) and washed with EtOAc (15 mL). The water phase was acidified with 1 N HCl to Ph ~5, extracted with $CH_2Cl_2$ (2×15 mL), dried over $MgSO_4$ and concentrated to give a white solid (36 mg, 30% yield). $^1H$ NMR (400 MHz, DMSO-$d_6$) δ 13.17 (br. s., 1 H) 11.04 (s, 1 H) 8.88 (s, 1 H) 8.28-8.35 (m, 2 H) 7.20 (s, 1 H) 6.98 (s, 1 H) 3.88 (d, J=6.57 Hz, 2 H) 2.96 (s, 2 H) 1.99-2.09 (m, 1 H) 1.43 (s, 6 H) 1.00 (d, J=6.57 Hz, 6 H); LCMS for $C_{21}H_{24}N_2O_5$ m/z 385.10 (M+H$^+$); Anal. Calcd. for $C_{21}H_{24}N_2O_5 \cdot 0.10$ EtOAc: C, 65.36; H, 6.36; N, 7.12; Found: C, 65.26; H, 6.21; N, 6.91.

Preparation of Intermediate 14a

4-Isobutoxy-2,2-dimethyl-2,3-dihydro-benzofuran-6-carbo-xylic acid methyl ester

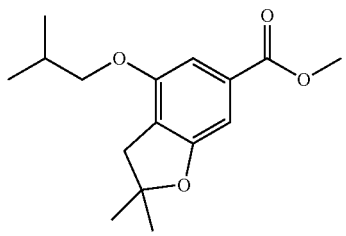

To a solution of 4-hydroxy-2,2-dimethyl-2,3-dihydrobenzofuran-6-carboxylic acid methyl ester (3e) (167 mg, 0.75 mmol) in DMF (3 mL) was added 1-bromo-2-methylpropane (0.090 mL, 0.83 mmol) and cesium carbonate (520 mg, 1.6 mmol). The reaction mixture was stirred at 85° C. for 2 hr and cooled to room temperature. The mixture was quenched with $H_2O$ (10 mL), extracted with EtOAc (2×10 mL), dried over $MgSO_4$ and concentrated. The residue was purified by flash column chromatography eluting with 5% EtOAc in hexanes to give colorless oil (193 mg, 92% yield). $^1H$ NMR (400 MHz, CDCl$_3$) δ 7.09 (s, 1 H) 7.05 (s, 1 H) 3.89 (s, 3 H) 3.80 (d, J=6.57 Hz, 2 H) 2.99 (s, 2 H) 2.02-2.16 (m, 1 H) 1.49 (s, 6 H) 1.04 (s, 3 H) 1.02 (s, 3 H); LCMS for $C_{16}H_{22}O_4$ m/z 279.10 (M+H$^+$).

Preparation of Intermediate 14b

6-[(4-Isobutoxy-2,2-dimethyl-2,3-dihydro-benzofuran-6-carbonyl)-amino]-nicotinic acid methyl ester

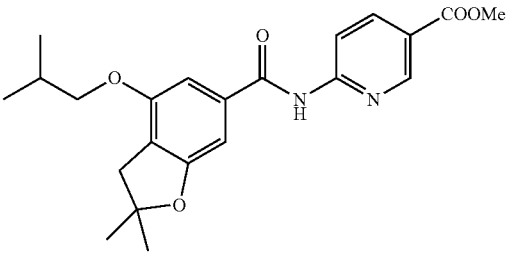

The title compound was prepared in a similar manner as described for Example 1, from 6-aminonicotinic acid methyl ester (1.0 g, 6.57 mmol) and 4-isobutoxy-2,2-dimethyl-2,3-dihydro-benzofuran-6-carboxylic acid methyl ester (14a) (185 mg, 0.66 mmol). Purification by column chromatography eluting with 15-25% EtOAc in hexane gave a pale yellow solid (127 mg, 48% yield). $^1H$ NMR (400 MHz, CDCl$_3$) δ 8.93 (d, J=1.52 Hz, 1 H) 8.69 (s, 1 H) 8.42-8.48 (m, 1 H) 8.35 (dd, J=8.72, 2.15 Hz, 1 H) 6.96 (s, 1 H) 6.87 (s, 1H) 3.95 (s, 3 H) 3.82 (d, J=6.32 Hz, 2 H) 3.01 (s, 2 H) 2.06-2.14 (m, J=13.33, 6.60, 6.60 Hz, 1 H) 1.51 (s, 6 H) 1.04 (d, J=6.82 Hz, 6 H); LCMS for $C_{22}H_{26}N_2O_5$ m/z 399.10 (M+H$^+$).

Example 15

6-{[4-(4-Methanesulfonyl-phenoxy)-2,2-dimethyl-2,3-dihydro-benzofuran-6-carbonyl]-amino}-nicotinamide

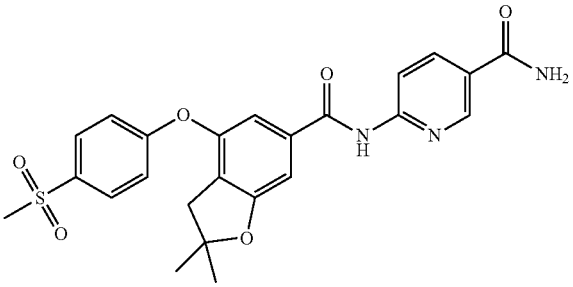

To a solution of 4-(4-methanesulfonyl-phenoxy)-2,2-dimethyl-2,3-dihydro-benzofuran-6-carboxylic acid (15a) (77 mg, 0.21 mmol) in DMF (3 mL) was added Et$_3$N (90.0 uL, 0.65 mmol), 4-aminonicotinic amide (60.0 mg, 0.44 mmol) and HATU (250 mg, 0.66 mmol). The mixture was stirred at room temperature for 3 hr. The mixture was quenched with $H_2O$ (10 mL), extracted with EtOAc (2×10 mL). The organic layers was washed with $H_2O$ (2×20 mL), dried over $MgSO_4$ and concentrated. The residue was purified by flash column chromatography eluting with 15-30% EtOAc in hexanes to give colorless oil (39 mg, 38% yield). $^1H$ NMR (400 MHz, CDCl$_3$) δ 8.74 (dd, J=4.42, 1.39 Hz, 1 H) 8.46 (dd, J=8.34, 1.26 Hz, 1 H) 7.96 (d, J=8.84 Hz, 2 H) 7.52 (s, 1 H) 7.42-7.50 (m, 2 H) 7.15 (d, J=8.84 Hz, 2 H) 3.08 (s, 3 H) 2.99 (s, 2 H) 1.54 (s, 6 H); LCMS for $C_{24}H_{23}N_3O_6S$ m/z 482.00 (M+H)$^+$.

Preparation of Intermediate 15a 4-(4-Methanesulfonyl-phenoxy)-2,2-dimethyl-2,3-dihydro-benzofuran-6-carboxylic acid

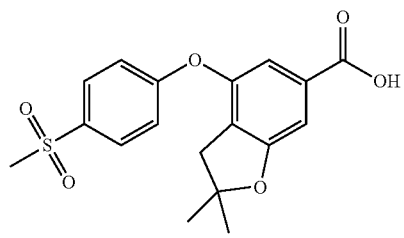

To a solution of 4-(4-methanesulfonyl-phenoxy)-2,2-dimethyl-2,3-dihydro-benzofuran-6-carboxylic acid methyl ester (3f) (76 mg, 0.20 mmol) in MeOH (5 mL) was added 3N aqueous NaOH (0.20 mL, 0.60 mmol). The mixture was heated to 60° C. overnight, and concentrated. The residue was diluted with H$_2$O (10 mL) extracted with EtOAc (10 mL). The water phase was acidified with 1N HCl to Ph ~1, extracted with CH$_2$Cl$_2$ (2×10 mL). The organic layers were dried over MgSO$_4$ and concentrated to give an off-white solid (77 mg, 100% yield). LCMS for $C_{24}H_{23}N_3O_6S$ m/z 385.00 (M+Na)$^+$.

Examples 16-21 were prepared in a similar manner as described for Example 1, from 4-(4-methanesulfonyl-phenoxy)-2,2-dimethyl-2,3-dihydro-benzofuran-6-carboxylic acid methyl ester (3f) and the appropriate amino heterocycles.

Example 16

4-(4-Methanesulfonyl-phenoxy)-2,2-dimethyl-2,3-dihydro-benzofuran-6-carbo-xylic acid(1-methyl-1H-pyrazol-3-yl)-amide

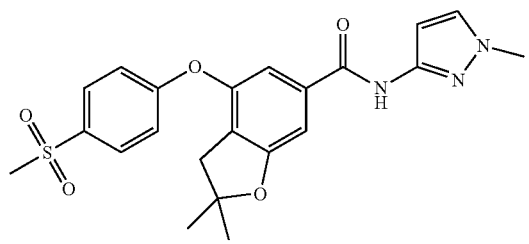

Example 17

4-(4-Methanesulfonyl-phenoxy)-2,2-dimethyl-2,3-dihydrobenzofuran-6-carboxy-lic acid pyrazin-2-ylamide

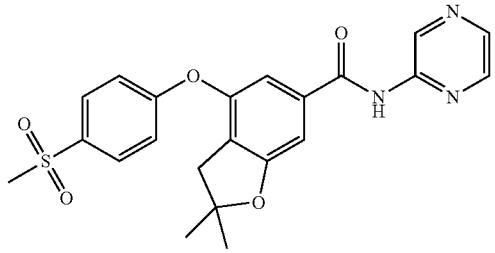

Example 18

4-(4-Methanesulfonyl-phenoxy)-2,2-dimethyl-2,3-dihydro-benzofuran-6-carbo-xylic acid(4-methoxy-pyridin-2-yl)-amide

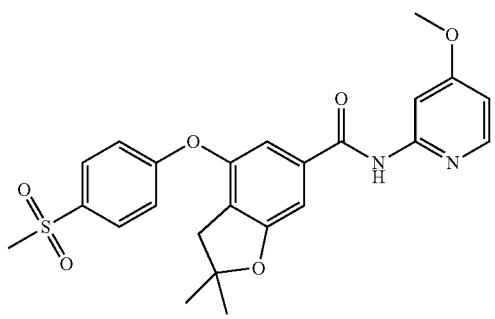

Example 19

4-(4-Methanesulfonyl-phenoxy)-2,2-dimethyl-2,3-dihydro-benzofuran-6-carbo-xylic acid pyridin-2-ylamide

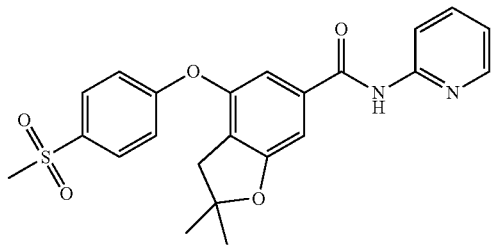

Example 20

4-(4-Methanesulfonyl-phenoxy)-2,2-dimethyl-2,3-dihydro-benzofuran-6-carbo-xylic acid(2-methyl-2H-[1,2,3]triazol-4-yl)-amide

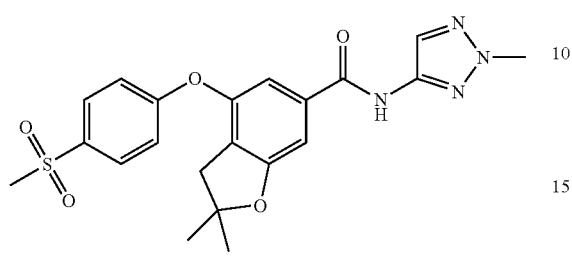

Example 21

4-(4-Methanesulfonyl-phenoxy)-2,2-dimethyl-2,3-dihydro-benzofuran-6-carboxylic acid (6-methyl-pyridazin-3-yl)-amide

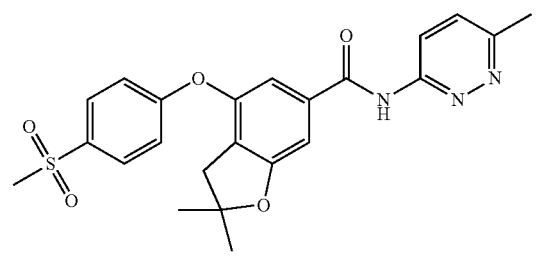

| Example | MW | MF | NMR | m/z | Elemental Analysis |
|---|---|---|---|---|---|
| 16 | 441.5 | C22H23N3O5S | $^1$H NMR (400 MHz, CDCl$_3$)) δ 8.55 (s, 1 H) 7.91 (d, J = 8.34 Hz, 2 H) 7.07 (dd, J = 16.67, 8.34 Hz, 4 H) 6.78 (s, 1 H) 3.78 (s, 3 H) 3.08 (s, 3 H) 2.90 (s, 2 H) 1.50 (s, 6 H); | 442.10 (M + H$^+$) | Calcd. for C$_{22}$H$_{23}$N$_3$O$_5$S•0.07 EtOAc: C, 59.78; H, 5.30; N, 9.39; Found: C, 59.78; H, 5.24; N, 9.28 |
| 17 | 439.5 | C22H21N3O5S | $^1$H NMR (400 MHz, CDCl$_3$)) δ 9.66 (s, 1 H) 8.41 (d, J = 13.64 Hz, 2 H) 8.27 (s, 1 H) 7.93 (d, J = 8.59 Hz, 2 H) 7.09-7.18 (m, 4 H) 3.09 (s, 3 H) 2.92 (s, 2 H) 1.51 (s, 6 H); | 440.10 (M + H$^+$) | Calcd. for C$_{22}$H$_{21}$N$_3$O$_5$S•0.20 H$_2$O: C, 59.64; H, 4.87; N, 9.48; Found: C, 59.72; H, 5.07; N, 9.47 |
| 18 | 468.5 | C24H24N2O6S | $^1$H NMR (400 MHz, CDCl$_3$)) δ 8.56 (s, 1 H) 8.05 (d, J = 4.80 Hz, 1 H) 7.95 (d, J = 14.91 Hz, 2 H) 7.91 (s, 1 H) 7.07-7.18 (m, 4 H) 6.63 (s, 1 H) 3.90 (s, 3 H) 3.08 (s, 3 H) 2.91 (s, 2 H) 1.51 (s, 6 H); | 469.10 (M + H$^+$) | Calcd. for C$_{24}$H$_{24}$N$_2$O$_6$S•0.10 H$_2$O: C, 61.29; H, 5.19; N, 5.96; Found: C, 61.24; H, 5.24; N, 6.05. |
| 19 | 438.5 | C23H22N2O5S | $^1$H NMR (400 MHz, CDCl$_3$)) δ 8.56 (s, 1 H) 8.34 (d, J = 8.59 Hz, 1 H) 8.30 (d, J = 4.04 Hz, 1 H) 7.89-7.97 (m, 2 H) 7.72-7.83 (m, 1 H) 7.16 (s, 1 H) 7.07-7.14 (m, 4 H) 3.09 (s, 3 H) 2.91 (s, 2 H) 1.51 (s, 6 H); | 439.10 (M + H$^+$) | Calcd. for C$_{23}$H$_{22}$N$_2$O$_5$S•0.30 H$_2$O: C, 62.23; H, 5.13; N, 6.31; Found: C, 62.18; H, 5.19; N, 6.14. |
| 20 | 442.5 | C21H22N4O5S | $^1$H NMR (400 MHz, CDCl$_3$)) δ 8.31 (s, 1 H) 8.08 (s, 1 H) 7.93 (d, J = 8.84 Hz, 2 H) 7.11 (d, J = 8.84 Hz, 2 H) 7.07 (d, J = 1.26 Hz, 2 H) 4.14 (s, 3 H) 3.09 (s, 3 H) 2.92 (s, 2 H) 1.51 (s, 6 H); | 443.10 (M + H$^+$) | Calcd. for C$_{21}$H$_{22}$N$_4$O$_5$S•0.55 H$_2$O: C, 55.75; H, 5.15; N, 12.38; Found: C, 55.89; H, 5.09; N, 12.20. |
| 21 | 453.5 | C23H23N3O5S | $^1$H NMR (400 MHz, CDCl$_3$) δ 8.92 (s, 1 H) 8.46 (d, J = 9.09 Hz, 1 H) 7.94 (d, J = 8.59 Hz, 2 H) 7.39 (d, J = 9.09 Hz, 1 H) 7.18 (s, 1 H) 7.11-7.15 (m, 2 H) 7.11 (s, 1 H) 3.09 (s, 3 H) 2.92 (s, 2 H) 2.68 (s, 3 H) 1.52 (s, 6 H); | 454.10 (M + H$^+$) | |

Example 22

4-(4-Methanesulfonyl-phenoxy)-2,2-dimethyl-2,3-dihydro-benzofuran-6-carboxylic acid (5-hydroxymethyl-pyridin-2-yl)-amide

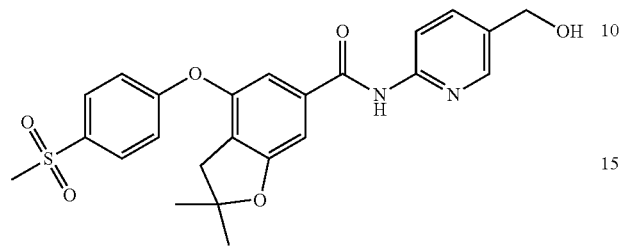

To a solution of 4-(4-methanesulfonyl-phenoxy)-2,2-dimethyl-2,3-dihydro-benzofuran-6-carboxylic acid[5-(tert-butyl-dimethyl-silanyloxymethyl)-pyridin-2-yl]-amide (22b) (85 mg, 0.15 mmol) in $CH_2Cl_2$ (5 mL) was added TBAF in THF (220 uL, 0.22 mmol). The reaction mixture was stirred at room temperature for 1 hr, quenched with $H_2O$ (20 mL), and extracted with $CH_2Cl_2$ (2×20 mL). The organic layers were dried over $MgSO_4$ and concentrated. The residue was purified by flash column chromatograph eluting with 50% EtOAc in hexanes to give a white solid (23 mg, 34% yield). $^1$H NMR (400 MHz, $CDCl_3$) δ 8.48 (s, 1 H) 8.34 (d, J=8.34 Hz, 1 H) 8.30 (s, 1 H) 7.93 (d, J=8.84 Hz, 2 H) 7.74-7.83 (m, 1 H) 7.08-7.17 (m, 4 H) 4.72 (s, 2 H) 3.09 (s, 3 H) 2.91 (s, 2 H) 1.51 (s, 6 H); LCMS for $C_{24}H_{24}N_2O_6S$ m/z 469.10 $(M+H)^+$.

Preparation of Intermediate 22a

5-(tert-Butyl-dimethyl-silanyloxymethyl)-pyridin-2-ylamine

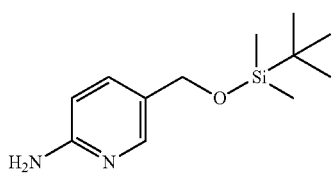

A mixture of (6-aminopyridin-3-yl)methanol (1.76 g, 14.2 mmol), TBDMSCl (2.18 g, 14.5 mmol), and imidazole (2.90 g, 42.6 mmol) in 20 mL DMF was stirred at room temperature for 2 hr. $H_2O$ was added, extracted with 3×EtOAc. The combined organic layer was washed with 2×$H_2O$, dried with $Na_2SO_4$, and concentrated to give an off-white solid (2.57 g, 76% yield). $^1$H NMR (400 MHz, $CDCl_3$)) δ 8.01 (d, J=1.77 Hz, 1 H) 7.44 (dd, J=8.34, 2.27 Hz, 1 H) 6.50 (d, J=8.34 Hz, 1 H) 4.60 (s, 2 H) 4.38 (br. s., 2 H) 0.93 (s, 9H) 0.11 (s, 6 H); LCMS for $C_{12}H_{22}N_2OSi$ m/z 239.00 (M+H).

Preparation of Intermediate 22b

4-(4-Methanesulfonyl-phenoxy)-2,2-dimethyl-2,3-dihydro-benzofuran-6-carboxylic acid[5-(tert-butyl-dimethyl-silanyloxymethyl)-pyridin-2-yl]-amide

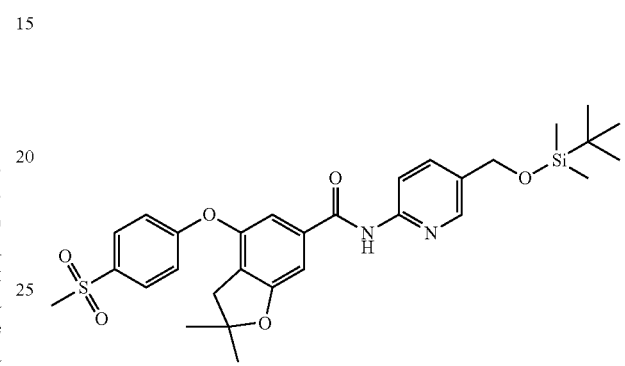

To a solution of 4-(4-methanesulfonyl-phenoxy)-2,2-dimethyl-2,3-dihydro-benzofuran-6-carboxylic acid (15a) (723 mg, 2.0 mmol) in DMF (5 mL) was added $Et_3N$ (600 uL. 4.30 mmol), HATU (1.52 g, 4.00 mmol) and 5-(tert-butyl-dimethyl-silanyloxymethyl)-pyridin-2-ylamine (22a) (338 mg, 1.42 mmol). The reaction mixture was stirred at 40° C. overnight, quenched with $H_2O$ (80 mL), and extracted with EtOAc (2×80 mL). The combined organic layers were washed with $H_2O$ (2×100 mL), dried over $MgSO_4$ and concentrated to give a brown solid which was purified by flash chromatography to give an off-white solid (91 mg, 8% yield). $^1$H NMR (400 MHz, $CDCl_3$) δ 8.48 (s, 1 H) 8.30 (d, J=8.59 Hz, 1 H) 8.25 (s, 1 H) 7.93 (d, J=8.84 Hz, 2 H) 7.71 (dd, J=8.59, 2.27 Hz, 1 H) 7.14 (d, J=1.26 Hz, 1 H) 7.12 (s, 1 H) 7.10 (d, J=1.77 Hz, 2 H) 4.73 (s, 2 H) 3.08 (s, 3 H) 2.91 (s, 2 H) 1.47-1.53 (m, 6 H) 0.94 (s, 9 H) 0.11 (s, 6 H); LCMS for $C_{30}H_{38}N_2O_6SSi$ m/z 582.20 $(M+H)^+$.

Examples 23 and 24 were prepared in parallel from 4-(4-methanesulfonyl-phenoxy)-2,2-dimethyl-2,3-dihydro-benzofuran-6-carbonyl chloride (23a) and the appropriate amino heterocycles: To appropriate 20 mL vials were delivered the amine solution (1.2 mL, 0.656 mmol, 0.5M in anhydrous DMA solution, 5 equiv.) and pyridine (0.032 mL, 0.394 mmol, 3 equiv). The acid chloride stock solution (260 µL, 0.13 mmol, 1 equiv, 0.5M in anhydrous acetonitrile solution) was delivered to each vial. The reaction vials were transferred to a heating block that had been preheated to 50° C. and stirred for 8 h at that temperature. Then the reaction mixtures were concentrated in vacuo at 35-40° C. to remove volatiles. The dried residues were dissolved DCM for further analysis and purification by flash chromatography. Fractions were collected in pre-tared tubes and lyophilized to dryness.

Example 23

4-(4-Methanesulfonyl-phenoxy)-2,2-dimethyl-2,3-dihydro-benzofuran-6-carboxylic acid(4-methyl-pyridin-2-yl)-amide

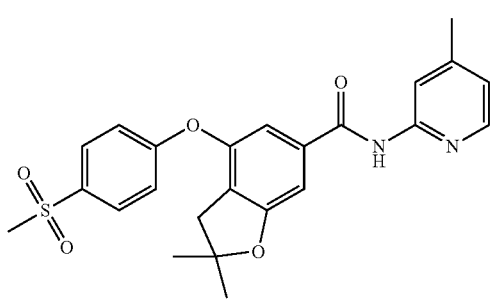

Yield: 10 mg (17%). LC-MS 453 (M+H)+, $^1$H NMR (400 MHz, ACETONITRILE-d$_3$) δ 1.46 (s, 6 H) 2.36 (s, 3H) 2.87 (s, 2 H) 3.05 (s, 3 H) 6.94 (s, J=4.53 Hz, 1 H) 7.07-7.23 (m, 4 H) 7.89 (d, J=8.81 Hz, 2H) 8.10 (2, 2 H).

Preparation of Intermediate 23a 4-(4-Methanesulfonyl-phenoxy)-2,2-dimethyl-2,3-dihydro-benzofuran-6-carbonyl chloride

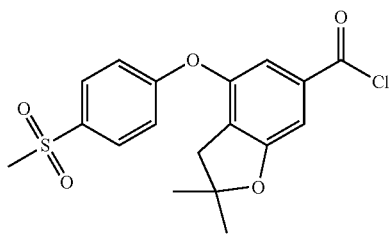

4-(4-Methanesulfonyl-phenoxy)-2,2-dimethyl-2,3-dihydro-benzofuran-6-carboxylic acid (15a) (3.35 g, 9.24 mmol) was dissolved in SOCl$_2$ (50 mL) and DCM (20 mL) and stirred at room temperature for 2 hr. The volatiles were removed to give 3.3 g of a yellow solid (94% yield). $^1$H NMR (400 MHz, CHLOROFORM-d) δ 1.51 (s, 6 H) 2.91 (s, 2 H) 3.06 (s, 3 H) 7.10 (d, J=8.56 Hz, 2 H) 7.30 (s, 1 H) 7.35 (s, 1 H) 7.93 (d, J=8.56 Hz, 2 H).

Example 24

4-(4-Methanesulfonyl-phenoxy)-2,2-dimethyl-2,3-dihydro-benzofuran-6-carboxylic acid(5-methyl-[1,3,4]thiadiazol-2-yl)-amide

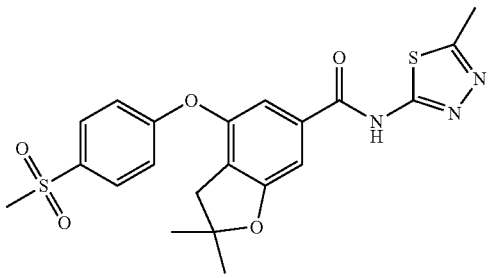

Yield: 10 mg (17%). LCMS 460 (M+H)+, $^1$H NMR (400 MHz, ACETONITRILE-d$_3$) δ 1.46 (s, 6 H) 2.63 (s, 3H) 2.90 (s, 2 H) 3.06 (s, 3 H) 7.17 (d, J=8 Hz, 2 H) 7.23 (s, 2 H) 7.91 (d, J=12 Hz, 2H) 10.47 (s, 1H).

Examples 25-30 were prepared in parallel from 4-(4-methanesulfonyl-phenoxy)-2,2-dimethyl-2,3-dihydro-benzofuran-6-carbonyl chloride (23a) and the appropriate amino heterocycles: To appropriate test tubes were delivered the amine stock solution (700 μL, 0.35 mmol, 0.5M in anhydrous DMA solution, 5 equiv.) and 2.5 M pyridine in DMA (84 μL, 0.21 mmol, 3 equiv). The acid chloride stock solution (200 μL, 0.07 mmol, 1 equiv, 0.5M in anhydrous acetonitrile solution) was delivered to each test tube. The tubes were transferred from the rack to a reactor block that had been preheated to 50° C. and stirred for 8 h at that temperature. Then the reaction mixtures were concentrated in vacuo at 35-40° C. to remove volatiles. The dried residues were dissolved in DMSO for further analysis and purification by preparative HPLC. Fractions were collected in pre-tared tubes and lyophilized to dryness.

Example 25

4-(4-Methanesulfonyl-phenoxy)-2,2-dimethyl-2,3-dihydro-benzofuran-6-carboxylic acid(5-methyl-isoxazol-3-yl)-amide

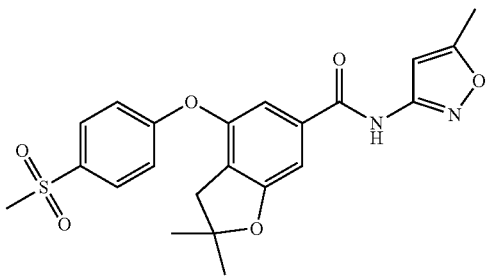

Example 26

4-(4-Methanesulfonyl-phenoxy)-2,2-dimethyl-2,3-dihydro-benzofuran-6-carboxylic acid isoxazol-3-ylamide

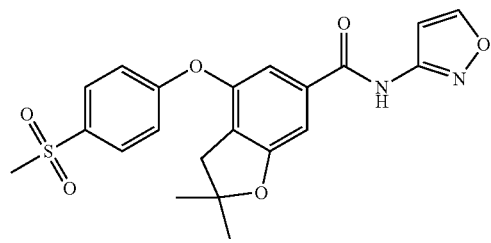

Example 27

4-(4-Methanesulfonyl-phenoxy)-2,2-dimethyl-2,3-dihydro-benzofuran-6-carboxylic acid(5-ethyl-[1,3,4]thiadiazol-2-yl)-amide

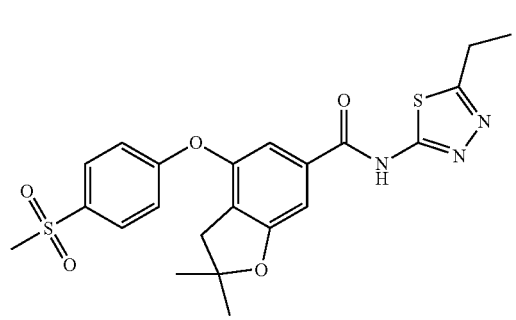

Example 28

4-(4-Methanesulfonyl-phenoxy)-2,2-dimethyl-2,3-dihydro-benzofuran-6-carboxylic acid(5-cyclopropyl-[1,3,4]thiadiazol-2-yl)-amide

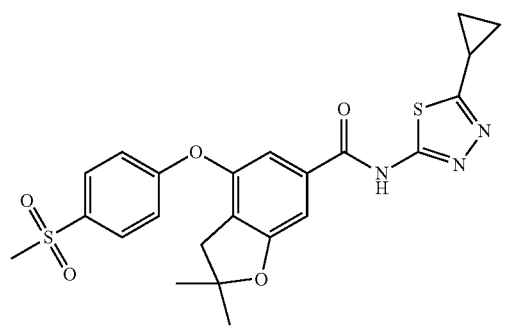

Example 29

4-(4-Methanesulfonyl-phenoxy)-2,2-dimethyl-2,3-dihydro-benzofuran-6-carboxylic acid(2-ethyl-2H-[1,2,3]triazol-4-yl)-amide

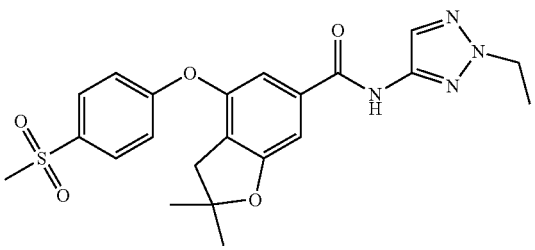

Example 30

4-(4-Methanesulfonyl-phenoxy)-2,2-dimethyl-2,3-dihydro-benzofuran-6-carboxylic acid(5-methoxymethyl-[1,3,4]thiadiazol-2-yl)-amide

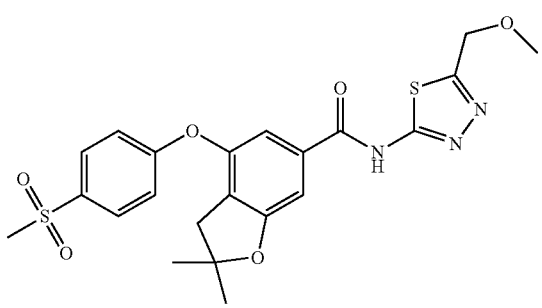

| Example | MW | MF | NMR | m/z |
|---|---|---|---|---|
| 25 | 442.5 | C22H22N2O6S | ¹H NMR (500 MHz, DMSO-d6, ppm) δ 1.37 (s, 6H), 2.32 (s, 3H), 2.60-2.85 (m, 2H), 3.12 (s, 3H), 6.61 (s, 1H), 7.10-7.20 (m, 4H), 7.83-7.90 (m, 2H). | 443.1 (M + H⁺) |
| 26 | 428.5 | C21H20N2O6S | ¹H NMR (500 MHz, DMSO-d6, ppm) δ 1.38 (s, 6H), 2.85 (s, 2H), 3.14 (s, 3H), 6.90-6.95 (m, 1H), 7.15-7.21 (m, 4H), 7.85-7.90 (m, 2H), 8.72 (s, 1H). | 429.1 (M + H⁺) |
| 27 | 473.6 | C22H23N3O5S2 | ¹H NMR (500 MHz, DMSO-d6, ppm) δ 1.23-1.28 (m, 3H), 1.39 (s, 6H), 2.84-2.88 (m, 2H), 2.90-2.97 (m, 2H), 3.13 (s, 3H), 7.15-7.20 (m, 2H), 7.25-7.30 (m, 2H), 7.86-7.91 (m, 2H). | 474.1 (M + H⁺) |
| 28 | 485.6 | C23H23N3O5S2 | ¹H NMR (500 MHz, DMSO-d6, ppm) δ 0.9-0.95 (m, 2H), 1.07-1.15 (m, 2H), 1.34-1.41 (s, 7H), 2.84-2.88 (m, 2H), 3.13 (s, 3H), 7.15-7.20 (m, 2H), 7.24-7.28 (m, 2H), 7.86-7.91 (m, 2H). | 486.1 (M + H⁺) |
| 29 | 456.5 | C22H24N4O5S | ¹H NMR (500 MHz, DMSO-d6, ppm) δ 1.36-1.41 (m, 9H), 2.83-2.88 (m, 2H), 3.34 (s, 3H), 4.26-4.35 (m, 2H), 7.15-7.25 (m, 4H), 7.85-7.93 (m, 2H). | 457.1 (M + H⁺) |
| 30 | 489.6 | C22H23N3O6S2 | ¹H NMR (500 MHz, DMSO-d6, ppm) δ 1.41 (s, 6H), 2.60-2.90 (m, 2H), 3.30-3.36 (m, 6H), 4.70-4.75 (m, 2H), 7.16-7.18 (m, 2H), 7.30-7.34 (m, 2H), 7.87-7.94 (m, 2H). | 490.1 (M + H⁺) |

Example 31

4-(4-Cyano-2-fluoro-phenoxy)-2,2-dimethyl-2,3-dihydro-benzofuran-6-carbo-xylic acid(1-methyl-1H-pyrazol-3-yl)-amide

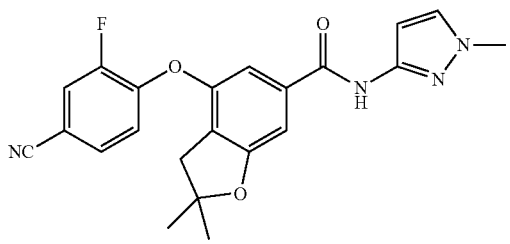

The title compound was prepared in a similar manner as described for Intermediate 1f, from 3,4-difluorobenzonitrile (11 mg, 0.080 mmol) and 4-hydroxy-2,2-dimethyl-2,3-dihydro-benzofuran-6-carboxylic acid(1-methyl-1H-pyrazol-3-yl)-amide (31a) (23 mg, 0.080 mmol) to give a colorless oil (8 mg, 20% yield). ¹H NMR (400 MHz, CDCl₃) δ 8.49 (s, 1 H) 7.50 (dd, J=10.11, 1.77 Hz, 1 H) 7.42 (d, J=8.59 Hz, 1 H) 7.28 (d, J=2.02 Hz, 1 H) 7.00-7.08 (m, 2 H) 6.95 (s, 1 H) 6.77 (d, J=1.77 Hz, 1 H) 3.78 (s, 3 H) 2.97 (s, 2 H) 1.51 (s, 6 H); LCMS for C₂₂H₁₉FN₄O₃ m/z (M+H)⁺407.10.

Preparation of Intermediate 31a

4-Hydroxy-2,2-dimethyl-2,3-dihydro-benzofuran-6-carbo-xylic acid(1-methyl-1H-pyrazol-3-yl)-amide

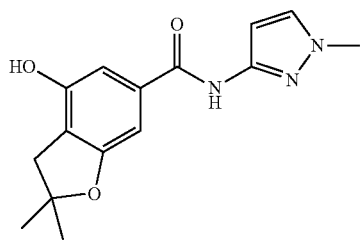

The title compound was prepared in a similar manner as described for Example 1, from 3-amino-1-methylpyrazole (201 mg, 2.07 mmol) and 4-hydroxy-2,2-dimethyl-2,3-dihydro-benzofuran-6-carboxylic acid methyl ester (3e) (45 mg, 0.22 mmol) to give a white solid (28 mg, 48% yield). ¹H NMR (400 MHz, CDCl₃) δ 8.53 (s, 1 H) 7.30 (d, J=1.77 Hz, 1 H)

7.05-7.12 (m, 1 H) 7.00 (s, 1 H) 6.80 (d, J=2.02 Hz, 1 H) 3.81 (s, 3 H) 3.00 (s, 2 H) 1.50 (s, 6 H); LCMS for $C_{15}H_{17}N_3O_3$ m/z 288.10 (M+H)+.

Example 32

4-[4-(Azetidine-1-carbonyl)-2-fluoro-phenoxy]-2,2-dimethyl-2,3-dihydro-benzo-furan-6-carboxylic acid (1-methyl-1H-pyrazol-3-yl)-amide

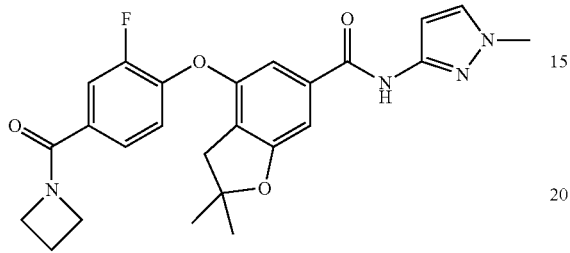

The title compound was prepared in a similar manner as described for Example 1, from 3-amino-1-methylpyrazole (250 mg, 2.57 mmol) and 4-[4-(azetidine-1-carbonyl)-2-fluoro-phenoxy]-2,2-dimethyl-2,3-dihydro-benzofuran-6-carboxylic acid(1-methyl-1 H-pyrazol-3-yl)-amide (32b) (103 mg, 0.26 mmol). Purification by reverse phase column chromatography gave a white solid (50 mg, 42% yield). $^1$H NMR (400 MHz, CDCl$_3$) δ 8.36 (s, 1 H) 7.49-7.58 (m, 1 H) 7.40 (dd, J=8.46, 1.14 Hz, 1 H) 6.98-7.05 (m, 2 H) 6.93 (s, 1 H) 6.77 (d, J=2.02 Hz, 1 H) 4.32-4.43 (m, 2 H) 4.21-4.32 (m, 2 H) 3.78-3.82 (m, 3 H) 2.98 (s, 2 H) 2.34-2.43 (m, 2 H) 1.51 (s, 6 H); LCMS for $C_{25}H_{25}FN_4O_4$ m/z 465.10 (M+H)+; Anal. Calcd. for $C_{25}H_{25}FN_4O_4$: C, 64.65; H, 5.43; N, 12.06; Found: C, 64.36; H, 5.31; N, 11.78.

Preparation of Intermediate 32a

Azetidin-1-yl-(3,4-difluoro-phenyl)-methanone

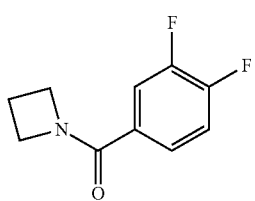

3,4-Difluorobenzoic acid (1.03 g, 6.51 mmol) in CH$_2$Cl$_2$ (10 ml) was added SOCl$_2$ (600 uL, 8.26 mmol) and DMF (3 drop). The reaction mixture was heated to reflux for 3 hr. The mixture was evaporated under vacuum and dried. The oil/solid mixture was taken into CH$_2$Cl$_2$ (20 mL) and added azetidine hydrochloride (731 mg, 7.82 mmol) and triethylamine (2.75 mL, 19.7 mmol). The reaction mixture was stirred at room temperature for 2 hr, quenched with 1 N HCl (60 mL) and extracted with EtOAc. The organic layers were dried over MgSO$_4$ and concentrated to give pale yellow oil which was purified by flash column chromatography eluting with 30% EtOAc in hexanes to give a white solid (553 mg, 48% yield). $^1$H NMR (400 MHz, CDCl$_3$) δ 7.50 (m, 1 H) 7.40 (m 1 H) 7.16-7.25 (m, 1 H) 4.32 (d, J=6.82 Hz, 2 H) 4.24 (d, J=7.07 Hz, 2 H) 2.33-2.42 (m, 2 H).

Preparation of Intermediate 32b

4-[4-(Azetidine-1-carbonyl)-2-fluoro-phenoxy]-2,2-dimethyl-2,3-dihydro-benzofuran-6-carboxylic acid methyl ester

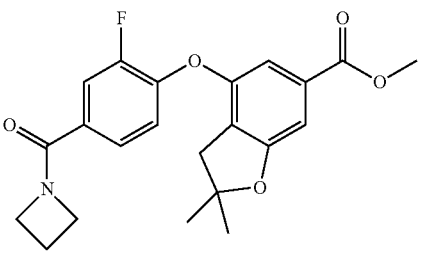

The title compound was prepared in a similar manner as described for Intermediate 1f, from azetidin-1-yl-(3,4-difluoro-phenyl)-methanone (32a) (90 mg, 0.46 mmol) and 4-hydroxy-2,2-dimethyl-2,3-dihydro-benzofuran-6-carboxylic acid methyl ester (3e) (117 mg, 0.53 mmol) to give a pale yellow oil (106 mg, 59% yield). $^1$H NMR (400 MHz, CDCl$_3$) δ 7.51 (dd, J=10.86, 2.02 Hz, 1 H) 7.38-7.42 (m, 1 H) 7.21 (d, J=1.01 Hz, 1 H) 7.09 (d, J=1.01 Hz, 1 H) 6.99 (t, J=8.21 Hz, 1 H) 4.30-4.40 (m, 2 H) 4.20-4.29 (m, 2 H) 3.86 (s, 3 H) 2.97 (s, 2 H) 2.33-2.43 (m, 2 H) 1.50 (s, 6 H).

Example 33

4-[4-(Azetidine-1-carbonyl)-3-fluoro-phenoxy]-2,2-dimethyl-2,3-dihydro-benzofuran-6-carboxylic acid (1-methyl-1H-pyrazol-3-yl)-amide and Example 34

4-[2-(Azetidine-1-carbonyl)-5-fluoro-phenoxy]-2,2-dimethyl-2,3-dihydro-benzofuran-6-carboxylic acid (1-methyl-1H-pyrazol-3-yl)-amide

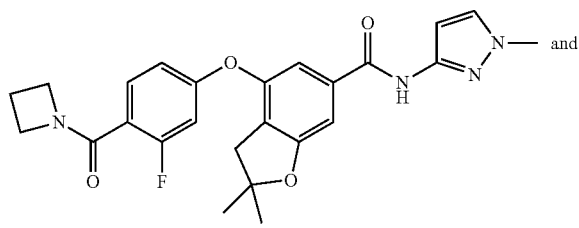

-continued

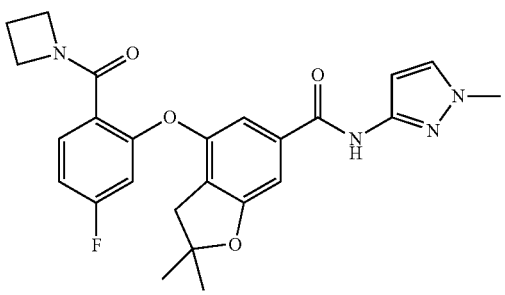

4-Hydroxy-2,2-dimethyl-2,3-dihydro-benzofuran-6-carboxylic acid(1-methyl-1H-pyrazol-3-yl)-amide (31a) (421 mg, 1.47 mmol) and Cs$_2$CO$_3$ (965 mg, 2.96 mmol) was added to a solution of azetidin-1-yl(2,4-difluorophenyl)methanone (33a) (292 mg, 1.48 mmol). The reaction mixture was heated to 160° C. for 2 hr in a microwave. The mixture was filtered and concentrated. The residue was purified by SFC chromatography to give 4-[4-(azetidine-1-carbonyl)-3-fluoro-phenoxy]-2,2-dimethyl-2,3-dihydro-benzofuran-6-carboxylic acid(1-methyl-1H-pyrazol-3-yl)-amide (315 mg, 46% yield) and 4-[2-(azetidine-1-carbonyl)-5-fluoro-phenoxy]-2,2-dimethyl-2,3-dihydro-benzofuran-6-carboxylic acid(1-methyl-1H-pyrazol-3-yl)-amide (34 mg, 5% yield) as white solid.

Example 33: $^1$H NMR (400 MHz, CDCl$_3$) δ 8.36 (s, 1 H) 7.50-7.57 (m, 1 H) 7.29 (d, J=2.53 Hz, 1 H) 7.05 (d, J=2.27 Hz, 2 H) 6.76-6.85 (m, 2 H) 6.67 (dd, J=11.12, 2.53 Hz, 1 H) 4.13-4.24 (m, 4 H) 3.81 (s, 3 H) 2.89 (s, 2 H) 2.30-2.39 (m, 2 H) 1.49 (s, 6 H); LCMS for C$_{25}$H$_{25}$FN$_4$O$_4$ m/z 465.20 (M+H)$^+$.

Example 34: $^1$H NMR (400 MHz, CDCl$_3$) δ 8.48 (s, 1 H) 7.46 (dd, J=8.46, 6.44 Hz, 1H) 7.29 (d, J=2.02 Hz, 1 H) 7.04 (d, J=2.02 Hz, 2 H) 6.87 (td, J=8.15, 2.40 Hz, 1 H) 6.78 (d, J=2.02 Hz, 1 H) 6.58 (dd, J=9.85, 2.27 Hz, 1 H) 4.07-4.16 (m, 4 H) 3.82 (s, 3 H) 2.91 (s, 2 H) 2.23-2.33 (m, 2 H) 1.49 (s, 6 H); LCMS for C$_{25}$H$_{25}$FN$_4$O$_4$ m/z 465.20 (M+H)$^+$.

Preparation of Intermediate 33a

Azetidin-1-yl-(2,4-difluoro-phenyl)-methanone

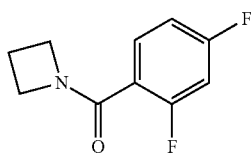

To a solution of 2,4-difluorobenzoyl chloride (1.14 g, 6.46 mmol) in CH$_2$Cl$_2$ was added azetidine hydrochloride (1.46 g, 15.6 mmol) and Et$_3$N (2.70 mL, 19.4 mmol). The reaction mixture was stirred at room temperature for 1 hr, quenched with H$_2$O (100 mL), and extracted with CH$_2$Cl$_2$ (2×100 mL). The organic layers were dried over MgSO$_4$ and concentrated to give an off-white solid (896 mg, 76% yield) which was used without further purification. $^1$H NMR (400 MHz, CDCl$_3$) δ 7.52-7.59 (m, 1 H) 6.91-6.98 (m, 1 H) 6.81-6.87 (m, 1 H) 4.21 (t, J=7.71 Hz, 2 H) 4.11 (t, J=7.71 Hz, 2H) 2.30-2.38 (m, 2 H).

Example 35

4-[4-(Azetidine-1-carbonyl)-phenoxy]-2,2-dimethyl-2,3-dihydro-benzofuran-6-carboxylic acid(1-methyl-1H-pyrazol-3-yl)-amide

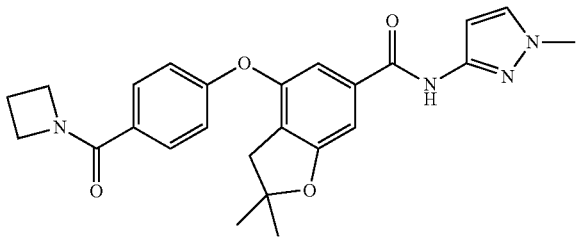

The title compound was prepared in a similar manner as described for Example 15, from 4-[4-(azetidine-1-carbonyl)-phenoxy]-2,2-dimethyl-2,3-dihydro-benzofuran-6-carboxylic acid (35c) (598 mg, 1.63 mmol) and 1-methyl-3-aminopyrazole (236 mg, 2.43 mmol) to give a white solid (315 mg, 41% yield). $^1$H NMR (400 MHz, CDCl$_3$) δ 8.31 (s, 1 H) 7.65 (ddd, J=9.22, 2.78, 2.40 Hz, 2 H) 7.28 (d, J=2.27 Hz, 1 H) 7.02 (dd, J=9.85, 1.26 Hz, 2 H) 6.98 (ddd, J=9.22, 2.78, 2.40 Hz, 2 H) 6.78 (d, J=2.02 Hz, 1 H) 4.30-4.40 (m, 2 H) 4.19-4.30 (m, 2 H) 3.81 (s, 3 H) 2.89 (s, 2 H) 2.32-2.40 (m, 2 H) 1.49 (s, 6 H); LCMS for C$_{25}$H$_{26}$N$_4$O$_4$ m/z 447.20 (M+H)$^+$; Anal. Calcd. for C$_{25}$H$_{26}$N$_4$O$_4$.0.31 H2O: C, 65.38; H, 6.02; N, 12.20; Found: C, 65.37; H, 5.85; N, 12.38.

Preparation of Intermediate 35a

Azetidin-1-yl-(4-bromo-phenyl)-methanone

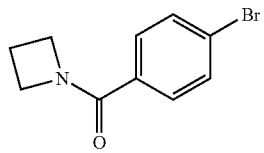

Et$_3$N (2.00 mL, 14.3 mmol) and azetidine hydrochloride (462 mg, 4.94 mmol) were added to a solution of 4-bromobenzoyl chloride (1.07 g, 4.88 mmol) in CH$_2$Cl$_2$ (20 mL). The mixture was stirred at room temperature for 2 hr, diluted with CH$_2$Cl$_2$ (100 mL), and washed with 1N aqueous HCl (100 mL), H$_2$O (100 mL), and brine (100 mL). The organic layer was dried over MgSO$_4$ and concentrated to give a colorless oil (1.10 g, 94% yield). $^1$H NMR (400 MHz, CDCl$_3$) δ

7.53 (ddd, J=17.43, 6.57, 2.27 Hz, 4 H) 4.21-4.32 (m, 4 H) 2.32-2.40 (m, 2 H);); LCMS for $C_{10}H_{10}BrNO$ m/z 241.00 $(M+H)^+$.

Preparation of Intermediate 35b

4-[4-(Azetidine-1-carbonyl)-phenoxy]-2,2-dimethyl-2,3-dihydro-benzofuran-6-carboxylic acid methyl ester

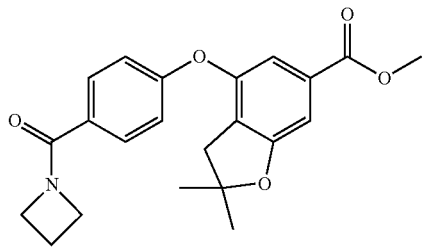

$K_3PO_4$ (1.23 g, 5.79 mmol), $Pd(OAc)_2$ (41 mg, 0.81 mmol) and 2-di-t-butylphosphino-2',4'6'-tri-i-propyl-1,1'-biphenyl (68 mg, 0.16 mmol) was added to a solution of 4-hydroxy-2,2-dimethyl-2,3-dihydro-benzofuran-6-carboxylic acid methyl ester (3e) (646 mg, 2.91 mmol) and azetidin-1-yl-(4-bromo-phenyl)-methanone (35a) (697 mg, 2.90 mmol) in toluene (10 mL). The reaction mixture was heated to 110° C. overnight. The mixture was filtered, washed with EtOAc, and concentrated. The residue was purified by flash column chromatograph eluting with 10-25 % EtOAc in hexanes to give a white solid (802 mg, 72% yield). $^1$H NMR (400 MHz, $CDCl_3$) δ 7.64 (d, J=6.82 Hz, 2 H) 7.23 (s, 1 H) 7.20 (s, 1 H) 6.97 (d, J=7.33 Hz, 2 H) 4.24-4.34 (m, 4 H) 3.87 (s, 3 H) 2.88 (s, 2 H) 2.50-2.61 (m, 1 H) 2.32-2.42 (m, 1H) 1.47 (s, 6 H); LCMS for $C_{22}H_{23}NO_5$ m/z 382.00 $(M+H)^+$.

Preparation of Intermediate 35c

4-[4-(Azetidine-1-carbonyl)-phenoxy]-2,2-dimethyl-2,3-dihydro-benzofuran-6-carboxylic acid

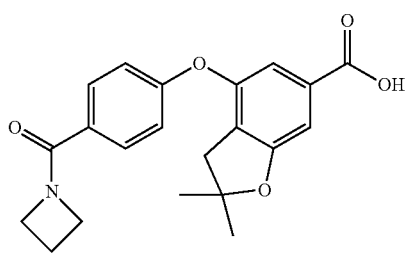

Aqueous NaOH (3 N, 2.1 mL, 6.3 mmol) was added to a solution of 4-[4-(azetidine-1-carbonyl)-phenoxy]-2,2-dimethyl-2,3-dihydro-benzofuran-6-carboxylic acid methyl ester (35b) (802 mg, 2.10 mmol) in 10 mL $CH_3OH$. The mixture was heated to 60° C. for 3 hr, concentrated, diluted with $H_2O$ (60 mL) and acidified with 1N aqueous HCl to Ph ~1. The aqueous phase was extracted with $CH_2Cl_2$ (60 mL), dried with $MgSO_4$ and concentrated to give a white solid (598 mg, 74% yield). $^1$H NMR (400 MHz, DMSO-$d_6$) δ 12.99 (s, 1 H) 7.67 (d, J=7.33 Hz, 2 H) 7.02-7.10 (m, 3 H) 6.99 (s, 1 H) 4.32 (s, 2 H) 4.03 (s, 2 H) 2.89 (s, 2 H) 2.21-2.30 (m, 2 H) 1.42 (s, 6 H); LCMS for $C_{21}H_{21}NO_5$ m/z 468.00 $(M+H)^+$.

Example 36

4-(3-Methanesulfonyl-phenoxy)-2,2-dimethyl-2,3-dihydro-benzofuran-6-carboxylic acid(1-methyl-1H-pyrazol-3-yl)-amide

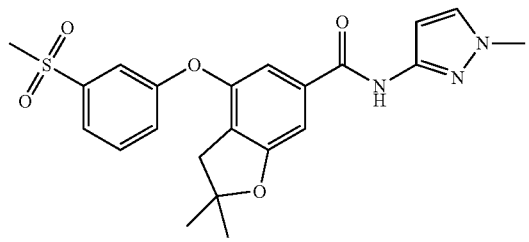

To a solution of 4-hydroxy-2,2-dimethyl-2,3-dihydro-benzofuran-6-carboxylic acid(1-methyl-1H-pyrazol-3-yl)-amide (31a) (117 mg, 0.41 mmol) in $CH_2Cl_2$ (5 mL) was added (3-methylsulfonyl)boronic acid (163 mg, 0.814 mmol), $Cu(OAc)_2$ (74 mg, 2.04 mmol), 4A Molecular Sieves (500 mg) and $Et_3N$ (0.300 mL, 2.15 mmol). The reaction mixture was stirred at room temperature overnight. LCMS showed about 50% conversion. More (3-methylsulfonyl)boronic acid (81 mg) was added, and the mixture was stirred at room temperature for 48 hrs, filtered, and concentrated. The residue was purified by flash column chromatograph eluting with 20-60% EtOAc in hexanes to give a white solid (57 mg, 32% yield). $^1$H NMR (400 MHz, DMSO-$d_6$) δ 10.62-10.73 (m, 1 H) 8.20 (s, 1 H) 8.02 (d, J=8.59 Hz, 1 H) 7.88-7.97 (m, 2 H) 7.64 (d, J=8.59 Hz, 1 H) 7.40 (d, J=1.26 Hz, 1 H) 7.27-7.36 (m, 1 H) 7.12-7.25 (m, 2 H) 4.85-4.99 (m, 1 H) 3.87-4.19 (m, 2 H) 3.20 (s, 3 H) 2.80 (dd, J=16.93, 4.29 Hz, 1 H) 2.48-2.60 (m, 1 H) 2.46-2.56 (m, 2 H) 2.27 (s, 3 H); LCMS for $C_{22}H_{23}N_3O_5S$ m/z 442.00 $(M+H)^+$; Anal. Calcd. for $C_{22}H_{23}N_3O_5S.0.28 H_2O$: C, 59.17; H, 5.32; N, 9.41; Found: C, 59.18; H, 5.31; N, 9.32.

Example 37

4-[3-(Azetidine-1-carbonyl)-phenoxy]-2,2-dimethyl-2,3-dihydro-benzofuran-6-carboxylic acid(1-methyl-1H-pyrazol-3-yl)-amide

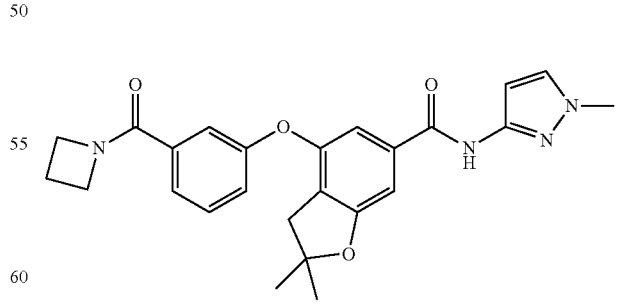

$Al(CH_3)_2Cl$ (4.85 mL, 1.85 mmol, 1.0M solution in hexane) was added to a solution of azetidine hydrochloride (173 mg, 1.85 mmol) in 1,2-dichloroethane (5 mL) at 0° C. The mixture was stirred at room temperature for 15 min, and then added 3-[2,2-dimethyl-6-(1-methyl-1H-pyrazol-3-ylcarbamoyl)-2,3-dihydro-benzofuran-4-yloxy]-benzoic acid methyl ester (37a) (78 mg, 0.19 mmol) in 1,2-dichloroethane (2 mL). The resulting mixture was stirred at room temperature overnight. LCMS show about 30% conversion. The mixture was heated to 60° C. overnight. The reaction mixture was quenched with 20% potassium sodium tartrate tetrahydrate (5 mL) and diluted with $H_2O$ (30 mL). The resulted suspension was extracted with $CHCl_3$ (2×30 mL), dried over $MgSO_4$ and concentrated. The residue was purified by flash column chromatograph eluting with 50-70% EtOAc in hexanes to give a white solid (42 mg, 51% yield). $^1$H NMR (400 MHz, $CDCl_3$) δ 8.44 (s, 1 H) 7.33-7.43 (m, 3 H) 7.10 (dd, J=7.45, 1.89 Hz, 1H) 7.01 (s, 1 H) 6.96 (s, 1 H) 6.76 (d, J=2.27 Hz, 1 H) 4.30 (t, J=7.45 Hz, 2 H) 4.22 (t, J=7.71 Hz, 2 H) 3.80 (s, 3H) 2.94 (s, 2 H) 2.30-2.41 (m, 2 H) 1.50 (s, 6 H); LCMS for $C_{25}H_{26}N_4O_4$ m/z 447.20 (M+H)$^+$; Anal. Calcd. for $C_{25}H_{26}N_4O_4$·0.50 $H_2O$·0.10 EtOAc: C, 65.70; H, 6.03; N, 12.07; Found: C, 65.80; H, 5.87; N, 11.85.

Preparation of Intermediate 37a

3-[2,2-Dimethyl-6-(1-methyl-1H-pyrazol-3-ylcarbamoyl)-2,3-dihydro-benzofuran-4-yloxy]-benzoic acid methyl ester

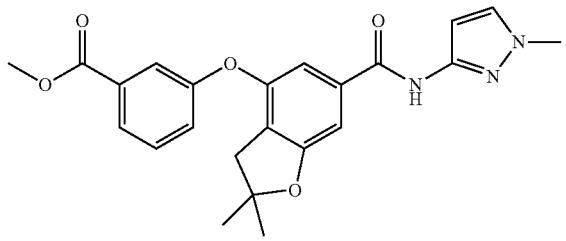

A flask is charged with 4-hydroxy-2,2-dimethyl-2,3-dihydro-benzofuran-6-carboxylic acid (1-methyl-1H-pyrazol-3-yl)-amide (31a) (233 mg, 0.811 mmol), $Cu(OAc)_2$ (147 mg, 0.811 mmol), (3-methoxy-carbonylphenol)boronic acid (438 mg, 2.43 mmol), and powdered 4A molecular sieves (500 mg). $CH_2Cl_2$ (8 mL) was added to yield a solution, followed by $Et_3N$ (0.56 mL, 4.02 mmol). The reaction mixture was stirred at room temperature overnight. Additional boronic acid (146 mg, 0.811 mmol) was added. The mixture was stirred at room temperature for 2 days, filtered, washes with EtOAc. The filtrated was concentrated. The residue was purified by flash column chromatograph eluting with 60-80% EtOAc in hexanes to give a white solid (79 mg, 23% yield). $^1$H NMR (400 MHz, $CDCl_3$) δ 9.05 (s, 1 H) 7.81 (d, J=6.82 Hz, 1 H) 7.65 (s, 1 H) 7.42 (t, J=7.96 Hz, 1H) 7.22 (dd, J=8.08, 2.53 Hz, 1 H) 7.09 (s, 1 H) 7.01 (s, 1 H) 6.81 (d, J=2.02 Hz, 1 H) 3.87-3.97 (m, 4 H) 3.80 (s, 3 H) 2.92 (s, 2 H) 1.50 (s, 6 H). LCMS for $C_{23}H_{23}N_3O_5$ m/z 422.20 (M+H)$^+$.

Example 38

4-(4-Difluoromethyl-phenoxy)-2,2-dimethyl-2,3-dihydro-benzofuran-6-carboxylic acid(1-methyl-1H-pyrazol-3-yl)-amide

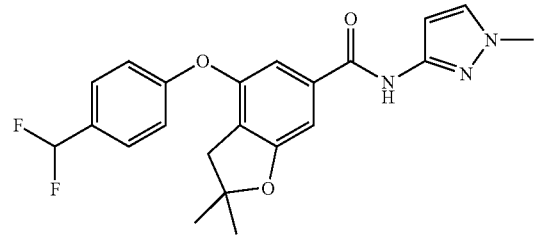

A mixture of 4-hydroxy-2,2-dimethyl-2,3-dihydro-benzofuran-6-carboxylic acid (1-methyl-1H-pyrazol-3-yl)-amide (31a) (102 mg, 0.36 mmol), 1-bromo-4-difluoromethyl benzene (110 mg, 0.53 mmol), $Cs_2CO_3$ (174 mg, 0.53 mmol) and CuI (1 mg) in DMF (5 mL) was heated for 2 hr at 160° C. in the microwave. The mixture was filtered and the filtrate was purified by reverse phase chromatograph to give a white solid (18 mg, 12% yield). $^1$H NMR (400 MHz, $CDCl_3$) δ 9.92 (d, J=2.02 Hz, 1 H) 8.52 (s, 1 H) 7.72 (dd, J=10.36, 1.77 Hz, 1 H) 7.64 (d, J=8.34 Hz, 1 H) 7.28 (s, 1 H) 7.09 (t, J=7.96 Hz, 1 H) 7.05 (s, 1 H) 6.97 (s, 1 H) 6.77 (d, J=2.02 Hz, 1 H) 3.78 (s, 3 H) 2.98 (s, 2 H) 1.51 (s, 6 H); LCMS for $C_{22}H_{21}F_2N_3O_3$ m/z 414.00 (M+H)$^+$.

Example 39

4-(4-Dimethylaminomethyl-2-fluoro-phenoxy)-2,2-dimethyl-2,3-dihydro-benzofuran-6-carboxylic acid (1-methyl-1H-pyrazol-3-yl)-amide and Example 40

4-(2-Fluoro-4-hydroxymethyl-phenoxy)-2,2-dimethyl-2,3-dihydro-benzofuran-6-carboxylic acid(1-methyl-1H-pyrazol-3-yl)-amide

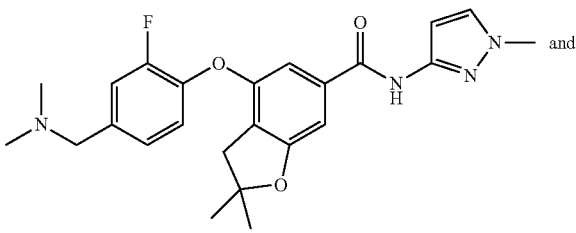

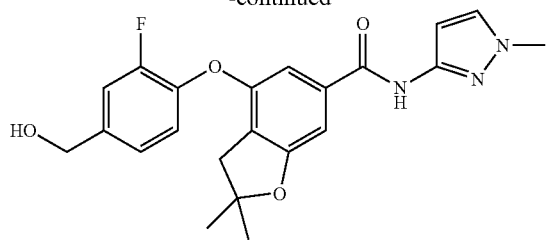

To dimethylamine (0.6 mL, 2.0 M, 1.0 mmol) in MeOH (5 mL) was added NaCNBH$_3$ (31 mg, 0.49 mmol). The mixture was heated to 50° C. for 1 hr, and then 4-(2-fluoro-4-formyl-phenoxy)-2,2-dimethyl-2,3-dihydro-benzofuran-6-carboxylic acid(1-methyl-1H-pyrazol-3-yl)-amide (39a) (100 mg, 0.24 mmol) was added. The reaction mixture was heated to 50° C. for 1 hr. Additional NaCNBH$_3$ (31 mg, 0.49 mmol) and dimethylamine (0.3 mL, 2.0 M, 0.5 mmol) were added to the reaction mixture. The mixture was heated at 50° C. for 1 hr, then concentrated and purified by reverse phase chromatograph to give 4-(4-dimethylaminomethyl-2-fluoro-phenoxy)-2,2-dimethyl-2,3-dihydro-benzofuran-6-carboxylic acid(1-methyl-1H-pyrazol-3-yl)-amide (26 mg, 24% yield) and 4-(2-Fluoro-4-hydroxymethyl-phenoxy)-2,2-dimethyl-2,3-dihydro-benzofuran-6-carboxylic acid(1-methyl-1H-pyrazol-3-yl)-amide (25 mg, 25% yield) as white solid.

Example 39: $^1$H NMR (400 MHz, DMSO-d$_6$) δ 10.72 (s, 1 H) 7.54-7.61 (m, 2 H) 7.28-7.37 (m, 2 H) 7.21 (d, J=1.01 Hz, 1 H) 6.97 (s, 1 H) 6.50 (d, J=2.27 Hz, 1 H) 4.27 (s, 2 H) 3.75 (s, 3 H) 2.97 (s, 2H) 2.74 (s, 6H) 1.46 (s, 6 H); LCMS for C$_{24}$H$_{27}$FN$_4$O$_3$ m/z 439.20 (M+H)$^+$.

Example 40: $^1$H NMR (400 MHz, DMSO-d$_6$) δ 10.70 (s, 1 H) 7.57 (d, J=2.27 Hz, 1 H) 7.28-7.35 (m, 1 H) 7.16-7.22 (m, 2 H) 7.15 (d, J=1.01 Hz, 1 H) 6.86 (s, 1 H) 6.50 (d, J=2.27 Hz, 1 H) 5.36 (t, J=5.81 Hz, 1 H) 4.52 (d, J=5.81 Hz, 2 H) 3.75 (s, 3 H) 2.99 (s, 2 H) 1.45 (s, 6 H); LCMS for C$_{22}$H$_{22}$FN$_3$O$_4$ m/z 412.00 (M+H)$^+$; Anal. Calcd. for C$_{22}$H$_{22}$FN$_3$O$_4$.0.08 TFA: C, 63.29; H, 5.29; N, 9.99; Found: C, 63.27; H, 5.29; N, 9.91.

Preparation of Intermediate 39a 4-(2-Fluoro-4-formyl-phenoxy)-2,2-dimethyl-2,3-dihydro-benzofuran-6-carboxylic acid(1-methyl-1H-pyrazol-3-yl)-amide

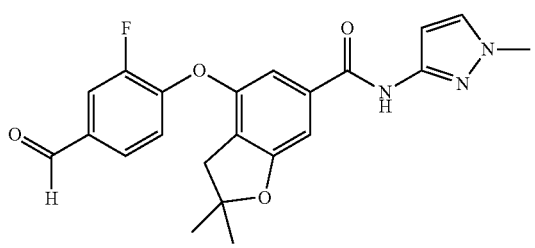

The title compound was prepared in a similar manner as described for Intermediate 1f, from 3,4-difluoro-benzaldehyde and 4-hydroxy-2,2-dimethyl-2,3-dihydro-benzofuran-6-carbo-xylic acid(1-methyl-1H-pyrazol-3-yl)-amide (31a). $^1$H NMR (400 MHz, CDCl$_3$) δ 9.92 (d, J=2.02 Hz, 1 H) 8.52 (s, 1 H) 7.72 (dd, J=10.36, 1.77 Hz, 1 H) 7.64 (d, J=8.34 Hz, 1 H) 7.28 (s, 1 H) 7.09 (t, J=7.96 Hz, 1 H) 7.05 (s, 1 H) 6.97 (s, 1 H) 6.77 (d, J=2.02 Hz, 1 H) 3.78 (s, 3 H) 2.98 (s, 2 H) 1.51 (s, 6 H); LCMS for C$_{22}$H$_{20}$FN$_3$O$_4$ m/z 410.00 (M+H)$^+$.

Examples 41-46 were prepared in a similar manner as described for Intermediate 1f, from 4-hydroxy-2,2-dimethyl-2,3-dihydro-benzofuran-6-carbo-xylic acid(1-methyl-1H-pyrazol-3-yl)-amide (31a) and the appropriate fluorophenyl amides. The appropriate fluorophenyl amide intermediates were prepared in a similar manner as described for Intermediate 32a, 33a or 35a, from the appropriate carboxylic acids or acid chlorides and amines.

Example 41

4-[2-Fluoro-4-(morpholine-4-carbonyl)-phenoxy]-2,2-dimethyl-2,3-dihydro-benzofuran-6-carboxylic acid(1-methyl-1H-pyrazol-3-yl)-amide

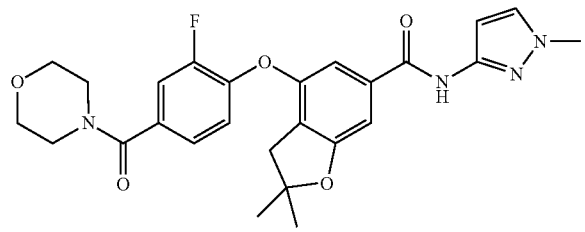

Example 42

4-[2-Fluoro-4-(4-methyl-piperazine-1-carbonyl)-phenoxy]-2,2-dimethyl-2,3-dihydro-benzofuran-6-carboxylic acid(1-methyl-1H-pyrazol-3-yl)-amide

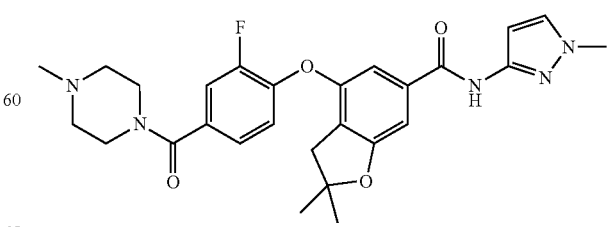

Example 43

4-[4-(3,3-Difluoro-azetidine-1-carbonyl)-2-fluoro-phenoxy]-2,2-dimethyl-2,3-dihydro-benzofuran-6-carboxylic acid(1-methyl-1H-pyrazol-3-yl)-amide

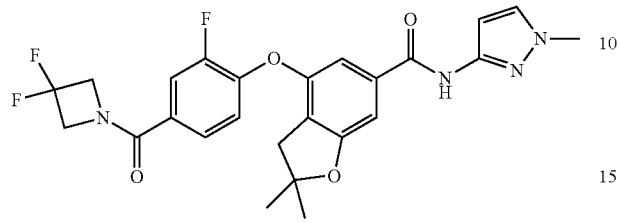

Example 44

4-[4-(3-Dimethylamino-azetidine-1-carbonyl)-2-fluoro-phenoxy]-2,2-dimethyl-2,3-dihydro-benzofuran-6-carboxylic acid(1-methyl-1H-pyrazol-3-yl)-amide

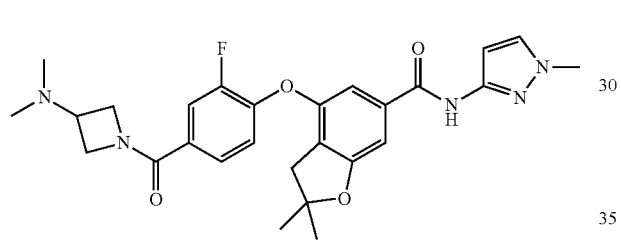

Example 45

4-[2-Fluoro-4-(3-hydroxy-azetidine-1-carbonyl)-phenoxy]-2,2-dimethyl-2,3-dihydro-benzofuran-6-carboxylic acid(1-methyl-1H-pyrazol-3-yl)-amide

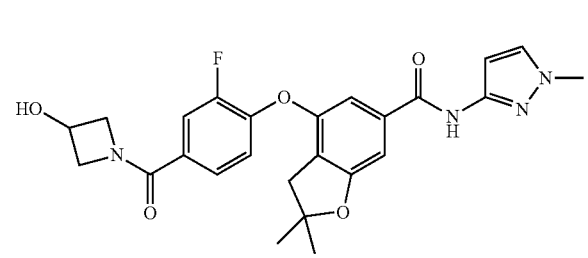

Example 46

4-(4-Dimethylcarbamoyl-2-fluoro-phenoxy)-2,2-dimethyl-2,3-dihydro-benzofuran-6-carboxylic acid (1-methyl-1H-pyrazol-3-yl)-amide

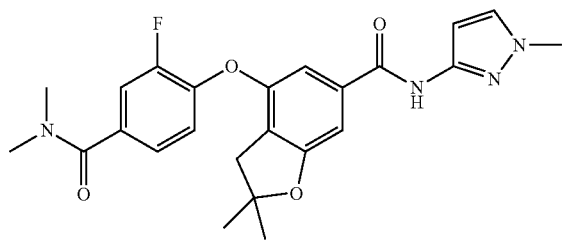

| Example | MW | MF | NMR | m/z | Elemental Analysis |
|---|---|---|---|---|---|
| 41 | 494.5 | C26H27FN4O5 | $^1$H NMR (400 MHz, CDCl$_3$) δ 8.68 (s, 1 H) 7.27-7.31 (m, 2 H) 7.18 (d, J = 8.34 Hz, 1 H) 7.06 (t, J = 8.21 Hz, 1 H) 7.03 (s, 1 H) 6.96 (s, 1 H) 6.77 (d, J = 2.02 Hz, 1 H) 3.80 (s, 3 H) 3.67-3.78 (m, 8 H) 3.02 (s, 2 H) 1.52 (s, 6 H); | 495.00 (M + H)$^+$ | Calcd. for C$_{26}$H$_{27}$FN$_4$O$_5$•0.29 AcOH•0.23 H$_2$O: C, 61.86; H, 5.59; N, 10.86; Found: C, 61.84; H, 5.41; N, 10.99. |
| 42 | 507.6 | C27H30FN5O4 | $^1$H NMR (400 MHz, CDCl$_3$) δ 9.49 (s, 1 H) 7.30-7.34 (m, 2 H) 7.17-7.21 (m, 1 H) 7.11 (d, J = 8.08 Hz, 1 H) 7.08 (s, 1 H) 6.96 (d, J = 1.26 Hz, 1 H) 6.86 (d, J = 2.27 Hz, 1 H) 3.84 (s, 3 H) 3.55-3.63 (m, 4 H) 3.04 (s, 2 H) 2.86 (s, 3 H) 2.77-2.88 (m, 4 H) 1.53 (s, 6 H); | 508.20 (M + H)$^+$ | Calcd. for C$_{27}$H$_{30}$FN$_5$O$_4$•1.82 TFA: C, 51.44; H, 4.49; N, 9.81; Found: C, 51.46; H, 4.49; N, 9.79. |
| 43 | 500.5 | C25H23F3N4O4 | $^1$H NMR (400 MHz, CDCl$_3$) δ 10.16 (s, 1 H) 7.50-7.55 (m, 1 H) 7.36-7.40 (m, 1 H) 7.35 (d, J = 2.53 Hz, 1 H) 7.17 (d, J = 1.26 Hz, 1 H) 7.11 (t, J = 8.08 Hz, 1 H) 7.04 (d, J = 1.26 Hz, 1 H) 6.95 (d, J = 2.53 Hz, 1 H) 4.58 (t, J = 11.87 Hz, 4 H) 3.88 (s, 3 H) 3.01 (s, 2 H) 1.48-1.55 (m, 6 H); | 501.00 (M + H)$^+$ | |
| 44 | 507.6 | C27H30FN5O4 | $^1$H NMR (400 MHz, CDCl$_3$) δ 8.48 (s, 1 H) 7.51 (d, J = 11.12 Hz, 1 H) 7.39 (d, J = 8.34 Hz, 1 H) 6.98-7.05 (m, 2 H) 6.94 (s, 1 H) 6.76 (s, 1 H) 4.27-4.36 (m, 1 H) 4.15-4.27 (m, 2 H) 3.99-4.11 (m, 1 H) 3.80 (s, 3 H) 3.10-3.19 (m, 1 H) 2.98 (s, 2 H) 2.20 (s, 6 H) 1.51 (s, 6 H); | 508.20 (M + H)$^+$ | Calcd. for C$_{27}$H$_{30}$FN$_5$O$_4$•0.40 AcOH: C, 62.81; H, 5.99; N, 13.17; Found: C, 62.94; H, 5.89; N, 13.17. |
| 45 | 480.5 | C25H25FN4O5 | $^1$H NMR (400 MHz, CDCl$_3$) δ 1.52 (s, 6 H) 3.01 (s, 2 H) 3.71 (s, 3 H) 3.93-4.03 (m, 1 H) 4.19-4.30 (m, 1 H) 4.42-4.54 (m, 2 | 481.00 (M + H)$^+$ | Calcd. for C$_{25}$H$_{25}$FN$_4$O$_5$•0.48 TFA: C, 58.26; H, 4.80; N, 10.47; Found: C, 58.30; |

| Example | MW | MF | NMR | m/z | Elemental Analysis |
|---|---|---|---|---|---|
| 46 | 452.5 | C24H25FN4O4 | H) 4.67-4.74 (m, 1 H) 6.78 (d, J = 2.27 Hz, 1 H) 6.82 (d, J = 1.01 Hz, 1 H) 7.01-7.07 (m, 2 H) 7.41 (d, J = 8.59 Hz, 1 H) 7.46 (dd, J = 10.99, 1.89 Hz, 1 H) 8.80 (s, 1 H); $^1$H NMR (400 MHz, CDCl$_3$) δ 8.54 (s, 1 H) 7.30 (dd, J = 10.74, 1.89 Hz, 1 H) 7.28 (s, 1 H) 7.19 (d, J = 8.34 Hz, 1 H) 7.00-7.05 (m, 2 H) 6.96 (s, 1 H) 6.77 (d, J = 2.27 Hz, 1 H) 3.80 (s, 3 H) 3.10 (s, 3 H) 3.06 (s, 3 H) 3.00 (s, 2 H) 1.51 (s, 6 H); | 453.00 (M + H)$^+$ | H, 4.93; N, 10.28. Calcd. for C$_{24}$H$_{25}$FN$_4$O$_4$•0.25 H$_2$O•0.5 AcOH: C, 61.66; H, 5.69; N, 11.50; Found: C, 61.65; H, 5.41; N, 11.51. |

Examples 47-50 were prepared in a similar manner as described for Intermediate 1f, from 4-hydroxy-2,2-dimethyl-2,3-dihydro-benzofuran-6-carbo-xylic acid(1-methyl-1H-pyrazol-3-yl)-amide (31a) and the appropriate fluorophenyl amides. The appropriate fluorophenyl amide intermediates were prepared in a similar manner as described for Intermediate 32a, 33a or 35a, from the appropriate carboxylic acids or acid chlorides and amines.

Example 47

2,2-Dimethyl-4-[4-(morpholine-4-carbonyl)-phenoxy]-2,3-dihydro-benzofuran-6-carboxylic acid(1-methyl-1H-pyrazol-3-yl)-amide

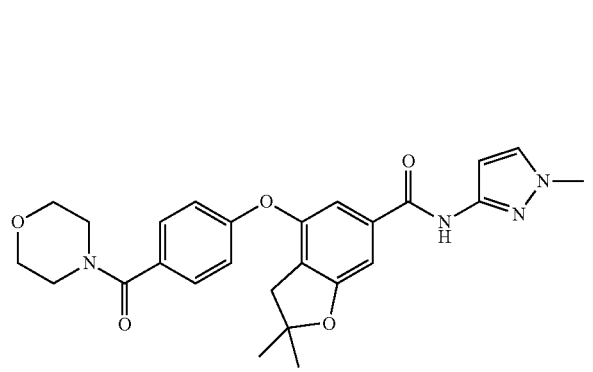

Example 48

2,2-Dimethyl-4-[4-(pyrrolidine-1-carbonyl)-phenoxy]-2,3-dihydro-benzofuran-6-carboxylic acid(1-methyl-1H-pyrazol-3-yl)-amide

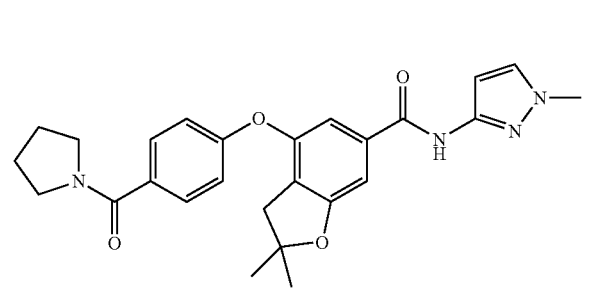

Example 49

4-[4-(3-Dimethylamino-azetidine-1-carbonyl)-phenoxy]-2,2-dimethyl-2,3-dihydro-benzofuran-6-carboxylic acid(1-methyl-1H-pyrazol-3-yl)-amide

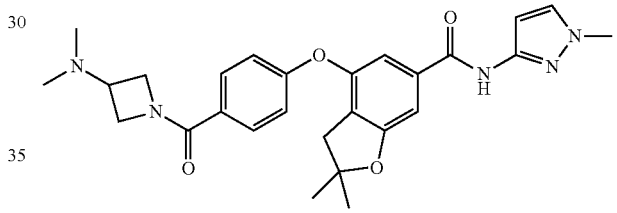

Example 50

4-[4-(3,3-Difluoro-azetidine-1-carbonyl)-phenoxy]-2,2-dimethyl-2,3-dihydro-benzofuran-6-carboxylic acid(1-methyl-1H-pyrazol-3-yl)-amide

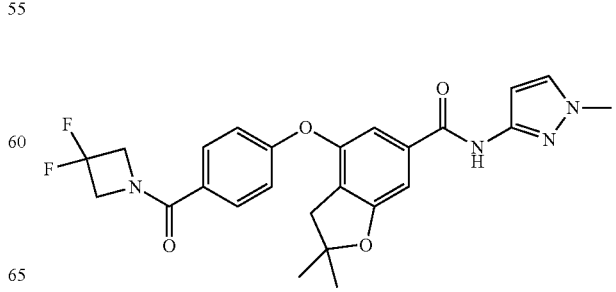

| Example | MW | MF | NMR | m/z | Elemental Analysis |
|---|---|---|---|---|---|
| 47 | 476.5 | C26H28N4O5 | $^1$H NMR (400 MHz, CDCl$_3$) δ 8.66 (s, 1 H) 7.43 (s, 1 H) 7.41 (s, 1 H) 7.28 (s, 1 H) 6.96-7.07 (m, 4 H) 6.79 (d, J = 2.27 Hz, 1 H) 3.81 (s, 3 H) 3.65-3.76 (m, 8 H) 2.93 (s, 2 H) 1.50 (s, 6 H); | 477.20 (M + H)$^+$ | Calcd. for C$_{26}$H$_{28}$N$_4$O$_5$•0.61 AcOH: C, 63.71; H, 5.98; N, 10.92; Found: C, 63.70; H, 5.73; N, 11.00. |
| 48 | 460.5 | C26H28N4O4 | $^1$H NMR (400 MHz, CDCl$_3$) δ 8.83 (s, 1 H) 7.51-7.56 (m, 2 H) 7.29 (d, J = 2.27 Hz, 1 H) 7.05 (dd, J = 9.73, 1.39 Hz, 2 H) 6.97-7.01 (m, 2 H) 6.82 (d, J = 2.53 Hz, 1 H) 3.82 (s, 3 H) 3.66 (t, J = 6.82 Hz, 2 H) 3.50 (t, J = 6.44 Hz, 2 H) 2.91 (s, 2 H) 1.88-2.00 (m, 4 H) 1.49 (s, 6 H); | 461.20 (M + H)$^+$ | Calcd. for C$_{26}$H$_{28}$N$_4$O$_4$•0.50 AcOH: C, 62.66; H, 5.53; N, 10.84; Found: C, 62.66; H, 5.55; N, 10.83. |
| 49 | 489.6 | C27H31N5O4 | $^1$H NMR (400 MHz, CDCl$_3$) δ 8.53 (s, 1 H) 7.60-7.66 (m, 2 H) 7.28 (s, 1 H) 7.02-7.07 (m, 2 H) 6.96-7.01 (m, 2 H) 6.78 (d, J = 2.27 Hz, 1 H) 4.22-4.34 (m, 3 H) 4.06-4.18 (m, 1 H) 3.80 (s, 3 H) 3.20-3.30 (m, 1 H) 2.90 (s, 2 H) 2.29 (s, 6 H) 1.49 (s, 6 H); | 490.20 (M + H)$^+$ | |
| 50 | 482.5 | C25H24F2N4O4 | $^1$H NMR (400 MHz, CDCl$_3$) δ 8.83 (s, 1 H) 7.63-7.67 (m, 2 H) 7.28 (d, J = 2.27 Hz, 1 H) 7.10 (d, J = 1.26 Hz, 1 H) 7.06 (d, J = 1.26 Hz, 1 H) 7.00-7.04 (m, 2 H) 6.81 (d, J = 2.27 Hz, 1 H) 4.56 (t, J = 12.00 Hz, 4 H) 3.80 (s, 3 H) 2.91 (s, 2 H) 1.50 (s, 6 H); | 483.00 (M + H)$^+$ | Calcd. for C$_{25}$H$_{24}$F$_2$N$_4$O$_4$•0.22 H2O•0.17 AcOH: C, 61.28; H, 5.10; N, 11.28; Found: C, 61.28; H, 5.00; N, 11.38. |

Examples 51-64 were prepared in a similar manner as described for Intermediate 1f, from 4-hydroxy-2,2-dimethyl-2,3-dihydro-benzofuran-6-carbo-xylic acid(1-methyl-1H-pyrazol-3-yl)-amide (31a) and the appropriate fluorophenyl amides. The appropriate fluorophenyl amide intermediates were prepared in a similar manner as described for Intermediate 32a, 33a or 35a, from the appropriate carboxylic acids or acid chlorides and amines.

Example 65 was prepared in a similar manner as described for Example 1, from 1-methyl-3-aminopyrazole and 4-(4-benzyloxycarbonyl-3-fluoro-phenoxy)-2,2-dimethyl-2,3-dihydro-benzofuran-6-carboxylic acid methyl ester (65b).

Preparation of Intermediate 65a

4-Bromo-2-fluoro-benzoic acid benzyl ester

Benzyl bromide (2.80 mL, 23.6 mmol) was added to a solution of 2-fluro-4-bromobenzoic acid (4.34 g, 19.8 mmol) and Cs$_2$CO$_3$ (9.79 g, 30.0 mmol) in CH$_2$Cl$_2$ (50 mL). The mixture was heated to reflux for 4 hr. The reaction was quenched with H$_2$O (150 mL) and extracted with CH$_2$Cl$_2$ (150 mL). The organic layer was dried over MgSO$_4$ and concentrated. The residue was purified by flash column chromatograph eluting with 10% EtOAc in hexanes to give a colorless oil (6.27 g, 100% yield). $^1$H NMR (400 MHz, CDCl$_3$) δ 7.82-7.88 (m, 1 H) 7.44-7.47 (m, 2 H) 7.34-7.42 (m, 5 H) 5.38 (s, 2 H).

Preparation of Intermediate 65b 4-(4-Benzyloxycarbonyl-3-fluoro-phenoxy)-2,2-dimethyl-2,3-dihydro-benzofuran-6-carboxylic acid methyl ester

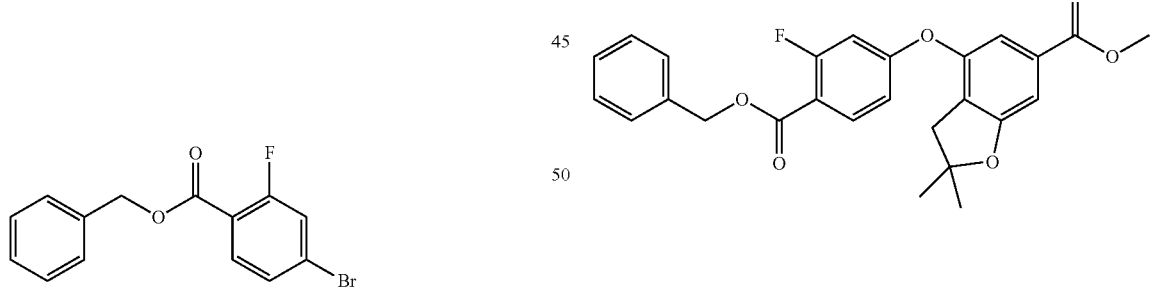

The title compound was prepared in a similar manner as described for Intermediate 35b, from 4-bromo-2-fluoro-benzoic acid benzyl ester (65a) and 4-hydroxy-2,2-dimethyl-2,3-dihydro-benzofuran-6-carboxylic acid methyl ester (3e). $^1$H NMR (400 MHz, CDCl$_3$) δ 7.96 (t, J=8.46 Hz, 1 H) 7.44-7.49 (m, 2 H) 7.32-7.43 (m, 3 H) 7.28 (s, 1 H) 7.25 (s, 1 H) 6.76 (dd, J=8.72, 2.40 Hz, 1 H) 6.68 (dd, J=11.75, 2.40 Hz, 1 H) 5.38 (s, 2H) 3.88 (s, 3 H) 2.87 (s, 2 H) 1.48 (s, 6 H); LCMS for C$_{26}$H$_{23}$FO$_6$ m/z 450.00 (M+H)$^+$.

Examples 66-76 were prepared in a similar manner as described for Example 15, from 4-[2,2-dimethyl-6-(1-methyl-1H-pyrazol-3-ylcarbamoyl)-2,3-dihydro-benzofuran-4-yloxy]-2-fluoro-benzoic acid (66d) and the appropriate amines.

Preparation of Intermediate 66a 4-(4-tert-Butoxycarbonyl-3-fluoro-phenoxy)-2,2-dimethyl-2,3-dihydro-benzofuran-6-carboxylic acid methyl ester

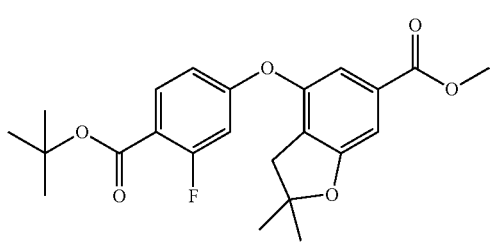

The title compound was prepared in a similar manner as described for Intermediate 35b, from 4-bromo-2-fluoro-benzoic acid tert-butyl ester and 4-hydroxy-2,2-dimethyl-2,3-dihydro-benzofuran-6-carboxylic acid methyl ester (3e). $^1$H NMR (400 MHz, CDCl$_3$) δ 7.86 (t, J=8.59 Hz, 1 H) 7.25-7.31 (m, 1 H) 7.24 (s, 1 H) 6.74 (dd, J=8.84, 2.02 Hz, 1H) 6.65 (dd, J=11.87, 2.27 Hz, 1 H) 3.88 (s, 3 H) 2.87 (s, 2 H) 1.59 (s, 9 H) 1.48 (s, 6 H); LCMS for C$_{23}$H$_{25}$FO$_6$ m/z 439.00 (M+Na)$^+$.

Preparation of Intermediate 66b 4-(4-tert-Butoxycarbonyl-3-fluoro-phenoxy)-2,2-dimethyl-2,3-dihydro-benzofuran-6-carboxylic acid

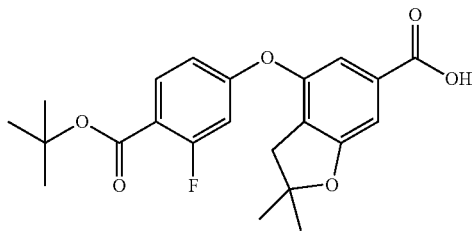

NaOH (6.20 mL, 19.0 mmol, 3N aqueous solution) was added to a solution of 4-(4-tert-butoxycarbonyl-3-fluoro-phenoxy)-2,2-dimethyl-2,3-dihydro-benzofuran-6-carboxylic acid methyl ester (66a) (2.56 g, 5.91 mmol) in 30 mL MeOH. The reaction mixture was heated to 60° C. for 2 hr, concentrated, diluted with H$_2$O (100 mL), acidified with 1N aqueous HCl to Ph ~1, and extracted with CH$_2$Cl$_2$ (2×100 mL). The combined organic layer was dried over MgSO$_4$, concentrated in vacuo to give a white solid (2.46 g, 98% yield). $^1$H NMR (400 MHz, DMSO-d$_6$) δ 13.08 (br. s., 1 H) 7.85 (t, J=8.72 Hz, 1 H) 7.11 (d, J=1.26 Hz, 1 H) 7.06 (d, J=1.01 Hz, 1 H) 6.99 (dd, J=12.13, 2.27 Hz, 1 H) 6.89 (dd, J=8.72, 2.40 Hz, 1 H) 2.87 (s, 2 H) 1.53 (s, 9H) 1.42 (s, 6 H); LCMS for C$_{22}$H$_{23}$FO$_6$ m/z 425.00 (M+Na)$^+$.

Preparation of Intermediate 66c

4-[2,2-Dimethyl-6-(1-methyl-1H-pyrazol-3-ylcarbamoyl)-2,3-dihydro-benzofuran-4-yloxy]-2-fluoro-benzoic acid tert-butyl ester

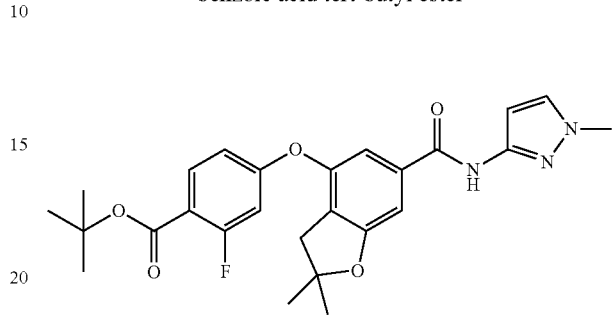

The title compound was prepared in a similar manner as described for Example 15 except that the reaction was carried out at 75° C. for 2 hr, from 1-methyl-3-aminopyrazole (892 mg, 9.18 mmol) and 4-(4-tert-butoxycarbonyl-3-fluoro-phenoxy)-2,2-dimethyl-2,3-dihydro-benzofuran-6-carboxylic acid (66b) (2.46 g, 6.11 mmol) to give a white solid (1.77 g, 60% yield). $^1$H NMR (400 MHz, CDCl$_3$) δ 8.38 (s, 1 H) 7.87 (t, J=8.59 Hz, 1 H) 7.28 (d, J=2.27 Hz, 1 H) 7.07 (s, 1 H) 7.04 (s, 1 H) 6.79 (d, J=2.02 Hz, 1 H) 6.75 (dd, J=8.84, 2.27 Hz, 1 H) 6.68 (dd, J=11.75, 2.40 Hz, 1H) 3.80 (s, 3 H) 2.87 (s, 2 H) 1.60 (s, 9 H) 1.49 (s, 6H); LCMS for C$_{26}$H$_{28}$FN$_3$O$_5$ m/z 505.00 (M+Na)$^+$.

Preparation of Intermediate 66d

4-[2,2-Dimethyl-6-(1-methyl-1H-pyrazol-3-ylcarbamoyl)-2,3-dihydro-benzofuran-4-yloxy]-2-fluoro-benzoic acid

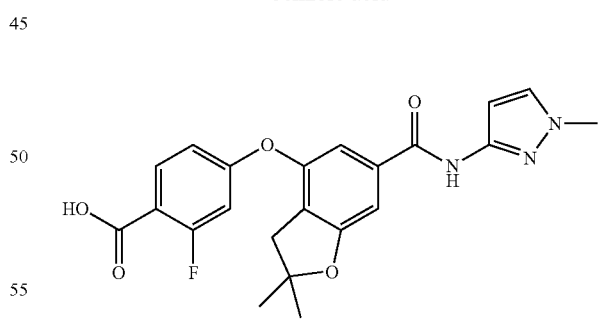

To a solution of 4-[2,2-dimethyl-6-(1-methyl-1H-pyrazol-3-ylcarbamoyl)-2,3-dihydro-benzofuran-4-yloxy]-2-fluoro-benzoic acid tert-butyl ester (66c) (1.77 g, 3.68 mmol) in CH$_2$Cl$_2$ (10 mL) was added TFA (4 mL). The mixture was stirred at room temperature for 2 hr, concentrated, and dried under vacuum to give an off-white solid (TFA salt) (2.0 g, 100% yield). $^1$H NMR (400 MHz, DMSO-d$_6$) δ 10.75 (s, 1 H) 7.91 (t, J=8.72 Hz, 1 H) 7.59 (d, J=2.02 Hz, 1 H) 7.25 (s, 2 H) 6.98 (dd, J=12.13, 2.02 Hz, 1 H) 6.89 (dd, J=8.72, 2.15 Hz, 1

H) 6.55 (d, J=1.77 Hz, 1 H) 3.76 (s, 3 H) 2.87 (s, 2 H) 1.43 (s, 6 H); LCMS for $C_{22}H_{20}FN_3O_5$ m/z 425.00 (M+H)$^+$.

Example 51

4-[3-Fluoro-4-(morpholine-4-carbonyl)-phenoxy]-2,2-dimethyl-2,3-dihydro-benzofuran-6-carboxylic acid(1-methyl-1H-pyrazol-3-yl)-amide

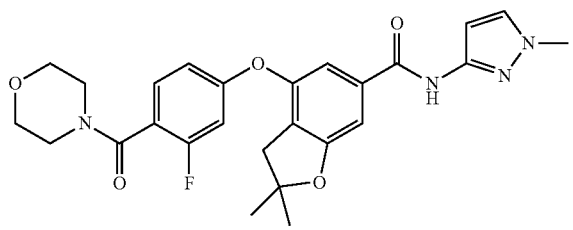

Example 52

4-[4-(3,3-Difluoro-azetidine-1-carbonyl)-3-fluoro-phenoxy]-2,2-dimethyl-2,3-dihydro-benzofuran-6-carboxylic acid(1-methyl-1H-pyrazol-3-yl)-amide

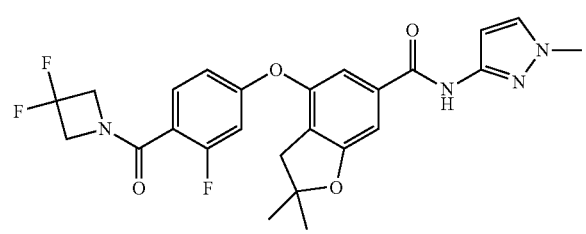

Example 53

4-[3-Fluoro-4-(4-methyl-piperazine-1-carbonyl)-phenoxy]-2,2-dimethyl-2,3-dihydro-benzofuran-6-carboxylic acid(1-methyl-1H-pyrazol-3-yl)-amide

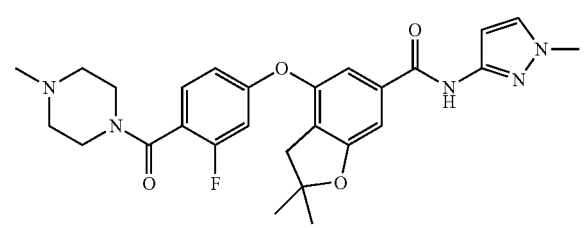

Example 54

4-(4-Dimethylcarbamoyl-3-fluoro-phenoxy)-2,2-dimethyl-2,3-dihydro-benzofuran-6-carboxylic acid (1-methyl-1H-pyrazol-3-yl)-amide

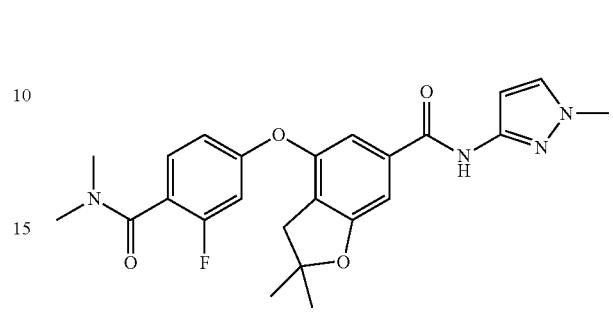

Example 55

4-[3-Fluoro-4-(3-hydroxy-azetidine-1-carbonyl)-phenoxy]-2,2-dimethyl-2,3-dihydro-benzofuran-6-carboxylic acid(1-methyl-1H-pyrazol-3-yl)-amide

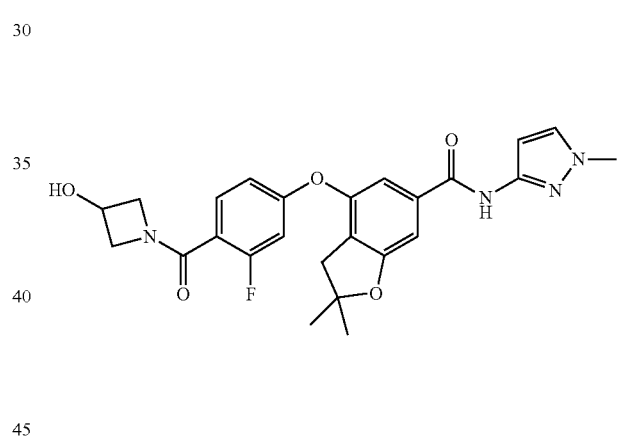

Example 56

4-[3-Fluoro-4-(pyrrolidine-1-carbonyl)-phenoxy]-2,2-dimethyl-2,3-dihydro-benzofuran-6-carboxylic acid(1-methyl-1H-pyrazol-3-yl)-amide

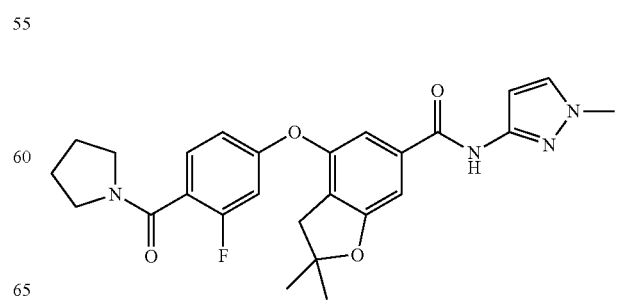

Example 57

4-[4-(3-Dimethylamino-azetidine-1-carbonyl)-3-fluoro-phenoxy]-2,2-dimethyl-2,3-dihydro-benzofuran-6-carboxylic acid(1-methyl-1H-pyrazol-3-yl)-amide

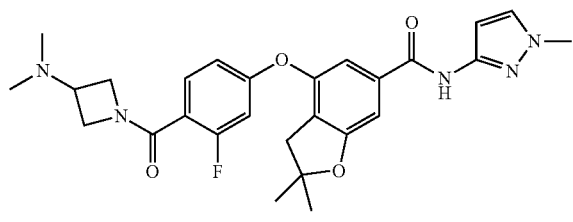

Example 58

4-[3-Fluoro-4-((R)-3-fluoro-pyrrolidine-1-carbonyl)-phenoxy]-2,2-dimethyl-2,3-dihydro-benzofuran-6-carboxylic acid(1-methyl-1H-pyrazol-3-yl)-amide

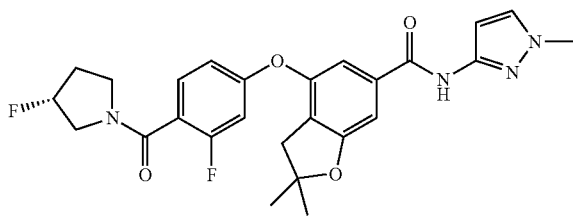

Example 59

4-[3-Fluoro-4-((R)-3-methoxy-pyrrolidine-1-carbonyl)-phenoxy]-2,2-dimethyl-2,3-dihydro-benzofuran-6-carboxylic acid(1-methyl-1H-pyrazol-3-yl)-amide

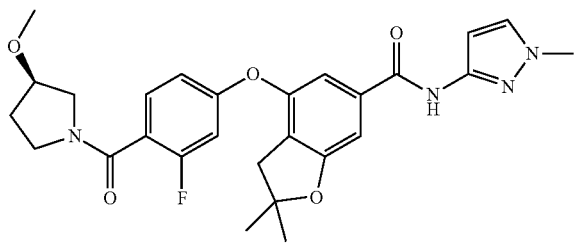

Example 60

4-[3-Fluoro-4-((S)-3-methoxy-pyrrolidine-1-carbonyl)-phenoxy]-2,2-dimethyl-2,3-dihydro-benzofuran-6-carboxylic acid(1-methyl-1H-pyrazol-3-yl)-amide

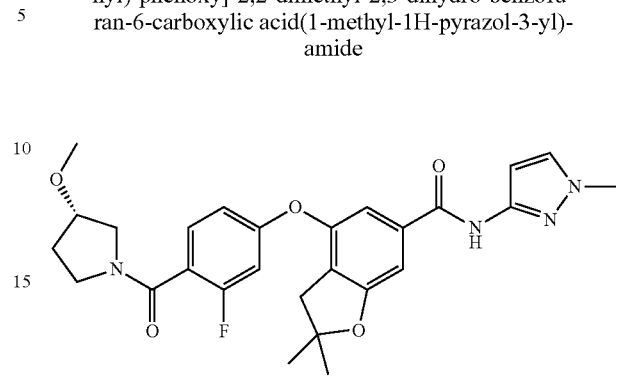

Example 61

4-[3-Fluoro-4-(piperidine-1-carbonyl)-phenoxy]-2,2-dimethyl-2,3-dihydro-benzofuran-6-carboxylic acid (1-methyl-1H-pyrazol-3-yl)-amide

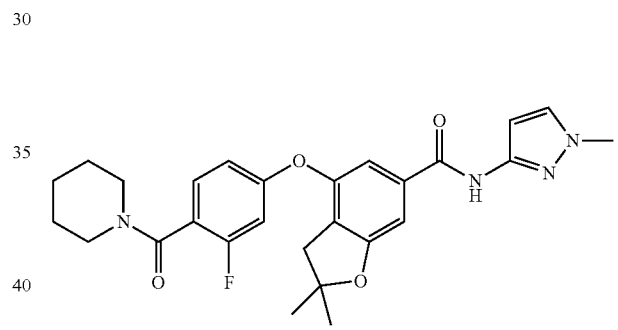

Example 62

4-[3-Fluoro-4-((S)-3-hydroxy-pyrrolidine-1-carbonyl)-phenoxy]-2,2-dimethyl-2,3-dihydro-benzofuran-6-carboxylic acid(1-methyl-1H-pyrazol-3-yl)-amide

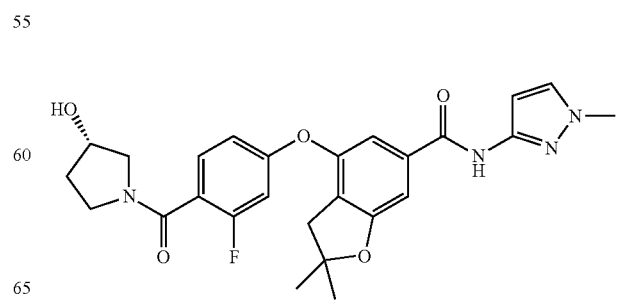

Example 63

4-[3-Fluoro-4-((S)-3-fluoro-pyrrolidine-1-carbonyl)-phenoxy]-2,2-dimethyl-2,3-dihydro-benzofuran-6-carboxylic acid(1-methyl-1H-pyrazol-3-yl)-amide

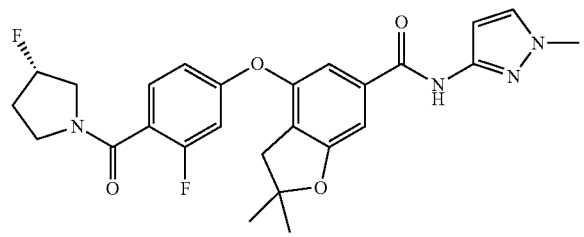

Example 64

4-{3-Fluoro-4-[(2-methoxy-ethyl)-methyl-carbamoyl]-phenoxy}-2,2-dimethyl-2,3-dihydro-benzofuran-6-carboxylic acid(1-methyl-1H-pyrazol-3-yl)-amide

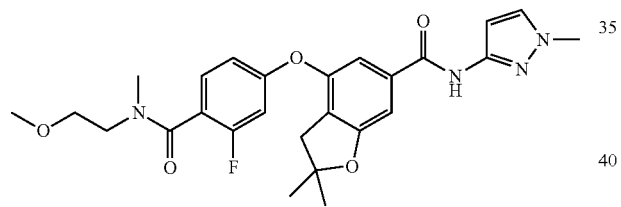

Example 65

4-[3-Fluoro-4-(1-methyl-1H-pyrazol-3-ylcarbamoyl)-phenoxy]-2,2-dimethyl-2,3-dihydro-benzofuran-6-carboxylic acid(1-methyl-1H-pyrazol-3-yl)-amide

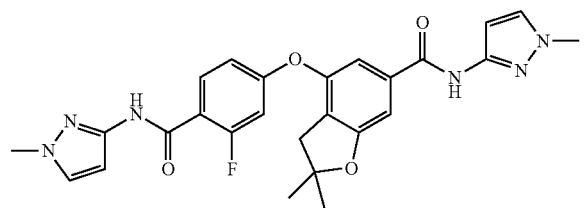

Example 66

4-{3-Fluoro-4-[(2-hydroxy-ethyl)-methyl-carbamoyl]-phenoxy}-2,2-dimethyl-2,3-dihydro-benzofuran-6-carboxylic acid(1-methyl-1H-pyrazol-3-yl)-amide

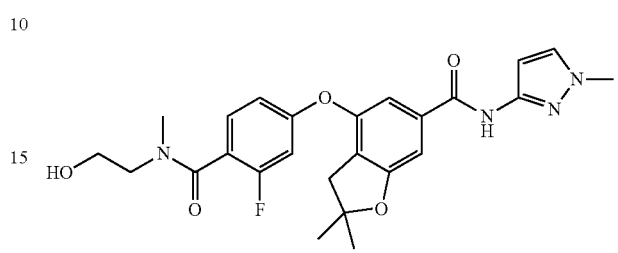

Example 67

4-[4-(Cyanomethyl-methyl-carbamoyl)-3-fluorophenoxy]-2,2-dimethyl-2,3-dihydro-benzofuran-6-carboxylic acid(1-methyl-1H-pyrazol-3-yl)-amide


Example 68

4-[3-Fluoro-4-(2-methoxy-ethylcarbamoyl)-phenoxy]-2,2-dimethyl-2,3-dihydro-benzofuran-6-carboxylic acid(1-methyl-1H-pyrazol-3-yl)-amide

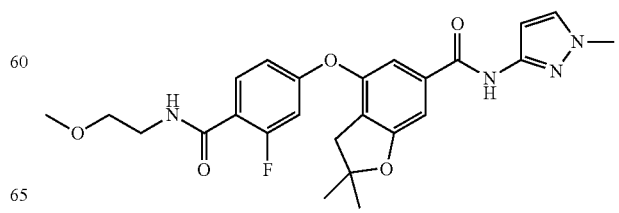

Example 69

4-(3-Fluoro-4-methylcarbamoyl-phenoxy)-2,2-dimethyl-2,3-dihydro-benzofuran-6-carboxylic acid(1-methyl-1H-pyrazol-3-yl)-amide

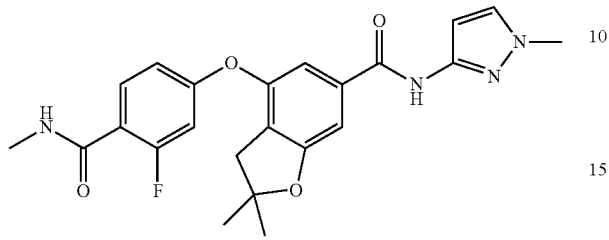

Example 70

4-(4-Ethylcarbamoyl-3-fluoro-phenoxy)-2,2-dimethyl-2,3-dihydro-benzofuran-6-carboxylic acid(1-methyl-1H-pyrazol-3-yl)-amide

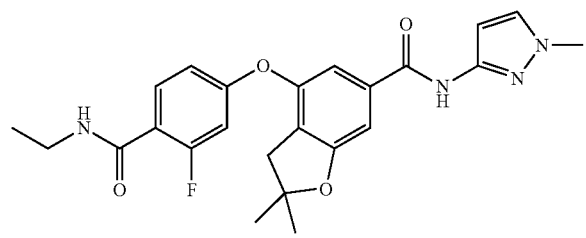

Example 71

4-(3-Fluoro-4-isopropylcarbamoyl-phenoxy)-2,2-dimethyl-2,3-dihydro-benzofuran-6-carboxylic acid (1-methyl-1H-pyrazol-3-yl)-amide

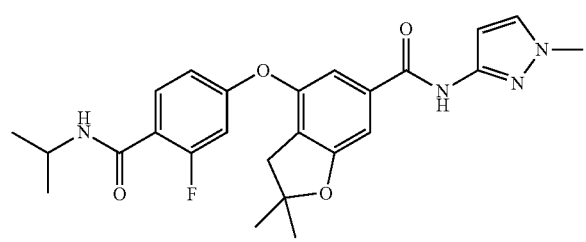

Example 72

4-[3-Fluoro-4-(2-hydroxy-ethylcarbamoyl)-phenoxy]-2,2-dimethyl-2,3-dihydro-benzofuran-6-carboxylic acid(1-methyl-1H-pyrazol-3-yl)-amide

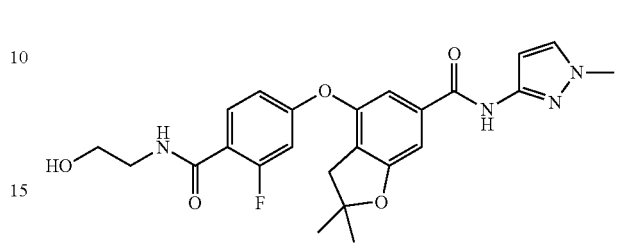

Example 73

4-(4-Cyclopropylcarbamoyl-3-fluoro-phenoxy)-2,2-dimethyl-2,3-dihydro-benzofuran-6-carboxylic acid (1-methyl-1H-pyrazol-3-yl)-amide

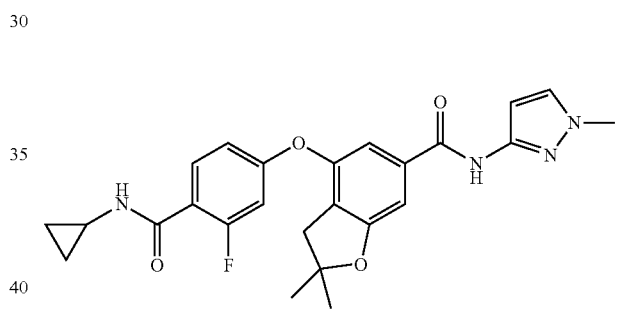

Example 74

4-(4-Cyclobutylcarbamoyl-3-fluoro-phenoxy)-2,2-dimethyl-2,3-dihydro-benzofuran-6-carboxylic acid (1-methyl-1H-pyrazol-3-yl)-amide

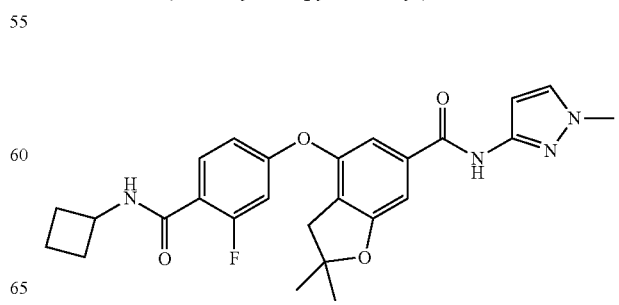

Example 75

4-[3-Fluoro-4-(2-fluoro-ethylcarbamoyl)-phenoxy]-2,2-dimethyl-2,3-dihydro-benzofuran-6-carboxylic acid(1-methyl-1H-pyrazol-3-yl)-amide

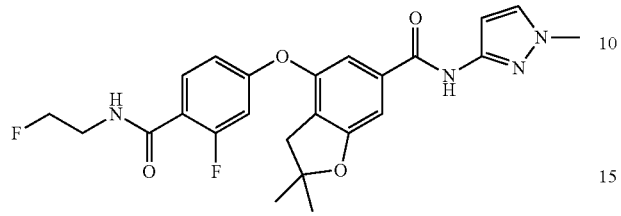

Example 76

4-[4-(2,2-Difluoro-ethylcarbamoyl)-3-fluoro-phenoxy]-2,2-dimethyl-2,3-dihydro-benzofuran-6-carboxylic acid(1-methyl-1H-pyrazol-3-yl)-amide

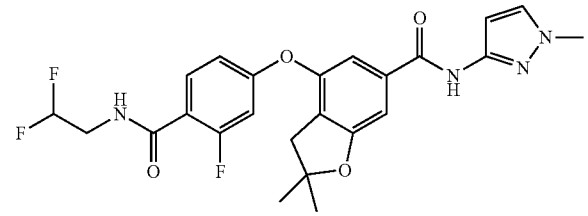

| Example | MW | MF | NMR | m/z | Elemental Analysis |
|---|---|---|---|---|---|
| 51 | 494.5 | C26H27FN4O5 | $^1$H NMR (400 MHz, CDCl$_3$) δ 10.16 (s, 1 H) 7.50-7.55 (m, 1 H) 7.36-7.40 (m, 1 H) 7.35 (d, J = 2.53 Hz, 1 H) 7.17 (d, J = 1.26 Hz, 1 H) 7.11 (t, J = 8.08 Hz, 1 H) 7.04 (d, J = 1.26 Hz, 1 H) 6.95 (d, J = 2.53 Hz, 1 H) 4.58 (t, J = 11.87 Hz, 4 H) 3.88 (s, 3 H) 3.01 (s, 2 H) 1.48-1.55 (m, 6 H); | 495.00 (M + H)$^+$ | Calcd. for C$_{26}$H$_{27}$FN$_4$O$_5$•0.43 AcOH: C, 62.00; H, 5.56; N, 10.77; Found: C, 61.99; H, 5.46; N, 10.99. |
| 52 | 500.5 | C25H23F3N4O4 | $^1$H NMR (400 MHz, CDCl$_3$) δ 8.38 (s, 1 H) 7.64 (t, J = 8.21 Hz, 1 H) 7.29 (d, J = 2.27 Hz, 1 H) 7.08 (dd, J = 9.47, 1.39 Hz, 2 H) 6.84 (dd, J = 8.72, 2.40 Hz, 1 H) 6.79 (d, J = 2.27 Hz, 1 H) 6.70 (dd, J = 11.62, 2.27 Hz, 1 H) 4.44-4.55 (m, 4 H) 3.82 (s, 3 H) 2.91 (s, 2 H) 1.50 (s, 6 H); | 501.00 (M + H)$^+$ | Calcd. for C$_{25}$H$_{23}$F$_3$N$_4$O$_4$•0.75 H$_2$O: C, 58.42; H, 4.80; N, 10.90; Found: C, 58.62; H, 4.59; N, 10.62. |
| 53 | 507.6 | C27H30FN5O4 | $^1$H NMR (400 MHz, CDCl$_3$) δ 8.52 (s, 1 H) 7.34-7.40 (m, 1 H) 7.29 (d, J = 2.27 Hz, 1 H) 7.05-7.09 (m, 2 H) 6.77-6.82 (m, 2 H) 6.70 (dd, J = 10.61, 2.27 Hz, 1 H) 3.82-3.85 (m, 2 H) 3.81 (s, 3 H) 3.36-3.46 (m, 2 H) 2.91 (s, 2 H) 2.47-2.57 (m, 2 H) 2.37-2.46 (m, 2 H) 2.34 (s, 3 H) 1.50 (s, 6 H); | 508.20 (M + H)$^+$ | Calcd. for C$_{27}$H$_{30}$FN$_5$O$_4$•0.42 AcOH: C, 62.76; H, 5.99; N, 13.14; Found: C, 62.76; H, 5.82; N, 13.22. |
| 54 | 452.5 | C24H25FN4O4 | $^1$H NMR (400 MHz, CDCl$_3$) δ 8.48 (s, 1 H) 7.33-7.41 (m, 1 H) 7.28 (d, J = 2.02 Hz, 1 H) 7.05-7.09 (m, 2 H) 6.77-6.82 (m, 2 H) 6.69 (dd, J = 10.61, 2.27 Hz, 1 H) 3.81 (s, 3 H) 3.13 (s, 3 H) 2.99 (d, J = 1.77 Hz, 3 H) 2.90 (s, 2 H) 1.50 (s, 6 H); | 453.00 (M + H)$^+$ | Calcd. for C$_{24}$H$_{25}$FN$_4$O$_4$•0.34 AcOH: C, 62.68; H, 5.62; N, 11.85; Found: C, 62.66; H, 5.60; N, 11.97. |
| 55 | 480.5 | C25H25FN4O5 | $^1$H NMR (400 MHz, CDCl$_3$) δ 7.91-7.99 (m, 2 H) 7.34 (t, J = 6.69 Hz, 2 H) 7.09-7.17 (m, 2 H) 5.05 (d, J = 2.78 Hz, 1 H) 3.88-3.97 (m, 1 H) 3.73-3.82 (m, 1 H) 3.15-3.24 (m, 1 H) 3.09-3.15 (m, 4 H) 2.99 (dd, J = 16.55, 7.20 Hz, 1 H) 1.62 (s, 9 H); | 481.00 (M + H)$^+$ | Calcd. for C$_{25}$H$_{25}$FN$_4$O$_5$•0.34 AcOH: C, 62.68; H, 5.62; N, 11.85; Found: C, 62.66; H, 5.60; N, 11.97. |
| 56 | 478.5 | C26H27FN4O4 | $^1$H NMR (400 MHz, CDCl$_3$) δ 8.77 (s, 1 H) 7.40 (t, J = 8.08 Hz, 1 H) 7.29 (d, J = 2.02 Hz, 1 H) 7.09 (d, J = 3.03 Hz, 2 H) 6.77-6.83 (m, 2 H) 6.70 (dd, J = 10.74, 2.15 Hz, 1 H) 3.82 (s, 3 H) 3.65 (t, J = 6.95 Hz, 2 H) 3.38 (t, J = 6.57 Hz, 2 H) 2.90 (s, 2 H) 1.89-2.00 (m, 4 H) 1.50 (s, 6 H); | 479.00 (M + H)$^+$ | |
| 57 | 507.6 | C27H30FN5O4 | $^1$H NMR (400 MHz, CDCl$_3$) δ 8.56 (s, 1 H) 7.54 (t, J = 8.21 Hz, 1 H) 7.28 (d, J = 2.27 Hz, 1 H) 7.08 (d, J = 2.53 Hz, 2 H) 6.79 (d, J = 1.77 Hz, 1 H) 6.67 (dd, J = 11.12, 2.27 Hz, 1 H) 4.23 (dd, J = 10.11, 7.58 Hz, 1 H) 4.09-4.17 (m, 1 H) 4.01-4.09 (m, 2 H) 3.81 (s, 3 H) 3.15-3.25 (m, 1 H) 2.89 (s, 2 H) 2.24 (s, 6 H) 2.06 (s, 1 H) 1.49 (s, 6 H); | 508.20 (M + H)$^+$ | Calcd. for C$_{27}$H$_{30}$FN$_5$O$_4$•0.60 H2O: C, 61.95; H, 6.08; N, 13.14; Found: C, 61.87; H, 5.87; N, 13.16. |
| 58 | 496.5 | C26H26F2N4O4 | $^1$H NMR (400 MHz, CDCl$_3$) δ 8.40 (s, 1 H) 7.40-7.47 (m, 1 H) 7.29 (d, J = 2.27 Hz, 1 H) 7.06-7.08 (m, 2 H) 6.77-6.83 (m, 2 H) 6.65-6.74 (m, 1 H) 4.86-5.64 (m, 1 H) 3.87-3.96 (m, 1 H) 3.82 (s, 3 H) 3.60-3.71 (m, 2 H) 3.54 (t, J = 9.47 Hz, 1 H) | 496.00 (M + H)$^+$ | Calcd. for C$_{26}$H$_{26}$F$_2$N$_4$O$_4$•0.82 H2O: C, 61.08; H, 5.45; N, 10.96; Found: C, 61.07; H, 5.17; N, 10.79. |

| Example | MW | MF | NMR | m/z | Elemental Analysis |
|---|---|---|---|---|---|
| | | | 2.91 (d, J = 1.77 Hz, 2 H) 2.29 (d, J = 4.55 Hz, 1 H) 2.01-2.13 (m, 1 H) 1.50 (s, 6 H); | | |
| 59 | 508.6 | C27H29FN4O5 | $^1$H NMR (400 MHz, CDCl$_3$) δ 8.85 (d, J = 4.04 Hz, 1 H) 7.39-7.44 (m, 1 H) 7.28 (d, J = 2.27 Hz, 1 H) 7.08-7.12 (m, 2 H) 6.81 (d, J = 2.27 Hz, 1 H) 6.79 (t, J = 2.15 Hz, 1 H) 6.68-6.73 (m, 1 H) 4.02-4.11 (m, 0.5 H) 3.94-4.00 (m, 0.5 H) 3.81 (s, 3 H) 3.68-3.78 (m, 2 H) 3.49-3.62 (m, 1 H) 3.38-3.46 (m, 1 H) 3.37 (s, 1.5 H) 3.28-3.32 (m, 1.5 H) 2.90 (s, 2 H) 1.92-2.16 (m, 2 H) 1.50 (s, 6 H); | 509.00 (M + H)$^+$ | Calcd. for C$_{27}$H$_{29}$FN$_4$O$_5$•0.44 AcOH: C, 62.60; H, 5.80; N, 10.47; Found: C, 62.60; H, 5.69; N, 10.45. |
| 60 | 508.6 | C27H29FN4O5 | $^1$H NMR (400 MHz, CDCl$_3$) δ 8.59 (s, 1 H) 7.38-7.45 (m, 1 H) 7.28 (d, J = 2.27 Hz, 1 H) 7.04-7.09 (m, 2 H) 6.76-6.83 (m, 2 H) 6.62-6.72 (m, 1 H) 4.02-4.09 (m, 0.5 H) 3.92-4.01 (m, 05 H) 3.80 (s, 3 H) 3.71-3.78 (m, 2 H) 3.49-3.58 (m, 1 H) 3.39-3.46 (m, 1 H) 3.37 (s, 1.5 H) 3.27-3.32 (m, 1.5 H) 2.89 (s, 2 H) 1.90-2.19 (m, 2 H) 1.49 (s, 6 H); | 509.00 (M + H)$^+$ | Calcd. for C$_{27}$H$_{29}$FN$_4$O$_5$•0.25 H$_2$O•0.37 AcOH: C, 62.25; H, 5.83; N, 10.47; Found: C, 62.24; H, 5.47; N, 10.69. |
| 61 | 492.6 | C27H29FN4O4 | $^1$H NMR (400 MHz, CDCl$_3$) δ 8.51 (s, 1 H) 7.30-7.37 (m, 1 H) 7.28 (d, J = 2.27 Hz, 1 H) 7.05-7.08 (m, 2 H) 6.76-6.82 (m, 2 H) 6.69 (dd, J = 10.61, 2.27 Hz, 1 H) 3.81 (s, 3 H) 3.69-3.78 (m, 2 H) 3.27-3.37 (m, 2 H) 2.91 (s, 2 H) 1.62-1.73 (m, 4 H) 1.52-1.62 (m, 2 H) 1.50 (s, 6 H); | 493.00 (M + H)$^+$ | Calcd. for C$_{27}$H$_{29}$FN$_4$O$_4$•0.40 H$_2$O: C, 64.89; H, 6.01; N, 11.21; Found: C, 64.88; H, 5.89; N, 10.98. |
| 62 | 494.5 | C26H27FN4O5 | $^1$H NMR (400 MHz, CDCl$_3$) δ 8.59 (s, 1 H) 7.38-7.45 (m, 1 H) 7.28 (d, J = 2.27 Hz, 1 H) 7.04-7.09 (m, 2 H) 6.76-6.83 (m, 2 H) 6.62-6.72 (m, 1 H) 4.02-4.09 (m, 0.5 H) 3.92-4.01 (m, 05 H) 3.80 (s, 3 H) 3.71-3.78 (m, 2 H) 3.49-3.58 (m, 1 H) 3.39-3.46 (m, 1 H) 3.37 (s, 1.5 H) 3.27-3.32 (m, 1.5 H) 2.89 (s, 2 H) 1.90-2.19 (m, 2 H) 1.49 (s, 6 H); | 495.00 (M + H)$^+$ | |
| 63 | 496.5 | C26H26F2N4O4 | $^1$H NMR (400 MHz, CDCl$_3$) δ 8.65 (s, 1 H) 7.40-7.48 (m, 1 H) 7.28 (d, J = 2.27 Hz, 1 H) 7.05-7.11 (m, 2 H) 6.82 (t, J = 2.15 Hz, 1 H) 6.80 (d, J = 2.02 Hz, 1 H) 6.71 (ddd, J = 10.61, 7.83, 2.27 Hz, 1 H) 4.83-5.83 (m, 1 H) 3.86-3.96 (m, 2 H) 3.81 (s, 3 H) 3.59-3.71 (m, 2 H) 2.91 (s, 2 H) 2.29-2.41 (m, 1 H) 2.01-2.12 (m, 1 H) 1.50 (s, 6 H); | 497.20 (M + H)$^+$ | Calcd. for C$_{26}$H$_{26}$F$_2$N$_4$O$_4$•0.65 H$_2$O•0.60 AcOH: C, 60.03; H, 5.50; N, 10.29; Found: C, 59.86; H, 5.16; N, 10.33. |
| 64 | 496.5 | C26H29FN4O5 | $^1$H NMR (400 MHz, CDCl$_3$) δ 8.46 (s, 1 H) 7.31-7.39 (m, 1 H) 7.28 (d, J = 2.27 Hz, 1 H) 7.07 (s, 2 H) 6.76-6.81 (m, 2 H) 6.69 (dt, J = 10.42, 2.75 Hz, 1 H) 3.80 (s, 3 H) 3.73 (t, J = 4.93 Hz, 1 H) 3.67 (t, J = 4.80 Hz, 1 H) 3.42-3.47 (m, 1 H) 3.40 (s, 2 H) 3.28 (s, 1 H) 3.15 (s, 1 H) 3.01-3.07 (m, 2 H) 2.90 (s, 2 H) 1.49 (s, 6 H); | 497.00 (M + H)$^+$ | Calcd. for C$_{26}$H$_{29}$FN$_4$O$_5$•0.30 AcOH: C, 62.09; H, 5.92; N, 10.89; Found: C, 61.95; H, 5.90; N, 10.99. |
| 65 | 504.5 | C26H25FN6O4 | $^1$H NMR (400 MHz, CDCl$_3$) δ 8.89 (d, J = 14.15 Hz, 1 H) 8.53 (t, J = 8.84 Hz, 1 H) 8.15 (t, J = 8.84 Hz, 1 H) 7.29 (d, J = 2.27 Hz, 1 H) 7.28 (s, 1 H) 7.09 (s, 2 H) 6.87 (dd, J = 8.59, 2.27 Hz, 1 H) 6.81 (d, J = 2.27 Hz, 1 H) 6.78 (d, J = 2.02 Hz, 1 H) 6.73 (dd, J = 13.14, 2.27 Hz, 1 H) 3.83 (s, 3 H) 3.78 (s, 3 H) 2.88 (s, 2 H) 1.49 (s, 6 H); | 505.00 (M + H)$^+$ | Calcd. for C$_{26}$H$_{25}$FN$_6$O$_4$•0.35 H2O•0.10EtOAc: C, 61.02; H, 5.17; N, 16.14; Found: C, 61.02; H, 5.14; N, 16.17. |
| 66 | 482.5 | C25H27FN4O5 | $^1$H NMR (400 MHz, CDCl$_3$) δ 8.93-9.59 (m, 1 H) 7.31-7.46 (m, 1 H) 7.28 (d, J = 2.02 Hz, 1 H) 7.09-7.18 (m, 2 H) 6.76-6.88 (m, 2 H) 6.71 (dd, J = 10.61, 2.27 Hz, 1 H) 3.92 (t, J = 5.18 Hz, 2 H) 3.80 (s, 3 H) 3.67-3.77 (m, 2 H) 3.43 (t, J = 5.56 Hz, 1 H) 3.16 (s, 1 H) 3.04 (d, J = 1.77 Hz, 2 H) 2.90 (s, 2 H) 1.50 (s, 6 H); | 483.00 (M + H)$^+$ | Calcd. for C$_{25}$H$_{27}$FN$_4$O$_5$•0.69 H$_2$O: C, 60.67; H, 5.78; N, 11.32; Found: C, 60.68; H, 5.52; N, 11.09. |
| 67 | 477.5 | C25H24FN5O4 | $^1$H NMR (400 MHz, CDCl$_3$) δ 8.94 (s, 1 H) 7.43 (t, J = 8.21 Hz, 1 H) 7.29 (d, J = 2.02 Hz, 1 H) 7.13 (s, 1 H) 7.12 (s, 1 H) 6.85 (dd, J = 8.46, 1.64 Hz, 1 H) 6.81 (d, J = 2.27 Hz, 1 H) 6.73 (d, J = 10.86 Hz, 1 H) 4.52 (s, 2 H) 3.81 (s, 3 H) 3.13 (s, 3 H) 2.91 (s, 2 H) 1.50 (s, 6 H); | 478.00 (M + H)$^+$ | Calcd. for C$_{25}$H$_{24}$FN$_5$O$_4$•0.45 AcOH: C, 61.66; H, 5.15; N, 13.88; Found: C, 61.65; H, 5.05; N, 13.95. |

-continued

| Example | MW | MF | NMR | m/z | Elemental Analysis |
|---|---|---|---|---|---|
| 68 | 482.5 | C25H27FN4O5 | $^1$H NMR (400 MHz, CDCl$_3$) δ 8.75 (s, 1 H) 8.09 (t, J = 8.84 Hz, 1 H) 7.28 (d, J = 2.27 Hz, 1 H) 7.12 (s, 1 H) 7.09 (s, 1 H) 6.97-7.07 (m, 1 H) 6.85 (dd, J = 8.59, 2.27 Hz, 1 H) 6.80 (d, J = 2.02 Hz, 1 H) 6.71 (dd, J = 13.14, 2.27 Hz, 1 H) 3.81 (s, 3 H) 3.68 (q, J = 5.05 Hz, 2 H) 3.58 (t, J = 5.05 Hz, 2 H) 3.41 (s, 3 H) 2.88 (s, 2 H) 1.49 (s, 6 H); | 483.00 (M + H)$^+$ | Calcd. for C$_{25}$H$_{27}$FN$_4$O$_5$•0.69 H$_2$O: C, 60.66; H, 5.53; N, 11.10; Found: C, 60.67; H, 5.78; N, 11.32. |
| 69 | 438.5 | C23H23FN4O4 | $^1$H NMR (400 MHz, CDCl$_3$) δ 9.19 (s, 1 H) 8.10 (t, J = 8.97 Hz, 1 H) 7.29 (d, J = 2.27 Hz, 1 H) 7.16 (d, J = 1.26 Hz, 1 H) 7.13 (d, J = 1.26 Hz, 1 H) 6.86 (dd, J = 8.72, 2.40, 1 H) 6.82 (d, J = 2.27 Hz, 1 H) 6.70 (dd, J = 13.14, 2.27 Hz, 1 H) 3.81 (s, 3 H) 3.04 (d, J = 4.04 Hz, 2 H) 2.89 (s, 2 H) 2.07 (s, 2 H) 1.49 (s, 6 H); | 439.00 (M + H)$^+$ | Calcd. for C$_{23}$H$_{23}$FN$_4$O$_4$•0.50 H$_2$O•0.78 AcOH: C, 59.68; H, 5.53; N, 11.33; Found: C, 59.66; H, 5.34; N, 11.50. |
| 70 | 452.5 | C24H25FN4O4 | $^1$H NMR (400 MHz, CDCl$_3$) δ 8.78 (s, 1 H) 8.09 (t, J = 8.97 Hz, 1 H) 7.28 (d, J = 2.27 Hz, 1 H) 7.11 (d, J = 1.01 Hz, 1 H) 7.08 (d, J = 1.26 Hz, 1 H) 6.85 (dd, J = 8.84, 2.27 Hz, 1 H) 6.80 (d, J = 2.27 Hz, 1 H) 6.70 (dd, J = 13.14, 2.53 Hz, 1 H) 6.65 (br. s., 1 H) 3.80 (s, 3 H) 3.48-3.56 (m, 2 H) 2.88 (s, 2 H) 1.49 (s, 6 H) 1.27 (t, J = 7.33 Hz, 3 H); | 453.00 (M + H)$^+$ | Calcd. for C$_{24}$H$_{25}$FN$_4$O$_4$•0.43 AcOH: C, 62.42; H, 5.63; N, 11.71; Found: C, 62.42; H, 5.59; N, 11.87. |
| 71 | 466.5 | C25H27FN4O4 | $^1$H NMR (400 MHz, CDCl$_3$) δ 9.05 (s, 1 H) 8.08 (t, J = 8.97 Hz, 1 H) 7.28 (d, J = 2.27 Hz, 1 H) 7.13-7.16 (m, 1 H) 7.11 (d, J = 1.26 Hz, 1 H) 6.86 (dd, J = 8.72, 2.40 Hz, 1 H) 6.82 (d, J = 2.27 Hz, 1 H) 6.70 (dd, J = 13.26, 2.40 Hz, 1 H) 6.48 (dd, J = 12.51, 7.71 Hz, 1 H) 4.26-4.36 (m, 1 H) 3.80 (s, 3 H) 2.88 (s, 2 H) 1.49 (s, 6 H) 1.28 (d, J = 6.57 Hz, 6 H); | 467.00 (M + H)$^+$ | Calcd. for C$_{25}$H$_{27}$FN$_4$O$_4$•0.75 AcOH: C, 62.22; H, 5.91; N, 10.95; Found: C, 62.17; H, 5.74; N, 11.06. |
| 72 | 468.5 | C24H25FN4O5 | $^1$H NMR (400 MHz, CDCl$_3$) δ 9.24 (s, 1 H) 8.05 (t, J = 8.84 Hz, 1 H) 7.26 (d, J = 2.27 Hz, 1 H) 7.18 (br. s., 1 H) 7.15 (s, 1 H) 7.10 (s, 1 H) 6.85 (dd, J = 8.72, 2.40 Hz, 1 H) 6.78 (d, J = 2.02 Hz, 1 H) 6.69 (dd, J = 13.14, 2.27 Hz, 1 H) 3.82-3.87 (m, 2 H) 3.76 (s, 3 H) 3.66 (q, J = 4.80 Hz, 2 H) 2.89 (s, 2 H) 1.49 (s, 6 H); | 469.00 (M + H)$^+$ | Calcd. for C$_{24}$H$_{25}$FN$_4$O$_5$•0.60 AcOH: C, 59.99; H, 5.47; N, 11.10; Found: C, 59.83; H, 5.47; N, 11.27. |
| 73 | 464.5 | C25H25FN4O4 | $^1$H NMR (400 MHz, CDCl$_3$) δ 8.03-8.13 (m, 1 H) 7.49 (s, 1 H) 7.20 (s, 1 H) 7.06-7.14 (m, 2 H) 6.77-6.87 (m, 2 H) 6.65-6.74 (m, 1 H) 4.03 (s, 3 H) 2.91-2.97 (m, 1 H) 2.88 (s, 2 H) 1.48 (s, 6 H) 0.83-0.91 (m, 2 H) 0.59-0.68 (m, 2 H); | 465.00 (M + H)$^+$ | Calcd. for C$_{25}$H$_{25}$FN$_4$O$_4$•0.75 H$_2$O•0.33 EtOAc: C, 62.34; H, 5.79; N, 11.05; Found: C, 62.35; H, 5.59; N, 10.98. |
| 74 | 478.5 | C26H27FN4O4 | $^1$H NMR (400 MHz, CDCl$_3$) δ 8.05 (d, J = 9.60 Hz, 1 H) 7.51 (s, 1 H) 7.21 (s, 1 H) 7.10 (s, 2 H) 6.84 (d, J = 7.83 Hz, 2 H) 6.66-6.78 (m, 1 H) 4.54-4.65 (m, 1 H) 4.05 (s, 3 H) 2.88 (s, 2 H) 2.39-2.49 (m, 2 H) 1.93-2.05 (m, 2 H) 1.73-1.83 (m, 2 H) 1.48 (s, 6 H); | 479.00 (M + H)$^+$ | Calcd. for C$_{26}$H$_{27}$FN$_4$O$_4$•0.69 H$_2$O: C, 63.61; H, 5.83; N, 11.41; Found: C, 63.66; H, 5.58; N, 10.06. |
| 75 | 470.5 | C24H24F2N4O4 | $^1$H NMR (400 MHz, CDCl$_3$) δ 8.63 (s, 1 H) 8.07 (t, J = 8.97 Hz, 1 H) 7.27 (d, J = 2.27 Hz, 1 H) 7.10 (s, 1 H) 7.07 (s, 1 H) 6.96-7.05 (m, 1 H) 6.83 (dd, J = 8.84, 2.27 Hz, 1 H) 6.78 (d, J = 2.27 Hz, 1 H) 6.69 (dd, J = 13.14, 2.53 Hz, 1 H) 4.66 (t, J = 4.80 Hz, 1 H) 4.54 (t, J = 4.80 Hz, 1 H) 3.80-3.87 (m, 1 H) 3.78 (s, 3 H) 3.72-3.77 (m, 1 H) 2.86 (s, 2 H) 1.47 (s, 6 H); | 471.20 (M + H)$^+$ | Calcd. for C$_{24}$H$_{24}$F$_2$N$_4$O$_4$•0.73 H2O•0.40 EtOAc: C, 59.26; H, 5.57; N, 10.80; Found: C, 59.25; H, 5.54; N, 10.73. |
| 76 | 488.5 | C24H23F3N4O4 | $^1$H NMR (400 MHz, CDCl$_3$) δ 8.53 (s, 1 H) 8.08 (t, J = 8.84 Hz, 1 H) 7.28 (s, 1 H) 7.09 (s, 1 H) 7.06 (d, J = 1.26 Hz, 1 H) 6.90-7.01 (m, 1 H) 6.86 (dd, J = 8.72, 2.40 Hz, 1 H) 6.78 (d, J = 2.27 Hz, 1 H) 6.71 (dd, J = 13.26, 2.40 Hz, 1 H) 5.66-6.26 (m, 1 H) 3.81-3.91 (m, 2 H) 3.79 (s, 3 H) 2.89 (s, 2 H) 1.49 (s, 6 H); | 489.00 (M + H)$^+$ | Calcd. for C$_{24}$H$_{23}$F$_3$N$_4$O$_4$•0.09 H$_2$O: C, 58.82; H, 4.77; N, 11.43; Found: C, 58.88; H, 4.75; N, 11.33. |

Example 77

6-[(4-Benzyloxy-2,2-dimethyl-2,3-dihydro-benzofuran-6-carbonyl)-amino]-nicotinic acid

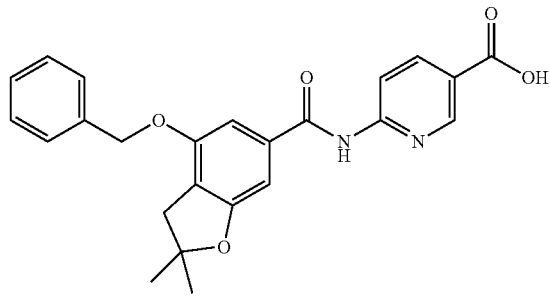

NaOH (110 uL, 0.1 mmol, 3N aqueous solution) was added to a solution of 6-[(4-benzyloxy-2,2-dimethyl-2,3-dihydro-benzofuran-6-carbonyl)-amino]-nicotinic acid methyl ester (77c) (48 mg, 0.11 mol). The reaction mixture was stirred at room temperature overnight. The mixture was concentrated and purified by reverse phase chromatograph to give a white solid (10 mg, 22% yield). $^1$H NMR (400 MHz, CD$_3$OD) δ 8.93 (s, 1 H) 8.31-8.41 (m, 1 H) 8.21-8.31 (m, 1 H) 7.47-7.54 (m, 2 H) 7.42 (t, J=7.33 Hz, 1 H) 7.35 (t, J=7.07 Hz, 1 H) 7.23 (s, 1 H) 7.00 (s, 1 H) 5.24 (s, 2 H) 3.06 (s, 2 H) 1.51 (s, 6 H); LCMS for C$_{24}$H$_{22}$N$_2$O$_5$ m/z 419.00 (M+H)$^+$.

Preparation of Intermediate 77a

4-Benzyloxy-2,2-dimethyl-2,3-dihydro-benzofuran-6-carboxylic acid methyl ester

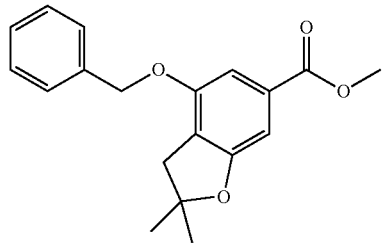

4-Hydroxy-2,2-dimethyl-2,3-dihydro-benzofuran-6-carboxylic acid methyl ester (3e) was dissolved in DMF (50 mL). K$_2$CO$_3$ (6.48 g, 46.9 mmol) and benzyl bromide (2.80 mL, 23.6 mmol) were added. The reaction mixture was stirred at room temperature overnight, quenched with H$_2$O (150 mL), and extracted with EtOAc (2×150 mL). The organic layers were dried over MgSO$_4$ and concentrated to give a white solid (7.18g, 98% yield) which was used as it is for the next step. $^1$H NMR (400 MHz, CDCl$_3$) δ 7.34-7.46 (m, 5 H) 7.21 (s, 1 H) 7.08 (s, 1 H) 5.13 (s, 2 H) 3.90 (s, 3 H) 3.02 (s, 2 H) 1.49 (s, 6 H); LCMS for C$_{19}$H$_{20}$O$_4$ m/z 313.20 (M+H)$^+$.

Preparation of Intermediate 77b

4-Benzyloxy-2,2-dimethyl-2,3-dihydro-benzofuran-6-carboxylic acid

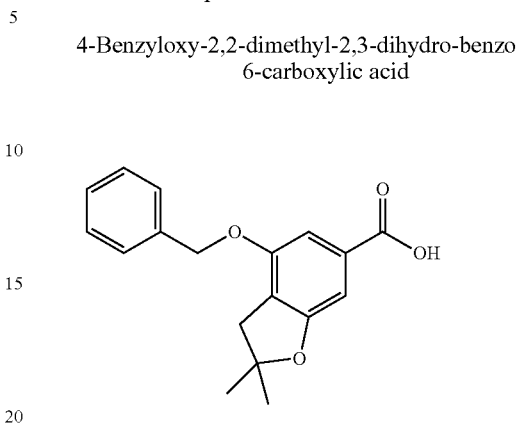

NaOH (23 mL, 69 mmol, 3N aqueous solution) was added to a solution of 4-benzyloxy-2,2-dimethyl-2,3-dihydro-benzofuran-6-carboxylic acid methyl ester (77a) (7.18 g, 23 mmol) in MeOH (80 mL). The reaction mixture was heated to 60° C. for 3 hr, and concentrated in vacuo. The residue was diluted with H$_2$O (100 mL) and washed with EtOAc (100 mL). The aqueous phase was acidified with 3N aqueous HCl to Ph ~2 to form a white precipitate, which was filtered and dried to give a white solid (6.05 g, 88% yield). $^1$H NMR (400 MHz, DMSO-d$_6$) δ 12.88 (s, 1 H) 7.38-7.48 (m, 4 H) 7.33 (t, J=7.07 Hz, 1 H) 7.14 (s, 1 H) 6.88 (s, 1H) 5.17 (s, 2 H) 2.98 (s, 2 H) 1.42 (s, 6 H); LCMS for C$_{18}$H$_{18}$O$_5$ m/z 299.10 (M+H)$^+$.

Preparation of Intermediate 77c

6-[(4-Benzyloxy-2,2-dimethyl-2,3-dihydro-benzofuran-6-carbonyl)-amino]-nicotinic acid methyl ester

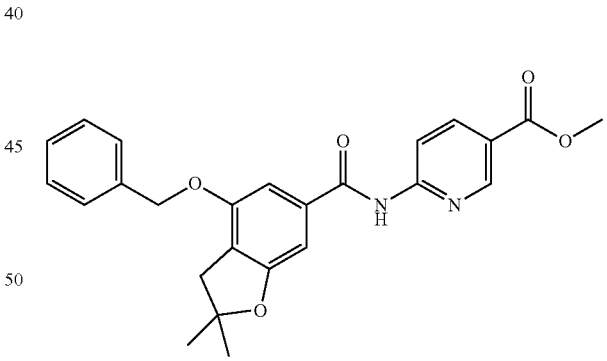

Thionyl chloride (40 uL, 0.55 mmol) and DMF (3 drops) were added to a solution of 4-benzyloxy-2,2-dimethyl-2,3-dihydro-benzofuran-6-carboxylic acid (77b) (130 mg, 0.44 mmol) in CH$_2$Cl$_2$ (20 mL). The mixture was concentrated and dried to give an off-white solid (130 mg). The solid was dissolved in CH$_2$Cl$_2$ (10 mL) and added pyridine (40 uL, 0.49 mmol) and methyl 6-aminonicotinate (65 mg, 0.43 mmol). The reaction mixture was stirred at room temperature for 2 hr, then quenched with H$_2$O (15 mL), and extracted with EtOAc (2×15 mL). The organic layers were dried over MgSO$_4$ and concentrated. The residue was purified by flash column chromatograph eluting with 25% EtOAc in hexanes to give a white solid (44 mg, 25% yield). $^1$H NMR (400 MHz, CDCl$_3$)

δ 1.51 (s, 6 H) 3.05 (s, 2 H) 3.95 (s, 3 H) 5.16 (s, 2 H) 6.90 (d, J=1.26 Hz, 1 H) 7.09 (d, J=1.26 Hz, 1 H) 7.34-7.38 (m, 1 H) 7.39-7.47 (m, 4 H) 8.36 (dd, J=8.72, 2.15 Hz, 1 H) 8.40-8.47 (m, 1 H) 8.65 (s, 1 H) 8.94 (d, J=1.52 Hz, 1 H); LCMS for $C_{25}H_{24}N_2O_5$ m/z 433.00 (M+H)$^+$.

Example 78

2,2-Dimethyl-4-((S)-1-methyl-2-phenyl-ethoxy)-2,3-dihydro-benzofuran-6-carboxylic acid (1-methyl-1H-pyrazol-3-yl)-amide

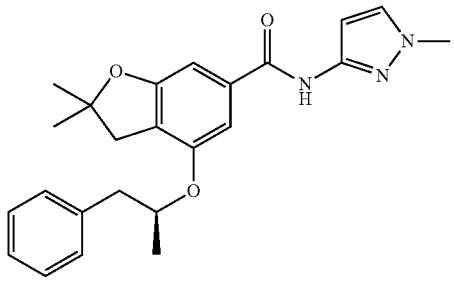

The title compound was prepared in a similar manner as described for Example 1, from 2,2-dimethyl-4-((S)-1-methyl-2-phenyl-ethoxy)-2,3-dihydro-benzofuran-6-carboxylic acid methyl ester (78a). $^1$H NMR (400 MHz, CDCl$_3$) δ 8.42 (s, 1 H) 7.26-7.32 (m, 3 H) 7.20-7.25 (m, 3 H) 6.95 (s, 1 H) 6.81 (d, J=2.02 Hz, 1 H) 6.76 (s, 1 H) 4.63-4.71 (m, 1 H) 3.79 (s, 3 H) 3.04 (dd, J=13.77, 6.44 Hz, 1 H) 2.85-2.93 (m, 3 H) 1.48 (d, J=3.79 Hz, 6 H) 1.33 (d, J=6.06 Hz, 3 H); LCMS for $C_{24}H_{27}N_3O_3$ m/z 406.20 (M+H)$^+$; Anal. Calcd. for $C_{24}H_{27}N_3O_3 \cdot 0.24$ H$_2$O: C, 70.34; H, 6.76; N, 10.25; Found: C, 70.40; H, 6.72; N, 10.26.

Preparation of Intermediate 78a 2,2-Dimethyl-4-((S)-1-methyl-2-phenyl-ethoxy)-2,3-dihydro-benzofuran-6-carboxylic acid methyl ester

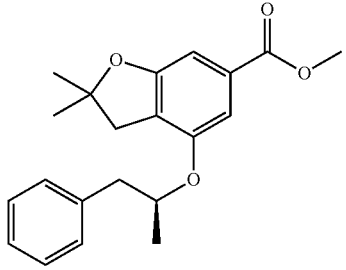

4-Hydroxy-2,2-dimethyl-2,3-dihydrobenzofuran-6-carboxy-lic acid methyl ester (3e) (1.04 g, 4.69 mmol) was dissolved in CH$_2$Cl$_2$ (25 mL) and cooled to 0° C. whilst stirring under a N$_2$ atmosphere. The solution was treated with Ph$_3$P (1.85 g, 7.04 mmol), (R)-(–)-1-phenyl-2-propane (959 mg, 7.04 mmol) and DIAD (1.40 mL, 7.11 mmol) added drop wise. The resulting solution was stirred at RT for 2 h. The reaction mixture was filtered and washed with CH$_2$Cl$_2$, concentrated in vacuo and purified by flash column chromatography eluting with 20% EtOAc/hexane to afford a colorless oil (1.27 g, 80% yield). $^1$H NMR (400 MHz, CDCl$_3$) δ 1.34 (d, J=6.06 Hz, 3 H) 1.47 (d, J=3.54 Hz, 6 H) 2.83-2.89 (m, 3 H) 3.02-3.09 (m, 1 H) 3.88 (s, 3 H) 4.62-4.71 (m, 1 H) 7.02 (s, 1 H) 7.12 (s, 1 H) 7.21-7.32 (m, 5 H); LCMS for $C_{21}H_{24}O_4$ m/z 341.20 (M+H)$^+$.

Example 79

4-[2-(4-Methoxy-phenyl)-1-methyl-ethoxy]-2,2-dimethyl-2,3-dihydro-benzofuran-6-carboxylic acid (1-methyl-1H-pyrazol-3-yl)-amide

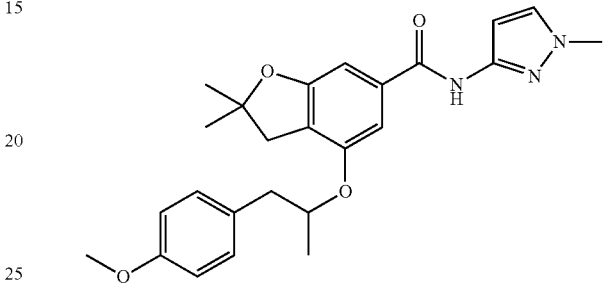

The title compound was prepared in a similar manner as described for Intermediate 78a, from 4-hydroxy-2,2-dimethyl-2,3-dihydro-benzofuran-6-carbo-xylic acid (1-methyl-1H-pyrazol-3-yl)-amide (31a). $^1$H NMR (400 MHz, CDCl$_3$) δ 9.32 (s, 1 H) 7.33 (s, 1 H) 7.15 (d, J=8.59 Hz, 2 H) 7.02 (s, 1 H) 6.92 (s, 1 H) 6.87 (s, 1 H) 6.83 (d, J=8.84 Hz, 2 H) 4.68-4.77 (m, 1 H) 3.86 (s, 3 H) 3.78 (s, 3 H) 2.90-2.99 (m, 3 H) 2.82-2.88 (m, 1 H) 1.49 (s, 3 H) 1.48 (s, 3 H) 1.32 (d, J=6.06 Hz, 3H); LCMS for $C_{25}H_{29}N_3O_4$ m/z 436.20 (M+H)$^+$.

Example 80

4-Benzyloxy-2,2-dimethyl-2,3-dihydro-benzofuran-6-carboxylic acid (1-methyl-1H-pyrazol-3-yl)-amide

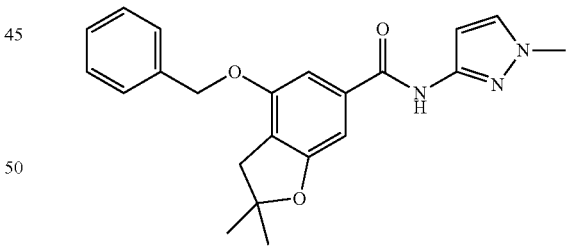

To a solution of 4-benzyloxy-2,2-dimethyl-2,3-dihydro-benzofuran-6-carboxylic acid (77b) (6.98 g, 23.40 mmol) in CH$_2$Cl$_2$ (100 mL) was added thionyl chloride (2.04 mL, 28.1 mmol), followed by 10 drops of DMF. The mixture was refluxed for 2 h, then concentrated and dried under vacuum. The residue was dissolved in CH$_2$Cl$_2$ (100 mL), and 3-amino-1-methyl-pyrazole (2.73 g, 28.1 mmol) was added at 0° C., followed by triethylamine (6.52 ml, 46.80 mmol). The mixture was stirred at 0° C. to room temperature for 1 hr. The reaction was quenched with H$_2$O, extracted with 3×CH$_2$Cl$_2$. The combined organic layers were dried over Na$_2$SO$_4$, concentrated and purified by flash column chromatography with 1-3% MeOH in CHCl$_3$ to give a white solid (5.31 g, 60% yield). ¹H NMR (400 MHz, CDCl₃) δ 8.43 (s, 1 H) 7.29-7.50 (m, 6 H) 7.09 (d, J=1.01 Hz, 1 H) 6.84 (dd, J=8.08, 1.77 Hz, 2 H) 5.14 (s, 2 H) 3.83 (s, 3 H) 2.95-3.06 (m, 2 H) 1.50 (s, 6 H); LCMS for C₂₂H₂₃N₃O₃ m/z 378.20 (M+H⁺).

Example 81

2,2-Dimethyl-4-(1-pyridin-2-yl-ethoxy)-2,3-dihydro-benzofuran-6-carboxylic acid (1-methyl-1H-pyrazol-3-yl)-amide

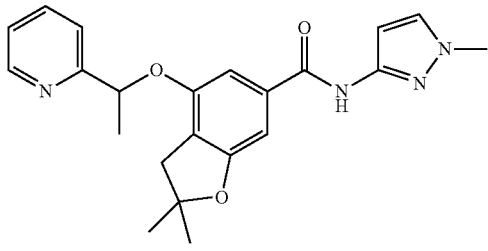

To a solution of 4-hydroxy-2,2-dimethyl-2,3-dihydro-benzofuran-6-carboxylic acid (1-methyl-1H-pyrazol-3-yl)-amide (31a) (80 mg, 0.28 mmol) and 1-pyridin-2-yl-ethanol (81a) (48 mg, 0.39 mmol) in 4 mL of THF was added PPh₃ (110 mg, 0.42 mmol) at 0° C., followed by DIAD (0.082 mL, 0.42 mmol) drop-wise. The mixture was stirred at room temperature overnight, concentrated, and purified by reverse phase HPLC to give a white solid (30 mg, 27% yield). ¹H NMR (400 MHz, CDCl₃) δ 9.61 (br. s., 1 H) 8.79 (d, J=4.55 Hz, 1 H) 7.94-8.06 (m, 1 H) 7.69 (d, J=8.08 Hz, 1 H) 7.45-7.53 (m, 1 H) 7.27-7.31 (m, 1 H) 6.94-7.00 (m, 2 H) 6.81-6.86 (m, 1 H) 5.84 (q, J=6.40 Hz, 1 H) 3.80 (s, 3 H) 3.09 (s, 2 H) 1.70-1.77 (m, 3 H) 1.48 (d, J=4.80 Hz, 6 H); LCMS for C₂₂H₂₄N₄O₃ m/z 393.20 (M+H⁺).

Preparation of Intermediate 81a

1-Pyridin-2-yl-ethanol

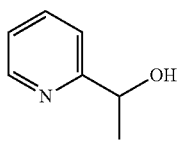

To a solution of 1-(pyridin-2-yl)ethanone (1.00 g, 8.255 mmol) in 20 mL of MeOH was added NaBH₄ (625 mg, 16.5 mmol) at 0° C. The mixture was stirred at 0° C. to room temperature for 2 h, then quenched with H₂O, extracted with 3×EtOAc, dried over Na₂SO₄, and concentrated to give a colorless oil (1.00 g, 98% yield). ¹H NMR (400 MHz, CDCl₃) δ 8.55 (d, J=4.80 Hz, 1 H) 7.62-7.76 (m, 1 H) 7.26-7.31 (m, 1 H) 7.21 (dd, J=7.07, 4.80 Hz, 1 H) 4.90 (d, J=6.57 Hz, 1 H) 4.30 (br. s., 1 H) 1.45-1.57 (m, 3 H); LCMS for C₇H₉NO m/z 124.20 (M+H⁺).

Examples 82-87 were prepared in a similar manner as described for Example 81, from 4-hydroxy-2,2-dimethyl-2,3-dihydro-benzofuran-6-carboxylic acid (1-methyl-1H-pyrazol-3-yl)-amide (31a) and the appropriate alcohols.

Example 82

2,2-Dimethyl-4-(1-pyrazin-2-yl-ethoxy)-2,3-dihydro-benzofuran-6-carboxylic acid (1-methyl-1H-pyrazol-3-yl)-amide

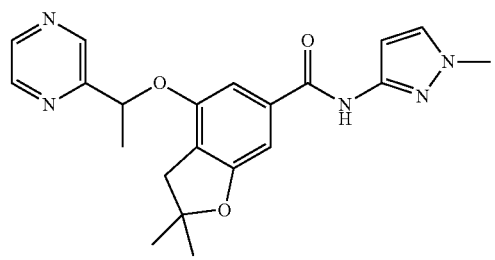

Example 83

2,2-Dimethyl-4-[1-(3-methyl-pyrazin-2-yl)-ethoxy]-2,3-dihydro-benzofuran-6-carboxylic acid (1-methyl-1H-pyrazol-3-yl)-amide

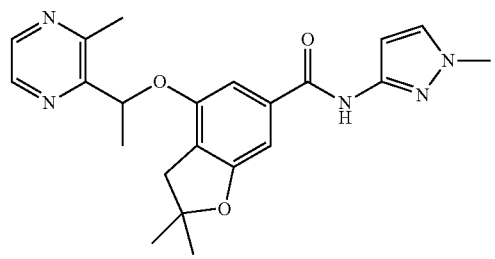

Example 84

4-(2-Methoxy-1-methyl-ethoxy)-2,2-dimethyl-2,3-dihydro-benzofuran-6-carboxylic acid (1-methyl-1H-pyrazol-3-yl)-amide

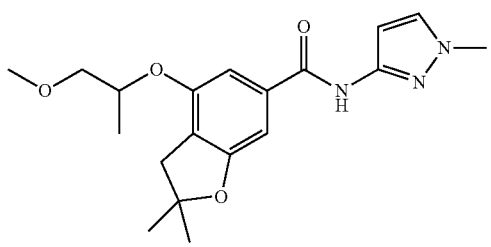

Example 85

2,2-Dimethyl-4-(1-methyl-2-morpholin-4-yl-ethoxy)-2,3-dihydro-benzofuran-6-carboxylic acid (1-methyl-1H-pyrazol-3-yl)-amide

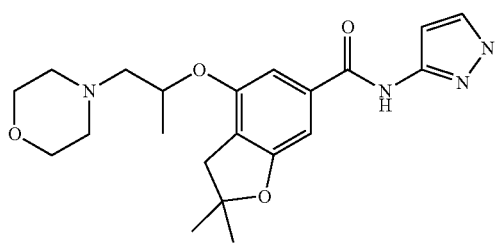

Example 86

2,2-Dimethyl-4-(1-pyrimidin-4-yl-ethoxy)-2,3-dihydro-benzofuran-6-carboxylic acid (1-methyl-1H-pyrazol-3-yl)-amide

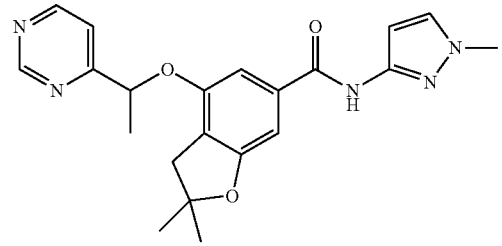

Example 87

2,2-Dimethyl-4-[1-(4-methyl-pyridin-2-yl)-ethoxy]-2,3-dihydro-benzofuran-6-carboxylic acid (1-methyl-1H-pyrazol-3-yl)-amide

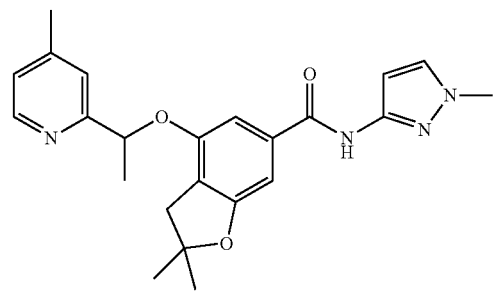

| Example | MW | MF | NMR | m/z |
|---|---|---|---|---|
| 82 | 393.5 | C21H23N5O3 | $^1$H NMR (400 MHz, CDCl$_3$)) δ 8.73 (d, J = 1.26 Hz, 1 H) 8.53-8.57 (m, 1 H) 8.51 (d, J = 2.53 Hz, 1 H) 8.39 (s, 1 H) 7.27 (s, 1 H) 6.93 (s, 1 H) 6.80 (s, 1 H) 6.77 (d, J = 2.02 Hz, 1 H) 5.61 (q, J = 6.57 Hz, 1 H) 3.80 (s, 3 H) 3.08 (s, 2 H) 1.73 (d, J = 6.57 Hz, 3 H) 1.52 (d, J = 4.80 Hz, 6 H); | 394.20 (M + H$^+$) |
| 83 | 407.5 | C22H25N5O3 | $^1$H NMR (400 MHz, CDCl$_3$)) δ 8.35-8.46 (m, 3 H) 7.26-7.31 (m, 1 H) 6.96 (s, 1 H) 6.72-6.83 (m, 2 H) 5.72 (q, J = 6.57 Hz, 1 H) 3.81 (s, 3 H) 3.01 (s, 2 H) 2.67 (s, 3 H) 1.75 (d, J = 6.57 Hz, 3 H) 1.49 (d, J = 4.80 Hz, 6 H); | 408.20 (M + H$^+$) |
| 84 | 359.4 | C19H25N3O4 | $^1$H NMR (400 MHz, CDCl$_3$)) δ 8.98 (br. s., 1 H) 7.31 (d, J = 2.27 Hz, 1 H) 7.06 (s, 1 H) 6.87 (dd, J = 4.29, 1.77 Hz, 2 H) 4.62-4.74 (m, 1 H) 3.84 (s, 3 H) 3.55-3.62 (m, 1 H) 3.48-3.53 (m, 1 H) 3.41 (s, 3 H) 2.99 (d, J = 4.04 Hz, 2 H) 1.49 (d, J = 8.84 Hz, 6 H) 1.32 (d, J = 6.32 Hz, 3 H); | 360.20 (M + H$^+$) |
| 85 | 414.5 | C22H30N4O4 | $^1$H NMR (400 MHz, CDCl$_3$)) 9.60 (br. s., 1 H) 7.33 (d, J = 1.77 Hz, 1 H) 7.11 (s, 1 H) 7.00 (s, 1 H) 6.88 (s, 1 H) 5.08-5.19 (m, 1 H) 3.96-4.05 (m, 4 H) 3.85 (s, 3 H) 3.45 (dd, J = 13.64, 9.35 Hz, 2 H) 3.15-3.26 (m, 2 H) 2.89-3.01 (m, 4 H) 1.48 (d, J = 8.84 Hz, 6 H) 1.34 (d, J = 6.06 Hz, 3 H); | 415.20 (M + H$^+$) |

-continued

| Example | MW | MF | NMR | m/z |
|---|---|---|---|---|
| 86 | 393.5 | C21H23N5O3 | $^1$H NMR (400 MHz, CDCl$_3$)) δ 9.20 (d, J = 1.26 Hz, 1 H) 8.72 (d, J = 5.05 Hz, 1 H) 8.37 (br. s., 1 H) 7.44 (dd, J = 5.05, 1.26 Hz, 1 H) 7.27 (s, 1 H) 6.86 (s, 1 H) 6.82 (s, 1 H) 6.76 (d, J = 2.27 Hz, 1 H) 5.47 (d, J = 6.57 Hz, 1 H) 3.81 (s, 3 H) 3.09 (s, 2 H) 1.69 (d, J = 6.57 Hz, 3 H) 1.53 (d, J = 4.80 Hz, 6 H); | 394.00 (M + H$^+$) |
| 87 | 406.5 | C23H26N4O3 | $^1$H NMR (400 MHz, CDCl$_3$)) δ 9.79 (br. s., 1 H) 8.80 (d, J = 5.81 Hz, 1 H) 7.62 (s, 1 H) 7.40-7.51 (m, 1 H) 7.27-7.38 (m, 1 H) 7.04 (d, J = 4.04 Hz, 2 H) 6.86 (d, J = 2.27 Hz, 1 H) 5.99 (q, J = 6.57 Hz, 1 H) 3.89 (s, 3 H) 3.12 (s, 2 H) 2.59 (s, 3 H) 1.77 (d, J = 6.32 Hz, 3 H) 1.51 (s, 6 H); | 407.00 (M + H$^+$) |

The following intermediates were prepared in a similar manner as described for Intermediate 81a from the appropriate ketones:

| Intermediate | Structure | Name | MW | NMR | m/z |
|---|---|---|---|---|---|
| 82a | 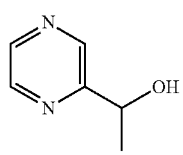 | 1-Pyrazin-2-yl-ethanol | 124 | $^1$H NMR (400 MHz, CDCl$_3$)) δ 8.68 (s, 1 H) 8.49-8.58 (m, 2 H) 5.01 (q, J = 6.65 Hz, 1 H) 3.47 (br. s., 1 H) 1.53-1.63 (m, 3 H); | 125.20 (M + H$^+$) |
| 83a | 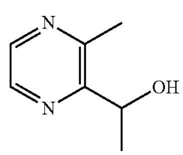 | 1-(3-Methyl-pyrazin-2-yl)-ethanol | 138 | $^1$H NMR (400 MHz, CDCl$_3$)) δ 8.42 (d, J = 2.53 Hz, 1 H) 8.38 (d, J = 2.53 Hz, 1 H) 5.04 (s, 1 H) 4.22 (d, J = 7.83 Hz, 1 H) 2.58 (s, 3 H) 1.46 (d, J = 6.57 Hz, 3 H); | 139.20 (M + H$^+$) |
| 86a | 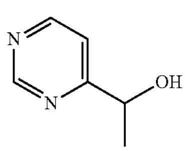 | 1-Pyrimidin-4-yl-ethanol | 124 | $^1$H NMR (400 MHz, CDCl$_3$)) δ 9.18 (d, J = 1.26 Hz, 1 H) 8.72 (d, J = 5.30 Hz, 1 H) 7.33-7.45 (m, 1 H) 4.81-4.95 (m, 1 H) 3.69 (br. s., 1 H) 1.54 (d, J = 6.57 Hz, 3 H); | 125.20 (M + H$^+$) |
| 87a | 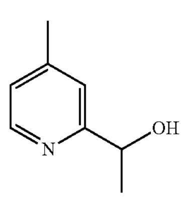 | 1-(4-Methyl-pyridin-2-yl)-ethanol | 137 | $^1$H NMR (400 MHz, CDCl$_3$)) δ 8.39 (d, J = 5.05 Hz, 1 H) 7.09 (s, 1 H) 7.03 (d, J = 5.05 Hz, 1 H) 4.85 (d, J = 6.06 Hz, 1 H) 4.29 (br. s., 1 H) 2.38 (s, 3 H) 1.50 (d, J = 6.57 Hz, 3 H); | 138.20 (M + H$^+$) |

Example 88

4-(6-Hydroxy-2-pyrazin-2-yl-pyrimidin-4-yl-methoxy)-2,2-dimethyl-2,3-dihydro-benzofuran-6-carboxylic acid (1-methyl-1H-pyrazol-3-yl)-amide

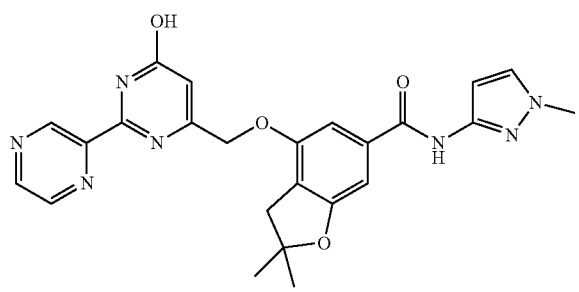

To a solution of 4-hydroxy-2,2-dimethyl-2,3-dihydro-benzofuran-6-carboxylic acid (1-methyl-1H-pyrazol-3-yl)-amide (31a) (80 mg, 0.280 mmol) and 6-(chloromethyl)-2-(pyrazin-2-yl)pyrimidin-4-ol (124 mg, 0.557 mmol) in 3 mL of DMF was added $Cs_2CO_3$ (181 mg, 0.557 mmol). The mixture was heated at 60° C. overnight, then filtered, washed with EtOAc, concentrated, and purified by reverse phase HPLC to give a white solid (13 mg, 10% yield). $^1$H NMR (400 MHz, $CDCl_3$) δ 9.67 (d, J=1.52 Hz, 1 H) 8.83 (d, J=2.53 Hz, 1 H) 8.65-8.67 (m, 1 H) 8.50 (s, 1 H) 7.27-7.31 (m, 1 H) 7.06 (d, J=1.01 Hz, 1 H) 6.88 (s, 1 H) 6.76-6.82 (m, 1 H) 6.72 (s, 1 H) 5.13 (s, 2 H) 3.81 (s, 3 H) 3.11 (s, 2 H) 1.49-1.55 (m, 6 H); LCMS for $C_{24}H_{23}N_7O_4$ m/z 474.00 (M+H$^+$).

Example 89

4-Cyclopropylmethoxy-2,2-dimethyl-2,3-dihydro-benzofuran-6-carboxylic acid (1-methyl-1H-pyrazol-3-yl)-amide

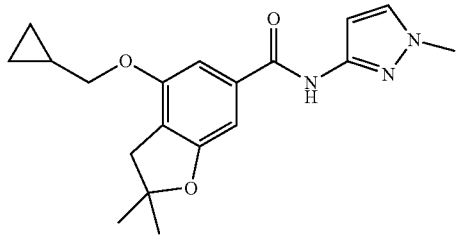

To 60 mg of cesium carbonate (180 µmol) in a test tube (10×95 mm) was added 0.8 mL of 0.1 M solution of 4-hydroxy-2,2-dimethyl-2,3-dihydro-benzofuran-6-carbo-xylic acid (1-methyl-1H-pyrazol-3-yl)-amide (31a) in acetonitrile followed by 1 mL of 0.1 M solution of chloromethyl cyclopropane in acetonitrile and the reaction was stirred at 80° C. for 8 h. After the removal of solid cesium carbonate, the acetonitrile was removed, the residue was reconstituted in 1.2 mL of DMSO and subjected to HPLC purification to obtain the title compound. $^1$H NMR (500 MHz, DMSO-$d_6$) δ 10.56 (s, 1 H) 7.57 (s, 1 H) 6.92 (s, 1 H) 6.54 (s, 1 H) 3.92-3.93 (d, J=5.00 Hz, 2 H) 2.94 (s, 2 H) 1.42 (s, 6 H) 0.55-0.60 (m, 2 H) 0.30-0.35 (m, 1H); LCMS for $C_{19}H_{23}N_3O_3$ m/z 342 (M+H)$^+$.

Examples 90-106 were prepared in parallel in a similar manner as described for Example 89, from 4-hydroxy-2,2-dimethyl-2,3-dihydro-benzofuran-6-carbo-xylic acid (1-methyl-1H-pyrazol-3-yl)-amide (31a) and the appropriate alkylating reagents.

Example 90

2,2-Dimethyl-4-(2-methyl-thiazol-4-ylmethoxy)-2,3-dihydro-benzofuran-6-carboxylic acid (1-methyl-1H-pyrazol-3-yl)-amide

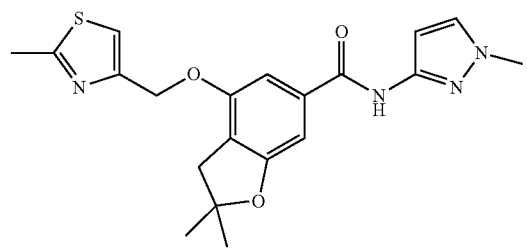

Example 91

4-(5-tert-Butyl-[1,2,4]oxadiazol-3-ylmethoxy)-2,2-dimethyl-2,3-dihydro-benzofuran-6-carboxylic acid (1-methyl-1H-pyrazol-3-yl)-amide

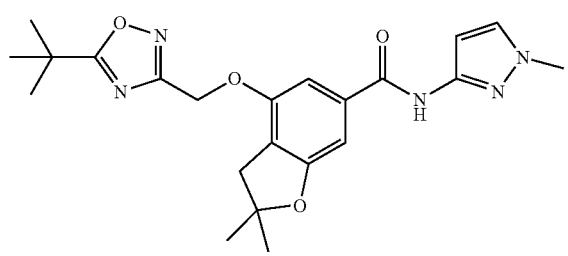

Example 92

4-Ethoxy-2,2-dimethyl-2,3-dihydro-benzofuran-6-carboxylic acid (1-methyl-1H-pyrazol-3-yl)-amide

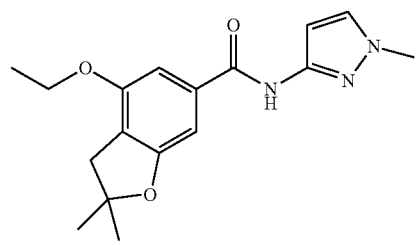

Example 93

4-(3-Cyano-propoxy)-2,2-dimethyl-2,3-dihydro-benzofuran-6-carboxylic acid (1-methyl-1H-pyrazol-3-yl)-amide

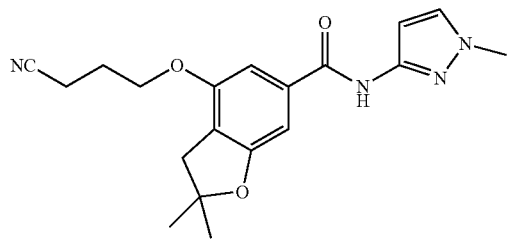

Example 94

2,2-Dimethyl-4-(3-methyl-[1,2,4]oxadiazol-5-yl-methoxy)-2,3-dihydro-benzofuran-6-carboxylic acid (1-methyl-1H-pyrazol-3-yl)-amide

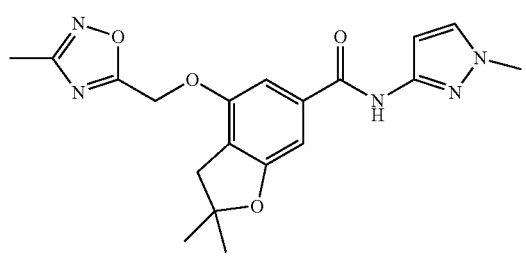

Example 95

4-(2-Cyclopropyl-6-hydroxy-pyrimidin-4-yl-methoxy)-2,2-dimethyl-2,3-dihydro-benzofuran-6-carboxylic acid (1-methyl-1H-pyrazol-3-yl)-amide

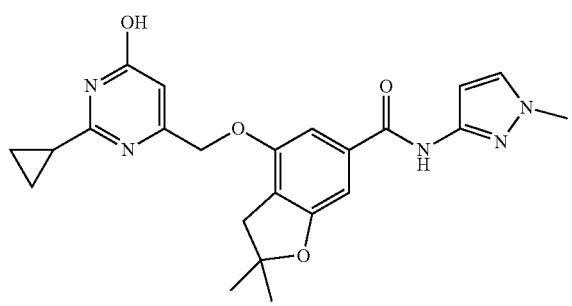

Example 96

2,2-Dimethyl-4-(5-methyl-[1,2,4]oxadiazol-3-yl-methoxy)-2,3-dihydro-benzofuran-6-carboxylic acid (1-methyl-1H-pyrazol-3-yl)-amide

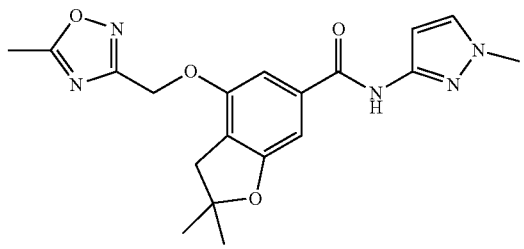

Example 97

4-[2-(4-Hydroxymethyl-phenyl)-2-oxo-ethoxy]-2,2-dimethyl-2,3-dihydro-benzofuran-6-carboxylic acid (1-methyl-1H-pyrazol-3-yl)-amide

Example 98

2,2-Dimethyl-4-(3-pyridin-2-yl-[1,2,4]oxadiazol-5-ylmethoxy)-2,3-dihydro-benzofuran-6-carboxylic acid (1-methyl-1H-pyrazol-3-yl)-amide

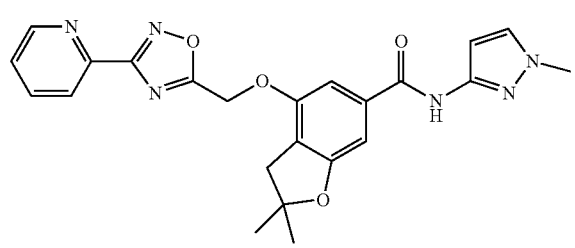

Example 99

2,2-Dimethyl-4-[2-(4-methyl-thiazol-5-yl)-ethoxy]-2,3-dihydro-benzofuran-6-carboxylic acid (1-methyl-1H-pyrazol-3-yl)-amide

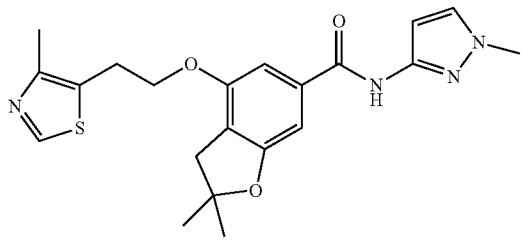

Example 100

2,2-Dimethyl-4-(3-propyl-[1,2,4]oxadiazol-5-yl-methoxy)-2,3-dihydro-benzofuran-6-carboxylic acid (1-methyl-1H-pyrazol-3-yl)-amide

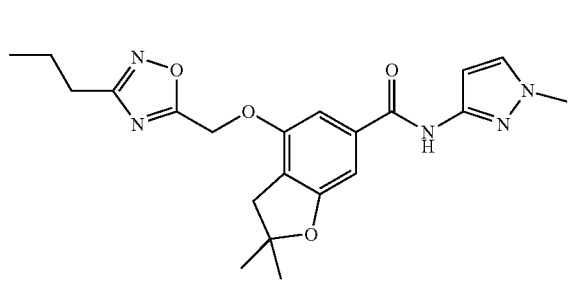

Example 101

4-(3-Methoxy-butoxy)-2,2-dimethyl-2,3-dihydro-benzofuran-6-carboxylic acid (1-methyl-1H-pyrazol-3-yl)-amide

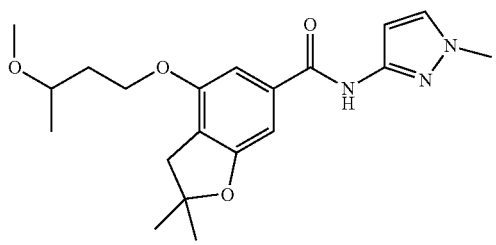

Example 102

4-((S)-3-Hydroxy-2-methyl-propoxy)-2,2-dimethyl-2,3-dihydro-benzofuran-6-carboxylic acid (1-methyl-1H-pyrazol-3-yl)-amide

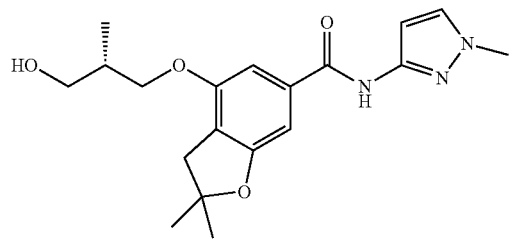

Example 103

2,2-Dimethyl-4-[2-(6-methyl-pyridin-3-yl)-2-oxo-ethoxy]-2,3-dihydro-benzofuran-6-carboxylic acid (1-methyl-1H-pyrazol-3-yl)-amide

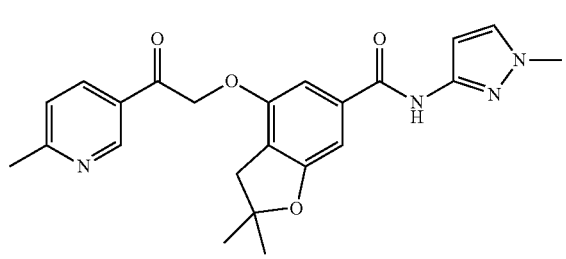

Example 104

4-(2-Ethyl-6-hydroxy-pyrimidin-4-ylmethoxy)-2,2-dimethyl-2,3-dihydro-benzofuran-6-carboxylic acid (1-methyl-1H-pyrazol-3-yl)-amide

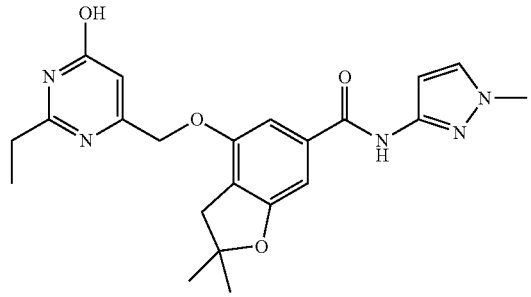

Example 105

2,2-Dimethyl-4-[2-(1-methyl-1H-pyrazol-4-yl)-2-oxo-ethoxy]-2,3-dihydro-benzofuran-6-carboxylic acid (1-methyl-1H-pyrazol-3-yl)-amide

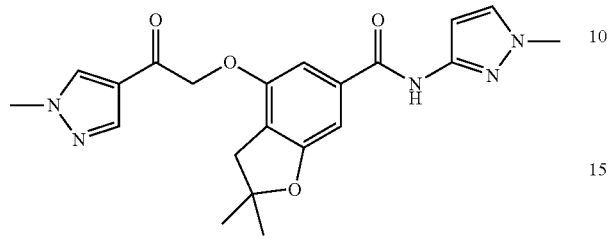

Example 106

2,2-Dimethyl-4-(2-methyl-pyridin-3-ylmethoxy)-2,3-dihydro-benzofuran-6-carboxylic acid (1-methyl-1H-pyrazol-3-yl)-amide

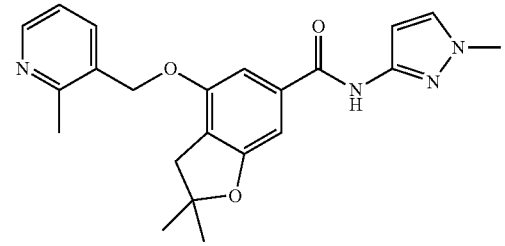

| Example | MW | MF | NMR | m/z |
|---|---|---|---|---|
| 90 | 398.5 | C20H22N4O3S | $^1$H NMR (500 MHz,, DMSO-$d_6$)) δ 10.60 (s, 1 H) 7.58 (s, 1 H) 7.50 (s, 1H) 7.28 (s, 1 H) 6.95 (s, 1H) 6.55 (s, 1 H) 5.21 (s, 2 H) 2.95 (s, 2 H) 1.40-1.44 (m, 9 H); | 399 (M + H)$^+$ |
| 91 | 425.5 | C22H27N5O4 | $^1$H NMR (500 MHz,, DMSO-$d_6$)) δ 10.59 (s, 1 H) 7.58 (s, 1 H) 7.30 (s, 1 H) 6.98 (s, 1H) 6.55 (s, 1 H) 6.39 (s, 2 H) 2.95 (s, 2 H) 1.37-1.44 (m, 15 H); | 426 (M + H)$^+$ |
| 92 | 315.4 | C17H21N3O3 | $^1$H NMR (500 MHz,, DMSO-$d_6$)) δ 10.58 (s, 1 H) 7.57 (s, 1 H) 7.12 (s, 1H) 6.92 (s, 1 H) 6.54 (s, 1 H) 4.10-4.15 (m, 2 H) 2.92 (s, 2 H) 1.42 (m, 6 H) 1.32-1.36 (m, 3H); | 316 (M + H)$^+$ |
| 93 | 354.4 | C19H22N4O3 | $^1$H NMR (500 MHz,, DMSO-$d_6$)) δ 10.60 (s, 1 H) 7.57 (s, 1 H) 7.14 (s, 1 H) 6.95 (s, 1 H) 6.55 (s, 1 H) 4.15 (s, 2 H) 2.96 (s, 2 H) 2.00-2.10 (m, 2 H) 1.42 (s, 6 H); | 355 (M + H)$^+$ |
| 94 | 383.4 | C19H21N5O4 | $^1$H NMR (500 MHz,, DMSO-$d_6$)) δ 10.59 (s, 1 H) 7.57 (s, 1 H) 7.25 (s, 1 H), 7.00 (s, 1H) 6.55 (s, 1 H) 5.56 (s, 2 H) 2.98 (s, 2 H) 2.36 (s, 3 H) 1.43 (m, 6 H); | 384 (M + H)$^+$ |
| 95 | 435.5 | C23H25N5O4 | $^1$H NMR (400 MHz, CDCl$_3$) δ 8.53 (s, 1 H) 7.20-7.34 (m, 1 H) 6.97 (s, 1 H) 6.86 (s, 1 H) 6.81 (d, J = 2.27 Hz, 1 H) 6.43 (s, 1 H) 4.92 (s, 2 H) 3.82 (s, 3 H) 3.06 (s, 2 H) 1.83-1.95 (m, 1 H) 1.46-1.54 (m, 6 H) 1.19-1.28 (m, 2 H) 1.07-1.16 (m, 2 H); | 436 (M + H)$^+$ |
| 96 | 383.4 | C19H21N5O4 | $^1$H NMR (500 MHz,, DMSO-$d_6$)) δ 10.60 (s, 1 H) 7.58 (s, 1H), 7.28 (s, 1 H) 6.97 (s, 1 H) 6.55 (s, 1 H) 5.34 (s, 2H) 2.94 (s, 2 H) 2.36 (s, 3 H) 1.42 (s, 6 H); | 384 (M + H)$^+$ |
| 97 | 435.5 | C24H25N3O5 | $^1$H NMR (500 MHz,, DMSO-$d_6$)) δ 10.49 (s, 1 H) 7.98-7.99 (m, 2 H) 7.55 (s, 1 H), 7.51-7.52 (m, 2 H) 7.03 (s, 1H) 6.95 (s, 1 H) 6.51 (s, 1 H) 5.64 (s, 2 H) 5.44-5.45 (m, 1 H) 4.60-4.62 (m, 2 H) 3.00 (s, 2 H) 2.36 (s, 3 H) 1.44 (m, 6 H); | 436 (M + H)$^+$ |
| 98 | 446.5 | C23H22N6O4 | $^1$H NMR (500 MHz,, DMSO-$d_6$)) δ 10.60 (s, 1 H) 7.99-8.10 (m, 2 H), 7.55-7.65 (m, 2 H) 7.30-6.97 (s, 1 H) 6.55 (s, 1 H) 5.70 (s, 2 H) 3.03 (s, 2 H) 1.44 (s, 6 H); | 447 (M + H)$^+$ |
| 99 | 412.5 | C21H24N4O3S | $^1$H NMR (500 MHz,, DMSO-$d_6$)) δ 10.59 (s, 1 H) 8.82 (s, 1 H), 7.57 (s, 1 H) 7.13 (s, 1 H) 6.92 (s, 1 H) 6.54 (s, 1 H) 4.25 (s, 2 H) 2.91 (s, 2 H) 2.36 (s, 3 H) 1.42 (s, 6 H); | 413 (M + H)$^+$ |
| 100 | 411.5 | C21H25N5O4 | $^1$H NMR (500 MHz,, DMSO-$d_6$)) δ 10.58 (s, 1 H) 7.57 (s, 1 H) 7.24 (s, 1 H) 7.00 (s, 1 H) 6.55 (s, 1 H) 5.56 (s, 2 H) 2.98 (s, 2 H) 2.67-2.72 (m, 2 H) 1.63-1.72 (m, 2 H) 1.43 (s, 6 H) 0.86-0.91 (m, 3 H); | 412 (M + H)$^+$ |
| 101 | 373.5 | C20H27N3O4 | $^1$H NMR (500 MHz,, DMSO-$d_6$)) δ 10.59 (s, 1 H) 7.57 (s, 1 H) 7.12 (s, 1 H) 6.92 (s, | 374 (M + H)$^+$ |

| Example | MW | MF | NMR | m/z |
|---|---|---|---|---|
| | | | 1 H) 6.54 (s, 1 H) 4.09-4.15 (m, 2 H) 3.20-3.25 (m, 1 H) 2.92 (s, 2 H) 1.82-1.90 (m, 2 H) 1.42 (br s, 8 H) 1.14-1.15 (d, J = 10 Hz, 3 H); | |
| 102 | 359.4 | C19H25N3O4 | $^1$H NMR (500 MHz,, DMSO-$d_6$)) δ 10.58 (s, 1 H) 7.57 (s, 1 H) 7.12 (s, 1 H) 6.92 (s, 1 H) 6.54 (s, 1 H) 3.9-4.1 (m, 1 H) 3.88-3.92 (m, 1 H) 2.93 (s, 2 H) 1.97-2.02 (m, 1 H) 1.42 (br s, 8 H) 0.96-0.98 (d, J = 10 Hz, 3 H); | 360 (M + H)$^+$ |
| 103 | 420.5 | C23H24N4O4 | $^1$H NMR (500 MHz,, DMSO-$d_6$)) δ 10.48 (s, 1 H) 9.05 (s, 1 H) 8.21-8.23 (d, J = 10 Hz, 1 H), 7.55 (s, 1 H) 7.46-7.48 (d, J = 10 Hz, 1 H) 7.06 (s, 1 H) 6.95 (s, 1 H) 6.54 (s, 1 H) 5.65 (s, 2 H) 3.00 (s, 2 H) 1.82-1.90 (m, 2 H) 1.44 (s, 6 H); | 421 (M + H)$^+$ |
| 104 | 423.5 | C22H25N5O4 | $^1$H NMR (500 MHz,, DMSO-$d_6$)) δ 10.63 (s, 1 H) 7.57 (s, 1 H) 7.21 (s, 1 H) 6.96 (s, 1 H) 6.54 (s, 1 H) 6.18 (s, 1 H) 5.01 (s, 2 H) 3.04 (s, 2 H) 1.44 (s, 6 H) 1.15-1.25 (m, 3 H); | 424 (M + H)$^+$ |
| 105 | 409.4 | C21H23N5O4 | $^1$H NMR (500 MHz,, DMSO-$d_6$)) δ 10.51 (s, 1 H) 8.45 (s, 1 H) 8.03 (s, 1 H) 7.56 (s, 1 H) 7.00 (s, 1 H) 6.95 (s, 1 H) 6.52 (s, 1 H) 5.26 (s, 2 H) 3.90 (s, 3 H) 3.02 (s, 2 H) 1.44 (s, 6 H); | 410 (M + H)$^+$ |
| 106 | 392.5 | C22H24N4O3 | $^1$H NMR (500 MHz,, DMSO-$d_6$)) δ 10.59 (s, 1 H) 8.40 (s, 1 H) 7.80-8.03 (m, 1 H) 7.58 (s, 1 H) 7.25-7.30 (m, 2 H) 6.97 (s, 1 H) 6.55 (s, 1 H) 5.22 (s, 2 H) 2.96 (s, 2 H) 1.42 (s, 9 H); | 393 (M + H)$^+$ |

Examples 107-111 were prepared in a similar manner as described for Intermediate 1f, from 4-hydroxy-2,2-dimethyl-2,3-dihydro-benzofuran-6-carbo-xylic acid (1-methyl-1H-pyrazol-3-yl)-amide (31a) and the corresponding fluorophenyl amide intermediates. The appropriate fluorophenyl amide intermediates were prepared in a similar manner as described for Intermediate 32a, 33a, or 35a, from the appropriate carboxylic acids or acid chlorides and amines.

Example 112 was prepared in a similar manner as described for Example 1, from 4-(4-ethylcarbamoyl-3,5-difluoro-phenoxy)-2,2-dimethyl-2,3-dihydro-benzofuran-6-carboxylic acid methyl ester (112b).

Preparation of Intermediate 112a 4-(4-tert-Butoxycarbonyl-3,5-difluoro-phenoxy)-2,2-dimethyl-2,3-dihydro-benzofuran-6-carboxylic acid methyl ester

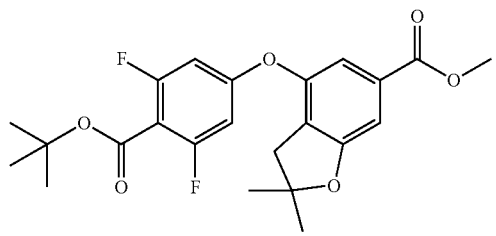

The title compound was prepared in a similar manner as described for Intermediate 35b, from 4-hydroxy-2,2-dimethyl-2,3-dihydro-benzofuran-6-carboxylic acid methyl ester (3e) and 4-bromo-2,6-difluoro-benzoic acid tert-butyl ester. $^1$H NMR (400 MHz, CDCl$_3$) δ 7.29 (s, 1 H) 7.23 (s, 1 H) 6.48 (d, J=8.84 Hz, 2 H) 3.89 (s, 3 H) 2.88 (s, 2 H) 1.59 (s, 9 H) 1.49 (s, 6 H); LCMS for C$_{23}$H$_{24}$F$_2$O$_6$ m/z 457.20 (M+Na)$^+$.

Preparation of Intermediate 112b 4-(4-Ethylcarbamoyl-3,5-difluoro-phenoxy)-2,2-dimethyl-2,3-dihydro-benzofuran-6-carboxylic acid methyl ester

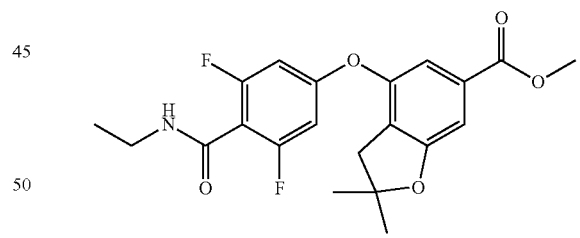

TFA (2 mL) was added to a solution of 4-(4-tert-butoxy-carbonyl-3,5-difluoro-phenoxy)-2,2-dimethyl-2,3-dihydro-benzofuran-6-carboxylic acid methyl ester (870 mg, 2.00 mmol) in CH$_2$Cl$_2$ (8 mL). The mixture was stirred at room temperature for 2 hr, concentrated in vacuo, and dried to give an off-white solid (TFA salt) (735 mg, 75% yield). The solid was then dissolved in DMF (3 mL) and added Et$_3$N (320 uL, 2.30 mmol), HATU (425 mg, 1.12 mmol) and ethyl amine (600 uL, 1.2 mmol). The mixture was stirred at room temperature for 1 hr, quenched with H$_2$O (30 mL), and extracted with EtOAc (2×30 mL). The organic layers were washed with H$_2$O (2×50 mL), dried over MgSO$_4$ and concentrated. The residue was purified by flash column chromatograph eluting with 80% EtOAc in hexanes to give an off-white solid (213 mg, 94% yield). ¹H NMR (400 MHz, CDCl₃) δ 7.21 (d, J=1.13 Hz, 1 H) 6.50 (d, J=9.04 Hz, 2 H) 3.89 (s, 3 H) 3.50 (dd, J=7.25, 5.75 Hz, 2 H) 2.88 (s, 2 H) 2.86 (d, J=3.77 Hz, 1 H) 1.48 (s, 6 H) 1.25 (t, J=7.25 Hz, 3 H).

Example 107

4-(2-Chloro-4-dimethylcarbamoyl-phenoxy)-2,2-dimethyl-2,3-dihydro-benzofuran-6-carboxylic acid (1-methyl-1H-pyrazol-3-yl)-amide

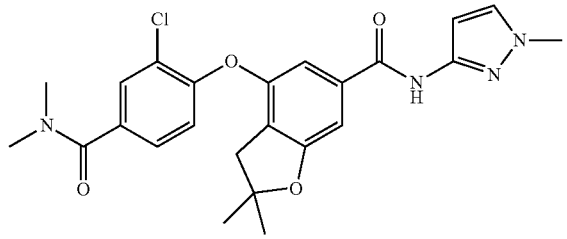

Example 108

4-(3-Chloro-4-dimethylcarbamoyl-phenoxy)-2,2-dimethyl-2,3-dihydro-benzofuran-6-carboxylic acid (1-methyl-1H-pyrazol-3-yl)-amide

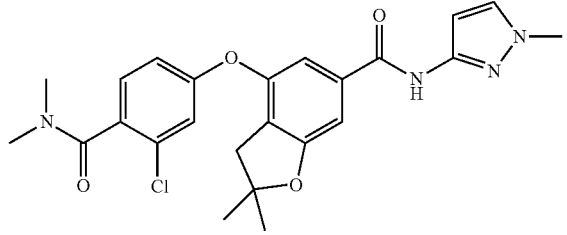

Example 109

4-(4-Dimethylcarbamoyl-2,5-difluoro-phenoxy)-2,2-dimethyl-2,3-dihydro-benzofuran-6-carboxylic acid (1-methyl-1H-pyrazol-3-yl)-amide

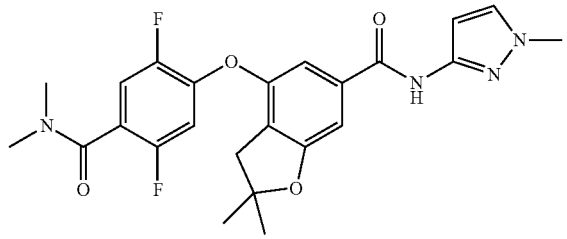

Example 110

4-[4-(Azetidine-1-carbonyl)-3,5-difluoro-phenoxy]-2,2-dimethyl-2,3-dihydro-benzofuran-6-carboxylic acid (1-methyl-1H-pyrazol-3-yl)-amide

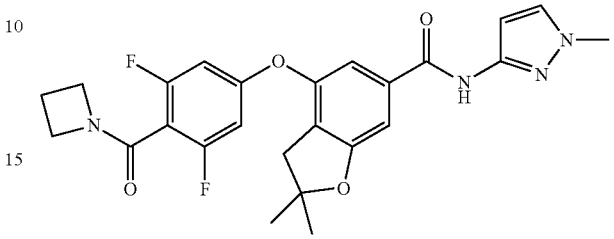

Example 111

4-(4-Dimethylcarbamoyl-3,5-difluoro-phenoxy)-2,2-dimethyl-2,3-dihydro-benzofuran-6-carboxylic acid (1-methyl-1H-pyrazol-3-yl)-amide

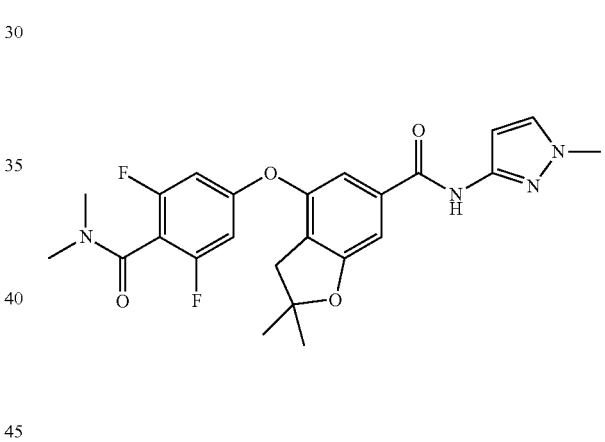

Example 112

4-(4-Ethylcarbamoyl-3,5-difluoro-phenoxy)-2,2-dimethyl-2,3-dihydro-benzofuran-6-carboxylic acid (1-methyl-1H-pyrazol-3-yl)-amide

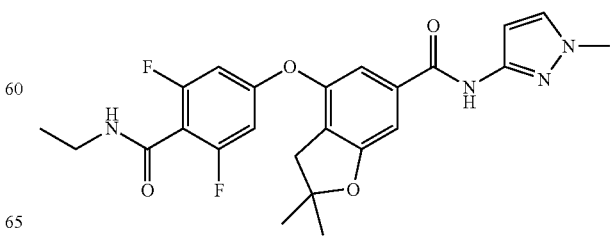

| Example | MW | MF | NMR | m/z | Elemental Analysis |
|---|---|---|---|---|---|
| 107 | 468.9 | C24H25ClN4O4 | $^1$H NMR (400 MHz, CDCl$_3$) δ 8.81 (s, 1 H) 7.57 (d, J = 2.02 Hz, 1 H) 7.30 (dd, J = 8.34, 2.02 Hz, 1 H) 7.28 (s, 1 H) 7.07 (d, J = 1.26 Hz, 1 H) 6.98 (d, J = 1.26 Hz, 1 H) 6.96 (d, J = 8.34 Hz, 1 H) 6.79 (d, J = 2.27 Hz, 1 H) 3.80 (s, 3 H) 3.10 (s, 3 H) 3.06 (s, 3 H) 2.96 (s, 2 H) 1.51 (s, 6 H); | 469.00 (M + H)$^+$ | Calcd. for C$_{24}$H$_{25}$ClN$_4$O$_4$•0.56 AcOH: C, 60.03; H, 5.47; N, 11.15; Found: C, 60.03; H, 5.37; N, 11.34 |
| 108 | 468.9 | C24H25ClN4O4 | $^1$H NMR (400 MHz, CDCl$_3$) δ 8.76 (s, 1 H) 7.29 (d, J = 2.27 Hz, 1 H) 7.25 (s, 1 H) 7.10 (dd, J = 9.09, 1.26 Hz, 2 H) 7.00 (d, J = 2.27 Hz, 1 H) 6.91 (dd, J = 8.46, 2.40 Hz, 1 H) 6.80 (d, J = 2.02 Hz, 1 H) 3.82 (s, 3 H) 3.14 (s, 3 H) 2.92 (s, 3 H) 2.90 (s, 2 H) 1.50 (s, 6 H); | 469.00 (M + H)$^+$ | Calcd. for C$_{24}$H$_{25}$ClN$_4$O$_4$•0.76 AcOH: C, 59.57; H, 5.49; N, 10.89; Found: C, 59.33; H, 5.23; N, 11.10. |
| 109 | 470.5 | C24H24F2N4O4 | $^1$H NMR (400 MHz, CDCl$_3$) δ 8.73 (s, 1 H) 7.24-7.29 (m, 2 H) 7.08 (s, 1 H) 7.03 (s, 1 H) 6.79 (d, J = 2.02 Hz, 1 H) 6.73 (dd, J = 9.47, 6.44 Hz, 1 H) 3.81 (s, 3 H) 3.13 (s, 3 H) 2.95-3.01 (m, 5 H) 1.52 (s, 6 H); | 471.00 (M + H)$^+$ | Calcd. for C$_{24}$H$_{24}$F$_2$N$_4$O$_4$•0.53 AcOH: C, 59.92; H, 5.24; N, 11.15; Found: C, 59.92; H, 5.14; N, 11.12. |
| 110 | 482.5 | C25H24F2N4O4 | $^1$H NMR (400 MHz, CDCl$_3$) δ 8.56 (s, 1 H) 7.29 (d, J = 2.02 Hz, 1 H) 7.04-7.11 (m, 2 H) 6.80 (d, J = 2.27 Hz, 1 H) 6.52 (d, J = 8.59 Hz, 1 H) 4.02-4.28 (m, 4 H) 3.82 (s, 3 H) 2.88 (s, 2 H) 2.34 (ddd, J = 15.79, 8.08, 7.96 Hz, 2 H) 1.50 (s, 6 H); | 483.00 (M + H)$^+$ | Calcd. for C$_{25}$H$_{24}$F$_2$N$_4$O$_4$•0.36 AcOH: C, 61.28; H, 5.09; N, 11.11; Found: C, 61.29; H, 5.07; N, 11.12. |
| 111 | 470.5 | C24H24F2N4O4 | $^1$H NMR (400 MHz, CDCl$_3$) δ 8.37 (s, 1 H) 7.29 (s, 1 H) 7.08 (s, 2 H) 6.78 (d, J = 2.02 Hz, 1 H) 6.53 (d, J = 8.08 Hz, 2 H) 3.82 (s, 3 H) 3.15 (s, 3 H) 2.99 (s, 3 H) 2.90 (s, 2 H) 1.50 (s, 6 H); | 471.00 (M + H)$^+$ | Calcd. for C$_{24}$H$_{24}$F$_2$N$_4$O$_4$•0.33 H2O: C, 60.51; H, 5.22; N, 11.76; Found: C, 60.51; H, 5.37; N, 11.67 |
| 112 | 470.5 | C24H24F2N4O4 | $^1$H NMR (400 MHz, CDCl$_3$) δ 8.96 (br. s., 1 H) 7.12 (s, 1 H) 7.03 (s, 1 H) 6.76 (s, 1 H) 6.50 (d, J = 8.84 Hz, 2 H) 6.26-6.42 (m, 1 H) 3.76 (s, 3 H) 3.46-3.55 (m, 2 H) 2.91 (s, 2 H) 1.50 (s, 6 H) 1.28 (t, J = 6.69 Hz, 3 H); | 471.20 (M + H)$^+$ | Calcd. for C$_{24}$H$_{24}$F$_2$N$_4$O$_4$•1.14 H$_2$O•0.63 EtOAc: C, 58.28; H, 5.78; N, 10.25; Found: C, 58.28; H, 5.62; N, 10.26. |

Example 113

4-(3,5-Difluoro-phenoxy)-2,2-dimethyl-2,3-dihydro-benzofuran-6-carboxylic acid (1-methyl-1H-pyrazol-3-yl)-amide

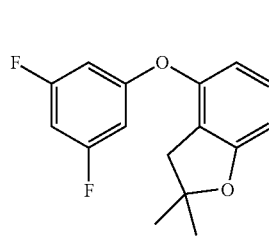

To a mixture of 4-(3,5-difluoro-phenoxy)-2,2-dimethyl-2,3-dihydro-benzofuran-6-carboxylic acid (113b) (0.308 g, 0.00096 mol), EDCl (0.28 g, 0.0015 mol), HOBt (0.21 g, 0.0015 mol) and NMM (0.49 g, 0.0048 mol) in CH$_2$Cl$_2$ (15 mL) was added 1-methyl-1H-pyrazol-3-amine (0.11 g, 0.001 mol) in one portion. The mixture was stirred at room temperature overnight. The reaction mixture was washed with water, aq. citric acid and then sat. NaHCO$_3$. The organic phase was dried over Na$_2$SO$_4$ and concentrated to give a brown oil. The crude oil was purified by prep. HPLC to give the title compound (95 mg, 51% yield) as a white solid. $^1$H NMR (400 MHz, CDCl$_3$): δ 8.82 (s, 1H), 7.20 (m, 2H), 7.03 (d, 2H), 6.73 (s, 1H), 6.42 (m, 3H), 3.72 (s, 3H), 2.84 (s, 2H), 1.42 (s, 6H);
LCMS for C$_{21}$H$_{19}$F$_2$N$_3$O$_3$ m/z 400.4 (M+H)$^+$.

Preparation of Intermediate 113a 4-(3,5-Difluoro-phenoxy)-2,2-dimethyl-2,3-dihydro-benzofuran-6-carboxylic acid methyl ester

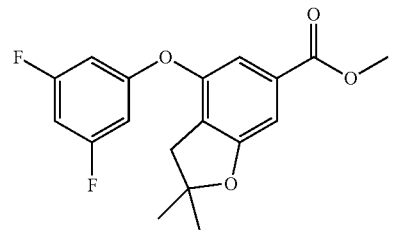

A mixture of 4-hydroxy-2,2-dimethyl-2,3-dihydrobenzofuran-6-carboxy-lic acid methyl ester (3e) (1 g, 0.0045 mol), 3,5-difluorophenylboronic acid (1.07 g, 0.0068 mol), Cu(OAc)$_2$ (0.9 g, 0.005 mol), freshly activated 4 Å molecular sieves (4 g) and Et$_3$N (4 mL) in CH$_2$Cl$_2$ (25 mL) was stirred at room temperature under N$_2$ for 48 hrs. The mixture was filtered through Celite and the filter cake was washed with CH$_2$Cl$_2$. The filtrate was concentrated to give a dark liquid. The crude liquid was purified by column chromatography eluting with EtOAc/petroleum ether (1/5) to give the title compound (0.4 g, 26.6%) as a colorless oil. $^1$H NMR (400

MHz, CDCl₃): δ 7.18 (s, 1H), δ 7.14 (s, 1H), 6.47(m, 1H), δ 6.36 (dd, 2H), 3.81 (s, 3H), 2.83 (s, 2H), 1.41 (s, 6H).

Preparation of Intermediate 113b 4-(3,5-Difluoro-phenoxy)-2,2-dimethyl-2,3-dihydro-benzofuran-6-carboxylic acid

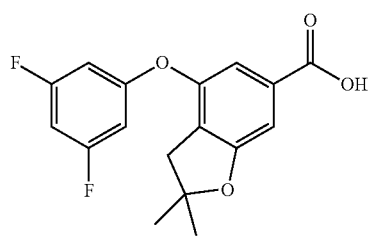

To a solution of 4-(3,5-difluoro-phenoxy)-2,2-dimethyl-2,3-dihydro-benzofuran-6-carboxylic acid methyl ester (113a) (0.4 g, 0.0012 mol) in MeOH (5 mL) was added NaOH (0.5 g, 0.012 mol) in one portion. The mixture was stirred at room temperature overnight. TLC (EtOAc/petroleum ether=1/10) showed the starting material was still present. The mixture was refluxed for another 3 hrs. After TLC indicated the reaction was complete. The solvents were removed in vacuo. The residue was dissolved in water and acidified with conc. HCl to pH 1. The aqueous phase was extracted with EtOAc (2×15 mL). The organic phase was dried over Na₂SO₄ and concentrated to give an off-white solid (0.308 g, 80% yield).

Example 114

4-(3-Fluoro-4-methanesulfonyl-phenoxy)-2,2-dimethyl-2,3-dihydro-benzofuran-6-carboxylic acid (1-methyl-1H-pyrazol-3-yl)-amide and Example 115

4-(5-Fluoro-2-methanesulfonyl-phenoxy)-2,2-dimethyl-2,3-dihydro-benzofuran-6-carboxylic acid (1-methyl-1H-pyrazol-3-yl)-amide

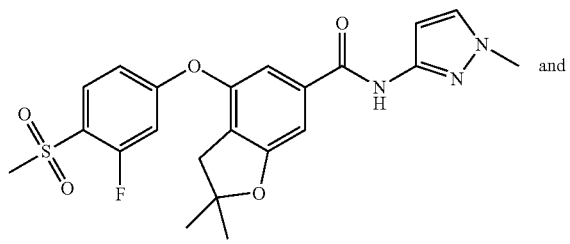
and

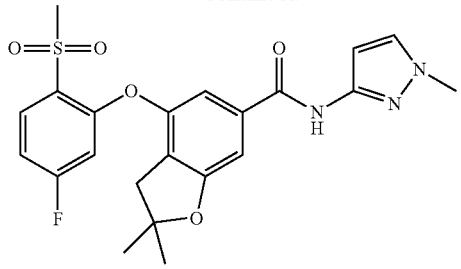

A mixture of 2,4-difluorophenyl methyl sulfone (67 mg, 0.35 mmol), 4-hydroxy-2,2-dimethyl-2,3-dihydro-benzofuran-6-carboxylic acid (1-methyl-1H-pyrazol-3-yl)-amide (31a) (100 mg, 0.35 mmol), and Cs₂CO₃ (227 mg, 0.70 mmol) in DMF (2 mL) was heated to 120° C. overnight, then cooled to room temperature, quenched with H₂O (50 mL), and extracted with EtOAc (2×50 mL). The organic layers were washed with H₂O (2×80 mL), dried over Na₂SO₄ and concentrated. The residue was purified by SFC column chromatography to give Example 114 (49 mg, 31% yield) and Example 115 (15 mg) as white solids.

Example 114: ¹H NMR (400 MHz, CDCl₃) δ 8.31 (s, 1 H) 7.92 (t, J=8.46 Hz, 1 H) 7.29 (d, J=2.27 Hz, 1 H) 7.09 (d, J=7.58 Hz, 2 H) 6.88 (dd, J=8.72, 2.15 Hz, 1 H) 6.76-6.83 (m, 2 H) 3.82 (s, 3 H) 3.23 (s, 3 H) 2.90 (s, 2 H) 1.51 (s, 6 H); LCMS for C₂₂H₂₂FN₃O₅S m/z 460.20 (M+H)⁺;

Example 115: ¹H NMR (400 MHz, CDCl₃) δ 8.43 (s, 1H) 8.09 (dd, J=8.84, 6.06 Hz, 1 H) 7.26-7.34 (m, 1 H) 7.14 (d, J=18.44 Hz, 2 H) 6.89-6.97 (m, 1 H) 6.79 (d, J=2.27 Hz, 1 H) 6.60 (dd, J=9.60, 2.27 Hz, 1 H) 3.81 (s, 3 H) 3.30 (s, 3 H) 2.92 (s, 2 H) 1.49 (s, 6H); LCMS for C₂₂H₂₂FN₃O₅S m/z 460.20 (M+H)⁺.

Example 116

4-(3-Fluoro-4-methanesulfonyl-phenoxy)-2,2-dimethyl-2,3-dihydro-benzofuran-6-carboxylic acid (5-methyl-pyridin-2-yl)-amide

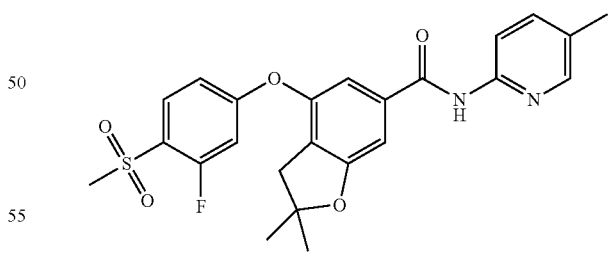

The title compound was prepared in a similar manner as described for Example 1, from 4-(3-fluoro-4-methanesulfonyl-phenoxy)-2,2-dimethyl-2,3-dihydro-benzofuran-6-carboxylic acid methyl ester (116a) (233 mg, 0.591 mmol) to give a white solid (140 mg, 50% yield). ¹H NMR (400 MHz, CDCl₃) δ 8.43 (s, 1 H) 8.22 (d, J=8.59 Hz, 1 H) 8.11 (d, J=2.27 Hz, 1 H) 7.86-8.00 (m, 1 H) 7.57 (dd, J=8.46, 2.15 Hz, 1 H) 7.14 (dd, J=18.95, 1.52 Hz, 2 H) 6.71-6.92 (m, 2 H) 3.23 (s, 3 H) 2.90 (s, 2 H) 2.32 (s, 3 H) 1.51 (s, 6 H); LCMS for $C_{24}H_{23}FN_2O_5S$ m/z 471.20 (M+H+); Anal. Calcd. for $C_{24}H_{23}FN_2O_5S$: C, 61.27; H, 4.93; N, 5.95; Found: C, 61.55; H, 4.86; N, 5.99.

Preparation of Intermediate 116a 4-(3-Fluoro-4-methanesulfonyl-phenoxy)-2,2-dimethyl-2,3-dihydro-benzofuran-6-carboxylic acid methyl ester

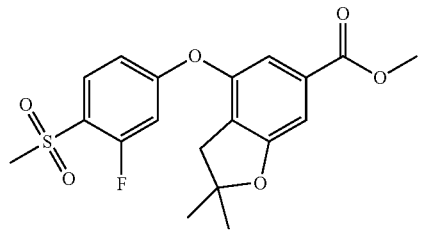

A mixture of 2,4-difluorophenyl methyl sulfone (865 mg, 4.50 mmol), 4-hydroxy-2,2-dimethyl-2,3-dihydro-benzofuran-6-carboxylic acid methyl ester (3e) (1.00 g, 4.50 mmol), and $Cs_2CO_3$ (2.93 g, 9.00 mmol) in DMF (2 mL) was heated to 80° C. for 2.5 h, cooled to room temperature, quenched with $H_2O$ and extracted with 3×EtOAc. The organic layers were washed with 2×$H_2O$, dried over $Na_2SO_4$ and concentrated. The residue was purified by Biotage column chromatography with 15%-40% EtOAc in hexanes to give a white solid (1.20 g, 68% yield). $^1$H NMR (400 MHz, $CDCl_3$) δ 7.82-7.95 (m, 1 H) 7.21-7.34 (m, 2 H) 6.72-6.88 (m, 2 H) 3.90 (s, 3 H) 3.22 (s, 3 H) 2.90 (s, 2 H) 1.48 (s, 6 H); LCMS for $C_{19}H_{19}FO_6S$ m/z 395.00 (M+H)+.

Example 117

4-(3-Fluoro-4-methanesulfonyl-phenoxy)-2,2-dimethyl-2,3-dihydro-benzofuran-6-carboxylic acid (2-methyl-2H-[1,2,3]triazol-4-yl)-amide

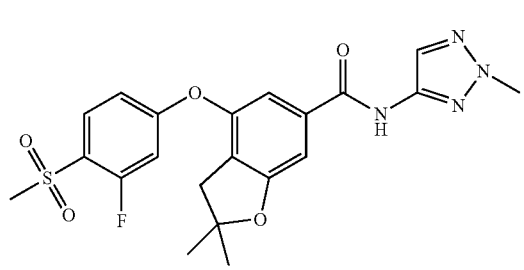

The title compound was prepared in a similar manner as described for Example 1 from 4-(3-fluoro-4-methanesulfonyl-phenoxy)-2,2-dimethyl-2,3-dihydro-benzofuran-6-carboxylic acid methyl ester (116a) (146 mg, 0.37 mmol) to give a white solid (87 mg, 51% yield). $^1$H NMR (300 MHz, $CD_3OD$) δ 7.93-7.98 (m, 1 H) 7.90 (d, J=3.96 Hz, 1 H) 7.18-7.25 (m, 1 H) 7.14-7.27 (m, 1 H) 6.86-7.07 (m, 2 H) 4.09 (d, J=0.94 Hz, 3 H) 3.23 (s, 3 H) 2.93 (s, 2 H) 1.48 (s, 6 H); LCMS for $C_{21}H_{21}FN_4O_5S$ m/z 461.00 (M+H+); Anal. Calcd. for $C_{21}H_{21}FN_4O_5S$: C, 54.78; H, 4.60; N, 12.17; Found: C, 54.64; H, 4.55; N, 12.10.

Example 118

4-(3-Chloro-4-methanesulfonyl-phenoxy)-2,2-dimethyl-2,3-dihydro-benzofuran-6-carboxylic acid (2-methyl-2H-[1,2,3]triazol-4-yl)-amide

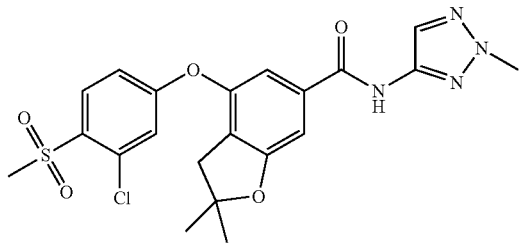

The title compound was prepared in a similar manner as described for Example 1 from 4-(3-chloro-4-methanesulfonyl-phenoxy)-2,2-dimethyl-2,3-dihydro-benzofuran-6-carboxylic acid methyl ester (118a) (154 mg, 0.370 mmol) to give a white solid (154 mg, 87% yield). $^1$H NMR (400 MHz, $CDCl_3$) δ 8.42 (s, 1 H) 8.08 (s, 2 H) 7.70-7.86 (m, 1H) 6.89-7.14 (m, 3H) 4.12 (s, 3 H) 3.11 (s, 3 H) 2.96 (s, 2 H) 1.53 (s, 6H); LCMS for $C_{21}H_{21}ClN_4O_5S$ m/z 477.00 and 479.00 (M+H+); Anal. Calcd. for $C_{21}H_{21}ClN_4O_5S \cdot 0.15CHCl_3$: C, 51.33; H, 4.31; N, 11.32; Found: C, 51.16; H, 4.35; N, 11.47.

Preparation of Intermediate 118a 4-(3-Chloro-4-methanesulfonyl-phenoxy)-2,2-dimethyl-2,3-dihydro-benzofuran-6-carboxylic acid methyl ester

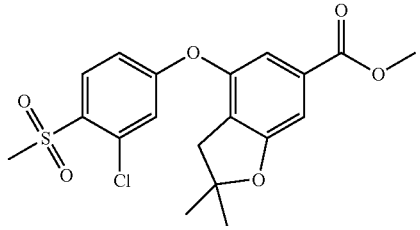

A mixture of 2-chloro-4-fluoro-1-(methylsulfonyl)benzene (939 mg, 4.50 mmol), 4-hydroxy-2,2-dimethyl-2,3-dihydro-benzofuran-6-carboxylic acid methyl ester (3e) (1.00 g, 4.50 mmol) and $Cs_2CO_3$ (2.93 g, 9.00 mmol) in DMF (5 mL) was heated to 80° C. for 1.5 h, cooled to room temperature, quenched with $H_2O$ and extracted with 3×EtOAc. The organic layers were washed with 2×$H_2O$, dried over $Na_2SO_4$ and concentrated. The residue was purified by Biotage column chromatography with 25-50% EtOAc in hexanes to give a white solid (1.70 g, 92% yield). $^1$H NMR (400 MHz, $CDCl_3$) δ 8.11 (d, J=8.84 Hz, 1H) 7.31 (d, J=1.26 Hz, 1 H) 7.25 (d, J=1.26 Hz, 1 H) 7.10 (d, J=2.27 Hz, 1 H) 6.88-7.03

(m, 1 H) 3.89 (s, 3 H) 3.28 (s, 3 H) 2.88 (s, 2 H) 1.50 (s, 6 H); LCMS for $C_{19}H_{19}ClO_6S$ m/z 411.00 and 413.00 (M+H)$^+$.

Example 119

4-(2-Chloro-4-methanesulfonyl-phenoxy)-2,2-dimethyl-2,3-dihydro-benzofuran-6-carboxylic acid (2-methyl-2H-[1,2,3]triazol-4-yl)-amide

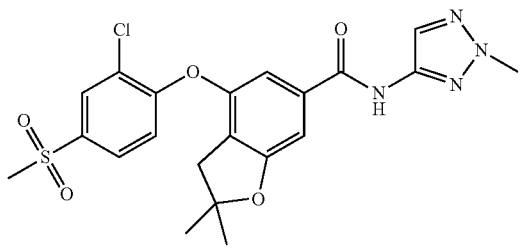

To a solution of 4-(2-chloro-4-methanesulfonyl-phenoxy)-2,2-dimethyl-2,3-dihydro-benzofuran-6-carboxylic acid (119b) (138 mg, 0.348 mmol), 2-methyl-2H-1,2,3-triazol-4-amine hydrochloride (93.6 mg, 0.695 mmol) and triethylamine (0.145 mL, 1.040 mmol) in 2 mL of DMF was added HATU (264 mg, 0.695 mmol). The mixture was stirred at 50° C. for 1.5 h, and purified by reverse phase column chromatography to give a white solid (100 mg, 60% yield). $^1$H NMR (400 MHz, CDCl$_3$) δ 8.80 (s, 1 H) 8.00-8.08 (m, 2 H) 7.05-7.17 (m, 3 H) 6.95 (dd, J=8.84, 2.53 Hz, 1 H) 4.07 (s, 3 H) 3.26 (s, 3 H) 2.88 (s, 2 H) 1.48 (s, 6 H); LCMS for $C_{21}H_{21}ClN_4O_5S$ m/z 476.8, 477.80, and 478.70 (M+H$^+$); Anal. Calcd. for $C_{21}H_{21}ClN_4O_5S \cdot 0.65$ TFA: C, 48.61; H, 3.96; N, 10.17; Found: C, 48.41; H, 4.07; N, 10.51.

Preparation of Intermediate 119a 4-(2-Chloro-4-methanesulfonyl-phenoxy)-2,2-dimethyl-2,3-dihydro-benzofuran-6-carboxylic acid methyl ester

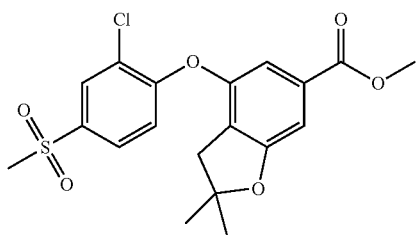

The title compound was prepared in a similar manner as described for Intermediate 118a, from 3-chloro-4-fluoro-1-(methylsulfonyl)benzene and 4-hydroxy-2,2-dimethyl-2,3-dihydro-benzofuran-6-carboxylic acid methyl ester (3e). $^1$H NMR (400 MHz, CDCl$_3$) δ 8.07 (d, J=2.27 Hz, 1 H) 7.77 (dd, J=8.59, 2.27 Hz, 1 H) 7.29 (d, J=1.01 Hz, 1 H) 7.18 (d, J=1.26 Hz, 1 H) 6.98 (d, J=8.59 Hz, 1 H) 3.88 (s, 3 H) 3.10 (s, 3 H) 2.93 (s, 2 H) 1.50 (s, 6 H); LCMS for $C_{19}H_{19}ClO_6S$ m/z 411.00 (M+H)$^+$.

Preparation of Intermediate 119b 4-(2-Chloro-4-methanesulfonyl-phenoxy)-2,2-dimethyl-2,3-dihydro-benzofuran-6-carboxylic acid

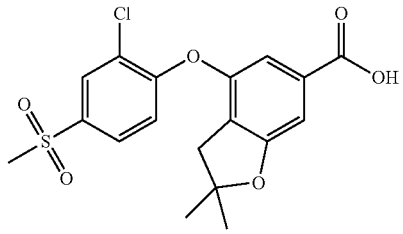

The title compound was prepared in a similar manner as described for Intermediate 15a, from 4-(2-chloro-4-methanesulfonyl-phenoxy)-2,2-dimethyl-2,3-dihydro-benzofuran-6-carboxylic acid methyl ester (119a). $^1$H NMR (400 MHz, CDCl$_3$) δ 8.08 (d, J=2.27 Hz, 1 H) 7.78 (dd, J=8.59, 2.27 Hz, 1 H) 7.34 (d, J=1.26 Hz, 1 H) 7.23 (d, J=1.26 Hz, 1 H) 7.00 (d, J=8.59 Hz, 1 H) 3.11 (s, 3 H) 2.95 (s, 2 H) 1.52 (s, 6 H); LCMS for $C_{18}H_{17}ClO_6S$ m/z 397.00 (M+H)$^+$.

Examples 120, 121, 124-130, 139-141 were prepared in a similar manner as described for Example 1, from the corresponding methyl ester intermediates and the appropriate amino heterocycles.

Examples 122 and 123 were prepared in a similar manner as described for Intermediate 1f, from 4-hydroxy-2,2-dimethyl-2,3-dihydro-benzofuran-6-carbo-xylic acid (1-methyl-1H-pyrazol-3-yl)-amide (31a) and the appropriate fluorophenyl intermediates.

Examples 131-138 were prepared in a similar manner as described for Example 15, from the corresponding carboxylic acid intermediates and the appropriate amino heterocycles. The appropriate carboxylic acid intermediates were prepared in a similar manner as described for Intermediate 35c, from the corresponding methyl ester intermediates.

Example 120

4-(2-Fluoro-4-methanesulfonyl-phenoxy)-2,2-dimethyl-2,3-dihydro-benzofuran-6-carboxylic acid (5-methyl-pyridin-2-yl)-amide

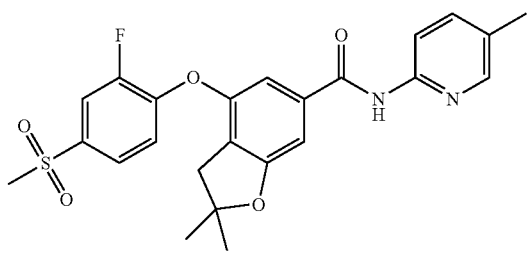

Example 121

4-(2-Fluoro-4-methanesulfonyl-phenoxy)-2,2-dimethyl-2,3-dihydro-benzofuran-6-carboxylic acid (1-methyl-1H-pyrazol-3-yl)-amide

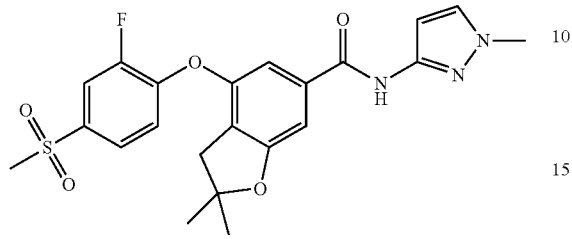

Example 122

4-(4-Dimethylsulfamoyl-phenoxy)-2,2-dimethyl-2,3-dihydro-benzofuran-6-carboxylic acid (1-methyl-1H-pyrazol-3-yl)-amide

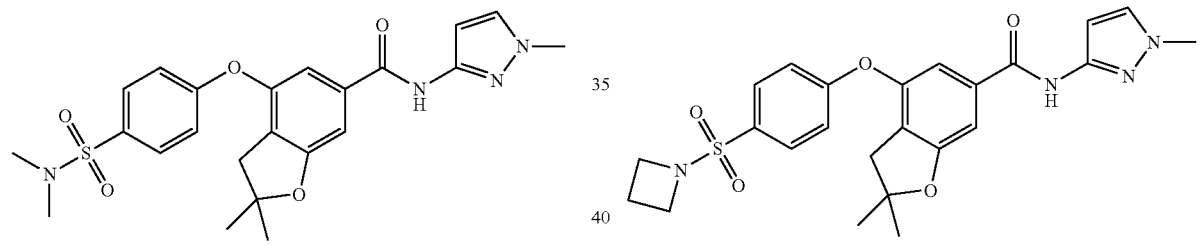

Example 123

4-(4-Cyclobutanesulfonyl-phenoxy)-2,2-dimethyl-2,3-dihydro-benzofuran-6-carboxylic acid (1-methyl-1H-pyrazol-3-yl)-amide

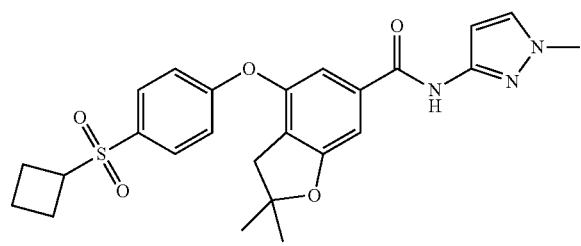

Example 124

4-[4-(Azetidine-1-sulfonyl)-phenoxy]-2,2-dimethyl-2,3-dihydro-benzofuran-6-carboxylic acid (5-methyl-pyridin-2-yl)-amide

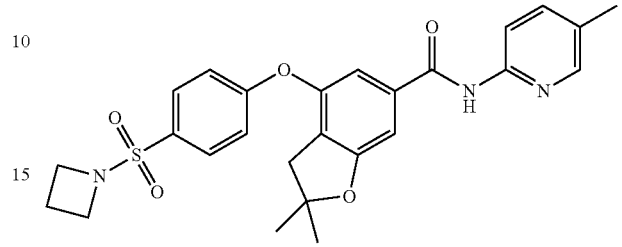

Example 125

4-[4-(Azetidine-1-sulfonyl)-phenoxy]-2,2-dimethyl-2,3-dihydro-benzofuran-6-carboxylic acid (1-methyl-1H-pyrazol-3-yl)-amide

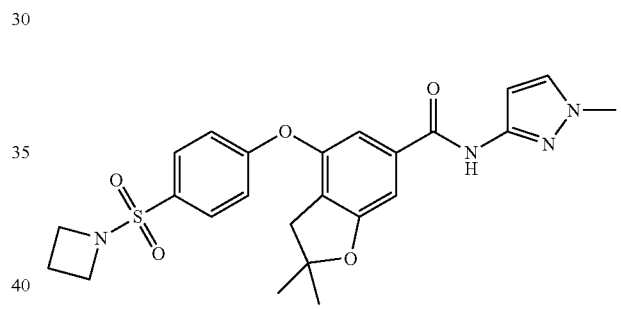

Example 126

4-(4-Ethanesulfonyl-phenoxy)-2,2-dimethyl-2,3-dihydro-benzofuran-6-carboxylic acid (5-methyl-pyridin-2-yl)-amide

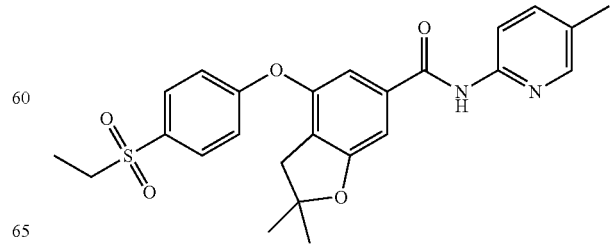

Example 127

4-(4-Ethanesulfonyl-phenoxy)-2,2-dimethyl-2,3-dihydro-benzofuran-6-carboxylic acid (1-methyl-1H-pyrazol-3-yl)-amide

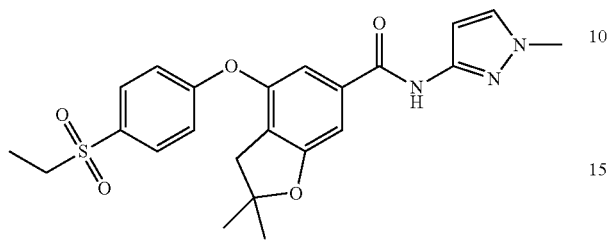

Example 128

4-(4-Dimethylsulfamoyl-phenoxy)-2,2-dimethyl-2,3-dihydro-benzofuran-6-carboxylic acid (5-methyl-pyridin-2-yl)-amide

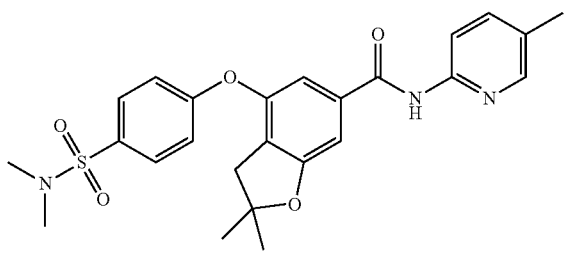

Example 129

4-(4-Cyclopropanesulfonyl-phenoxy)-2,2-dimethyl-2,3-dihydro-benzofuran-6-carboxylic acid (1-methyl-1H-pyrazol-3-yl)-amide

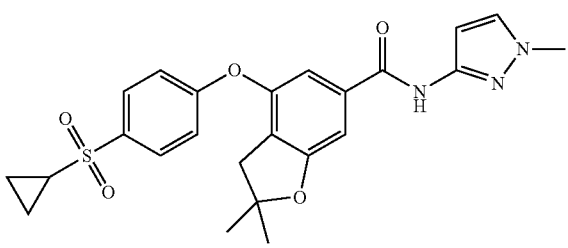

Example 130

4-(4-Dimethylsulfamoyl-3-fluoro-phenoxy)-2,2-dimethyl-2,3-dihydro-benzofuran-6-carboxylic acid (1-methyl-1H-pyrazol-3-yl)-amide

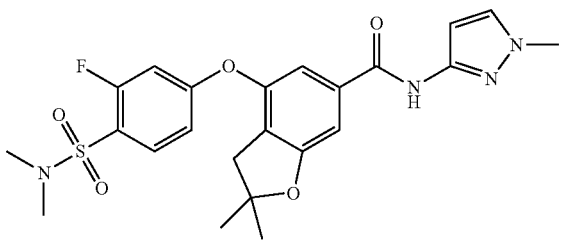

Example 131

4-(4-Cyclopropanesulfonyl-phenoxy)-2,2-dimethyl-2,3-dihydro-benzofuran-6-carboxylic acid (2-methyl-2H-[1,2,3]triazol-4-yl)-amide

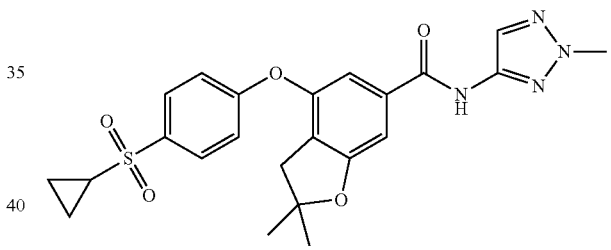

Example 132

4-(4-Dimethylsulfamoyl-3-fluoro-phenoxy)-2,2-dimethyl-2,3-dihydro-benzofuran-6-carboxylic acid (2-methyl-2H-[1,2,3]triazol-4-yl)-amide

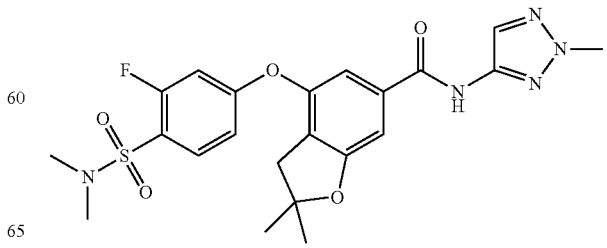

Example 133

4-(4-Ethanesulfonyl-phenoxy)-2,2-dimethyl-2,3-dihydro-benzofuran-6-carboxylic acid (2-methyl-2H-[1,2,3]triazol-4-yl)-amide

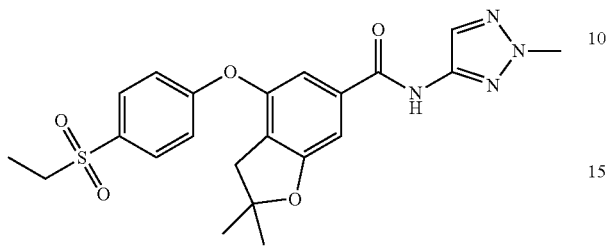

Example 134

4-(4-Dimethylsulfamoyl-phenoxy)-2,2-dimethyl-2,3-dihydro-benzofuran-6-carboxylic acid (2-methyl-2H-[1,2,3]triazol-4-yl)-amide

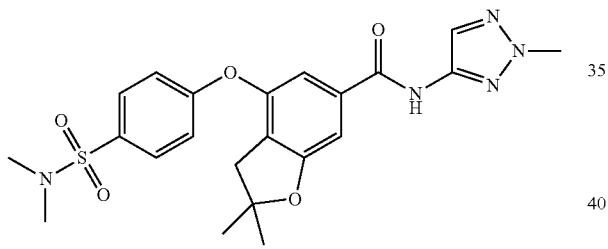

Example 135

4-(4-Ethanesulfonyl-3-fluoro-phenoxy)-2,2-dimethyl-2,3-dihydro-benzofuran-6-carboxylic acid (2-methyl-2H-[1,2,3]triazol-4-yl)-amide

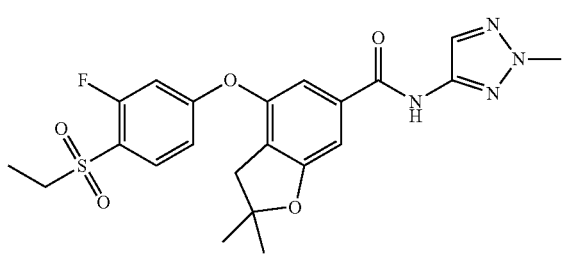

Example 136

4-(4-Ethanesulfonyl-3-fluoro-phenoxy)-2,2-dimethyl-2,3-dihydro-benzofuran-6-carboxylic acid (1-methyl-1H-pyrazol-3-yl)-amide

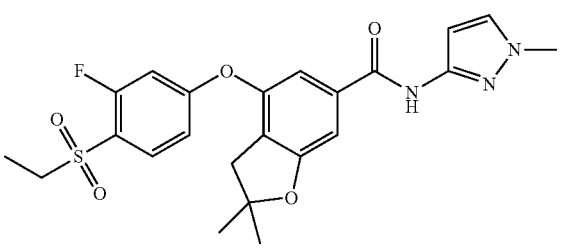

Example 137

4-(2-Chloro-4-methanesulfonyl-phenoxy)-2,2-dimethyl-2,3-dihydro-benzofuran-6-carboxylic acid (1-methyl-1H-pyrazol-3-yl)-amide

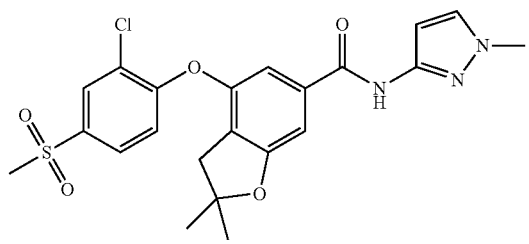

Example 138

4-(4-Dimethylsulfamoyl-2,5-difluoro-phenoxy)-2,2-dimethyl-2,3-dihydro-benzofuran-6-carboxylic acid (2-methyl-2H-[1,2,3]triazol-4-yl)-amide

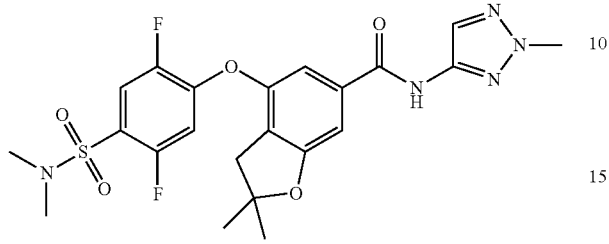

Example 139

4-(3-Chloro-4-methanesulfonyl-phenoxy)-2,2-dimethyl-2,3-dihydro-benzofuran-6-carboxylic acid (1-methyl-1H-pyrazol-3-yl)-amide

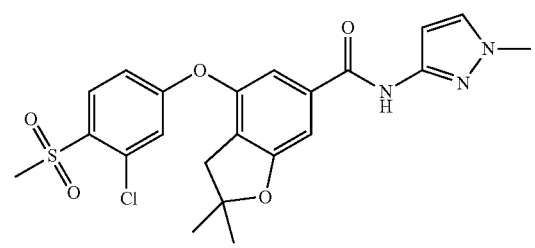

Example 140

4-(4-Cyclopropanesulfonyl-3-fluoro-phenoxy)-2,2-dimethyl-2,3-dihydro-benzofuran-6-carboxylic acid (2-methyl-2H-[1,2,3]triazol-4-yl)-amide

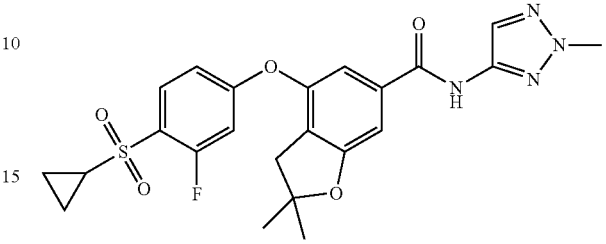

Example 141

4-(4-Cyclopropanesulfonyl-3-fluoro-phenoxy)-2,2-dimethyl-2,3-dihydro-benzofuran-6-carboxylic acid (1-methyl-1H-pyrazol-3-yl)-amide

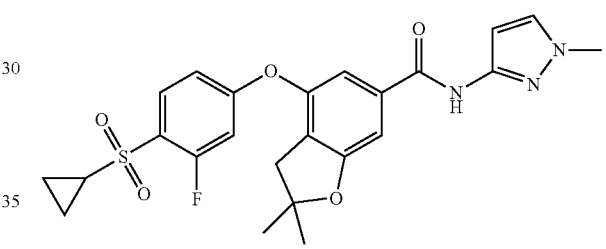

| Example | MW | MF | NMR | m/z | Elemental Analysis |
|---|---|---|---|---|---|
| 120 | 470.5 | C24H23FN2O5S | $^1$H NMR (400 MHz, CDCl$_3$) δ 8.41 (s, 1 H) 8.21 (d, J = 8.59 Hz, 1 H) 8.11 (s, 1 H) 7.80 (dd, J = 9.60, 2.02 Hz, 1 H) 7.70 (d, J = 8.59 Hz, 1 H) 7.56 (dd, J = 8.59, 2.02 Hz, 1 H) 7.09-7.15 (m, 2 H) 7.03 (s, 1 H) 3.11 (s, 3 H) 2.99 (s, 2 H) 2.32 (s, 3 H) 1.53 (s, 6 H); | 471.00 (M + H)$^+$ | Calcd. for C$_{24}$H$_{23}$FN$_2$O$_5$S•0.23 H$_2$O: C, 60.73; H, 4.98; N, 5.90; Found: C, 60.74; H, 4.93; N, 5.91. |
| 121 | 459.5 | C22H22FN3O5S | $^1$H NMR (400 MHz, CDCl$_3$) δ 8.39 (s, 1 H) 7.79 (dd, J = 9.60, 2.27 Hz, 1 H) 7.68-7.72 (m, 1 H) 7.28 (d, J = 2.27 Hz, 1 H) 7.10-7.16 (m, 1 H) 7.04 (s, 1 H) 6.98 (s, 1 H) 6.76 (d, J = 2.27 Hz, 1 H) 3.80 (s, 3 H) 3.11 (s, 3 H) 2.99 (s, 2 H) 1.52 (s, 6 H); | 460.00 (M + H)$^+$ | Calcd. for C$_{22}$H$_{22}$FN$_3$O$_5$S•0.44 H$_2$O: C, 56.53; H, 4.93; N, 8.99; Found: C, 56.53; H, 4.87; N, 8.81 |
| 122 | 470.6 | C23H26N4O5S | $^1$H NMR (400 MHz, CDCl$_3$) δ 8.92 (s, 1 H) 7.73-7.78 (m, 2 H) 7.29 (d, J = 2.27 Hz, 1 H) 7.13 (s, 2 H) 7.07-7.11 (m, 2 H) 6.81 (d, J = 2.27 Hz, 1 H) 3.81 (s, 3 H) 2.90 (s, 2 H) 2.74 (s, 6 H) 1.50 (s, 6 H); | 471.00 (M + H)$^+$ | Calcd. for C$_{23}$H$_{26}$N$_4$O$_5$S•0.54 AcOH: C, 57.54; H, 5.56; N, 11.11; Found: C, 57.50; H, 5.64; N, 11.14. |
| 123 | 481.6 | C25H27N3O5S | $^1$H NMR (400 MHz, CDCl$_3$) δ 8.37 (s, 1 H) 7.84 (ddd, J = 9.22, 2.78, 2.40 Hz, 2 H) 7.29 (d, J = 2.27 Hz, 1 H) 7.05-7.09 (m, 4 H) 6.78 (d, J = 2.27 Hz, 1 H) 3.81 (s, 3 H) 2.89 (s, 2 H) 2.53-2.63 (m, 2 H) 2.18-2.27 (m, 2 H) 1.97-2.05 (m, 2 H) 1.50 (s, 6 H); | 482.00 (M + H)$^+$ | Calcd. for C$_{25}$H$_{27}$N$_3$O$_5$S•0.46 H$_2$O: C, 61.30; H, 5.74; N, 8.58; Found: C, 61.30; H, 5.43; N, 8.30. |
| 124 | 493.6 | C26H27N3O5S | $^1$H NMR (400 MHz, CDCl$_3$) δ 8.40 (s, 1 H) 8.22 (d, J = 8.59 Hz, 1 H) 8.11 (d, J = 2.27 Hz, 1 H) 7.81-7.85 (m, 2 H) 7.57 (dd, J = 8.46, 2.15 Hz, 1 H) 7.11-7.14 (m, 3 H) 7.09-7.11 (m, 1 H) 3.82 (t, J = 7.71 Hz, 4 | 494.00 (M + H)$^+$ | Calcd. for C$_{26}$H$_{27}$N$_3$O$_5$S•0.1 EtOAc: C, 63.25; H, 5.38; N, 8.17; Found: C, 63.12; H, 5.58; N, 8.36. |

| Example | MW | MF | NMR | m/z | Elemental Analysis |
|---|---|---|---|---|---|
| 125 | 482.6 | C24H26N4O5S | H) 2.91 (s, 2 H) 2.32 (s, 3 H) 2.09-2.18 (m, 2 H) 1.51 (s, 6 H); <br> $^1$H NMR (400 MHz, CDCl$_3$) δ 8.35 (s, 1 H) 7.80-7.85 (m, 2 H) 7.29 (d, J = 2.02 Hz, 1 H) 7.10-7.13 (m, 1 H) 7.10 (d, J = 1.77 Hz, 2 H) 7.07 (s, 1 H) 6.78 (d, J = 2.27 Hz, 1 H) 3.79-3.84 (m, 7 H) 2.91 (s, 2 H) 2.09-2.18 (m, 2 H) 1.50 (s, 6 H); | 483.00 (M + H)$^+$ | Calcd. for C$_{24}$H$_{26}$N$_4$O$_5$S•0.24 EtOAc: C, 59.49; H, 5.40; N, 11.12; Found: C, 59.49; H, 5.40; N, 11.12. |
| 126 | 466.6 | C25H26N2O5S | $^1$H NMR (400 MHz, CDCl$_3$) δ 8.41 (s, 1 H) 8.22 (d, J = 8.34 Hz, 1 H) 8.11 (d, J = 2.27 Hz, 1 H) 7.88 (ddd, J = 9.22, 2.78, 2.40 Hz, 2 H) 7.57 (dd, J = 8.46, 2.15 Hz, 1 H) 7.14 (d, J = 1.26 Hz, 1 H) 7.08-7.12 (m, 3 H) 3.14 (q, J = 7.33 Hz, 2 H) 2.90 (s, 2 H) 2.32 (s, 3 H) 1.50 (s, 6 H) 1.32 (t, J = 7.45 Hz, 3 H); | 467.00 (M + H)$^+$ | Calcd. for C$_{25}$H$_{26}$N$_2$O$_5$S•0.11 H$_2$O: C, 64.09; H, 5.59; N, 5.92; Found: C, 64.09; H, 5.59; N, 5.92. |
| 127 | 455.5 | C23H25N3O5S | $^1$H NMR (400 MHz, CDCl$_3$) δ 8.36 (s, 1 H) 7.85-7.90 (m, 2 H) 7.29 (d, J = 2.27 Hz, 1 H) 7.11 (s, 1 H) 7.09 (s, 1 H) 7.07 (d, J = 2.53 Hz, 2 H) 6.78 (d, J = 2.27 Hz, 1 H) 3.81 (s, 3 H) 3.14 (q, J = 7.33 Hz, 2 H) 2.90 (s, 2 H) 1.50 (s, 6 H) 1.32 (t, J = 7.45 Hz, 3 H); | 456.00 (M + H)$^+$ | Calcd. for C$_{23}$H$_{25}$N$_3$O$_5$S•0.25 H$_2$O: C, 60.10; H, 5.55; N, 8.95; Found: C, 60.05; H, 5.59; N, 9.13. |
| 128 | 481.6 | C25H27N3O5S | $^1$H NMR (400 MHz, CDCl$_3$) δ 8.41 (s, 1 H) 8.22 (d, J = 8.34 Hz, 1 H) 8.11 (d, J = 2.02 Hz, 1 H) 7.74-7.79 (m, 2 H) 7.57 (dd, J = 8.46, 2.15 Hz, 1 H) 7.12 (dd, J = 10.61, 1.26 Hz, 2 H) 7.07-7.10 (m, 2 H) 2.90 (s, 2 H) 2.74 (s, 6 H) 2.32 (s, 3 H) 1.51 (s, 6 H); | 482.00 (M + H)$^+$ | Calcd. for C$_{25}$H$_{27}$N$_3$O$_5$S•0.12 EtOAc: C, 62.19; H, 5.73; N, 8.54; Found: C, 62.24; H, 5.67; N, 8.48. |
| 129 | 467.5 | C24H25N3O5S | $^1$H NMR (400 MHz, CDCl$_3$) δ 8.38 (s, 1 H) 7.87 (d, J = 8.84 Hz, 2 H) 7.28 (d, J = 2.27 Hz, 1 H) 7.10 (s, 1 H) 7.08 (s, 1 H) 7.06 (d, J = 1.26 Hz, 2 H) 6.78 (d, J = 2.02 Hz, 1 H) 3.81 (s, 3 H) 2.91 (s, 2 H) 2.49 (ddd, J = 12.76, 7.96, 4.80 Hz, 1 H) 1.50 (s, 6 H) 1.36 (dt, J = 6.76, 4.71 Hz, 2 H) 1.03-1.11 (m, 2 H); | 468.00 (M + H)$^+$ | Calcd. for C$_{24}$H$_{25}$N$_3$O$_5$S•0.16 H2O: C, 61.28; H, 5.43; N, 8.93; Found: C, 61.23; H, 5.29; N, 8.77. |
| 130 | 488.5 | C23H25FN4O5S | $^1$H NMR (400 MHz, CDCl$_3$) δ 10.17 (s, 1 H) 7.81 (t, J = 8.21 Hz, 1 H) 7.48 (s, 1 H) 7.24 (s, 1 H) 7.02 (s, 1 H) 6.83 (d, J = 8.84 Hz, 1 H) 6.75-6.80 (m, 1 H) 4.00 (s, 3 H) 2.90 (s, 2 H) 2.85 (d, J = 1.26 Hz, 6 H) 1.49 (s, 6 H); | 489.00 (M + H)$^+$ | Calcd. for C$_{23}$H$_{25}$FN$_4$O$_5$S: C, 56.55; H, 5.16; N, 11.47; Found: C, 56.65; H, 5.11; N, 11.27. |
| 131 | 468.5 | C23H24N4O5S | $^1$H NMR (400 MHz, CD$_3$OD) δ 7.93 (s, 1 H) 7.90-7.92 (m, 1 H) 7.88-7.90 (m, 1 H) 7.18 (d, J = 1.77 Hz, 2 H) 7.17 (d, J = 2.27 Hz, 2 H) 4.08 (s, 3 H) 2.91 (s, 2 H) 2.63-2.70 (m, 1 H) 1.47 (s, 6 H) 1.22 (ddd, J = 7.01, 4.48, 4.17 Hz, 2 H) 1.02-1.12 (m, 2 H); | 469.10 (M + H)$^+$ | Calcd. for C$_{23}$H$_{24}$N$_4$O$_5$S•1.05 H$_2$O: C, 56.67; H, 5.40; N, 11.49; Found: C, 56.68; H, 5.18; N, 11.36. |
| 132 | 489.5 | C22H24FN5O5S | $^1$H NMR (400 MHz, DMSO-d$_6$) δ 11.21 (s, 1 H) 7.95 (s, 1 H) 7.78 (t, J = 8.46 Hz, 1 H) 7.31 (s, 1 H) 7.29 (s, 1 H) 7.21 (dd, J = 11.62, 2.27 Hz, 1 H) 6.99 (dd, J = 8.84, 2.27 Hz, 1 H) 4.09 (s, 3 H) 2.91 (s, 2 H) 2.72 (s, 3 H) 2.72 (s, 3 H) 1.44 (s, 6 H); | 490.00 (M + H)$^+$ | Calcd. for C$_{22}$H$_{24}$FN$_5$O$_5$S: C, 53.98; H, 4.94; N, 14.31; Found: C, 54.31; H, 5.11; N, 14.20. |
| 133 | 456.5 | C22H24N4O5S | $^1$H NMR (400 MHz, CDCl$_3$) δ 8.33 (s, 1 H) 8.08 (s, 1 H) 7.88 (s, 2 H) 7.09 (s, 4 H) 4.13 (s, 3 H) 2.92 (s, 2 H) 1.49 (s, 6 H) 1.32 (s, 3 H); | 457.00 (M + H)$^+$ | |
| 134 | 471.5 | C22H25N5O5S | $^1$H NMR (400 MHz, CDCl$_3$) δ 8.30 (s, 1 H) 8.08 (s, 1 H) 7.73-7.80 (m, 1 H) 7.77 (d, J = 8.84 Hz, 1 H) 7.09 (d, J = 1.01 Hz, 1 H) 7.10 (s, 1 H) 7.08 (s, 1 H) 7.05-7.07 (m, 1 H) 4.12 (s, 3 H) 2.91 (s, 2 H) 2.74 (s, 6 H) 1.51 (s, 6 H); | 472.00 (M + H)$^+$ | |
| 135 | 474.5 | C22H23FN4O5S | $^1$H NMR (400 MHz, CDCl$_3$) δ 8.32 (s, 1 H) 8.09 (s, 1 H) 7.86-7.93 (m, 1 H) 7.06-7.13 (m, 2 H) 6.88 (dd, J = 8.59, 2.27 Hz, 1 H) 6.80 (dd, J = 10.99, 2.40 Hz, 1 H) 4.13 (s, 3 H) 3.32 (q, J = 7.58 Hz, 2 H) 2.91 (s, 2 H) 1.51 (s, 6 H) 1.34 (t, J = 7.45 Hz, 3 H); | 475.00 (M + H)$^+$ | Calcd. for C$_{22}$H$_{23}$FN$_4$O$_5$S: C, 55.43; H, 4.91; N, 11.75; Found: C, 55.44; H, 4.93; N, 11.80. |
| 136 | 473.5 | C23H24FN3O5S | $^1$H NMR (400 MHz, CDCl$_3$) δ 8.33 (s, 1 H) 7.89 (t, J = 8.21 Hz, 1 H) 7.30 (s, 1 H) 7.10 (s, 2 H) 6.84-6.91 (m, 1 H) | 474.20 (M + H)$^+$ | Calcd. for C$_{23}$H$_{24}$FN$_3$O$_5$S: C, 58.34; H, 5.11; N, 8.87; Found: C, 58.34; H, 5.12; N, |

-continued

| Example | MW | MF | NMR | m/z | Elemental Analysis |
|---|---|---|---|---|---|
| | | | 6.74-6.83 (m, 2 H) 3.82 (s, 3 H) 3.32 (q, J = 7.49 Hz, 2 H) 2.90 (s, 2 H) 1.51 (s, 6 H) 1.34 (t, J = 7.45 Hz, 3 H); | | 8.88. |
| 137 | 476 | C22H22ClN3O5S | $^1$H NMR (400 MHz, CD$_3$OD) δ 8.11 (d, J = 2.27 Hz, 1 H) 7.86 (dd, J = 8.59, 2.27 Hz, 1 H) 7.47 (d, J = 2.27 Hz, 1 H) 7.15 (d, J = 8.84 Hz, 2 H) 7.07 (d, J = 1.26 Hz, 1 H) 6.55 (d, J = 2.27 Hz, 1 H) 3.80 (s, 3 H) 3.15 (s, 3 H) 2.94 (s, 2 H) 1.48 (s, 6 H); | 478.00 (M + H)$^+$ | Calcd. for C$_{22}$H$_{22}$ClN$_3$O$_5$S•0.35 H$_2$O•0.75 AcOH: C, 53.53; H, 4.91; N, 7.97; Found: C, 53.52; H, 4.98; N, 8.15. |
| 138 | 507.5 | C22H23F2N5O5S | $^1$H NMR (400 MHz, CD$_3$OD) δ 7.96 (s, 1 H) 7.76 (dd, J = 9.98, 6.19 Hz, 1 H) 7.22 (d, J = 1.26 Hz, 1 H) 7.16 (s, 1 H) 7.08 (dd, J = 10.48, 6.44 Hz, 1 H) 4.11 (s, 3 H) 3.04 (s, 2 H) 2.84 (d, J = 1.77 Hz, 6 H) 1.52 (s, 6 H); | 508.00 (M + H)$^+$ | Calcd. for C$_{22}$H$_{23}$F$_2$N$_5$O$_5$S•1.25 H$_2$O: C, 49.85; H, 4.85; N, 13.21; Found: C, 49.49; H, 4.47; N, 13.09. |
| 139 | 476 | C22H22ClN3O5S | $^1$H NMR (400 MHz, CD$_3$OD) δ 8.10 (d, J = 8.84 Hz, 1 H) 7.48 (d, J = 2.27 Hz, 1 H) 7.26 (d, J = 2.53 Hz, 1 H) 7.18 (d, J = 10.86 Hz, 2 H) 7.09 (dd, J = 8.84, 2.27 Hz, 1 H) 6.56 (d, J = 2.27 Hz, 1 H) 3.81 (s, 3 H) 3.28 (s, 3 H) 2.91 (s, 2 H) 1.47 (s, 6 H); | 476.00 (M + H)$^+$ | |
| 140 | 486.5 | C23H23FN4O5S | $^1$H NMR (400 MHz, CD$_3$OD) δ 7.94 (s, 1 H) 7.82-7.89 (m, 1 H) 7.19-7.22 (m, 2 H) 6.93-7.02 (m, 2 H) 4.09 (s, 3 H) 2.93 (s, 2 H) 2.83 (ddd, J = 8.84, 4.04, 1.26 Hz, 1 H) 1.48 (s, 6 H) 1.21-1.31 (m, 2 H) 1.07-1.16 (m, 2 H); | 487.20 (M + H)$^+$ | Calcd. for C$_{23}$H$_{23}$FN$_4$O$_5$S•0.24 H2O: C, 56.28; H, 4.82; N, 11.41; Found: C, 56.29; H, 4.74; N, 11.31. |
| 141 | 485.5 | C24H24FN3O5S | $^1$H NMR (400 MHz, CDCl$_3$) δ 8.44 (s, 1 H) 7.85 (t, J = 8.34 Hz, 1 H) 7.29 (d, J = 2.27 Hz, 1 H) 7.08 (s, 2 H) 6.85 (dd, J = 8.84, 2.27 Hz, 1 H) 6.77-6.82 (m, 2 H) 3.80 (s, 3 H) 2.91 (s, 2 H) 2.74 (dd, J = 12.00, 3.66 Hz, 1 H) 1.51 (s, 6 H) 1.40 (dd, J = 4.67, 2.15 Hz, 2 H) 1.10 (dd, J = 7.71, 1.89 Hz, 2 H); | 486.00 (M + H)$^+$ | Calcd. for C$_{24}$H$_{24}$FN$_3$O$_5$S•0.27 H$_2$O: C, 58.70; H, 5.04; N, 8.55; Found: C, 58.71; H, 5.19; N, 8.42. |

The appropriate methyl ester intermediates to the above compounds were prepared in a similar manner as described for Intermediate 1f, from 4-hydroxy-2,2-dimethyl-2,3-dihydrobenzofuran-6-carboxylic acid methyl ester (3e) and the appropriate fluorophenyl sulfones or sulfonamides.

| # | Structure | Name | NMR | m/z |
|---|---|---|---|---|
| 120a | 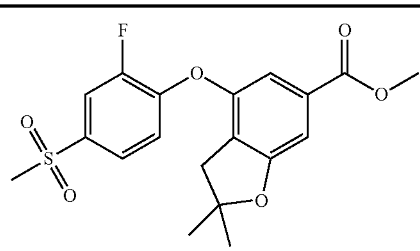 | 4-(2-Fluoro-4-methanesulfonyl-phenoxy)-2,2-dimethyl-6-carboxylic acid methyl ester | $^1$H NMR (400 MHz, CDCl$_3$) δ 7.79 (dd, J = 9.60, 2.02 Hz, 1 H) 7.69 (dd, J = 8.46, 1.14 Hz, 1 H) 7.25-7.28 (m, 1 H) 7.16 (s, 1 H) 7.08 (t, J = 8.08 Hz, 1 H) 3.88 (s, 3 H) 3.10 (s, 3 H) 2.97 (s, 2 H) 1.51 (s, 6 H); | 395.00 (M + H)$^+$ |
| 124a | 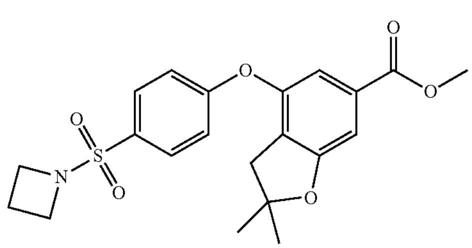 | 4-[4-(Azetidine-1-sulfonyl)-phenoxy]-2,2-dimethyl-2,3-dihydro-benzofuran-6-carboxylic acid methyl ester | $^1$H NMR (400 MHz, CDCl$_3$) δ 7.82 (d, J = 8.84 Hz, 2 H) 7.28 (s, 1 H) 7.27 (s, 1 H) 7.09 (d, J = 8.84 Hz, 2 H) 3.89 (s, 3 H) 3.81 (t, J = 7.58 Hz, 4 H) 2.90 (s, 2 H) 2.08-2.17 (m, 2 H) 1.49 (s, 6 H); | 418.00 (M + H)$^+$ |

-continued

| # | Structure | Name | NMR | m/z |
|---|---|---|---|---|
| 126a | 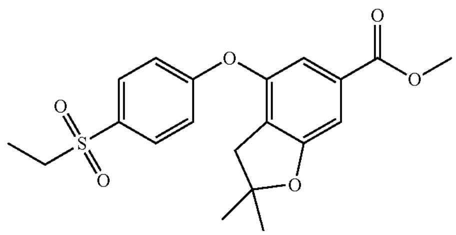 | 4-(4-Ethanesulfonyl-phenoxy)-2,2-dimethyl-2,3-dihydro-benzofuran-6-carboxylic acid methyl ester | $^1$H NMR (400 MHz, CDCl$_3$) δ 7.87 (d, J = 8.84 Hz, 2 H) 7.27 (s, 1 H) 7.24 (s, 1 H) 7.07 (d, J = 8.84 Hz, 2 H) 3.88 (s, 3 H) 3.13 (q, J = 7.33 Hz, 2 H) 2.88 (s, 2 H) 1.48 (s, 6 H) 1.31 (t, J = 7.45 Hz, 3 H); | 391.00 (M + H)$^+$ |
| 128a | 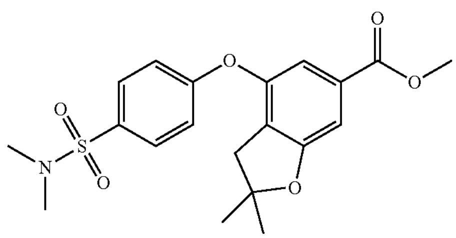 | 4-(4-Dimethylsulfamoyl-phenoxy)-2,2-dimethyl-2,3-dihydro-benzofuran-6-carboxylic acid methyl ester | $^1$H NMR (400 MHz, CDCl$_3$) δ 7.75 (d, J = 8.84 Hz, 2 H) 7.27 (d, 1 H) 7.24 (d, J = 1.26 Hz, 1 H) 7.06 (d, J = 8.84 Hz, 2 H) 3.88 (s, 3 H) 2.89 (s, 2 H) 2.73 (s, 6 H) 1.49 (s, 6 H); | 406.00 (M + H)$^+$ |
| 129a | 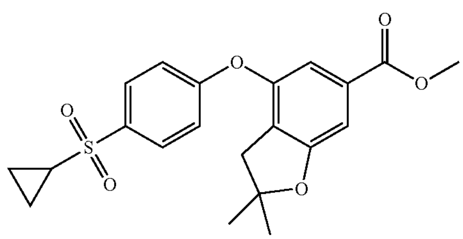 | 4-(4-Cyclopropanesulfonyl-phenoxy)-2,2-dimethyl-2,3-dihydro-benzofuran-6-carboxylic acid methyl ester | $^1$H NMR (400 MHz, CDCl$_3$) δ 7.86 (d, J = 8.84 Hz, 2 H) 7.26-7.28 (m, 1 H) 7.24 (s, 1 H) 7.07 (d, J = 8.84 Hz, 2 H) 3.85-3.91 (m, 3 H) 2.89 (s, 2 H) 2.48 (tt, J = 7.96, 4.80 Hz, 1 H) 1.49 (s, 6 H) 1.35 (dt, J = 6.57, 4.67 Hz, 2 H) 1.02-1.10 (m, 2 H); | 403.00 (M + H)$^+$ |
| 130a | 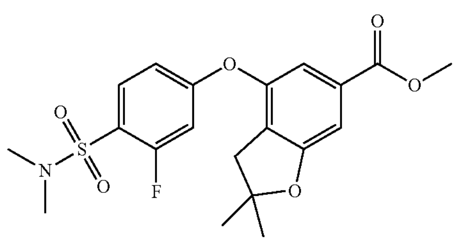 | 4-(4-Dimethylsulfamoyl-3-fluoro-phenoxy)-2,2-dimethyl-2,3-dihydro-benzofuran-6-carboxylic acid methyl ester | $^1$H NMR (400 MHz, CDCl$_3$) δ 7.78-7.84 (m, 1 H) 7.30 (d, J = 1.01 Hz, 1 H) 7.26 (d, J = 1.26 Hz, 1 H) 6.81 (dd, J = 8.72, 2.40 Hz, 1 H) 6.75 (dd, J = 11.12, 2.27 Hz, 1 H) 3.90 (s, 3 H) 2.89 (s, 2 H) 2.85 (s, 3 H) 2.84 (s, 3 H) 1.49 (s, 6 H); | 424.00 (M + H)$^+$ |
| 135a | 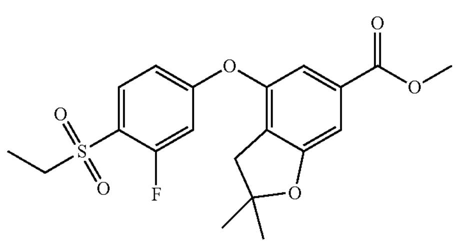 | 4-(4-Ethanesulfonyl-3-fluoro-phenoxy)-2,2-dimethyl-2,3-dihydro-benzofuran-6-carboxylic acid methyl ester | $^1$H NMR (400 MHz, CDCl$_3$) δ 7.87 (d, J = 8.08 Hz, 1 H) 7.31 (d, J = 1.26 Hz, 1 H) 7.27 (d, J = 1.26 Hz, 1 H) 6.85 (dd, J = 8.72, 2.15 Hz, 1 H) 6.77 (dd, J = 11.12, 2.27 Hz, 1 H) 3.90 (s, 3 H) 3.31 (q, J = 7.33 Hz, 2 H) 2.88 (s, 2 H) 1.49 (s, 6 H) 1.27 (t, J = 7.20 Hz, 3 H); | 409.00 (M + H)$^+$ |
| 138a | 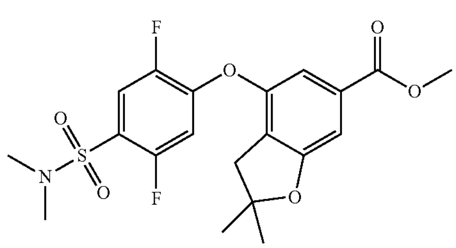 | 4-(4-Dimethylsulfamoyl-2,5-difluoro-phenoxy)-2,2-dimethyl-2,3-dihydro-benzofuran-6-carboxylic acid methyl ester | $^1$H NMR (400 MHz, CDCl$_3$) δ 7.70 (dd, J = 9.73, 6.19 Hz, 1 H) 7.29 (d, J = 1.26 Hz, 1 H) 7.21 (d, J = 1.26 Hz, 1 H) 6.73 (dd, J = 10.11, 6.32 Hz, 1 H) 3.90 (s, 3 H) 2.97 (s, 2 H) 2.82-2.90 (m, 6 H) 1.51 (s, 6 H); | 442.00 (M + H)$^+$ |

| # | Structure | Name | NMR | m/z |
|---|---|---|---|---|
| 140a | 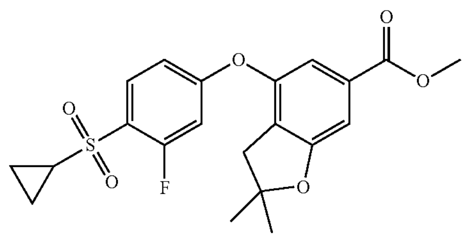 | 4-(4-Cyclopropanesulfonyl-3-fluoro-phenoxy)-2,2-dimethyl-2,3-dihydro-benzofuran-6-carboxylic acid methyl ester | $^1$H NMR (400 MHz, CDCl$_3$) δ 7.81-7.89 (m, 1 H) 7.29-7.33 (m, 1 H) 7.26 (s, 1 H) 6.83 (dd, J = 8.84, 2.27 Hz, 1 H) 6.78 (dd, J = 10.99, 2.40 Hz, 1 H) 3.90 (s, 3 H) 2.89 (s, 2 H) 2.73 (d, J = 1.26 Hz, 1 H) 1.50 (s, 6 H) 1.34-1.43 (m, 2 H) 1.04-1.13 (m, 2 H); | 421.00 (M + H)$^+$ |

Example 142

4-(4-Dimethylcarbamoyl-3-fluoro-phenoxy)-2,2-dimethyl-2,3-dihydro-benzofuran-6-carboxylic acid (2-methyl-2H-[1,2,3]triazol-4-yl)-amide

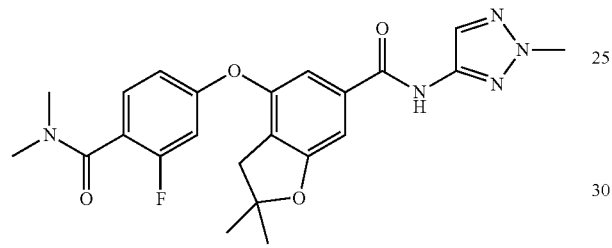

The title compound was prepared in a similar manner as described for Example 1 from 4-(4-dimethylcarbamoyl-3-fluoro-phenoxy)-2,2-dimethyl-2,3-dihydro-benzofuran-6-carboxylic acid methyl ester (142a) (80 mg, 0.21 mmol) to give a white solid (91 mg, 97% yield). $^1$H NMR (400 MHz, CDCl$_3$) δ 8.87 (s, 1 H) 8.06 (s, 1 H) 7.35 (t, J=8.08 Hz, 1 H) 7.08 (s, 2 H) 6.77 (dd, J=8.34, 2.27 Hz, 1 H) 6.66 (dd, J=10.61, 2.27 Hz, 1 H) 4.08 (s, 3 H) 3.11 (s, 3 H) 2.97 (s, 3 H) 2.89 (s, 2 H) 1.48 (s, 6 H); LCMS for C$_{23}$H$_{24}$FN$_5$O$_4$ m/z 454.20 (M+H)$^+$); Anal. Calcd. for C$_{23}$H$_{24}$FN$_5$O$_4$·0.47 H$_2$O: C, 59.80; H, 5.44; N, 15.16; Found: C, 59.77; H, 5.21; N, 15.06.

Preparation of Intermediate 142a

4-(4-Dimethylcarbamoyl-3-fluoro-phenoxy)-2,2-dimethyl-2,3-dihydro-benzofuran-6-carboxylic acid methyl ester

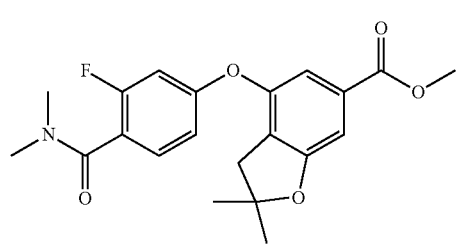

The title compound was prepared in a similar manner as described for Intermediate 35b, from 4-bromo-2-fluoro-N,N-dimethyl-benzamide (589 mg, 2.65 mmol) and 4-hydroxy-2,2-dimethyl-2,3-dihydro-benzofuran-6-carboxylic acid methyl ester (3e) (652 mg, 2.65 mmol) to give a white solid (861 mg, 84% yield). $^1$H NMR (400 MHz, CDCl$_3$) δ 7.33-7.43 (m, 1 H) 7.25 (s, 1 H) 7.22 (s, 1 H) 6.75-6.84 (m, 1 H) 6.66-6.73 (m, 1 H) 3.88 (s, 3 H) 3.13 (s, 3 H) 2.98 (s, 3 H) 2.90 (s, 2 H) 1.49 (s, 6 H); LCMS for C$_{21}$H$_{22}$FNO$_5$ m/z 388.00 (M+H)$^+$.

Example 143

4-(4-Dimethylcarbamoyl-3-fluoro-phenoxy)-2,2-dimethyl-2,3-dihydro-benzofuran-6-carboxylic acid (5-methyl-isoxazol-3-yl)-amide

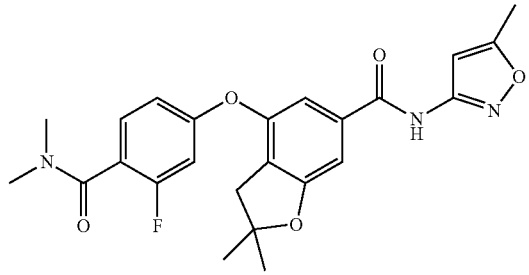

To a solution of 4-(4-dimethylcarbamoyl-3-fluoro-phenoxy)-2,2-dimethyl-2,3-dihydro-benzofuran-6-carboxylic acid (143a) (66 mg, 0.177 mmol) in 3 mL of CH$_2$Cl$_2$ was added thionyl chloride (0.0154 mL, 0.212 mmol), followed by 3 drops of DMF. The mixture was refluxed for 1.5 h, then concentrated and dried under vacuum. The residue was dissolved in 3 mL of CH$_2$Cl$_2$, added 3-amino-5-methylisoxazole (22.6 mg, 0.230 mmol) at 0° C., followed by DMAP (52 mg, 0.354 mmol). The mixture was stirred at 0° C. to room temperature for 1 hr and heated at 40° C. overnight, then concentrated and purified by flash column chromatography with 40-55% EtOAc in hexanes to give a white solid (8 mg, 10% yield). $^1$H NMR (400 MHz, CDCl$_3$) δ 9.06 (s, 1 H) 7.38 (t, J=8.08 Hz, 1 H) 7.11 (d, J=1.77 Hz, 2 H) 6.76-6.84 (m, 2 H) 6.70 (dd, J=10.61, 2.27 Hz, 1 H) 3.13 (s, 3 H) 2.98 (br. s., 3 H)

2.91 (s, 2 H) 2.42 (s, 3 H) 1.50 (s, 6 H); LCMS for $C_{24}H_{24}FN_3O_5$ m/z 454.00 (M+H+).

Preparation of Intermediate 143a 4-(4-Dimethylcarbamoyl-3-fluoro-phenoxy)-2,2-dimethyl-2,3-dihydro-benzofuran-6-carboxylic acid

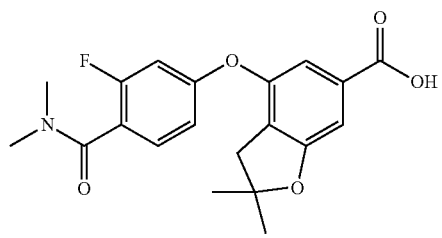

The title compound was prepared in a similar manner as described for Intermediate 15a, from 4-(4-dimethylcarbamoyl-3-fluoro-phenoxy)-2,2-dimethyl-2,3-dihydro-benzofuran-6-carboxylic acid methyl ester (142a). $^1$H NMR (400 MHz, CDCl$_3$)) δ 7.40 (t, J=7.96 Hz, 1 H) 7.27-7.33 (m, 2 H) 6.80 (dd, J=8.34, 2.02 Hz, 1 H) 6.70 (dd, J=10.61, 2.27 Hz, 1 H) 3.10-3.18 (m, 3 H) 3.00 (br. s., 3 H) 2.92 (s, 2 H) 1.49 (s, 6 H); LCMS for $C_{20}H_{20}FNO_5$ m/z 374.00 (M+H).

Example 144

4-(4-Dimethylcarbamoyl-3-fluoro-phenoxy)-2,2-dimethyl-2,3-dihydro-benzofuran-6-carboxylic acid isoxazol-3-ylamide

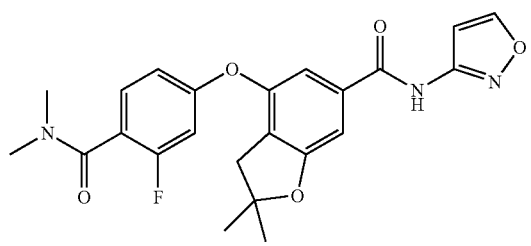

To a solution of 4-(4-dimethylcarbamoyl-3-fluoro-phenoxy)-2,2-dimethyl-2,3-dihydro-benzofuran-6-carboxylic acid (143a) (80 mg, 0.21 mmol), 3-aminoisoxazole (36 mg, 0.429 mmol) and triethylamine (0.0597 mL, 0.4294 mmol) in 2 mL of DMF was added HATU (163 mg, 0.429 mmol). The mixture was stirred at 50° C. overnight, and purified by reverse phase column chromatography to give a white solid (3.3 mg, 4% yield). $^1$H NMR (400 MHz, CDCl$_3$) δ 9.23 (s, 1 H) 7.39 (t, J=8.08 Hz, 1 H) 7.27 (s, 1 H) 7.20 (d, J=1.77 Hz, 1 H) 7.13 (d, J=4.55 Hz, 2 H) 6.82 (dd, J=8.59, 2.27 Hz, 1 H) 6.71 (dd, J=10.61, 2.27 Hz, 1 H) 3.16 (s, 3 H) 3.00 (s, 3 H) 2.92 (s, 2 H) 1.51 (s, 6 H); LCMS for $C_{23}H_{22}FN_3O_5$ m/z 440.20 (M+H+).

Example 145

4-(4-Dimethylcarbamoyl-3-fluoro-phenoxy)-2,2-dimethyl-2,3-dihydro-benzofuran-6-carboxylic acid (5-hydroxymethyl-pyridin-2-yl)-amide

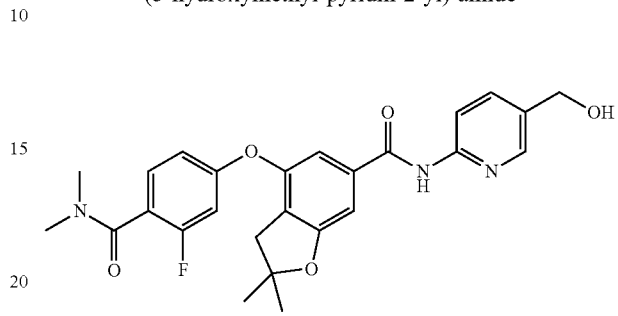

To a solution of 4-(4-dimethylcarbamoyl-3-fluoro-phenoxy)-2,2-dimethyl-2,3-dihydro-benzofuran-6-carboxylic acid (143a) (381 mg, 1.02 mmol), 5-(tert-butyl-dimethyl-silanyloxymethyl)-pyridin-2-ylamine (22a) (365 mg, 1.53 mmol) and triethylamine (0.284 mL, 2.04 mmol) in 5 mL of DMF was added HATU (776 mg, 2.04 mmol). The mixture was stirred at 50° C. overnight, quenched with water, extracted with 3×EtOAc. The combined organic layer was washed with 2×H$_2$O, dried with Na$_2$SO$_4$, concentrated and the resulting oil was purified by Biotage column chromatography with 50-100% EtOAc in hexanes to give a yellow solid (120 mg, 25% yield). $^1$H NMR (400 MHz, CDCl$_3$) δ 8.76 (br. s., 1 H) 8.29 (d, J=8.59 Hz, 1 H) 8.21 (d, J=1.77 Hz, 1 H) 7.74 (dd, J=8.59, 2.27 Hz, 1 H) 7.35 (t, J=8.08 Hz, 1 H) 7.27 (s, 1 H) 7.11 (d, J=5.81 Hz, 1 H) 6.78 (dd, J=8.46, 2.40 Hz, 1 H) 6.68 (dd, J=10.61, 2.27 Hz, 1 H) 4.66 (s, 2 H) 3.11 (s, 3 H) 2.96 (s, 3 H) 2.88 (s, 2 H) 1.48 (s, 6 H); LCMS for $C_{26}H_{26}FN_3O_5$ m/z 480.20 (M+H).

Example 146

6-{[4-(4-Dimethylcarbamoyl-3-fluoro-phenoxy)-2,2-dimethyl-2,3-dihydro-benzofuran-6-carbonyl]-amino}-nicotinamide

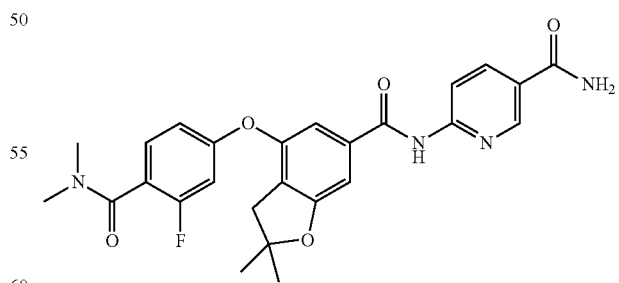

The title compound was prepared in a similar manner as described for Example 144, from 4-(4-dimethylcarbamoyl-3-fluoro-phenoxy)-2,2-dimethyl-2,3-dihydro-benzofuran-6-carboxylic acid (143a) (80 mg, 0.21 mmol) and 6-aminonicotinamide (58.8 mg, 0.429 mmol) to give a brown solid (5 mg, 5% yield). $^1$H NMR (400 MHz, MeOD.) δ 8.82 (d, J=1.52 Hz, 1 H) 8.14-8.32 (m, 2 H) 7.31-7.44 (m, 1 H) 7.18 (dd, J=8.34, 1.26 Hz, 2 H) 6.80-6.97 (m, 2 H) 3.10 (s, 3 H) 2.98 (s, 3 H) 2.93 (s, 2 H) 1.47 (s, 6 H); LCMS for $C_{26}H_{25}FN_4O_5$ m/z 493.20 (M+H$^+$).

Example 147

4-(4-Dimethylcarbamoyl-3-fluoro-phenoxy)-2,2-dimethyl-2,3-dihydro-benzofuran-6-carboxylic acid (5-cyclopropylaminomethyl-pyridin-2-yl)-amide

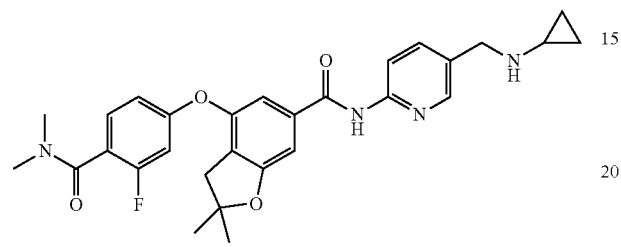

To a solution of 4-(4-dimethylcarbamoyl-3-fluoro-phenoxy)-2,2-dimethyl-2,3-dihydro-benzofuran-6-carboxylic acid (5-formyl-pyridin-2-yl)-amide (147a) (88 mg, 0.18 mmol) in 3 mL of MeOH was added aminocyclopropane (31.6 mg, 0.553 mmol). The mixture was heated at 40° C. for 1 hr, then NaCNBH$_3$ (29 mg, 0.461 mmol) was added. The reaction mixture was heated at 40° C. for 1 hr, and quenched with 14 drops of AcOH, concentrated and purified by reverse phase column chromatography to give a white solid (26 mg, 27% yield). $^1$H NMR (400 MHz, MeOD.) δ 8.38 (d, J=2.02 Hz, 1 H) 8.21 (d, J=8.59 Hz, 1 H) 7.88 (dd, J=8.59, 2.27 Hz, 1 H) 7.40 (t, J=8.08 Hz, 1 H) 7.10-7.24 (m, 2 H) 6.80-6.98 (m, 2 H) 4.08 (s, 2 H) 3.11 (s, 3 H) 2.99 (s, 3 H) 2.94 (s, 2 H) 2.38-2.51 (m, 1 H) 1.48 (s, 6 H) 0.67-0.74 (m, 2 H) 0.58-0.65 (m, 2 H); LCMS for $C_{29}H_{31}FN_4O_4$ m/z 519.20 (M+H$^+$); Anal. Calcd. for $C_{29}H_{31}FN_4O_4$.0.35 TFA.0.9 H$_2$O: C, 62.07; H, 5.81; N, 9.75; Found: C, 61.98; H, 5.95; N, 10.05.

Preparation of Intermediate 147a 4-(4-Dimethylcarbamoyl-3-fluoro-phenoxy)-2,2-dimethyl-2,3-dihydro-benzofuran-6-carboxylic acid (5-formyl-pyridin-2-yl)-amide

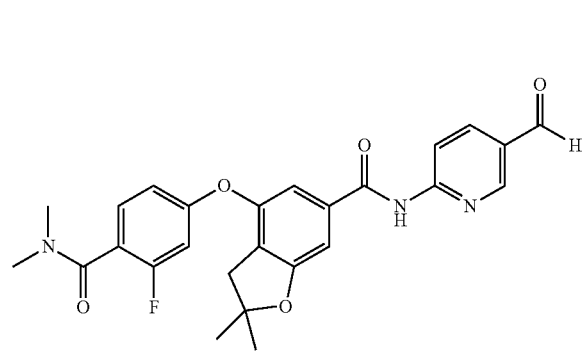

To a solution of 4-(4-Dimethylcarbamoyl-3-fluoro-phenoxy)-2,2-dimethyl-2,3-dihydro-benzofuran-6-carboxylic acid (5-hydroxymethyl-pyridin-2-yl)-amide (145) (88 mg, 0.18 mmol) in 3 mL CH$_2$Cl$_2$ was added Dess-Martin periodinane (93.4 mg, 0.22 mmol) at 0° C. The mixture was stirred at 0° C. for 1.5 hr. The reaction was quenched with water, extracted with 3×CHCl$_3$. The combined organic layer was dried with Na$_2$SO$_4$ and concentrated. The resulting oil was taken into the next step without further purification. LCMS for $C_{26}H_{24}FN_3O_5$ m/z 478.20 (M+H$^+$).

Example 148

4-(4-Dimethylcarbamoyl-3-fluoro-phenoxy)-2,2-dimethyl-2,3-dihydro-benzofuran-6-carboxylic acid (5-methyl-pyridin-2-yl)-amide

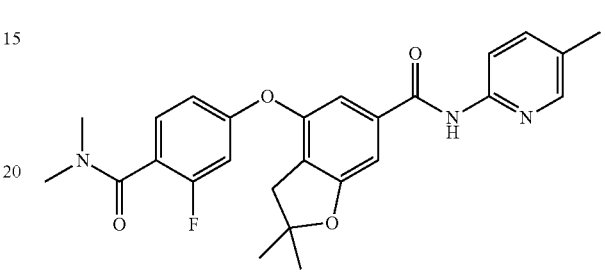

The title compound was prepared in a similar manner as described for Example 144, from 4-(4-dimethylcarbamoyl-3-fluoro-phenoxy)-2,2-dimethyl-2,3-dihydro-benzofuran-6-carboxylic acid (143a) (60 mg, 0.16 mmol) and 2-amino-5-methylpyridine (34.8 mg, 0.321 mmol) to give a brown solid (25 mg, 34% yield). $^1$H NMR (400 MHz, CDCl$_3$) δ 8.98 (br. s., 1 H) 8.19 (d, J=8.34 Hz, 1 H) 8.11 (s, 1 H) 7.66 (dd, J=8.46, 1.89 Hz, 1 H) 7.31-7.43 (m, 1 H) 7.12 (s, 1 H) 7.07 (d, J=1.26 Hz, 1 H) 6.80 (dd, J=8.59, 2.27 Hz, 1 H) 6.69 (dd, J=10.61, 2.27 Hz, 1 H) 3.14 (s, 3 H) 2.98 (s, 3 H) 2.91 (s, 2 H) 2.35 (s, 3 H) 1.50 (s, 6 H); LCMS for $C_{26}H_{26}FN_3O_4$ m/z 464.20 (M+H$^+$); Anal. Calcd. for $C_{26}H_{26}FN_3O_4$.0.27 TFA.1.0 H$_2$O: C, 62.22; H, 5.56; N, 8.20; Found: C, 61.87; H, 5.36; N, 8.56.

Example 149

4-(4-Dimethylcarbamoyl-phenoxy)-2,2-dimethyl-2,3-dihydro-benzofuran-6-carboxylic acid (1-methyl-1H-pyrazol-3-yl)-amide

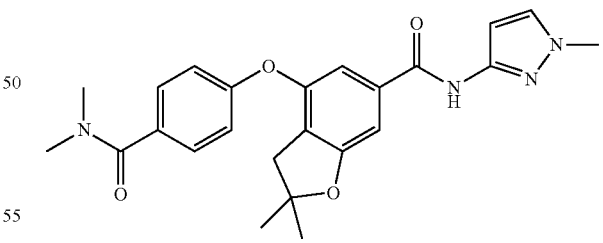

To a solution of 4-(4-dimethylcarbamoyl-phenoxy)-2,2-dimethyl-2,3-dihydro-benzofuran-6-carboxylic acid (149c) (130 mg, 0.366 mmol), 3-amino-1-methyl-pyrazole (71.1 mg, 0.732 mmol) and triethylamine (0.102 ml, 0.732 mmol) in 3 mL of DMF was added HATU (278 mg, 0.732 mmol). The mixture was stirred at 50° C. for 2 hr, quenched with water, extracted with 3×EtOAc. The combined organic layer was washed with 2×H$_2$O, dried with Na$_2$SO$_4$, concentrated and purified by Biotage column chromatography with 75-100% EtOAc in hexanes to give a white solid (134 mg, 84% yield). ¹H NMR (400 MHz, CDCl₃) δ 8.69 (s, 1 H) 7.38-7.46 (m, 2 H) 7.24-7.28 (m, 1 H) 7.01 (d, J=2.78 Hz, 2 H) 6.97 (d, J=8.59 Hz, 2 H) 6.77 (d, J=2.02 Hz, 1 H) 3.76 (d, 3 H) 3.07 (d, J=22.48 Hz, 6 H) 2.89 (s, 2 H) 1.47 (s, 6 H); LCMS for C₂₄H₂₆N₄O₄ m/z 435.20 (M+H⁺); Anal. Calcd. for C₂₄H₂₆N₄O₄·0.7 H₂O: C, 64.47; H, 6.18; N, 12.53; Found: C, 64.22; H, 6.11; N, 12.54.

Preparation of Intermediate 149a

4-Bromo-N,N-dimethyl-benzamide

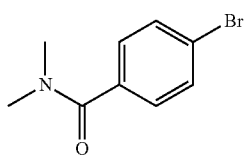

To a solution of 4-bromobenzoyl chloride (2.00 g, 9.11 mmol) and dimethyl amine hydrochloride (892 mg, 10.90 mmol) in 20 mL of CH₂Cl₂ was added triethylamine (3.81 mL, 27.30 mmol). The mixture was stirred at room temperature for 2 h, quenched with water, extracted with 3×CHCl₃, dried with Na₂SO₄, concentrated and purified by Biotage column chromatography with 1-4% MeOH in 1:1 EtOAc/CH₂Cl₂ to give a white solid (1.73 g, 83% yield). ¹H NMR (400 MHz, CDCl₃) δ 7.48-7.65 (m, 2 H) 7.20-7.37 (m, 2 H) 3.05 (d, J=50.78 Hz, 6 H); LCMS for C₉H₁₀BrNO m/z 228.00 and 230.00 (M+H)⁺

Preparation of Intermediate 149b 4-(4-Dimethylcarbamoyl-phenoxy)-2,2-dimethyl-2,3-dihydro-benzofuran-6-carboxylic acid methyl ester

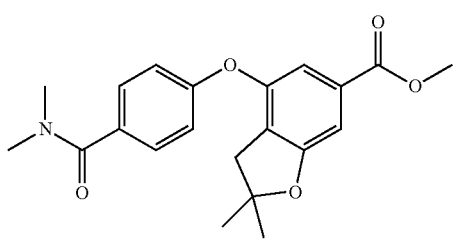

A mixture of 4-bromo-N,N-dimethyl-benzamide (149a) (428 mg, 1.87 mmol), 4-hydroxy-2,2-dimethyl-2,3-dihydrobenzofuran-6-carboxylic acid methyl ester (3e) (500 mg, 2.25 mmol), K₃PO₄ (796 mg, 3.75 mmol), 2-di-t-butylphosphino-2',4',6'-tri-i-propyl-1,1'-biphyl (21 mg, 0.094 mmol), and Pd(OAc)₂ (39.8 mg, 0.094 mmol) in toluene (10 mL) was heated to 100° C. in a microwave for 5 hr, cooled to room temperature, filtered through celite, washed with EtOAc, concentrated, and purified by Biotage column chromatography with 20-55% EtOAc in hexanes to give a yellow foam (662 mg, 80% yield). ¹H NMR (400 MHz, CDCl₃) δ 7.36-7.50 (m, 2 H) 7.20 (dd, J=10.36, 1.26 Hz, 2 H) 6.92-7.04 (m, 2 H) 3.86 (s, 3 H) 3.07 (br. s., 6 H) 2.90 (s, 2 H) 1.48 (s, 6 H); LCMS for C₂₁H₂₃NO₅ m/z 370.20 (M+H⁺).

Preparation of Intermediate 149c 4-(4-Dimethylcarbamoyl-phenoxy)-2,2-dimethyl-2,3-dihydro-benzofuran-6-carboxylic acid

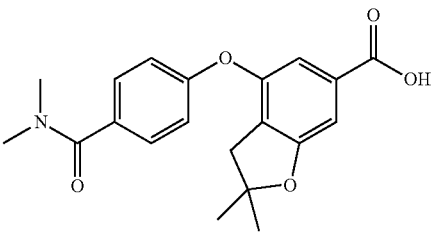

To a solution of 4-(4-dimethylcarbamoyl-phenoxy)-2,2-dimethyl-2,3-dihydro-benzofuran-6-carboxylic acid methyl ester (149b) (662 mg, 1.79 mmol) in 10 mL MeOH was added 1N aqueous NaOH (3.58 mL, 3.58 mmol). The mixture was stirred at room temperature overnight, then acidified to pH ~1 with 1N aqueous HCl, extracted with 3×EtOAc, dried over Na₂SO₄, concentrated to give a white solid (624 mg, 98% yield). ¹H NMR (400 MHz, CDCl₃) δ 7.44 (d, J=8.59 Hz, 2 H) 7.25 (dd, J=8.08, 1.26 Hz, 2 H) 6.92-7.02 (m, 2 H) 3.08 (br. s., 6 H) 2.92 (s, 2 H) 1.49 (s, 6 H); LCMS for C₂₀H₂₁NO₅ m/z 356.20 (M+H⁺).

Examples 150-158 were prepared in a similar manner as described for Example 144 from 4-(4-dimethylcarbamoyl-phenoxy)-2,2-dimethyl-2,3-dihydro-benzofuran-6-carboxylic acid (149c) and the appropriate amino heterocycles.

Example 155 was prepared from 4-(4-dimethylcarbamoyl-phenoxy)-2,2-dimethyl-2,3-dihydro-benzofuran-6-carboxylic acid (149c) and 5-(tert-butyl-dimethyl-silanyloxymethyl)-pyridin-2-ylamine (22a).

Example 150

4-(4-Dimethylcarbamoyl-phenoxy)-2,2-dimethyl-2,3-dihydro-benzofuran-6-carboxylic acid (5-methyl-pyridin-2-yl)-amide

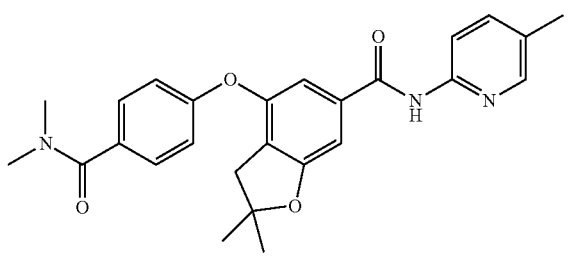

Example 151

4-(4-Dimethylcarbamoyl-phenoxy)-2,2-dimethyl-2,3-dihydro-benzofuran-6-carboxylic acid pyrazin-2-ylamide

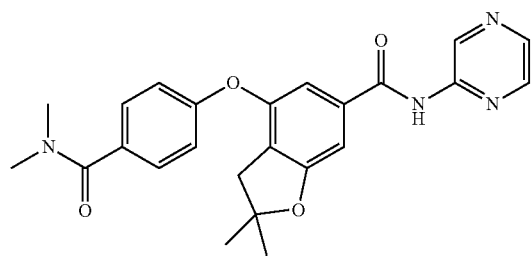

Example 152

4-(4-Dimethylcarbamoyl-phenoxy)-2,2-dimethyl-2,3-dihydro-benzofuran-6-carboxylic acid (1H-pyrazol-3-yl)-amide

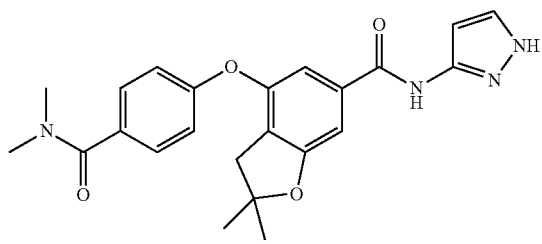

Example 153

4-(4-Dimethylcarbamoyl-phenoxy)-2,2-dimethyl-2,3-dihydro-benzofuran-6-carboxylic acid (2-methyl-2H-[1,2,3]triazol-4-yl)-amide

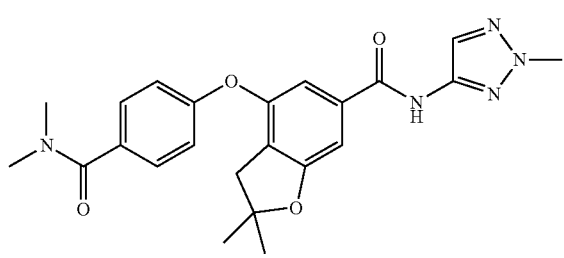

Example 154

4-(4-Dimethylcarbamoyl-phenoxy)-2,2-dimethyl-2,3-dihydro-benzofuran-6-carboxylic acid (5-methyl-isoxazol-3-yl)-amide

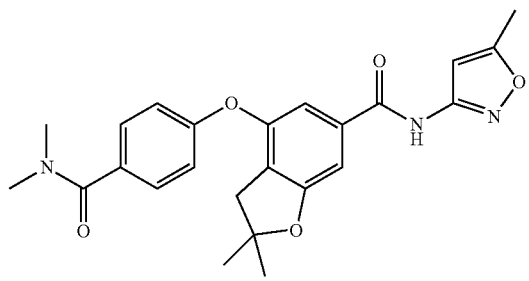

Example 155

4-(4-Dimethylcarbamoyl-phenoxy)-2,2-dimethyl-2,3-dihydro-benzofuran-6-carboxylic acid (5-hydroxymethyl-pyridin-2-yl)-amide

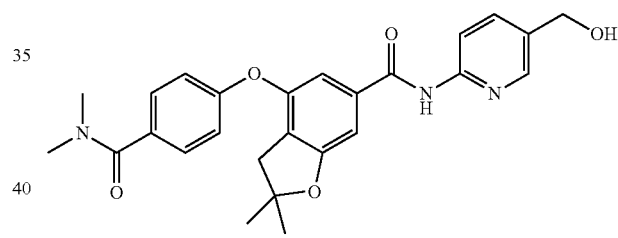

Example 156

4-(4-Dimethylcarbamoyl-phenoxy)-2,2-dimethyl-2,3-dihydro-benzofuran-6-carboxylic acid pyrimidin-4-ylamide

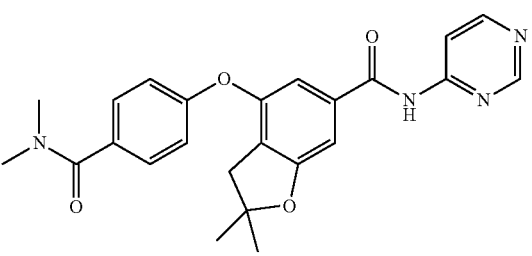

Example 157

4-(4-Dimethylcarbamoyl-phenoxy)-2,2-dimethyl-2,3-dihydro-benzofuran-6-carboxylic acid pyridin-2-ylamide

Example 158

4-(4-Dimethylcarbamoyl-phenoxy)-2,2-dimethyl-2,3-dihydro-benzofuran-6-carboxylic acid isoxazol-3-ylamide

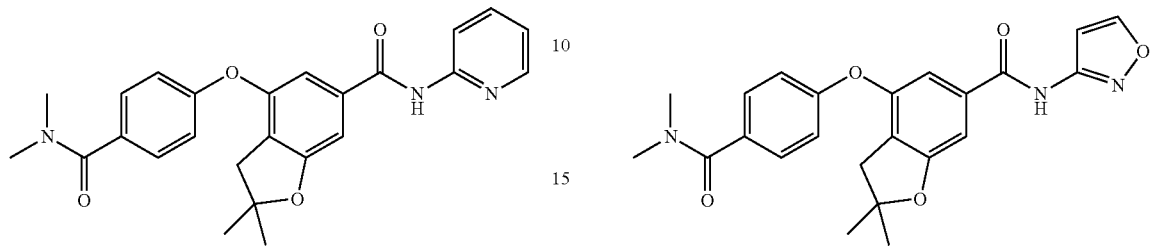

| Example | MW | MF | NMR | m/z | Elemental Analysis |
|---|---|---|---|---|---|
| 150 | 445.5 | C26H27N3O4 | $^1$H NMR (400 MHz, CDCl$_3$)) δ 8.99 (br. s., 1 H) 8.20 (d, J = 8.59 Hz, 1 H) 8.10 (d, J = 2.02 Hz, 1 H) 7.64 (dd, J = 8.59, 2.02 Hz, 1 H) 7.34-7.47 (m, 2 H) 6.92-7.13 (m, 4 H) 3.05 (br. s., 6 H) 2.92 (s, 2 H) 2.33 (s, 3 H) 1.49 (s, 6 H); | 446.00 (M + H$^+$) | Calcd. for C$_{26}$H$_{27}$N$_3$O$_4$•0.3 TFA•0.4 H$_2$O: C, 65.61; H, 5.82; N, 8.63; Found: C, 65.22; H, 5.79; N, 8.93. |
| 151 | 432.5 | C24H24N4O4 | $^1$H NMR (400 MHz, CDCl$_3$)) δ 9.60 (s, 1 H) 8.63 (br. s., 1 H) 8.27-8.41 (m, 2 H) 7.37-7.53 (m, 2 H) 6.92-7.12 (m, 4 H) 3.06 (br. s., 6 H) 2.95 (s, 2 H) 1.49 (s, 6 H); | 433.20 (M + H)$^+$ | |
| 152 | 420.5 | C23H24N4O4 | $^1$H NMR (400 MHz, CDCl$_3$)) δ 7.99 (d, J = 2.78 Hz, 1 H) 7.45 (d, J = 8.59 Hz, 2 H) 7.27 (s, 1 H) 7.12 (s, 1 H) 7.02-7.07 (m, 3 H) 6.03 (d, J = 3.03 Hz, 1 H) 3.08 (br. s., 6 H) 2.96 (s, 2 H) 1.48-1.53 (m, 6 H); | 421.20 (M + H$^+$) | |
| 153 | 435.5 | C23H25N5O4 | $^1$H NMR (400 MHz, CDCl$_3$)) δ 8.54 (s, 1 H) 8.09 (s, 1 H) 7.44 (d, J = 8.59 Hz, 2 H) 7.03 (t, J = 7.71 Hz, 4 H) 4.11 (s, 3 H) 3.10 (br. s., 6 H) 2.92 (s, 2 H) 1.50 (s, 6 H); | 436.00 (M + H$^+$) | Calcd. for C$_{23}$H$_{25}$N$_5$O$_4$•0.9 TFA: C, 55.36; H, 4.85; N, 13.01; Found: C, 55.05; H, 5.11; N, 13.15. |
| 154 | 435.5 | C24H25N3O5 | $^1$H NMR (400 MHz, CDCl$_3$)) δ 9.06 (br. s., 1 H) 7.44 (d, J = 8.34 Hz, 2 H) 7.04-7.12 (m, 2 H) 7.00 (d, J = 8.59 Hz, 2 H) 6.81 (s, 1 H) 3.06 (br. s., 6 H) 2.91 (s, 2 H) 2.41 (s, 3 H) 1.49 (s, 6 H); | 436.00 (M + H$^+$) | Calcd. for C$_{24}$H$_{25}$N$_3$O$_5$•0.3 TFA•0.4 H$_2$O: C, 61.96; H, 5.52; N, 8.81; Found: C, 61.82; H, 5.62; N, 9.02. |
| 155* | 461.5 | C26H27N3O5 | $^1$H NMR (400 MHz, CDCl$_3$)) δ 9.03 (br. s., 1 H) 8.15-8.37 (m, 2 H) 7.84 (dd, J = 8.46, 1.89 Hz, 1 H) 7.36-7.47 (m, 2 H) 6.94-7.14 (m, 4 H) 4.71 (s, 2 H) 3.11 (br. s., 6 H) 2.94 (s, 2 H) 1.50 (s, 6 H); | 462.00 (M + H)$^+$ | |
| 156 | 432.5 | C24H24N4O4 | $^1$H NMR (400 MHz, CDCl$_3$)) δ 8.87 (s, 1 H) 8.57-8.71 (m, 2 H) 8.29 (dd, J = 5.81, 1.26 Hz, 1 H) 7.39-7.49 (m, 2 H) 6.89-7.11 (m, 4 H) 3.05 (br. s., 6 H) 2.93 (s, 2 H) 1.50 (s, 6 H); | 433.00 (M + H)$^+$ | Calcd. for C$_{24}$H$_{24}$N$_4$O$_4$•0.1 TFA•0.4 H$_2$O: C, 64.44; H, 5.56; N, 12.42; Found: C, 64.33; H, 5.48; N, 12.46. |
| 157 | 431.5 | C25H25N3O4 | $^1$H NMR (400 MHz, CDCl$_3$)) δ 9.02 (br. s., 1 H) 8.22-8.41 (m, 2 H) 7.73-7.87 (m, 1 H) 7.37-7.48 (m, 2 H) 6.93-7.14 (m, 5 H) 3.05 (br. s., 6 H) 2.92 (s, 2 H) 1.47 (s, 6 H); | 432.20 (M + H)$^+$ | Calcd. for C$_{25}$H$_{25}$N$_3$O$_4$•0.33 TFA•0.4 H$_2$O: C, 64.70; H, 5.53; N, 8.82; Found: C, 64.74; H, 5.57; N, 8.89. |
| 158 | 421.5 | C23H23N3O5 | $^1$H NMR (400 MHz, CDCl$_3$) δ 8.61 (s, 1 H) 8.32 (d, J = 1.26 Hz, 1 H) 7.41-7.48 (m, 2 H) 7.27 (s, 1 H) 7.17 (d, J = 1.77 Hz, 1 H) 6.96-7.06 (m, 3 H) 3.06 (br. s., 6 H) 2.92 (s, 2 H) 1.50 (s, 6 H); | 422.00 (M + H$^+$) | |

Example 159

4-[4-(Azetidine-1-carbonyl)-3-fluoro-phenoxy]-2,2-dimethyl-2,3-dihydro-benzofuran-6-carboxylic acid (2-methyl-2H-[1,2,3]triazol-4-yl)-amide

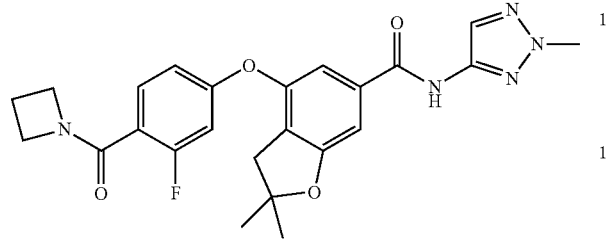

The title compound was prepared in a similar manner as described for Example 1, from 4-[4-(azetidine-1-carbonyl)-3-fluoro-phenoxy]-2,2-dimethyl-2,3-dihydro-benzofuran-6-carboxylic acid methyl ester (159a) (92 mg, 0.23 mmol) to give a white solid (60 mg, 56% yield). $^1$H NMR (400 MHz, CDCl$_3$) δ 8.57 (s, 1 H) 8.08 (s, 1 H) 7.43-7.59 (m, 1 H) 7.07 (s, 2 H) 6.78 (d, J=8.59 Hz, 1 H) 6.67 (dd, J=10.99, 2.40 Hz, 1 H) 4.11-4.25 (m, 4 H) 4.10 (s, 3 H) 2.89 (s, 2 H) 2.34 (s, 2 H) 1.49 (s, 6 H); LCMS for C$_{24}$H$_{24}$FN$_5$O$_4$ m/z 466.20 (M+H$^+$); Anal. Calcd. for C$_{24}$H$_{24}$FN$_5$O$_4$.0.2 CHCl$_3$: C, 59.35; H, 4.98; N, 14.31; Found: C, 59.68; H, 5.19; N, 14.08.

Preparation of Intermediate 159a

4-[4-(Azetidine-1-carbonyl)-3-fluoro-phenoxy]-2,2-dimethyl-2,3-dihydro-benzofuran-6-carboxylic acid methyl ester

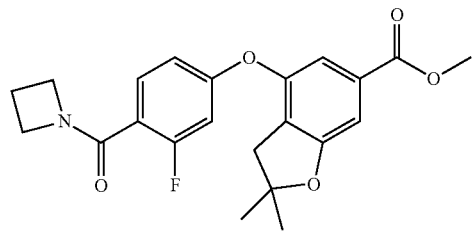

The title compound was prepared in a similar manner as described for Intermediate 35b, from 4-hydroxy-2,2-dimethyl-2,3-dihydrobenzofuran-6-carboxylic acid methyl ester (3e) and azetidin-1-yl-(4-bromo-2-fluoro-phenyl)-methanone. $^1$H NMR (400 MHz, CDCl$_3$) δ 7.53 (t, J=8.21 Hz, 1 H) 7.25 (s, 1 H) 7.22 (s, 1 H) 6.78 (dd, J=8.59, 2.27 Hz, 1 H) 6.66 (dd, J=11.12, 2.27 Hz, 1 H) 4.18-4.29 (m, 2 H) 4.15 (t, J=7.58 Hz, 2 H) 3.88 (s, 3 H) 2.88 (s, 2 H) 2.30-2.41 (m, J=7.75, 7.75, 7.75, 7.58 Hz, 2 H) 1.48 (s, 6 H); LCMS for C$_{22}$H$_{22}$FNO$_5$ m/z 400.20 (M+H)$^+$.

Example 160

4-[4-(Azetidine-1-carbonyl)-phenoxy]-2,2-dimethyl-2,3-dihydro-benzofuran-6-carboxylic acid (2-methyl-2H-[1,2,3]triazol-4-yl)-amide

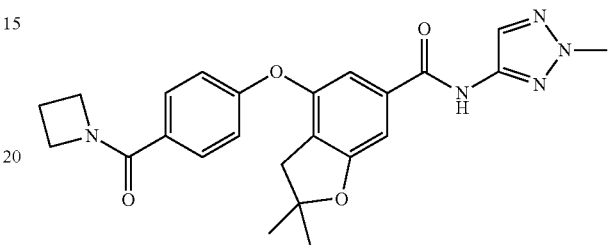

The title compound was prepared in a similar manner as described for Example 1, from 4-[4-(azetidine-1-carbonyl)-phenoxy]-2,2-dimethyl-2,3-dihydro-benzofuran-6-carboxylic acid methyl ester (35b) (94 mg, 0.250 mmol) to give a white solid (66 mg, 60% yield). $^1$H NMR (400 MHz, CDCl$_3$) δ 8.43 (s, 1 H) 8.01-8.15 (m, 1 H) 7.64 (t, J=8.21 Hz, 2 H) 7.02-7.05 (m, 2 H) 6.99 (d, J=8.59 Hz, 2 H) 4.25-4.35 (m, 4 H) 4.11 (s, 3 H) 2.90 (s, 2 H) 2.37 (t, J=7.71 Hz, 2 H) 1.49 (s, 6 H); LCMS for C$_{24}$H$_{25}$N$_5$O$_4$ m/z 448.20 (M+H$^+$); Anal. Calcd. for C$_{24}$H$_{25}$N$_5$O$_4$.0.3 H$_2$O: C, 63.65; H, 5.70; N, 15.46; Found: C, 63.90; H, 5.58; N, 15.40.

Example 161

5-[2,2-Dimethyl-6-(1-methyl-1H-pyrazol-3-ylcarbamoyl)-2,3-dihydro-benzofuran-4-yloxy]-pyridine-2-carboxylic acid dimethylamide

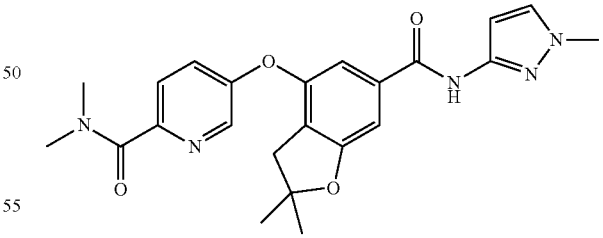

The title compound was prepared in a similar manner as described for Example 1 from 4-(6-dimethylcarbamoyl-pyridin-3-yloxy)-2,2-dimethyl-2,3-dihydro-benzofuran-6-carboxylic acid methyl ester (161b) (111 mg, 0.30 mmol) to give a white solid (87 mg, 67% yield). $^1$H NMR (400 MHz, CDCl$_3$) δ 8.93 (s, 1 H) 8.30 (d, J=2.27 Hz, 1 H) 7.67 (d, J=8.59 Hz, 1 H) 7.18-7.33 (m, 2 H) 7.03 (s, 2 H) 6.76 (d, J=2.27 Hz, 1 H) 3.72 (s, 3 H) 3.13 (d, J=7.33 Hz, 6 H) 2.89 (s, 2 H) 1.47 (s, 6 H); LCMS for C$_{23}$H$_{25}$N$_5$O$_4$ m/z 436.30 (M+H$^+$); Anal.

Calcd. for $C_{23}H_{25}N_5O_4 \cdot 0.22\ H_2O$: C, 62.86; H, 5.84; N, 15.94; Found: C, 62.90; H, 5.89; N, 16.01.

Preparation of Intermediate 161a

5-Bromo-pyridine-2-carboxylic acid dimethylamide

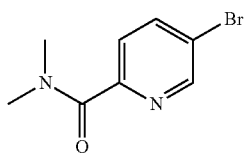

To a solution of 5-bromopyridine-2-caboxylic acid (3.00 g, 14.85 mmol), dimethyl amine hydrochloride (1.82 g, 22.30 mmol) and triethylamine (6.21 ml, 44.60 mmol) in 20 mL of DMF was added HATU (8.47 g, 22.30 mmol). The mixture was stirred at room temperature overnight, quenched with water, extracted with 3×EtOAc. The combined organic layer was washed with 2×H$_2$O, dried with Na$_2$SO$_4$, concentrated and purified by Biotage column chromatography with 60-70% EtOAc in hexanes to give a yellow oil (1.56 g, 46% yield). $^1$H NMR (400 MHz, CDCl$_3$) δ 8.59 (d, J=1.77 Hz, 1 H) 7.88 (dd, J=8.34, 2.27 Hz, 1 H) 7.52 (d, J=8.34 Hz, 1 H) 3.06 (d, J=14.15 Hz, 6 H); LCMS for C$_8$H$_9$BrN$_2$O m/z 229.00 (M+H$^+$).

Preparation of Intermediate 161b 4-(6-Dimethylcarbamoyl-pyridin-3-yloxy)-2,2-dimethyl-2,3-dihydro-benzofuran-6-carboxylic acid methyl ester

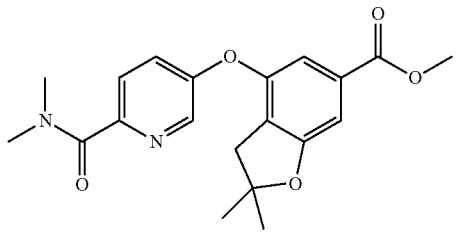

A mixture of 5-bromo-pyridine-2-carboxylic acid dimethylamide (161a) (1.14 g, 4.95 mmol), 4-hydroxy-2,2-dimethyl-2,3-dihydrobenzofuran-6-carboxylic acid methyl ester (3e) (1.10 g, 4.95 mmol), and K$_3$PO$_4$ (2.10 g, 9.91 mmol), 2-di-t-butylphosphino-2',4',6'-tri-i-propyl-1,1'-biphyl (210 mg, 0.495 mmol), and Pd(OAc)$_2$ (111 mg, 0.495 mmol) in toluene (10 mL) was heated to 100° C. in a microwave for 6 hr, cooled to room temperature, filtered through celite, washed with EtOAc, concentrated, and purified by Biotage column chromatography with 35-70% EtOAc in hexanes to give a white foam (238 mg, 13% yield). $^1$H NMR (400 MHz, CDCl$_3$) δ 8.32 (d, J=2.78 Hz, 1 H) 7.70 (d, J=8.59 Hz, 1 H) 7.31 (dd, J=8.72, 2.91 Hz, 1 H) 7.25 (d, J=1.26 Hz, 1 H) 7.19 (d, J=1.26 Hz, 1 H) 3.87 (s, 3 H) 3.15 (d, J=4.29 Hz, 6 H) 2.92 (s, 2 H) 1.49 (s, 6 H); LCMS for C$_{20}$H$_{22}$N$_2$O$_5$ m/z 371.20 (M+H$^+$).

Example 162

6-[2,2-Dimethyl-6-(1-methyl-1H-pyrazol-3-ylcarbamoyl)-2,3-dihydro-benzofuran-4-yloxy]-N,N-dimethyl-nicotinamide

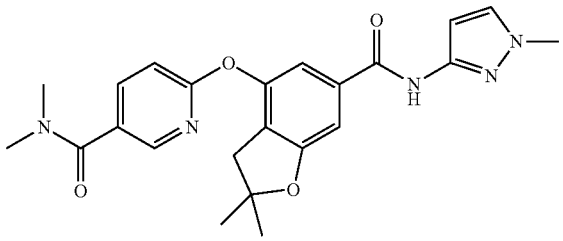

The title compound was prepared in a similar manner as described for Example 1, from 4-(5-dimethylcarbamoyl-pyridin-2-yloxy)-2,2-dimethyl-2,3-dihydro-benzofuran-6-carboxylic acid methyl ester (162b) (100 mg, 0.27 mmol), to give a white solid (67 mg, 57% yield). $^1$H NMR (400 MHz, CDCl$_3$) δ 8.57 (s, 1 H) 8.28 (d, J=1.77 Hz, 1 H) 7.85 (dd, J=8.46, 2.40 Hz, 1 H) 7.27 (s, 1 H) 7.11 (d, 1 H) 7.14 (dd, J=24.51, 1.26 Hz, 1 H) 6.99 (d, J=9.09 Hz, 1 H) 6.80 (d, J=2.27 Hz, 1 H) 3.80 (s, 3 H) 3.10 (d, J=17.94 Hz, 6 H) 2.87 (s, 2 H) 1.48 (s, 6 H); LCMS for C$_{23}$H$_{25}$N$_5$O$_4$ m/z 436.30 (M+H$^+$); Anal. Calcd. for C$_{23}$H$_{25}$N$_5$O$_4 \cdot 0.33\ H_2O$: C, 62.56; H, 5.86; N, 15.87; Found: C, 62.57; H, 5.93; N, 15.87.

Preparation of Intermediate 162a

6-Bromo-N,N-dimethyl-nicotinamide

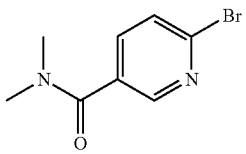

The title compound was prepared in a similar manner as described for Intermediate 161a, from 6-bromo-nicotinic acid (1.00 g, 4.95 mmol) to give a colorless oil (780 mg, 69% yield). $^1$H NMR (400 MHz, CDCl$_3$) δ 8.46 (d, J=2.53 Hz, 1 H)

7.61-7.71 (m, 1 H) 7.56 (d, J=8.08 Hz, 1 H) 3.08 (d, J=41.68 Hz, 6 H); LCMS for $C_8H_9BrN_2O$ m/z 229.00 (M+H)$^+$.

Preparation of Intermediate 162b 4-(5-Dimethylcarbamoyl-pyridin-2-yloxy)-2,2-dimethyl-2,3-dihydro-benzofuran-6-carboxylic acid methyl ester

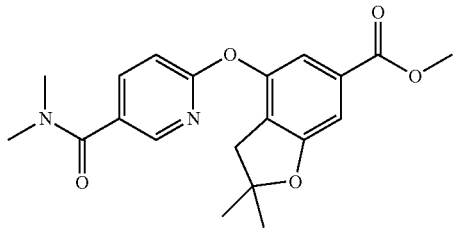

The title compound was prepared in a similar manner as described for Intermediate 161b, from 6-bromo-N,N-dimethyl-nicotinamide (162a) (335 mg, 1.46 mmol) and 4-hydroxy-2,2-dimethyl-2,3-dihydrobenzofuran-6-carboxylic acid methyl ester (3e) (250 mg, 1.12 mmol) to give a white foam (200 mg, 50% yield). $^1$H NMR (400 MHz, CDCl$_3$) δ 8.26 (d, J=2.02 Hz, 1 H) 7.83 (dd, J=8.46, 2.40 Hz, 1 H) 7.34 (d, J=1.01 Hz, 1 H) 7.27 (s, 1 H) 6.97 (d, J=8.34 Hz, 1 H) 3.86 (s, 3 H) 3.08 (d, J=21.47 Hz, 6 H) 2.82 (s, 2 H) 1.46 (s, 6 H); LCMS for $C_{20}H_{22}N_2O_5$ m/z 371.20 (M+H$^+$).

Example 163

5-[2,2-Dimethyl-6-(1-methyl-1H-pyrazol-3-ylcarbamoyl)-2,3-dihydro-benzofuran-4-yloxy]-pyridine-2-carboxylic acid (1-methyl-1H-pyrazol-3-yl)-amide The title compound was prepared in a similar manner as described for Example 149, from 5-(6-carboxy-2,2-dimethyl-2,3-dihydro-benzofuran-4-yloxy)-pyridine-2-carboxylic acid (163b) (111 mg, 0.288 mmol) and 3-amino-1-methyl-pyrazole (56 mg, 0.576 mmol) to give a white solid (112 mg, 80% yield). $^1$H NMR (400 MHz, CDCl$_3$) δ 10.19 (s, 1 H) 8.98 (s, 1 H) 8.30 (d, J=2.53 Hz, 1 H) 8.22 (d, J=8.59 Hz, 1 H) 7.28-7.38 (m, 2 H) 7.24-7.28 (m, 1 H) 7.07 (d, J=3.03 Hz, 2 H) 6.79 (d, J=2.02 Hz, 1 H) 6.83 (d, J=2.27 Hz, 1 H) 3.84 (s, 3 H) 3.74 (s, 3 H) 2.89 (s, 2 H) 1.49 (s, 6 H); LCMS for $C_{25}H_{25}N_7O_4$ m/z 488.20 (M+H$^+$); Anal. Calcd. for $C_{25}H_{25}N_7O_4$·0.1 CHCl$_3$: C, 59.50; H, 5.15; N, 19.35; Found: C, 59.77; H, 5.17; N, 18.96.

Preparation of Intermediate 163a 5-(6-Methoxycarbonyl-2,2-dimethyl-2,3-dihydro-benzofuran-4-yloxy)-pyridine-2-carboxylic acid tert-butyl ester

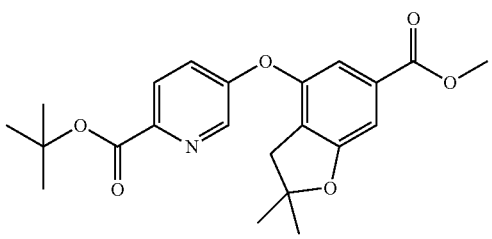

A mixture of t-butyl 5-bromopicolinate (581 mg, 2.25 mmol), 4-hydroxy-2,2-dimethyl-2,3-dihydro-benzofuran-6-carboxylic acid methyl ester (3e) (500 mg, 2.25 mmol), K$_3$PO$_4$ (956 mg, 4.50 mmol), 2-di-t-butylphosphino-2',4',6'-tri-i-propyl-1,1'-biphyl (96 mg, 0.225 mmol), and Pd(OAc)$_2$ (51 mg, 0.225 mmol) in toluene (10 mL) was heated to 100° C. in a microwave for 3 h, cooled to room temperature, filtered through celite, washed with EtOAc, concentrated, and purified by Biotage column chromatography with 15-30% EtOAc in hexanes to give 26 mg of 5-(6-Methoxycarbonyl-2,2-dimethyl-2,3-dihydro-benzofuran-4-yloxy)-pyridine-2-carboxylic acid tert-butyl ester and 400 mg mixture of the title compound with ~40% of 4-hydroxy-2,2-dimethyl-2,3-dihydrobenzofuran-6-carboxylic acid methyl ester as a yellow foam. $^1$H NMR (400 MHz, CDCl$_3$) δ 8.47 (d, J=2.53 Hz, 1 H) 8.05 (d, J=8.84 Hz, 1 H) 7.23-7.36 (m, 2 H) 7.19 (d, J=1.26 Hz, 1 H) 3.87 (s, 3 H) 2.89 (s, 2 H) 1.64 (s, 9 H) 1.48 (s, 6 H); LCMS for $C_{22}H_{25}NO_6$ m/z 344.00 (M-tBu+H$^+$).

Preparation of Intermediate 163b 5-(6-Carboxy-2,2-dimethyl-2,3-dihydro-benzofuran-4-yloxy)-pyridine-2-carboxylic acid

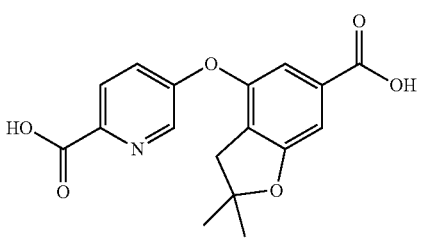

To a solution of 5-(6-methoxycarbonyl-2,2-dimethyl-2,3-dihydro-benzofuran-4-yloxy)-pyridine-2-carboxylic acid tert-butyl ester (163a) (110 mg, 0.275 mmol) in 2 mL MeOH and 1 mL THF was added 1N aqueous NaOH (0.55 mL, 0.55 mmol). The mixture was stirred at room temperature overnight, heated at 60° C. for 6 hr, then concentrated, acidified to pH ~3 with 1N aqueous HCl, extracted with 3×EtOAc, dried over Na₂SO₄, and concentrated to give 113 mg white solid. LCMS for C₁₇H₁₅NO₆ m/z 330.00 (M+H⁺).

Example 164

5-[2,2-Dimethyl-6-(1-methyl-1H-pyrazol-3-ylcarbamoyl)-2,3-dihydro-benzofuran-4-yloxy]-pyrimidine-2-carboxylic acid dimethylamide

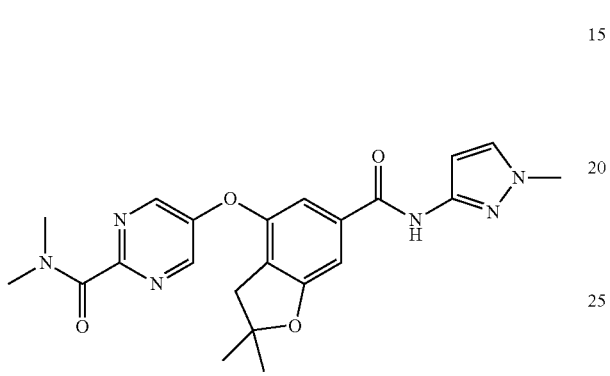

The title compound was prepared in a similar manner as described for Example 1, from 3-amino-1-methyl-pyrazole (152 mg, 1.56 mmol) and 4-(2-dimethylcarbamoyl-pyrimidin-5-yloxy)-2,2-dimethyl-2,3-dihydro-benzofuran-6-carboxylic acid methyl ester (164b) (58 mg, 0.16 mmol) to give a white solid (64 mg, 94% yield). ¹H NMR (400 MHz, CDCl₃) δ 8.96 (s, 1 H) 8.47 (s, 2 H) 7.20-7.34 (m, 1 H) 7.07 (d, J=1.52 Hz, 2 H) 6.76 (d, J=2.02 Hz, 1 H) 3.73 (s, 3 H) 3.14 (s, 3 H) 2.98 (s, 3 H) 2.92 (s, 2 H) 1.49 (s, 6 H); LCMS for C₂₂H₂₄N₆O₄ m/z 437.00 (M+H⁺); Anal. Calcd. for C₂₂H₂₄N₆O₄·0.15 CHCl₃: C, 58.55; H, 5.36; N, 18.50; Found: C, 58.59; H, 5.45; N, 18.61.

Preparation of Intermediate 164a

5-Bromo-pyrimidine-2-carboxylic acid dimethylamide

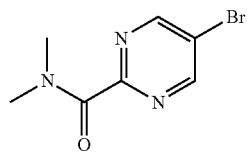

The title compound was prepared in a similar manner as described for Intermediate 161a, from 5-bromopyrimidine-2-caboxylic acid (1.03 g, 5.074 mmol) to give a yellow oil (308 mg, 26% yield). ¹H NMR (400 MHz, CDCl₃) δ 8.50 (s, 2 H) 3.17 (s, 3 H) 3.00 (s, 3 H); LCMS for C₇H₈BrN₃O m/z 230.00 and 232.00 (M+H⁺).

Preparation of Intermediate 164b 4-(2-Dimethylcarbamoyl-pyrimidin-5-yloxy)-2,2-dimethyl-2,3-dihydro-benzofuran-6-carboxylic acid methyl ester

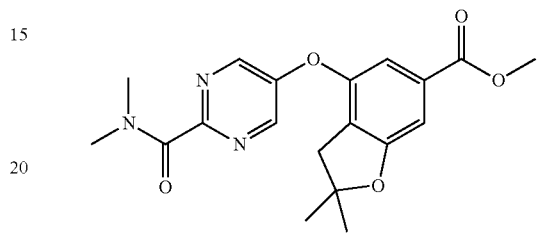

The title compound was prepared in a similar manner as described for Intermediate 161b, from 5-bromo-pyrimidine-2-carboxylic acid dimethylamide (164a) (271 mg, 1.18 mmol) and 4-hydroxy-2,2-dimethyl-2,3-dihydro-benzofuran-6-carboxylic acid methyl ester (3e) (262 mg, 1.18 mmol) to give a white foam (110 mg, 25% yield). ¹H NMR (400 MHz, CDCl₃) δ 8.50 (s, 2 H) 7.24-7.36 (m, 1 H) 7.20 (s, 1 H) 3.88 (s, 3 H) 3.17 (s, 3 H) 3.00 (s, 3 H) 2.95 (s, 2 H) 1.51 (s, 6 H); LCMS for C₁₉H₂₁N₃O₅ m/z 372.00 (M+H⁺).

Example 165

5-[2,2-Dimethyl-6-(5-methyl-pyridin-2-ylcarbamoyl)-2,3-dihydro-benzofuran-4-yloxy]-pyridine-2-carboxylic acid dimethylamide

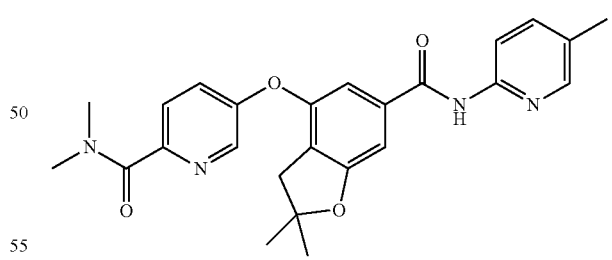

The title compound was prepared in a similar manner as described for Example 1, from 4-(6-dimethylcarbamoyl-pyridin-3-yloxy)-2,2-dimethyl-2,3-dihydro-benzofuran-6-carboxylic acid methyl ester (161b) (93 mg, 0.25 mmol) to give a white solid (57 mg, 51% yield). ¹H NMR (400 MHz, CDCl₃) δ 8.72 (s, 1 H) 8.31 (d, J=2.78 Hz, 1 H) 8.20 (d, J=8.34 Hz, 1 H) 8.02 (d, J=2.27 Hz, 1 H) 7.53 (dd, J=8.46, 2.15 Hz, 1 H) 7.23-7.35 (m, 2 H) 7.08 (dd, J=13.64, 1.26 Hz, 2 H) 3.13 (d, J=8.34 Hz, 6 H) 2.89 (s, 2 H) 2.27 (s, 3 H) 1.48 (s, 6 H);

LCMS for $C_{25}H_{26}N_4O_4$ m/z 447.00 (M+H$^+$); Anal. Calcd. for $C_{25}H_{26}N_4O_4 \cdot 0.5$ CHCl$_3$: C, 60.50; H, 5.28; N, 11.07; Found: C, 60.31; H, 5.31; N, 11.00.

Example 166

5-[2,2-Dimethyl-6-(1-methyl-1H-pyrazol-3-ylcarbamoyl)-2,3-dihydro-benzofuran-4-yloxy]-pyridine-2-carboxylic acid methylamide

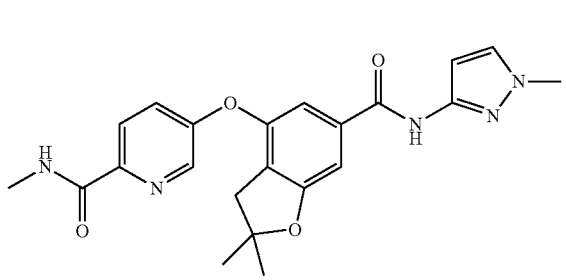

The title compound was prepared in a similar manner as described for Example 1, from 2,2-dimethyl-4-(6-methylcarbamoyl-pyridin-3-yloxy)-2,3-dihydro-benzofuran-6-carboxylic acid methyl ester (166b) (174 mg, 0.488 mmol) to give a white solid (147 mg, 71% yield). $^1$H NMR (400 MHz, CDCl$_3$) δ 8.38 (s, 1 H) 8.29 (d, J=2.53 Hz, 1 H) 8.20 (d, J=8.59 Hz, 1 H) 8.08 (s, 1 H) 7.86 (br. s., 1 H) 7.37 (dd, J=8.59, 2.78 Hz, 1 H) 7.26 (d, J=2.27 Hz, 1 H) 6.98-7.10 (m, 2 H) 4.12 (s, 3 H) 3.04 (d, J=5.05 Hz, 3 H) 2.92 (s, 2 H) 1.51 (s, 6 H): LCMS for $C_{22}H_{23}N_5O_4$ m/z 422.20 (M+H$^+$); Anal. Calcd. for $C_{22}H_{23}N_5O_4 \cdot 0.15$ CHCl$_3$: C, 60.55; H, 5.31; N, 15.94; Found: C, 60.68; H, 5.45; N, 15.98.

Preparation of Intermediate 166a 5-(6-Methoxycarbonyl-2,2-dimethyl-2,3-dihydro-benzofuran-4-yloxy)-pyridine-2-carboxylic acid

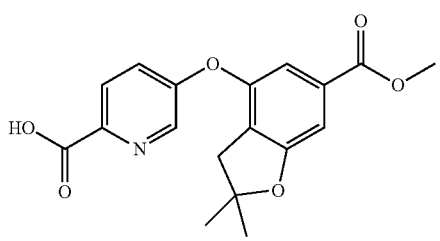

A solution of 5-(6-methoxycarbonyl-2,2-dimethyl-2,3-dihydro-benzofuran-4-yloxy)-pyridine-2-carboxylic acid tert-butyl ester (163a) (260 mg, 0.65 mmol) in 4 mL CH$_2$Cl$_2$ and 2 mL TFA was stirred at room temperature for 2 hr. The mixture was concentrated, dried under vacuum, and taken to the next step as it is.

Preparation of Intermediate 166b 2,2-Dimethyl-4-(6-methylcarbamoyl-pyridin-3-yloxy)-2,3-dihydro-benzofuran-6-carboxylic acid methyl ester

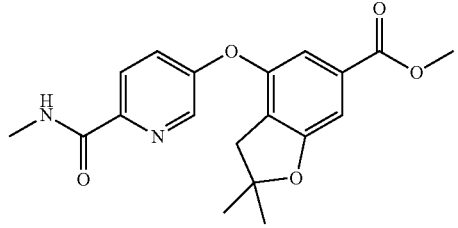

To a solution of 5-(6-methoxycarbonyl-2,2-dimethyl-2,3-dihydro-benzofuran-4-yloxy)-pyridine-2-carboxylic acid (166a) (74 mg, 0.22 mmol) 3 mL CH$_2$Cl$_2$ was added 2.0 M oxalyl chloride in THF (0.22 mL, 0.44 mmol), followed by 3 drops of DMF. The mixture was stirred at room temperature for 1 hr. Another 2.0 eq of oxalyl chloride was added. The mixture was stirred at room temperature for 30 min, concentrated, and dried under vacuum. The residue was dissolved in 3 mL CH$_2$Cl$_2$, and 2 mL 2.0 M methyl amine in THF was introduced. The mixture was stirred at room temperature overnight, concentrated, and purified by Biotage column chromatography with 30-50% EtOAc in hexanes to give a white solid (37 mg, 48% yield). $^1$H NMR (400 MHz, CDCl$_3$) δ 8.28 (d, J=2.78 Hz, 1 H) 8.19 (d, J=8.59 Hz, 1 H) 7.88 (d, J=3.79 Hz, 1 H) 7.34 (dd, J=8.72, 2.65 Hz, 1 H) 7.26-7.30 (m, 2 H) 3.88 (s, 3 H) 3.05 (d, J=5.05 Hz, 3 H) 2.90 (s, 2 H) 1.49 (s, 6 H); LCMS for $C_{19}H_{20}N_2O_5$ m/z 357.00 (M+H$^+$).

Example 167

4-[6-(Azetidine-1-carbonyl)-pyridin-3-yloxy]-2,2-dimethyl-2,3-dihydro-benzofuran-6-carboxylic acid (1-methyl-1H-pyrazol-3-yl)-amide

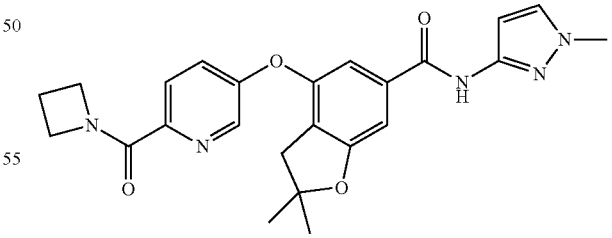

The title compound was prepared in a similar manner as described for Example 1, from 4-[6-(azetidine-1-carbonyl)-pyridin-3-yloxy]-2,2-dimethyl-2,3-dihydro-benzofuran-6-carboxylic acid methyl ester (167b) (68 mg, 0.178 mmol) to give a white solid (37 mg, 46% yield). $^1$H NMR (400 MHz, CDCl$_3$) δ 8.76 (s, 1 H) 8.29 (d, J=2.78 Hz, 1 H) 8.10 (d, J=8.59 Hz, 1 H) 7.31 (dd, 1 H) 7.23-7.33 (m, 1 H) 7.03 (s, 1 H) 7.04 (d, J=7.83 Hz, 1 H) 6.78 (d, J=2.27 Hz, 1 H) 4.70 (t, J=7.71

Hz, 2 H) 4.24 (t, J=7.83 Hz, 2 H) 3.76 (s, 3 H) 2.89 (s, 2 H) 2.29-2.41 (m, 2 H) 1.49 (s, 6 H); LCMS for $C_{24}H_{25}N_5O_4$ m/z 448.20 (M+H$^+$); Anal. Calcd. for $C_{24}H_{25}N_5O_4$·0.2 AcOH: C, 61.32; H, 5.45; N, 15.05; Found: C, 62.35; H, 5.50; N, 14.94.

Preparation of Intermediate 167a

Azetidin-1-yl-(5-bromo-pyridin-2-yl)-methanone

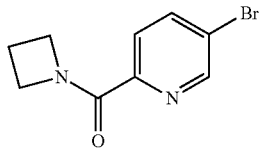

The title compound was prepared in a similar manner as described for Intermediate 161a, from 5-bromopyridine-2-caboxylic acid (1.50 g, 7.43 mmol) and azetidine hydrochloride (954 mg, 10.2 mmol) to give a yellow solid (1.38 g, 77% yield). $^1$H NMR (400 MHz, CDCl$_3$) δ 8.58 (d, J=2.02 Hz, 1 H) 7.93-7.99 (m, 1 H) 7.90 (d, J=2.27 Hz, 1 H) 4.65 (t, J=7.71 Hz, 2 H) 4.20 (dd, J=8.34, 7.33 Hz, 2 H) 2.27-2.36 (m, 2 H); LCMS for $C_9H_9BrN_2O$ m/z 241.00 (M+H)$^+$.

Preparation of Intermediate 167b

4-[6-(Azetidine-1-carbonyl)-pyridin-3-yloxy]-2,2-dimethyl-2,3-dihydro-benzofuran-6-carboxylic acid methyl ester

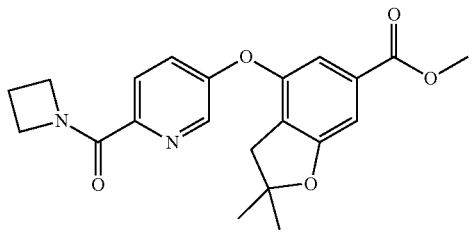

The title compound was prepared in a similar manner as described for Intermediate 161b, from azetidin-1-yl-(5-bromo-pyridin-2-yl)-methanone (167a) (1.37 g, 5.68 mmol) and 4-hydroxy-2,2-dimethyl-2,3-dihydro-benzofuran-6-carboxylic acid methyl ester (3e) (1.26 g, 5.58 mmol) to give a white foam (738 mg, 34% yield). $^1$H NMR (400 MHz, CDCl$_3$) δ 8.32 (d, J=2.78 Hz, 1 H) 8.12 (d, J=8.59 Hz, 1 H) 7.31-7.38 (m, 1 H) 7.27 (s, 1 H) 7.21 (s, 1 H) 4.72 (t, J=7.71 Hz, 2 H) 4.27 (t, J=7.71 Hz, 2 H) 3.89 (s, 3 H) 2.92 (s, 2 H) 2.38 (t, J=7.71 Hz, 2 H) 1.50 (s, 6 H); LCMS for $C_{21}H_{22}N_2O_5$ m/z 383.20 (M+H$^+$).

Example 168

5-[2,2-Dimethyl-6-(1-methyl-1H-pyrazol-3-ylcarbamoyl)-2,3-dihydro-benzofuran-4-yloxy]-pyridine-2-carboxylic acid ethylamide

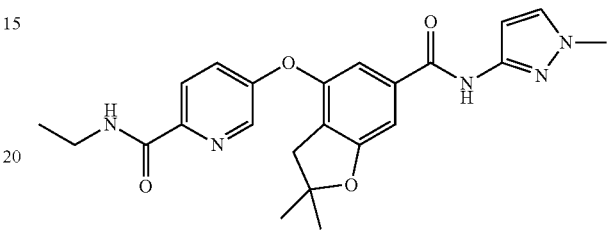

The title compound was prepared in a similar manner as described for Example 1 from 4-(6-ethylcarbamoyl-pyridin-3-yloxy)-2,2-dimethyl-2,3-dihydro-benzofuran-6-carboxylic acid methyl ester (168a) (28 mg, 0.076 mmol) to give a white solid (22 mg, 65% yield). $^1$H NMR (400 MHz, CDCl$_3$) δ 8.83 (s, 1 H) 8.24 (d, J=2.27 Hz, 1 H) 8.17 (d, J=8.59 Hz, 1 H) 7.88 (br. s., 1 H) 7.34 (dd, J=8.59, 2.78 Hz, 1 H) 7.26 (d, J=2.27 Hz, 1 H) 7.05 (d, J=1.26 Hz, 1 H) 6.99 (d, J=1.26 Hz, 1 H) 6.78 (d, J=2.02 Hz, 1 H) 3.73 (s, 3 H) 3.49 (dd, J=7.20, 5.94 Hz, 2 H) 2.89 (s, 2 H) 1.48 (s, 6 H) 1.19-1.30 (m, 3 H); LCMS for $C_{23}H_{25}N_5O_4$ m/z 436.20 (M+H$^+$); Anal. Calcd. for $C_{23}H_{25}N_5O_4$·0.12 CHCl$_3$: C, 61.73; H, 5.63; N, 15.57; Found: C, 61.55; H, 5.63; N, 15.12.

Preparation of Intermediate 168a 4-(6-Ethylcarbamoyl-pyridin-3-yloxy)-2,2-dimethyl-2,3-dihydro-benzofuran-6-carboxylic acid methyl ester

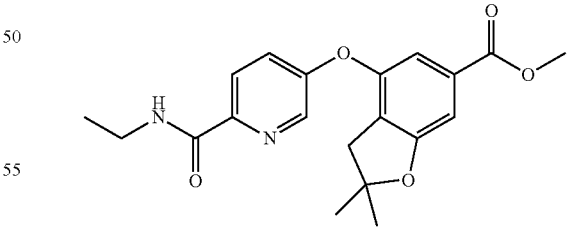

The title compound was prepared in a similar manner as described for Intermediate 166b, from 5-(6-methoxycarbonyl-2,2-dimethyl-2,3-dihydro-benzofuran-4-yloxy)-pyridine-2-carboxylic acid (166a) (74 mg, 0.22 mmol) and ethyl amine (2.0 M in THF, 1 mL) to give a white solid (28 mg, 35% yield). $^1$H NMR (400 MHz, CDCl$_3$) δ 8.28 (d, J=2.78 Hz, 1 H) 8.18 (d, J=8.59 Hz, 1 H) 7.82-7.91 (m, 1 H) 7.34 (dd, J=8.59, 2.78 Hz, 1 H) 7.25 (s, 1 H) 7.19 (d, J=1.01 Hz, 1 H) 3.87 (s, 3

H) 3.52 (dd, J=7.33, 6.06 Hz, 2 H) 2.90 (s, 2 H) 1.49 (s, 6 H) 1.22-1.33 (m, 3 H); LCMS for $C_{20}H_{22}N_2O_5$ m/z 371.00 (M+H$^+$).

Example 169

4-[6-(Azetidine-1-carbonyl)-pyridin-3-yloxy]-2,2-dimethyl-2,3-dihydro-benzofuran-6-carboxylic acid (2-methyl-2H-[1,2,3]triazol-4-yl)-amide

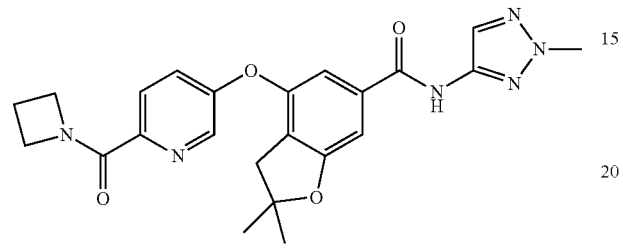

The title compound was prepared in a similar manner as described for Example 1, from 4-[6-(azetidine-1-carbonyl)-pyridin-3-yloxy]-2,2-dimethyl-2,3-dihydro-benzofuran-6-carboxylic acid methyl ester (167b) (68 mg, 0.18 mmol) to give a white solid (46 mg, 69% yield). $^1$H NMR (400 MHz, CDCl$_3$) δ 8.37 (s, 1 H) 8.31 (d, J=2.27 Hz, 1 H) 8.08 (s, 1 H) 8.12 (d, J=8.59 Hz, 1 H) 7.33 (dd, J=8.72, 2.91 Hz, 1 H) 7.05 (dd, J=7.33, 1.26 Hz, 2 H) 4.71 (t, J=7.71 Hz, 2 H) 4.26 (t, J=7.83 Hz, 2 H) 4.12 (s, 3 H) 2.91 (s, 2 H) 2.36 (t, J=7.71 Hz, 2 H) 1.51 (s, 6 H); LCMS for $C_{23}H_{24}N_6O_4$ m/z 449.20 (M+H$^+$); Anal. Calcd. for $C_{23}H_{24}N_6O_4$·0.2 AcOH: C, 61.03; H, 5.43; N, 18.25; Found: C, 61.14; H, 5.54; N, 18.39.

Example 170

5-[2,2-Dimethyl-6-(2-methyl-2H-[1,2,3]triazol-4-ylcarbamoyl)-2,3-dihydro-benzofuran-4-yloxy]-pyridine-2-carboxylic acid methylamide

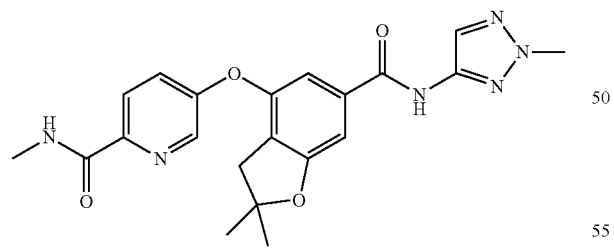

The title compound was prepared in a similar manner as described for Example 1, from 2,2-dimethyl-4-(6-methylcarbamoyl-pyridin-3-yloxy)-2,3-dihydro-benzofuran-6-carboxylic acid methyl ester (166b) (104 mg, 0.292 mmol) to give a white solid (60 mg, 46% yield). $^1$H NMR (400 MHz, CDCl$_3$) δ 8.40 (s, 1 H) 8.29 (d, J=2.78 Hz, 1 H) 8.19 (d, J=8.84 Hz, 1 H) 8.08 (s, 1 H) 7.87 (d, J=4.55 Hz, 1 H) 7.37 (dd, J=8.59, 2.78 Hz, 1 H) 7.06 (s, 1 H) 7.04 (s, 1 H) 4.11 (s, 3 H) 3.04 (d, J=5.31 Hz, 3 H) 2.91 (s, 2 H) 1.51 (s, 6 H); LCMS for $C_{21}H_{22}N_6O_4$ m/z 423.20 (M+H$^+$); Anal. Calcd. for $C_{21}H_{22}N_6O_4$·0.2 AcOH·0.2 H$_2$O: C, 58.67; H, 5.34; N, 19.19; Found: C, 58.48; H, 5.25; N, 19.34.

Example 171

5-[2,2-Dimethyl-6-(1-methyl-1H-pyrazol-3-ylcarbamoyl)-2,3-dihydro-benzofuran-4-yloxy]-pyrimidine-2-carboxylic acid methylamide

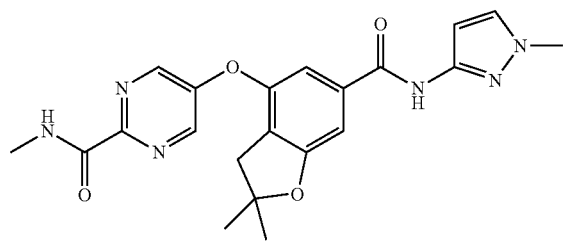

The title compound was prepared in a similar manner as described for Example 1, from 2,2-dimethyl-4-(2-methylcarbamoyl-pyrimidin-5-yloxy)-2,3-dihydro-benzofuran-6-carboxylic acid methyl ester (171d) (45 mg, 0.16 mmol) to give a white solid (15 mg, 28% yield). $^1$H NMR (400 MHz, CDCl$_3$) δ 8.54 (s, 2 H) 7.89 (br. s., 2 H) 7.38 (s, 1 H) 7.27 (s, 1 H) 7.08-7.19 (m, 2 H) 3.86 (s, 3 H) 3.08 (d, J=4.80 Hz, 3 H) 2.93 (s, 2 H) 1.51 (s, 6 H); LCMS for $C_{21}H_{22}N_6O_4$ m/z 423.00 (M+H$^+$).

Preparation of Intermediate 171a

5-Bromo-pyrimidine-2-carboxylic acid tert-butyl ester

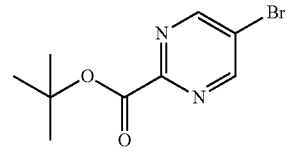

A suspension of 5-bromopyrimidine-2-carboxylic acid (690 mg, 3.40 mmol) in 6.8 mL t-BuOH and 1.9 mL pyridine was stirred at room temperature to 50° C. for 1 hr, and cooled to room temperature. 4-Toluenesulfonyl chloride (1.55 g, 8.12 mmol) was added portion wise. The mixture was stirred at room temperature for 1.5 h. The reaction was quenched with saturated aqueous NaHCO$_3$ slowly, extracted with 3×Et$_2$O, dried over Na$_2$SO$_4$, and concentrated. The residue was purified by Biotage column chromatography with 15-25% EtOAc in hexanes to give a yellow solid (497 mg, 56% yield). $^1$H NMR (400 MHz, CDCl$_3$) δ 8.94 (s, 2 H) 1.64 (s, 9 H).

Preparation of Intermediate 171b 5-(6-Methoxycarbonyl-2,2-dimethyl-2,3-dihydro-benzofuran-4-yloxy)-pyrimidine-2-carboxylic acid tert-butyl ester

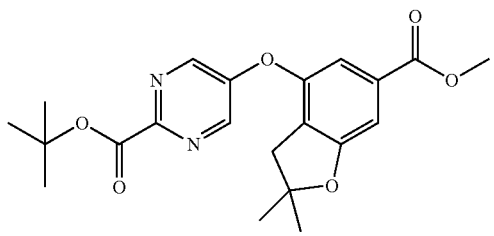

The title compound was prepared in a similar manner as described for Intermediate 161b, from 5-bromo-pyrimidine-2-carboxylic acid tert-butyl ester (171a) (497 mg, 1.92 mmol) and 4-hydroxy-2,2-dimethyl-2,3-dihydro-benzofuran-6-carboxylic acid methyl ester (3e) (426 mg, 1.92 mmol) to give a yellow oil (83 mg, 11% yield). $^1$H NMR (400 MHz, CDCl$_3$) δ 8.57 (s, 2 H) 7.30 (d, J=1.26 Hz, 1 H) 7.19 (d, J=1.26 Hz, 1 H) 3.88 (s, 3 H) 2.92 (s, 2 H) 1.68 (s, 9 H) 1.50 (s, 6 H); LCMS for C$_{21}$H$_{24}$N$_2$O$_6$ m/z 345.00 (M-tBu+H$^+$).

Preparation of Intermediate 171c 5-(6-Methoxycarbonyl-2,2-dimethyl-2,3-dihydro-benzofuran-4-yloxy)-pyrimidine-2-carboxylic acid

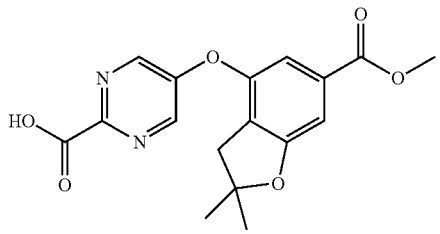

A solution of 5-(6-methoxycarbonyl-2,2-dimethyl-2,3-dihydro-benzofuran-4-yloxy)-pyrimidine-2-carboxylic acid tert-butyl ester (171b) (83 mg, 0.21 mmol) in 2 mL CH$_2$Cl$_2$ and 1 mL TFA was stirred at room temperature for 2 hr. The mixture was concentrated, dried under vacuum, and taken to the next step as it is.

Preparation of Intermediate 171d 2,2-Dimethyl-4-(2-methylcarbamoyl-pyrimidin-5-yloxy)-2,3-dihydro-benzofuran-6-carboxylic acid methyl ester

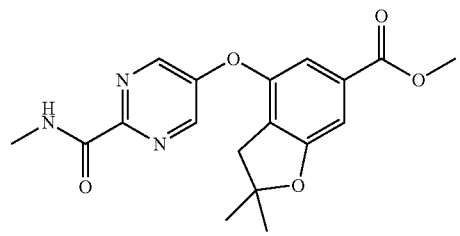

The title compound was prepared in a similar manner as described for Intermediate 166b, from 5-(6-methoxycarbonyl-2,2-dimethyl-2,3-dihydro-benzofuran-4-yloxy)-pyrimidine-2-carboxylic acid (171c) (72.3 mg, 0.21 mmol) and methyl amine (2 mL, 2.0 M solution in THF) to give a white solid (45 mg, 60% yield). $^1$H NMR (400 MHz, CDCl$_3$) δ 8.53 (s, 2 H) 7.88 (d, J=3.79 Hz, 1 H) 7.28 (d, J=10.11 Hz, 1 H) 7.19 (s, 1 H) 3.88 (s, 3 H) 3.08 (d, J=5.05 Hz, 3 H) 2.92 (s, 2 H) 1.49 (s, 6 H); LCMS for C$_{18}$H$_{19}$N$_3$O$_5$ m/z 358.20 (M+H$^+$).

Example 172

4-[2-(Azetidine-1-carbonyl)-pyrimidin-5-yloxy]-2,2-dimethyl-2,3-dihydro-benzofuran-6-carboxylic acid (1-methyl-1H-pyrazol-3-yl)-amide

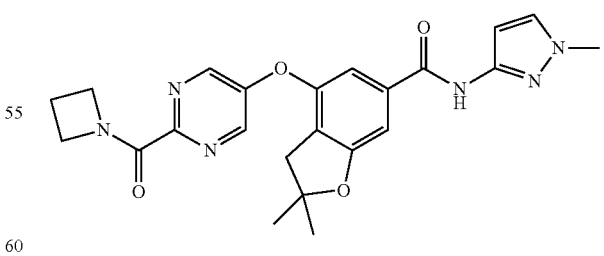

The title compound was prepared in a similar manner as described for Example 1, from 4-[2-(azetidine-1-carbonyl)-pyrimidin-5-yloxy]-2,2-dimethyl-2,3-dihydro-benzofuran-6-carboxylic acid methyl ester (172b) (76 mg, 0.20 mmol) to give a white solid (18 mg, 20% yield). $^1$H NMR (400 MHz, CDCl$_3$) δ 8.57 (br. s., 2 H) 7.22-7.33 (m, 3 H) 7.09-7.19 (m, 2 H) 4.64 (br. s., 2 H) 4.31 (br. s., 2 H) 3.88 (s, 3 H) 2.97 (s, 2 H) 2.29-2.42 (m, 2 H) 1.50 (s, 6 H); LCMS for $C_{23}H_{24}N_8O_4$ m/z 449.00 (M+H$^+$).

Preparation of Intermediate 172a

Azetidin-1-yl-(5-bromo-pyrimidin-2-yl)-methanone

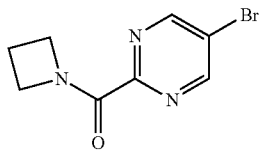

The title compound was prepared in a similar manner as described for Intermediate 161a, from 5-bromopyrimidine-2-caboxylic acid (1.60 g, 7.877 mmol) and azetidine hydrochloride (1.11 g, 11.8 mmol) to give a yellow solid (331 mg, 17% yield). $^1$H NMR (400 MHz, CDCl$_3$) δ 8.92 (s, 2 H) 4.64 (t, J=7.71 Hz, 2 H) 4.29 (t, J=7.83 Hz, 2 H) 2.29-2.41 (m, 2 H); LCMS for $C_8H_8BrN_3O$ m/z 241.00 and 243.00 (M+H)$^+$.

Preparation of Intermediate 172b

4-[2-(Azetidine-1-carbonyl)-pyrimidin-5-yloxy]-2,2-dimethyl-2,3-dihydro-benzofuran-6-carboxylic acid methyl ester

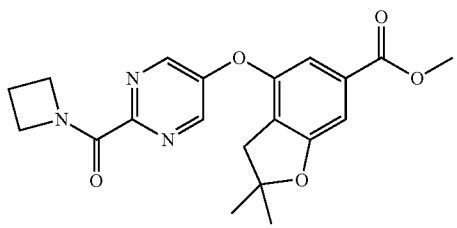

The title compound was prepared in a similar manner as described for Intermediate 161b, from azetidin-1-yl-(5-bromo-pyrimidin-2-yl)-methanone (172a) (331 mg, 1.37 mmol) and 4-hydroxy-2,2-dimethyl-2,3-dihydro-benzofuran-6-carboxylic acid methyl ester (3e) (304 mg, 1.37 mmol) to give a white foam (136 mg, 36% yield). $^1$H NMR (400 MHz, CDCl$_3$) δ 8.91 (s, 1 H) 8.53 (s, 2 H) 7.29 (s, 1 H) 4.64 (t, J=7.45 Hz, 2 H) 4.30 (t, J=7.58 Hz, 2 H) 3.88 (s, 3 H) 2.93 (s, 2 H) 2.36 (t, J=7.45 Hz, 2 H) 1.50 (s, 6 H); LCMS for $C_{20}H_{21}N_3O_5$ m/z 384.00 (M+H$^+$).

Example 173

4-[6-(Azetidine-1-carbonyl)-5-fluoro-pyridin-3-yloxy]-2,2-dimethyl-2,3-dihydro-benzofuran-6-carboxylic acid (1-methyl-1H-pyrazol-3-yl)-amide

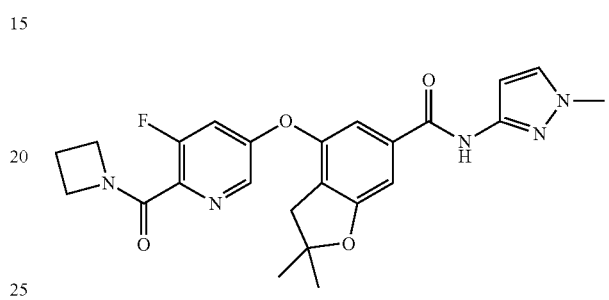

A mixture of azetidin-1-yl-(3,5-difluoro-pyridin-2-yl)-methanone (173a) (174 mg, 0.877 mmol), 4-hydroxy-2,2-dimethyl-2,3-dihydro-benzofuran-6-carboxylic acid (1-methyl-1H-pyrazol-3-yl)-amide (31a) (210 mg, 0.731 mmol), and Cs$_2$CO$_3$ (476 mg, 1.46 mmol) in DMF was heated to 160° C. in a microwave for 30 min, cooled to room temperature, quenched with H$_2$O, and extracted with 3×EtOAc. The combined organic layer was washed with 2×H$_2$O, dried over Na$_2$SO$_4$ and concentrated. The residue was purified by SFC column chromatography to give a white solid (241 mg, 68% yield). $^1$H NMR (400 MHz, CDCl$_3$) δ 9.64 (br. S, 1 H) 8.20 (d, J=1.76 Hz, 1 H) 7.28 (d, J=2.27 Hz, 1 H) 7.21 (s, 1H) 7.18 (d, J=1.01 Hz, 1 H) 7.08 (dd, J=10.83, 2.27 Hz, 1 H) 6.84 (d, J=2.27 Hz, 1 H) 4.38 (t, J=7.68 Hz, 2 H) 4.25 (t, J=7.81 Hz, 2 H) 3.80 (s, 3 H) 2.97 (s, 2 H) 2.24-2.43 (m, 2 H) 1.50 (s, 6 H); LCMS for $C_{24}H_{24}FN_8O_4$ m/z 466.20 (M+H)$^+$; Anal. Calcd. for $C_{24}H_{24}FN_8O_4$·0.40 AcOH: C, 60.85; H, 5.27; N, 14.31; Found: C, 60.87; H, 5.23; N, 14.42.

Preparation of Intermediate 173a

Azetidin-1-yl-(3,5-difluoro-pyridin-2-yl)-methanone

The title compound was prepared in a similar manner as described for Intermediate 161a, from 3,4-difluoropyridine-2-caboxylic acid (1.00 g, 6.29 mmol) and azetidine hydrochloride (882 mg, 9.43 mmol) to give a white solid (630 mg, 51% yield). $^1$H NMR (400 MHz, CDCl$_3$) δ 8.32-8.51 (m, 1 H) 7.66 (dd, J=9.09, 1.77 Hz, 1 H) 4.26 (d, J=7.58 Hz, 2 H) 4.18

(t, J=7.83 Hz, 2 H) 2.29 (dt, J=15.66, 7.83 Hz, 2 H); LCMS for C₉H₈F₂N₂O m/z 199.00 (M+H)⁺.

Example 174

5-[2,2-Dimethyl-6-(2-methyl-2H-[1,2,3]triazol-4-ylcarbamoyl)-2,3-dihydro-benzofuran-4-yloxy]-pyridine-2-carboxylic acid ethylamide

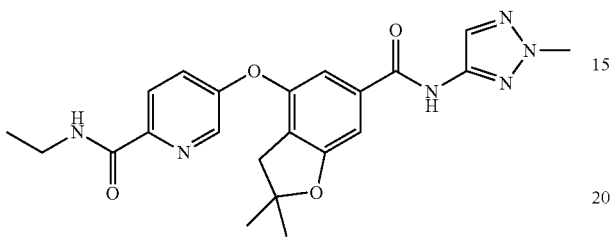

The title compound was prepared in a similar manner as described for Example 1, from 4-(6-ethylcarbamoyl-pyridin-3-yloxy)-2,2-dimethyl-2,3-dihydro-benzofuran-6-carboxylic acid methyl ester (168a) to give a white solid (287 mg, 36% yield). ¹H NMR (400 MHz, CDCl₃) δ 8.46 (br. s., 1 H) 8.29 (d, J=2.02 Hz, 1 H) 8.19 (d, J=8.59 Hz, 1 H) 8.08 (s, 1 H) 7.86 (br. s., 1 H) 7.36 (dd, J=8.59, 2.78 Hz, 1 H) 7.28 (s, 1 H) 7.04 (d, J=1.26 Hz, 1 H) 4.11 (s, 3 H) 3.51 (d, J=6.06 Hz, 2 H) 2.91 (s, 2 H) 1.51 (s, 6 H) 1.28 (t, J=7.33 Hz, 3 H); LCMS for C₂₂H₂₄N₆O₄ m/z 437.00 (M+H⁺); Anal. Calcd. for C₂₂H₂₄N₆O₄.0.2 AcOH: C, 59.99; H, 5.57; N, 18.97; Found: C, 59.84; H, 5.47; N, 18.97.

Example 175

5-[2,2-Dimethyl-6-(1-methyl-1H-pyrazol-3-ylcarbamoyl)-2,3-dihydro-benzofuran-4-yloxy]-3-ethylamino-pyridine-2-carboxylic acid ethylamide

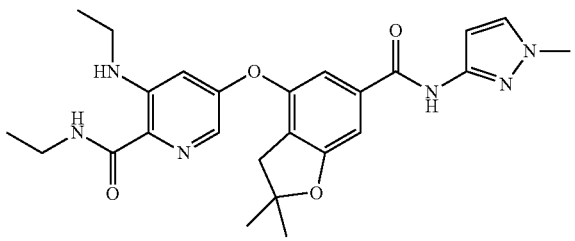

The title compound was prepared in a similar manner as described for Example 1, from ethyl amine hydrochloride (278 mg, 3.41 mmol) and 5-[2,2-dimethyl-6-(1-methyl-1H-pyrazol-3-ylcarbamoyl)-2,3-dihydro-benzofuran-4-yloxy]-3-fluoro-pyridine-2-carboxylic acid methyl ester (175b) (150 mg, 0.341 mmol) to give a white solid (111 mg, 68% yield). ¹H NMR (400 MHz, CDCl₃) δ 8.36-8.50 (m, 2 H) 7.91 (t, J=5.56 Hz, 1 H) 7.47 (d, J=2.27 Hz, 1 H) 7.27 (s, 1H) 7.04 (s, 1 H) 7.00 (d, J=1.26 Hz, 1 H) 6.78 (d, J=2.27 Hz, 1 H) 6.50 (d, J=2.27 Hz, 1 H) 3.79 (s, 3 H) 3.33-3.51 (m, 2 H) 3.01-3.15 (m, 2 H) 2.94 (s, 2 H) 1.50 (s, 6 H) 1.19-1.34 (m, 6 H); LCMS for C₂₅H₃₀N₆O₄ m/z 479.20 (M+H⁺); Anal. Calcd. for C₂₅H₃₀N₆O₄: C, 62.75; H, 6.32; N, 17.56; Found: C, 62.63; H, 6.37; N, 17.35.

Preparation of Intermediate 175a 3,5-Difluoro-pyridine-2-carboxylic acid methyl ester

3,5-Difluoropicolinic acid (1.40 g, 8.78 mmol) was dissolved in 30 mL MeOH and 0.5 mL 4.0 M HCl in 1,4-dioxane. The mixture was heated at 60° C. for 1.5 h and concentrated. Saturated aqueous NaHCO₃ was added. The mixture was extracted with EtOAc, dried over Na₂SO₄, and concentrated to give a yellow solid (1.30 g, 86% yield). ¹H NMR (400 MHz, CDCl₃) δ 8.48 (d, J=2.27 Hz, 1 H) 7.28-7.47 (m, 1 H) 4.03 (s, 3 H); LCMS for C₇H₅F₂NO₂ m/z 174.00 (M+H⁺).

Preparation of Intermediate 175b

5-[2,2-Dimethyl-6-(1-methyl-1H-pyrazol-3-ylcarbamoyl)-2,3-dihydro-benzofuran-4-yloxy]-3-fluoro-pyridine-2-carboxylic acid methyl ester

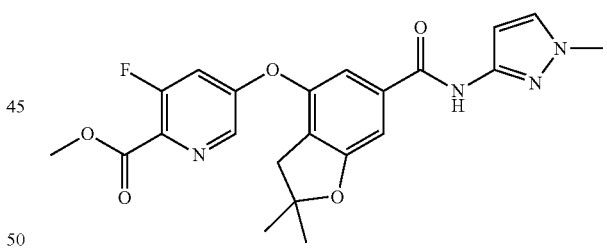

A mixture of 3,5-difluoro-pyridine-2-carboxylic acid methyl ester (175a) (422 mg, 2.44 mmol), 4-hydroxy-2,2-dimethyl-2,3-dihydro-benzofuran-6-carboxylic acid (1-methyl-1H-pyrazol-3-yl)-amide (31a) (700 mg, 2.44 mmol), and Cs₂CO₃ (1.59 g, 4.88 mmol) in DMF was heated to 160° C. in a microwave for 30 min, cooled to room temperature, quenched with H₂O and extracted with 3×EtOAc. The combined organic layer was washed with 2×H₂O, dried over Na₂SO₄ and concentrated. The residue was purified by Biotage column chromatography with 40-70% EtOAc in hexanes to give a white solid (607 mg, 57% yield). ¹H NMR (400 MHz, CDCl₃) δ 9.12 (br. s., 1 H) 8.31 (d, J=2.02 Hz, 1 H) 7.27 (d, J=2.27 Hz, 1 H) 7.12 (d, J=5.81 Hz, 2 H) 6.97-7.07 (m, 1

H) 6.78 (d, J=1.77 Hz, 1 H) 4.00 (s, 3 H) 3.73 (s, 3 H) 2.88 (s, 2 H) 1.49 (s, 6 H); LCMS for $C_{22}H_{21}FN_4O_5$ m/z 441.20 (M+H)$^+$.

Example 176

5-[2,2-Dimethyl-6-(1-methyl-1H-pyrazol-3-ylcarbamoyl)-2,3-dihydro-benzofuran-4-yloxy]-3-fluoropyridine-2-carboxylic acid methylamide

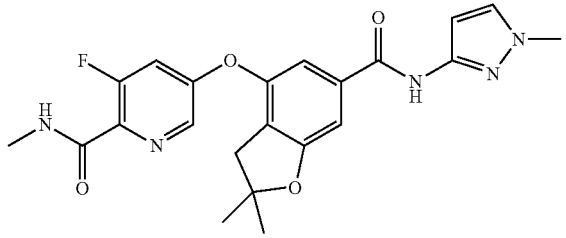

To a solution of 5-[2,2-dimethyl-6-(1-methyl-1H-pyrazol-3-ylcarbamoyl)-2,3-dihydro-benzofuran-4-yloxy]-3-fluoro-pyridine-2-carboxylic acid (176a) (97 mg, 0.23 mmol) in 3 mL $CH_2Cl_2$ was added 2.0 M oxalyl chloride in THF (0.23 mL, 0.46 mmol), followed by 3 drops of DMF. The mixture was stirred at room temperature for 1 hr, concentrated, and dried under vacuum. The residue was dissolved in 3 mL $CH_2Cl_2$, and 1 mL 2.0 M methyl amine in THF was added at 0° C., followed by $Et_3N$ (0.091 mL, 0.46 mmol). The mixture was stirred at 0° C. for 1.5 hr. The reaction was quenched with $H_2O$, extracted with 3×$CHCl_3$, concentrated, and purified by reverse phase column chromatography to give a white solid (48 mg, 48% yield). $^1$H NMR (400 MHz, $CDCl_3$) δ 8.51 (s, 1 H) 8.14 (d, J=2.02 Hz, 1 H) 7.63 (br. s., 1 H) 7.25-7.33 (m, 1 H) 7.03-7.12 (m, 3 H) 6.79 (d, J=1.77 Hz, 1 H) 3.81 (s, 3 H) 2.98-3.06 (m, 3 H) 2.91 (s, 2 H) 1.51 (s, 6 H); LCMS for $C_{22}H_{22}FN_5O_4$ m/z 440.20 (M+H$^+$); Anal. Calcd. for $C_{22}H_{22}FN_5O_4$·0.25 AcOH: C, 59.47; H, 5.10; N, 15.41; Found: C, 59.41; H, 5.04; N, 15.52.

Preparation of Intermediate 176a

5-[2,2-Dimethyl-6-(1-methyl-1H-pyrazol-3-ylcarbamoyl)-2,3-dihydro-benzofuran-4-yloxy]-3-fluoropyridine-2-carboxylic acid

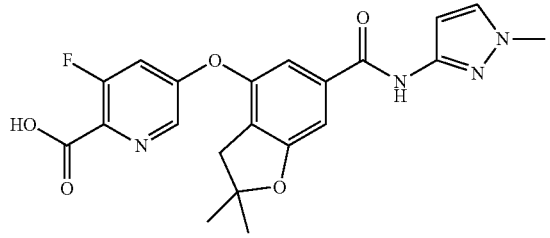

To a solution of 5-[2,2-dimethyl-6-(1-methyl-1H-pyrazol-3-ylcarbamoyl)-2,3-dihydro-benzofuran-4-yloxy]-3-fluoro-pyridine-2-carboxylic acid methyl ester (175b) (949 mg, 2.15 mmol) in 12 mL THF was added 4 mL of 1.0 N aqueous NaOH. The mixture was heated at 60° C. for 1 hr, and concentrated in vacuo. The residue was acidified to pH ~1 with 1N aqueous HCl, filtered, washed with water, and dried under vacuum at 60° C. overnight to give an off-white solid (800 mg, 87% yield). LCMS for $C_{21}H_{19}FN_4O_5$ m/z 427.20 (M+H$^+$).

Example 177

5-[2,2-Dimethyl-6-(1-methyl-1H-pyrazol-3-ylcarbamoyl)-2,3-dihydro-benzofuran-4-yloxy]-3-fluoropyridine-2-carboxylic acid ethylamide

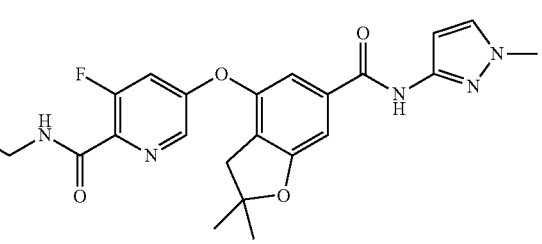

The title compound was prepared in a similar manner as described for Example 176, from 5-[2,2-dimethyl-6-(1-methyl-1H-pyrazol-3-ylcarbamoyl)-2,3-dihydro-benzofuran-4-yloxy]-3-fluoro-pyridine-2-carboxylic acid (176a) and ethyl amine (1.0 mL, 2.0 M solution in THF) to give a white solid (203 mg, 64% yield). $^1$H NMR (400 MHz, $CDCl_3$) δ 8.70 (s, 1 H) 8.12 (d, J=2.02 Hz, 1 H) 7.65 (t, J=5.43 Hz, 1 H) 7.23-7.32 (m, 1 H) 6.96-7.12 (m, 3 H) 6.78 (d, J=2.02 Hz, 1 H) 3.77 (s, 3 H) 3.40-3.58 (m, 2 H) 2.89 (s, 2 H) 1.50 (s, 6 H) 1.26 (t, J=7.20 Hz, 3 H); LCMS for $C_{23}H_{24}FN_5O_4$ m/z 454.20 (M+H$^+$); Anal. Calcd. for $C_{23}H_{24}FN_5O_4$·0.10 AcOH: C, 60.65; H, 5.35; N, 15.24; Found: C, 60.62; H, 5.36; N, 15.28.

Example 178

5-[2,2-Dimethyl-6-(1-methyl-1H-pyrazol-3-ylcarbamoyl)-2,3-dihydro-benzofuran-4-yloxy]-3-fluoropyridine-2-carboxylic acid dimethylamide

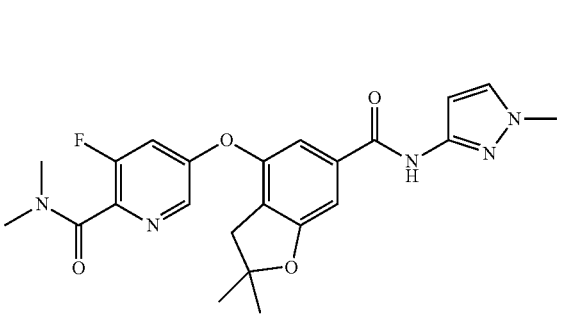

The title compound was prepared in a similar manner as described for Example 1, from dimethyl amine hydrochloride (278 mg, 3.41 mmol) and 5-[2,2-dimethyl-6-(1-methyl-1H-pyrazol-3-ylcarbamoyl)-2,3-dihydro-benzofuran-4-yloxy]-3-fluoro-pyridine-2-carboxylic acid methyl ester (175b) (150 mg, 0.341 mmol) to give a white solid (74 mg, 48% yield). $^1$H NMR (400 MHz, $CDCl_3$) δ 8.39 (s, 1 H) 8.22 (d, J=1.77 Hz, 1 H) 7.27-7.31 (m, 1 H) 7.01-7.13 (m, 3 H) 6.78 (d, J=2.02 Hz, 1 H) 3.81 (s, 3 H) 3.16 (s, 3 H) 3.00 (s, 3 H) 2.92 (s, 2 H) 1.50

(s, 6 H); LCMS for $C_{23}H_{24}FN_5O_4$ m/z 454.20 (M+H⁺); Anal. Calcd. for $C_{23}H_{24}FN_5O_4$: C, 60.92; H, 5.33; N, 15.44; Found: C, 60.66; H, 5.37; N, 15.26.

Example 179

5-[2,2-Dimethyl-6-(1-methyl-1H-pyrazol-3-ylcarbamoyl)-2,3-dihydro-benzofuran-4-yloxy]-pyridine-2-carboxylic acid methyl ester

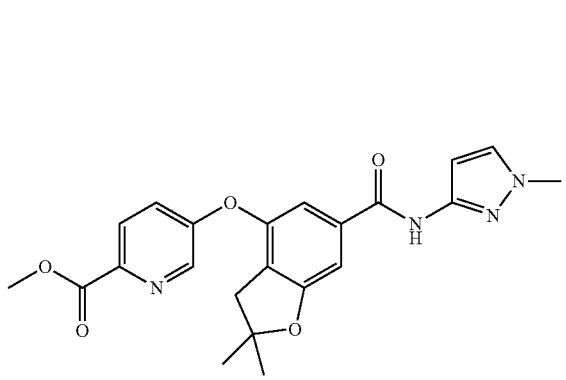

A mixture of 5-fluoro-pyridine-2-carboxylic acid methyl ester (179a) (342 mg, 2.20 mmol), 4-hydroxy-2,2-dimethyl-2,3-dihydro-benzofuran-6-carboxylic acid (1-methyl-1H-pyrazol-3-yl)-amide (31a) (633 mg, 2.20 mmol), and $Cs_2CO_3$ (1.44 g, 4.40 mmol) in DMF was heated to 160° C. in a microwave for 30 min, cooled to room temperature, quenched with $H_2O$, and extracted with 3×EtOAc. The combined organic layer was washed with 2×$H_2O$, dried over $Na_2SO_4$ and concentrated. The residue was purified by Biotage column chromatography with 75-90% EtOAc in hexanes to give a white solid (524 mg, 56% yield). ¹H NMR (400 MHz, $CDCl_3$) δ 8.49 (d, J=3.03 Hz, 2 H) 8.13 (d, J=8.59 Hz, 1 H) 7.22-7.36 (m, 2 H) 7.06 (d, J=5.05 Hz, 2 H) 6.77 (d, J=2.27 Hz, 1 H) 4.01 (s, 3 H) 3.78 (s, 3 H) 2.89 (s, 2 H) 1.49 (s, 6 H); LCMS for $C_{22}H_{22}N_4O_6$ m/z 423.20 (M+H⁺).

Preparation of Intermediate 179a

5-Fluoro-pyridine-2-carboxylic acid methyl ester

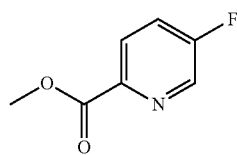

The title compound was prepared in a similar manner as described for Intermediate 175a, from 5-fluoropicolinic acid (1.05 g, 7.44 mmol) to give a yellow solid (980 mg, 85% yield). ¹H NMR (400 MHz, $CDCl_3$) δ 8.59 (d, J=2.78 Hz, 1 H) 8.21 (dd, J=8.72, 4.42 Hz, 1 H) 7.55 (d, J=3.03 Hz, 1 H) 4.02 (s, 3 H); LCMS for $C_7H_6FNO_2$ m/z 156.00 (M+H⁺).

Example 180

5-[2,2-Dimethyl-6-(1-methyl-1H-pyrazol-3-ylcarbamoyl)-2,3-dihydro-benzofuran-4-yloxy]-pyridine-2-carboxylic acid

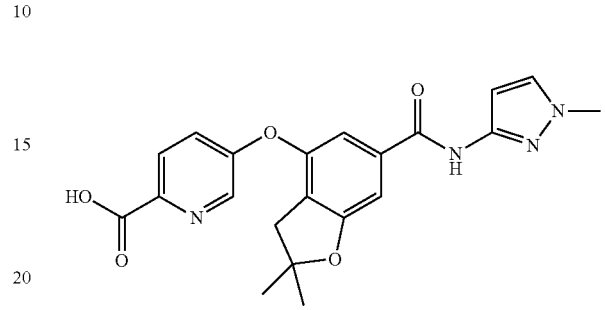

To a solution of 5-[2,2-dimethyl-6-(1-methyl-1H-pyrazol-3-ylcarbamoyl)-2,3-dihydro-benzofuran-4-yloxy]-pyridine-2-carboxylic acid methyl ester (179) (524 mg, 1.24 mmol) in 10 mL THF was added 2 mL 1 N aqueous NaOH. The mixture was heated at 60° C. for 1 hr, and concentrated in vacuo. The residue was acidified to pH ~1 with 1N aqueous HCl, filtered, washed with water, and dried under vacuum at 60° C. overnight to give an off-white solid (400 mg, 79% yield). ¹H NMR (400 MHz, DMSO-$d_6$) δ 10.74 (br. s., 1 H) 8.51 (br. s., 2 H) 7.97-8.17 (m, 1 H) 7.46-7.64 (m, 2 H) 7.23 (br. s., 2 H) 6.54 (br, s, 1 H) 3.76 (s, 3 H) 2.91 (s, 2 H) 1.44 (s, 6 H); LCMS for $C_{21}H_{20}N_4O_5$ m/z 409.20 (M+H⁺).

Example 181

4-(6-Cyano-pyridin-3-yloxy)-2,2-dimethyl-2,3-dihydro-benzofuran-6-carboxylic acid (1-methyl-1H-pyrazol-3-yl)-amide

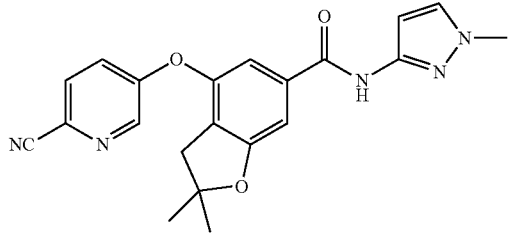

A mixture of 5-(4,4,5,5-tetramethyl-1,3,2-dioxaborolan-2-yl)picolinonitrile (634 mg, 2.76 mmol), 4-hydroxy-2,2-dimethyl-2,3-dihydro-benzofuran-6-carboxylic acid (1-methyl-1H-pyrazol-3-yl)-amide (31a) (396 mg, 1.33 mmol), $Et_3N$ (0.96 mL, 6.89 mmol), and $Cu(OAc)_2$ (501 mg, 2.76 mmol) in $CH_2Cl_2$ (15 mL) was stirred at room temperature with 4 A molecular sieves for 4 days, then filtered through celite, washed with $CHCl_3$, concentrated, and purified by column chromatography with 30-60% EtOAc in hexanes to give a white foam (246 mg, 46% yield). ¹H NMR (400 MHz, $CDCl_3$) δ 9.23 (s, 1 H) 8.45 (d, J=2.53 Hz, 1 H) 7.65 (d, J=8.59 Hz, 1 H) 7.21-7.35 (m, 2H) 7.10 (d, J=11.37 Hz, 2 H) 6.78 (d, J=2.02 Hz, 1 H) 3.73 (s, 3 H) 2.89 (s, 2 H)) 1.48 (s, 6 H); LCMS for $C_{21}H_{19}N_5O_3$ m/z 390.00 (M+H$^+$).

Example 182

2,2-Dimethyl-4-(6-[1,2,4]oxadiazol-3-yl-pyridin-3-yloxy)-2,3-dihydro-benzofuran-6-carboxylic acid (1-methyl-1H-pyrazol-3-yl)-amide

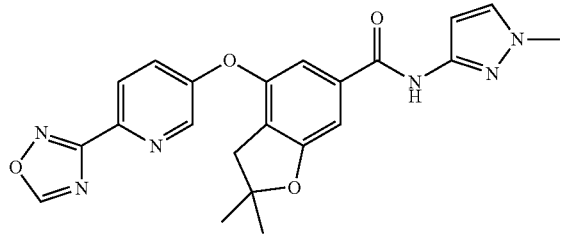

To a suspension of 4-[6-(N-hydroxycarbamimidoyl)-pyridin-3-yloxy]-2,2-dimethyl-2,3-dihydro-benzofuran-6-carboxylic acid (1-methyl-1H-pyrazol-3-yl)-amide (182a) (63.4 mg, 0.15 mmol) in 3 mL trimethyl orthoformate was added 2 drops of boron trifluoride diethyl etherate. The resulting solution was stirred at 55° C. for 1 hr, concentrated, and purified by column chromatography with 60-70% EtOAc in hexanes to give a white solid (31 mg, 48% yield). $^1$H NMR (400 MHz, CDCl$_3$) δ 8.89 (s, 1 H) 8.83 (s, 1 H) 8.57 (d, J=2.53 Hz, 1 H) 8.14 (d, J=8.84 Hz, 1 H) 7.38 (dd, J=8.72, 2.91 Hz, 1 H) 7.27 (s, 1 H) 7.09 (s, 2 H) 6.79 (d, J=2.27 Hz, 1 H) 3.78 (s, 3 H) 2.92 (s, 2 H) 1.49 (s, 6 H); LCMS for $C_{22}H_{20}N_6O_4$ m/z 433.00 (M+H$^+$); Anal. Calcd. for $C_{22}H_{20}N_6O_4 \cdot 0.4$ CHCl$_3$: C, 56.03; H, 4.28; N, 17.50; Found: C, 56.03; H, 4.46; N, 17.07.

Preparation of Intermediate 182a

4-[6-(N-Hydroxycarbamimidoyl)-pyridin-3-yloxy]-2,2-dimethyl-2,3-dihydro-benzofuran-6-carboxylic acid (1-methyl-1H-pyrazol-3-yl)-amide

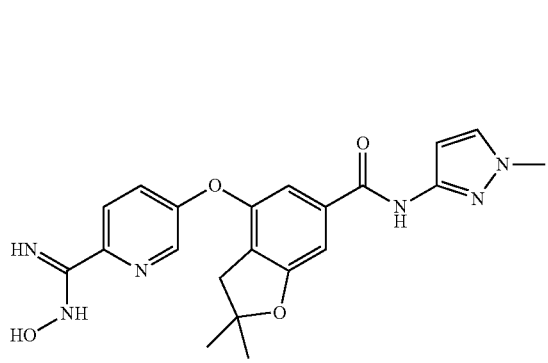

To a solution of 4-(6-cyano-pyridin-3-yloxy)-2,2-dimethyl-2,3-dihydro-benzofuran-6-carboxylic acid (1-methyl-1H-pyrazol-3-yl)-amide (181) in 3 mL EtOH was added 1 mL 50% NH$_4$OH in water. The resulting mixture was stirred at room temperature for 2 hr, concentrated in vacuo, dried under vacuum, and used as it is for the next step.

Example 183

4-(4-Cyano-3-fluoro-phenoxy)-2,2-dimethyl-2,3-dihydro-benzofuran-6-carboxylic acid (1-methyl-1H-pyrazol-3-yl)-amide

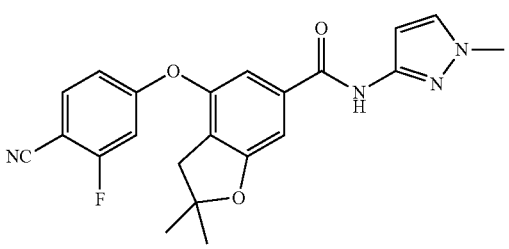

The title compound was prepared in a similar manner as described for Example 1, from 3-amino-1-methyl-pyrazole (478 mg, 4.92 mmol) and 4-(4-cyano-3-fluoro-phenoxy)-2,2-dimethyl-2,3-dihydro-benzofuran-6-carboxylic acid methyl ester (183a) (168 mg, 0.49 mmol) to give a white solid (176 mg, 88% yield). $^1$H NMR (400 MHz, CDCl$_3$) δ 9.19 (s, 1 H) 7.56 (dd, J=8.59, 7.33 Hz, 1 H) 7.16-7.32 (m, 1 H) 7.07 (d, J=3.03 Hz, 2 H) 6.68-6.83 (m, 3 H) 3.71 (s, 3 H) 2.87 (s, 2 H) 1.48 (s, 6 H); LCMS for $C_{22}H_{19}FN_4O_3$ m/z 407.00 (M+H$^+$).

Preparation of Intermediate 183a 4-(4-Cyano-3-fluoro-phenoxy)-2,2-dimethyl-2,3-dihydro-benzofuran-6-carboxylic acid methyl ester

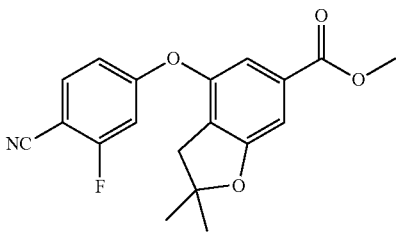

The title compound was prepared in a similar manner as described for Intermediate 161b, from 4-bromo-2-fluoro-benzonitrile (270 mg, 1.35 mmol) and 4-hydroxy-2,2-dimethyl-2,3-dihydro-benzofuran-6-carboxylic acid methyl ester (3e) (300 mg, 1.35 mmol) to give a white foam (336 mg, 73% yield). $^1$H NMR (400 MHz, CDCl$_3$) δ 7.57 (dd, J=8.84, 7.33 Hz, 1 H) 7.28 (s, 1 H) 7.24 (d, J=1.26 Hz, 1 H) 6.81 (dd, J=8.34, 2.02 Hz, 1 H) 6.75 (dd, J=10.23, 2.40 Hz, 1 H) 3.88 (s, 3 H) 2.87 (s, 2 H) 1.48 (s, 6 H); LCMS for $C_{19}H_{16}FNO_4$ m/z 342.00 (M+H$^+$).

Example 184

4-(4-Cyano-3-fluoro-phenoxy)-2,2-dimethyl-2,3-dihydro-benzofuran-6-carboxylic acid (2-methyl-2H-[1,2,3]triazol-4-yl)-amide

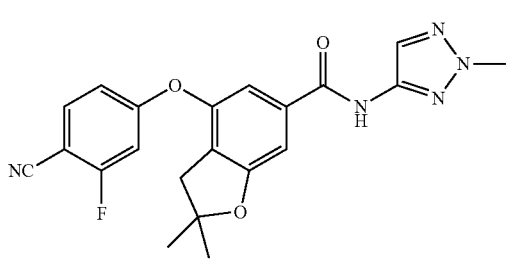

The title compound was prepared in a similar manner as described for Example 1, from 2-methyl-2H-1,2,3-triazol-4-amine hydrochloride (662 mg, 4.92 mmol) and 4-(4-cyano-3-fluoro-phenoxy)-2,2-dimethyl-2,3-dihydro-benzofuran-6-carboxylic acid methyl ester (183a) (168 mg, 0.49 mmol) to give a white solid (154 mg, 77% yield). $^1$H NMR (400 MHz, CDCl$_3$) δ 8.67 (s, 1 H) 8.06 (s, 1 H) 7.57 (dd, J=8.59, 7.33 Hz, 1 H) 7.06-7.15 (m, 2 H) 6.67-6.88 (m, 2 H) 4.10 (s, 3 H) 2.88 (s, 2 H) 1.49 (s, 6 H); LCMS for $C_{21}H_{18}FN_5O_3$ m/z 408.00 and 409.00 (M+H$^+$).

Example 185

4-(3-Fluoro-4-[1,2,4]oxadiazol-3-yl-phenoxy)-2,2-dimethyl-2,3-dihydro-benzofuran-6-carboxylic acid (1-methyl-1H-pyrazol-3-yl)-amide

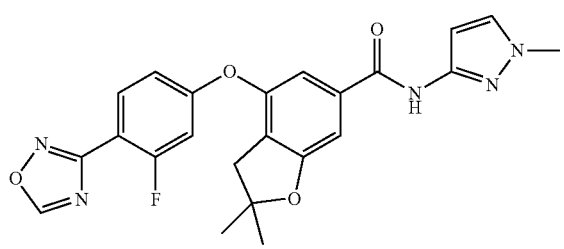

The title compound was prepared in a similar manner as described for Example 182, from 4-[3-fluoro-4-(N-hydroxy-carbamimidoyl)-phenoxy]-2,2-dimethyl-2,3-dihydro-benzofuran-6-carboxylic acid (1-methyl-1H-pyrazol-3-yl)-amide (185a) (178 mg, 0.40 mmol) to give white solid (82 mg, 45% yield). $^1$H NMR (400 MHz, CDCl$_3$) δ 8.80 (s, 1 H) 8.76 (s, 1 H) 8.06 (t, J=8.34 Hz, 1 H) 7.25-7.30 (m, 1 H) 7.10 (d, J=2.02 Hz, 2 H) 6.71-6.93 (m, 3 H) 3.77 (s, 3 H) 2.90 (s, 2 H) 1.49 (s, 6 H); LCMS for $C_{23}H_{20}FN_5O_4$ m/z 450.00 and 451.00 (M+H$^+$); Anal. Calcd. for $C_{23}H_{20}FN_5O_4 \cdot 0.4 H_2O$: C, 60.49; H, 4.59; N, 15.34; Found: C, 60.31; H, 4.45; N, 15.49.

Preparation of Intermediate 185a

4-[3-Fluoro-4-(N-hydroxycarbamimidoyl)-phenoxy]-2,2-dimethyl-2,3-dihydro-benzofuran-6-carboxylic acid (1-methyl-1H-pyrazol-3-yl)-amide

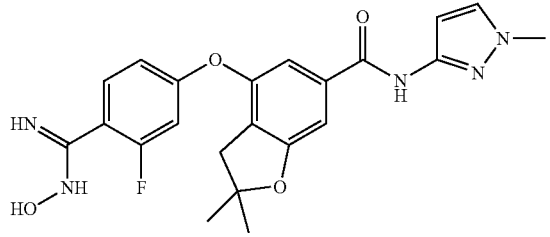

To a solution of 4-(4-cyano-3-fluoro-phenoxy)-2,2-dimethyl-2,3-dihydro-benzofuran-6-carboxylic acid (1-methyl-1H-pyrazol-3-yl)-amide (183) (164 mg, 0.404 mmol) in 3 mL EtOH was added 1 mL 50% NH$_4$OH in water. The resulting mixture was stirred at 55° C. for 2 hr, concentrated in vacuo, dried under vacuum, and used as it is for the next step.

Example 186

4-(3-Fluoro-4-[1,2,4]oxadiazol-3-yl-phenoxy)-2,2-dimethyl-2,3-dihydro-benzofuran-6-carboxylic acid (2-methyl-2H-[1,2,3]triazol-4-yl)-amide

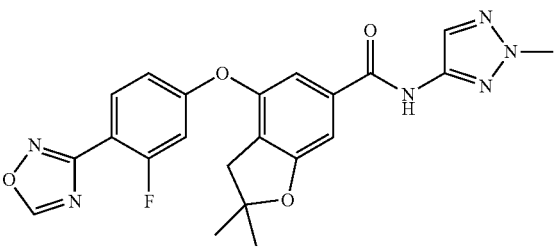

The title compound was prepared in a similar manner as described for Example 182, from 4-[3-fluoro-4-(N-hydroxy-carbamimidoyl)-phenoxy]-2,2-dimethyl-2,3-dihydro-benzofuran-6-carboxylic acid (2-methyl-2H-[1,2,3]triazol-4-yl)-amide (186a) (162 mg, 0.368 mmol) to give a white solid (155 mg, 85% yield). $^1$H NMR (400 MHz, CDCl$_3$) δ 8.75-8.87 (m, 2 H) 8.00-8.10 (m, 2 H) 7.12 (d, J=2.27 Hz, 2 H) 6.86

(d, J=3.28 Hz, 2 H) 4.09 (s, 3 H) 2.91 (s, 2 H) 1.49 (s, 6 H); LCMS for $C_{22}H_{19}FN_6O_4$ m/z 451.20 and 452.00 (M+H$^+$).

Preparation of Intermediate 186a

4-[3-Fluoro-4-(N-hydroxycarbamimidoyl)-phenoxy]-2,2-dimethyl-2,3-dihydro-benzofuran-6-carboxylic acid (2-methyl-2H-[1,2,3]triazol-4-yl)-amide

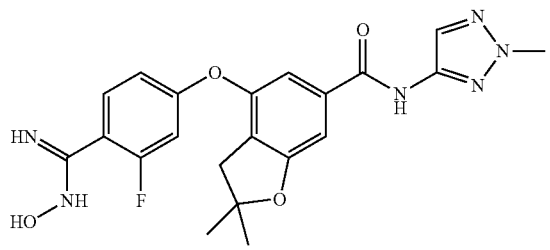

The title compound was prepared in a similar manner as described for Intermediate 185a, from 4-(4-cyano-3-fluoro-phenoxy)-2,2-dimethyl-2,3-dihydro-benzofuran-6-carboxylic acid (2-methyl-2H-[1,2,3]triazol-4-yl)-amide (184) (150 mg, 0.368 mmol) and used without further purification for the next step.

Example 187

2,2-Dimethyl-4-(4-[1,2,4]oxadiazol-3-yl-phenoxy)-2,3-dihydro-benzofuran-6-carboxylic acid (1-methyl-1H-pyrazol-3-yl)-amide

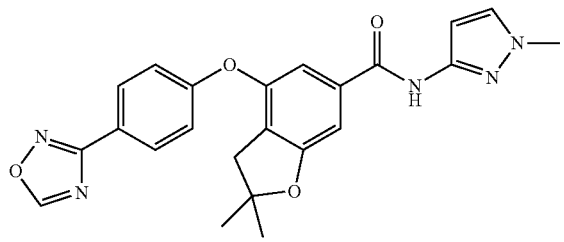

The title compound was prepared in a similar manner as described for Example 182, from 4-[4-(N-hydroxycarbamimidoyl)-phenoxy]-2,2-dimethyl-2,3-dihydro-benzofuran-6-carboxylic acid (1-methyl-1H-pyrazol-3-yl)-amide (187c) (135 mg, 0.321 mmol) to a give white solid (19 mg, 14% yield). $^1$H NMR (400 MHz, CDCl$_3$) δ 8.75 (s, 1 H) 8.43 (s, 1 H) 8.08-8.13 (m, 2 H) 7.27 (s, 1 H) 7.07-7.11 (m, 2 H) 7.04 (d, J=4.29 Hz, 2 H) 6.78 (d, J=2.27 Hz, 1 H) 3.78 (s, 3 H) 2.92 (s, 2 H) 1.49 (s, 6 H); LCMS for $C_{23}H_{21}N_5O_4$ m/z 432.00 (M+H$^+$).

Preparation of Intermediate 187a 4-(4-Cyano-phenoxy)-2,2-dimethyl-2,3-dihydro-benzofuran-6-carboxylic acid methyl ester

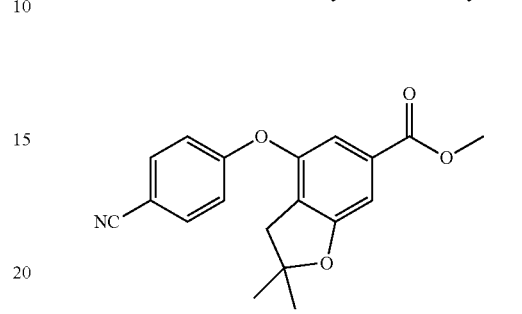

The title compound was prepared in a similar manner as described for Intermediate 161b, from 4-bromo benzonitrile (246 mg, 1.35 mmol) and 4-hydroxy-2,2-dimethyl-2,3-dihydro-benzofuran-6-carboxylic acid methyl ester (3e) (300 mg, 1.35 mmol) to give a white foam (257 mg, 59% yield). $^1$H NMR (400 MHz, CDCl$_3$) δ 7.58-7.71 (m, 2 H) 7.20-7.30 (m, 2 H) 6.95-7.06 (m, 2 H) 3.88 (s, 3 H) 2.88 (s, 2 H) 1.49 (s, 6 H); LCMS for $C_{19}H_{17}NO_4$ m/z 324.00 (M+H$^+$).

Preparation of Intermediate 187b 4-(4-Cyano-phenoxy)-2,2-dimethyl-2,3-dihydro-benzofuran-6-carboxylic acid (1-methyl-1H-pyrazol-3-yl)-amide

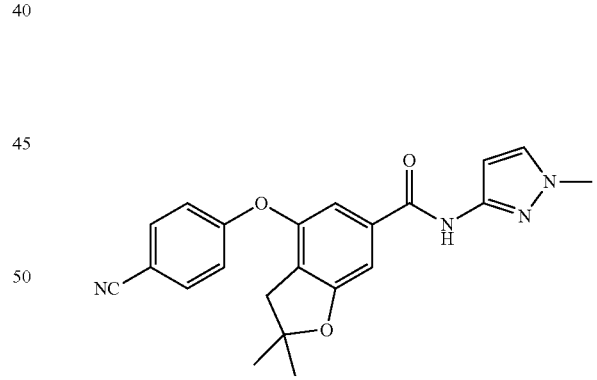

The title compound was prepared in a similar manner as described for Example 1, from 3-amino-1-methyl-pyrazole (366 mg, 3.96 mmol) and 4-(4-cyano-phenoxy)-2,2-dimethyl-2,3-dihydro-benzofuran-6-carboxylic acid methyl ester (187a) (128 mg, 0.396 mmol) to give a white solid (121 mg, 77% yield). $^1$H NMR (400 MHz, CDCl$_3$) δ 8.80 (s, 1 H) 7.56-7.69 (m, 2 H) 7.21-7.33 (m, 1 H) 6.97-7.09 (m, 4 H) 6.79

(d, J=2.02 Hz, 1 H) 3.75 (s, 3 H) 2.88 (s, 2 H) 1.49 (s, 6 H); LCMS for C$_{22}$H$_{20}$N$_4$O$_3$ m/z 389.20 (M+H$^+$).

Preparation of Intermediate 187c

4-[4-(N-Hydroxycarbamimidoyl)-phenoxy]-2,2-dimethyl-2,3-dihydro-benzofuran-6-carboxylic acid (1-methyl-1H-pyrazol-3-yl)-amide

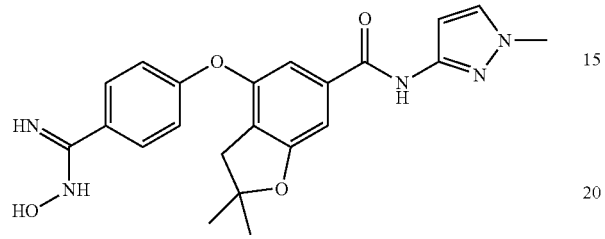

The title compound was prepared in a similar manner as described for Intermediate 185a, from 4-(4-cyano-phenoxy)-2,2-dimethyl-2,3-dihydro-benzofuran-6-carboxylic acid (1-methyl-1H-pyrazol-3-yl)-amide (187b) (212 mg, 0.321 mmol) and used without further purification for the next step.

Example 188

2,2-Dimethyl-4-(4-[1,2,4]oxadiazol-3-yl-phenoxy)-2,3-dihydro-benzofuran-6-carboxylic acid (2-methyl-2H-[1,2,3]triazol-4-yl)-amide

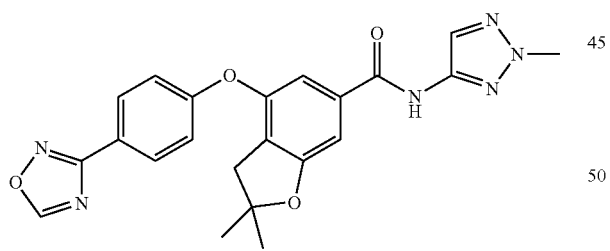

The title compound was prepared in a similar manner as described for Example 182, from 4-[4-(N-hydroxycarbamimidoyl)-phenoxy]-2,2-dimethyl-2,3-dihydro-benzofuran-6-carboxylic acid (2-methyl-2H-[1,2,3]triazol-4-yl)-amide (188b) (141 mg, 0.334 mmol) to a give white solid (82 mg, 57% yield). $^1$H NMR (400 MHz, CDCl$_3$) δ 8.76 (s, 2 H) 7.96-8.16 (m, 3 H) 6.99-7.12 (m, 4 H) 4.06 (s, 3 H) 2.91 (s, 2 H) 1.49 (s, 6 H); LCMS for C$_{22}$H$_{20}$N$_6$O$_4$ m/z 433.20 (M+H$^+$);

Anal. Calcd. for C$_{22}$H$_{20}$N$_6$O$_4$.0.45H$_2$O: C, 59.98; H, 4.78; N, 19.08; Found: C, 60.08; H, 4.64; N, 18.86.

Preparation of Intermediate 188a 4-(4-Cyano-phenoxy)-2,2-dimethyl-2,3-dihydro-benzofuran-6-carboxylic acid (2-methyl-2H-[1,2,3] triazol-4-yl)-amide

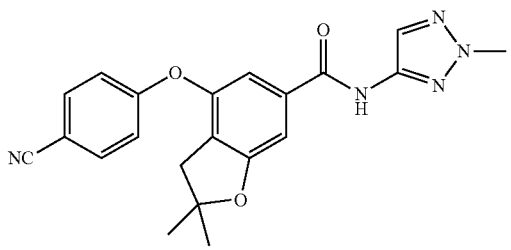

The title compound was prepared in a similar manner as described for Example 1, from 2-methyl-2H-1,2,3-triazol-4-amine hydrochloride (533 mg, 1.78 mmol) and 4-(4-cyano-phenoxy)-2,2-dimethyl-2,3-dihydro-benzofuran-6-carboxylic acid methyl ester (187a) (128 mg, 0.396 mmol) to give a white solid (130 mg, 84% yield). $^1$H NMR (400 MHz, CDCl$_3$) δ 8.82 (s, 1 H) 8.07 (s, 1 H) 7.62 (d, J=8.59 Hz, 2 H) 7.09 (d, J=10.36 Hz, 2 H) 7.02 (d, J=8.59 Hz, 2 H) 4.07 (s, 3 H) 2.88 (s, 2 H) 1.49 (s, 6 H); LCMS for C$_{21}$H$_{19}$N$_5$O$_3$ m/z 390.20 (M+H$^+$).

Preparation of Intermediate 188b

4-[4-(N-Hydroxycarbamimidoyl)-phenoxy]-2,2-dimethyl-2,3-dihydro-benzofuran-6-carboxylic acid (2-methyl-2H-[1,2,3]triazol-4-yl)-amide

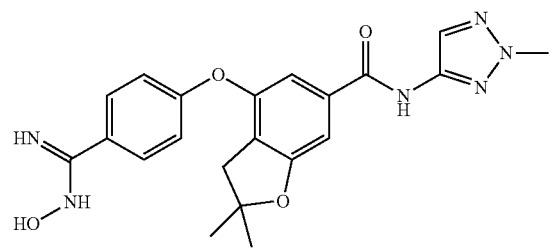

The title compound was prepared in a similar manner as described for Intermediate 185a, from 4-(4-cyano-phenoxy)-2,2-dimethyl-2,3-dihydro-benzofuran-6-carboxylic acid (2-methyl-2H-[1,2,3]triazol-4-yl)-amide (188a) (130 mg, 0.334 mmol) and used without further purification for the next step.

Example 189

4-(3-Chloro-4-[1,2,4]oxadiazol-3-yl-phenoxy)-2,2-dimethyl-2,3-dihydro-benzofuran-6-carboxylic acid (1-methyl-1H-pyrazol-3-yl)-amide

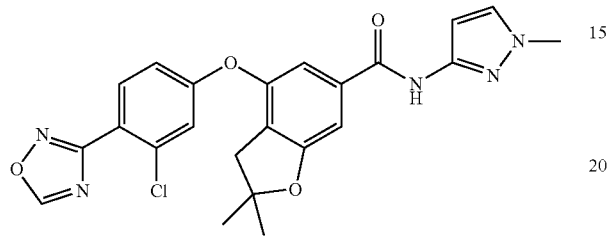

The title compound was prepared in a similar manner as described for Example 182, from 4-[3-Chloro-4-(N-hydroxycarbamimidoyl)-phenoxy]-2,2-dimethyl-2,3-dihydro-benzofuran-6-carboxylic acid (1-methyl-1H-pyrazol-3-yl)-amide (189c) (153 mg, 0.335 mmol) to a give white solid (37 mg, 24% yield). $^1$H NMR (400 MHz, CDCl$_3$) δ 8.83 (s, 1 H) 8.81 (s, 1 H) 7.95 (d, J=8.59 Hz, 1 H) 7.27 (s, 1 H) 7.15 (d, J=2.53 Hz, 1 H) 7.10 (s, 2 H) 6.97 (dd, J=8.84, 2.53 Hz, 1 H) 6.80 (d, J=2.02 Hz, 1 H) 3.77 (s, 3 H) 2.90 (s, 2 H) 1.49 (s, 6 H); LCMS for C$_{23}$H$_{20}$ClN$_5$O$_4$ m/z 465.90, 466.90 and 467.80 (M+H$^+$); Anal. Calcd. for C$_{23}$H$_{20}$ClN$_5$O$_4$·0.7 H$_2$O: C, 57.73; H, 4.51; N, 14.64; Found: C, 57.66; H, 4.51; N, 14.92.

Preparation of Intermediate 189a 4-(3-Chloro-4-cyano-phenoxy)-2,2-dimethyl-2,3-dihydro-benzofuran-6-carboxylic acid methyl ester

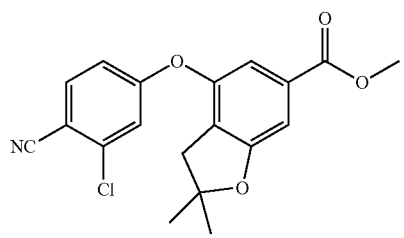

The title compound was prepared in a similar manner as described for Intermediate 161b, from 4-bromo-2-chlorobenzonitrile (292 mg, 1.35 mmol) and 4-hydroxy-2,2-dimethyl-2,3-dihydro-benzofuran-6-carboxylic acid methyl ester (3e) (300 mg, 1.35 mmol) to give a white foam (116 mg, 24% yield). $^1$H NMR (400 MHz, CDCl$_3$) δ 7.62 (d, J=8.59 Hz, 1 H) 7.25-7.34 (m, 1 H) 7.23 (d, J=1.01 Hz, 1 H) 7.04 (d, J=2.27 Hz, 1 H) 6.90 (dd, J=8.72, 2.40 Hz, 1 H) 3.88 (s, 3 H) 2.87 (s, 2 H) 1.48 (s, 6 H); LCMS for C$_{19}$H$_{16}$ClNO$_4$ m/z 380.00 (M+Na$^+$).

Preparation of Intermediate 189b 4-(3-Chloro-4-cyano-phenoxy)-2,2-dimethyl-2,3-dihydro-benzofuran-6-carboxylic acid (1-methyl-1H-pyrazol-3-yl)-amide

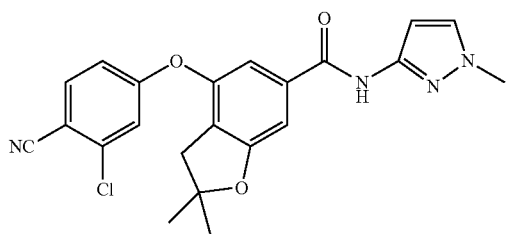

The title compound was prepared in a similar manner as described for Example 1, from 3-amino-1-methyl-pyrazole (157 mg, 1.62 mmol) and 4-(3-chloro-4-cyano-phenoxy)-2,2-dimethyl-2,3-dihydro-benzofuran-6-carboxylic acid methyl ester (189a) (58 mg, 0.16 mmol) to give a white solid (53 mg, 77% yield). $^1$H NMR (400 MHz, CDCl$_3$) δ 8.55 (s, 1 H) 7.91 (d, J=8.34 Hz, 2 H) 7.07 (dd, J=16.67, 8.34 Hz, 4 H) 6.78 (s, 1 H) 3.78 (s, 3 H) 2.90 (s, 2 H) 1.50 (s, 6 H); LCMS for C$_{22}$H$_{19}$ClN$_4$O$_3$ m/z 423.00 (M+H$^+$).

Preparation of Intermediate 189c

4-[3-Chloro-4-(N-hydroxycarbamimidoyl)-phenoxy]-2,2-dimethyl-2,3-dihydro-benzofuran-6-carboxylic acid (1-methyl-1H-pyrazol-3-yl)-amide

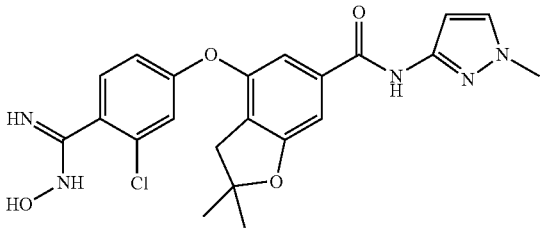

The title compound was prepared in a similar manner as described for Intermediate 185a, from 4-(3-chloro-4-cyano-phenoxy)-2,2-dimethyl-2,3-dihydro-benzofuran-6-carboxylic acid (1-methyl-1H-pyrazol-3-yl)-amide (189b) and used without further purification for the next step.

Example 190

7-Fluoro-4-(4-methanesulfonyl-phenoxy)-2,2-dimethyl-2,3-dihydro-benzofuran-6-carboxylic acid (1-methyl-1H-pyrazol-3-yl)-amide

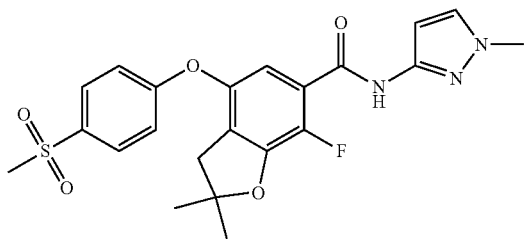

The title compound was prepared in a similar manner as described for Example 1, from 7-fluoro-4-(4-methanesulfonyl-phenoxy)-2,2-dimethyl-2,3-dihydro-benzofuran-6-carboxylic acid methyl ester (190c). $^1$H NMR (400 MHz, CDCl$_3$) δ 8.83 (d, J=13.64 Hz, 1 H) 7.89-7.94 (m, 2 H) 7.28-7.31 (m, 2 H) 7.06-7.12 (m, 2 H) 6.76 (d, J=2.27 Hz, 1 H) 3.84 (s, 3 H) 3.08 (s, 3 H) 2.97 (s, 2 H) 1.56 (s, 6 H); LCMS for C$_{22}$H$_{22}$FN$_3$O$_5$S m/z 460.20 (M+H)$^+$; Anal. Calcd. for C$_{22}$H$_{22}$FN$_3$O$_5$S.0.83 H$_2$O: C, 55.69; H, 5.03; N, 8.86; Found: C, 55.69; H, 4.74; N, 8.63.

Preparation of Intermediate 190a

7-Fluoro-4-hydroxy-2,2-dimethyl-2,3-dihydro-benzofuran-6-carboxylic acid methyl ester and Intermediate 190b: 5-Fluoro-4-hydroxy-2,2-dimethyl-2,3-dihydro-benzofuran-6-carboxylic acid methyl ester

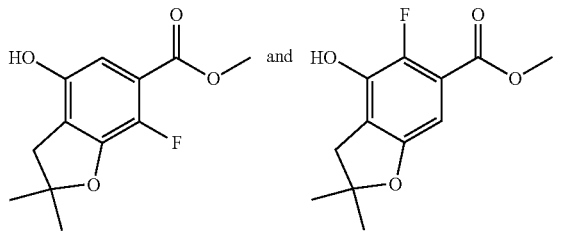

A mixture of 4-hydroxy-2,2-dimethyl-2,3-dihydrobenzofuran-6-carboxylic acid methyl ester (3e) (1.5 g, 6.7 mmol) and SelectFluoro (2.39 g, 6.75 mmol) in CH$_3$CN (10 mL) was heated to reflux overnight. The mixture was quenched with H$_2$O (100 mL) and extracted with CH$_2$Cl$_2$ (100 mL). The organic layer was dried over MgSO$_4$ and concentrated. The residue was purified by Biotage column chromatography, eluting with 5-25% EtOAc in hexanes to give a ~1:1 mixture of starting material (3e) and 5-fluoro-4-hydroxy-2,2-dimethyl-2,3-dihydro-benzofuran-6-carboxylic acid methyl ester (190b) (810 mg) and 7-fluoro-4-hydroxy-2,2-dimethyl-2,3-dihydro-benzofuran-6-carboxylic acid methyl ester (190a) (372 mg, 23% yield) as a pale yellow color solid. $^1$H NMR (for 190a) (400 MHz, CDCl3) δ 6.87 (d, J=4.29 Hz, 1 H) 5.23 (s, 1 H) 3.92 (s, 3 H) 3.04 (s, 2 H) 1.55 (s, 6 H); LCMS for C$_{22}$H$_{22}$FN$_3$O$_5$S m/z 241.20 (M+H)$^+$

Preparation of Intermediate 190c

7-Fluoro-4-(4-methanesulfonyl-phenoxy)-2,2-dimethyl-2,3-dihydro-benzofuran-6-carboxylic acid methyl ester

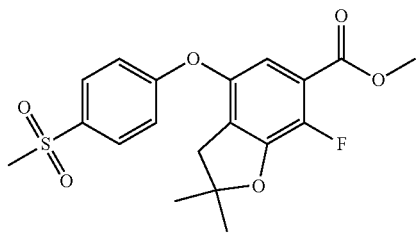

The title compound was prepared in a similar manner as described for Intermediate 1f, from 7-fluoro-4-hydroxy-2,2-dimethyl-2,3-dihydro-benzofuran-6-carboxylic acid methyl ester (190a). $^1$H NMR (400 MHz, CDCl$_3$) δ 7.89-7.94 (m, 2 H) 7.10 (d, J=4.55 Hz, 1 H) 7.04-7.09 (m, 2 H) 3.92 (s, 3 H) 3.07 (s, 3 H) 2.92 (s, 2 H) 1.54 (s, 6 H); LCMS for C$_{22}$H$_{22}$FN$_3$O$_5$S m/z 395.00 (M+H)$^+$.

Example 191

4-[4-(Azetidine-1-carbonyl)-phenoxy]-7-fluoro-2,2-dimethyl-2,3-dihydro-benzofuran-6-carboxylic acid (1-methyl-1H-pyrazol-3-yl)-amide

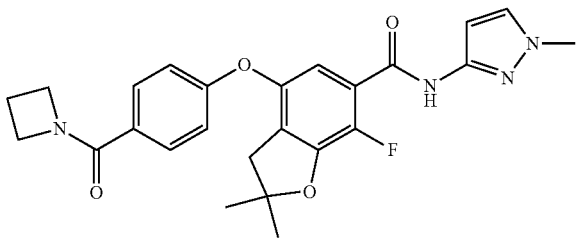

The title compound was prepared in a similar manner as described for Example 1, from 4-[4-(azetidine-1-carbonyl)-phenoxy]-7-fluoro-2,2-dimethyl-2,3-dihydro-benzofuran-6-carboxylic acid methyl ester (191a). $^1$H NMR (400 MHz, CDCl$_3$) δ 8.81 (d, J=13.39 Hz, 1 H) 7.61-7.65 (m, 2 H) 7.27-7.30 (m, 2 H) 6.96 (d, J=8.84 Hz, 2 H) 6.77 (d, J=2.27 Hz, 1 H) 4.34 (s, 2 H) 4.20-4.29 (m, 2 H) 3.81-3.86 (m, 3 H) 2.94 (s, 2 H) 2.32-2.40 (m, 2 H) 1.54 (s, 6 H); LCMS for $C_{25}H_{25}FN_4O_4$ m/z 465.00 (M+H)$^+$; Anal. Calcd. for $C_{25}H_{25}FN_4O_4$·0.36 $H_2O$: C, 63.76; H, 5.50; N, 11.90; Found: C, 63.76; H, 5.46; N, 11.63.

Preparation of Intermediate 191a

4-[4-(Azetidine-1-carbonyl)-phenoxy]-7-fluoro-2,2-dimethyl-2,3-dihydro-benzofuran-6-carboxylic acid methyl ester

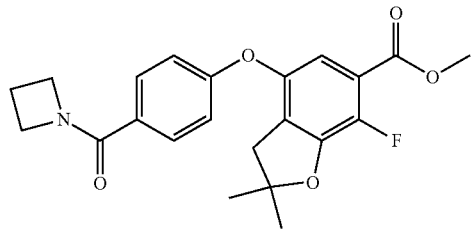

The title compound was prepared in a similar manner as described for Intermediate 35b, from 7-fluoro-4-hydroxy-2,2-dimethyl-2,3-dihydro-benzofuran-6-carboxylic acid methyl ester (190a) and azetidin-1-yl-(4-bromo-phenyl)-methanone. $^1$H NMR (400 MHz, CDCl$_3$) δ 7.61-7.65 (m, 2 H) 7.05 (d, J=4.55 Hz, 1 H) 6.94 (ddd, J=9.22, 2.78, 2.40 Hz, 2 H) 4.27-4.37 (m, 2 H) 4.23 (s, 2 H) 3.90 (s, 3 H) 2.91 (s, 2 H) 2.32-2.40 (m, 2 H) 1.52 (s, 6 H); LCMS for $C_{22}H_{22}FNO_5$ m/z 400.20 (M+H)$^+$.

Example 192

5-Fluoro-4-(4-methanesulfonyl-phenoxy)-2,2-dimethyl-2,3-dihydro-benzofuran-6-carboxylic acid (1-methyl-1H-pyrazol-3-yl)-amide

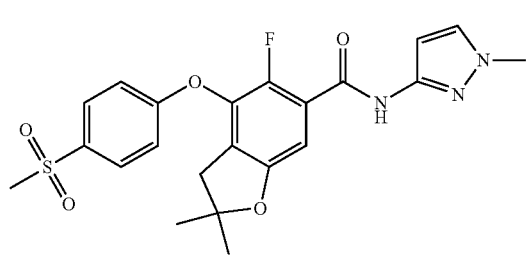

The title compound was prepared in two steps as described for Example 190, from 5-fluoro-4-hydroxy-2,2-dimethyl-2,3-dihydro-benzofuran-6-carboxylic acid methyl ester (190b) and purified by reverse phase HPLC to yield the desired compound. $^1$H NMR (400 MHz, CD$_3$OD) δ 7.92-7.98 (m, 2 H) 7.48 (d, J=2.27 Hz, 1 H) 7.18 (d, J=8.84 Hz, 2 H) 6.92 (d, J=4.55 Hz, 1 H) 6.59 (d, J=2.27 Hz, 1 H) 3.80 (s, 3 H) 3.10 (s, 3 H) 2.92 (s, 2 H) 1.44 (s, 6 H); LCMS for $C_{22}H_{22}FN_3O_5S$ m/z 460.00 (M+H)$^+$; Anal. Calcd. for $C_{22}H_{22}FN_3O_5S$: C, 57.17; H, 4.86; N, 9.09; Found: C, 57.17; H, 5.04; N, 8.95.

Example 193

4-(1-Methanesulfonyl-azetidin-3-yloxy)-2,2-dimethyl-2,3-dihydro-benzofuran-6-carboxylic acid (1-methyl-1H-pyrazol-3-yl)-amide

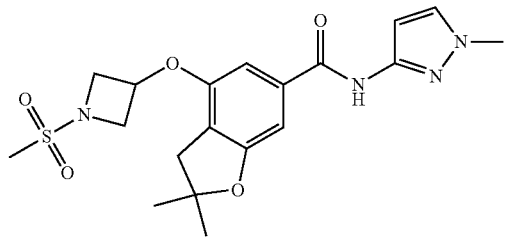

The title compound was prepared in a similar manner as described for Example 1, from 4-(1-methanesulfonyl-azetidin-3-yloxy)-2,2-dimethyl-2,3-dihydro-benzofuran-6-carboxylic acid methyl ester (193d). $^1$H NMR (400 MHz, CDCl$_3$) δ 8.33 (s, 1 H) 8.09 (s, 1 H) 6.80 (d, J=1.01 Hz, 1 H) 6.70 (d, J=1.01 Hz, 1 H) 4.99-5.06 (m, 1 H) 4.33 (dd, J=9.60, 6.32 Hz, 2 H) 4.13 (s, 3 H) 4.07-4.12 (m, 2 H) 3.02 (s, 2 H) 2.93 (s, 3 H) 1.52 (s, 6 H); LCMS for $C_{19}H_{24}N_4O_5S$ m/z 421.20 (M+H)$^+$; Anal. Calcd. for $C_{19}H_{24}N_4O_5S$·0.23 H2O: C, 53.74; H, 5.81; N, 13.19; Found: C, 53.76; H, 5.87; N, 12.99.

Preparation of Intermediate 193a

Methanesulfonic acid 1-benzhydryl-azetidin-3-yl ester

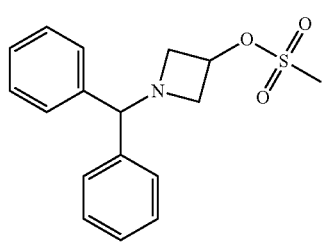

Methane sulphonyl chloride (0.5 mL, 6.43 mmol) was added to a solution of 1-(diphenylmethyl)-3-hydroxyazetidine (1.38 g, 5.77 mmol) and Et$_3$N (0.9 mL, 6.46 mmol) in toluene (10 mL) at 0° C. The reaction mixture was stirred and warmed to room temperature overnight. The mixture was quenched with H$_2$O (100 mL) and extracted with EtOAc (100 mL). The organic layer was dried over MgSO$_4$ and concentrated to give pale yellow oil (756 mg, 41%) which was used without further purification.

Preparation of Intermediate 193b 4-(1-Benzhydryl-azetidin-3-yloxy)-2,2-dimethyl-2,3-dihydro-benzofuran-6-carboxylic acid methyl ester

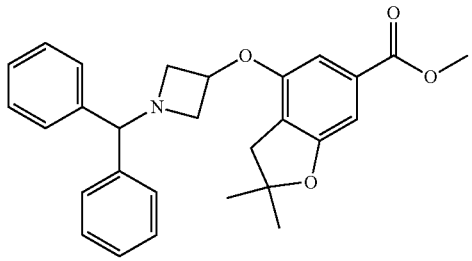

Cs$_2$CO$_3$ (1.16 g, 4.95 mmol) was added to a solution of methanesulfonic acid 1-benzhydryl-azetidin-3-yl ester (193a) (756 mg, 2.38 mmol) and 4-hydroxy-2,2-dimethyl-2,3-dihydro-benzofuran-6-carboxylic acid methyl ester (3e) (440 mg, 1.98 mmol) in DMF (6 mL). The mixture was heated to 100° C. for 4 hr, quenched with H$_2$O (100 mL) and extracted with EtOAc (100 mL). The organic layer was washed with H$_2$O, dried over MgSO$_4$ and concentrated. The residue was purified by flash column chromatograph eluting with 30-40% EtOAc in hexanes to give a white sold (740 mg, 84% yield). $^1$H NMR (400 MHz, CDCl$_3$) δ 7.44 (d, J=7.07 Hz, 4 H) 7.27-7.32 (m, 4 H) 7.18-7.25 (m, 2 H) 7.04 (d, J=1.01 Hz, 1 H) 6.81 (d, J=1.01 Hz, 1 H) 4.87 (t, J=5.81 Hz, 1 H) 3.85 (s, 3 H) 3.76 (ddd, J=7.52, 5.87, 2.02 Hz, 2 H) 3.12 (ddd, J=7.33, 5.56, 1.77 Hz, 2 H) 2.99 (s, 2 H) 1.49 (s, 6 H); LCMS for C$_{28}$H$_{29}$NO$_4$ m/z 444.20 (M+H)$^+$.

Preparation of Intermediate 193c 4-(Azetidin-3-yloxy)-2,2-dimethyl-2,3-dihydro-benzofuran-6-carboxylic acid methyl ester

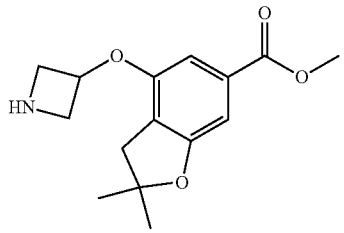

Palladium on carbon (108 mg) was added to a solution of 4-(1-benzhydryl-azetidin-3-yloxy)-2,2-dimethyl-2,3-dihydro-benzofuran-6-carboxylic acid methyl ester (193b) (740 mg, 1.67 mmol) in 1:1 EtOAc and MeOH. The mixture was stirred under H$_2$ balloon overnight. The mixture was filtered through Celite and concentrated to give a pale yellow solid (526 mg, 100% yield). LCMS for C$_{15}$H$_{19}$NO$_4$ m/z 278.10 (M+H)$^+$.

Preparation of Intermediate 193d 4-(1-Methanesulfonyl-azetidin-3-yloxy)-2,2-dimethyl-2,3-dihydro-benzofuran-6-carboxylic acid methyl ester

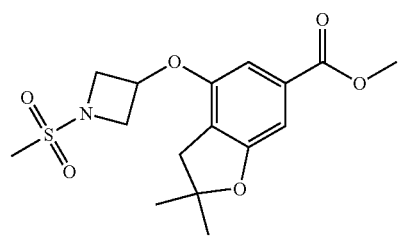

Et$_3$N (400 mg, 2.87 mmol) and methane sulfonyl chloride (75 uL, 0.97 mmol) were added to a solution of 4-(azetidin-3-yloxy)-2,2-dimethyl-2,3-dihydro-benzofuran-6-carboxylic acid methyl ester (193c) (303 mg, 0.97 mmol) in CH$_2$Cl$_2$ (15 mL). The mixture was stirred at room temperature for 2 hr, quenched with 1N aqueous HCl (60 mL) and extracted with CH$_2$Cl$_2$ (60 mL). The organic layer was dried over MgSO$_4$, filtered, and concentrated. The residue was purified by flash column chromatograph to give a white solid (197 mg, 57% yield). $^1$H NMR (400 MHz, CDCl$_3$) δ 7.10 (s, 1 H) 6.75 (s, 1 H) 5.02 (d, J=6.06 Hz, 1 H) 4.34 (dd, J=8.46, 6.69 Hz, 2 H) 4.08 (dd, J=8.72, 4.93 Hz, 2 H) 3.89 (s, 3 H) 3.00 (s, 2 H) 2.93 (s, 3 H) 1.50 (s, 6 H).

Example 194

4-(1-Methanesulfonyl-azetidin-3-yloxy)-2,2-dimethyl-2,3-dihydro-benzofuran-6-carboxylic acid (2-methyl-2H-[1,2,3]triazol-4-yl)-amide

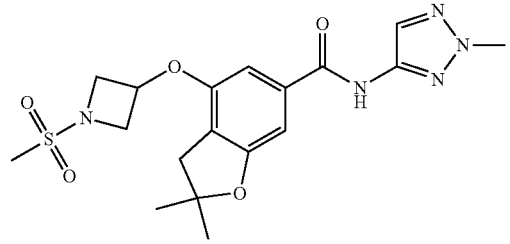

The title compound was prepared in a similar manner as described for Example 1, from 4-(1-methanesulfonyl-azetidin-3-yloxy)-2,2-dimethyl-2,3-dihydro-benzofuran-6-carboxylic acid methyl ester (193d). $^1$H NMR (400 MHz, CDCl$_3$) δ 8.33 (s, 1 H) 8.09 (s, 1 H) 6.80 (d, J=1.01 Hz, 1 H) 6.70 (d, J=1.01 Hz, 1 H) 4.99-5.06 (m, 1 H) 4.33 (dd, J=9.60, 6.32 Hz, 2 H) 4.13 (s, 3 H) 4.07-4.12 (m, 2 H) 3.02 (s, 2H) 2.93 (s, 3 H) 1.52 (s, 6 H); LCMS for C$_{18}$H$_{23}$N$_5$O$_5$S m/z 422.20 (M+H)+; Anal. Calcd. for $C_{18}H_{23}N_5O_5S \cdot 0.10$ EtOAc: C, 51.36; H, 5.58; N, 16.28; Found: C, 51.36; H, 5.71; N, 16.31.

Example 195

4-(1-Acetyl-azetidin-3-yloxy)-2,2-dimethyl-2,3-dihydro-benzofuran-6-carboxylic acid (2-methyl-2H-[1,2,3]triazol-4-yl)-amide

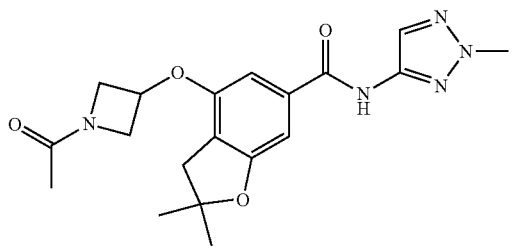

The title compound was prepared in a similar manner as described for Example 1, from 4-(1-acetyl-azetidin-3-yloxy)-2,2-dimethyl-2,3-dihydro-benzofuran-6-carboxylic acid methyl ester (195a). $^1$H NMR (400 MHz, CDCl$_3$) δ 8.50 (s, 1 H) 8.09 (s, 1 H) 6.81 (d, J=1.01 Hz, 1 H) 6.69 (d, J=1.26 Hz, 1 H) 5.03 (dd, J=10.36, 2.53 Hz, 1 H) 4.57 (ddd, J=9.47, 6.19, 1.01 Hz, 1 H) 4.42 (dd, J=10.99, 6.69 Hz, 1 H) 4.06-4.18 (m, 5 H) 3.02 (s, 2 H) 1.92 (s, 3 H) 1.51 (s, 6 H); LCMS for $C_{19}H_{23}N_5O_4$ m/z 386.20 (M+H)+; Anal. Calcd. for $C_{19}H_{23}N_5O_4 \cdot 0.33$ H$_2$O: C, 58.31; H, 6.09; N, 17.89; Found: C, 58.31; H, 6.06; N, 17.87.

Preparation of Intermediate 195a 4-(1-Acetyl-azetidin-3-yloxy)-2,2-dimethyl-2,3-dihydro-benzofuran-6-carboxylic acid methyl ester

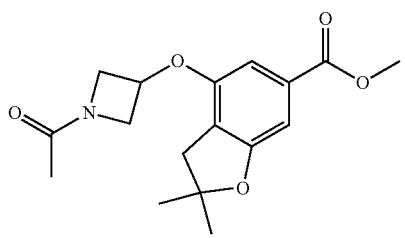

Et$_3$N (400 uL, 2.87 mmol) and acetyl chloride (70 uL, 0.99 mmol) were added to a solution of 4-(azetidin-3-yloxy)-2,2-dimethyl-2,3-dihydro-benzofuran-6-carboxylic acid methyl ester (193c) (300 mg, 0.96 mmol) in CH$_2$Cl$_2$ (15 mL). The mixture was stirred at room temperature for 4 hr, then quenched with 1N aqueous HCl (80 mL), and extracted with CH$_2$Cl$_2$ (80 mL). The organic layer was dried over MgSO$_4$ and concentrated. The residue was purified by flash column chromatograph eluting with 80% EtOAc in hexanes to give a colorless oil (239 mg, 73% yield). $^1$H NMR (400 MHz, CDCl$_3$) δ 7.12 (br. s., 1 H) 6.76 (br. s., 1 H) 5.03 (br. s., 1 H) 4.55 (br. s., 1 H) 4.43 (br. s., 1 H) 4.03-4.19 (m, 2 H) 3.89 (s, 3 H) 3.00 (s, 2 H) 1.92 (s, 3 H) 1.51 (br. s., 6 H).

Example 196

4-(1-Acetyl-azetidin-3-yloxy)-2,2-dimethyl-2,3-dihydro-benzofuran-6-carboxylic acid (1-methyl-1H-pyrazol-3-yl)-amide

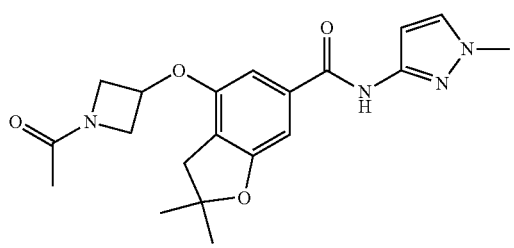

The title compound was prepared in a similar manner as described for Example 1, from 4-(1-acetyl-azetidin-3-yloxy)-2,2-dimethyl-2,3-dihydro-benzofuran-6-carboxylic acid methyl ester (195a). $^1$H NMR (400 MHz, CDCl$_3$) δ 8.56 (s, 1 H) 7.30 (d, J=2.27 Hz, 1 H) 6.82 (s, 1 H) 6.80 (d, J=2.02 Hz, 1 H) 6.67 (d, J=1.26 Hz, 1 H) 5.01 (ddd, J=10.23, 6.44, 3.79 Hz, 1 H) 4.51-4.59 (m, 1 H) 4.42 (dd, J=10.74, 6.69 Hz, 1 H) 4.07-4.16 (m, 2 H) 3.81 (s, 3 H) 3.01 (s, 2 H) 1.91 (s, 3 H) 1.51 (s, 6 H); LCMS for $C_{20}H_{24}N_4O_4$ m/z 385.00 (M+H)+; Anal. Calcd. for $C_{20}H_{24}N_4O_4 \cdot 0.45$ H$_2$O: C, 61.20; H, 6.39; N, 14.27; Found: C, 61.20; H, 6.32; N, 14.16.

Example 197

6-[4-(Azetidine-1-carbonyl)-3-fluoro-phenoxy]-2,2-dimethyl-2,3-dihydro-benzofuran-4-carboxylic acid (1-methyl-1H-pyrazol-3-yl)-amide

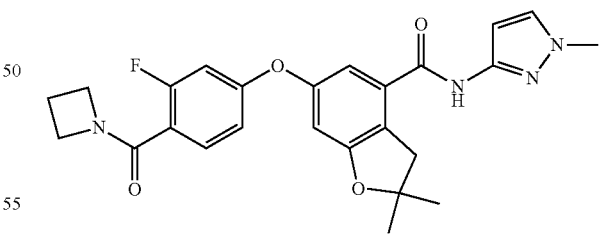

The title compound was prepared in a similar manner as described for Example 1, from 6-[4-(azetidine-1-carbonyl)-3-fluoro-phenoxy]-2,2-dimethyl-2,3-dihydro-benzofuran-4-carboxylic acid methyl ester (197f). $^1$H NMR (400 MHz, CDCl$_3$) δ 8.30 (s, 1 H) 7.53 (t, J=8.21 Hz, 1 H) 7.29 (d, J=2.27 Hz, 1 H) 6.85 (d, J=2.02 Hz, 1 H) 6.83 (dd, J=8.59, 2.27 Hz, 1 H) 6.77 (d, J=1.77 Hz, 1 H) 6.68 (dd, J=11.37, 2.27 Hz, 1 H) 6.59 (d, J=2.02 Hz, 1 H) 4.12-4.24 (m, 4 H) 3.81 (s, 3 H) 3.37 (s, 2 H) 2.34 (dt, J=15.41, 7.71 Hz, 2 H) 1.51 (s, 6 H); LCMS for $C_{25}H_{25}FN_4O_4$ m/z 465.20 (M+H)$^+$; Anal. Calcd. for $C_{25}H_{25}FN_4O_4 \cdot 0.93 H_2O$: C, 62.39; H, 5.63; N, 11.63; Found: C, 62.39; H, 5.49; N, 11.56.

Preparation of Intermediate 197a

4-Bromo-3,5-dihydroxy-benzoic acid methyl ester

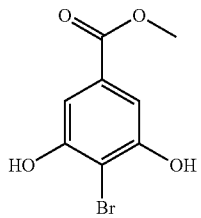

To a solution of 4-bromo-3,5-dihydroxy-benzoic acid (450 g, 1.94 mol) in MeOH (3.5 L) was added drop wise conc. $H_2SO_4$ (20 mL) at room temperature, and the mixture was refluxed overnight. TLC (petroleum ether/EtOAc=1/1) showed the reaction was complete. MeOH was removed under vacuum to about 250 mL and the resulting solid was filtered. The filter cake was dried under vacuum to give the title compound (450 g, 94% yield) as a white solid Preparation of Intermediate 197b 4-Bromo-3-hydroxy-5-(2-methyl-allyloxy)-benzoic acid methyl ester

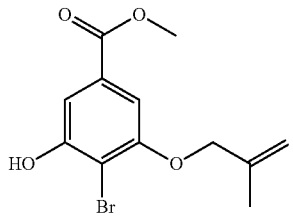

Na pieces (41.4 g, 1.82 mol) were added slowly to MeOH (3 L). The resulting mixture was stirred at room temperature for 30 min and then 4-bromo-3,5-dihydroxy-benzoic acid methyl ester (197a) (450 g, 1.82 mol) was added portion wise. The mixture was warmed to 60° C. 3-Chloro-2-methyl-propene (202.5 mL, 2 mol) was added drop wise. The mixture was refluxed for 6 h. TLC (petroleum ether/EtOAc=5/1) showed the reaction was complete. The solvent was removed and the residue was purified by column chromatography (petroleum ether/EtOAc=15/1) to give the title compound (75 g, 13.6% yield). $^1$H NMR (400 MHz, CDCl$_3$) δ 7.27 (s, 1H), 7.06(s, 1H), 5.72(s, 1H), 5.11(s, 1H), 4.96(s, 1H), 4.47(s, 2H), 3.84(s, 3H), 1.79(s, 3H).

Preparation of Intermediate 197c

4-Bromo-3,5-dihydroxy-2-(2-methyl-allyl)-benzoic acid methyl ester

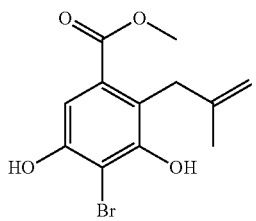

A solution of 4-bromo-3-hydroxy-5-(2-methyl-allyloxy)-benzoic acid methyl ester (197b) (148 g, 0.49 mol) in NMP (1.5 L) was refluxed for 0.5 h. After TLC (petroleum ether/EtOAc=5/1) indicated complete consumption of 197b, the reaction mixture was cooled to room temperature and 20% aq. HCl was added until pH=1. The resulting mixture was extracted with EtOAc (3×500 mL). The combined organic phases were dried over Na$_2$SO$_4$ and concentrated to give a brown oil. The crude oil was purified by column chromatography (petroleum ether/EtOAc=15/1) to give the title compound (139 g, 94% yield) as a white solid.

Preparation of Intermediate 197d

7-Bromo-6-hydroxy-2,2-dimethyl-2,3-dihydro-benzofuran-4-carboxylic acid methyl ester

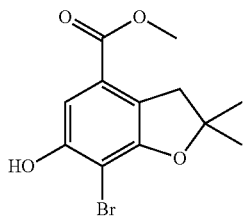

To a stirred solution of 4-bromo-3,5-dihydroxy-2-(2-methyl-allyl)-benzoic acid methyl ester (197c) (85 g, 0.28 mol) in CH$_2$Cl$_2$ (1500 mL) was added drop wise BF$_3$.Et$_2$O (180 mL, 1.41 mol) at 0° C. The mixture was stirred at room temperature for 2 hr. After TLC (petroleum ether/EtOAc=5/1) showed the reaction was complete, the reaction mixture was poured into water (1 L). The organic phase was separated and washed with saturated aqueous NaHCO$_3$, dried over Na$_2$SO$_4$ and concentrated to give a yellow solid. The crude solid was purified by column chromatography (petroleum ether/EtOAc=15/1) to give the title compound (37 g, 44% yield) as a white solid. ¹H NMR (400 MHz, CDCl₃) δ 7.07 (s, 1H), 5.43 (s, 1H), 3.80 (s, 3H), 3.29 (s, 2H), 1.45 (s, 6H) (s, 2 H) 2.29-2.39 (m, 2 H) 1.51 (s, 6 H); LCMS for C₂₂H₂₂FNO₅ m/z 441.30 (M+H)⁺.

Preparation of Intermediate 197e

6-Hydroxy-2,2-dimethyl-2,3-dihydro-benzofuran-4-carboxylic acid methyl ester

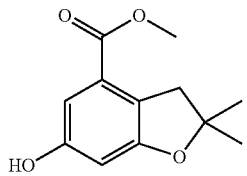

A suspension of 7-bromo-6-hydroxy-2,2-dimethyl-2,3-dihydro-benzofuran-4-carboxylic acid methyl ester (197d) (52 g, 0.17 mol) and 10% Pd on Carbon (5 g) in MeOH (1 L) was stirred under 50 Psi of H₂ at 35-40° C. for 3 days. After HPLC indicated complete consumption of 197d, the reaction mixture was filtered through Celite and the filtrate was concentrated to give the title compound (30.6 g, 79.6%) as a yellow solid. ¹H NMR (400 MHz, CDCl₃) δ 6.93 (s, 1H), 6.39 (s, 1H), 5.32 (s, 1H), 3.81 (s, 3H), 3.17 (s, 2 H), 1.40 (s, 6H).

Preparation of Intermediate 197f

6-[4-(Azetidine-1-carbonyl)-3-fluoro-phenoxy]-2,2-dimethyl-2,3-dihydro-benzofuran-4-carboxylic acid methyl ester

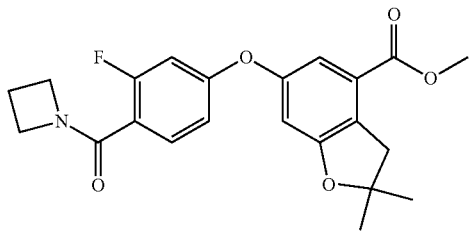

The title compound was prepared in a similar manner as described for Intermediate 35b, from azetidin-1-yl-(4-bromo-2-fluoro-phenyl)-methanone and 6-hydroxy-2,2-dimethyl-2,3-dihydro-benzofuran-4-carboxylic acid methyl ester (197e). ¹H NMR (400 MHz, CDCl₃) δ 7.42 (d, J=7.07 Hz, 1 H) 7.37 (d, J=1.77 Hz, 1 H) 7.29 (dd, J=9.35, 1.52 Hz, 1 H) 7.15 (d, J=2.27 Hz, 1 H) 6.62 (d, J=2.27 Hz, 1 H) 4.16-4.25 (m, 2 H) 4.07-4.16 (m, 2 H) 3.87-3.88 (m, 3 H) 3.33

Example 198

6-(4-Methanesulfonyl-phenoxy)-2,2-dimethyl-2,3-dihydro-benzofuran-4-carboxylic acid (2-methyl-2H-[1,2,3]triazol-4-yl)-amide

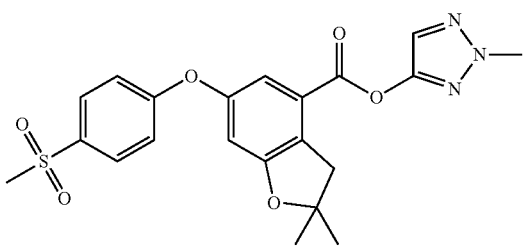

The title compound was prepared in a similar manner as described for Example 1, from 6-(4-methanesulfonyl-phenoxy)-2,2-dimethyl-2,3-dihydro-benzofuran-4-carboxylic acid methyl ester (198a). ¹H NMR (400 MHz, CDCl₃) δ 8.26 (s, 1 H) 8.08 (s, 1 H) 7.87-7.96 (m, 2 H) 7.13 (d, J=8.84 Hz, 1 H) 7.13 (q, J=4.80 Hz, 1 H) 6.86 (d, J=2.02 Hz, 1 H) 6.64 (d, J=2.02 Hz, 1 H) 4.12 (s, 3 H) 3.39 (s, 2 H) 3.08 (s, 3 H) 1.53 (s, 6 H); LCMS for C₂₁H₂₂N₄O₅S m/z 443.20 (M+H)⁺; Anal. Calcd. for C₂₁H₂₂N₄O₅S.0.70 H2O: C, 55.42; H, 5.18; N, 12.31; Found: C, 55.31; H, 4.90; N, 12.39.

Preparation of Intermediate 198a 6-(4-Methanesulfonyl-phenoxy)-2,2-dimethyl-2,3-dihydro-benzofuran-4-carboxylic acid methyl ester

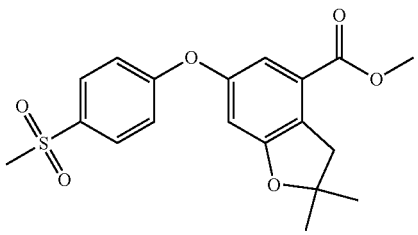

The title compound was prepared in a similar manner as described for Intermediate 1f, from 6-hydroxy-2,2-dimethyl-2,3-dihydro-benzofuran-4-carboxylic acid methyl ester (197e). ¹H NMR (400 MHz, CDCl₃) δ 7.90 (d, J=9.09 Hz, 2 H) 7.17 (d, J=2.27 Hz, 1 H) 7.10 (d, J=8.84 Hz, 2 H) 6.64 (d, J=2.02 Hz, 1 H) 3.89 (s, 3 H) 3.35 (s, 2 H) 3.06 (s, 3 H) 1.52 (s, 6 H); LCMS for $C_{19}H_{20}O_5S$ m/z 377.20 $(M+H)^+$.

Example 199

6-(4-Methanesulfonyl-phenoxy)-2,2-dimethyl-2,3-dihydro-benzofuran-4-carboxylic acid (1-methyl-1H-pyrazol-3-yl)-amide

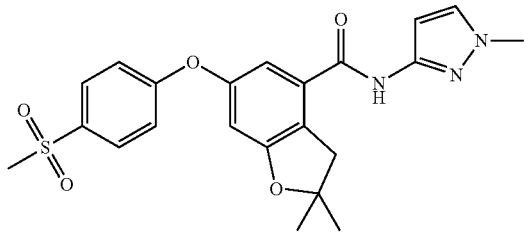

The title compound was prepared in a similar manner as described for Example 1, from 6-(4-methanesulfonyl-phenoxy)-2,2-dimethyl-2,3-dihydro-benzofuran-4-carboxylic acid methyl ester (198a). $^1$H NMR (400 MHz, $CDCl_3$) δ 8.30 (s, 1 H) 7.91 (d, J=8.84 Hz, 2 H) 7.29 (d, J=2.27 Hz, 1 H) 7.06-7.15 (m, 2 H) 6.85 (d, J=2.02 Hz, 1 H) 6.76 (d, J=2.02 Hz, 1 H) 6.62 (d, J=2.02 Hz, 1 H) 3.79 (s, 3 H) 3.38 (s, 2 H) 3.07 (s, 3 H) 1.52 (s, 6 H); LCMS for $C_{22}H_{23}N_3O_5S$ m/z 442.20 $(M+H)^+$; Anal. Calcd. for $C_{22}H_{23}N_3O_5S \cdot 0.17 H_2O$: C, 59.45; H, 5.32; N, 9.43; Found: C, 59.45; H, 5.32; N, 9.43.

Example 200

2-Hydroxymethyl-4-(4-methanesulfonyl-phenoxy)-2,3-dihydro-benzofuran-6-carboxylic acid (1-methyl-1H-pyrazol-3-yl)-amide

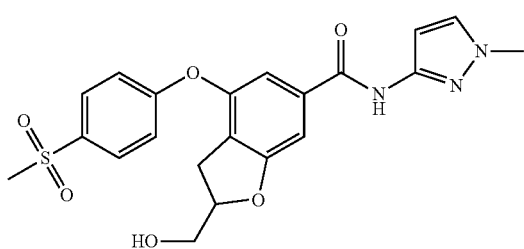

To a solution of 2-hydroxymethyl-4-(4-methanesulfonyl-phenoxy)-2,3-dihydro-benzofuran-6-carboxylic acid tert-butyl ester (200g) (422 mg, 1.0 mmol) in $CH_2Cl_2$ (4 mL) was added TFA (2 mL). The reaction mixture was stirred at room temperature for 3 hr, then concentrated and dried to give an off-white solid (424 mg, 100% yield) which was used without purification. To a solution of this crude solid (242 mg, 0.66 mmol) in DMF (5 mL) was added $Et_3N$ (0.50 mL, 3.59 mmol), HATU (507 mg, 1.33 mmol) and 1-methyl-3-aminopyrazole (130 mg, 1.34 mmol). The reaction mixture was heated to 50° C. for 2 hr, quenched with $H_2O$ (20 mL), and extracted with EtOAc (2×20 mL). The organic layers were washed with $H_2O$ (2×40 mL), dried over $MgSO_4$ and concentrated. The residue was purified by flash column chromatograph eluting with 0-3% $CH_3OH$ in 1:1 $EtOAc/CH_2Cl_2$ to give a white solid (139 mg, 47% yield). $^1$H NMR (400 MHz, $CDCl_3$) δ 8.41 (s, 1 H) 7.92 (ddd, J=9.22, 2.78, 2.40 Hz, 2 H) 7.29 (d, J=2.27 Hz, 1 H) 7.11-7.13 (m, 2 H) 7.09-7.11 (m, 1 H) 7.06 (d, J=1.52 Hz, 1 H) 6.77 (d, J=2.27 Hz, 1 H) 5.00-5.07 (m, 1 H) 3.88-3.98 (m, 1 H) 3.81 (s, 3 H) 3.75 (ddd, J=12.25, 6.06, 5.94 Hz, 1 H) 3.12-3.21 (m, 1 H) 3.09 (s, 3 H) 2.96-3.07 (m, 1 H); LCMS for $C_{21}H_{21}N_3O_6S$ m/z 444.00 $(M+H)^+$; Anal. Calcd. for $C_{21}H_{21}N_3O_6S \cdot 0.34 H_2O$: C, 56.13; H, 4.86; N, 9.06; Found: C, 56.08; H, 4.85; N, 9.05.

Preparation of Intermediate 200a 3,5-Bis-benzyloxy-4-bromo-benzoic acid benzyl ester

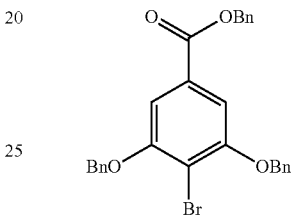

To a stirred solution of 4-bromo-3,5-dihydroxy-benzoic acid (350 g, 1.5 mol) in dry DMF (2 L) were added $K_2CO_3$ (725 g, 5.25 mL) and BnBr (769 g, 4.5 mol) in one portion. The mixture was stirred at room temperature for 2 days and then filtered. The filter cake was washed with $CH_2Cl_2$. The combined filtrates were concentrated to give the title compound (225 g, 40% yield) as a white solid. $^1$H NMR (400 MHz, $CDCl_3$): δ 7.22-7.52 (m, 17H), 5.38(s, 2H), 5.21 (s, 4H).

Preparation of Intermediate 200b 3,5-Bis-benzyloxy-4-bromo-benzoic acid

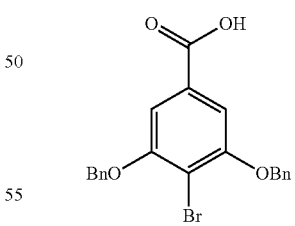

To a stirred solution of 3,5-bis-benzyloxy-4-bromo-benzoic acid benzyl ester (200a) (225 g, 0.45 mol) in THF (400 mL) and $H_2O$ (500 mL) was added NaOH (89.4 g, 2.24 mol) in one portion. The mixture was refluxed for 4 hr. TLC (EtOAc/petroleum ether=1/4) showed that the reaction was complete. $Et_2O$ (100 mL) was added to the mixture and the organic layer was separated. The aqueous layer was acidified with conc. HCl, and the resulting solid was filtered and dried in vacuo to give the title compound (150 g, 85% yield) as a white solid. $^1$H NMR (400 MHz, CDCl$_3$): δ 7.48 (dd, 4H), 7.39(t, 4H), 7.31 (m, 4H), 5.27(s, 4H).

Preparation of Intermediate 200c 3,5-Bis-benzyloxy-4-bromo-benzoic acid tert-butyl ester

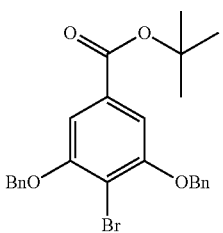

To a stirred solution of 3,5-bis-benzyloxy-4-bromo-benzoic acid (200b) (153 g, 0.37 mol) in DMF (1 L) was added CDI (90 g, 0.56 mol) in several portions. The solution was stirred at 40° C. for 1 hr. t-BuOH (55 g, 0.74 mol) was added to the mixture and then followed by the drop wise addition of DBU (56.3 g, 0.37 mol). The resulting solution was stirred at 40° C. for 2 days. TLC (EtOAc/petroleum ether=1/10) showed that the reaction was complete. The mixture was cooled to room temperature and poured into ice water (1 L). The mixture was acidified to pH 5 with conc. HCl and stirred for 1 hr. The formed solid was filtered and washed with water, then dried in vacuo to give the title compound (165 g, 86% yield) as a brown solid. $^1$H NMR (400 MHz, CDCl$_3$): δ 7.57-7.25 (m, 12H), 5.21(s, 4H), 1.58 (s, 9H).

Preparation of Intermediate 200d

4-Allyl-3,5-bis-benzyloxy-benzoic acid tert-butyl ester

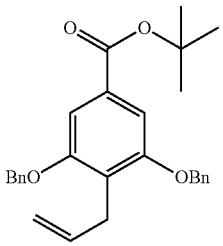

To a suspension of Mg pieces (5.76 g, 0.24 mol) in Et$_2$O (250 mL) was added catalytic I$_2$, followed by i-PrMgBr (19.7 g, 0.16 mol) in one portion. The mixture was irradiated with heating. After stirring for 2 hr, the resulting solution was added to THF (200 mL). n-BuLi (128 mL, 2.5 M in hexane, 0.32 mol) was added drop wise to the mixture at 0° C. The mixture was cooled to −78° C. and 3,5-bis-benzyloxy-4-bromo-benzoic acid tert-butyl ester (200c) (50 g, 0.107 mol) was added drop wise. After the mixture was stirred for 1 hr, CuCN (2.9 g, 0.032 mol), LiCl (2.7 g, 0.064 mol) and allyl bromide (51.5 g, 0.43 mol) were added sequentially. After stirring for another 30 min at −78° C., TLC (EtOAc/petroleum oil=1/10) showed the reaction was complete. The mixture was quenched with saturated aqueous NH$_4$Cl (150 mL). The aqueous layer was extracted with EtOAc (2×100 mL). The combined organic layers were washed with brine, dried over Na$_2$SO$_4$ and concentrated to give the title compound (35 g, 76.4% yield) as a yellow oil. $^1$H NMR (400 MHz, CDCl$_3$): δ 7.57-7.25 (m, 12H), 5.98(m, 1H), 5.13 (s, 4H), 5.04-4.88 (m, 2H), 3.57 (m, 2H), 1.59 (s, 9H).

Preparation of Intermediate 200e 3,5-Bis-benzyloxy-4-oxiranylmethyl-benzoic acid tert-butyl ester

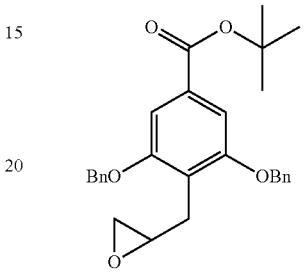

To a solution of 4-allyl-3,5-bis-benzyloxy-benzoic acid tert-butyl ester (200d) (125 g, 0.29 mol) in CH$_2$Cl$_2$ was added m-CPBA (100 g, 0.58 mol) in several portions. The mixture was refluxed overnight. The solid was filtered and washed with CH$_2$Cl$_2$. The combined filtrates were washed with saturated aqueous Na$_2$S$_2$O$_4$ (250 mL) and brine (250 mL). The organic layer was dried over Na$_2$SO$_4$ and concentrated to give a yellow oil. The crude oil was purified by flash column chromatography (EtOAc/petroleum ether=1/20) to give the title compound (75 g, 57.8%) as a white solid. $^1$H NMR (400 MHz, CDCl$_3$): δ 7.40 (m, 12H), 5.09(s, 4H), 3.53 (dd, 1H), 3.17 (m, 1H), 2.80 (dd, H), 2.63 (t, 1H), 2.51 (dd, 1H), 1.60 (s, 9H).

Preparation of Intermediate 200f

4-Hydroxy-2-hydroxymethyl-2,3-dihydro-benzofuran-6-carboxylic acid tert-butyl ester

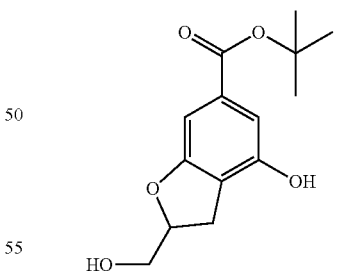

A mixture of 3,5-bis-benzyloxy-4-oxiranylmethyl-benzoic acid tert-butyl ester (200e) (55 g, 0.12 mol), 10% Pd on Carbon (5 g), Et$_3$N (15 g, 0.14 mol), and K$_2$CO$_3$ (20 g, 0.14 mol) in MeOH (250 mL) was stirred under 760 mmHg of H$_2$ at room temperature for 4 hr. TLC (EtOAc/petroleum oil=1/2) showed the reaction was complete. The mixture was filtered through Celite. The filtrate was concentrated and the residue was purified by column chromatography (EtOAc/petroleum ether=1/3) to give the title compound (18 g, 55% yield) as an off-white solid.

¹H NMR (400 MHz, CDCl₃): δ 7.12 (s, 1H), 6.94(s, H), 6.74 (s, 1H), 4.97 (m, 1H), 3.86 (m, 1H), 3.75 (m, 1H), 3.22 (m, 1H), 3.02 (m, 1H), 2.47 (s, 1H), 1.56 (s, 9H).

Preparation of Intermediate 200g

2-Hydroxymethyl-4-(4-methanesulfonyl-phenoxy)-2,3-dihydro-benzofuran-6-carboxylic acid tert-butyl ester

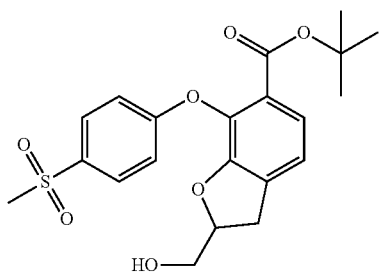

The mixture of 4-hydroxy-2-hydroxymethyl-2,3-dihydro-benzofuran-6-carboxylic acid tert-butyl ester (200f) (921 mg, 3.46 mmol), 4-flurophenyl methylsulfone (602 mg, 3.46 mmol), and Cs₂CO₃ (2.37 g, 7.27 mmol) in DMF (6 mL) was heated to 120° C. for 5 hr. The mixture was quenched with H₂O (60 mL) and extracted with EtOAc (2×60 mL). The organic layers were washed with H₂O (2×80 mL), dried over MgSO₄ and concentrated. The residue was purified by flash column chromatography eluting with 40-50% EtOAc in hexanes to give a colorless oil (1.05 mg, 72% yield). ¹H NMR (400 MHz, CDCl₃) δ 7.91-7.99 (m, 2 H) 7.34 (t, J=6.69 Hz, 2 H) 7.09-7.17 (m, 2 H) 5.05 (d, J=2.78 Hz, 1 H) 3.88-3.97 (m, 1 H) 3.73-3.82 (m, 1 H) 3.14-3.23 (m, 1 H) 3.12 (s, 3 H) 3.07-3.11 (m, 1 H) 2.99 (dd, J=16.55, 7.20 Hz, 1 H) 1.62 (s, 9 H); LCMS for C₂₁H₂₄O₇S m/z 443.00 (M+Na)⁺.

Example 201

4-(4-Methanesulfonyl-phenoxy)-2-methoxymethyl-2,3-dihydro-benzofuran-6-carboxylic acid (1-methyl-1H-pyrazol-3-yl)-amide

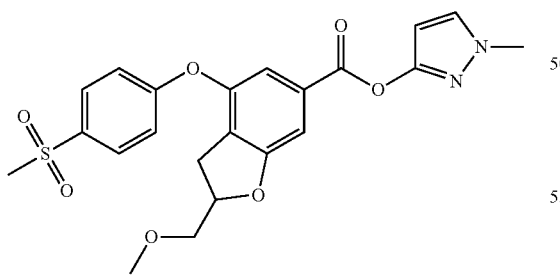

The title compound was prepared in a similar manner as described for Example 200, from 4-(4-methanesulfonyl-phenoxy)-2-methoxymethyl-2,3-dihydro-benzofuran-6-carboxylic acid tert-butyl ester (201a). ¹H NMR (400 MHz, CDCl₃) δ 8.41 (s, 1H) 7.89-7.95 (m, 2 H) 7.28 (d, J=2.27 Hz, 1 H) 7.12 (t, J=2.02 Hz, 2 H) 7.09-7.11 (m, 1 H) 7.06 (d, J=1.52 Hz, 1 H) 6.77 (d, J=2.27 Hz, 1 H) 5.01-5.10 (m, 1 H) 3.80 (s, 3 H) 3.61 (d, J=4.80 Hz, 2 H) 3.43 (s, 3 H) 3.17 (dd, J=16.42, 9.60 Hz, 1 H) 3.08 (s, 3 H) 2.89-2.99 (m, 1 H); LCMS for C₂₂H₂₃N₃O₆S m/z 458.00 (M+H)⁺.

Preparation of Intermediate 201a 4-(4-Methanesulfonyl-phenoxy)-2-methoxymethyl-2,3-dihydro-benzofuran-6-carboxylic acid tert-butyl ester

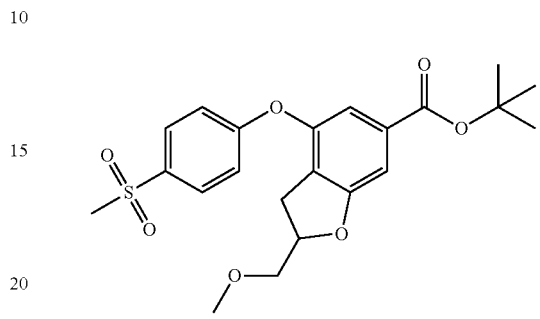

NaH (50 mg, 60% in mineral oil, 1.3 mmol) was added to a solution of 2-hydroxymethyl-4-(4-methanesulfonyl-phenoxy)-2,3-dihydro-benzofuran-6-carboxylic acid tert-butyl ester (200g) (409 mg, 0.97 mmol) in THF (5 mL). The resulting mixture was stirred at 0° C. for 10 min and then methyl iodide (80 uL, 1.3 mmol) was added. The mixture was stirred at room temperature for 2 hr and then quenched with H₂O (20 mL), extracted with EtOAc (2×20 mL). The organic layers were dried over MgSO₄ and concentrated. The residue was purified by flash column chromatograph eluting with 20-30% EtOAc in hexanes to give a colorless oil (295 mg, 70% yield). ¹H NMR (400 MHz, CHLOROFORM-d) δ 1.56 (s, 9 H) 2.89 (dd, J=16.55, 7.20 Hz, 1 H) 3.07 (s, 3 H) 3.08-3.17 (m, 1 H) 3.39-3.44 (m, 3 H) 3.58 (d, J=5.05 Hz, 2 H) 4.99-5.08 (m, 1 H) 7.04-7.10 (m, 2 H) 7.21 (d, J=1.01 Hz, 1 H) 7.30 (d, J=1.26 Hz, 1 H) 7.86-7.93 (m, 2 H); LCMS for C₂₂H₂₆O₇S m/z 457.00 (M+Na)⁺.

Example 202

4-[4-(Azetidine-1-carbonyl)-3-fluoro-phenoxy]-2-hydroxymethyl-2,3-dihydro-benzofuran-6-carboxylic acid (1-methyl-1H-pyrazol-3-yl)-amide

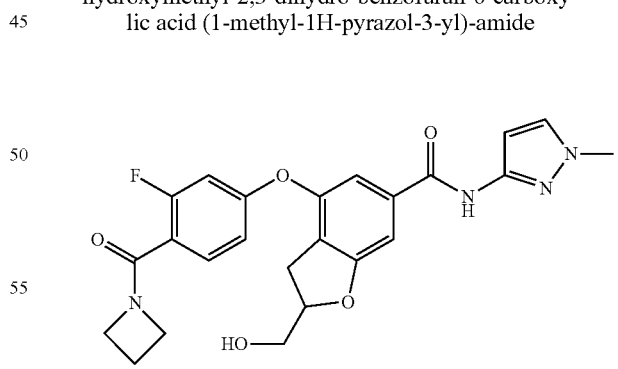

The title compound was prepared in a similar manner as described for Example 200, from 4-[4-(azetidine-1-carbonyl)-3-fluoro-phenoxy]-2-hydroxymethyl-2,3-dihydro-benzofuran-6-carboxylic acid tert-butyl ester (202a). ¹H NMR (400 MHz, CDCl₃) δ 8.54 (s, 1H) 7.52 (t, J=8.08 Hz, 1 H) 7.28 (s, 1 H) 7.05-7.14 (m, 2 H) 6.74-6.81 (m, 2 H) 6.68 (dd, J=10.99, 2.15 Hz, 1 H) 5.00 (ddd, J=12.76, 9.47, 3.03 Hz, 1 H) 4.18-4.25 (m, 2 H) 4.11-4.18 (m, 2 H) 3.89 (ddd, J=12.19, 6.25, 3.03 Hz, 1 H) 3.79 (s, 3 H) 3.73 (dt, J=12.13, 6.06 Hz, 1 H) 3.13 (dd, J=16.55, 9.47 Hz, 1 H) 2.92-3.01 (m, 1 H) 2.47 (t, J=6.32 Hz, 1 H) 2.29-2.38 (m, 2 H); LCMS for $C_{24}H_{23}FN_4O_5$ m/z 467.00 (M+H)$^+$.

Preparation of Intermediate 202a

4-[4-(Azetidine-1-carbonyl)-3-fluoro-phenoxy]-2-hydroxymethyl-2,3-dihydro-benzofuran-6-carboxylic acid tert-butyl ester

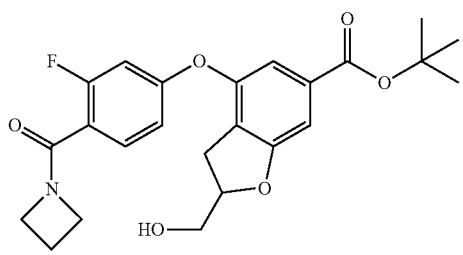

The title compound was prepared in a similar manner as described for Intermediate 1f, from 4-hydroxy-2-hydroxymethyl-2,3-dihydro-benzofuran-6-carboxylic acid tert-butyl ester (200f) and azetidin-1-yl-(2,4-difluoro-phenyl)-methanone. $^1$H NMR (400 MHz, CDCl$_3$) δ 1.57 (s, 9 H) 2.26-2.38 (m, 2 H) 3.06-3.17 (m, 1 H) 3.67-3.78 (m, 1 H) 3.81-3.90 (m, 1 H) 4.09-4.18 (m, 3 H) 4.18-4.25 (m, 2 H) 4.92-5.02 (m, 1 H) 6.63-6.68 (m, 1 H) 6.78 (dd, J=8.59, 2.27 Hz, 1 H) 7.21 (d, J=1.26 Hz, 1 H) 7.49-7.56 (m, 1 H) 8.02 (s, 1 H); LCMS for $C_{24}H_{24}FNO_6$ m/z 444.00 (M+H)$^+$.

Example 203

4-[4-(Azetidine-1-carbonyl)-3-fluoro-phenoxy]-2-hydroxymethyl-2,3-dihydro-benzofuran-6-carboxylic acid (5-methyl-pyridin-2-yl)-amide

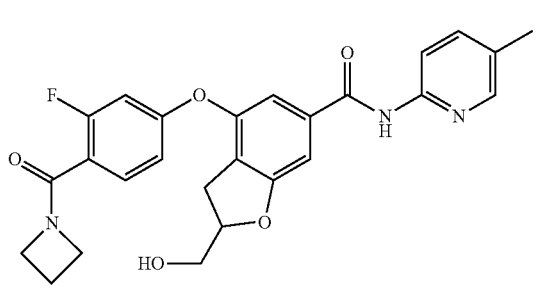

The title compound was prepared in a similar manner as described for Example 200, from 4-[4-(azetidine-1-carbonyl)-3-fluoro-phenoxy]-2-hydroxymethyl-2,3-dihydro-benzofuran-6-carboxylic acid tert-butyl ester (202a). $^1$H NMR (400 MHz, CDCl$_3$) δ 8.41-8.85 (m, 1 H) 8.19-8.24 (m, 1 H) 8.11 (s, 1 H) 7.59 (dd, J=8.59, 1.77 Hz, 1 H) 7.54 (t, J=8.21 Hz, 1 H) 7.18 (d, J=1.01 Hz, 1 H) 7.11 (d, J=1.26 Hz, 1 H) 6.80 (dd, J=8.59, 2.27 Hz, 1 H) 6.66-6.72 (m, 1 H) 4.98-5.06 (m, 1 H) 4.22 (t, J=7.83 Hz, 2 H) 4.16 (t, J=7.71 Hz, 2 H) 3.86-3.94 (m, 1 H) 3.75 (dd, J=12.38, 5.56 Hz, 1 H) 3.15 (dd, J=16.67, 9.60 Hz, 1 H) 2.93-3.01 (m, 1H) 2.31-2.34 (m, 5 H); LCMS for $C_{26}H_{24}FN_3O_5$ m/z 478.00 (M+H)$^+$.

Example 204

4-[4-(Azetidine-1-carbonyl)-3-fluoro-phenoxy]-2-methoxymethyl-2,3-dihydro-benzofuran-6-carboxylic acid (1-methyl-1H-pyrazol-3-yl)-amide

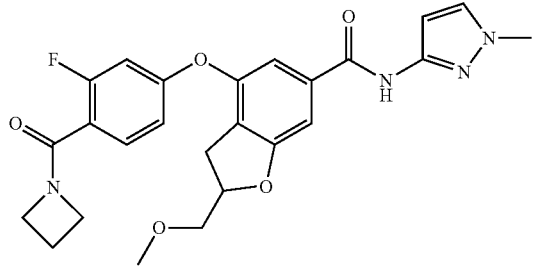

The title compound was prepared in a similar manner as described for Intermediate 1f, from 4-hydroxy-2-methoxymethyl-2,3-dihydro-benzofuran-6-carboxylic acid (1-methyl-1H-pyrazol-3-yl)-amide (204d) and azetidin-1-yl-(2,4-difluoro-phenyl)-methanone. $^1$H NMR (400 MHz, CDCl$_3$) δ 8.43 (s, 1 H) 7.54 (t, J=8.08 Hz, 1 H) 7.28 (d, J=2.27 Hz, 1 H) 7.13 (s, 1 H) 7.08 (s, 1 H) 6.81 (dd, J=8.59, 2.27 Hz, 1 H) 6.78 (d, J=2.02 Hz, 1 H) 6.68 (dd, J=11.12, 2.27 Hz, 1 H) 5.00-5.08 (m, 1 H) 4.22 (t, J=7.71 Hz, 2 H) 4.16 (t, J=7.71 Hz, 2 H) 3.81 (s, 3 H) 3.60 (d, J=5.05 Hz, 2 H) 3.43 (s, 3 H) 3.15 (dd, J=16.42, 9.60 Hz, 1 H) 2.92 (dd, J=16.42, 7.33 Hz, 1 H) 2.27-2.38 (m, 2 H); LCMS for $C_{25}H_{25}FN_4O_5$ m/z 481.00 (M+H)$^+$.

Preparation of Intermediate 204a

4-Benzyloxy-2-hydroxymethyl-2,3-dihydro-benzofuran-6-carboxylic acid tert-butyl ester

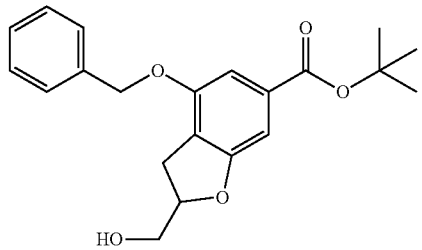

Benzyl bromide (1.8 mL, 15.2 mmol) and Cs$_2$CO$_3$ (4.89 g, 15.0 mmol) were added to a solution of 4-hydroxy-2-hydroxymethyl-2,3-dihydro-benzofuran-6-carboxylic acid tert-butyl ester (200f) (4.0 g, 15.0 mmol) in DMF (10 mL). The reaction mixture was stirred at room temperature overnight. The mixture was quenched with H$_2$O (60 mL) and extracted EtOAc (2×60 mL). The organic layers were washed with H$_2$O (2×100 mL), dried over MgSO$_4$ and concentrated. The residue was purified by flash column chromatograph eluting with 30-40% EtOAc in hexanes to give a pale yellow oil (4.43 g, 83% yield). $^1$H NMR (400 MHz, CDCl$_3$) δ 7.34-7.45 (m, 5 H) 7.19 (s, 1 H) 7.09 (s, 1 H) 5.13 (s, 2 H) 4.96-5.03 (m, 1 H) 3.85 (ddd, J=12.00, 6.95, 3.28 Hz, 1 H) 3.74 (dt, J=12.13, 6.06 Hz, 1 H) 3.27 (dd, J=16.42, 9.60 Hz, 1 H) 3.01 (dd, J=16.42, 7.07 Hz, 1 H) 1.58 (s, 9 H); LCMS for $C_{21}H_{24}O_5$ m/z 357.00 $(M+H)^+$.

Preparation of Intermediate 204b

4-Benzyloxy-2-methoxymethyl-2,3-dihydro-benzofuran-6-carboxylic acid tert-butyl ester

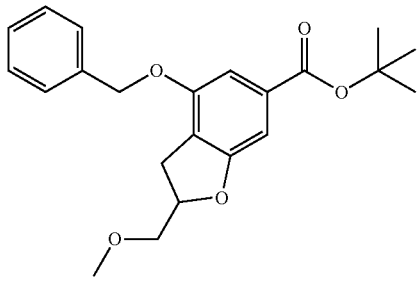

NaH (134 mg, 3.35 mmol) was added to a solution of 4-benzyloxy-2-hydroxymethyl-2,3-dihydro-benzofuran-6-carboxylic acid tert-butyl ester (204a) (994 mg, 2.79 mmol) in THF (10 mL). The resulting mixture was stirred at 0° C. for 10 min and methyl iodide (210 uL, 3.37 mmol) was added. The mixture was stirred at room temperature for 2 hr, quenched with $H_2O$ (50 mL) and extracted with EtOAc (2×50 mL). The organic layers were dried over $MgSO_4$ and concentrated. The residue was purified by flash column chromatograph eluting with 20-30% EtOAc in hexanes to give a colorless oil (295 mg, 70% yield). $^1$H NMR (400 MHz, $CDCl_3$) δ 7.34-7.45 (m, 5 H) 7.19 (d, J=1.01 Hz, 1 H) 7.11 (d, J=1.01 Hz, 1 H) 5.13 (s, 2 H)) 4.99-5.09 (m, 1 H) 3.54-3.64 (m, 2 H) 3.44 (s, 3 H) 3.23-3.33 (m, 1 H) 2.98 (dd, J=16.42, 7.33 Hz, 1 H) 1.57 (s, 9 H); LCMS for $C_{22}H_{26}O_5$ m/z 371.20 $(M+H)^+$.

Preparation of Intermediate 204c

4-Benzyloxy-2-methoxymethyl-2,3-dihydro-benzofuran-6-carboxylic acid (1-methyl-1H-pyrazol-3-yl)-amide

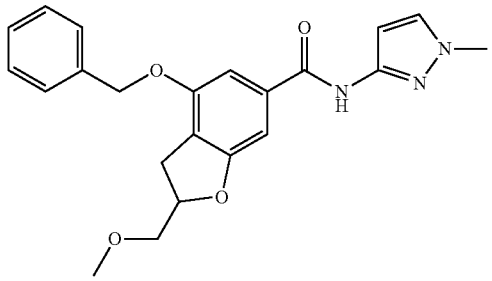

The title compound was prepared in a similar manner as described for Example 200, from 4-benzyloxy-2-methoxymethyl-2,3-dihydro-benzofuran-6-carboxylic acid tert-butyl ester (204b) and 1-methyl-3-aminopyrazole (268 mg, 2.95 mmol) to give a white solid (645 mg, 83% yield). $^1$H NMR (400 MHz, $CDCl_3$) δ 8.53 (s, 1 H) 7.34-7.44 (m, 5 H) 7.29 (d, J=2.27 Hz, 1 H) 7.09 (d, J=1.26 Hz, 1 H) 6.89 (s, 1 H) 6.82 (d, J=2.27 Hz, 1 H) 5.12 (s, 2 H) 5.01-5.09 (m, 1 H) 3.79 (s, 3 H) 3.56-3.66 (m, 2 H) 3.45 (s, 3 H) 3.29 (dd, J=16.42, 9.60 Hz, 1 H) 3.01 (dd, J=16.42, 7.33 Hz, 1 H); LCMS for $C_{22}H_{23}N_3O_4$ m/z 394.00 $(M+H)^+$.

Preparation of Intermediate 204d

4-Hydroxy-2-methoxymethyl-2,3-dihydro-benzofuran-6-carboxylic acid (1-methyl-1H-pyrazol-3-yl)-amide

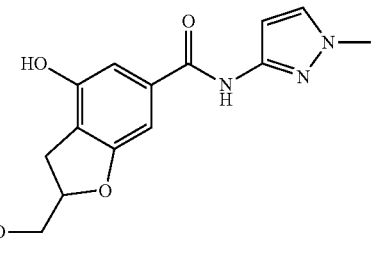

10% Pd on Carbon (100 mg) was added to a solution of 4-benzyloxy-2-methoxymethyl-2,3-dihydro-benzofuran-6-carboxylic acid (1-methyl-1H-pyrazol-3-yl)-amide (204c) (640 mg, 1.63 mmol) in EtOAc (15 mL). The reaction mixture was stirred under $H_2$ balloon overnight. The mixture was filtered through Celite, washed with EtOAc and concentrated to give a white solid (508 mg, 100% yield). $^1$H NMR (400 MHz, $CDCl_3$) δ 8.77 (s, 1 H) 7.96 (s, 1 H) 7.28 (d, J=2.27 Hz, 1 H) 6.98 (s, 1 H) 6.82 (s, 1 H) 6.78 (d, J=2.27 Hz, 1 H) 4.98-5.07 (m, 1 H) 3.76 (s, 3 H) 3.56-3.65 (m, 2 H) 3.44 (s, 3 H) 3.25 (dd, J=15.92, 9.60 Hz, 1 H) 2.97 (dd, J=16.04, 7.20 Hz, 1 H); LCMS for $C_{15}H_{17}N_3O_4$ m/z 304.00 $(M+H)^+$.

Example 205

4-(4-Dimethylcarbamoyl-3-fluoro-phenoxy)-2-methoxymethyl-2,3-dihydro-benzofuran-6-carboxylic acid (1-methyl-1H-pyrazol-3-yl)-amide

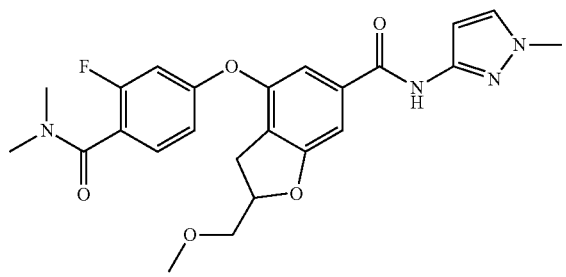

The title compound was prepared in a similar manner as described for Intermediate 1f, from 4-hydroxy-2-methoxymethyl-2,3-dihydro-benzofuran-6-carboxylic acid (1-methyl-1H-pyrazol-3-yl)-amide (204d) and 2,4-difluoro-N,N-dimethyl-benzamide. $^1$H NMR (400 MHz, DMSO-$d_6$) δ 10.75 (s, 1 H) 7.58 (d, J=1.77 Hz, 1 H) 7.40 (t, J=8.21 Hz, 1 H) 7.26 (s, 1 H) 7.21 (s, 1 H) 7.00 (dd, J=11.12, 1.52 Hz, 1 H) 6.91 (dd, J=8.46, 1.89 Hz, 1 H) 6.54 (d, J=1.52 Hz, 1 H) 5.01-5.09 (m, 1 H) 3.76 (s, 3 H) 3.50-3.59 (m, 2 H) 3.29 (s, 3 H) 3.10-3.21 (m, 1 H) 2.99 (s, 3 H) 2.85-2.89 (m, 4 H); LCMS for $C_{24}H_{25}FN_4O_5$ m/z 469.20 (M+H)$^+$; Anal. Calcd. for $C_{24}H_{25}FN_4O_5$.0.63 H2O: C, 60.08; H, 5.52; N, 11.68; Found: C, 60.08; H, 5.19; N, 11.53.

Example 206

(−)-4-(4-Dimethylcarbamoyl-3-fluoro-phenoxy)-2-methoxymethyl-2,3-dihydro-benzofuran-6-carboxylic acid (1-methyl-1H-pyrazol-3-yl)-amide and

Example 207

(+)-4-(4-Dimethylcarbamoyl-3-fluoro-phenoxy)-2-methoxymethyl-2,3-dihydro-benzofuran-6-carboxylic acid (1-methyl-1H-pyrazol-3-yl)-amide

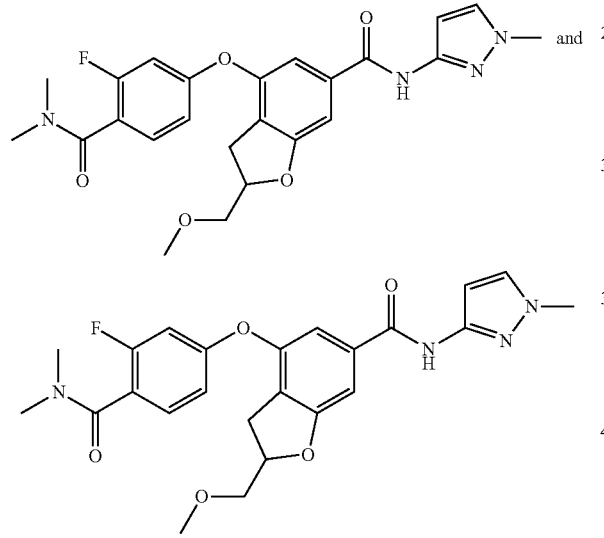

The title compounds were prepared by the chiral separation of Example 205 by SFC column chromatography.

Example 206: [α]$_D$=−29.9; 100% ee; $^1$H NMR (400 MHz, CDCl$_3$) δ 8.33 (s, 1 H) 7.38 (t, J=8.08 Hz, 1 H) 7.28 (d, J=2.27 Hz, 1 H) 7.12 (s, 1 H) 7.07 (d, J=1.26 Hz, 1 H) 6.82 (dd, J=8.46, 2.15 Hz, 1 H) 6.77 (d, J=2.02 Hz, 1 H) 6.70 (dd, J=10.61, 2.27 Hz, 1 H) 5.01-5.08 (m, J=9.60, 7.26, 4.71, 4.71 Hz, 1 H) 3.81 (s, 3 H) 3.61 (d, J=5.05 Hz, 2 H) 3.43 (s, 3 H) 3.14-3.20 (m, 1 H) 3.13 (s, 3 H) 2.99 (d, J=1.77 Hz, 3 H) 2.93 (dd, J=16.42, 7.33 Hz, 1 H); LCMS for $C_{24}H_{25}FN_4O_5$ m/z 469.00 (M+H)$^+$; Anal. Calcd. for $C_{24}H_{25}FN_4O_5$.0.55 H2O: C, 60.26; H, 5.50; N, 11.71; Found: C, 60.21; H, 5.33; N, 11.55.

Example 207: [α]$_D$=+35.7; 99.5% ee; $^1$H NMR (400 MHz, CDCl$_3$) δ 8.33 (s, 1 H) 7.38 (t, J=8.08 Hz, 1 H) 7.28 (d, J=2.02 Hz, 1 H) 7.12 (s, 1 H) 7.07 (s, 1 H) 6.82 (dd, J=8.46, 2.15 Hz, 1 H) 6.77 (d, J=1.77 Hz, 1 H) 6.70 (dd, J=10.61, 2.27 Hz, 1 H) 5.01-5.08 (m, 1 H) 3.81 (s, 3 H) 3.61 (d, J=5.05 Hz, 2 H) 3.44 (s, 3 H) 3.14-3.20 (m, 1 H) 3.13 (s, 3 H) 2.99 (d, J=1.52 Hz, 3 H) 2.89-2.97 (m, 1 H); LCMS for $C_{24}H_{25}FN_4O_5$ m/z 469.00 (M+H)$^+$; Anal. Calcd. for $C_{24}H_{25}FN_4O_5$.0.26 H$_2$O: C, 60.92; H, 5.44; N, 11.84; Found: C, 60.92; H, 5.32; N, 11.77.

Example 208

4-[4-(Azetidine-1-carbonyl)-phenoxy]-2-methoxymethyl-2,3-dihydro-benzofuran-6-carboxylic acid (1-methyl-1H-pyrazol-3-yl)-amide

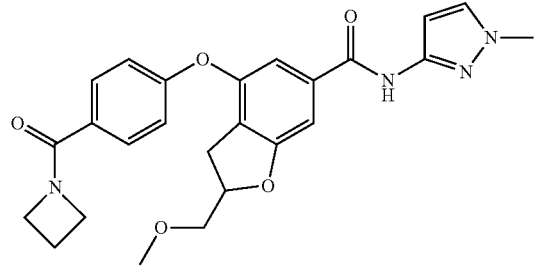

The title compound was prepared in a similar manner as described for Intermediate 1f, from 4-hydroxy-2-methoxymethyl-2,3-dihydro-benzofuran-6-carboxylic acid (1-methyl-1H-pyrazol-3-yl)-amide (204d) and azetidin-1-yl-(4-fluoro-phenyl)-methanone. $^1$H NMR (400 MHz, CDCl$_3$) δ 8.60 (s, 1 H) 7.59-7.67 (m, 2 H) 7.28 (d, J=2.53 Hz, 1 H) 7.13 (d, J=1.26 Hz, 1 H) 7.06 (d, J=1.26 Hz, 1 H) 6.97-7.02 (m, 2 H) 6.79 (d, J=2.27 Hz, 1 H) 4.99-5.08 (m, 1 H) 4.29-4.39 (m, 2 H) 4.19-4.29 (m, 2 H) 3.80-3.82 (m, 3 H) 3.56-3.64 (m, 2 H) 3.44 (s, 3 H) 3.16 (dd, J=16.55, 9.47 Hz, 1H) 2.92 (dd, J=16.42, 7.33 Hz, 1 H) 2.31-2.41 (m, 2 H); LCMS for $C_{25}H_{26}N_4O_5$ m/z 463.20 (M+H)$^+$.

Example 209

(−)-4-[4-(Azetidine-1-carbonyl)-phenoxy]-2-methoxymethyl-2,3-dihydro-benzofuran-6-carboxylic acid (1-methyl-1H-pyrazol-3-yl)-amide and

Example 210

(+)-4-[4-(Azetidine-1-carbonyl)-phenoxy]-2-methoxymethyl-2,3-dihydro-benzofuran-6-carboxylic acid (1-methyl-1H-pyrazol-3-yl)-amide

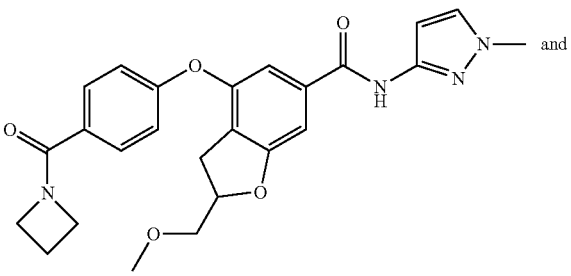

221

-continued

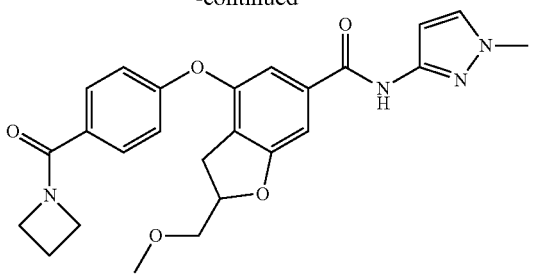

The title compounds were prepared by the chiral separation of Example 208 by SFC column chromatography.

Example 209: $[\alpha]_D$=−29.72; $^1$H NMR (400 MHz, CDCl$_3$) δ 8.33 (s, 1 H) 7.58-7.70 (m, 2 H) 7.22-7.30 (m, 1 H) 7.09 (s, 1 H) 6.95-7.04 (m, 3 H) 6.77 (d, J=2.02 Hz, 1 H) 4.99-5.08 (m, 1 H) 4.35 (br. s., 2 H) 4.23 (d, J=9.09 Hz, 2 H) 3.80 (s, 3 H) 3.55-3.63 (m, 2 H) 3.44 (s, 3 H) 3.16 (dd, J=16.42, 9.60 Hz, 1 H) 2.84-2.95 (m, 1 H) 2.28-2.41 (m, 2 H); LCMS for C$_{25}$H$_{26}$N$_4$O$_5$ m/z 463.00 (M+H$^+$).

Example 210: $[\alpha]_D$=+28.85; $^1$H NMR (400 MHz, CDCl$_3$) δ 8.35 (s, 1 H) 7.65 (d, J=8.84 Hz, 2 H) 7.23-7.31 (m, 1 H) 7.09 (s, 1 H) 6.96-7.06 (m, 3 H) 6.77 (d, J=2.27 Hz, 1 H) 5.04 (dd, J=4.55, 2.78 Hz, 1 H) 4.35 (br. s., 2 H) 4.24 (br. s., 2 H) 3.80 (s, 3 H) 3.54-3.66 (m, 2 H) 3.43 (s, 3 H) 3.15 (dd, J=16.67, 9.60 Hz, 1 H) 2.92 (dd, J=16.42, 7.33 Hz, 1 H) 2.29-2.42 (m, 2 H); LCMS for C$_{25}$H$_{26}$N$_4$O$_5$ m/z 463.00 (M+H$^+$).

Example 211

4-(4-Dimethylcarbamoyl-phenoxy)-2-methoxymethyl-2,3-dihydro-benzofuran-6-carboxylic acid (1-methyl-1H-pyrazol-3-yl)-amide

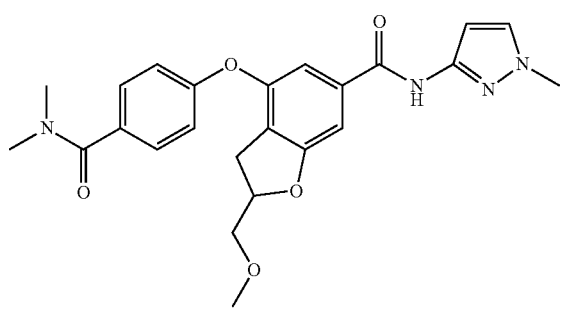

The title compound was prepared in a similar manner as described for Example 200, from and 3-amino-1-methyl-pyrazole and 4-(4-dimethylcarbamoyl-phenoxy)-2-methoxymethyl-2,3-dihydro-benzofuran-6-carboxylic acid tert-butyl ester (211b) to give a white solid. $^1$H NMR (400 MHz, CDCl$_3$) δ 8.26 (s, 1 H) 7.37-7.49 (m, 2 H) 7.23-7.30 (m, 1 H) 7.09 (d, J=1.26 Hz, 1 H) 6.95-7.06 (m, 3 H) 6.77 (d, J=2.27 Hz, 1 H) 4.99-5.09 (m, 1 H) 3.81 (s, 3 H) 3.59-3.62 (m, 2 H)

222

3.45 (s, 3 H) 3.14-3.21 (m, 1 H) 3.06 (d, J=1.52 Hz, 6H) 2.93 (dd, J=16.55, 7.45 Hz, 1H); LCMS for C$_{24}$H$_{26}$N$_4$O$_5$ m/z 451.20 (M+H$^+$).

Preparation of Intermediate 211a 4-(4-Dimethylcarbamoyl-phenoxy)-2-hydroxymethyl-2,3-dihydro-benzofuran-6-carboxylic acid tert-butyl ester

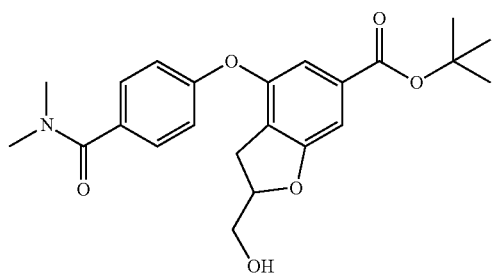

The title compound was prepared in a similar manner as described for Intermediate 1f, from 4-fluoro-N,N-dimethyl-benzamide (989 mg, 5.91 mmol) and 4-hydroxy-2-hydroxymethyl-2,3-dihydro-benzofuran-6-carboxylic acid tert-butyl ester (200f) (1.500 g, 5.633 mmol) to give a white solid (154 mg, 7% yield). $^1$H NMR (400 MHz, CDCl$_3$) δ 7.41 (d, J=8.59 Hz, 2 H) 7.20 (d, J=16.17 Hz, 2 H) 6.96 (d, J=8.59 Hz, 2 H) 4.87-5.03 (m, 1 H) 3.77-3.87 (m, 1 H) 3.71 (br. s., 1 H) 2.99-3.13 (m, 7 H) 2.90 (dd, J=16.55, 7.20 Hz, 1 H) 1.54 (s, 9 H); LCMS for C$_{23}$H$_{27}$NO$_6$ m/z 358.20 (M-tBu+H)$^+$.

Preparation of Intermediate 211b 4-(4-Dimethylcarbamoyl-phenoxy)-2-methoxymethyl-2,3-dihydro-benzofuran-6-carboxylic acid tert-butyl ester

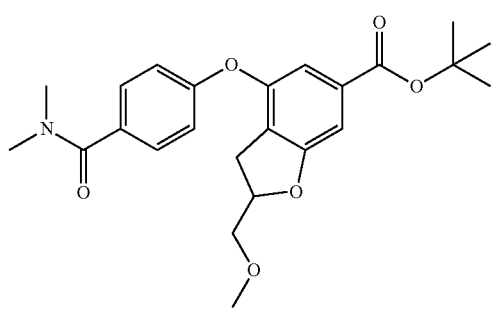

The title compound was prepared in a similar manner as described for Intermediate 204b, from 4-(4-dimethylcarbamoyl-phenoxy)-2-hydroxymethyl-2,3-dihydro-benzofuran-6-carboxylic acid tert-butyl ester (211a) and methyl iodide. $^1$H NMR (400 MHz, CDCl$_3$) δ 7.40-7.43 (m, 2 H) 7.24 (d, J=1.26 Hz, 1 H) 7.17 (d, J=1.26 Hz, 1 H) 6.92-7.01 (m, 2 H) 4.92-

5.05 (m, 1 H) 3.51-3.59 (m, 2 H) 3.41 (s, 3 H) 2.99-3.15 (m, 7 H) 2.81-2.90 (m, 1 H) 1.54 (s, 9 H); LCMS for $C_{24}H_{29}NO_6$ m/z 428.20 (M+H$^+$).

Example 212

(+)-4-(4-Dimethylcarbamoyl-phenoxy)-2-methoxymethyl-2,3-dihydro-benzofuran-6-carboxylic acid (1-methyl-1H-pyrazol-3-yl)-amide and Example 213: (−)-4-(4-Dimethylcarbamoyl-phenoxy)-2-methoxymethyl-2,3-dihydro-benzofuran-6-carboxylic acid (1-methyl-1H-pyrazol-3-yl)-amide

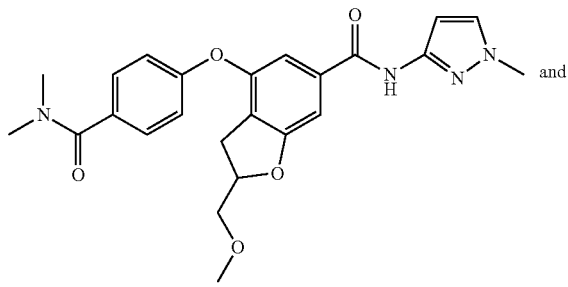

and

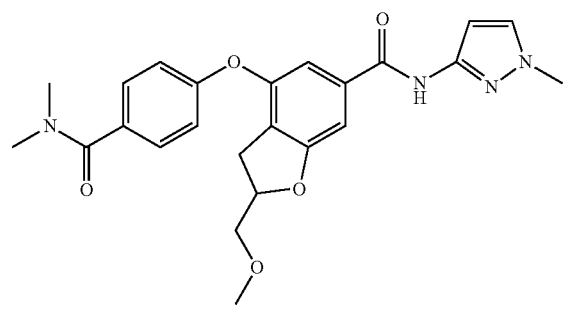

The title compounds were prepared by the chiral separation of Example 211 by SFC column chromatography.

Example 212: $[\alpha]_D$=+30.5; $^1$H NMR (400 MHz, CDCl$_3$) δ 8.30 (s, 1 H) 7.37-7.49 (m, 2 H) 7.22-7.30 (m, 1 H) 6.97-7.04 (m, 4 H) 6.77 (d, J=2.27 Hz, 1 H) 4.99-5.09 (m, 1 H) 3.81 (s, 3 H) 3.58-3.62 (m, 2H) 3.44 (s, 3 H) 3.13-3.21 (m, 1 H) 3.10 (br. s., 3 H) 3.06 (br. s., 3 H) 2.93 (dd, J=16.55, 7.45 Hz, 1 H); LCMS for $C_{24}H_{26}N_4O_5$ m/z 451.20 (M+H$^+$).

Example 213 $[\alpha]_D$=−33.9; $^1$H NMR (400 MHz, CDCl$_3$) δ 8.26 (s, 1 H) 7.37-7.49 (m, 2 H) 7.23-7.30 (m, 1 H) 7.09 (d, J=1.26 Hz, 1 H) 6.95-7.06 (m, 3 H) 6.77 (d, J=2.27 Hz, 1 H) 4.99-5.09 (m, 1 H) 3.81 (s, 3H) 3.59-3.62 (m, 2 H) 3.45 (s, 3 H) 3.14-3.21 (m, 1 H) 3.06 (d, J=1.52 Hz, 6H) 2.93 (dd, J=16.55, 7.45 Hz, 1 H); LCMS for $C_{24}H_{26}N_4O_5$ m/z 451.20 (M+H$^{30}$).

Example 214

4-Isopropoxy-2-phenoxymethyl-2,3-dihydro-benzofuran-6-carboxylic acid (1-methyl-1H-pyrazol-3-yl)-amide

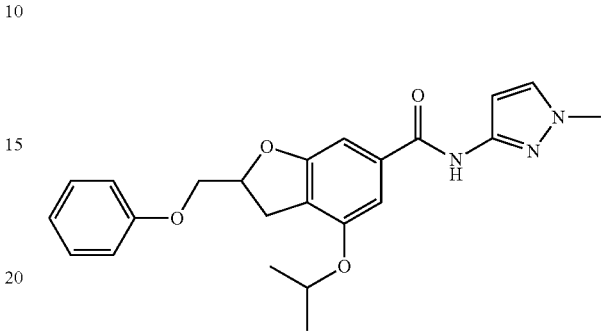

The title compound was prepared in a similar manner as described for Example 200 from 4-isopropoxy-2-phenoxymethyl-2,3-dihydro-benzofuran-6-carboxylic acid tert-butyl ester (214c) and 1-methyl-3-aminopyrazole. $^1$H NMR (400 MHz, CDCl$_3$) δ 8.69 (s, 1 H) 7.28-7.32 (m, 3 H) 7.05 (s, 1 H) 6.93-7.00 (m, 3 H) 6.89 (s, 1 H) 6.84 (s, 1 H) 5.19-5.27 (m, 1 H) 4.64-4.72 (m, 1 H) 4.20-4.26 (m, 1 H) 4.11 (dd, J=9.98, 4.67 Hz, 1 H) 3.82 (s, 3 H) 3.35 (dd, J=16.42, 9.35 Hz, 1 H) 3.11 (dd, J=16.55, 6.95 Hz, 1 H) 1.36 (d, J=5.81 Hz, 6 H); LCMS for $C_{23}H_{25}N_3O_4$ m/z 408.20 (M+H)$^+$; Anal. Calcd. for $C_{23}H_{25}N_3O_4$·0.50 H2O: C, 66.33; H, 6.29; N, 10.09; Found: C, 66.29; H, 6.05; N, 9.87.

Preparation of Intermediate 214a

4-Benzyloxy-2-phenoxymethyl-2,3-dihydro-benzofuran-6-carboxylic acid tert-butyl ester

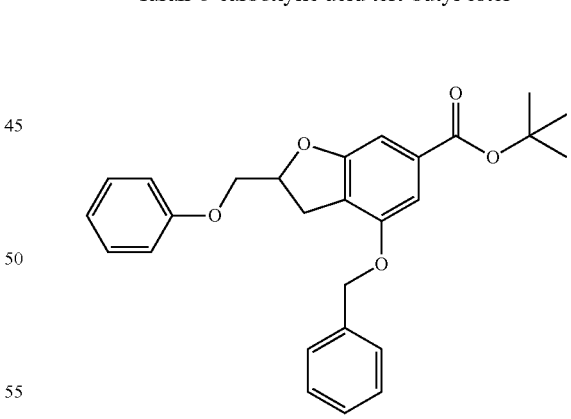

4-Benzyloxy-2-hydroxymethyl-2,3-dihydro-benzofuran-6-carboxylic acid tert-butyl ester (204a) (414 mg, 1.16 mmol) was dissolved in CH$_2$Cl$_2$ (25 mL) and cooled to 0° C. whilst stirring under a N$_2$ atmosphere. The solution was treated with Ph$_3$P (457 mg, 1.74 mmol), phenol (164 mg, 1.74 mmol) and DIAD (350 uL, 1.78 mmol) added drop-wise. The resulting solution was stirred at room temperature for 2 hr. The reaction mixture was concentrated in vacuo and purified by column chromatography, eluting with 5-10% EtOAc in hexanes to give a colorless oil (480 mg, 95% yield). $^1$H NMR (400 MHz, CDCl$_3$) δ 7.37-7.46 (m, 5 H) 7.21-7.26 (m, 2 H) 7.11-7.14 (m, 1 H) 6.91-6.96 (m, 2 H) 6.83-6.87 (m, 1H) 5.17-5.27 (m, 1 H) 5.12-5.15 (m, 3 H) 4.17-4.23 (m, 1 H) 4.07-4.15 (m, 1 H) 3.40 (dd, J=16.67, 9.60 Hz, 1H) 3.15 (dd, J=16.67, 6.82 Hz, 1 H) 1.59 (s, 9 H); LCMS for C$_{27}$H$_{28}$C$_5$ m/z 433.00 (M+H)$^+$.

Preparation of Intermediate 214b

4-Hydroxy-2-phenoxymethyl-2,3-dihydro-benzofuran-6-carboxylic acid tert-butyl ester

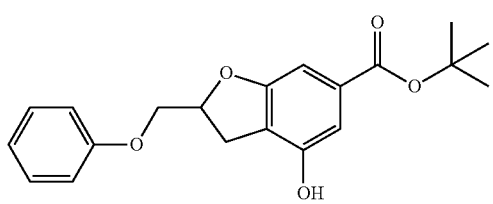

10% Pd on Carbon (50 mg) was added to a solution of 4-benzyloxy-2-phenoxymethyl-2,3-dihydro-benzofuran-6-carboxylic acid tert-butyl ester (214a) (500 mg, 1.16 mmol) in EtOAc (10 mL). The mixture was stirred under H$_2$ balloon for 3 days. The mixture was filtered through Celite and concentrated to give a colorless oil (400 mg, 88% yield). $^1$H NMR (400 MHz, CDCl$_3$) δ 7.22-7.32 (m, 2 H) 7.18 (s, 1 H) 7.04 (s, 1 H) 6.91-6.95 (m, 2 H) 6.85 (d, J=7.58 Hz, 1 H) 5.18-5.28 (m, 1 H) 4.09-4.17 (m, 2 H) 3.38 (dd, J=16.17, 9.60 Hz, 1 H) 3.15 (dd, J=16.29, 6.69 Hz, 1 H) 1.58 (s, 9 H); LCMS for C$_{20}$H$_{22}$O$_5$ m/z 365.00 (M+Na)$^+$.

Preparation of Intermediate 214c

4-Isopropoxy-2-phenoxymethyl-2,3-dihydro-benzofuran-6-carboxylic acid tert-butyl ester

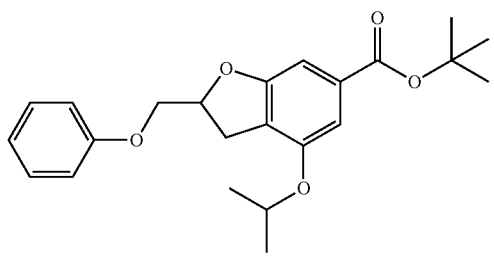

2-Iodopropane (174 mg, 1.02 mmol)) was added to a mixture of 4-hydroxy-2-phenoxymethyl-2,3-dihydro-benzofuran-6-carboxylic acid tert-butyl ester (214b) (350 mg, 1.02 mmol) and K$_2$CO$_3$ (141 mg, 1.02 mmol) in DMF (5 mL). The reaction mixture was stirred at 60° C. overnight. The mixture was diluted with H$_2$O (50 mL) and extracted with EtOAc (2×50 mL). The organic layers were washed with H$_2$O (2×70 mL), dried over MgSO$_4$ and concentrated. The residue was purified by flash column chromatograph eluting with 5% EtOAc in hexanes to give a white solid (182 mg, 46% yield). $^1$H NMR (400 MHz, CDCl$_3$) δ 7.29 (d, J=1.26 Hz, 1 H) 7.22-7.26 (m, 1 H) 7.13 (s, 1 H) 7.07 (s, 1 H) 6.91-7.00 (m, 3 H) 6.85 (d, J=7.58 Hz, 1 H) 5.17-5.25 (m, 1 H) 4.59-4.68 (m, 1 H) 4.07-4.17 (m, 1 H) 3.34 (dd, J=16.55, 9.47 Hz, 1 H) 3.09 (dd, J=16.55, 6.95 Hz, 1 H) 1.58 (s, 9 H) 1.35 (d, J=6.06 Hz, 6 H); LCMS for C$_{23}$H$_{28}$O$_5$ m/z 385.20 (M+H$^+$).

Example 215

2-Hydroxymethyl-4-isopropoxy-2,3-dihydro-benzofuran-6-carboxylic acid (1-methyl-1H-pyrazol-3-yl)-amide

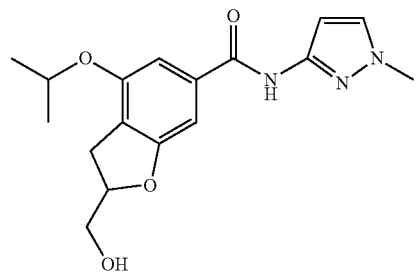

The title compound was prepared in a similar manner as described for Example 200, from 2-hydroxymethyl-4-isopropoxy-2,3-dihydro-benzofuran-6-carboxylic acid tert-butyl ester (215a) and 3-amino-1-methyl-pyrazole. $^1$H NMR (400 MHz, CDCl$_3$) δ 8.34 (s, 1 H) 7.26-7.35 (m, 1 H) 6.95-7.05 (m, 1H) 6.76-6.86 (m, 2 H) 4.93-5.08 (m, 1 H) 4.59-4.71 (m, 1 H) 3.84-3.91 (m, 1 H) 3.83 (s, 3 H), 3.22 (dd, J=16.42, 9.60 Hz, 1 H) 2.89-3.02 (m, 1 H) 1.98 (t, J=6.44 Hz, 1 H) 1.35 (d, J=6.06 Hz, 6 H); LCMS for C$_{17}$H$_{21}$N$_3$O$_4$ m/z 332.20 (M+H$^+$).

Preparation of Intermediate 215a

2-Hydroxymethyl-4-isopropoxy-2,3-dihydro-benzofuran-6-carboxylic acid tert-butyl ester

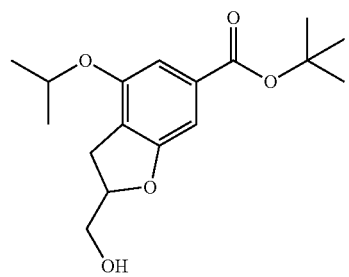

A mixture of 2-iodopropane (0.826 mL, 8.26 mmol), 4-hydroxy-2-hydroxymethyl-2,3-dihydro-benzofuran-6-carboxylic acid tert-butyl ester (200f) (2.00 g, 7.51 mmol), and K$_2$CO$_3$ (1.56 g, 11.3 mmol) in DMF (20 mL) was heated to 60° C. overnight. Additional 2-iodopropane (0.9 mL) and K$_2$CO$_3$ (0.9 g) were added. The resulting mixture was heated to 50° C. for 4 days, then cooled to room temperature, quenched with H$_2$O and extracted with 3×EtOAc. The organic layers were washed with 2×H$_2$O, dried over Na$_2$SO$_4$, and concentrated. The residue was purified by flash column chromatography with 50-70% EtOAc in hexanes to give a yellow syrup (2.0 g, 86% yield). $^1$H NMR (400 MHz, CDCl$_3$) δ 7.11 (s, 1 H) 7.03 (d, J=1.01 Hz, 1H) 4.90-5.05 (m, 1 H) 4.58-4.66 (m, 1 H) 3.81-3.88 (m, 1 H) 3.67-3.77 (m 1 H) 3.21

(dd, J=16.42, 9.60 Hz, 1 H) 2.94 (dd, J=16.42, 7.07 Hz, 1 H) 1.60 (s, 9 H) 1.32-1.34 (m, 6 H); LCMS for $C_{17}H_{24}O_5$ m/z 253.00 (M-tBu+H+).

Example 216

4-Isopropoxy-2-methoxymethyl-2,3-dihydro-benzofuran-6-carboxylic acid (1-methyl-1H-pyrazol-3-yl)-amide

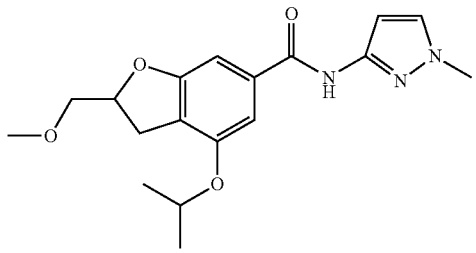

To a solution of toluene-4-sulfonic acid 4-isopropoxy-6-(1-methyl-1H-pyrazol-3-ylcarbamoyl)-2,3-dihydro-benzofuran-2-ylmethyl ester (216a) (84 mg, 0.17 mmol) in anhydrous MeOH (2 mL) was added NaOMe (1.4 mL, 25% wt). The mixture was stirred at room temperature overnight, then heated at 50° C. for 3 hr, concentrated, and purified by reverse phase HPLC to give a white glass (33 mg, 56% yield). $^1$H NMR (400 MHz, CDCl$_3$) δ 8.93 (s, 1 H) 7.21-7.31 (m, 1 H) 7.00 (s, 1 H) 6.84 (dd, J=7.20, 1.64 Hz, 2 H) 5.01 (s, 1 H) 4.55-4.63 (m, 1 H) 3.75 (s, 3 H) 3.53-3.64 (m, 2 H) 3.44 (s, 3 H) 3.22 (dd, J=16.42, 9.60 Hz, 1 H) 2.92 (dd, J=16.29, 7.45 Hz, 1 H) 1.32 (dd, J=6.06, 1.26 Hz, 6 H); LCMS for $C_{18}H_{23}N_3O_4$ m/z 346.20 (M+H+).

Preparation of Intermediate 216a

Toluene-4-sulfonic acid 4-isopropoxy-6-(1-methyl-1H-pyrazol-3-ylcarbamoyl)-2,3-dihydro-benzofuran-2-ylmethyl ester

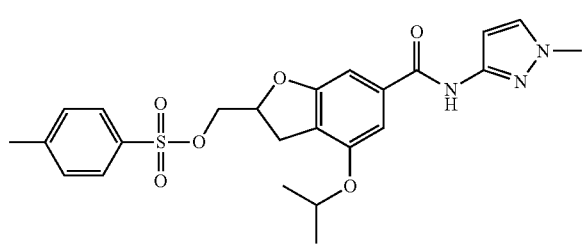

To a solution of 2-hydroxymethyl-4-isopropoxy-2,3-dihydro-benzofuran-6-carboxylic acid (1-methyl-1H-pyrazol-3-yl)-amide (215) (506 mg, 1.530 mmol) in pyridine (10 mL) was added DMAP (20 mg), followed by p-toluenesulfonyl chloride (533 mg, 2.79 mmol). The mixture was stirred at room temperature overnight. The reaction was quenched with water, extracted with 3×EtOAc, dried over Na$_2$SO$_4$, concentrated and purified by flash column chromatography with 35-60% EtOAc in hexanes to give a white solid (580 mg, 78% yield). $^1$H NMR (400 MHz, CDCl$_3$) δ 8.38 (s, 1 H) 7.78 (d, J=8.34 H) 7.35 (d, J=8.08 Hz, 2 H) 7.29 (d, J=2.27 Hz, 1 H) 6.96 (s, 1 H) 6.80 (d, J=2.27 Hz, 1 H) 6.69 (d, J=1.26 Hz, 1 H) 5.01 (dd, J=4.93, 1.89 Hz, 1 H) 4.56-4.66 (m, 1 H) 4.19 (dd, J=5.05, 2.27 Hz, 2 H) 3.81 (s, 3 H) 3.24 (dd, J=16.55, 9.73 Hz, 1 H) 2.95 (dd, J=16.42, 6.82 Hz, 1 H) 2.45 (s, 3 H) 1.30-1.35 (m, 6 H); LCMS for $C_{24}H_{27}N_3O_6S$ m/z 486.20 (M+H+).

Example 217

2-Ethoxymethyl-4-isopropoxy-2,3-dihydro-benzofuran-6-carboxylic acid (1-methyl-1H-pyrazol-3-yl)-amide

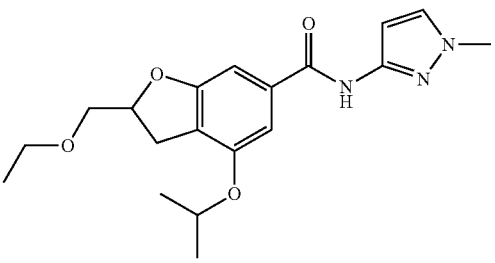

To a solution of toluene-4-sulfonic acid 4-isopropoxy-6-(1-methyl-1H-pyrazol-3-ylcarbamoyl)-2,3-dihydro-benzofuran-2-ylmethyl ester (216a) (84 mg, 0.17 mmol) in anhydrous EtOH (2 mL) was added NaOEt (1.5 mL, 21% wt). The mixture was heated at 50° C. for 4 hr, then quenched with H$_2$O and extracted with 3×EtOAc. The organic layers were washed with 2×H$_2$O, dried over Na$_2$SO$_4$, and concentrated. The residue was purified by reverse phase HPLC to give a white glass (22 mg, 36% yield). $^1$H NMR (400 MHz, CDCl$_3$) δ 8.99 (s, 1 H) 7.20-7.34 (m, 1 H) 7.02 (s, 1 H) 6.86 (dd, J=13.26, 1.64 Hz, 2 H) 4.92-5.09 (m, 1 H) 4.57-4.69 (m, 1 H) 3.78 (s, 3 H) 3.63-3.72 (m, 1 H) 3.54-3.62 (m, 3 H) 3.22 (dd, J=16.42, 9.60 Hz, 1 H) 2.92 (dd, J=16.29, 7.45 Hz, 1 H) 1.34 (dd, J=5.81, 1.77 Hz, 6 H) 1.23 (t, J=7.07 Hz, 3 H); LCMS for $C_{19}H_{25}N_3O_4$ m/z 360.20 (M+H+).

Example 218

2-Dimethylaminomethyl-4-isopropoxy-2,3-dihydro-benzofuran-6-carboxylic acid (1-methyl-1H-pyrazol-3-yl)-amide

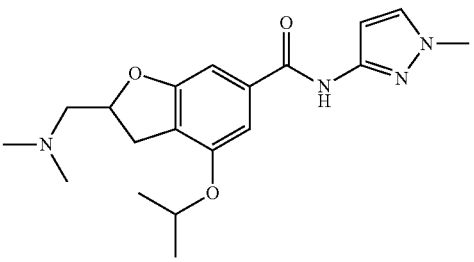

To a solution of toluene-4-sulfonic acid 4-isopropoxy-6-(1-methyl-1H-pyrazol-3-ylcarbamoyl)-2,3-dihydro-benzofuran-2-ylmethyl ester (216a) (84 mg, 0.17 mmol) in THF (2 mL) was added dimethyl amine hydrochloride (190 mg) and triethylamine (0.4 mL). The mixture was heated at 50° C. for 2 days, then concentrated, and purified by reverse phase HPLC to give a white solid (6 mg, 10% yield). $^1$H NMR (400 MHz, CDCl$_3$) δ 8.94 (s, 1 H) 7.25-7.32 (m, 1 H) 7.04 (s, 1 H)

6.90 (d, J=1.01 Hz, 1 H) 6.84 (d, J=2.27 Hz, 1 H) 5.03-5.14 (m, 1 H) 4.61-4.71 (m, 1 H) 3.81 (s, 3 H) 3.29 (dd, J=16.42, 9.35 Hz, 1 H) 2.75-2.92 (m, 2 H) 2.60-2.70 (m, 1 H) 2.47 (s, 6 H) 1.34 (d, J=6.06 Hz, 6 H); LCMS for $C_{19}H_{26}N_4O_3$ m/z 359.20 (M+H$^+$).

Example 219

2-Cyclopropylaminomethyl-4-isopropoxy-2,3-dihydro-benzofuran-6-carboxylic acid (1-methyl-1H-pyrazol-3-yl)-amide

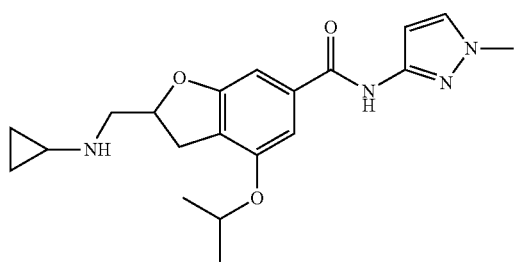

To a solution of toluene-4-sulfonic acid 4-isopropoxy-6-(1-methyl-1H-pyrazol-3-ylcarbamoyl)-2,3-dihydro-benzofuran-2-ylmethyl ester (216a) (84 mg, 0.17 mmol) in THF (2 mL) was added aminopropane (0.5 mL). The mixture was heated at 50° C. for 2 days, then concentrated, and purified by reverse phase HPLC to give a white solid (10 mg, 16% yield). $^1$H NMR (400 MHz, CDCl$_3$) δ 8.71 (s, 1 H) 7.26-7.34 (m, 1 H) 7.01 (s, 1 H) 6.80-6.87 (m, 1 H) 4.98-5.07 (m, 1 H) 4.59-4.69 (m, 1 H) 3.81 (s, 3 H) 3.23 (dd, J=16.42, 9.35 Hz, 1 H) 2.93-3.05 (m, 2 H) 2.86 (dd, J=16.42, 7.07 Hz, 1 H) 2.20-2.27 (m, 1 H) 1.34 (dd, J=5.94, 1.14 Hz, 6 H) 0.36-0.54 (m, 4 H); LCMS for $C_{20}H_{26}N_4O_3$ m/z 371.20 (M+H$^+$).

Example 220

2-Benzyl-4-isopropoxy-2,3-dihydro-benzofuran-6-carboxylic acid pyridin-2-ylamide

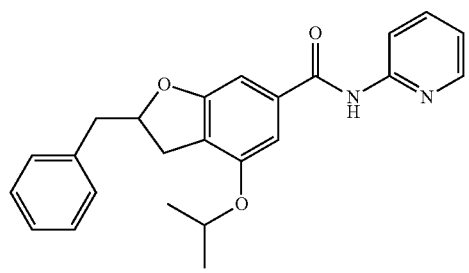

A mixture of 2-benzyl-4-isopropoxy-2,3-dihydro-benzofuran-6-carboxylic acid (220j) (0.5 g, 1.9 mmol), DIPEA (0.37 g, 2.85 mmol) and HATU (0.74 g, 1.94 mmol) in DMF (15 mL) was stirred at room temperature for 1 hr, and then pyridin-2-amine (0.18 g, 1.94 mmol) was added in one portion. The mixture was stirred at room temperature overnight. TLC (EtOAc/petroleum ether=1/2) indicated that the reaction was complete. The mixture was concentrated. The residue was purified by prep. HPLC to give the title compound (73 mg, 21% yield, TFA salt) as a white solid. $^1$H NMR (400 MHz, CDCl$_3$): δ11.71 (br, 1H), 8.76 (d, 1H), 8.27 (d, 1H), 8.14 (t, 1H), 7.17~7.46 (m, 9H), 4.96 (d, 1H), 4.78 (t, 1H), 2.82 (m, 1H), 2.67 (m, 1H), 2.19 (m, 1H), 1.96 (m, 1H), 1.32 (d, 6H).

Preparation of Intermediate 220a 3,5-Bis-methoxymethoxy-benzoic acid methyl ester

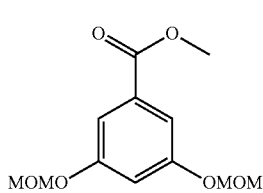

To a suspension of methyl 3,5-dihydroxybenzoate (250 g, 1.5 mol) and K$_2$CO$_3$ (500 g, 3.6 mol) in MeCN (2 L) was added drop wise MOMCl (270 g, 3.35 mol) at 0° C. The mixture was stirred at room temperature for 1.5 hr. TLC (EtOAc/petroleum ether=1/2) showed that no starting material was present. The reaction mixture was filtered and the filtrate was concentrated to give a brown oil. The oil was suspended in CH$_2$Cl$_2$. The resulting solid was filtered off. The filtrate was concentrated again to give the title compound (200 g, 57%) as a brown oil. $^1$H NMR (400 MHz, CDCl$_3$): δ 7.36 (d, 2H), 6.91 (t, 1H), 5.19 (s, 4H), 3.90 (s, 3H), 3.47 (s, 6H).

Preparation of Intermediate 220b (3,5-Bis-methoxymethoxy-phenyl)-methanol

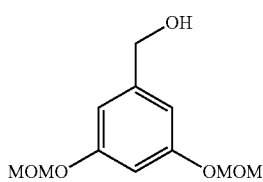

To a solution of 3,5-bis-methoxymethoxy-benzoic acid methyl ester (220a) (350 g, 1.37 mol) in THF (1.8 L) was added portion wise LiAlH$_4$ (62 g, 1.64 mol) at 0° C. The mixture was stirred at 0° C. for another 1 hr. TLC (EtOAc/petroleum ether=1/2) showed that the reaction was complete. The reaction was quenched with 2 N aqueous NaOH. The mixture was filtered through Celite. The filtrate was dried over Na$_2$SO$_4$ and concentrated to give the title compound (290 g, 76%) as a brown oil. $^1$H NMR (400 MHz, CDCl$_3$): δ 6.70 (d, 2H), 6.64 (d, 1H), 5.22 (s, 4H), 4.61 (s, 2H), 3.46 (s, 6H).

Preparation of Intermediate 220c (3,5-Bis-methoxymethoxy-benzyloxy)-tert-butyl-dimethyl-silane

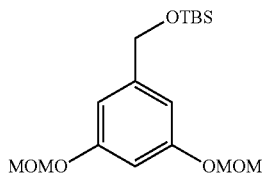

To a solution of (3,5-bis-methoxymethoxy-phenyl)-methanol (220b) (290 g, 1.27 mol) and imidazole (129 g, 1.9 mol) in CH$_2$Cl$_2$ (1.5 L) was added TBSCl (286 g, 1.9 mol) at 5° C. in several portion was stirred at room temperature overnight. TLC (EtOAc/petroleum ether=1/2) showed that the reaction was complete. The mixture was filtered and the filtrate was washed with water, dried over Na$_2$SO$_4$ and concentrated under high vacuum to give the title compound (320 g, 97%) as a brown oil. $^1$H NMR (400 MHz, CDCl$_3$): δ 6.68 (d, 2H), 6.57(t, 1H), 5.14 (s, 4H), 4.66 (s, 2H), 3.48 (s, 6H), 0.94 (s, 9H), 0.07 (s, 6H).

Preparation of Intermediate 220d

[3,5-Bis-methoxymethoxy-44(E)-3-phenyl-allyl)-benzyloxy]tert-butyl-dimethyl-silane

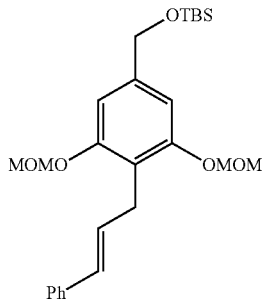

To a suspension of NaH (60%, 18 g, 0.45 mol) in THF (2 L) were added (3,5-bis-methoxymethoxy-benzyloxy)-tert-butyl-dimethyl-silane (220c) (100 g, 0.3 mol) and TMEDA (81.6 g, 0.6 mol) in one portion. The mixture was stirred at 0° C. for 1 hr. n-BuLi (2.5 M in hexane, 180 mL, 0.45 mol) was added drop wise to the mixture at −20° C. and the solution was stirred for 1 hr. CuI (114 g, 0.6mol) was added in one portion and the reaction was stirred at −20° C. for another 1 hr. Then the mixture was added drop wise cinamy bromide (65 g, 0.3 mol) at −20° C. After stirring for another 30 min, TLC (EtOAc/petroleum ether=1/10) showed that the reaction was complete. The reaction mixture was quenched with H$_2$O (500 mL). The organic layer was separated and the aqueous layer was extracted with EtOAc (2×500mL). The organic layers were combined, washed with brine (1 L), dried over Na$_2$SO$_4$ and concentrated to give a dark oil. The crude oil was purified by column chromatography (EtOAc/petroleum ether=1/10) to give the title compound (55 g, 34%) as a yellow liquid. $^1$H NMR (400 MHz, CDCl$_3$): δ 7.16~7.41 (m, 5H), 6.82 (s, 2H), 6.47 (m, 2H), 5.22(s, 4H), 4.71 (s, 2H), 3.62 (d, 2H), 3.45 (s, 6H), 0.94 (s, 9H), 0.12 (s, 6H).

Preparation of Intermediate 220e

[3,5-Bis-methoxymethoxy-4-((E)-3-phenyl-allyl)-phenyl]-methanol

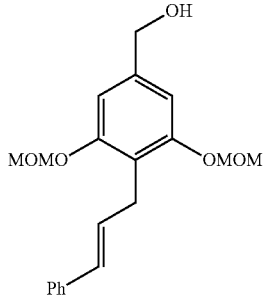

To a solution of [3,5-bis-methoxymethoxy-4-((E)-3-phenyl-allyl)-benzyloxy]-tert-butyl-dimethyl-silane (220d) (55 g, 0.12 mol) in THF (250 mL) was added TBAF (47.2 g, 0.18 mol) in one portion. The mixture was stirred at room temperature for 0.5 hr. TLC (EtOAc/petroleum ether=1/10) showed that the reaction was complete. The reaction mixture was washed with brine (50 mL) and the aqueous layer was extracted with EtOAc (2×100 mL). The combined organic layers were dried over Na$_2$SO$_4$ and concentrated in high vacuum to give the title compound (45 g, 92% yield) as a yellow oil. $^1$H NMR (400 MHz, CDCl$_3$): δ 7.16~7.41 (m, 5H), 6.82 (s, 2H), 6.47 (m, 2H), 5.22(s, 4H), 4.71 (s, 2H), 3.62 (d, 2H), 3.45 (s, 6H).

Preparation of Intermediate 220f 3,5-Bis-methoxymethoxy-4-((E)-3-phenyl-allyl)-benzaldehyde

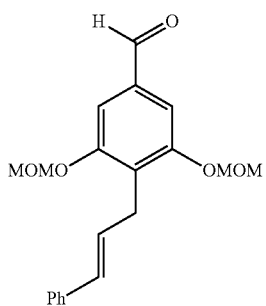

To a solution of pyridine (62 g, 0.78 mol) in CH$_2$Cl$_2$ (500 mL) were added CrO$_3$ (39 g, 0.39 mol) and Silica gel (40 g) in several portions at 0° C. After stirring for 10 min, [3,5-bis-methoxymethoxy-4-((E)-3-phenyl-allyl)-phenyl]-methanol (220e) (45 g, 0.13 mol) was added in one portion. The mixture was stirred at room temperature overnight. TLC (EtOAc/petroleum ether=1/2) indicated that the reaction was complete. The reaction mixture was filtered and the filter cake was washed with Et$_2$O. The combined filtrates were concentrated. The residue was suspended in Et$_2$O and filtered again. The filtrate was concentrated under vacuum to give the crude title compound (45 g, 100% yield) as a yellow oil, which was used directly in the next step without further purification. $^1$H NMR (400 MHz, CDCl$_3$): δ 9.89 (s, 1H), 7.16-7.41 (m, 5H), 6.25~6.44 (m, 2H), 5.36 (s, 4H), 3.66 (d, 2H), 3.47 (s, 6H).

Preparation of Intermediate 220g 3,5-Bis-methoxymethoxy-4-((E)-3-phenyl-allyl)-benzoic acid

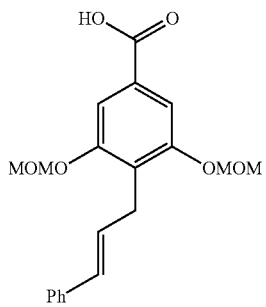

To a solution of 3,5-bis-methoxymethoxy-4-((E)-3-phenyl-allyl)-benzaldehyde (220f) (42 g, 0.12 mol) in MeOH/H$_2$O (500 mL) was added AgNO$_3$ (21 g, 0.12 mol), followed by NaOH (15 g, 0.36 mol) in one portion at room temperature. The mixture was stirred at room temperature overnight and then filtered. The filtrate was concentrated under vacuum to remove MeOH. The residue was extracted with Et$_2$O (2×100 mL) to remove impurities. The aqueous layer was acidified with conc. HCl to pH 4. The resulting white solid was filtered and dried under vacuum to give the title compound (31 g, 62% yield) as white solid.

Preparation of Intermediate 220h 3,5-Dihydroxy-4-((E)-3-phenyl-allyl)-benzoic acid methyl ester

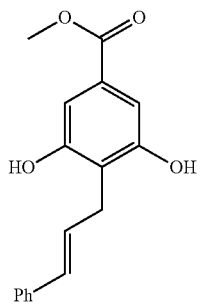

To a solution of 3,5-bis-methoxymethoxy-4-((E)-3-phenyl-allyl)-benzoic acid (220g) (18 g, 0.05 mol) in MeOH (300 mL) was added catalytic amount of conc. H$_2$SO$_4$ (3 mL) in one portion. The mixture was refluxed overnight. The solution was concentrated. The residue was dissolved in CH$_2$Cl$_2$ (75 mL) and washed with sat. NaHCO$_3$ (25 mL). The organic layers were dried and concentrated to give a brown solid (12 g, 73% yield). $^1$H NMR (400 MHz, CDCl$_3$): δ 9.63 (s, 2H), 7.11~7.34 (m, 5H), 6.93 (s, 2H), 6.32 (s, 2H), 3.77 (s, 3H), 3.42 (s, 2H).

Preparation of Intermediate 220i

2-Benzyl-4-hydroxy-2,3-dihydro-benzofuran-6-carboxylic acid methyl ester

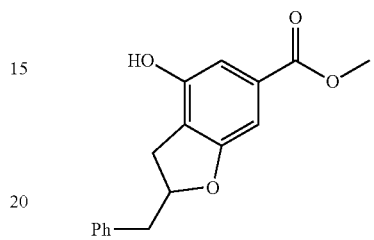

A solution of 3,5-dihydroxy-4-((E)-3-phenyl-allyl)-benzoic acid methyl ester (220h) (12 g, 0.032 mol) in HCl (g)/MeOH (4 N, 150 mL) was stirred at room temperature for 2 days. The reaction solution was concentrated to give a brown solid. The crude solid was re-crystallized from EtOAc to give the product (7 g) as a yellow solid. The mother liquid was concentrated to give a brown solid (5 g). The total yield is 98%. $^1$H NMR (400 MHz, CDCl$_3$): δ 9.90 (br, 1H), 7.27~7.46 (m, 5H), 7.00 (s, 1H), 6.87 (s, 1H), 5.07 (d, 1H), 3.78 (s, 3H), 2.65 (d, 2H), 2.16 (m, 1H), 1.92 (m, 1H).

Preparation of Intermediate 220j

2-Benzyl-4-isopropoxy-2,3-dihydro-benzofuran-6-carboxylic acid

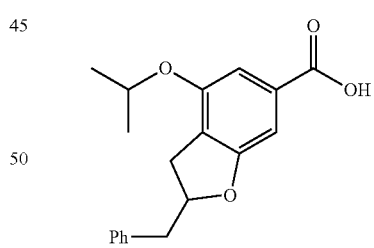

To a mixture of 2-benzyl-4-hydroxy-2,3-dihydro-benzofuran-6-carboxylic acid methyl ester (220i) (5 g, 0.018 mol) and NaH (60%, 1.4 g, 0.035 mol) in DMF (15 mL) was added isopropyl bromide (3.3 g, 0.027 mol) in one portion. The mixture was stirred at room temperature overnight. TLC (EtOAc/petroleum ether=1/2) indicated that the reaction was complete. The mixture was quenched with H$_2$O (50 mL). The aqueous phase was extracted with EtOAc. The combined organic phases were dried over Na$_2$SO$_4$ and concentrated to give brown solid (6 g). The crude solid was purified by column chromatography (EtOAc/petroleum ether=1/4) to give the title compound (2 g, 32% yield) as white solid.

Example 221: 2-Benzyl-4-isopropoxy-2,3-dihydro-benzofuran-6-carboxylic acid (1-methyl-1H-pyrazol-3-yl)-amide

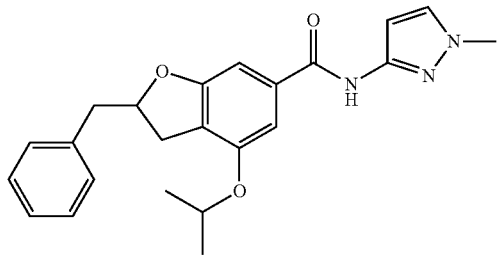

To a solution of 2-benzyl-4-isopropoxy-2,3-dihydro-benzofuran-6-carboxylic acid (220j) (0.5 g, 1.6 mmol) in $CH_2Cl_2$ (15 mL) were added 1-methyl-1H-pyrazol-3-ylamine (0.16 g, 1.7 mmol), EDCI (0.46 g, 2.4 mmol), HOBt (0.32 g, 2.4 mmol) and N-methylmorphiline (0.81 g, 8 mmol) sequentially. The mixture was stirred at room temperature overnight. The reaction solution was washed with water (5 mL), aq. HCl (1 N, 5 mL) and sat. $NaHCO_3$. The organic phase was dried over $Na_2SO_4$ and concentrated to give a yellow oil. The crude oil was purified by prep. HPLC to give the product as a white solid (98.6 mg, 16% yield, TFA salt). $^1$H NMR (400 MHz, $CDCl_3$): δ 10.71 (s, 1H), 7.58 (s, 1H), 7.30-7.48 (m, 5H), 7.01~7.19 (d, 2H), 6.57 (s, 1H), 5.08 (d, 1H), 4.74 (m, 1H), 3.74 (s, 3H), 2.66 (d, 2H), 2.17 (m, 1H), 1.96 (m, 1H), 1.28 (d, 6H).

Example 222: 4-Benzyloxy-2-difluoromethyl-2,3-dihydro-benzofuran-6-carboxylic acid (1-methyl-1H-pyrazol-3-yl)-amide

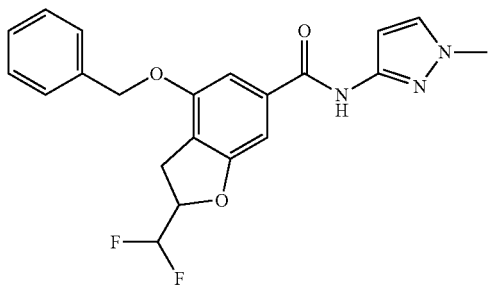

To a solution of 4-benzyloxy-2-formyl-2,3-dihydro-benzofuran-6-carboxylic acid (1-methyl-1H-pyrazol-3-yl)-amide (222b) (500 mg, 1.32 mmol) in $CH_2Cl_2$ (3 mL) was added a solution of DAST (340 mg, 2.11 mmol) in $CH_2Cl_2$ (1.5 mL), and rinsed with $CH_2Cl_2$ (2 mL). The mixture was stirred at room temperature for 30 min. The reaction was quenched with $H_2O$, extracted with 3×$CHCl_3$, dried over $Na_2SO_4$, concentrated and purified by reverse phase HPLC to give a white solid (200 mg, 38% yield). $^1$H NMR (400 MHz, $CDCl_3$) δ 8.75 (s., 1 H) 7.39-7.45 (m, 2 H) 7.37-7.41 (m, 1 H) 7.34-7.40 (m, 2 H) 7.30 (d, J=2.27 Hz, 1 H) 7.14 (d, J=1.01 Hz, 1 H) 6.92 (d, J=1.01 Hz, 1 H) 6.83 (d, J=2.27 Hz, 1 H) 5.65-6.09 (m, 1 H) 5.11 (s., 2 H) 4.87-5.07 (m, 1 H) 3.76 (s., 3 H) 3.27-3.42 (m, 2 H); LCMS for $C_{21}H_{19}F_2N_3O_3$ m/z 400.00 $(M+H)^+$.

Preparation of Intermediate 222a

4-Benzyloxy-2-hydroxymethyl-2,3-dihydro-benzofuran-6-carboxylic acid (1-methyl-1H-pyrazol-3-yl)-amide

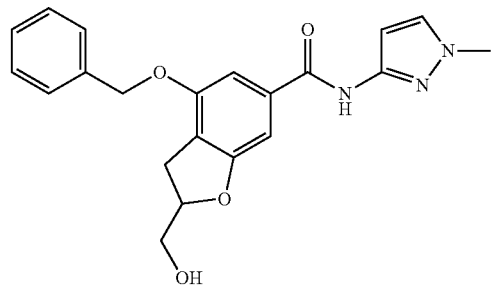

The title compound was prepared in a similar manner as described for Example 200, from 4-benzyloxy-2-hydroxymethyl-2,3-dihydro-benzofuran-6-carboxylic acid tert-butyl ester (204a) and 3-amino-1-methyl-pyrazole to give a white solid. $^1$H NMR (400 MHz, $CDCl_3$) δ 8.50 (s, 1 H) 7.33-7.45 (m, 5 H) 7.30 (d, J=2.27 Hz, 1 H) 7.09 (d, J=1.26 Hz, 1 H) 6.89 (d, J=1.01 Hz, 1 H) 6.82 (d, J=2.27 Hz, 1 H) 5.12 (s, 2 H) 4.95-5.03 (m, 1 H) 3.81 (s, 3 H) 3.73-3.79 (m, 1 H) 3.27 (dd, J=16.17, 9.60 Hz, 1H) 3.03 (dd, J=16.29, 7.20 Hz, 1 H) 2.13 (t, J=6.44 Hz, 1 H); LCMS for $C_{21}H_{21}N_3O_4$ m/z 380.00 $(M+H^+)$.

Preparation of Intermediate 222b

4-Benzyloxy-2-formyl-2,3-dihydro-benzofuran-6-carboxylic acid (1-methyl-1H-pyrazol-3-yl)-amide

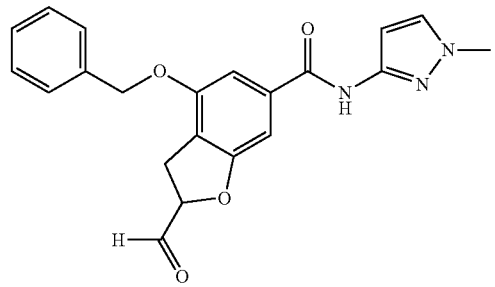

To a suspension of 4-benzyloxy-2-hydroxymethyl-2,3-dihydro-benzofuran-6-carboxylic acid (1-methyl-1H-pyrazol-3-yl)-amide (222a) (1.05 g, 2.77 mmol) in $CH_2Cl_2$ (25 mL) was added Dess-Martin periodinane (1.41 g, 3.32 mmol) at 0° C. The mixture was stirred at room temperature for 2 h. The reaction was quenched with saturated aqueous $NaHCO_3$, extracted with 3×EtOAc, dried over $Na_2SO_4$, concentrated, and purified by flash column chromatography eluting with 55-100% EtOAc in hexanes to give a yellow foam (850 mg).

Example 223

4-[4-(Azetidine-1-carbonyl)-3,5-difluoro-phenoxy]-2-difluoromethyl-2,3-dihydro-benzofuran-6-carboxylic acid (1-methyl-1H-pyrazol-3-yl)-amide

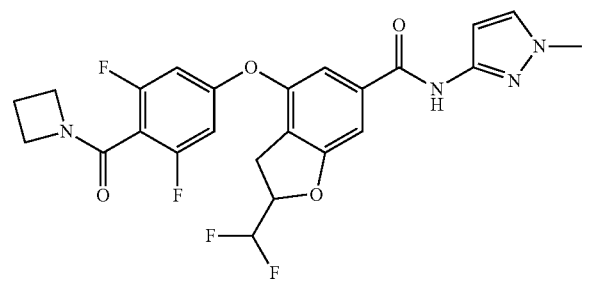

The title compound was prepared in a similar manner as described for Example 33, from azetidin-1-yl)2,4,6-trifluorophenyl)methanone (57.4 mg, 0.267 mmol) and 2-difluoromethyl-4-hydroxy-2,3-dihydro-benzofuran-6-carboxylic acid (1-methyl-1H-pyrazol-3-yl)-amide (223a) (75 mg, 0.24 mmol) to give a white solid (20 mg, 16% yield). $^1$H NMR (400 MHz, CDCl$_3$) δ 8.64 (s, 1 H) 7.25-7.35 (m, 1 H) 7.12-7.21 (m, 2H) 6.71-6.82 (m, 1 H) 6.54 (d, J=8.34 Hz, 2 H) 5.73-6.12 (m, 1 H) 5.02 (d, J=8.08 Hz, 1 H) 4.23 (t, J=7.83 Hz, 2 H) 4.00-4.10 (m, 2 H) 3.78 (s, 3 H) 3.17-3.29 (m, 2 H) 2.36 (t, J=7.71 Hz, 2 H); LCMS for C$_{24}$H$_{20}$F$_4$N$_4$O$_4$ m/z 505.00 and 506.00 (M+H)$^+$; Anal. Calcd. for C$_{24}$H$_{20}$F$_4$N$_4$O$_4$: C, 53.77; H, 4.01; N, 9.95; Found: C, 53.79; H, 3.91; N, 9.87.

Preparation of Intermediate 223a

2-Difluoromethyl-4-hydroxy-2,3-dihydro-benzofuran-6-carboxylic acid (1-methyl-1H-pyrazol-3-yl)-amide

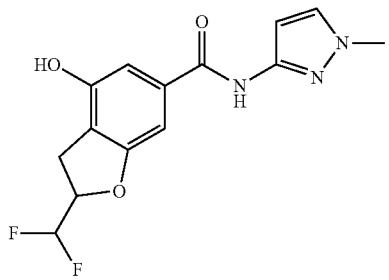

10% Pd on Carbon (20 mg) was added to a solution of 4-benzyloxy-2-difluoromethyl-2,3-dihydro-benzofuran-6-carboxylic acid (1-methyl-1H-pyrazol-3-yl)-amide (222) (186 mg, 0.466 mmol) in EtOAc (5 mL). The mixture was stirred at room temperature with a H$_2$ balloon overnight, then filtered through Celite, washed with EtOAc, and concentrated to give yellow solid (143 mg, 99% yield). $^1$H NMR (400 MHz, CDCl$_3$) δ 9.44 (br. s., 1 H) 7.27 (br. s., 1 H) 7.07 (br. s., 1 H) 6.90 (br. s., 1 H) 6.79 (br. s., 1 H) 5.67-6.04 (m, 1 H) 4.94 (br. s., 1 H) 3.73 (br. s., 3 H) 3.14-3.37 (m, 2 H); LCMS for C$_{14}$H$_{13}$F$_2$N$_3$O$_3$ m/z 310.00 (M+H)$^+$.

Example 224

2-Fluoromethyl-4-(4-methanesulfonyl-phenoxy)-2,3-dihydro-benzofuran-6-carboxylic acid (1-methyl-1H-pyrazol-3-yl)-amide

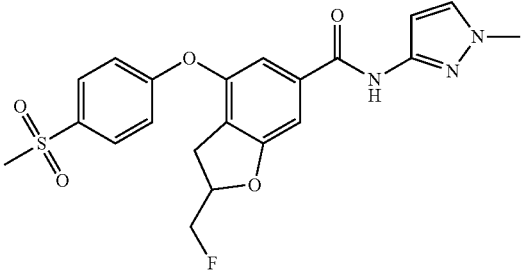

A solution of 2,4,6-collidine (0.0311 mL, 0.235 mmol) and 2-hydroxymethyl-4-(4-methanesulfonyl-phenoxy)-2,3-dihydro-benzofuran-6-carboxylic acid (1-methyl-1H-pyrazol-3-yl)-amide (200) (50 mg, 0.11 mmol) in CH$_2$Cl$_2$ (3 mL) was cooled to −15° C. DAST (0.0307 mL, 0.235 mmol) was added drop wise. The mixture was stirred at −15° C. to room temperature overnight, then quenched with MeOH at 0° C., concentrated, and purified by column chromatography eluting with 25-75% EtOAc in hexanes to give a white solid (9 mg, 18% yield). $^1$H NMR (400 MHz, CDCl$_3$) δ 8.48 (s, 1 H) 7.78-8.03 (m, 2 H) 7.20-7.34 (m, 2 H) 7.02-7.20 (m, 3 H) 6.77 (d, J=2.27 Hz, 1 H) 5.01-5.19 (m, 1 H) 4.42-4.78 (m, 2 H) 3.79 (s, 3H) 3.25 (dd, J=16.55, 9.73 Hz, 1 H) 3.08 (s, 3 H) 2.99-3.06 (m, 1 H); LCMS for C$_{21}$H$_{20}$FN$_3$O$_5$S m/z 446.00 (M+H$^+$).

Example 225

2-Difluoromethyl-4-(4-methanesulfonyl-phenoxy)-2,3-dihydro-benzofuran-6-carboxylic acid (1-methyl-1H-pyrazol-3-yl)-amide

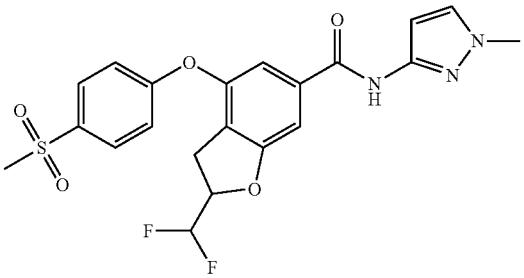

The title compound was prepared in a similar manner as described for Example 33, from 4-fluorophenyl methyl sulfone (28.2 mg, 0.162 mmol) and 2-difluoromethyl-4-hydroxy-2,3-dihydro-benzofuran-6-carboxylic acid (1-methyl-1H-pyrazol-3-yl)-amide (223a) (50 mg, 0.160 mmol) to give a white solid (18 mg, 24% yield). $^1$H NMR (400 MHz, CDCl$_3$) δ 8.57 (s, 1 H) 7.85-8.02 (m, 2 H) 7.22-7.38 (m, 2 H) 7.02-7.21 (m, 3 H) 6.77 (d, J=2.02 Hz, 1 H) 5.94 (t, 1 H) 5.02

(br. s., 1 H) 3.78 (s, 3 H) 3.55-3.65 (m, 1 H) 3.23-3.33 (m, 1 H) 3.09 (s, 3 H); LCMS for $C_{21}H_{19}F_2N_3O_5S$ m/z 464.00 $(M+H)^+$.

Example 226

4-[4-(Azetidine-1-carbonyl)-phenoxy]-2-difluoromethyl-2,3-dihydro-benzofuran-6-carboxylic acid (1-methyl-1H-pyrazol-3-yl)-amide

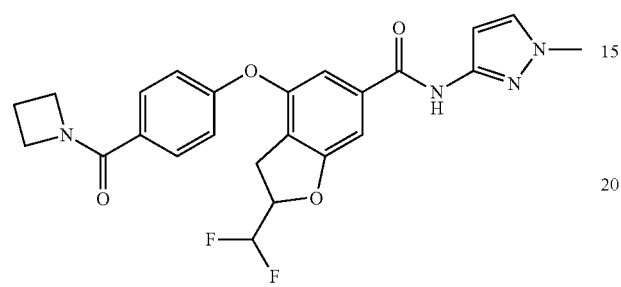

The title compound was prepared in a similar manner as described for Example 33, from azetidin-1-yl(4-fluorophenyl)methanone (57.4 mg, 0.32 mmol) and 2-difluoromethyl-4-hydroxy-2,3-dihydro-benzofuran-6-carboxylic acid (1-methyl-1H-pyrazol-3-yl)-amide (223a) (99 mg, 0.32 mmol) to give a white solid (12 mg, 8% yield). $^1$H NMR (400 MHz, CDCl$_3$) δ 8.86 (s, 1 H) 7.55-7.71 (m, 2 H) 7.22-7.31 (m, 1 H) 7.13-7.19 (m, 1 H) 7.06-7.12 (m, 1 H) 6.96-7.03 (m, 2 H) 6.79 (d, J=2.02 Hz, 1 H) 5.75-6.08 (m, 1 H) 4.93-5.19 (m, 1 H) 4.35 (br. s., 2 H) 4.24 (br. s., 2 H) 3.79 (s, 3 H) 3.57-3.63 (m, 1 H) 3.14-3.31 (m, 2 H) 2.30-2.42 (m, 1 H.); LCMS for $C_{24}H_{22}F_2N_4O_4$ m/z 469.00 $(M+H)^+$.

Example 227

2-Hydroxymethyl-4-(4-methanesulfonyl-phenoxy)-2-methyl-2,3-dihydro-benzofuran-6-carboxylic acid (1-methyl-1H-pyrazol-3-yl)-amide

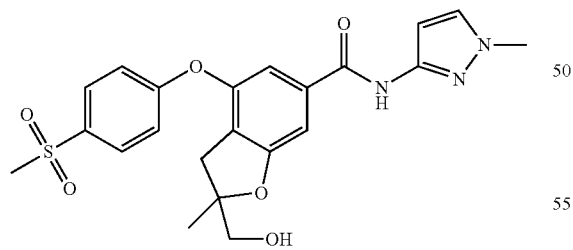

The title compound was prepared in a similar manner as described for Example 200, from 2-hydroxymethyl-4-(4-methanesulfonyl-phenoxy)-2-methyl-2,3-dihydro-benzofuran-6-carboxylic acid tert-butyl ester (227d). $^1$H NMR (400 MHz, CDCl$_3$) δ 8.50 (s, 1 H) 7.91 (d, J=8.84 Hz, 2 H) 7.28 (d, J=2.02 Hz, 1 H) 7.11 (s, 1 H) 7.08 (d, J=2.53 Hz, 2 H) 7.05 (s, 1 H) 6.77 (d, J=1.77 Hz, 1H) 3.79 (s, 3 H) 3.75 (d, J=11.87 Hz, 1 H) 3.61 (d, J=11.87 Hz, 1 H) 3.20 (d, J=16.42 Hz, 1 H) 3.08 (s, 3H) 2.81 (d, J=16.42 Hz, 1H) 1.45 (s, 3 H); LCMS for $C_{22}H_{23}N_3O_6S$ m/z 458.00 $(M+H)^+$; Anal. Calcd. for $C_{22}H_{23}N_3O_6S.0.48$ TFA: C, 53.83; H, 4.62; N, 8.20; Found: C, 53.62; H, 4.85; N, 8.36.

Preparation of Intermediate 227a 3,5-Bis-benzyloxy-4-(2-methyl-allyl)-benzoic acid tert-butyl ester

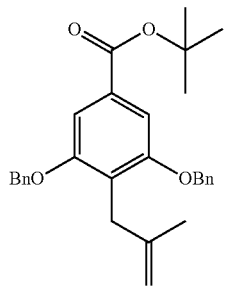

To a suspension of Mg pieces (7.9 g, 0.23 mol) in THF (250 mL) was added a catalytic amount of I$_2$, followed by addition of i-PrMgBr (15 mL, 0.16 mol) drop wise. The mixture was heated slowly until refluxed violently. After stirring for 2 hr, the resulting mixture was added to THF (200 mL) and cooled to 0° C. n-BuLi (128 mL, 2.5 M in hexane, 0.32 mol) was added drop wise at 0° C. The mixture was cooled to −78° C. and 3,5-bis-benzyloxy-4-bromo-benzoic acid tert-butyl ester (200c) (50 g, 0.107 mol) was added drop wise. After the mixture was stirred for 1 hr, CuCN (2.85 g, 0.032 mol), LiCl (2.7 g, 0.064 mol), and 3-bromo-2-methyl-propene (43 mL, 0.43 mol) were added sequentially. After stirring for another 30 min at −78° C., TLC (EtOAc/petroleum ether=1/10) showed the reaction was complete. The mixture was quenched with saturated aqueous NH$_4$Cl (150 mL). The aqueous layer was extracted with EtOAc (2×100 mL). The organic layer was washed with brine, dried over Na$_2$SO$_4$ and concentrated to give the title compound as a yellow oil (40 g, 84.4% yield).

Preparation of Intermediate 227b 3,5-Bis-benzyloxy-4-(2-methyl-oxiranylmethyl)-benzoic acid tert-butyl ester

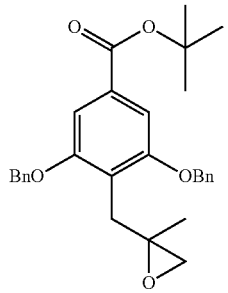

To a solution of 3,5-bis-benzyloxy-4-(2-methyl-allyl)-benzoic acid tert-butyl ester (227a) (80 g, 0.18 mmol) in CH$_2$Cl$_2$ (500 mL) was added m-CPBA (62 g, 0.36 mol) portion-wise. The mixture was refluxed overnight. The solid was filtered and washed with CH$_2$Cl$_2$. The filtrate was washed with saturated aqueous Na$_2$S$_2$O$_4$ (250 mL) and brine (250 mL). The organic layer was separated, dried over Na$_2$SO$_4$ and concentrated to give a brown oil. The crude oil was quickly purified by column chromatography (EtOAc/petroleum ether=1/10) to give the title compound (40 g, 48.2% yield) as a white solid.

Preparation of Intermediate 227c

4-Hydroxy-2-hydroxymethyl-2-methyl-2,3-dihydro-benzofuran-6-carboxylic acid tert-butyl ester

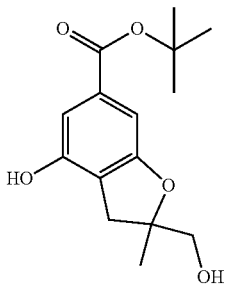

A mixture of 3,5-bis-benzyloxy-4-(2-methyl-oxiranylmethyl)-benzoic acid tert-butyl ester (227b) (158 g, 0.343 mol), 10% Pd/C (15 g), Et$_3$N (57.3 mL, 0.412 mol) and K$_2$Co$_3$ (56.94 g, 0.412 mol) in MeOH (1.5 L) was stirred under 760 mmHg of H$_2$ at room temperature overnight. TLC (EtOAc/petroleum ether=1/3) showed that the reaction was complete. The mixture was filtered through Celite. The filtrate was concentrated and the residue was purified by column chromatography (EtOAc/petroleum ether=1/3) to give a brown oil. The brown oil was further purified by prep. HPLC to give the title compound (18 g, 18.7% yield) as a brown oil. $^1$H NMR (400 MHz, CDCl$_3$): δ 6.98 (s, 1H), 6.82(s, 1H), 3.67 (d, 1 H), 3.56 (d, 1H), 2.80 (d, 1H), 1.48 (s, 9H), 1.35 (s, 3H).

Preparation of Intermediate 227d

2-Hydroxymethyl-4-(4-methanesulfonyl-phenoxy)-2-methyl-2,3-dihydro-benzofuran-6-carboxylic acid tert-butyl ester

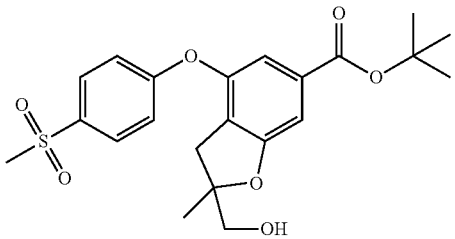

The title compound was prepared in a similar manner as described for Intermediate 1f, from 4-hydroxy-2-hydroxymethyl-2-methyl-2,3-dihydro-benzofuran-6-carboxylic acid tert-butyl ester (227c) and 4-fluorophenyl methylsulfone. $^1$H NMR (400 MHz, CDCl$_3$) δ 7.89-7.94 (m, 2 H) 7.26-7.27 (m, 1 H) 7.22 (d, J=1.26 Hz, 1 H) 7.02-7.11 (m, 2 H) 3.69-3.76 (m, 1 H) 3.60 (dd, J=11.87, 7.58 Hz, 1 H) 3.16 (d, J=16.42 Hz, 1 H) 3.07 (s, 3 H) 2.78 (d, J=16.67 Hz, 1 H) 1.86 (dd, J=7.58, 5.81 Hz, 1 H) 1.57 (s, 9 H) 1.44 (s, 3 H); LCMS for C$_{26}$H$_{26}$O$_7$S m/z 435.00 (M+H)$^+$.

Example 228

4-(4-Methanesulfonyl-phenoxy)-2-methoxymethyl-2-methyl-2,3-dihydro-benzofuran-6-carboxylic acid (1-methyl-1H-pyrazol-3-yl)-amide

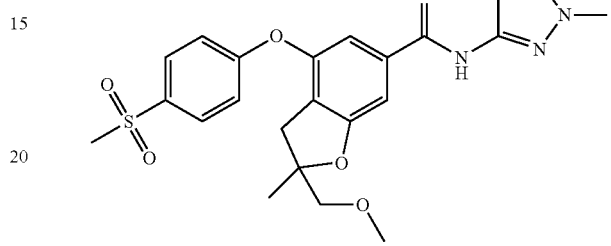

The title compound was prepared in a similar manner as described for Example 200, from 4-(4-methanesulfonyl-phenoxy)-2-methoxymethyl-2-methyl-2,3-dihydro-benzofuran-6-carboxylic acid tert-butyl ester (228a). $^1$H NMR (400 MHz, CDCl$_3$) δ 8.39 (s, 1 H) 7.89-7.94 (m, 2 H) 7.28 (d, J=2.27 Hz, 1 H) 7.08-7.13 (m, 3 H) 7.05 (d, J=1.26 Hz, 1 H) 6.77 (d, J=2.02 Hz, 1 H) 3.80 (s, 3 H) 3.42-3.52 (m, 2 H) 3.41 (s, 3 H) 3.15 (d, J=16.67 Hz, 1 H) 3.06-3.10 (m, 4 H) 1.47 (s, 3 H); LCMS for C$_{23}$H$_{25}$N$_3$O$_6$S m/z 472.00 (M+H)$^+$.

Preparation of Intermediate 228a 4-(4-Methanesulfonyl-phenoxy)-2-methoxymethyl-2-methyl-2,3-dihydro-benzofuran-6-carboxylic acid tert-butyl ester

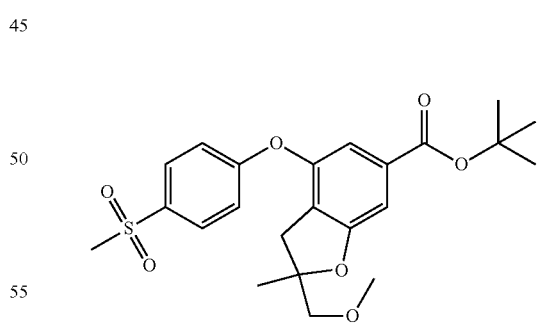

The title compound was prepared in a similar manner as described for Intermediate 201a, from 2-hydroxymethyl-4-(4-methanesulfonyl-phenoxy)-2-methyl-2,3-dihydro-benzofu ran-6-carboxylic acid tert-butyl ester (227d) and methyl iodide. $^1$H NMR (400 MHz, CDCl$_3$) δ 7.88-7.93 (m, J=9.47, 2.78, 2.40 Hz, 2 H) 7.28 (s, 1 H) 7.21 (d, J=1.26 Hz, 1 H) 7.04-7.10 (m, 2 H) 3.41-3.50 (m, 2 H) 3.40 (s, 3 H) 3.10 (d, J=16.67 Hz, 1 H) 3.07 (s, 3 H) 2.75 (d, J=16.67 Hz, 1 H) 1.56 (s, 9 H) 1.46 (s, 3 H); LCMS for C$_{23}$H$_{28}$O$_7$S m/z 449.00 (M+H)$^+$.

Example 229

4-(4-Dimethylcarbamoyl-3-fluoro-phenoxy)-2-hydroxymethyl-2-methyl-2,3-dihydro-benzofuran-6-carboxylic acid (1-methyl-1H-pyrazol-3-yl)-amide

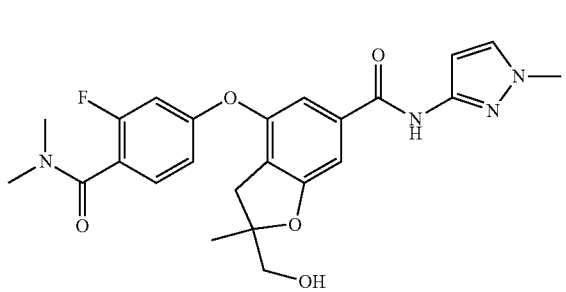

The title compound was prepared in a similar manner as described for Example 200, from 4-(4-dimethylcarbamoyl-3-fluoro-phenoxy)-2-hydroxymethyl-2-methyl-2,3-dihydro-benzofuran-6-carboxylic acid tert-butyl ester (229a). $^1$H NMR (400 MHz, CDCl$_3$) δ 8.38 (s, 1 H) 7.38 (t, J=8.08 Hz, 1 H) 7.28 (d, J=2.02 Hz, 1 H) 7.07 (d, J=7.83 Hz, 2 H) 6.80 (dd, J=8.59, 2.27 Hz, 1 H) 6.78 (d, J=2.02 Hz, 1 H) 6.70 (dd, J=10.61, 2.27 Hz, 1 H) 3.81 (s, 3 H) 3.69-3.76 (m, 1 H) 3.58-3.65 (m, 1 H) 3.19 (d, J=16.42 Hz, 1 H) 3.13 (s, 3 H) 2.93-3.01 (m, 4 H) 1.46 (s, 3 H); LCMS for C$_{24}$H$_{25}$FN$_4$O$_5$ m/z 469.00 (M+H)$^+$.

Preparation of Intermediate 229a 4-(4-Dimethylcarbamoyl-3-fluoro-phenoxy)-2-hydroxymethyl-2-methyl-2,3-dihydro-benzofuran-6-carboxylic acid tert-butyl ester

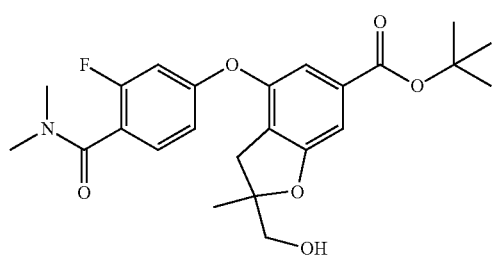

The title compound was prepared in a similar manner as described for Intermediate 1f, from 4-hydroxy-2-hydroxymethyl-2-methyl-2,3-dihydro-benzofuran-6-carboxylic acid tert-butyl ester (227c) and 2,4-difluoro-N,N-dimethyl-benzamide. $^1$H NMR (400 MHz, CDCl$_3$) δ 7.36 (t, J=8.08 Hz, 1 H) 7.24 (s, 1 H) 7.20 (d, J=1.26 Hz, 1 H) 6.78 (dd, J=8.59, 2.27 Hz, 1 H) 6.67 (dd, J=10.61, 2.27 Hz, 1 H) 3.67-3.73 (m, 1 H) 3.56-3.62 (m, 1 H) 3.08-3.18 (m, 4 H) 2.97 (d, J=1.52 Hz, 3 H) 2.77 (d, J=16.67 Hz, 1 H) 1.56 (s, 9 H) 1.43 (s, 3 H); LCMS for C$_{24}$H$_{28}$FNO$_6$ m/z 446.00 (M+H)$^+$.

Example 230

2-Hydroxymethyl-4-(4-methanesulfonyl-phenoxy)-2-methyl-2,3-dihydro-benzofuran-6-carboxylic acid (5-methyl-pyridin-2-yl)-amide

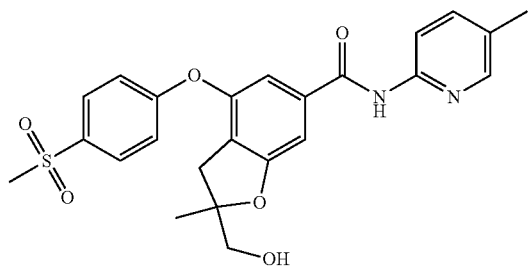

The title compound was prepared in a similar manner as described for Example 200, from 2-hydroxymethyl-4-(4-methanesulfonyl-phenoxy)-2-methyl-2,3-dihydro-benzofuran-6-carboxylic acid tert-butyl ester (227d) and 5-methyl-pyridin-2-ylamine. $^1$H NMR (400 MHz, CDCl$_3$) δ 8.60 (d, J=8.84 Hz, 1 H) 8.05 (s, 1 H) 7.92 (d, J=8.84 Hz, 3 H) 7.28 (s, 1 H) 7.24 (s, 1 H) 7.15 (d, J=8.84 Hz, 2 H) 3.76 (d, J=11.87 Hz, 1 H) 3.62 (d, J=11.87 Hz, 1 H) 3.22 (d, J=16.67 Hz, 1 H) 3.07 (s, 3 H) 2.83 (d, J=16.67 Hz, 1 H) 2.42 (s, 3 H) 1.47 (s, 3 H); LCMS for C$_{24}$H$_{24}$N$_2$O$_6$S m/z 469.00 (M+H)$^+$.

Example 231

4-(4-Methanesulfonyl-phenoxy)-2-methoxymethyl-2-methyl-2,3-dihydro-benzofuran-6-carboxylic acid (5-methyl-pyridin-2-yl)-amide

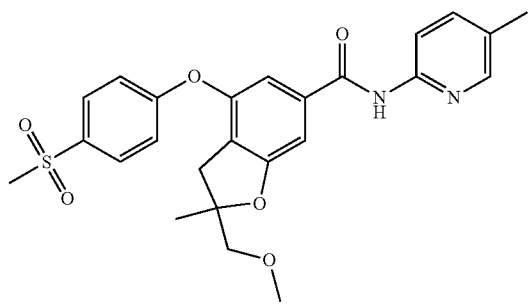

The title compound was prepared in a similar manner as described for Example 200, from 4-(4-methanesulfonyl-phenoxy)-2-methoxymethyl-2-methyl-2,3-dihydro-benzofuran-6-carboxylic acid tert-butyl ester (228a) and 5-methyl-pyridin-2-ylamine. $^1$H NMR (400 MHz, CDCl$_3$) δ 8.21 (d, J=8.59 Hz, 1 H) 8.09 (s, 1 H) 7.92 (ddd, J=9.22, 2.78, 2.40 Hz, 2 H) 7.65 (dd, J=8.59, 2.02 Hz, 1 H) 7.19 (s, 1 H) 7.13 (s, 2 H) 7.09-7.11 (m, 1 H) 3.43-3.53 (m, 2 H) 3.41 (s, 3 H) 3.16 (d, J=16.42 Hz, 1 H) 3.06-3.10 (m, 3 H) 2.80 (d, J=16.67 Hz, 1 H) 2.34 (s, 3 H) 1.48 (s, 3 H); LCMS for for C$_{25}$H$_{26}$N$_2$O$_6$S m/z 483.00 (M+H)+; Anal. Calcd. for C$_{25}$H$_{26}$N$_2$O$_6$S.0.37 TFA: C, 58.95; H, 5.18; N, 5.34; Found: C, 58.92; H, 5.07; N, 5.34.

Example 232

4-(3-Fluoro-4-methanesulfonyl-phenoxy)-2-hydroxymethyl-2-methyl-2,3-dihydro-benzofuran-6-carboxylic acid (1-methyl-1H-pyrazol-3-yl)-amide

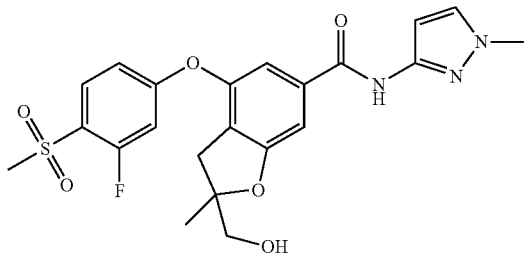

The title compound was prepared in a similar manner as described for Example 200, from 4-(3-fluoro-4-methanesulfonyl-phenoxy)-2-hydroxymethyl-2-methyl-2,3-dihydro-benzofuran-6-carboxylic acid tert-butyl ester (232a) and 3-amino-1-methyl-pyrazole. $^1$H NMR (400 MHz, CDCl$_3$) δ 8.36 (s, 1 H) 7.80-7.99 (m, 1H) 7.26-7.32 (m, 1 H) 7.11 (dd, J=17.05, 1.39 Hz, 2 H) 6.73-6.92 (m, 3 H) 3.82 (s, 3 H) 3.75 (d, J=5.56 Hz, 1 H) 3.63 (d, J=7.58 Hz, 1 H) 3.23 (s, 3 H) 2.81 (d, J=16.17 Hz, 1 H) 2.04 (d, J=1.77 Hz, 1 H) 1.47 (s, 3 H); LCMS for C$_{22}$H$_{22}$FN$_3$O$_6$S m/z 476.00 (M+H+).

Preparation of Intermediate 232a

Mixture of 4-(3-fluoro-4-methanesulfonyl-phenoxy)-2-hydroxymethyl-2-methyl-2,3-dihydro-benzofuran-6-carboxylic acid tert-butyl ester and 4-(5-fluoro-2-methanesulfonyl-phenoxy)-2-hydroxymethyl-2-methyl-2,3-dihydro-benzofuran-6-carboxylic acid tert-butyl ester

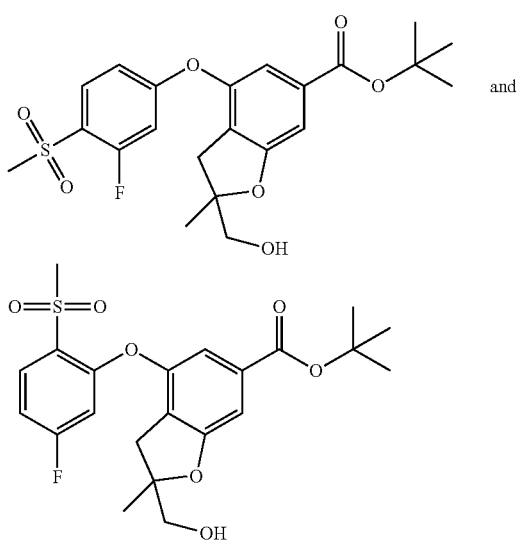

The title compound was prepared in a similar manner as described for Intermediate 1f, from 4-hydroxy-2-hydroxymethyl-2-methyl-2,3-dihydro-benzofuran-6-carboxylic acid tert-butyl ester (227c) and 2,4-difluorophenyl methyl sulfone. $^1$H NMR (400 MHz, CDCl$_3$) δ 7.89 (t, J=8.34 Hz, 1 H) 7.27-7.30 (m, 1H) 7.22 (d, J=1.01 Hz, 1 H) 6.85 (dd, J=8.84, 2.27 Hz, 1 H) 6.77 (dd, J=11.12, 2.27 Hz, 1 H) 3.66-3.76 (m, 1H) 3.51-3.63 (m, 1 H) 3.21 (s, 3 H) 3.16 (d, J=16.42 Hz, 1 H) 2.69-2.82 (m, 1H) 1.52-1.58 (m, 12 H); LCMS for C$_{22}$H$_{25}$FO$_7$S m/z 397.00 (M-tBu+H+).

Example 233

4-(3-Fluoro-4-methanesulfonyl-phenoxy)-2-hydroxymethyl-2-methyl-2,3-dihydro-benzofuran-6-carboxylic acid (5-methyl-pyridin-2-yl)-amide

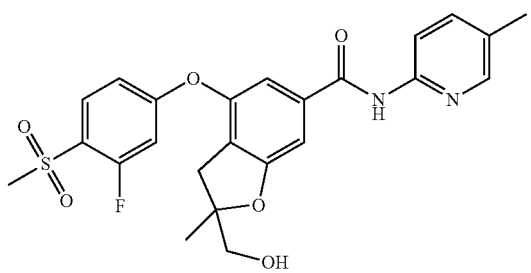

The title compound was prepared in a similar manner as described for Example 200, from 4-(3-fluoro-4-methanesulfonyl-phenoxy)-2-hydroxymethyl-2-methyl-2,3-dihydro-benzofuran-6-carboxylic acid tert-butyl ester (232a) and 2-amino-5-picoline. $^1$H NMR (400 MHz, CDCl$_3$) δ 8.39 (s, 1 H) 8.22 (d, J=8.59 Hz, 1 H) 8.12 (d, J=2.02 Hz, 1 H) 7.93 (t, J=8.46 Hz, 1 H) 7.58 (dd, J=8.34, 2.02 Hz, 1 H) 7.19 (d, J=1.26 Hz, 1 H) 7.13 (d, J=1.26 Hz, 1 H) 6.88 (dd, J=8.84, 2.27 Hz, 1 H) 6.82 (dd, J=10.86, 2.27 Hz, 1 H) 3.76 (d, J=5.56 Hz, 1 H) 3.64 (d, J=7.33 Hz, 1 H) 3.21 (s, 3 H) 2.81 (d, J=16.67 Hz, 1 H) 2.33 (s, 3 H) 1.97 (d, J=1.52 Hz, 1 H) 1.47 (s, 3 H); LCMS for C$_{24}$H$_{23}$FN$_2$O$_6$S m/z 487.00 (M+H+).

Example 234

4-(4-Dimethylcarbamoyl-3-fluoro-phenoxy)-2-methoxymethyl-2-methyl-2,3-dihydro-benzofuran-6-carboxylic acid (1-methyl-1H-pyrazol-3-yl)-amide

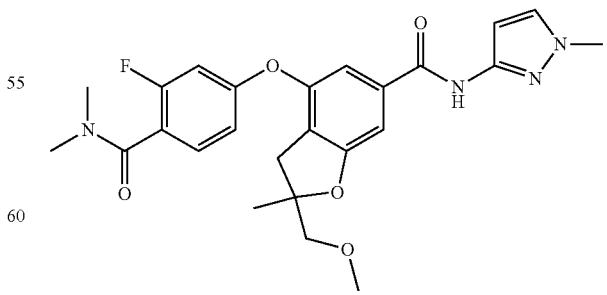

The title compound was prepared in a similar manner as described for Example 200, from 4-(4-Dimethylcarbamoyl-3-fluoro-phenoxy)-2-methoxymethyl-2-methyl-2,3-dihydro-benzofuran-6-carboxylic acid tert-butyl ester (234a). $^1$H NMR (400 MHz, CDCl$_3$) δ 8.34 (s, 1 H) 7.38 (t, J=8.08 Hz, 1 H) 7.28 (d, J=2.27 Hz, 1H) 7.08 (s, 1 H) 7.06 (s, 1 H) 6.81 (dd, J=8.46, 2.15 Hz, 1 H) 6.77 (d, J=2.02 Hz, 1 H) 6.69 (dd, J=10.61, 2.27 Hz, 1 H) 3.81 (s, 3 H) 3.41-3.51 (m, 2 H) 3.40 (s, 3 H) 3.13 (s, 3 H) 3.14 (d, J=16.42 Hz, 1 H) 2.98 (d, J=1.77 Hz, 3 H) 2.95-2.97 (m, 1 H) 1.47 (s, 3 H); LCMS for C$_{25}$H$_{27}$FN$_4$O$_5$ m/z 483.00 (M+H)$^+$; Anal. Calcd. for C$_{25}$H$_{27}$FN$_4$O$_5$.0.49 H2O: C, 61.11; H, 5.74; N, 11.40, Found: C, 61.11; H, 5.68; N, 11.20.

Preparation of Intermediate 234a 4-(4-Dimethylcarbamoyl-3-fluoro-phenoxy)-2-methoxymethyl-2-methyl-2,3-dihydro-benzofuran-6-carboxylic acid tert-butyl ester

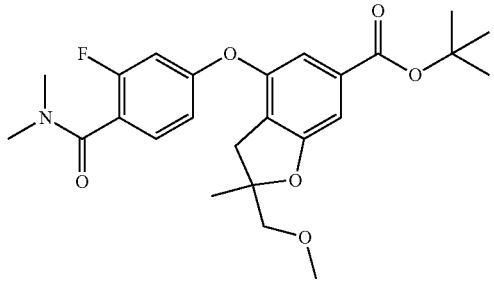

The title compound was prepared in a similar manner as described for Intermediate 201a, from 4-(4-dimethylcarbamoyl-3-fluoro-phenoxy)-2-hydroxymethyl-2-methyl-2,3-dihydro-benzofuran-6-carboxylic acid tert-butyl ester (229a) and methyl iodide. $^1$H NMR (400 MHz, CDCl$_3$) δ 7.36 (t, J=8.21 Hz, 1H) 7.26 (s, 1H) 7.20 (s, 1 H) 6.78 (dd, J=8.46, 1.89 Hz, 1 H) 6.66 (dd, J=10.74, 1.89 Hz, 1 H) 3.40-3.49 (m, 2 H) 3.39 (s, 3 H) 3.07-3.14 (m, 4 H) 2.97 (s, 3 H) 2.76 (d, J=16.67 Hz, 1 H) 1.56 (s, 9 H) 1.45 (s, 3 H); LCMS for C$_{25}$H$_{30}$FNO$_6$ m/z 482.00 (M+Na)$^+$.

Example 235

4-(5-Fluoro-2-methanesulfonyl-phenoxy)-2-hydroxymethyl-2-methyl-2,3-dihydro-benzofuran-6-carboxylic acid (1-methyl-1H-pyrazol-3-yl)-amide

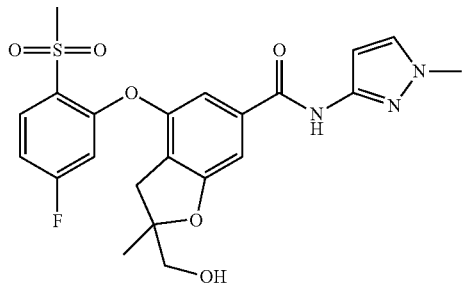

The title compound was prepared as a minor product to Example 232 from Intermediate 232a and purified by reverse phase HPLC. $^1$H NMR (400 MHz, CDCl$_3$)) δ 8.38 (s, 1 H) 8.08 (dd, J=8.84, 6.06 Hz, 1 H) 7.26-7.31 (m, 1 H) 7.15 (d, J=4.80 Hz, 2 H) 6.90-7.01 (m, 1 H) 6.77 (d, J=2.27 Hz, 1 H) 6.61 (dd, J=9.47, 2.40 Hz, 1 H) 3.81 (s, 3 H) 3.72 (d, J=5.81 Hz, 1 H) 3.60 (s, 1 H) 3.29 (s, 3 H) 3.18 (d, J=16.42 Hz, 1 H) 2.84 (d, J=16.67 Hz, 1 H) 1.96 (d, J=1.52 Hz, 1 H) 1.45 (s, 3 H); LCMS for C$_{22}$H$_{22}$FN$_3$O$_6$S m/z 476.00 (M+H$^+$).

Example 236

4-(5-Fluoro-2-methanesulfonyl-phenoxy)-2-hydroxymethyl-2-methyl-2,3-dihydro-benzofuran-6-carboxylic acid (5-methyl-pyridin-2-yl)-amide

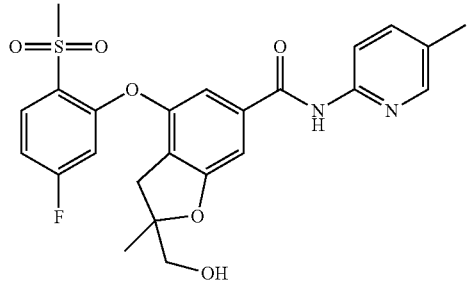

The title compound was prepared as a minor product to Example 233 from Intermediate 232a and purified by reverse phase HPLC. $^1$H NMR (400 MHz, CDCl$_3$)) δ 8.43 (s, 1 H) 8.23 (d, J=8.34 Hz, 1H) 8.05-8.16 (m, 2 H) 7.58 (dd, J=8.34, 2.02 Hz, 1 H) 7.21 (s, 2 H) 6.91-7.01 (m, 1 H) 6.61 (dd, J=9.47, 2.40 Hz, 1 H) 3.74 (dd, J=12.00, 5.68 Hz, 1 H) 3.61 (dd, J=11.87, 7.33 Hz, 1 H) 3.30 (s, 3 H) 3.19 (d, J=16.67 Hz, 1 H) 2.84 (d, J=16.67 Hz, 1 H) 2.33 (s, 3 H) 1.95 (t, J=6.57 Hz, 1 H) 1.46 (s, 3 H); LCMS for C$_{24}$H$_{23}$FN$_2$O$_6$S m/z 487.00 (M+H$^+$).

Example 237

4-(3-Fluoro-4-methanesulfonyl-phenoxy)-2-methoxymethyl-2-methyl-2,3-dihydro-benzofuran-6-carboxylic acid (1-methyl-1H-pyrazol-3-yl)-amide

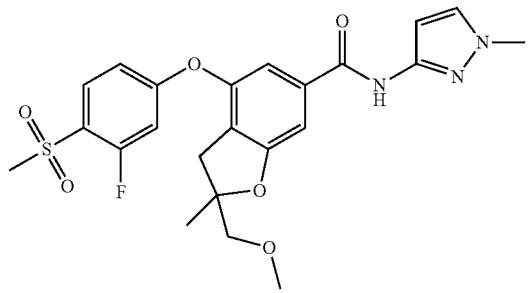

The title compound was prepared in a similar manner as described for Example 200, from 4-(3-fluoro-4-methanesulfonyl-phenoxy)-2-methoxymethyl-2-methyl-2,3-dihydro-benzofuran-6-carboxylic acid tert-butyl ester (237a) and 3-amino-1-methyl-pyrazole. $^1$H NMR (300 MHz, CDCl$_3$) δ

8.37 (s, 1 H) 7.92 (t, J=8.38 Hz, 1 H) 7.29 (d, J=2.26 Hz, 1 H) 7.12 (d, J=1.13 Hz, 1 H) 7.08 (d, J=1.13 Hz, 1 H) 6.88 (dd, J=8.76, 2.35 Hz, 1 H) 6.76-6.84 (m, 2 H) 3.81 (s, 3 H) 3.42-3.56 (m, 2 H) 3.41 (s, 3 H) 3.23 (s, 3 H) 3.15 (d, J=16.58 Hz, 1 H) 2.79 (d, J=16.58 Hz, 1 H) 1.48 (s, 3 H); LCMS for $C_{23}H_{24}FN_3O_6S$ m/z 490.00 (M+H$^+$).

Preparation of Intermediate 237a

Mixture of 4-(3-fluoro-4-methanesulfonyl-phenoxy)-2-methoxymethyl-2-methyl-2,3-dihydro-benzofuran-6-carboxylic acid tert-butyl ester and 4-(5-fluoro-2-methanesulfonyl-phenoxy)-2-methoxymethyl-2-methyl-2,3-dihydro-benzofuran-6-carboxylic acid tert-butyl ester

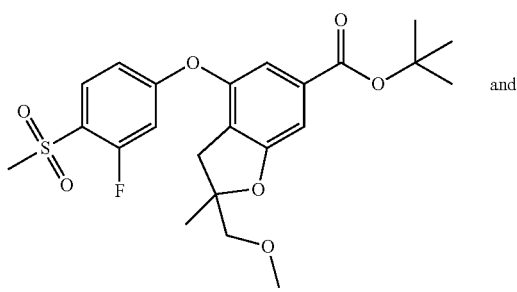

and

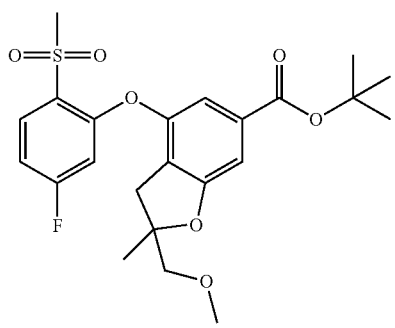

The title compound was prepared in a similar manner as described for Intermediate 201a, from Intermediate 232a and methyl iodide. $^1$H NMR (400 MHz, CDCl3) δ 8.07 (dd, J=8.72, 6.19 Hz, 1 H) 7.89 (t, J=8.34 Hz, 1 H) 7.27-7.32 (m, 3 H) 7.21 (d, J=1.01 Hz, 1 H) 6.89-6.95 (m, 1 H) 6.85 (dd, J=8.84, 2.27 Hz, 1 H) 6.77 (dd, J=11.24, 2.40 Hz, 1 H) 6.57 (dd, J=9.85, 2.27 Hz, 1 H) 3.40-3.50 (m, 4 H) 3.39 (s, 3 H) 3.37 (s, 3 H) 3.31 (s, 3 H) 3.21 (s, 3 H) 3.11 (d, J=5.05 Hz, 1 H) 3.07 (d, J=5.05 Hz, 1 H) 2.77 (t, J=16.55 Hz, 2 H) 1.57 (s, 9 H) 1.56 (s, 9 H) 1.45 (s, 3 H) 1.44 (s, 3 H); LCMS for $C_{23}H_{27}FO_7S$ m/z 422.00 (M-tBu+H$^+$).

Example 238

4-(5-Fluoro-2-methanesulfonyl-phenoxy)-2-methoxymethyl-2-methyl-2,3-dihydro-benzofuran-6-carboxylic acid (1-methyl-1H-pyrazol-3-yl)-amide

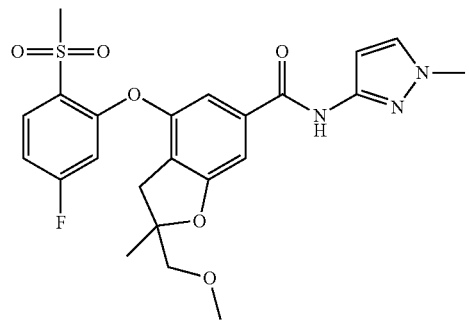

The title compound was prepared as a minor product to Example 237 from Intermediate 237a and purified by reverse phase HPLC. $^1$H NMR (300 MHz, CDCl$_3$)) δ 8.55 (s, 1 H) 8.08 (dd, J=8.85, 6.22 Hz, 1 H) 7.26-7.32 (m, 1 H) 7.08-7.22 (m, 2 H) 6.87-7.01 (m, 1 H) 6.78 (d, J=2.26 Hz, 1 H) 6.61 (dd, J=9.70, 2.35 Hz, 1 H) 3.79 (s, 3 H) 3.46-3.54 (m, 2 H) 3.39 (s, 3 H) 3.30 (s, 3 H) 3.14 (d, J=16.58 Hz, 1 H) 2.82 (d, J=16.58 Hz, 1 H) 1.46 (s, 3 H); LCMS for $C_{23}H_{24}FN_3O_6S$ m/z 490.00 (M+H$^+$).

Example 239

4-(4-Dimethylcarbamoyl-3-fluoro-phenoxy)-2-hydroxymethyl-2-methyl-2,3-dihydro-benzofuran-6-carboxylic acid (5-methyl-pyridin-2-yl)-amide

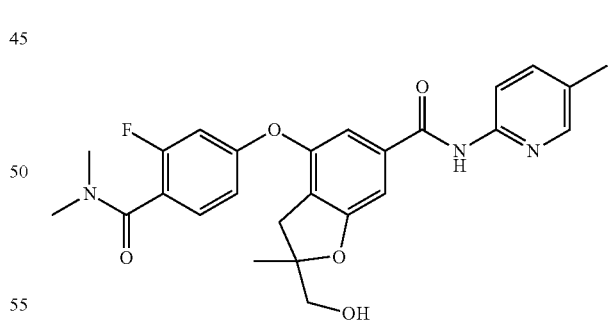

The title compound was prepared in a similar manner as described for Example 200, from 4-(4-dimethylcarbamoyl-3-fluoro-phenoxy)-2-hydroxymethyl-2-methyl-2,3-dihydro-benzofuran-6-carboxylic acid tert-butyl ester (229a) and 2-amino-5-methyl-pyridine. $^1$H NMR (400 MHz, CDCl$_3$) δ 8.56 (s, 1 H) 8.23 (d, J=8.59 Hz, 1 H) 8.09 (s, 1 H) 7.57 (dd, J=8.46, 1.89 Hz, 1 H) 7.38 (t, J=8.08 Hz, 1 H) 7.13 (s, 1 H) 7.10 (s, 1 H) 6.80 (dd, J=8.59, 2.27 Hz, 1 H) 6.71 (dd, J=10.61, 2.27 Hz, 1 H) 3.70-3.77 (m, 1 H) 3.57-3.66 (m, 1 H) 3.19 (d, J=16.67 Hz, 1 H) 3.13 (s, 3 H) 2.98 (d, J=1.52 Hz, 3

H) 2.81 (d, J=16.67 Hz, 1 H) 2.31 (s, 3H) 1.46 (s, 3 H); LCMS for $C_{26}H_{26}FN_3O_5$ m/z 480.00 (M+H)$^+$.

Example 240

4-[4-(Azetidine-1-carbonyl)-3-fluoro-phenoxy]-2-hydroxymethyl-2-methyl-2,3-dihydro-benzofuran-6-carboxylic acid (5-methyl-pyridin-2-yl)-amide

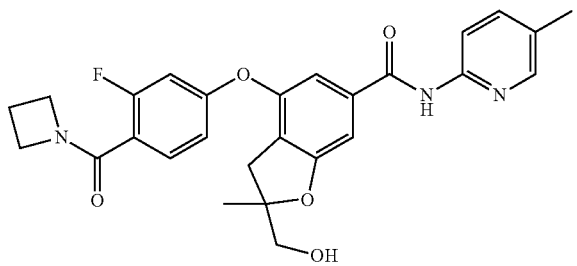

The title compound was prepared in a similar manner as described for Example 200, from 4-[4-(azetidine-1-carbonyl)-3-fluoro-phenoxy]-2-hydroxymethyl-2-methyl-2,3-dihydro-benzofuran-6-carboxylic acid tert-butyl ester (240a) and 2-amino-5-methyl-pyridine. $^1$H NMR (400 MHz, CDCl$_3$) δ 9.01 (br. s., 1 H) 8.23 (d, J=8.59 Hz, 1 H) 8.09 (s, 1 H) 7.62 (dd, J=8.59, 1.77 Hz, 1 H) 7.53 (t, J=8.08 Hz, 1 H) 7.15 (s, 1 H) 7.11 (s, 1 H) 6.80 (dd, J=8.59, 2.27 Hz, 1 H) 6.63-6.73 (m, 1 H) 4.22 (t, J=7.71 Hz, 2 H) 4.15 (t, J=7.71 Hz, 2 H) 3.74 (d, 1 H) 3.61 (d, J=11.87 Hz, 1 H) 3.18 (d, J=16.67 Hz, 1 H) 2.79 (d, J=16.67 Hz, 1 H) 2.28-2.38 (m, 5 H) 1.46 (s, 3 H); LCMS for $C_{27}H_{26}FN_3O_5$ m/z 492.00 (M+H)$^+$.

Preparation of Intermediate 240a

4-[4-(Azetidine-1-carbonyl)-3-fluoro-phenoxy]-2-hydroxymethyl-2-methyl-2,3-dihydro-benzofuran-6-carboxylic acid tert-butyl ester

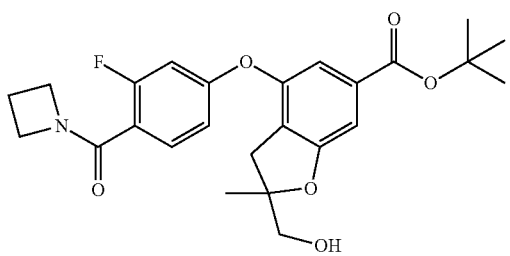

The title compound was prepared in a similar manner as described for Intermediate 1f, from 4-hydroxy-2-hydroxymethyl-2-methyl-2,3-dihydro-benzofuran-6-carboxylic acid tert-butyl ester (227c) and azetidin-1-yl-(2,4-difluoro-phenyl)-methanone. $^1$H NMR (400 MHz, CDCl$_3$) δ 7.48-7.56 (m, 1 H) 7.24 (s, 1 H) 7.20 (d, J=1.26 Hz, 1 H) 6.77 (dd, J=8.59, 2.53 Hz, 1 H) 6.66 (dd, J=11.24, 2.40 Hz, 1 H) 4.21 (t, J=7.83 Hz, 2 H) 4.11-4.17 (m, 2 H) 3.65-3.74 (m, 1 H) 3.55-3.63 (m, 1 H) 3.13 (d, J=16.67 Hz, 1 H) 2.76 (d, J=16.67 Hz, 1 H) 2.34 (dt, J=15.60, 7.74 Hz, 2 H) 1.89-1.97 (m, 1 H) 1.56 (s, 9 H) 1.44 (s, 3 H); LCMS for $C_{25}H_{28}FNO_6$ m/z 458.20 (M+H)$^+$.

Example 241

4-[4-(Azetidine-1-carbonyl)-3-fluoro-phenoxy]-2-hydroxymethyl-2-methyl-2,3-dihydro-benzofuran-6-carboxylic acid (1-methyl-1H-pyrazol-3-yl)-amide

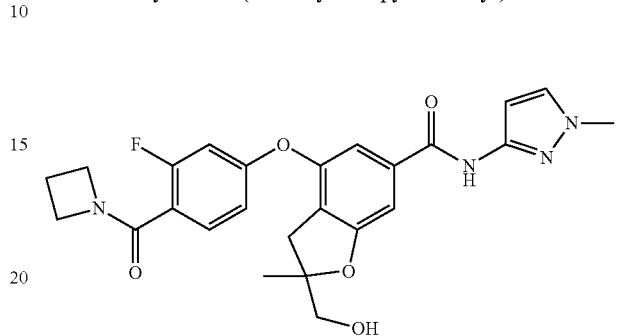

The title compound was prepared in a similar manner as described for Example 200, from 4-[4-(azetidine-1-carbonyl)-3-fluoro-phenoxy]-2-hydroxymethyl-2-methyl-2,3-dihydro-benzofuran-6-carboxylic acid tert-butyl ester (240a). $^1$H NMR (400 MHz, CDCl$_3$) δ 9.12 (s, 1 H) 7.53 (t, J=8.21 Hz, 1 H) 7.32 (d, J=2.27 Hz, 1 H) 7.15 (s, 1 H) 7.11 (s, 1 H) 6.86 (d, J=2.27 Hz, 1 H) 6.81 (dd, J=8.59, 2.27 Hz, 1 H) 6.70 (dd, J=10.99, 2.15 Hz, 1 H) 4.22 (t, J=7.83 Hz, 2 H) 4.16 (t, J=7.58 Hz, 2 H) 3.84 (s, 3 H) 3.71-3.76 (m, 1 H) 3.59-3.64 (m, 1 H) 3.18 (d, J=16.42 Hz, 1 H) 2.80 (d, J=16.67 Hz, 2 H) 2.29-2.40 (m, 2 H) 1.46 (s, 3 H); LCMS for $C_{25}H_{25}FN_4O_5$ m/z 481.20 (M+H)$^+$.

Example 242

4-[4-(Azetidine-1-carbonyl)-3-fluoro-phenoxy]-2-methoxymethyl-2-methyl-2,3-dihydro-benzofuran-6-carboxylic acid (1-methyl-1H-pyrazol-3-yl)-amide

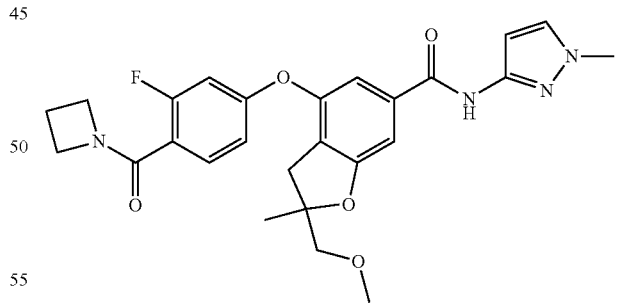

The title compound was prepared in a similar manner as described for Example 200, from 4-[4-(azetidine-1-carbonyl)-3-fluoro-phenoxy]-2-methoxymethyl-2-methyl-2,3-dihydro-benzofuran-6-carboxylic acid tert-butyl ester (242a). $^1$H NMR (400 MHz, CDCl$_3$) δ 8.37 (s, 1 H) 7.53 (t, J=8.21 Hz, 1 H) 7.28 (d, J=2.27 Hz, 1 H) 7.07 (d, J=9.35 Hz, 2 H) 6.80 (dd, J=8.59, 2.27 Hz, 1 H) 6.78 (d, J=2.27 Hz, 1 H) 6.67 (dd, J=11.12, 2.27 Hz, 1 H) 4.22 (t, J=7.71 Hz, 2 H) 4.10-4.19 (m, 3 H) 3.80 (s, 3 H) 3.40 (s, 3 H) 3.12 (d, J'16.67 Hz, 1 H) 2.74-2.82 (m, 1 H) 2.29-2.38 (m, 2 H) 1.47 (s, 3 H); LCMS for $C_{26}H_{27}FN_4O_5$ m/z 495.20 (M+H)$^+$; Anal. Calcd. for $C_{26}H_{27}FN_4O_5 \cdot 0.24 H_2O$: C, 62.60; H, 5.55; N, 11.23; Found: C, 62.64; H, 5.67; N, 10.93.

Preparation of Intermediate 242a

4-[4-(Azetidine-1-carbonyl)-3-fluoro-phenoxy]-2-methoxymethyl-2-methyl-2,3-dihydro-benzofuran-6-carboxylic acid tert-butyl ester

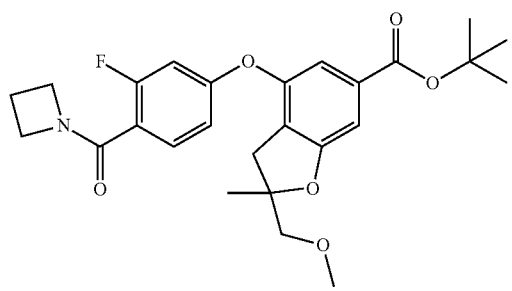

The title compound was prepared in a similar manner as described for Intermediate 201a, from 4-[4-(azetidine-1-carbonyl)-3-fluoro-phenoxy]-2-hydroxymethyl-2-methyl-2,3-dihydro-benzofuran-6-carboxylic acid tert-butyl ester (240a) and methyl iodide. $^1$H NMR (400 MHz, CDCl$_3$) δ 7.86 (d, J=8.84 Hz, 2 H) 7.22 (s, 1 H) 7.07 (d, J=8.84 Hz, 2 H) 3.41-3.52 (m, 2 H) 3.40 (s, 3 H) 3.11 (d, J=16.67 Hz, 1 H) 2.76 (d, J=16.67 Hz, 1 H) 2.48 (td, J=7.89, 4.67 Hz, 1 H) 1.56 (s, 9 H) 1.46 (s, 3 H) 1.32-1.43 (m, 2 H) 1.00-1.12 (m, 2 H); LCMS for $C_{26}H_{30}FNO_6$ m/z 472.20 (M+H)$^+$.

Example 243

(−)-4-[4-(Azetidine-1-carbonyl)-3-fluoro-phenoxy]-2-methoxymethyl-2-methyl-2,3-dihydro-benzofuran-6-carboxylic acid (1-methyl-1H-pyrazol-3-yl)-amide and Example 244: (+)-4-[4-(Azetidine-1-carbonyl)-3-fluoro-phenoxy]-2-methoxymethyl-2-methyl-2,3-dihydro-benzofuran-6-carboxylic acid (1-methyl-1H-pyrazol-3-yl)-amide

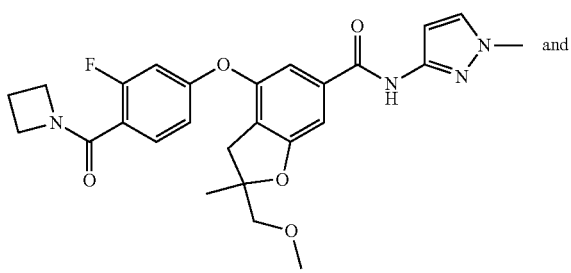

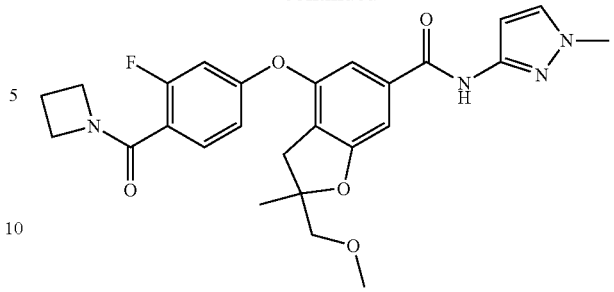

The title compounds were prepared by the chiral separation of Example 242 by SFC column chromatography.

Example 243: [α]$_D$=−20.49; 100% ee; $^1$H NMR (400 MHz, CDCl$_3$) δ 8.30 (s, 1 H) 7.50-7.57 (m, 1 H) 7.28 (d, J=2.27 Hz, 1 H) 7.07 (dd, J=11.24, 1.39 Hz, 2 H) 6.80 (dd, J=8.59, 2.53 Hz, 1 H) 6.78 (d, J=2.27 Hz, 1H) 6.67 (dd, J=11.12, 2.27 Hz, 1 H) 4.22 (t, J=7.71 Hz, 2 H) 4.16 (t, J=7.71 Hz, 2 H) 3.81 (s, 3 H) 3.41-3.51 (m, 2 H) 3.39-3.41 (m, 3 H) 3.12 (d, J=16.42 Hz, 1 H) 2.78 (d, J=16.42 Hz, 1 H) 2.34 (dt, J=15.47, 7.80 Hz, 2 H) 1.47 (s, 3 H); LCMS for $C_{26}H_{27}FN_4O_5$ m/z 495.20 (M+H)$^+$; Anal. Calcd, for $C_{26}H_{27}FN_4O_5 \cdot 0.23 H_2O$: C, 62.62; H, 5.55; N, 11.24; Found: C, 58.2862.61; H, 5.52; N, 11.25.

Example 244: [α]$_D$=+14.78; 100% ee; $^1$H NMR (400 MHz, CDCl$_3$) δ 8.31 (s, 1 H) 7.53 (t, J=8.21 Hz, 1 H) 7.28 (d, J=2.27 Hz, 1 H) 7.07 (d, J=9.85 Hz, 2 H) 6.76-6.85 (m, 2 H) 6.67 (dd, J=11.37, 2.27 Hz, 1 H) 4.19-4.26 (m, 2 H) 4.16 (t, J=7.71 Hz, 2 H) 3.81 (s, 3 H) 3.41-3.52 (m, 2 H) 3.40 (s, 3 H) 3.12 (d, J=16.42 Hz, 1 H) 2.77 (d, J=16.67 Hz, 1 H) 2.30-2.40 (m, 2 H) 1.47 (s, 3 H); LCMS for $C_{26}H_{27}FN_4O_5$ m/z 495.20 (M+H)$^+$; Anal. Calcd. for $C_{26}H_{27}FN_4O_5 \cdot 0.20 H_2O$: C, 62.69; H, 5.54; N, 11.25; Found: C, 62.76; H, 5.51; N, 11.14

Example 245

4-(4-Cyclopropanesulfonyl-phenoxy)-2-hydroxymethyl-2-methyl-2,3-dihydro-benzofuran-6-carboxylic acid (1-methyl-1H-pyrazol-3-yl)-amide

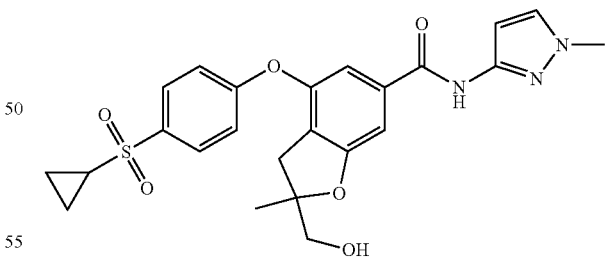

The title compound was prepared in a similar manner as described for Example 200, from 4-(4-cyclopropanesulfonyl-phenoxy)-2-hydroxymethyl-2-methyl-2,3-dihydro-benzofuran-6-carboxylic acid tert-butyl ester (245a). $^1$H NMR (400 MHz, CDCl$_3$) δ 8.36 (s, 1 H) 7.84-7.91 (m, 2 H) 7.29 (d, J=2.27 Hz, 1 H) 7.04-7.13 (m, 3 H) 3.81 (s, 3 H) 3.71-3.79 (m, 1 H) 3.62 (dd, J=11.87, 7.07 Hz, 1 H) 3.21 (d, J=16.42 Hz, 1 H) 2.87 (d, J=19.96 Hz, 1 H) 2.81 (s, 2 H) 2.44-2.53 (m, 1 H) 2.11 (t, J=6.44 Hz, 1 H) 1.6 (s, 3 H) 1.31-1.42 (m, 2 H) 1.01-1.11 (m, 2 H); LCMS for $C_{24}H_{25}N_3O_6S$ m/z 484.20

(M+H)⁺; Anal. Calcd, for $C_{24}H_{25}N_3O_6S \cdot 0.27 H_2O$: C, 58.70; H, 5.04; N, 8.55; Found: C, 58.71; H, 5.19; N, 8.42.

Preparation of Intermediate 245a 4-(4-Cyclopropanesulfonyl-phenoxy)-2-hydroxymethyl-2-methyl-2,3-dihydro-benzofuran-6-carboxylic acid tert-butyl ester

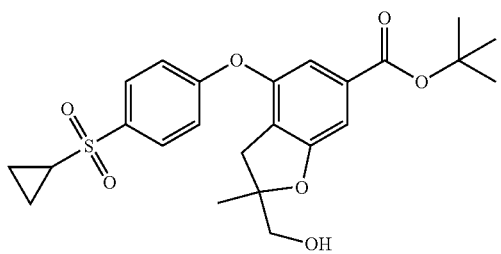

The title compound was prepared in a similar manner as described for Intermediate 1f, from 4-hydroxy-2-hydroxymethyl-2-methyl-2,3-dihydro-benzofuran-6-carboxylic acid tert-butyl ester (227c) and 1-cyclopropanesulfonyl-4-fluorobenzene. ¹H NMR (400 MHz, CDCl₃) δ 7.86 (d, J=8.59 Hz, 2 H) 7.23 (s, 1H) 7.07 (d, J=8.59 Hz, 2 H) 3.73 (dd, J=11.87, 5.81 Hz, 1 H) 3.62 (d, J=7.58 Hz, 1 H) 3.16 (d, J=16.67 Hz, 1 H) 2.78 (d, J=16.67 Hz, 1 H) 2.48 (td, J=8.02, 4.67 Hz, 1 H) 1.55-1.58 (m, 12H) 1.45 (s, 2 H) 1.36 (dd, J=4.67, 1.89 Hz, 2 H) 0.97-1.13 (m, 2 H); LCMS for $C_{24}H_{27}O_7S$ m/z 460.80 (M+H)⁺.

Example 246

4-(4-Cyclopropanesulfonyl-phenoxy)-2-hydroxymethyl-2-methyl-2,3-dihydro-benzofuran-6-carboxylic acid (2-methyl-2H-[1,2,3]triazol-4-yl)-amide

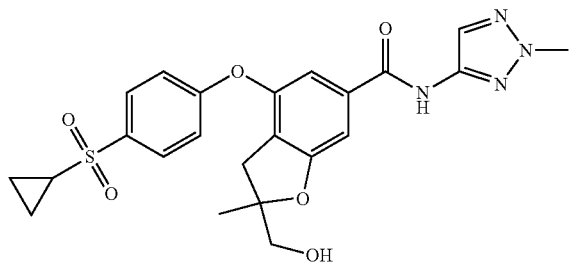

The title compound was prepared in a similar manner as described for Example 200, from 4-(4-cyclopropanesulfonyl-phenoxy)-2-hydroxymethyl-2-methyl-2,3-dihydro-benzofuran-6-carboxylic acid tert-butyl ester (245a). ¹H NMR (400 MHz, CDCl₃) δ 8.35 (s, 1 H) 8.08 (s, 1 H) 7.88 (d, J=8.84 Hz, 1 H) 7.82-7.92 (m, 1 H) 7.03-7.14 (m, 4 H) 4.12 (s, 3 H) 3.77 (dd, J=12.00, 5.68 Hz, 1 H) 3.63 (dd, J=12.00, 7.45 Hz, 1 H) 3.22 (d, J=16.42 Hz, 1 H) 2.83 (d, J=16.67 Hz, 1 H) 2.44-2.54 (m, 1 H) 1.96 (dd, J=7.45, 5.68 Hz, 1 H) 1.47 (s, 3 H) 1.37 (dd, J=4.80, 1.77 Hz, 2 H) 1.07 (dd, J=7.83, 2.02 Hz, 2H); LCMS for $C_{23}H_{24}N_4O_6S$ m/z 485.00 (M+H)⁺; Anal. Calcd. for $C_{23}H_{24}N_4O_6S \cdot 0.26 H_2O$: C, 56.47; H, 5.05; N, 11.45; Found: C, 56.46; H, 5.00; N, 11.40.

Example 247

(−)-4-(4-Cyclopropanesulfonyl-phenoxy)-2-methoxymethyl-2-methyl-2,3-dihydro-benzofuran-6-carboxylic acid (1-methyl-1H-pyrazol-3-yl)-amide and Example 248: (+)-4-(4-Cyclopropanesulfonyl-phenoxy)-2-methoxymethyl-2-methyl-2,3-dihydro-benzofuran-6-carboxylic acid (1-methyl-1H-pyrazol-3-yl)-amide

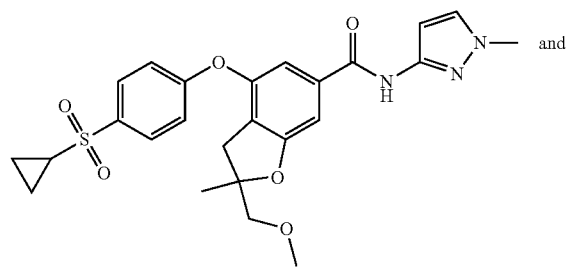

and

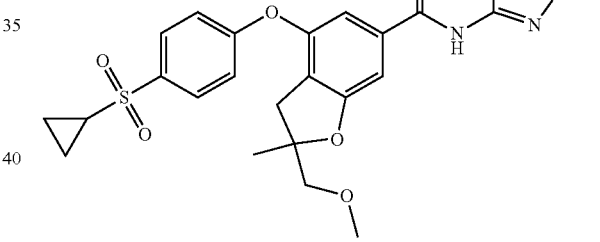

The title compounds were prepared in a similar manner as described for Example 200, from 4-(4-cyclopropanesulfonyl-phenoxy)-2-methoxymethyl-2-methyl-2,3-dihydro-benzofuran-6-carboxylic acid tert-butyl ester (247a), followed by chiral separation by SFC column chromatography.

Example 247: [α]$_D$ =−14.75; 100% ee; ¹H NMR (400 MHz, CDCl₃) δ 8.28 (s, 1H) 7.85-7.90 (m, 2 H) 7.29 (d, J=2.27 Hz, 1 H) 7.10-7.14 (m, 1 H) 7.09 (s, 2 H) 7.06 (d, J=1.26 Hz, 1 H) (d, J=2.27 Hz, 1 H) 3.81 (s, 3 H) 3.43-3.52 (m, 2 H) 3.41 (s, 3 H) 3.16 (d, J=16.67 Hz, 1 H) 2.80 (d, J=16.42 Hz, 1 H) 2.45-2.53 (m, 1 H) 1.48 (s, 3 H) 1.34-1.39 (m, 2 H) 1.07 (dd, J=7.83, 2.02 Hz, 2 H): LCMS for $C_{25}H_{27}N_3O_6S$ m/z 498.20 (M+H)⁺; Anal. Calcd. for $C_{25}H_{27}N_3O_6S$: C, 60.35; H, 5.47; N, 8.45; Found: C, 60.34; H, 5.51; N, 8.37.

Example 248: [α]$_D$=+14.49; 100% ee; ¹H NMR (400 MHz, CDCl₃) δ 8.30 (s, 1 H) 7.87 (ddd, J=9.22, 2.78, 2.40 Hz, 2 H) 7.29 (d, J=2.27 Hz, 1 H) 7.10-7.12 (m, 1 H) 7.08-7.10 (m, 2 H) 7.06 (d, J=1.52 Hz, 1 H) 6.77 (d, J=2.27 Hz, 1 H) 3.81 (s, 3 H) 3.42-3.52 (m, 2 H) 3.41 (s, 3 H) 3.16 (d, J=16.67 Hz, 1 H) 2.80 (d, J=16.42 Hz, 1 H) 2.49 (ddd, J=8.02, 4.86, 3.03 Hz, 1 H) 1.48 (s, 3 H) 1.31-1.39 (m, 2 H) 1.07 (ddd, J=14.15, 6.32, 1.26 Hz, 2 H); LCMS for $C_{25}H_{27}N_3O_6S$ m/z 498.20 (M+H)⁺;

Anal. Calcd. for $C_{25}H_{27}N_3O_6S \cdot 0.16 H_2O$: C, 60.00; H, 5.50; N, 8.40; Found: C, 60.01; H, 5.65; N, 8.38.

Preparation of Intermediate 247a 4-(4-Cyclopropanesulfonyl-phenoxy)-2-methoxymethyl-2-methyl-2,3-dihydro-benzofuran-6-carboxylic acid tert-butyl ester

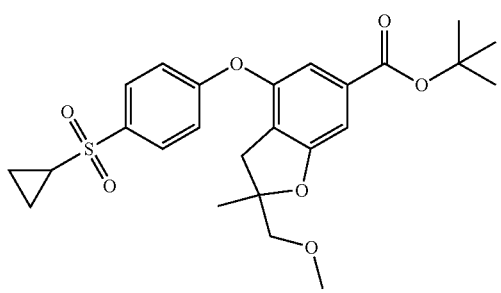

The title compound was prepared in a similar manner as described for Intermediate 201a, from 4-(4-cyclopropanesulfonyl-phenoxy)-2-hydroxymethyl-2-methyl-2,3-dihydro-benzofuran-6-carboxylic acid tert-butyl ester (245a) and methyl iodide. $^1$H NMR (400 MHz, CDCl$_3$) δ 7.86 (d, J=8.84 Hz, 2 H) 7.22 (s, 1 H) 7.07 (d, J=8.84 Hz, 2 H) 3.41-3.52 (m, 2 H) 3.40 (s, 3 H) 3.11 (d, J=16.67 Hz, 1 H) 2.76 (d, J=16.67 Hz, 1 H) 2.48 (td, J=7.89, 4.67 Hz, 1 H) 1.56 (s, 9 H) 1.46 (s, 3 H) 1.32-1.43 (m, 2 H) 1.00-1.12 (m, 2 H); LCMS for $C_{25}H_{30}O_7S$ m/z 475.20 (M+H)$^+$.

Example 249

(+)-4-(4-Cyclopropanesulfonyl-phenoxy)-2-methoxymethyl-2-methyl-2,3-dihydro-benzofuran-6-carboxylic acid (2-methyl-2H-[1,2,3]triazol-4-yl)-amide and Example 250: (+)-4-(4-Cyclopropanesulfonyl-phenoxy)-2-methoxymethyl-2-methyl-2,3-dihydro-benzofuran-6-carboxylic acid (2-methyl-2H-[1,2,3]triazol-4-yl)-amide

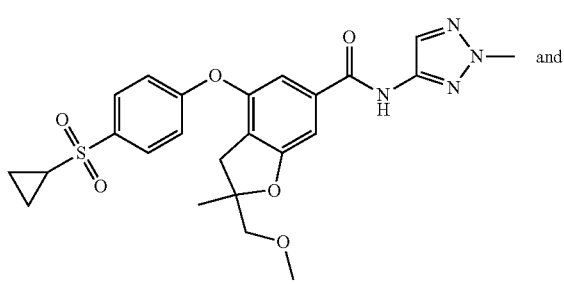

and

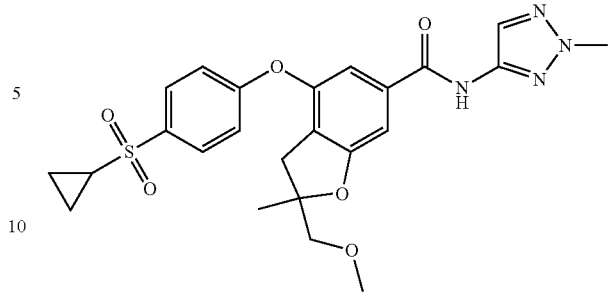

The title compounds were prepared in a similar manner as described for Example 200, from 4-(4-cyclopropanesulfonyl-phenoxy)-2-methoxymethyl-2-methyl-2,3-dihydro-benzofuran-6-carboxylic acid tert-butyl ester (247a), followed by chiral separation by SFC column chromatography.

Example 249: [α]$_D$=−11.16; 100% ee; $^1$H NMR (400 MHz, CDCl$_3$) δ 8.31 (s, 1 H) 8.08 (s, 1 H) 7.82-7.94 (m, 2 H) 7.11 (d, J=9.09 Hz, 2 H) 7.09 (s, 2 H) 4.12 (s, 3 H) 3.42-3.56 (m, 2 H) 3.41 (s, 3 H) 3.17 (d, J=16.67 Hz, 1 H) 2.81 (d, J=16.42 Hz, 1 H) 2.37-2.60 (m, 1 H) 1.48 (s, 3 H) 1.37 (dd, J=4.80, 2.02 Hz, 2H) 1.07 (dd, J=7.83, 2.02 Hz, 2 H); LCMS for $C_{24}H_{26}N_4O_6S$ m/z 499.00 (M+H)$^+$; Anal. Calcd. for $C_{24}H_{26}N_4O_6S$: C, 57.82; H, 5.26; N, 11.24; Found: C, 57.70; H, 5.31; N, 11.11.

Example 250: [α]$_D$=+13.33; >99% ee; $^1$H NMR (400 MHz, CDCl$_3$) δ 8.30 (s, 1 H) 8.08 (s, 1 H) 7.79-7.95 (m, 2 H) 7.05-7.14 (m, 4 H) 4.12 (s, 3 H) 3.42-3.55 (m, 2 H) 3.41 (s, 3 H) 3.17 (d, J=16.42 Hz, 1 H) 2.81 (d, J=16.67 Hz, 1 H) 2.45-2.54 (m, 1 H) 1.48 (s, 3 H) 1.37 (dd, J=4.55, 2.02 Hz, 2 H) 1.07 (dd, J=7.96, 1.89 Hz, 2 H); LCMS for $C_{24}H_{26}N_4O_6S$ m/z 499.00 (M+H)$^+$; Anal. Calcd. for $C_{24}H_{26}N_4O_6S \cdot 0.09 H_2O$: C, 58.82; H, 4.77; N, 11.43; Found: C, 58.88; H, 4.75; N, 11.33.

Example 251

2-Fluoromethyl-4-(4-methanesulfonyl-phenoxy)-2-methyl-2,3-dihydro-benzofuran-6-carboxylic acid (1-methyl-1H-pyrazol-3-yl)-amide

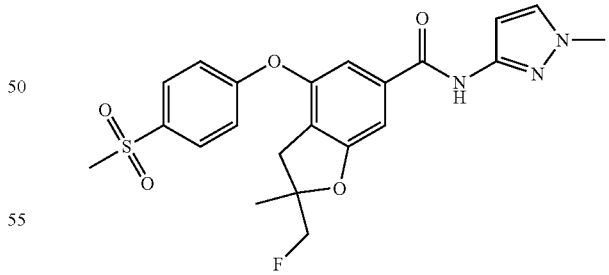

To a solution of 2-hydroxymethyl-4-(4-methanesulfonyl-phenoxy)-2-methyl-2,3-dihydro-benzofuran-6-carboxylic acid (1-methyl-1H-pyrazol-3-yl)-amide (227) (62 mg, 0.140 mmol) and 2,4,6-collidine (0.0359 mL, 0.271 mmol) in dry CH$_2$Cl$_2$ was added trifluoromethanesulfonic acid anhydride (0.0365 mL, 0.217 mmol) at 0° C. The mixture was stirred at 0° C. to room temperature for 1 hr. TLC indicated that the reaction was complete. The reaction was quenched with 0.5 N aqueous HCl, extracted with 3×CHCl$_3$, dried over Na$_2$SO$_4$, and concentrated. The residue was dissolved in anhydrous CH$_2$Cl$_2$ (3 mL), and TBAF (1 mL, 1 M in THF) was added. The resulting mixture was stirred at room temperature for 1.5 hr, quenched with H$_2$O, and extracted with 3×CHCl$_3$. The combined organic layer was dried over Na$_2$SO$_4$, concentrated, and purified by column chromatography eluting with 50-65% EtOAc in hexanes to give a white solid (18 mg, 28% yield). $^1$H NMR (400 MHz, CDCl$_3$) δ 8.55 (s, 1 H) 7.84-7.96 (m, 2 H) 7.25-7.31 (m, 2 H) 7.02-7.15 (m, 3 H) 6.72-6.83 (m, 1 H) 4.26-4.54 (m, 2 H) 3.79 (s, 3H) 3.20 (d, J=16.67 Hz, 1H) 3.08 (s, 3 H) 2.89 (dd, J=16.67, 1.77 Hz, 1 H) 1.52 (s, 3 H); LCMS for C$_{22}$H$_{22}$FN$_3$O$_5$S m/z 460.00 (M+H$^+$).

Example 252

2-Methyl-N-(5-methylpyridin-2-yl)-4-(4-(methylsulfonyl)-phenoxy)-benzofuran-6-carboxamide

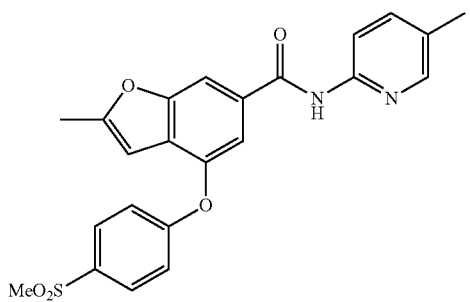

2-Amino-5-methyl pyridine (289 mg, 2.67 mmol) was dissolved in DCE (10 mL) at 0° C., then Al(CH$_3$)$_2$Cl (2.67 mL, 1M in hexanes) was added drop wise. After the addition, the ice-bath was removed, and the mixture was stirred for 30 min at room temperature. Ethyl 2-methyl-4-[4-(methylsulfonyl)phenoxy]-1-benzofuran-6-carboxylate (100 mg, 0.267 mmol) was added and the stirring was continued for 14 h. The reaction was quenched with potassium sodium tartrate tetrahydrate (20% w/w) cautiously. The product was extracted with CHCl$_3$, washed with brine and dried over MgSO$_4$. The crude product was purified by gradient silica gel chromatography using CHCl$_3$/MeOH (100/0 to 98/2) to give the title compound (100 mg, 86%) as a white solid. $^1$H NMR (300 MHz, CHLOROFORM-D) δ ppm 2.32 (s, 3 H) 2.48 (s, 3 H) 3.07 (s, 3H) 6.24 (s, 1 H) 7.08-7.16 (m, 2 H) 7.48 (d, J=1.32 Hz, 1 H) 7.57 (dd, J=8.29, 2.35 Hz, 1 H) 7.81-7.97 (m, 3 H) 8.12 (d, J=2.35 Hz, 1 H) 8.25 (d, J=8.29 Hz, 1 H) 8.44 (s, 1 H). LCMS for C$_{23}$H$_{20}$N$_2$O$_5$S m/z 437.4 (M+H)$^+$.

Preparation of Intermediate 252a 3-(Ethoxycarbonyl)-4-(5-methyl-2-furyl)but-3-enoic Acid

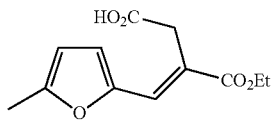

Sodium ethylate (74.2 g, 1.09 mol) was added under vigorous stirring to a solution of 5-methyl-2-furaldehyde 1 (100 g, 0.91 mol) and diethyl succinate (316 g, 1.81 mol) in ethanol (1 L). The reaction mixture was refluxed for 8 h and evaporated in vacuum (~20 mmHg) at 50° C. until the solvent distillation ceased. The obtained residue was diluted with 500 mL of 10% HCl and 500 mL of ethyl acetate. The mixture was shaken. The organic layer was separated, diluted with 500 mL of a saturated aqueous solution of NaHCO$_3$, and shaken. The aqueous layer was separated, acidified with 10% HCl to pH 2, and subjected to extraction with 1 L of ethyl acetate. The organic layer was evaporated in vacuum (~20 mmHg) at 60° C. and chromatographed on a layer of silica gel (200×150 mm) with hexane/ethyl acetate mixture, 1:1 as eluent. Fractions with the target product were collected and evaporated in vacuum to give 45 g (0.19 mol, 21%) of the desired compound as a yellow solid.

Preparation of Intermediate 252b

Ethyl 4-(Acetyloxy)-2-methyl-1-benzofuran-6-carboxylate

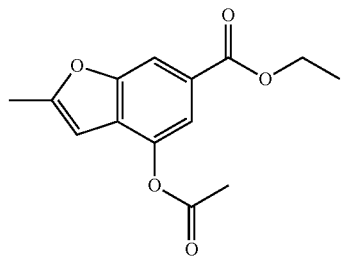

Sodium acetate (30 g, 0.36 mol) was added under vigorous stirring to a solution of 3-(ethoxycarbonyl)-4-(5-methyl-2-furyl)but-3-enoic acid (45 g, 0.19 mol) in 250 mL of acetic anhydride. The reaction mixture was refluxed for 2 h and evaporated in vacuum (~20 mmHg) at 70° C. until the solvent distillation ceased. The obtained crude product was suspended in 500 mL of dichloromethane. The suspension was filtered. The solid was washed with 200 mL of dichloromethane. The combined solutions were washed with 200 mL of a saturated aqueous solution of NaHCO$_3$ and evaporated in vacuum to dryness. The obtained crude product was chromatographed on a layer of silica gel (200×150 mm) with hexane/ethyl acetate mixture, 3:1 as eluent to give 25 g (95 mmol, 51%) of desired compound as a yellow solid.

Preparation of Intermediate 252c

Ethyl 4-hydroxy-2-methyl-1-benzofuran-6-carboxylate

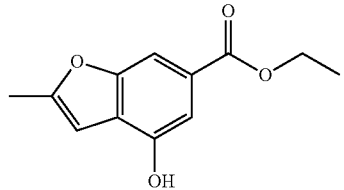

A mixture of ethyl 4-(acetyloxy)-2-methyl-1-benzofuran-6-carboxylate in absolute ethanol (500 mL) and potassium carbonate (18 g, 0.13 mol) was stirred for 3 h at 60° C. The mixture was diluted with 500 mL of dichloromethane and the suspension was filtered. The precipitate was washed with 200 mL of dichloromethane. The combined solutions was washed with 200 mL of a 10% aqueous solution of citric acid and evaporated in vacuum to dryness. The crude product introduced into a silica gel column and eluted with hexane/ethyl acetate mixture (2:1) to give 20 g (91 mmol, 95%) of desired compound as a yellow solid. ¹HNMR (DMSO d-6): 1.30 (t, 3H), 2.45 (s, 3H), 4.30 (qt, 2H), 6.65 (s, 1H), 7.28 (2, 1H) 7.53 (s, 1H), 10.25 (s, 1H).

Preparation of Intermediate 252d

Ethyl 2-methyl-4-[4-(methylsulfonyl)phenoxy]-1-benzofuran-6-carboxylate

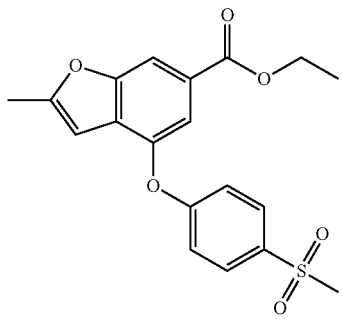

The mixture of ethyl 4-hydroxy-2-methylbenzofuran-6-carboxylate (4.5 g, 20.4 mmol), 1-fluoro-4-(methylsulfonyl)benzene (5.34 g, 30.7 mmol) and $Cs_2CO_3$ (9.99 g, 30.7 mmol) in DMF(10 mL) was heated in a microwave at 120° C. for 60 min. The sample was filtered and the filtrate was concentrated to give an oil residue. The oil was purified by HPLC to give the title compound (5.074 g, 66%) as an off-white solid. ¹H NMR (300 MHz, CHLOROFORM-D) d ppm 1.39 (t, J=7.16 Hz, 3 H) 2.46 (s, 3 H) 3.06 (s, 3H) 4.38 (q, J=7.16 Hz, 2 H) 6.21 (s, 1 H) 7.00-7.14 (m, 2 H) 7.62 (s, 1 H) 7.81-7.95 (m, 2 H) 8.01 (s, 1 H).

Examples 253-270 were prepared in a similar manner as described for Example 252, from Intermediate 252d and the appropriate amino heterocycles.

Example 253

2-Methyl-4-(4-(methylsulfonyl)phenoxy)-N-(5-(trifluoromethyl)-pyridin-2-yl)benzofuran-6-carboxamide

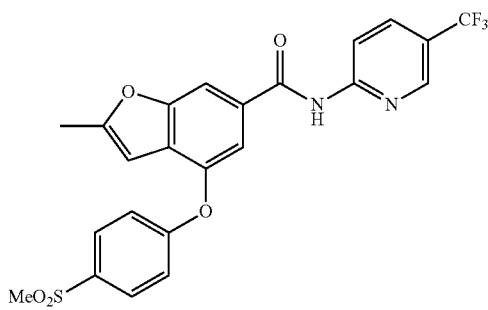

Example 254

N-(6,7-Dihydro-5H-cyclopenta[b]pyridin-2-yl)-2-methyl-4-(4-(methylsulfonyl)-phenoxy)benzofuran-6-carboxamide

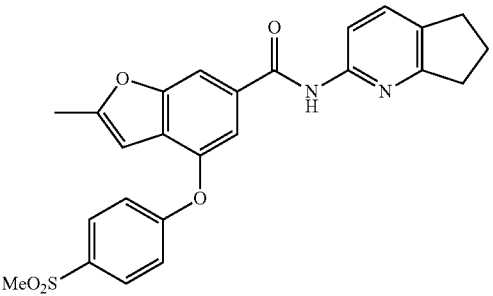

Example 255

2-Methyl-N-(5-methylisoxazol-3-yl)-4-(4-(methylsulfonyl)-phenoxy)-benzofuran-6-carboxamide

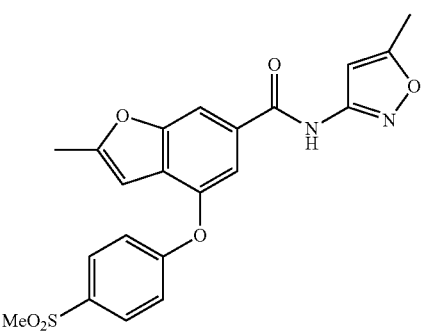

Example 256

N-(5-Fluoropyridin-2-yl)-2-methyl-4-(4-(methylsulfonyl)-phenoxy)benzofuran-6-carboxamide

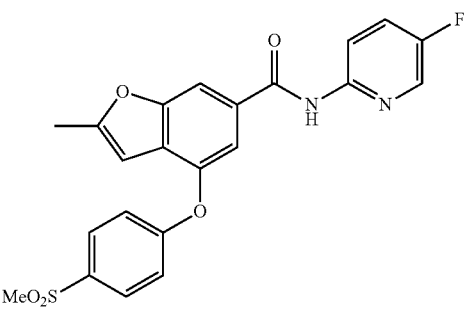

263

Example 257

2-Methyl-4-(4-(methylsulfonyl)phenoxy)-N-(pyridin-2-yl)-benzofuran-6-carboxamide

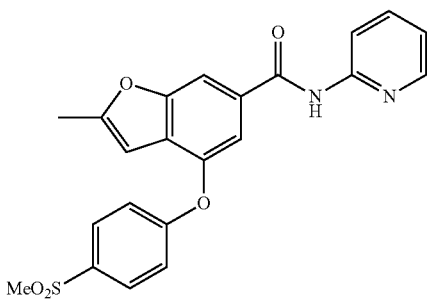

Example 258

N-(Isoxazol-3-yl)-2-methyl-4-(4-(methylsulfonyl)phenoxy)-benzofuran-6-carboxamide

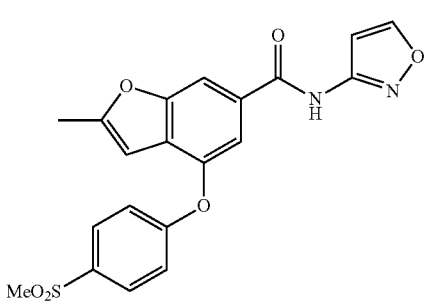

Example 259

N-(4-Methoxypyridin-2-yl)-2-methyl-4-(4-(methylsulfonyl)-phenoxy)-benzofuran-6-carboxamide

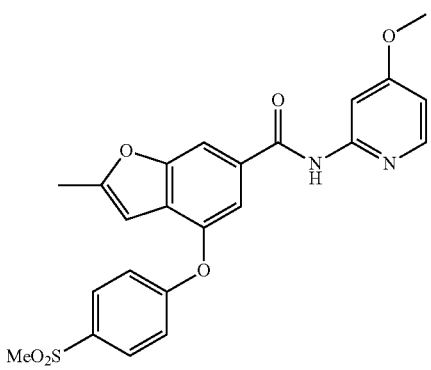

264

Example 260

N-(5-chloropyridin-2-yl)-2-methyl-4-(4-(methylsulfonyl)-phenoxy)benzofuran-6-carboxamide

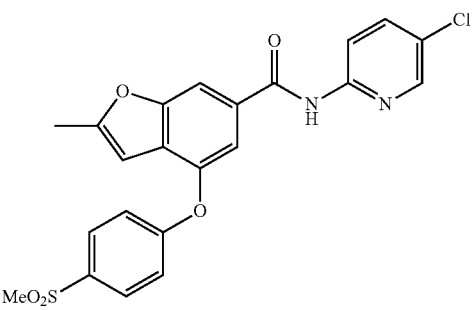

Example 261

N-(5-cyanopyridin-2-yl)-2-methyl-4-(4-(methylsulfonyl)-phenoxy)benzofuran-6-carboxamide

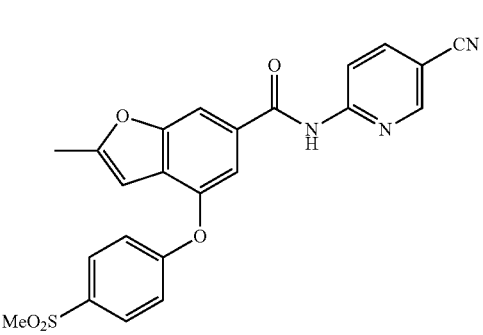

Example 262

N-(5-(Dimethylamino)pyrazin-2-yl)-2-methyl-4-(4-(methylsulfonyl)-phenoxy)-benzofuran-6-carboxamide

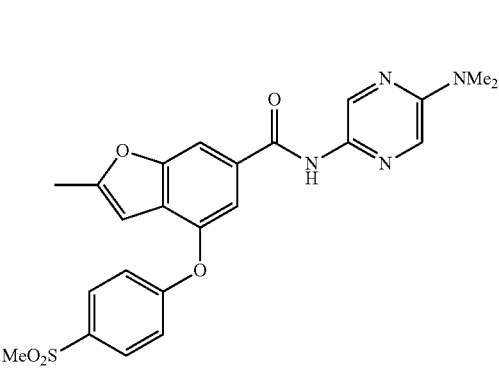

265

Example 263

N-(5-methoxypyrazin-2-yl)-2-methyl-4-(4-(methyl-sulfonyl)-phenoxy)-benzofuran-6-carboxamide

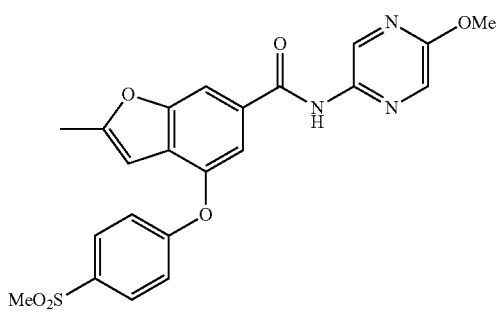

Example 264

Methyl 6-(2-methyl-4-(4-(methylsulfonyl)phenoxy)benzofuran-6-carboxamido)nicotinate

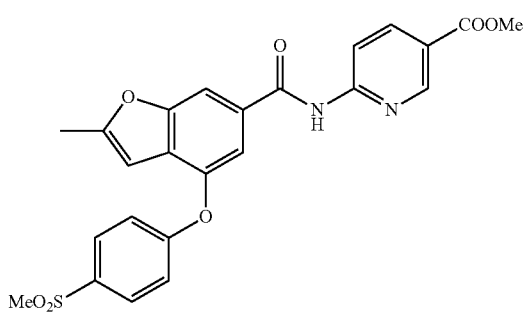

Example 265

N-(5-Ethylpyridin-2-yl)-2-methyl-4-(4-(methylsulfonyl)-phenoxy)benzofuran-6-carboxamide

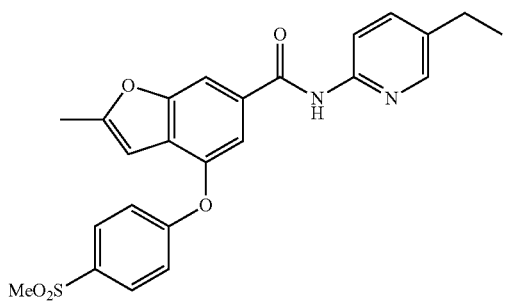

266

Example 266

N-(5-(Hydroxymethyl)pyridin-2-yl)-2-methyl-4-(4-(methylsulfonyl)-phenoxy)-benzofuran-6-carboxamide

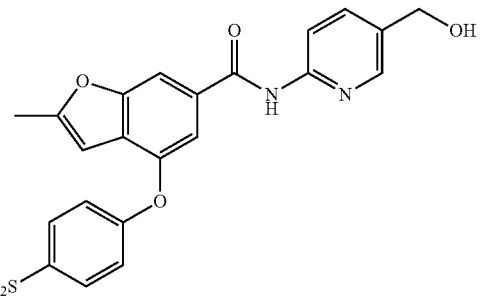

Example 267

2-Methyl-N-(2-methyl-2H-1,2,3-triazol-4-yl)-4-(4-(methylsulfonyl)phenoxy)-benzofuran-6-carboxamide

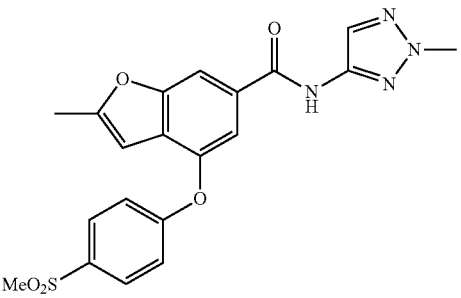

Example 268

N-(6-(Hydroxymethyl)pyridin-2-yl)-2-methyl-4-(4-(methylsulfonyl)phenoxy)-benzofuran-6-carboxamide

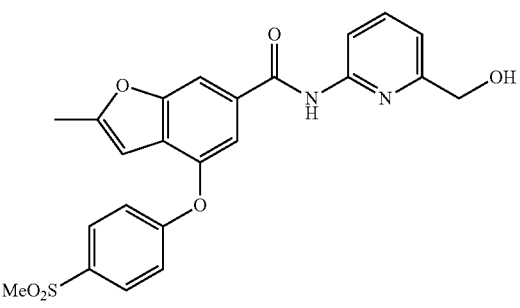

Example 269

N-(6-(1-Hydroxyethyl)pyridin-2-yl)-2-methyl-4-(4-(methylsulfonyl)phenoxy)-benzofuran-6-carboxamide

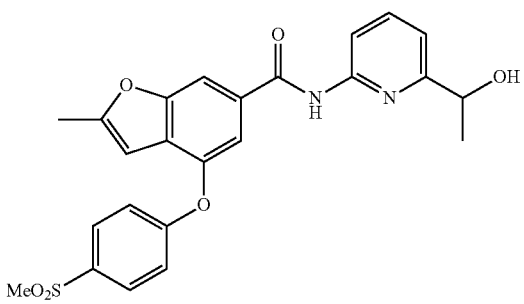

Example 270

N-(5-ethoxypyridin-2-yl)-2-methyl-4-(4-(methylsulfonyl)-phenoxy)benzofuran-6-carboxamide

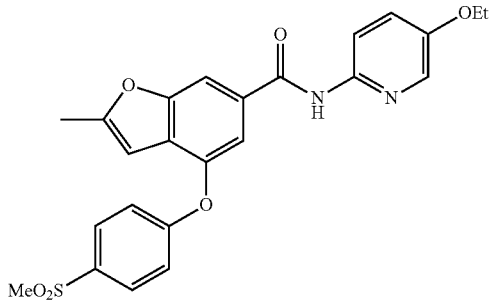

| Example | MW | MF | NMR | m/z |
|---|---|---|---|---|
| 253 | 490.5 | C23H17F3N2O5S | 1H NMR (300 MHz, CHLOROFORM-d) d ppm 2.50 (s, 3 H) 3.03-3.18 (m, 3 H) 6.25 (s, 1 H) 7.05-7.20 (m, 2 H) 7.51 (d, J = 1.13 Hz, 1 H) 7.86-7.97 (m, 3 H) 8.02 (d, 1 H) 8.49 (d, 1 H) 8.58 (s, 1 H) 8.72 (s, 1 H) | 491.00 |
| 254 | 462.5 | C25H22N2O5S | 1H NMR (300 MHz, CHLOROFORM-d) d ppm 2.16 (d, J = 7.35 Hz, 2 H) 2.48 (s, 3 H) 2.87-3.03 (m, 4 H) 3.08 (s, 3 H) 6.25 (s, 1 H) 7.11 (d, J = 8.67 Hz, 2 H) 7.49 (s, 1 H) 7.60 (d, 1 H) 7.85-8.04 (m, 3 H) 8.14 (d, J = 8.29 Hz, 1 H) 8.50 (s, 1 H) | 463.00 |
| 255 | 426.5 | C21H18N2O6S | 1H NMR (300 MHz, CHLOROFORM-d) d ppm 2.43 (s, 3 H) 2.48 (s, 3 H) 3.09 (s, 3 H) 6.24 (s, 1 H) 6.85 (s, 1 H) 7.12 (d, J = 8.85 Hz, 2 H) 7.57 (s, 1 H) 7.90 (d, J = 8.85 Hz, 2 H) 7.98 (s, 1 H) | 427.00 |
| 256 | 440.5 | C22H17FN2O5S | 1H NMR (300 MHz, CHLOROFORM-d) d ppm 2.49 (s, 3 H) 3.07 (s, 3 H) 6.24 (s, 1 H) 7.05-7.19 (m, 2 H) 7.45-7.63 (m, 2 H) 7.84-8.01 (m, 3 H) 8.16 (d, J = 2.83 Hz, 1 H) 8.32-8.46 (m, J = 9.23, 4.14 Hz, 1 H) 8.57 (s, 1 H) | 441.30 |
| 257 | 422.5 | C22H18N2O5S | 1H NMR (300 MHz, CHLOROFORM-d) d ppm 2.49 (s, 3 H) 3.08 (s, 3 H) 6.25 (s, 1 H) 7.04-7.20 (m, J = 8.85 Hz, 3 H) 7.51 (d, J = 1.32 Hz, 1 H) 7.78 (s, 1 H) 7.88-8.03 (m, 3 H) 8.27-8.45 (m, 2 H) 8.58 (s, 1 H) | 423.40 |
| 258 | 412.4 | C20H16N2O6S | 1H NMR (300 MHz, CHLOROFORM-d) d ppm 2.50 (s, 3 H) 3.09 (s, 3 H) 6.26 (s, 1 H) 7.13 (d, J = 8.85 Hz, 2 H) 7.19-7.25 (m, 1 H) 7.50 (s, 1 H) 7.82-8.02 (m, 3 H) 8.33 (s, 1 H) 9.01 (s, 1 H) | 413.40 |
| 259 | 452.5 | C23H20N2O6S | 1H NMR (300 MHz, CHLOROFORM-d) d ppm 2.49 (s, 3 H) 3.02-3.18 (m, 3 H) 3.85-4.03 (m, 3 H) 6.26 (s, 1 H) 6.64 (dd, J = 5.65, 2.26 Hz, 1 H) 7.02-7.20 (m, 2 H) 7.49 (d, J = 1.13 Hz, 1 H) 7.86-7.98 (m, 3 H) 7.98-8.17 (m, 2 H) 8.63 (s, 1 H) | 453.35 |
| 260 | 456.9 | C22H17ClN2O5S | 1H NMR (300 MHz, CHLOROFORM-d) d ppm 2.49 (s, 3 H) 3.08 (s, 3 H) 6.25 (s, 1 H) 7.10 (d, J = 1.51 Hz, 1 H) 7.50 (d, J = 0.94 Hz, 1 H) 7.63 (d, J = 0.94 Hz, 1 H) 7.69-7.78 (m, 1 H) 7.84-7.96 (m, 2 H) 8.02 (s, 1 H) 8.26 (d, J = 2.45 Hz, 1 H) 8.37 (d, J = 8.85 Hz, 1H), 8.63 (s, 1H) | 457.20 |
| 261 | 447.5 | C23H17N3O5S | 1H NMR (300 MHz, CHLOROFORM-d) d ppm 2.48 (s, 3 H) 3.08 (s, 3 H) 6.26 (s, 1 H) 7.07-7.20 (m, 2 H) 7.54 (d, J = 1.32 Hz, 1 H) 7.87-8.04 (m, 3 H) 8.33-8.44 (m, 1 H) 8.48 (d, J = 8.67 Hz, 1 H) 8.93 (d, J = 1.70 Hz, 1 H) 9.07 (s, 1 H) | 448.20 |
| 262 | 466.5 | C23H22N4O5S | 1H NMR (300 MHz, CHLOROFORM-d) d ppm 2.48 (s, 3 H) 3.08 (s, 3 H) 3.13 (s, 6 H) 6.25 (s, 1 H) 7.05-7.18 (m, 2 H) 7.49 (d, J = 1.13 Hz, 1 H) 7.71 (d, J = 1.51 Hz, 1 H) 7.84-8.01 (m, 3 H) 8.18 (s, 1 H) 9.15 (d, J = 1.32 Hz, 1 H) | 467.20 |
| 263 | 453.5 | C22H19N3O6S | 1H NMR (300 MHz, CHLOROFORM-d) d ppm 2.49 (s, 3 H) 2.99-3.23 (m, 3 H) 3.99 (s, 3 H) 6.25 (s, 1 | 454.20 |

| Example | MW | MF | NMR | m/z |
|---|---|---|---|---|
| | | | H) 7.12 (d, J = 8.67 Hz, 2 H) 7.50 (s, 1 H) 7.81-8.08 (m, 4 H) 8.41 (s, 1 H) 9.19 (s, 1 H) | |
| 264 | 480.5 | C24H20N2O7S | 1H NMR (300 MHz, CHLOROFORM-d) d ppm 2.44-2.61 (m, 3 H) 3.08 (s, 3 H) 3.95 (s, 3 H) 6.26 (s, 1 H) 7.07-7.20 (m, 2 H) 7.54 (d, J = 1.32 Hz, 1 H) 7.87-8.04 (m, 3 H) 8.33-8.44 (m, 1 H) 8.48 (d, J = 8.67 Hz, 1 H) 8.93 (d, J = 1.70 Hz, 1 H) 9.07 (s, 1 H) | 481.20 |
| 265 | 450.5 | C24H22N2O5S | 1H NMR (300 MHz, CHLOROFORM-d) d ppm 1.26 (t, J = 7.54 Hz, 3 H) 2.49 (s, 3 H) 2.65 (q, J = 7.72 Hz, 2 H) 3.08 (s, 3 H) 6.25 (s, 1 H) 7.12 (d, J = 8.67 Hz, 2 H) 7.50 (s, 1 H) 7.63 (s, 1 H) 7.84-8.03 (m, 3 H) 8.14 (s, 1 H) 8.28 (d, J = 8.48 Hz, 1 H) 8.54 (s, 1 H) | 451.40 |
| 266 | 452.5 | C23H20N2O6S | 1H NMR (300 MHz, CHLOROFORM-d) d ppm 2.48 (s, 3 H) 3.08 (s, 3 H) 4.72 (s, 2 H) 6.25 (s, 1 H) 7.03-7.20 (m, 2 H) 7.53 (s, 1 H) 7.78-7.87 (m, 1 H) 7.87-8.02 (m, 3 H) 8.41 (s, 2 H) 8.95 (s, 1 H) 11.85 (s, 1 H) | 453.20 |
| 267 | 426.5 | C20H18N4O5S | 1H NMR (300 MHz, CHLOROFORM-d) d ppm 2.49 (s, 3 H) 3.08 (s, 3 H) 4.13 (s, 3 H) 6.25 (s, 1 H) 7.12 (d, J = 8.85 Hz, 2 H) 7.46 (s, 1 H) 7.85 (s, 1 H) 7.92 (d, J = 8.67 Hz, 2 H) 8.11 (s, 1 H) 8.49 (s, 1 H) | 427.20 |
| 268 | 452.5 | C23H20N2O6S | 1H NMR (300 MHz, CHLOROFORM-d) d ppm 2.47 (s, 3 H) 3.07 (s, 3 H) 5.29 (s, 2 H) 6.23 (d, J = 0.94 Hz, 1 H) 6.46 (d, J = 8.10 Hz, 1 H) 6.78 (d, J = 7.35 Hz, 1 H) 7.03-7.16 (m, 2 H) 7.45 (t, J = 7.82 Hz, 1 H) 7.68 (d, J = 1.13 Hz, 1 H) 7.85-7.98 (m, 2 H) 8.09 (s, 1H) | 453.30 |
| 269 | 466.5 | C24H22N2O6S | 1H NMR (300 MHz, CHLOROFORM-d) d ppm 1.52 (d, J = 6.59 Hz, 3 H) 2.50 (s, 3 H) 3.09 (s, 3 H) 3.70 (d, 1 H) 4.87 (d, J = 6.22 Hz, 1 H) 6.25 (d, J = 0.94 Hz, 1 H) 7.02-7.23 (m, 3 H) 7.54 (d, J = 1.32 Hz, 1 H) 7.79 (t, J = 7.91 Hz, 1 H) 7.88-8.02 (m, 3 H) 8.27 (d, J = 8.29 Hz, 1 H) 8.58 (s, 1 H) | 467.20 |
| 270 | 466.5 | C24H22N2O6S | 1H NMR (300 MHz, CHLOROFORM-d) d ppm 1.44 (t, J = 6.97 Hz, 3 H) 2.48 (s, 3 H) 3.07 (s, 3 H) 4.08 (q, J = 6.97 Hz, 2 H) 6.24 (s, 1 H) 7.06-7.22 (m, 2 H) 7.31 (dd, J = 9.04, 3.01 Hz, 1 H) 7.50 (s, 1 H) 7.87-8.10 (m, 4 H) 8.30 (d, J = 9.04 Hz, 1 H) 8.59 (s, 1 H) | 467.00 |

Example 271

4-(4-(Methylsulfonyl)phenoxy)-2-methyl-N-(1-methyl-1H-pyrazol-3-yl)benzofuran-6-carboxamide

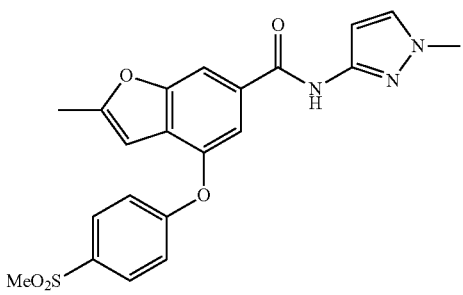

$Cs_2CO_3$ (0.806 g, 2.47 mmol) was added to a solution of ethyl 4-hydroxy-2-methylbenzofuran-6-carboxylate (0.273 g, 1.24 mmol) and 1-fluoro-4-(methylsulfonyl)benzene (0.22 g, 1.26 mmol) in DMF (5 ML). The mixture was stirred at 120° C. for 8 hours and then cooled to room temperature. 1-Methyl-1H-pyrazol-3-amine (0.18 g, 1.85 mmol) and HATU (0.7 g, 1.85 mmol) were added. The reaction mixture was stirred at 50° C. for one hour and then filtered. Purification by HPLC gave a solid (20 mg, 4% yield) as expected product. $^1$H NMR (400 MHz, $CD_3OD$) δ 7.99 (m, 1 H) 7.93-7.96 (m, 2 H) 7.56 (m, 1 H) 7.50 (m, 1 H) 7.18-7.20 (m, 2 H) 6.59-6.60 (m, 1 H) 6.33 (s, 1 H) 3.83 (s, 3 H), 3.12 (s, 3 H), 2.47 (s, 3 H). LCMS for $C_{21}H_{19}N_3O_5S$ m/z 426.10 $(M+H)^+$.

Example 272

4-(4-(Dimethylcarbamoyl)-3-fluorophenoxy)-2-methyl-N-(1-methyl-1H-pyrazol-3-yl)benzofuran-6-carboxamide

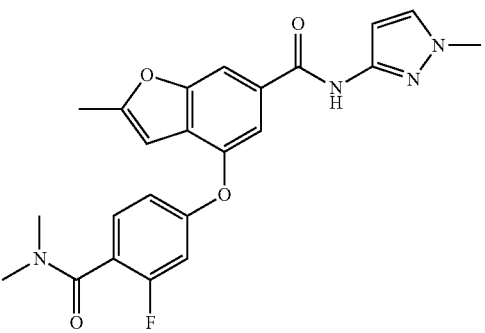

The title compound was prepared in a similar manner as described for Example 271, from ethyl 4-hydroxy-2-methylbenzofuran-6-carboxylate (0.275 g, 1.25 mmol), 2,4-difluoro-N,N-dimethylbenzamide (0.289 g, 1.56 mmol) and 1-methyl-1H-pyrazol-3-amine (0.21 g, 2.12 mmol) in two steps to give a solid (5 mg, 1% yield) as expected product. $^1$H NMR (400 MHz, DMSO-$d_6$) δ 10.90 (s, 1 H) 8.12 (s, 1H) 7.61-7.62 (m, 2 H) 7.38-7.42 (t, 1 H) 7.03-7.06 (m, 1 H) 6.88-6.91 (m, 1 H) 6.58-6.59 (m, 1 H) 6.50 (m, 1H) 3.78 (s, 3 H) 3.00 (s, 3 H) 2.88 (m, 3 H) 2.47-2.48 (m, 3 H). LCMS for $C_{23}H_{21}FN_4O_4$ m/z 437.20 (M+H)$^+$.

Example 273

4-(4-(Dimethylcarbamoyl)-3-fluorophenoxy)-2-methyl-N-(5-methylpyridin-2-yl)benzofuran-6-carboxamide

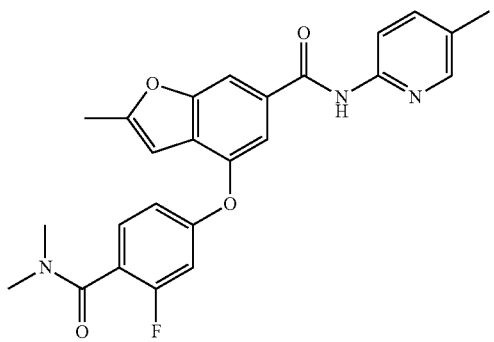

The title compound was prepared in a similar manner as described for Example 271, from ethyl 4-hydroxy-2-methylbenzofuran-6-carboxylate (0.275 g, 1.25 mmol), 2,4-difluoro-N,N-dimethylbenzamide (0.289 g, 1.56 mmol) and 2-amino-5-methyl pyridine (0.229 g, 2.1 mmol) in two steps to give an off-white solid (131 mg, 24% yield). $^1$H NMR (400 MHz, DMSO-$d_6$) δ 10.79 (s, 1 H) 8.21 (m, 1 H) 8.16 (s, 1 H) 8.06-8.08 (d, 1 H)) 7.66 (m, 1 H) 7.64 (m, 1 H) 7.37-7.41 (t, 1 H) 7.02-7.06 (m, 1H) 6.89-6.92 (m, 1 H) 6.50 (s, 1 H) 2.99 (s, 3 H) 2.87 (m, 3 H) 2.47 (m, 3 H) 2.27 (s, 3 H).

Example 274

2-Ethyl-N-(5-methylpyridin-2-yl)-4-[4-(methylsulfonyl)-phenoxy]-1-benzofuran-6-carboxamide

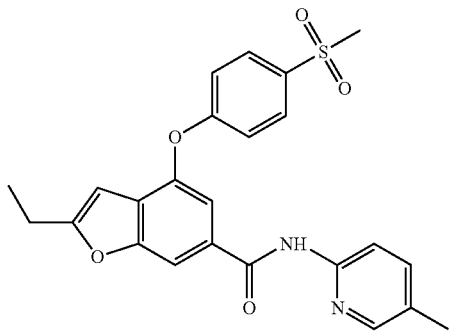

A solution of 2-ethyl-4-[4-(methylsulfonyl)phenoxy]-1-benzofuran-6-carboxylic acid (300 mg, 0.83 mmol), HATU (476 mg, 1.3 mmol) and DIPEA (162 mg, 1.3 mmol) in DMF (20 mL) was stirred for 1 h. After which 5-methylpyridin-2-amine (108 mg, 1.0 mmol) was added. The resulting mixture was stirred overnight. The reaction was monitored by TLC (petroleum ether/EtOAc 1:1). The mixture was poured into water (30 mL) and extracted with EtOAc (30 mL×3). The organic layer was washed with brine (20 mL×2), dried over $Na_2SO_4$ and concentrated. The residue was purified by preparative HPLC to afford the desired product (115.0 mg, 31%) as a white solid. $^1$H NMR (400 MHz, CDCl$_3$): δ 8.52 (s, 1H), 8.18 (d, 1H), 8.04 (s, 1H), 7.86 (d, 3H), 7.52 (d, 1H), 7.42 (s, 1H), 7.06 (d, 2H), 6.20 (s, 1H), 3.00 (s, 3H), 2.74 (q, 2H), 2.24 (s, 3H), 1.26 (t, 3H); MS (ACPI, pos): 451.2.

Preparation of Intermediate 274a (3E)-3-(Ethoxycarbonyl)-4-(5-ethyl-2-furyl)but-3-enoic acid

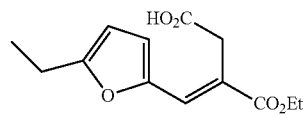

To a suspension of $^t$BuOK (61.4 g, 0.54 mol) in $^t$BuOH (180 mL) was added a suspension of 5-ethyl-2-furaldehyde (22.5 g, 0.18 mol) in succinic acid diethyl ester (142.1 g, 0.82 mol). The reaction mixture was refluxed for 1 h. Then the same amounts of $^t$BuOK, $^t$BuOH and succinic acid diethyl ester were added at the same temperature, and the reaction mixture was stirred at reflux for another 1 h. TLC (petroleum ether/EtOAc 2:1) indicated the complete consumption of the furaldehyde. The reaction mixture was allowed to cool to room temperature, acidified to a pH~2 by 20% aqueous HCl (200 mL) and extracted with EtOAc (500 mL×3). The organic phase was washed with 10% aqueous $Na_2CO_3$ (500 mL×3). The combined aqueous layers was washed with ethyl ether (500 mL) and acidified to a pH~2 with 20% aqueous HCl (100 mL). The aqueous phase was finally extracted with EtOAc (500 mL×4). The combined organic layers were dried over $Na_2SO_4$ and concentrated to give the crude acid (45.4 g, 100%), which was directly used to next step without further purification.

Preparation of Intermediate 274b

Ethyl 4-(acetyloxy)-2-ethyl-1-benzofuran-6-carboxylate

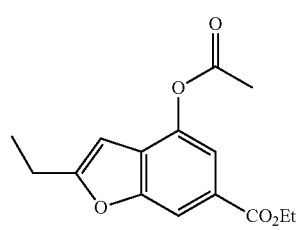

A mixture of (ethoxycarbonyl)-4-(5-ethyl-2-furyl)but-3-enoic acid (45.4 g, 0.18 mol) and sodium acetate (59.0, 0.72 mol) in acetic anhydride (450 mL) was heated to reflux for 5 hours. TLC (petroleum ether/EtOAc 4:1) indicated complete consumption of the starting material. The reaction mixture was concentrated and the residue was poured into 15% aq. $Na_2CO_3$ (500 mL), and extracted with EtOAc (500 mL×3). The combined organic layers was washed with brine (200 mL), dried over Na$_2$SO$_4$, and concentrated. The product was purified via silica gel column chromatography using petroleum ether/EtOAc (70:1) to afford the desired compound (13.0 g, 28%) as a yellow solid.

Preparation of Intermediate 274c

Ethyl 2-ethyl-4-hydroxy-1-benzofuran-6-carboxylate

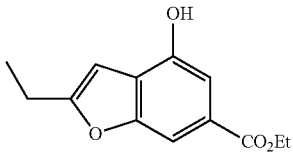

A suspension of ethyl 4-(acetyloxy)-2-ethyl-1-benzofuran-6-carboxylate (8.0 g, 29.0 mmol) and K$_2$CO$_3$ (4.81 g, 34.8 mmol) in ethanol (80 mL) was refluxed for 24 hours. TLC (petroleum ether/EtOAc 4:1) showed complete consumption of the acetate. The solvent was removed under reduced pressure and the residue was poured into water (30 mL). The aqueous phase was acidified to pH~2 with 10% aqueous HCl (50 mL) and extracted with EtOAc (100 mL×2). The organic layer was dried over Na$_2$SO$_4$ and concentrated. The residue was purified by column chromatography on silica gel eluted with petroleum ether/EtOAc (40:1) to afford the desired compound (6.0 g, 88%) as a yellow solid. $^1$H NMR (400 MHz, CDCl$_3$): δ 7.87 (s, 1H), 7.45 (s, 1H), 6.46 (s, 1H), 6.36 (s, 1H), 4.34-4.27 (q, 2H), 2.77-2.71 (q, 2H), 1.40-1.31 (t, 3H), 1.31-1.21 (t, 3H).

Preparation of Intermediate 274d

Ethyl 2-ethyl-4-[4-(methylsulfonyl)phenoxy]-1-benzofuran-6-carboxylate

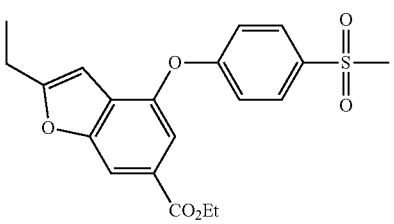

A mixture of ethyl 2-ethyl-4-hydroxy-1-benzofuran-6-carboxylate (0.80 g, 3.4 mmol), 4-fluorophenyl methyl sulfone (0.60 g, 3.4 mmol) and Cs$_2$CO$_3$ (1.12 g, 3.4 mmol) in DMF (40 mL) was heated to 100° C. overnight. The reaction was monitored by TLC (petroleum ether/EtOAc 4:1). The mixture was poured into water (50 mL) and extracted with EtOAc (90 mL×3). The organic layer was washed with brine (50 mL×2), dried over Na$_2$SO$_4$ and concentrated. The product was purified via column chromatography on silica gel eluted with petroleum ether/EtOAc (20:1) to afford the desired compound (0.80 g, 60%) as a colorless oil.

Preparation of Intermediate 274e

2-Ethyl-4-[4-(methylsulfonyl)phenoxy]-1-benzofuran-6-carboxylic acid

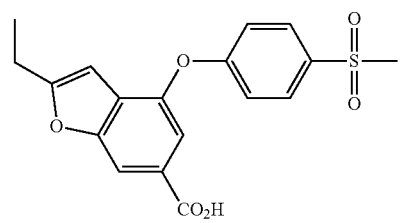

A mixture of ethyl 2-ethyl-4-[4-(methylsulfonyl)phenoxy]-1-benzofuran-6-carboxylate (0.80 g, 2.1 mmol) and KOH (0.35 g, 6.3 mmol) in MeOH (40 mL) and water (4 mL) was heated to reflux overnight. The reaction was monitored by TLC (petroleum ether/EtOAc 4:1). The reaction mixture was concentrated to dryness and poured into water (50 mL). The aqueous layer was acidified to pH~2 with concentrated HCl (4 mL) and extracted with EtOAc (50 mL×3). The organic layer was washed with brine (50 mL×2), dried over Na$_2$SO$_4$ and concentrated to afford the desired compound (0.70 g, 94%) as an off-white solid.

Example 275

2-Ethyl-N-(1-methyl-1H-pyrazol-3-yl)-4-[4-(methylsulfonyl)-phenoxy]-1-benzofuran-carboxamide

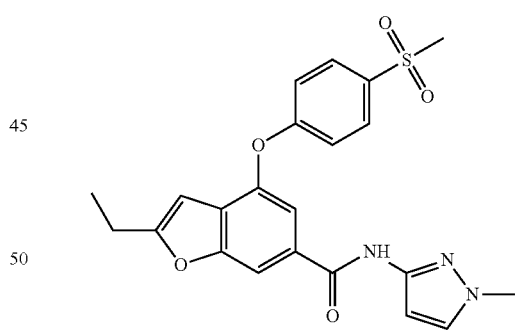

A solution of 2-ethyl-4-[4-(methylsulfonyl)phenoxy]-1-benzofuran-6-carboxylic acid (400 mg, 1.1 mmol), HATU (635 mg, 1.6 mmol) and DIPEA (214 mg, 1.6 mmol) in DMF (20 mL) was stirred for 1 h. Then, 1-methyl-1H-pyrazol-3-amine (129 mg, 1.3 mmol) was added. The resulting solution was stirred overnight. The reaction was monitored by TLC (petroleum ether/EtOAc 1:1). The mixture was poured into water (30 mL) and extracted with EtOAc (30 mL×3). The organic layer was washed with brine (20 mL×2), dried over Na$_2$SO$_4$, concentrated and purified by preparative HPLC to afford the desired product (109.5 mg, 22%) as a yellow solid. $^1$H NMR (400 MHz, DMSO): δ 10.89 (s, 1H), 8.15 (s, 1H), 7.94 (d, 2H), 7.65 (s, 1H), 7.00 (s, 1H), 7.24 (d, 2H), 6.61 (s, 1H), 6.55 (d, 2H), 3.77 (s, 3H), 3.20 (s, 3H), 2.82 (q, 2H), 1.25 (t, 3H); MS (APCl, pos): 440.3.

Example 276

4-{4-[(Dimethylamino)carbonyl]phenoxy}-2-ethyl-N-(5-methylpyridin-2-yl)-1-benzofuran-6-carboxamide

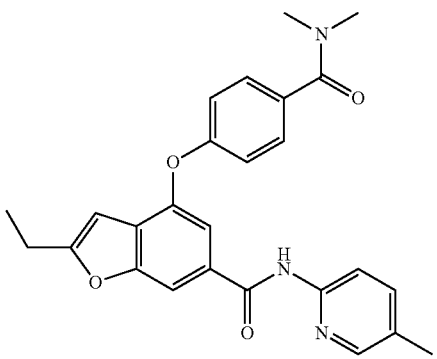

A solution of 4-{4-[(dimethylamino)carbonyl]phenoxy}-2-ethyl-1-benzofuran-6-carboxylic acid (400 mg, 1.13 mmol), HATU (671 mg, 1.70 mmol) and DIPEA (226 mg, 1.70 mmol) in DMF (20 mL) was stirred for 1 h. Then 5-methylpyridin-2-amine (146 mg, 2.26 mmol) was added. The resulting solution was stirred overnight. The reaction was monitored by TLC (petroleum ether/EtOAc 1:1). The mixture was poured into water (30 mL) and extracted with EtOAc (30 mL×3). The organic layer was washed with brine (20 mL×2), dried over $Na_2SO_4$ and concentrated. The product was purified via preparative HPLC to afford the desired compound (133.7 mg, 27%) as a yellow solid. $^1$H NMR (400 MHz, CDCl$_3$): δ 8.92 (bs, 1H), 8.25 (d, 1H), 8.03 (s, 1H), 7.82 (s, 1H), 7.55 (d, 2H), 7.44-7.37 (m, 3H), 6.96 (d, 2H), 6.22 (s, 1H), 3.10-2.93 (d, 6H), 2.74 (q, 2H), 2.26 (s, 3H), 1.26 (t, 3H). LCMS m/z 444.40 (M+H)$^+$.

Preparation of Intermediate 276a

4-Iodo-N,N-dimethylbenzamide

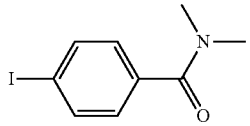

A solution of 4-iodobenzoic acid (2.0 g, 8.0 mmol), HATU (4.6 g, 12.0 mmol) and DIPEA (1.6 g, 12.0 mmol) in DMF (30 mL) was stirred for 1 h. Then, dimethylamine hydrochloride (0.98 mg, 12.0 mmol) was added. The resulting solution was stirred overnight. The reaction was monitored by TLC (petroleum ether/EtOAc 2:1). The reaction mixture was poured into water (30 mL) and extracted with EtOAc (40 mL×3). The organic layer was washed with brine (20 mL×2), dried over $Na_2SO_4$ and concentrated. The product was purified by silica gel column chromatography using petroleum ether/EtOAc (4:1) to afford the desired compound (1.5 g, 60%) as a yellow solid. $^1$H NMR (400 MHz, CDCl$_3$): δ 7.75 (d, 2H), 7.16 (d, 2H), 3.15-2.97 (d, 6H).

Preparation of Intermediate 276b

Ethyl 4-{4-[(dimethylamino)carbonyl]phenoxy}-2-ethyl-1-benzofuran-6-carboxylate

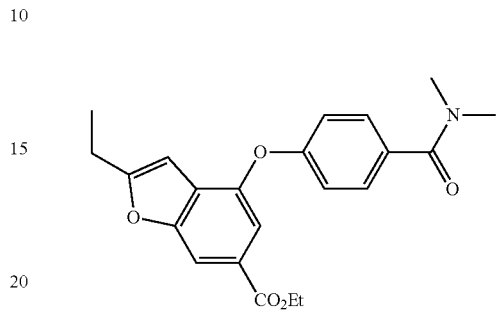

A mixture of ethyl 2-ethyl-4-hydroxy-1-benzofuran-6-carboxylate (0.8 g, 3.4 mmol), 4-iodo-N,N-dimethylbenzamide (0.9 g, 3.3 mmol), $Cs_2CO_3$ (1.12 g, 3.4 mmol) and CuI (400 mg, 2.1 mmol) in pyridine (30 mL) was heated to 100° C. for 24 hours. TLC (petroleum ether/EtOAc 4:1) indicated the complete consumption of the phenol. The solvent was removed under reduced pressure. The residue was poured into water (20 mL) and extracted with EtOAc (30 mL×2). The combined organic layers were washed with brine (20 mL×2), dried over $Na_2SO_4$ and concentrated. The product was purified via silica gel column chromatography using petroleum ether/EtOAc (20:1 to 1:1) to afford the desired compound (400 mg, 30%) as a yellow solid. $^1$H NMR (400 MHz, CDCl$_3$): δ 7.97 (s, 1H), 7.56 (s, 1H), 7.43 (d, 2H), 7.00 (d, 2H), 6.27 (s, 1H), 4.44-4.35 (q, 2H), 3.15-3.04 (d, 6H), 2.83-2.78 (q, 2H), 1.45-1.37 (t, 3H), 1.37-1.26 (t, 3H).

Preparation of Intermediate 276c

4-{4-[(Dimethylamino)carbonyl]phenoxy}-2-ethyl-1-benzofuran-6-carboxylic acid

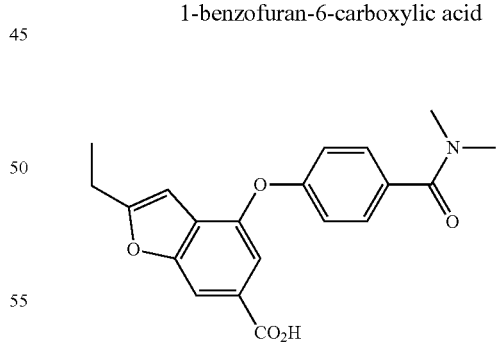

A suspension of ethyl 4-{4-[(dimethylamino)carbonyl]phenoxy}-2-ethyl-1-benzofuran-6-carboxylate (400 mg, 1.0 mmol) and LiOH.H$_2$O (200 mg, 4.7 mmol) in MeOH (20 mL) and water (2 mL) was stir for 4 hr at room temperature. TLC (petroleum ether/EtOAc 4:1) indicated the reaction was complete. The reaction mixture was concentrated to dryness and poured into water (30 mL). The aqueous layer was acidified to pH~2 with conc. HCl and extracted with EtOAc (20 mL×3). The organic layer was washed with brine (25 mL×2), dried over Na$_2$SO$_4$ and concentrated to afford the desired product (350 mg, 99%) as a yellow solid.

Example 277

N,N-Dimethyl-5-[(2-methyl-6-{[(5-methylpyridin-2-yl)amino]-carbonyl}-1-benzofuran-4-yl)oxy]pyridine-2-carboxamide

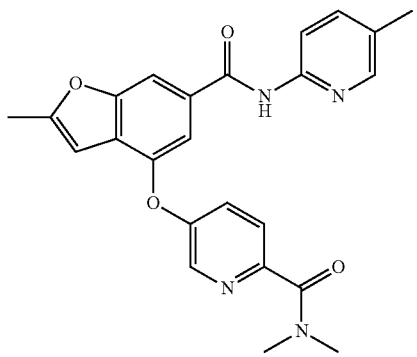

To a solution of 5-methylpyridin-2-amine (191 mg, 1.76 mmol) in DCE at 0° C. was added Al(CH$_3$)$_2$Cl drop-wise. After stirring the mixture at room temperature for 20 minutes ethyl 4-({6-[(dimethylamino)carbonyl]pyridin-3-yl}oxy)-2-methyl-1-benzofuran-6-carboxylate (65 mg, 0.18 mmol) was added. The reaction was stirred at room temperature for 14 hours. The sample was diluted with CH$_2$Cl$_2$ and quenched with potassium sodium tartrate tetrahydrate (20% w/w) (1 mL). Caution, addition was done slowly. The organic layer was washed with brine, dried over Na$_2$SO$_4$ and concentrated. The crude sample was introduced into a silica gel column and eluted with MeOH/CHCl$_3$ (3/97) to provide the product (35 mg, 85% yield) as white solid. $^1$H NMR (300 MHz, CHLOROFORM-d) δ ppm 2.32 (s, 3 H) 2.48 (s, 3 H) 3.16 (d, J=7.54 Hz, 6 H) 6.26 (s, 1 H) 7.31 (dd, J=8.67, 2.83 Hz, 1 H) 7.48 (d, J=1.13 Hz, 1 H) 7.58 (d, J=6.78 Hz, 1 H) 7.69 (d, J=8.67 Hz, 1 H) 7.87 (s, 1 H) 8.12 (s, 1 H) 8.26 (d, J=8.48 Hz, 1 H) 8.38 (e, J=2.64 Hz, 1H) 8.53 (s, 1 H); MS (ESI, pos): 431.

Preparation of Intermediate 277a

5-Bromo-N,N-dimethylpyridine-2-carboxamide

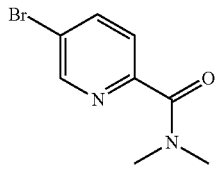

To a solution of 5-bromopyridine-2-carboxylic acid (1.5 g, 7.4 mmol), dimethyl amine (1.3 gm, 16 mmol), diisopropylethyl amine (excess) in DMF (10 mL) was added a solution of HATU in DMF (5 mL). After stirring the reaction for 14 hours at room temperature, the solvent was removed under reduced vacuum. The residue was taken up in ethyl acetate, washed with 1 N HCl (2×), brine (2×), 1 N NaOH (2×), brine (3×), dried over MgSO$_4$, and concentrated. The crude was product was used in subsequent steps without further purification.

Preparation of Intermediate 277b

5-Bromo-N,N-dimethylpyridine-2-carboxamide 1-oxide

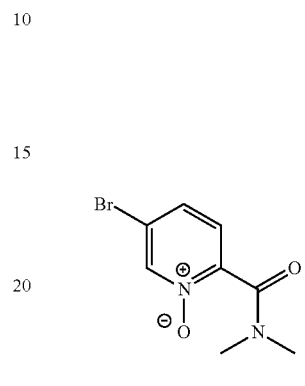

To a solution of 5-bromo-N,N-dimethylpyridine-2-carboxamide (730 mg, 3.19 mmol) in 10 mL of HOAc was added 1 ml of 35% H$_2$O$_2$. After stirring the mixture at 78° C. for 14 hours, it was cooled and concentrated under reduced pressure. The residue was made alkaline with excess solid Na$_2$CO$_3$ and diluted with 25 mL of CHCl$_3$ with stirring. The inorganic salts were filtered off, and the organic layer was dried over Na$_2$SO$_4$. The solvent was evaporated under reduced pressure to provided the product (750 mg, 98%), which was used without further purification. MS (ESI, pos): 247.00.

Preparation of Intermediate 277c

Ethyl 4-({6-[(dimethylamino)carbonyl]-1-oxidopyridin-3-yl}oxy)-2-methyl-1-benzofuran-6-carboxylate

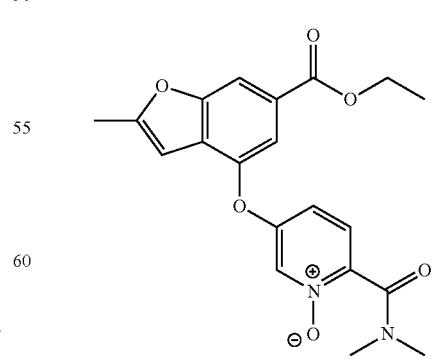

The title compound was synthesized in a similar fashion as described for Intermediate 252d, by reacting ethyl 4-hydroxy-2-methylbenzofuran-6-carboxylate and 5-bromo-N,N-dimethylpyridine-2-carboxamide 1-oxide. LC-MS (ESI, pos): 386.00.

Preparation of Intermediate 277d

Ethyl 4-({6-[(dimethylamino)carbonyl]pyridin-3-yl}oxy)-2-methyl-1-benzofuran-6-carboxylate

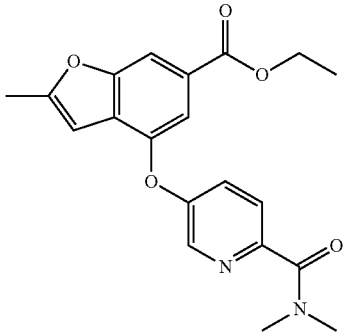

To a stirred solution of ethyl 4-({6-[(dimethylamino)carbonyl]-1-oxidopyridin-3-yl}oxy)-2-methyl-1-benzofuran-6-carboxylate (176 mg, 0.457 mmol) in 15 mL of acetic acid, was added powdered Fe while keeping the temperature at 70° C. for 2 hrs. LC-MS showed that the reaction was complete. The reaction was cooled to room temperature, and the insoluble material was filtered. The mother liquor was diluted with EtOAc, washed with NaHCO$_3$, brine, and dried over Na$_2$SO$_4$, and concentrated. The crude product was introduced into a silica gel column and eluted with MeOH/CHCl$_3$ (2/98 to 5/95) to provide the product (135 mg, 85% yield) as colorless oil. $^1$H NMR (300 MHz, CHLOROFORM-d) δ ppm 1.40 (t, J=7.16 Hz, 3H) 2.47 (s, 3 H) 3.15 (d, 6 H) 4.39 (q, J=7.03 Hz, 2 H) 6.25 (s, 1 H) 7.30 (d, J=2.45 Hz, 1 H) 7.55-7.64 (m, 1 H) 7.64-7.76 (m, 1 H) 8.00 (s, 1 H) 8.38 (s, 1 H); LC-MS (ESI)+m/z=369.00 (M+H)$^+$.

Example 278

N,N-Dimethyl-5-(2-methyl-6-((2-methyl-2H-1,2,3-triazol-4-yl)carbamoyl)-benzofuran-4-yloxy)picolinamide

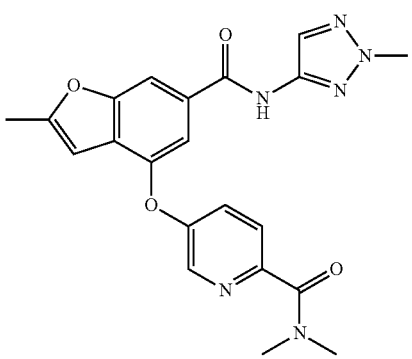

The title compound was prepared in a similar manner as described for Example 277, from Intermediate 277d and 2-methyl-2H-1,2,3-triazol-4-amine. $^1$H NMR (300 MHz, CHLOROFORM-d) δ 2.48 (s, 3H) 3.15 (d, J=7.16 Hz, 6 H) 4.12 (s, 3 H) 6.27 (s, 1 H) 7.31 (dd, J=8.67, 2.83 Hz, 1 H) 7.43 (s, 1 H) 7.69 (d, J=8.67 Hz, 1 H) 7.83 (s, 1 H) 8.10 (s, 1 H) 8.37 (d, J=2.64 Hz, 1 H) 8.51 (s, 1 H). LCMS m/z 421.00 (M+H)$^+$.

Example 279

5-(6-((5-Methoxypyrazin-2-yl)carbamoyl)-2-methyl-benzofuran-4-yloxy)-N,N-dimethylpicolinamide

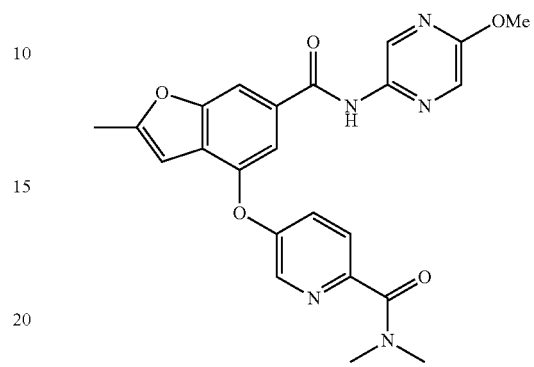

The title compound was prepared in a similar manner as described for Example 277, from Intermediate 277d and 5-methoxypyrazin-2-amine. $^1$H NMR (300 MHz, CHLOROFORM-d) δ 2.48 (s, 3 H) 3.15 (d, 6 H) 3.99 (s, 3 H) 6.27 (s, 1 H) 7.28-7.38 (m, 1 H) 7.48 (s, 1 H) 7.61-7.76 (m, 1 H) 7.79-8.02 (m, 2 H) 8.30-8.47 (m, 2 H) 9.19 (s, 1 H). LCMS m/z 448.00 (M+H)$^+$.

Example 280

N[5-(Dimethylamino)pyrazin-2-yl]-2-methyl-4-{[5-(methylsulfonyl)pyridin-2-yl]oxy}-1-benzofuran-6-carboxamide

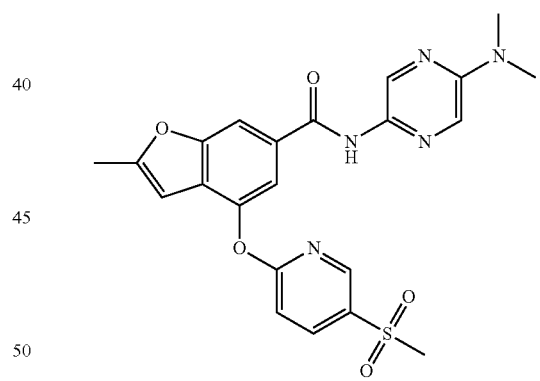

To a solution of N$^2$-N$^2$-dimethylpyrizane-diamine (368 mg, 2.66 mmol) in DCE at 0° C. was added Al(CH$_3$)$_2$Cl (3.0 mL, 1.0M) drop wise. After the reaction was stirred at room temperature for 20 minutes, ethyl 2-methyl-4-{[5-(methylsulfonyl)pyridin-2-yl]oxy}-1-benzofuran-6-carboxylate (100 mg, 0.26 mmol) was added. The reaction was stirred at room temperature for 14 hours. The sample was diluted with CH$_2$Cl$_2$ and quenched with potassium sodium tartrate tetrahydrate (20% w/w) (1 mL) slowly (caution). The organic layer was washed with brine and dried over Na$_2$SO$_4$ and concentrated. The crude sample was introduced into a silica gel column and eluted with (5-10% MeOH/CHCl$_3$) to provide the product (110 mg, 85% yield) as white solid. $^1$H NMR (300 MHz, CHLOROFORM-d) δ 1.59 (s, 3 H) 2.48 (s, 3 H) 3.12 (s, 6 H) 6.22 (s, 1 H) 7.16 (d, J=8.67 Hz, 1 H) 7.58 (d, J=1.13 Hz, 1 H) 7.70 (d, J=1.32 Hz, 1 H) 7.92 (s, 1H) 8.23 (dd, J=8.57, 2.54 Hz, 2 H) 8.69 (d, J=2.45 Hz, 1 H) 9.15 (d, J=1.32 Hz, 1 H); MS (ESI, pos): 468.

Preparation of Intermediate 280a

Ethyl 2-methyl-4-{[5-(methylsulfonyl)pyridin-2-yl]oxy}-1-benzofuran-6-carboxylate

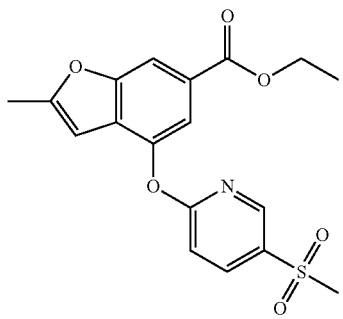

A mixture of ethyl 4-hydroxy-2-methyl-1-benzofuran-6-carboxylate (500 mg, 2.27 mmol), 2-bromo-5-methanesulfonyl pyridine (590 mg, 2.57 mmol), Cs$_2$CO$_3$ (1.1 g, 4.12 mmol) and CuI (100 mg, 1 mmol) in DMF (20 mL) was heated to 100° C. for 4 hours. The solvent was removed under reduced pressure. The residue was poured into water (20 mL) and extracted with EtOAc (50 mL×2). The combined organic layer was washed with brine (20 mL×2), dried over Na$_2$SO$_4$ and concentrated. The product was purified via gradient silica gel chromatography on silica gel using EtOAc/Hex (10/90 to 30/70) to afford the title compound (830 mg, 88%) as a white solid. $^1$H NMR (300 MHz, CHLOROFORM-d) δ ppm 1.42 (t, J=7.16 Hz, 3 H) 2.48 (s, 3 H) 3.01-3.19 (m, 3 H) 4.41 (q, J=7.16 Hz, 2 H) 6.23 (d, J=0.94 Hz, 1 H) 7.02-7.18 (m, 2 H) 7.64 (d, J=1.13 Hz, 1 H) 7.85-7.96 (m, 1 H) 8.02-8.10 (m, 1 H); (ESI, pos): 376.

Examples 281-284 were prepared in a similar manner as described for Example 280, from Intermediate 280a and the appropriate amino heterocycles.

Example 281

2-Methyl-N-(5-methylpyridin-2-yl)-4-(5-(methylsulfonyl)pyridin-2-yloxy)-benzofuran-6-carboxamide

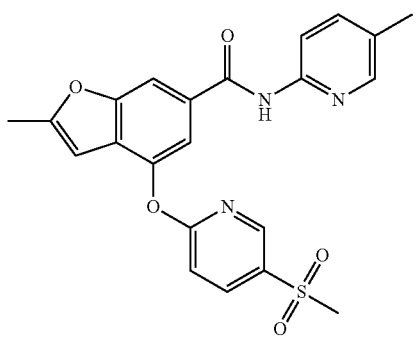

Example 282

2-Methyl-N-(2-methyl-2H-1,2,3-triazol-4-yl)-4-(5-(methylsulfonyl)pyridin-2-yloxy)benzofuran-6-carboxamide

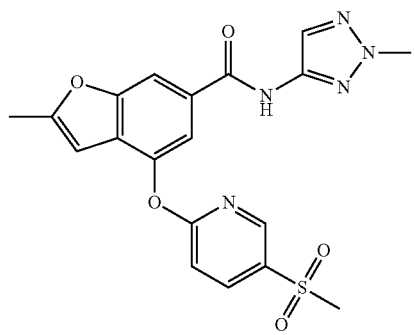

Example 283

2-Methyl-N-(1-methyl-1H-pyrazol-3-yl)-4-(5-(methylsulfonyl)-pyridin-2-yloxy)-benzofuran-6-carboxamide

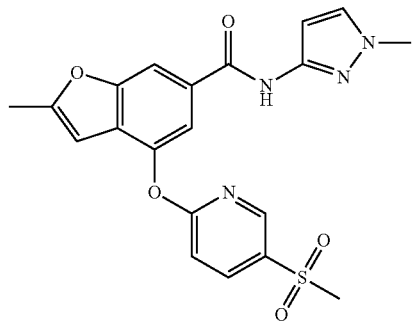

Example 284

N-(5-Methoxypyrazin-2-yl)-2-methyl-4-(5-(methylsulfonyl)-pyridin-2-yloxy)-benzofuran-6-carboxamide

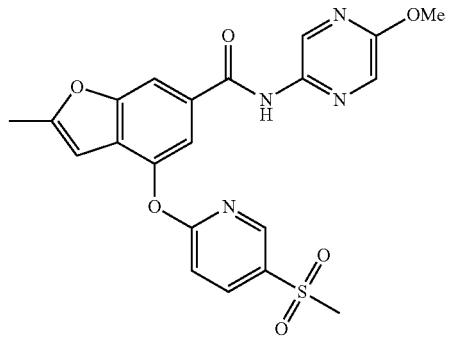

| Example | MW | MF | NMR | m/z |
|---|---|---|---|---|
| 281 | 437.5 | C22H19N3O5S | 1H NMR (300 MHz, CHLOROFORM-d) d ppm 2.32 (s, 3 H) 2.48 (s, 3 H) 3.11 (s, 3 H) 6.23 (s, 1 H) 7.17 (d, J = 8.67 Hz, 1 H) 7.55-7.68 (m, 2 H) 7.95 (s, 1 H) 8.11 (s, 1 H) 8.19-8.40 (m, 2 H) 8.64 (d, 1 H) 8.69 (d, J = 2.45 Hz, 1 H) | 438.00 |
| 282 | 427.4 | C19H17N5O5S | 1H NMR (300 MHz, DMSO-d6) d ppm 2.50 (s, 3 H) 3.33 (s, 3 H) 4.14 (s, 3 H) 6.50 (s, 1 H) 7.44 (d, J = 8.67 Hz, 1 H) 7.80 (s, 1 H) 8.02 (s, 1 H) 8.22 (s, 1 H) 8.42 (dd, J = 8.67, 2.64 Hz, 1 H) 8.66 (d, J = 2.45 Hz, 1 H) 11.35 (s, 1 H) | 428.00 |
| 283 | 426.5 | C20H18N4O5S | 1H NMR (300 MHz, CHLOROFORM-d) d ppm 2.47 (s, 3 H) 3.11 (s, 3 H) 3.77 (s, 3 H) 6.22 (s, 1 H) 6.82 (d, J = 2.26 Hz, 1 H) 7.05-7.21 (m, 1 H) 7.28 (d, J = 2.26 Hz, 1 H) 7.55 (d, J = 1.13 Hz, 1 H) 7.89 (s, 1 H) 8.22 (dd, J = 8.67, 2.45 Hz, 1 H) 8.68 (d, J = 2.45 Hz, 1 H) 8.86 (s, 1 H) | 427.00 |
| 284 | 454.5 | C21H18N4O6S | 1H NMR (300 MHz, DMSO-d6) d ppm 2.47 (s, 3 H) 3.32 (s, 3 H) 3.93 (s, 3 H) 6.47 (s, 1 H) 7.41 (d, J = 8.67 Hz, 1 H) 7.80 (s, 1 H) 8.20 (d, J = 7.16 Hz, 2 H) 8.39 (dd, J = 8.67, 2.64 Hz, 1 H) 8.63 (d, J = 2.45 Hz, 1 H) 8.94 (s, 1 H) 10.94 (s, 1 H) | 455.00 |

Example 285

N2,N2-Dimethyl-N6-(5-methylpyridin-2-yl)-4-(4-(methylsulfonyl)-phenoxy)-benzofuran-2,6-dicarboxamide

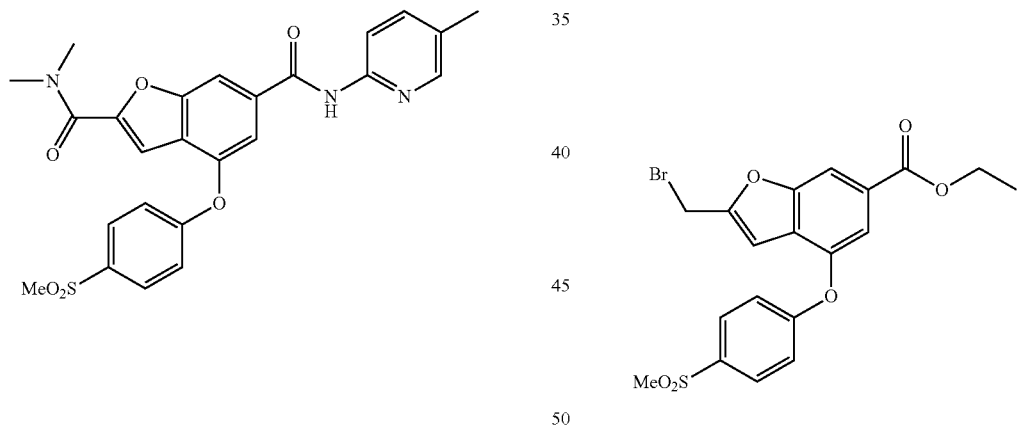

2-Amino-5-methyl pyridine (226 mg, 2.09 mmol) was dissolved in DCE (10 mL) at 0° C., and Al(CH$_3$)$_2$Cl (2.09 mL, 1M in hexanes) was then added drop-wise. After stirring the mixture at room temperature for 30 minutes, ethyl 2-(dimethylcarbamoyl)-4-(4-(methylsulfonyl)phenoxy)-benzofuran-6-carboxylate (90 mg, 0.21 mmol) was then added and the stirring was continued for another 14 h. The reaction was quenched with potassium sodium tartrate tetrahydrate (20% w/w) cautiously. The product was extracted with CHCl$_3$, washed with brine, and dried over MgSO$_4$. The product was purified by reverse phase HPLC to give the title compound (61 mg, 61%) as a white solid. $^1$H NMR (300 MHz, CHLOROFORM-D) δ ppm 2.32 (s, 3 H) 3.08 (s, 3 H) 3.15 (s, 3 H) 3.34 (s, 3 H) 7.12-7.18 (m, 2 H) 7.19 (s, 1 H) 7.58 (dd, J=8.48, 2.26 Hz, 1 H) 7.87-7.98 (m, 2 H) 7.99 (s, 1 H) 8.11 (s, 1 H) 8.24 (d, J=8.48 Hz, 1 H) 8.64 (s, 1 H). LCMS m/z 494.0 (M+H)$^+$.

Preparation of Intermediate 285a

Ethyl 2-(bromomethyl)-4-(4-(methylsulfonyl)phenoxy)-benzofuran-6-carboxylate

To a solution of ethyl 2-methyl-4-(4-(methylsulfonyl)phenoxy)benzofuran-6-carboxylate (252d) (226 mg, 0.604 mmol) and NBS (183 mg, 1.03 mmol) in CHCl$_3$ (10 mL) was added benzoyl peroxide (14.6 mg, 0.0604 mmol). After stirring the mixture at refluxed for 4 hr, the solvent was evaporated. The product was purified by gradient silica gel chromatography with hexanes/EtOAc (100/0 to 70/30) to give the title compound (200 mg, 73%) as a white solid. $^1$H NMR (300 MHz, CHLOROFORM-D) δ ppm 1.39 (t, J=7.16 Hz, 3 H) 3.07 (s, 3 H) 4.39 (q, J=7.16 Hz, 2 H) 4.53 (s, 2 H) 6.62 (s, 1

H) 7.05-7.18 (m, 2 H) 7.62 (d, J=0.75 Hz, 1 H) 7.86-7.98 (m, 2 H) 8.07 (d, J=0.75 Hz, 1 H).

Preparation of Intermediate 285b

Ethyl 2-formyl-4-(4-(methylsulfonyl)phenoxy)benzofuran-6-carboxylate

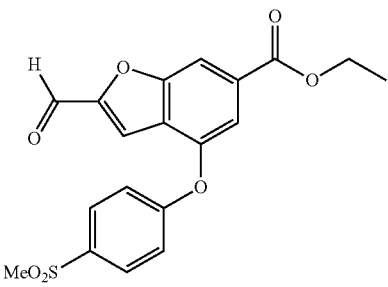

A solution of ethyl 2-(bromomethyl)-4-(4-(methylsulfonyl)phenoxy)benzofuran-6-carboxylate (320 mg, 0.706 mmol) and IBX (395 mg, 1.41 mmol) in DMSO (2 mL) was heated at 65° C. for 3 h. The reaction was quenched with water and the product was extracted with $CHCl_3$. The combined organic layers were washed with water (2×), dried over $MgSO_4$, and concentrated. The product was purified by gradient chromatography on silica gel using hexanes/EtOAc (100/0 to 40/60) to give the title compound (230 mg, 84%) as a white solid. $^1$H NMR (300 MHz, CHLOROFORM-D) δ ppm 1.40 (t, J=7.16 Hz, 3 H) 3.09 (s, 3H) 4.41 (q, J=7.16 Hz, 2 H) 7.14-7.23 (m, 2 H) 7.46 (d, J=0.94 Hz, 1 H) 7.62 (d, J=0.94 Hz, 1 H) 7.89-8.02 (m, 2 H) 8.15 (t, J=0.94 Hz, 1 H) 9.89 (s, 1 H).

Preparation of Intermediate 285c 6-(Ethoxycarbonyl)-4-(4-(methylsulfonyl)-phenoxy)-benzofuran-2-carboxylic acid

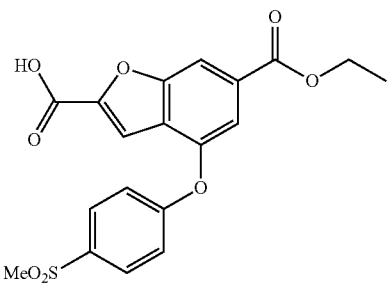

To 10 mL of acetonitrile was added periodic acid (232 mg, 1.02 mmol), and the solution was stirred vigorously at room temperature for 15 min. Ethyl 2-formyl-4-(4-(methylsulfonyl)phenoxy)-benzofuran-6-carboxylate (360 mg, 0.927 mmol) was then added at 0° C. followed by the addition of pyridium fluorochromate (3.69 mg, 0.0185 mmol) in $CH_3CN$ (1 mL). The reaction was stirred at 0° C. for 1 hour. The reaction was diluted with ethyl acetate and washed with brine. The organic layer was dried and concentrated to give the title compound (355 mg, 95%) as an orange solid. The crude product was used in the next step without further purification. $^1$H NMR (300 MHz, CHLOROFORM-D) δ ppm 1.40 (t, J=7.16 Hz, 3 H) 3.09 (s, 3 H) 4.41 (q, J=7.16 Hz, 2 H) 7.12-7.22 (m, 2 H) 7.55 (d, J=1.13 Hz, 1 H) 7.63 (d, J=1.13 Hz, 1 H) 7.92-8.02 (m, 2 H) 8.17 (s, 1 H).

Preparation of Intermediate 285d

Ethyl 2-(dimethylcarbamoyl)-4-(4-(methylsulfonyl)-phenoxy)-benzofuran-6-carboxylate

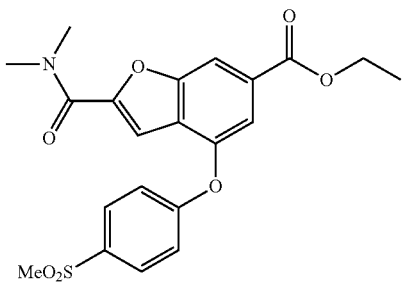

To a solution of 6-(ethoxycarbonyl)-4-(4-(methylsulfonyl)phenoxy)benzofuran-2-carboxylic acid (450 mg, 1.11 mmol) in DMF (10 mL) was added HATU (846 mg, 2.23 mmol), DIEA (719 mg, 5.56 mmol) and the solution was stirred at 0° C. for 15 min. Dimethylamine hydrochloride (136 mg, 1.67 mmol) was added and the solution was warmed gradually to room temperature and stirred for 14 h. Water was added and the product was extracted with $CHCl_3$. The combined organic layers were washed with water (2×), brine, dried over $Na_2SO_4$, and concentrated. The product was purified by gradient silica gel chromatography using $CHCl_3$/MeOH (100/0 to 95/5) to give the title compound (460 mg, 96%) as a light yellow solid. $^1$H NMR (300 MHz, CHLOROFORM-D) δ ppm 1.40 (t, J=7.16 Hz, 3 H) 3.07 (s, 3 H) 3.13 (s, 3 H) 3.33 (s, 3 H) 4.40 (q, J=7.16 Hz, 2 H) 7.07-7.15 (m, 2 H) 7.16 (d, J=0.75 Hz, 1 H) 7.65 (d, J=0.94 Hz, 1 H) 7.87-7.94 (m, 2H) 8.10-8.15 (d, J=0.94 Hz, 1 H).

Examples 286-292 were prepared in a similar manner as described for Example 285, from Intermediate 285d or ethyl 2-(azetidine-1-carbonyl)-4-(4-(methylsulfonyl)phenoxy) benzofuran-6-carboxylate, which was prepared in a similar manner as described for Intermediate 285d, from Intermediate 285c and azetidine hydrochloride.

Example 286

N2,N2-Dimethyl-N6-(1-methyl-1H-pyrazol-3-yl)-4-[4-(methylsulfonyl)phenoxy]-1-benzofuran-2,6-dicarboxamide

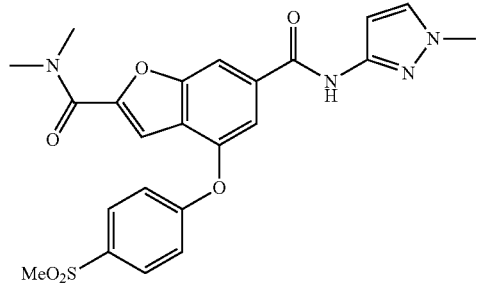

Example 287

N6-(5-Methoxypyrazin-2-yl)-N2,N2-dimethyl-4-[4-(methylsulfonyl)phenoxy]-1-benzofuran-2,6-dicarboxamide

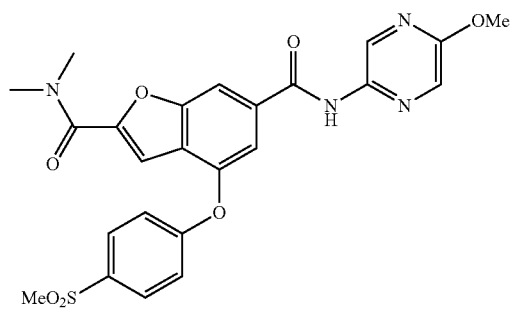

Example 288

N2,N2-Dimethyl-4-[4-(methylsulfonyl)phenoxy]-N6-(2-methyl-2H-1,2,3-triazol-4-yl)-1-benzofuran-2,6-dicarboxamide

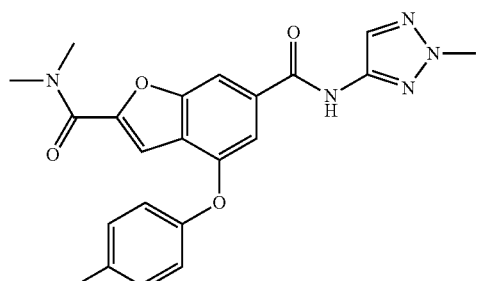

Example 289

N6-(4-Methoxypyridin-2-yl)-N2,N2-dimethyl-4-[4-(methylsulfonyl)phenoxy]-1-benzofuran-2,6-dicarboxamide

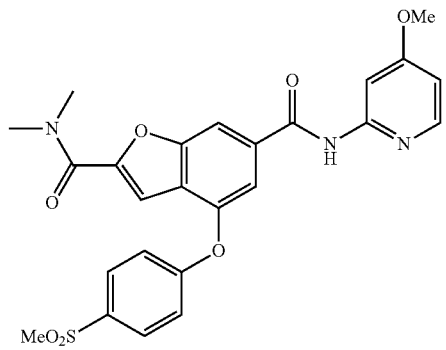

Example 290

2-(Azetidin-1-ylcarbonyl)-N-(5-methylpyridin-2-yl)-4-[4-(methylsulfonyl)-phenoxy]-1-benzofuran-6-carboxamide

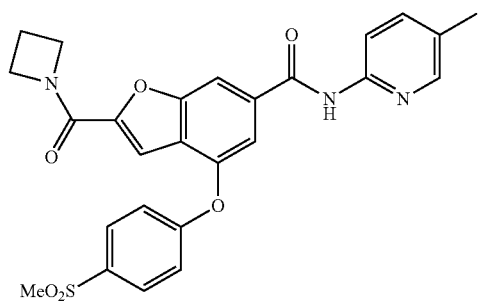

Example 291

2-(Azetidin-1-ylcarbonyl)-N-(1-methyl-1H-pyrazol-3-yl)-4-[4-(methylsulfonyl)-phenoxy]-1-benzofuran-6-carboxamide

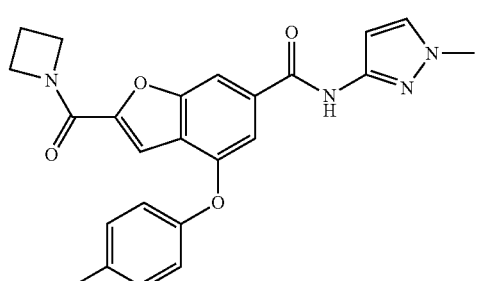

Example 292

2-(Azetidin-1-ylcarbonyl)-4-[4-(methylsulfonyl)phenoxy]-N-(2-methyl-2H-1,2,3-triazol-4-yl)-1-benzofuran-6-carboxamide

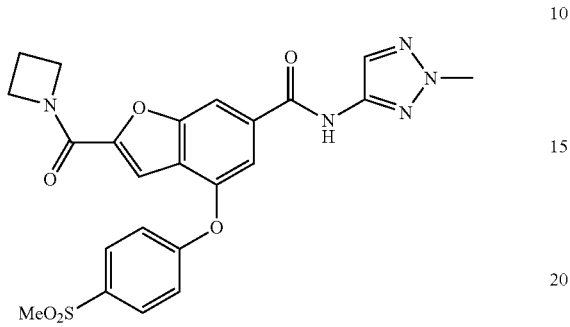

| Example | MW | MF | NMR | m/z |
|---|---|---|---|---|
| 286 | 482.5 | C23H22N4O6S | 1H NMR (300 MHz, CHLOROFORM-D) d ppm 3.08 (s, 3 H) 3.14 (s, 3 H) 3.33 (s, 3 H) 3.79 (s, 3 H) 6.79 (d, J = 2.26 Hz, 1 H) 7.11-7.20 (m, 3 H) 7.29 (d, J = 2.26 Hz, 1 H) 7.45 (d, J = 1.13 Hz, 1 H) 7.88-8.05 (m, 3 H) 8.58 (s, 1 H) | 483.00 |
| 287 | 510.5 | C24H22N4O7S | 1H NMR (300 MHz, CHLOROFORM-D) d ppm 3.08 (s, 3 H) 3.15 (s, 3 H) 3.34 (s, 3 H) 3.98 (s, 3 H) 7.16 (d, J = 8.67 Hz, 2 H) 7.19 (s, 1 H) 7.52 (s, 1 H) 7.88-7.97 (m, 3 H) 7.98 (s, 1 H) 8.40 (s, 1 H) 9.16 (s, 1 H) | 511.00 |
| 288 | 483.5 | C22H21N5O6S | 1H NMR (300 MHz, CHLOROFORM-D) d ppm 3.08 (s, 3 H) 3.15 (s, 3 H) 3.33 (s, 3 H) 4.11 (s, 3 H) 7.10-7.21 (m, 3 H) 7.48 (d, J = 1.13 Hz, 1 H) 7.88-7.99 (m, 3 H) 8.09 (s, 1 H) 8.64 (s, 1 H) | 484.00 |
| 289 | 509.5 | C25H23N3O7S | 1H NMR (300 MHz, CHLOROFORM-D) d ppm 3.08 (s, 3 H) 3.15 (s, 3 H) 3.34 (s, 3 H) 3.90 (s, 3 H) 6.64 (dd, J = 5.84, 2.26 Hz, 1 H) 7.17 (d, J = 8.67 Hz, 2 H) 7.20 (s, 1 H) 7.53 (s, 1 H) 7.93 (d, J = 8.67 Hz, 2 H) 7.97-8.03 (m, 2 H) 8.05 (d, J = 5.84 Hz, 1 H) 9.02 (s, 1H) | 510.00 |
| 290 | 505.6 | C26H23N3O6S | 1H NMR (300 MHz, CHLOROFORM-D) d ppm 2.32 (s, 3 H) 2.39-2.56 (m, 2 H) 3.08 (s, 3 H) 4.26 (t, J = 7.82 Hz, 2 H) 4.69 (t, J = 7.82 Hz, 2 H) 7.09-7.19 (m, 2 H) 7.28 (s, 1 H) 7.51 (d, J = 1.13 Hz, 1 H) 7.58 (dd, J = 8.29, 1.98 Hz, 1 H) 7.88-7.96 (m, 2 H) 7.97 (s, 1 H) 8.12 (s, 1 H) 8.23 (d, J = 8.29 Hz, 1 H) 8.49 (s, 1 H) | 506.00 |
| 291 | 494.5 | C24H22N4O6S | 1H NMR (300 MHz, CHLOROFORM-D) d ppm 2.38-2.53 (m, 2 H) 3.09 (s, 3 H) 3.81 (s, 3 H) 4.25 (t, J = 7.82 Hz, 2 H) 4.68 (t, J = 7.63 Hz, 2 H) 6.79 (d, J = 2.26 Hz, 1 H) 7.10-7.20 (m, 2 H) 7.27 (s, 1 H) 7.30 (d, J = 2.26 Hz, 1 H) 7.45 (d, J = 1.13 Hz, 1 H) 7.84-8.04 (m, 3 H) 8.50 (s, 1 H) | 495.00 |
| 292 | 495.5 | C23H21N5O6S | 1H NMR (300 MHz, CHLOROFORM-D) d ppm 2.37-2.55 (m, 2 H) 3.09 (s, 3 H) 4.12 (s, 3 H) 4.26 (t, J = 7.72 Hz, 2 H) 4.69 (t, J = 7.63 Hz, 2 H) 7.11-7.19 (m, 2 H) 7.27 (s, 1 H) 7.47 (d, J = 0.94 Hz, 1 H) 7.86-8.00 (m, 3 H) 8.10 (s, 1 H) 8.54 (s, 1 H) | 496.00 |

Example 293

4-{4-[(Dimethylamino)sulfonyl]-3-fluorophenoxy}-N-(4-methoxypyridin-2-yl)-2-methyl-1-benzofuran-6-carboxamide

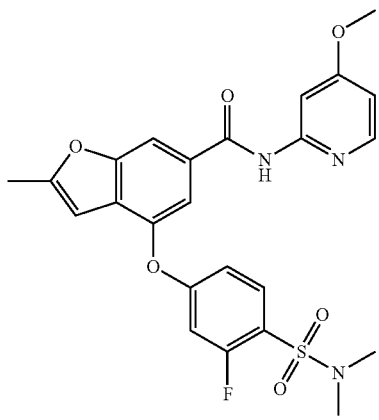

To a solution of 4-methoxypyridin-2-amine (295 mg, 2.37 mmol) in DCE at 0° C. was added Al(CH₃)₂Cl (3.0 mL, 1.0M) drop wise, and the reaction was stirred for 20 minutes at room temperature. Ethyl 4-{4-[(dimethylamino)sulfonyl]-3-fluorophenoxy}-2-methyl-1-benzofuran-6-carboxylate (100 mg, 0.24 mmol) was then added and the reaction was stirred at room temperature for an additional 14 hours. The sample was diluted with CH₂Cl₂ and quenched with potassium sodium tartrate tetrahydrate (20% w/w) (1 mL). The organic layer was washed with brine and dried over Na₂SO₄ and concentrated under reduced pressure. The crude sample was introduced into a silica gel column and eluted with MeOH/CHCl₃ (5/95-10/90) to provide the product (110 mg, 93% yield) as white solid. $^1$H NMR (300 MHz, CHLOROFORM-d) δ ppm 2.49 (s, 3 H) 2.84 (d, J=1.51 Hz, 6 H) 3.91 (s, 3 H) 6.26 (s, 1 H) 6.64 (dd, J=5.75, 2.35 Hz, 1 H) 6.71-6.91 (m, 2 H) 7.52 (s, 1 H) 7.81 (t, J=8.29 Hz, 1 H) 7.91 (s, 1 H) 8.01 (s, 1 H) 8.09 (d, J=5.84 Hz, 1 H) 8.59 (s, 1 H); MS (ESI, pos): 500.

Preparation of Intermediate 293a

Ethyl 4-{4-[(dimethylamino)sulfonyl]-3-fluorophenoxy}-2-methyl-1-benzofuran-6-carboxylate

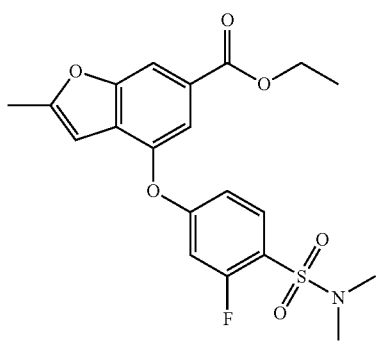

A mixture of ethyl 4-hydroxy-2-methyl-1-benzofuran-6-carboxylate (500 mg, 2.27 mmol), 2,4-difluoro-N,N-dimethylbenzenesulfonamide (553 mg, 2.75 mmol), Cs₂CO₃ (1.1 g, 4.12 mmol) and CuI (100 mg, 1 mmol) in DMF (20 mL) was heated to 100° C. for 4 hours. The solvent was removed under reduced pressure. The residue was poured into water (20 mL) and extracted with EtOAc (50 mL×2). The combined organic layers was washed with brine (20 mL×2), dried over Na₂SO₄ and concentrated. The product was purified via gradient silica gel column chromatography using EtOAc/Hex (10/90 to 30/70) to afford the desired compound (850 mg, 91%) as a white solid. $^1$H NMR (300 MHz, CHLOROFORM-d) δ ppm 1.41 (t, J=7.16 Hz, 3 H) 2.48 (s, 3 H) 2.78-2.94 (m, 6 H) 4.40 (q, J=7.10 Hz, 2 H) 6.24 (s, 1 H) 6.66-6.94 (m, 2 H) 7.65 (s, 1 H) 7.79 (t, J=8.38 Hz, 1 H) 8.04 (s, 1 H); MS (ESI, pos): 422.

Examples 294-308 were prepared in a similar manner as described for Example 293, from Intermediate 293a, or ethyl 4-(4-(azetidin-1-ylsulfonyl)phenoxy)-2-methylbenzofuran-6-carboxylate, which was prepared in a similar manner as described for Intermediate 293a, from ethyl 4-hydroxy-2-methyl-1-benzofuran-6-carboxylate and 1-(4-fluorophenylsulfonyl)azetidine.

Example 294

4-(4-(Azetidin-1-ylsulfonyl)phenoxy)-2-methyl-N-(1-methyl-1H-pyrazol-3-yl)benzofuran-6-carboxamide

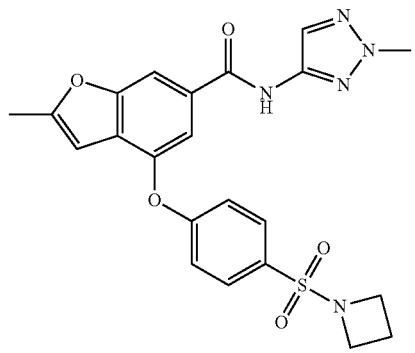

Example 295

4-(4-(Azetidin-1-ylsulfonyl)phenoxy)-N-(4-methoxypyridin-2-yl)-2-methyl-benzofuran-6-carboxamide

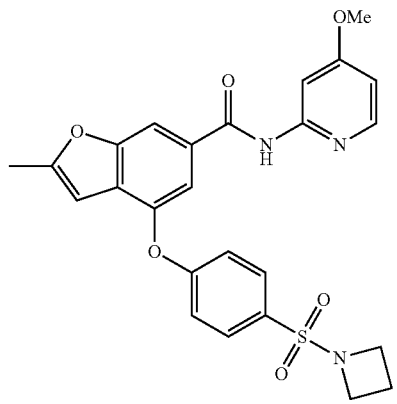

Example 296

4-(4-(Azetidin-1-ylsulfonyl)phenoxy)-2-methyl-N-(pyridin-2-yl)benzofuran-6-carboxamide

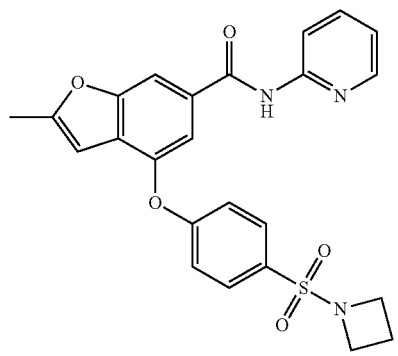

Example 297

4-(4-(Azetidin-1-ylsulfonyl)phenoxy)-2-methyl-N-(5-methylpyridin-2-yl)-benzofuran-6-carboxamide

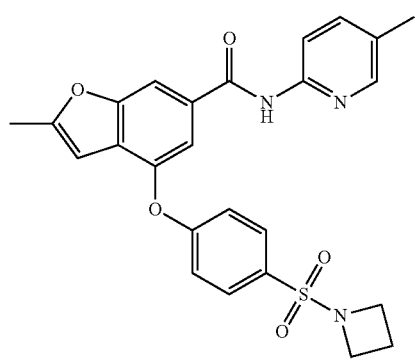

Example 298

4-(4-(Azetidin-1-ylsulfonyl)phenoxy)-2-methyl-N-(2-methyl-2H-1,2,3-triazol-4-yl)benzofuran-6-carboxamide

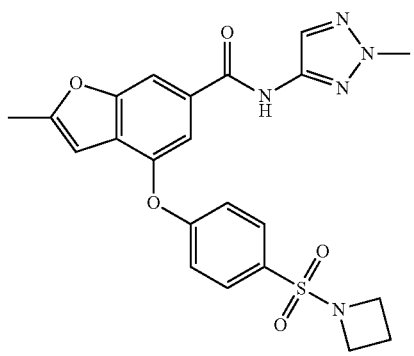

Example 299

4-(4-(Azetidin-1-ylsulfonyl)phenoxy)-N-(5-(dimethylamino)-pyrazin-2-yl)-2-methylbenzofuran-6-carboxamide

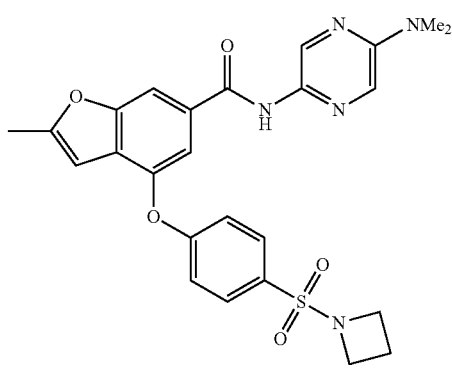

Example 300

4-(4-(Azetidin-1-ylsulfonyl)phenoxy)-N-(5-chloro-pyridin-2-yl)-2-methyl-benzofuran-6-carboxamide

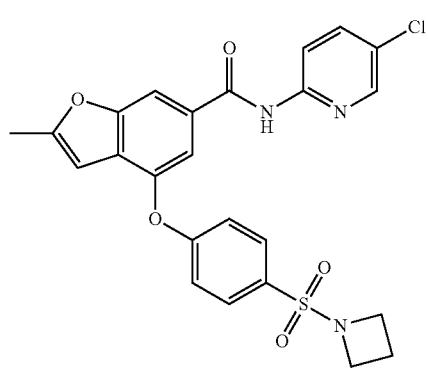

Example 301

4-(4-(Azetidin-1-ylsulfonyl)phenoxy)-N-(5-(hydroxymethyl)-pyridin-2-yl)-2-methylbenzofuran-6-carboxamide

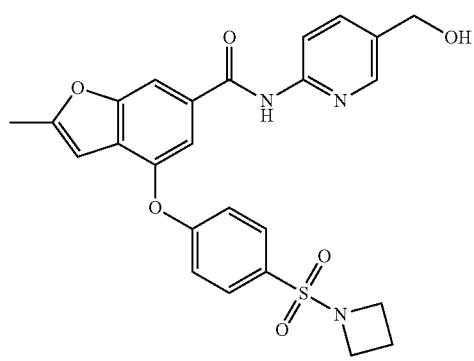

Example 302

4-(4-(Azetidin-1-ylsulfonyl)phenoxy)-N-(5-ethoxy-pyridin-2-yl)-2-methyl-benzofuran-6-carboxamide

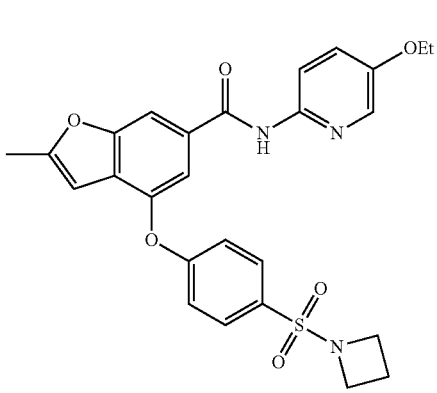

Example 303

4-(4-(Azetidin-1-ylsulfonyl)phenoxy)-N-(5-methoxypyrazin-2-yl)-2-methyl-benzofuran-6-carboxamide

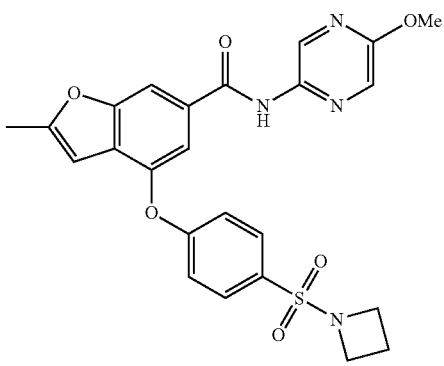

Example 304

4-{4-[(Dimethylamino)sulfonyl]-3-fluorophenoxy}-2-methyl-N-(5-methyl-pyridin-2-yl)-1-benzofuran-6-carboxamide

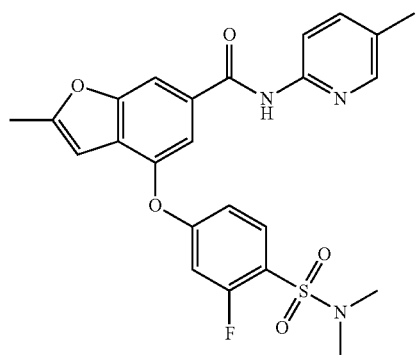

Example 305

4-{4-[(Dimethylamino)sulfonyl]-3-fluorophenoxy}-2-methyl-N-(1-methyl-1H-pyrazol-3-yl)-1-benzofuran-6-carboxamide

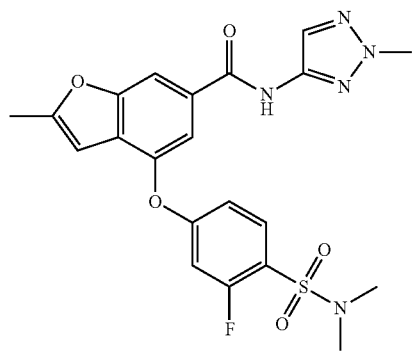

Example 306

4-{4-[(Dimethylamino)sulfonyl]-3-fluorophenoxy}-2-methyl-N-(2-methyl-2H-1,2,3-triazol-4-yl)-1-benzofuran-6-carboxamide

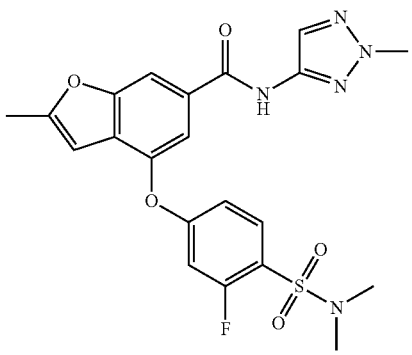

Example 307

4-{4-[(Dimethylamino)sulfonyl]-3-fluorophenoxy}-N-(5-methoxypyrazin-2-yl)-2-methyl-1-benzofuran-6-carboxamide

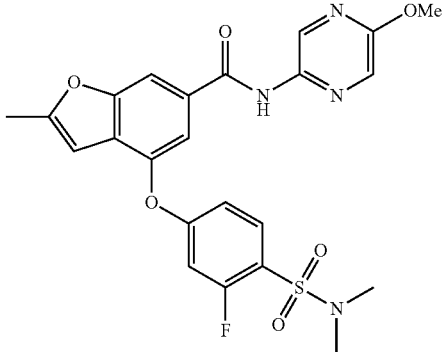

Example 308

N-[5-(Dimethylamino)pyrazin-2-yl]-4-{4-[(dimethylamino)-sulfonyl]-3-fluorophenoxy}-2-methyl-1-benzofuran-6-carboxamide

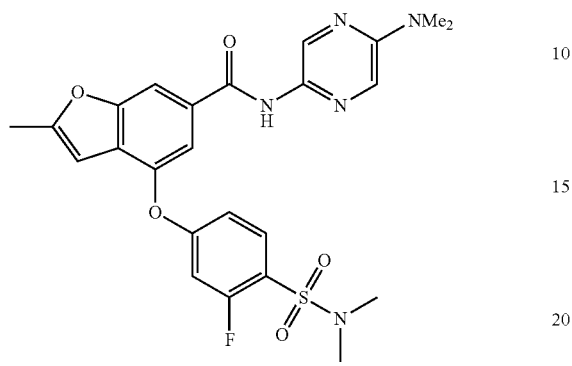

| Example | MW | MF | NMR | m/z |
|---|---|---|---|---|
| 294 | 466.5 | C23H22N4O5S | 1H NMR (300 MHz, CHLOROFORM-d) d ppm 2.02-2.25 (m, 2 H) 2.48 (s, 3 H) 3.71-3.93 (m, 7 H) 6.25 (d, J = 0.75 Hz, 1 H) 6.82 (d, J = 2.26 Hz, 1 H) 7.06-7.17 (m, 2 H) 7.30 (d, J = 2.26 Hz, 1 H) 7.48 (d, J = 1.13 Hz, 1 H) 7.75-7.92 (m, 3 H) 8.62 (s, 1 H) | 467.20 |
| 295 | 493.5 | C25H23N3O6S | 1H NMR (300 MHz, CHLOROFORM-d) d ppm 2.00-2.29 (m, 2 H) 2.50 (s, 3 H) 3.82 (t, J = 7.54 Hz, 4 H) 3.92 (s, 3 H) 6.27 (s, 1 H) 6.64 (dd, J = 5.84, 2.45 Hz, 1 H) 7.06-7.20 (m, 2 H) 7.52 (d, J = 1.13 Hz, 1 H) 7.78-7.87 (m, 2 H) 7.90 (s, 1 H) 8.02 (d, J = 2.26 Hz, 1 H) 8.09 (d, J = 5.84 Hz, 1 H) 8.63 (s, 1 H) | 494.00 |
| 296 | 463.5 | C24H21N3O5S | 1H NMR (300 MHz, CHLOROFORM-d) d ppm 2.03-2.22 (m, 2 H) 2.49 (s, 3 H) 3.81 (t, J = 7.63 Hz, 4 H) 6.26 (s, 1 H) 7.05-7.18 (m, 3 H) 7.53 (d, J = 1.13 Hz, 1 H) 7.72-7.87 (m, 3 H) 7.90 (s, 1 H) 8.37 (d, J = 8.29 Hz, 2 H) 8.57 (s, 1 H) | 464.00 |
| 297 | 477.5 | C25H23N3O5S | 1H NMR (300 MHz, CHLOROFORM-d) d ppm 2.03-2.21 (m, 2 H) 2.32 (s, 3 H) 2.44-2.58 (m, 3 H) 3.80 (t, J = 7.54 Hz, 4 H) 6.25 (s, 1 H) 7.05-7.20 (m, 2 H) 7.52 (d, J = 1.13 Hz, 1 H) 7.58 (dd, J = 8.67, 2.07 Hz, 1 H) 7.76-7.87 (m, 2 H) 7.90 (s, 1 H) 8.12 (s, 1 H) 8.26 (d, J = 8.48 Hz, 1 H) 8.57 (s, 1 H) | 478.00 |
| 298 | 467.5 | C22H21N5O5S | 1H NMR (300 MHz, CHLOROFORM-d) d ppm 2.05-2.28 (m, 2 H) 2.50 (s, 3 H) 3.75-3.99 (m, 4 H) 4.14 (s, 3 H) 6.23-6.38 (m, 1 H) 7.06-7.24 (m, 2 H) 7.47-7.62 (m, 1 H) 7.78-7.99 (m, 3 H) 8.13 (s, 1 H) 8.43 (s, 1 H) | 468.20 |
| 299 | 507.6 | C25H25N5O5S | 1H NMR (300 MHz, CHLOROFORM-d) d ppm 2.01-2.22 (m, 2 H) 2.48 (s, 3 H) 3.13 (s, 6 H) 3.80 (t, J = 7.63 Hz, 4 H) 6.25 (s, 1 H) 7.06-7.18 (m, 2 H) 7.52 (d, J = 1.13 Hz, 1 H) 7.71 (d, J = 1.13 Hz, 1 H) 7.76-7.85 (m, 2 H) 7.87 (s, 1 H) 8.22 (s, 1 H) 9.14 (d, J = 1.32 Hz, 1 H) | 508.00 |
| 300 | 498 | C24H20ClN3O5S | 1H NMR (300 MHz, CHLOROFORM-d) d ppm 2.06-2.23 (m, 2 H) 2.49 (s, 3 H) 3.81 (t, J = 7.63 Hz, 4 H) 6.26 (d, J = 0.75 Hz, 1 H) 7.07-7.20 (m, 2 H) 7.52 (d, J = 1.32 Hz, 1 H) 7.73 (dd, J = 8.95, 2.54 Hz, 1 H) 7.78-7.88 (m, 2 H) 7.89 (s, 1 H) 8.26 (d, J = 2.45 Hz, 1 H) 8.37 (d, J = 9.04 Hz, 1 H) 8.63 (s, 1 H) | 498.20 |
| 301 | 493.5 | C25H23N3O6S | 1HNMR: HB110684-1121H NMR (300 MHz, CHLOROFORM-d) d ppm 1.98-2.25 (m, 2 H) 2.49 (s, 3 H) 3.80 (t, J = 7.63 Hz, 4 H) 4.72 (s, 2 H) 6.26 (d, J = 0.75 Hz, 1 H) 7.04-7.19 (m, 2 H) 7.53 (s, 1 H) 7.75-7.88 (m, 3 H) 7.91 (s, 1 H) 8.23-8.47 (m, 2 H) 8.67 (s, 1 H) | 494.20 |
| 302 | 507.6 | C26H25N3O6S | 1H NMR (300 MHz, CHLOROFORM-d) d ppm −0.12 (t, J = 6.97 Hz, 3 H) 0.46-0.67 (m, 2 H) 0.92 (s, 3 H) 2.24 (t, J = 7.63 Hz, 4 H) 2.52 (q, J = 6.97 Hz, 2 H) 4.69 (s, 1 H) 5.51-5.63 (m, 2 H) 5.74-5.81 (m, 1 H) 5.95 (d, J = 1.13 Hz, 1 H) 6.25 (d, J = 8.85 Hz, 2 H) 6.30-6.37 (m, 1 H) 6.39-6.48 (m, 1 H) 6.72 (s, 1 H) 6.84-6.97 (m, 1 H) | 508.20 |
| 303 | 494.5 | C24H22N4O6S | 1H NMR (300 MHz, CHLOROFORM-d) d ppm 2.01-2.27 (m, 2 H) 2.49 (s, 3 H) 3.81 (t, J = 7.63 Hz, 4 H) 3.99 (s, 3 H) 6.26 (s, 1 H) 7.06-7.20 (m, 2 H) 7.52 (d, J = 1.32 Hz, 1 H) 7.75-7.87 (m, | 495.20 |

| Example | MW | MF | NMR | m/z |
|---|---|---|---|---|
| | | | 2 H) 7.88 (s, 1 H) 7.95 (d, J = 1.32 Hz, 1 H) 8.33 (s, 1 H) 9.19 (d, J = 1.32 Hz, 1 H) | |
| 304 | 483.5 | C24H22FN3O5S | 1H NMR (300 MHz, CHLOROFORM-d) d ppm 2.32 (s, 3 H) 2.49 (s, 3 H) 2.84 (d, J = 1.88 Hz, 6 H) 6.26 (d, J = 0.94 Hz, 1 H) 6.69-6.96 (m, 2 H) 7.53 (d, J = 1.32 Hz, 1 H) 7.59 (dd, J = 8.38, 2.17 Hz, 1 H) 7.74-7.87 (m, 1 H) 7.91 (s, 1 H) 8.13 (s, 1 H) 8.26 (d, J = 8.48 Hz, 1 H) 8.54 (s, 1 H) | 484.00 |
| 305 | 472.5 | C22H21FN4O5S | 1H NMR (300 MHz, CHLOROFORM-d) d ppm 2.48 (s, 3 H) 2.84 (d, J = 1.88 Hz, 6 H) 3.77-3.92 (m, 3 H) 6.25 (s, 1 H) 6.69-6.94 (m, 3 H) 7.30 (d, J = 2.07 Hz, 1 H) 7.45-7.56 (m, 1 H) 7.73-7.93 (m, 2 H) 8.58 (s, 1 H) | 473.00 |
| 306 | 473.5 | C21H20FN5O5S | 1H NMR (300 MHz, CHLOROFORM-d) d ppm 2.50 (s, 3 H) 2.84 (d, J = 1.70 Hz, 6 H) 4.13 (s, 3 H) 6.26 (d, J = 0.75 Hz, 1 H) 6.70-6.95 (m, 2 H) 7.49 (d, J = 1.32 Hz, 1 H) 7.81 (t, J = 8.38 Hz, 1 H) 7.87 (s, 1 H) 8.12 (s, 1 H) 8.47 (s, 1 H) | 474.00 |
| 307 | 500.5 | C23H21FN4O6S | 1H NMR (300 MHz, CHLOROFORM-d) d ppm 2.50 (s, 3 H) 2.84 (d, J = 1.70 Hz, 6 H) 3.99 (s, 3 H) 6.26 (s, 1 H) 6.70-6.97 (m, 2 H) 7.53 (s, 1 H) 7.81 (t, J = 8.29 Hz, 1 H) 7.91 (s, 1 H) 7.95 (d, J = 1.13 Hz, 1 H) 8.35 (s, 1 H) 9.19 (d, J = 1.13 Hz, 1 H) | 501.00 |
| 308 | 513.6 | C24H24FN5O5S | 1H NMR (300 MHz, CHLOROFORM-d) d ppm 2.49 (s, 3 H) 2.84 (d, J = 1.70 Hz, 6 H) 3.13 (s, 6 H) 6.26 (s, 1 H) 6.69-6.92 (m, 2 H) 7.53 (s, 1 H) 7.70 (d, J = 1.32 Hz, 1 H) 7.80 (t, J = 8.29 Hz, 1 H) 7.90 (s, 1 H) 8.28 (s, 1 H) 9.15 (s, 1 H) | 514.00 |

Example 309

2-(Methoxymethyl)-N-(5-methylpyridin-2-yl)-4-[4-(methylsulfonyl)-phenoxy]-1-benzofuran-6-carboxamide

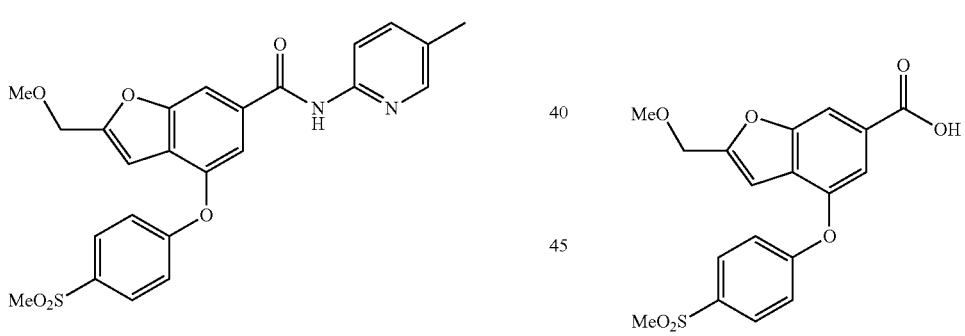

Preparation of Intermediate 309a 2-(Methoxymethyl)-4-(4-(methylsulfonyl)-phenoxy)-benzofuran-6-carboxylic acid To a solution of 2-(methoxymethyl)-4-(4-(methylsulfonyl) phenoxy)benzofuran-6-carboxylic acid (130 mg, 0.345 mmol) in DMF (5 mL) was added HATU (263 mg, 0.691 mmol) and DIEA (89.3 mg, 0.691 mmol). After stirring the solution at 0° C. for 15 minutes, 2-amino-5-methyl pyridine (74.7 mg, 0.691 mmol) was added. The solution was warmed gradually to room temperature and stirred for 14 h. The reaction was concentrated under high vacuum, and the product was purified by reverse phase HPLC to give the title compound (88 mg, 55%) as a white solid. $^1$H NMR (300 MHz, CHLOROFORM-D) δ ppm 2.36 (s, 3 H) 3.07 (s, 3 H) 3.46 (s, 3 H) 4.56 (s, 2 H) 6.59 (s, 1 H) 7.07-7.18 (m, 2 H) 7.53 (d, J=1.32 Hz, 1 H) 7.74 (dd, J=8.67, 1.32 Hz, 1 H) 7.85-7.95 (m, 2 H) 8.00 (s, 1 H) 8.09 (s, 1 H) 8.22 (d, J=8.67 Hz, 1 H) 9.10 (s, 1 H). LCMS m/z 467.20 (M+H)$^+$.

To a solution of ethyl 2-(bromomethyl)-4-(4-(methylsulfonyl)phenoxy)benzofuran-6-carboxylate (285a) (750 mg, 1.65 mmol) in THF and MeOH (3:1, 15 mL) was added NaOMe in MeOH(25% w/w, 1 mL) drop-wise at 0° C. After the solution was stirred at 0° C. for 2 hours, water was added and the stirring was continued for 14 h. The solvents were reduced under reduced pressure. To the aqueous solution was added 1N HCl until the pH ~1. The product was extracted with CHCl$_3$ and dried over MgSO$_4$. The solution was concentrated to give the title compound (610 mg, 98%) as a white solid. The product was usedin the next step without further purification. $^1$H NMR (300 MHz, CHLOROFORM-D) δ ppm 3.07 (s, 3 H) 3.46 (s, 3 H) 4.56 (s, 2 H) 6.58 (s, 1 H) 7.07-7.17 (m, 2 H) 7.67 (d, J=1.13 Hz, 1 H) 7.85-7.99 (m, 2 H) 8.13 (d, J=1.13 Hz, 1 H).

Examples 310-315 were prepared in a similar manner as described for Example 309, from Intermediate 309a and the appropriate amino heterocycles.

Example 310

2-(Methoxymethyl)-N-(1-methyl-1H-pyrazol-3-yl)-4-[4-(methylsulfonyl)-phenoxy]-1-benzofuran-6-carboxamide

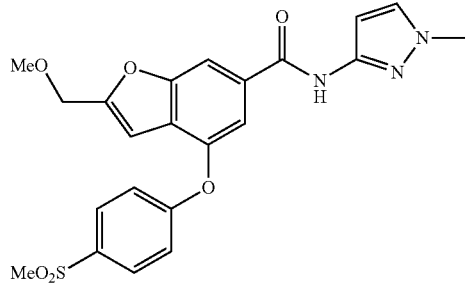

Example 311

N-[5-(Dimethylamino)pyrazin-2-yl]-2-(methoxymethyl)-4-[4-(methylsulfonyl)-phenoxy]-1-benzofuran-6-carboxamide

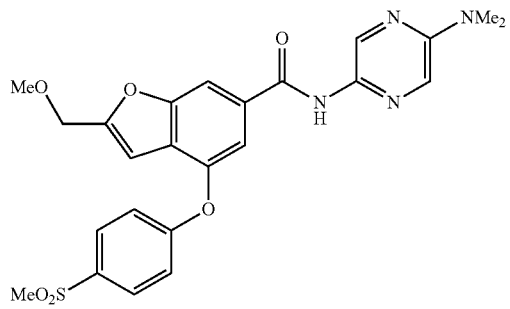

Example 312

2-(Methoxymethyl)-N-(5-methoxypyrazin-2-yl)-4-[4-(methylsulfonyl)phenoxy]-1-benzofuran-6-carboxamide

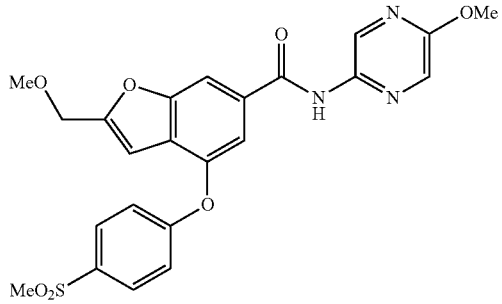

Example 313

2-(Methoxymethyl)-4-[4-(methylsulfonyl)phenoxy]-N-(2-methyl-2H-1,2,3-triazol-4-yl)-1-benzofuran-6-carboxamide

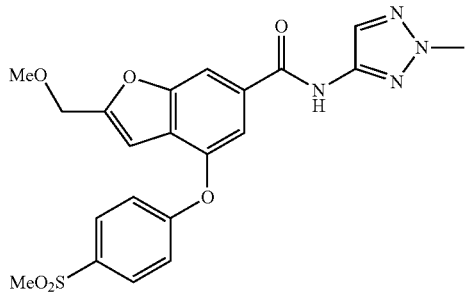

Example 314

2-(Methoxymethyl)-N-(4-methoxypyridin-2-yl)-4-[4-(methylsulfonyl)phenoxy]-1-benzofuran-6-carboxamide

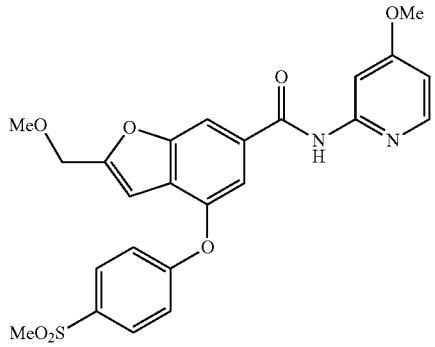

Example 315

2-(Methoxymethyl)-N-(5-methylisoxazol-3-yl)-4-[4-(methylsulfonyl)phenoxy]-1-benzofuran-6-carboxamide

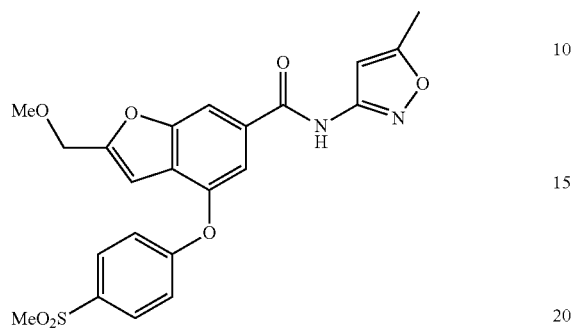

| Example | MW | MF | NMR | m/z |
|---|---|---|---|---|
| 310 | 455.5 | C22H21N3O6S | 1H NMR (300 MHz, CHLOROFORM-D) d ppm 3.07 (s, 3 H) 3.45 (s, 3 H) 3.80 (s, 3 H) 4.55 (s, 2 H) 6.58 (s, 1 H) 6.81 (d, J = 2.26 Hz, 1 H) 7.07-7.19 (m, 2 H) 7.29 (d, J = 2.26 Hz, 1 H) 7.47 (d, J = 1.13 Hz, 1 H) 7.84-8.00 (m, 3 H) 8.78 (s, 1 H) | 456.00 |
| 311 | 496.5 | C24H24N4O6S | 1H NMR (300 MHz, CHLOROFORM-D) d ppm 3.06 (s, 3 H) 3.11 (s, 6 H) 3.45 (s, 3 H) 4.54 (s, 2 H) 6.57 (s, 1 H) 7.04-7.19 (m, 2 H) 7.51 (d, J = 1.13 Hz, 1 H) 7.67 (d, J = 1.51 Hz, 1 H) 7.83-8.06 (m, 3 H) 8.43 (s, 1 H) 9.12 (d, J = 1.51 Hz, 1 H) | 497.00 |
| 312 | 483.5 | C23H21N3O7S | 1H NMR (300 MHz, CHLOROFORM-D) d ppm 3.07 (s, 3 H) 3.46 (s, 3 H) 3.99 (s, 3 H) 4.56 (s, 2 H) 6.58 (s, 1 H) 7.10-7.20 (m, 2 H) 7.53 (d, J = 1.13 Hz, 1 H) 7.90-8.00 (m, 4 H) 8.66 (s, 1 H) 9.21 (d, J = 1.32 Hz, 1 H) | 484.00 |
| 313 | 456.5 | C21H20N4O6S | 1H NMR (300 MHz, CHLOROFORM-D) d ppm 3.07 (s, 3 H) 3.45 (s, 3 H) 4.12 (s, 3 H) 4.55 (s, 2 H) 6.58 (s, 1 H) 7.08-7.20 (m, 2 H) 7.46 (d, J = 1.13 Hz, 1 H) 7.83-8.01 (m, 3 H) 8.10 (s, 1 H) 8.48 (s, 1 H) | 457.00 |
| 314 | 482.5 | C24H22N2O7S | 1H NMR (300 MHz, DMSO-D6) d ppm 3.21 (s, 3 H) 3.31 (s, 3 H) 3.86 (s, 3 H) 4.56 (s, 2 H) 6.78-6.86 (m, 2 H) 7.27 (d, J = 8.67 Hz, 2 H) 7.69 (s, 1 H) 7.77 (d, J = 1.70 Hz, 1 H) 7.94 (d, J = 8.67 Hz, 2 H) 8.21 (d, J = 5.65 Hz, 1 H) 8.26 (s, 1 H) 10.98 (s, 1 H) | 483.20 |
| 315 | 456.5 | C22H20N2O7S | 1H NMR (300 MHz, CHLOROFORM-D) d ppm 2.43 (s, 3 H) 3.08 (s, 3 H) 3.46 (s, 3 H) 4.56 (s, 2 H) 6.58 (s, 1 H) 6.82 (s, 1 H) 7.10-7.18 (m, 2 H) 7.46 (d, J = 1.32 Hz, 1 H) 7.88-7.99 (m, 3 H) 8.69 (s, 1 H) | 457.00 |

Example 316

2-(Hydroxymethyl)-N-(5-methylpyridin-2-yl)-4-(4-(methylsulfonyl)-phenoxy)benzofuran-6-carboxamide

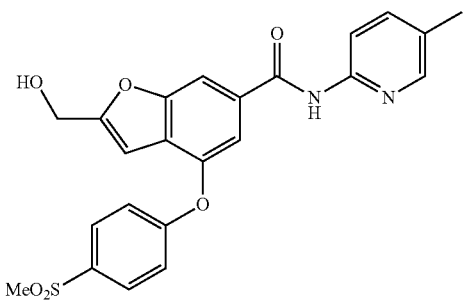

To a solution of 2-amino-5-methyl pyridine (305 mg, 2.82 mmol) in DCE (10 mL) at 0° C. was added dimethylaluminum chloride (1M in hexanes, 2.82 mL) drop-wise. After the addition, the ice-bath was removed, and the mixture was stirred for 30 minutes at room temperature. Ethyl 2-(hydroxymethyl)-4-(4-(methylsulfonyl)phenoxy)benzofuran-6-carboxylate (110 mg, 0.282 mmol) was then added, and the stirring was continued for another 14 h. The reaction was quenched with potassium sodium tartrate tetrahydrate (20% w/w) cautiously. The product was extracted with CHCl$_3$, washed with brine and dried over MgSO$_4$. The product was purified by reverse phase HPLC to give the title compound (90 mg, 71%) as a white solid. $^1$H NMR (300 MHz, DMSO-D6) δ ppm 2.27 (s, 3 H) 3.20 (s, 3 H) 4.58 (d, J=5.84 Hz, 2 H) 5.60 (t, J=5.84 Hz, 1 H) 6.61 (s, 1 H) 7.24 (d, J=8.67 Hz, 2 H) 7.66 (dd, J=8.48, 2.26 Hz, 1 H) 7.70 (s, 1 H) 7.93 (d, J=8.67 Hz, 2 H) 8.06 (d, J=8.48 Hz, 1 H) 8.22 (d, J=2.26 Hz, 1 H) 8.24 (s, 1 H) 10.83 (s, 1 H). LCMS m/z 453.0 (M+H)$^+$.

Preparation of Intermediate 316a

Ethyl 2-(hydroxymethyl)-4-(4-(methylsulfonyl)-phenoxy)-benzofuran-6-carboxylate

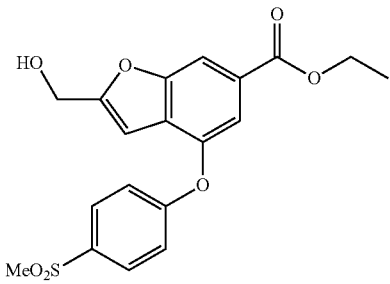

To a solution of ethyl 2-formyl-4-(4-(methylsulfonyl)phenoxy)benzofuran-6-carboxylate (285b) (230 mg, 0.592 mmol) in MeOH (10 mL) was added NaBH$_4$ (50 mg, 1.3 mmol). The mixture was stirred for half an hour. The solvent was evaporated, and the product was purified by gradient silica gel chromatography using CHCl$_3$/MeOH (100/0 to 98/2). The desired compound was isolated as a white solid (170 mg, 74%).

$^1$H NMR (300 MHz, CHLOROFORM-D) δ ppm 1.40 (t, J=7.16 Hz, 3 H) 1.99 (t, J=6.22 Hz, 1 H) 3.06 (s, 3 H) 4.39 (q, J=7.16 Hz, 2 H) 4.78 (d, J=6.22 Hz, 2 H) 6.52 (d, J=1.13 Hz, 1 H) 7.00-7.17 (m, 2 H) 7.64 (d, J=1.13 Hz, 1 H) 7.87-7.97 (m, 2 H) 8.06 (s, 1 H).

Example 317

2-(Hydroxymethyl)-N-(1-methyl-1H-pyrazol-3-yl)-4-[4-(methylsulfonyl)-phenoxy]-1-benzofuran-6-carboxamide

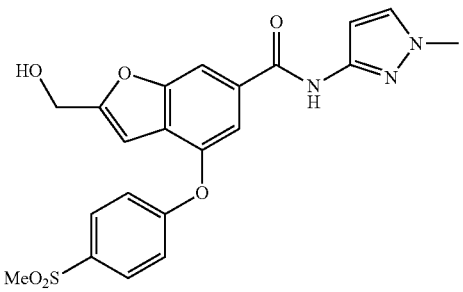

The title compound was prepared in a similar manner as described for Example 316, from Intermediate 316a and 1-methyl-1H-pyrazol-3-amine. $^1$H NMR (300 MHz, CHLOROFORM-D) δ ppm 3.07 (s, 3 H) 3.83 (s, 3 H) 4.78 (s, 2 H) 6.55 (s, 1 H) 6.84 (d, J=2.26 Hz, 1 H) 7.05-7.18 (m, 2 H) 7.31 (d, J=2.26 Hz, 1 H) 7.48 (d, J=1.13 Hz, 1 H) 7.79-8.06 (m, 3 H) 8.98 (s, 1 H); LCMS m/z 442.00 (M+H)$^+$.

Example 318

N-(1-Methyl-1H-pyrazol-3-yl)-4-[4-(methylsulfonyl)phenoxy]-2-[(2-oxopyrrolidin-1-yl)methyl]-1-benzofuran-6-carboxamide

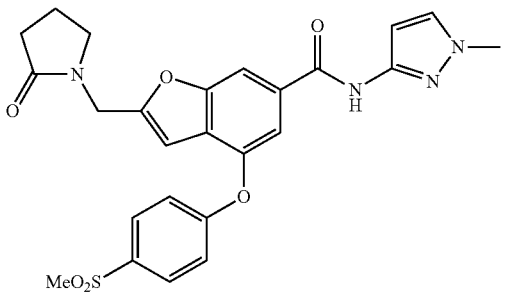

To a solution of 3-amino-1-methyl pyrazole (106 mg, 1.09 mmol) in DCE (10 mL) at 0° C. was added Al(CH$_3$)$_2$Cl (1.09 mL, 1M in hexanes) drop-wise. After removal of the ice-bath, the mixture was stirred for min at room temperature. Ethyl 4-(4-(methylsulfonyl)phenoxy)-2-((2-oxopyrrolidin-1-yl)methyl)benzofuran-6-carboxylate (50 mg, 0.11 mmol) was added and the stirring was continued for another 14 h. The reaction was quenched with potassium sodium tartrate tetrahydrate (20% w/w) cautiously. The product was extracted with CHCl$_3$, washed with brine and dried over MgSO$_4$. The product was purified by reverse phase HPLC to give the title compound (22 mg, 47%) as a white solid. $^1$H NMR (300

MHz, CHLOROFORM-D) δ ppm 1.97-2.13 (m, 2 H) 2.44 (t, J=8.01 Hz, 2 H) 3.08 (s, 3 H) 3.46 (t, J=6.97 Hz, 2 H) 3.81 (s, 3 H) 4.60 (s, 2 H) 6.54 (s, 1 H) 6.79 (d, J=2.26 Hz, 1 H) 7.09-7.17 (m, 2 H) 7.29 (d, J=2.26 Hz, 1 H) 7.44 (s, 1 H) 7.81-7.98 (m, 3 H) 8.54 (s, 1 H). LCMS m/z 509.0 (M+H)+.

Preparation of Intermediate 318a

Ethyl 4-(4-(methylsulfonyl)phenoxy)-2-((2-oxopyr-rolidin-1-yl)methyl)benzofuran-6-carboxylate

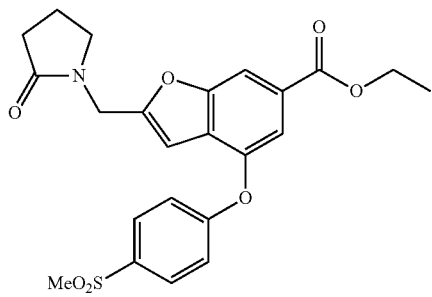

To a solution of 2-ketopyrrolidine (75.1 mg, 0.882 mmol) in DMF (10 mL) was added NaH (60% in mineral oil, 44 mg, 1.1 mmol) at room temperature. After stirring the reaction for 30 min, ethyl 2-(bromomethyl)-4-(4-(methylsulfonyl)phe-noxy)benzofuran-6-carboxylate (285a) (200 mg, 0.441 mmol) was added. The mixture was stirred at room temperature for another 2 h. Water was added to the reaction, and the product was extracted with CHCl₃. The combined organic layer was dried and concentrated. The product was purified by gradient silica gel chromatography using CHCl₃/MeOH (100/0 to 95/5) to give the title compound (50 mg, 25%) as a yellow oil. ¹H NMR (300 MHz, CHLOROFORM-D) δ ppm 1.38 (t, J=7.16 Hz, 3 H) 1.98-2.14 (m, 2 H) 2.42 (t, J=8.10 Hz, 2 H) 3.06 (s, 3 H) 3.44 (t, J=7.06 Hz, 2 H) 4.38 (q, J=7.16 Hz, 2 H) 4.58 (s, 2 H) 6.49 (d, J=0.75 Hz, 1 H) 7.04-7.12 (m, 2 H) 7.61 (d, J=1.13 Hz, 1 H) 7.83-7.94 (m, 2 H) 8.05 (t, J=1.13 Hz, 1 H).

Examples 319 and 320 were prepared in a similar manner as described for Example 318, from the corresponding ether ester intermediates, which were prepared in a similar manner as described for Intermediate 318a, starting from Intermediate 285a and dimethylamine or 2-methyl-1H-imidazole, respectively.

Example 319

2-[(Dimethylamino)methyl]-N-(5-methylpyridin-2-yl)-4-[4-(methylsulfonyl)-phenoxy]-1-benzofuran-6-carboxamide

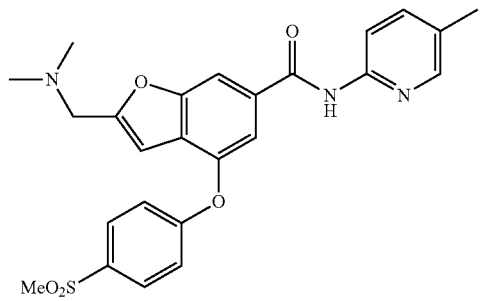

¹H NMR (300 MHz, CHLOROFORM-D) δ ppm 2.30 (s, 3 H) 2.32 (s, 6 H) 3.06 (s, 3 H) 3.61 (s, 2 H) 6.48 (s, 1 H) 7.07-7.18 (m, 2 H) 7.50 (d, J=1.13 Hz, 1 H) 7.57 (dd, J=8.48, 2.26 Hz, 1 H) 7.85-7.93 (m, 2 H) 7.94 (s, 1 H) 8.08 (s, 1 H) 8.25 (d, J=8.48 Hz, 1 H) 8.76 (s, 1 H); LCMS m/z 480.20 (M+H)+.

Example 320

2-[(2-Methyl-1H-imidazol-1-yl)methyl]-N-(5-meth-ylpyridin-2-yl)-4-[4-(methylsulfonyl)phenoxy]-1-benzofuran-6-carboxamide

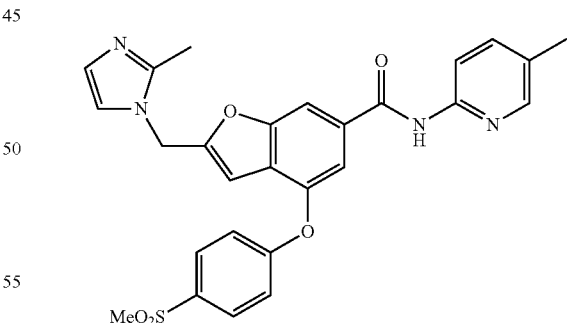

¹H NMR (300 MHz, CHLOROFORM-D) δ ppm 2.31 (s, 3 H) 2.46 (s, 3 H) 3.07 (s, 3 H) 5.16 (s, 2 H) 6.45 (s, 1 H) 6.91-6.94 (m, 1 H) 6.95 (d, J=1.32 Hz, 1 H) 7.08-7.19 (m, 2 H) 7.49 (d, J=1.32 Hz, 1 H) 7.58 (dd, J=8.67, 2.26 Hz, 1 H)

7.87-8.01 (m, 3 H) 8.10 (s, 1 H) 8.23 (d, J=8.48 Hz, 1 H) 8.67 (s, 1 H); LCMS m/z 517.00 (M+H)+.

Example 321

2-(Difluoromethyl)-N-(5-methylpyridin-2-yl)-4-[4-(methylsulfonyl)-phenoxy]-1-benzofuran-6-carboxamide

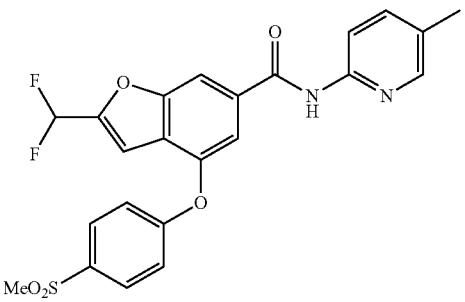

2-Amino-5-methyl pyridine (264 mg, 2.44 mmol) was dissolved in DCE (10 mL) at 0° C., then Al(CH₃)₂Cl (2.44 mL, 1M in hexanes) was added drop wise. After the addition, the ice-bath was removed, and the mixture was stirred for 30 minutes at room temperature. Ethyl 2-(difluoromethyl)-4-[4-(methylsulfonyl)phenoxy]-1-benzofuran-6-carboxylate (100 mg, 0.244 mmol) was added, and the stirring was continued for 14 h. The reaction was quenched with potassium sodium tartrate tetrahydrate (20% w/w) cautiously. The product was extracted with CHCl₃, washed with brine and dried over MgSO₄. The product was purified by reverse phase HPLC to give the title compound (92 mg, 80%) as a white solid. $^1$H NMR (400 MHz, CHLOROFORM-D) δ ppm 2.31 (s, 3 H) 3.08 (s, 3 H) 6.75 (t, J=53.94 Hz, 1 H) 6.98 (s, 1 H) 7.12-7.20 (m, 2 H) 7.51 (d, J=1.01 Hz, 1 H) 7.58 (dd, J=8.46, 2.15 Hz, 1 H) 7.91-7.96 (m, 2 H) 7.97 (s, 1 H) 8.11 (d, J=2.15 Hz, 1 H) 8.23 (d, J=8.46 Hz, 1 H) 8.54 (s, 1 H). LCMS m/z 473.0 (M+H)+.

Preparation of Intermediate 321a

Ethyl 2-(difluoromethyl)-4-[4-(methylsulfonyl)phenoxy]-1-benzofuran-6-carboxylate

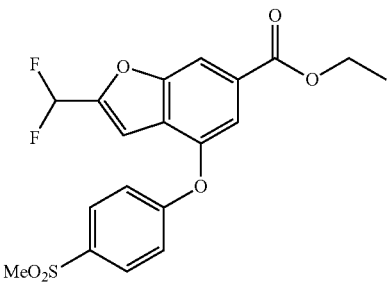

To a solution of ethyl 2-formyl-4-[4-(methylsulfonyl)phenoxy]-1-benzofuran-6-carboxylate (285b) (500 mg 1.14 mmol) in CH₂Cl₂ (15 mL) was added DAST (238 mg, 1.48 mmol) at room temperature. The mixture was stirred for 1 hour and water was added. The product was extracted with CHCl₃, dried over MgSO₄ and concentrated. The residue was passed through a silica gel column eluting with hexanes/EtOAc (100/0 to 70/30) to give the title compound (400 mg, 86%) as a colorless oil. $^1$H NMR (300 MHz, CHLOROFORM-D) δ ppm 1.40 (t, J=7.16 Hz, 3 H) 3.07 (s, 3 H) 4.40 (q, J=7.16 Hz, 2 H) 6.74 (t, J=53.78 Hz, 1 H) 6.95 (s, 1 H) 7.09-7.19 (m, 2 H) 7.65 (d, J=1.13 Hz, 1 H) 7.87-8.13 (s, 1 H).

Example 322

2-(Difluoromethyl)-N-(1-methyl-1H-pyrazol-3-yl)-4-[4-(methylsulfonyl)-phenoxy]-1-benzofuran-6-carboxamide

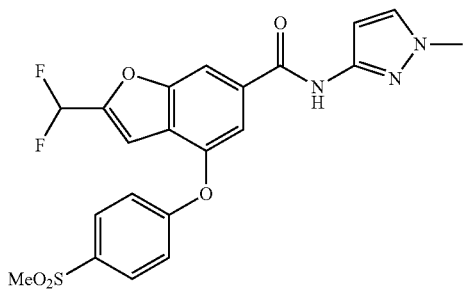

The title compound was prepared in a similar manner as described for Example 321, from Intermediate 321a and 1-methyl-1H-pyrazol-3-amine. $^1$H NMR (400 MHz, CHLOROFORM-D) δ ppm 3.06 (s, 3 H) 3.79 (s, 3 H) 6.73 (t, J=53.81 Hz, 1 H) 6.77 (d, J=2.27 Hz, 1 H) 6.95 (s, 1 H) 7.11-7.19 (m, 2 H) 7.28 (d, J=2.27 Hz, 1 H) 7.52 (d, J=1.26 Hz, 1 H) 7.87-7.95 (m, 2 H) 7.99 (s, 1 H); LCMS m/z 462.0 (M+H)+.

Example 323

4-[4-(Difluoromethyl)phenoxy]-N²,N²-dimethyl-N⁶-(5-methylpyridin-2-yl)-1-benzofuran-2,6-dicarboxamide

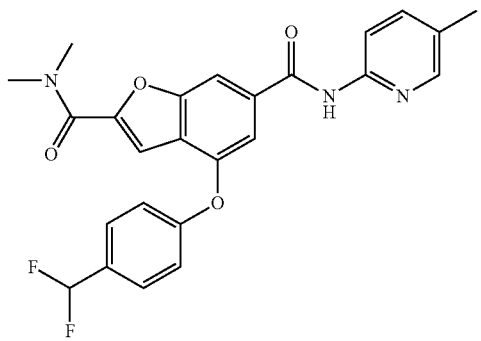

To a solution of 4-(4-formylphenoxy)-N²,N²-dimethyl-N⁶-(5-methylpyridin-2-yl)-1-benzofuran-2,6-dicarboxamide (40 mg, 0.09 mmol) in CH₂Cl₂ (5 mL) was added DAST (18.9 mg, 0.117 mmol) at room temperature. The mixture was stirred for 1 hour and water was added. The product was extracted with CHCl₃ three times, dried over MgSO₄, and concentrated. The product was purified by reverse phase HPLC to give the title compound (9 mg, 20%) as a white solid. ¹H NMR (400 MHz, CHLOROFORM-D) δ ppm 2.31 (s, 3 H) 3.14 (s, 3 H) 3.33 (s, 3 H) 6.64 (t, J=56.59 Hz, 1 H) 7.12 (d, J=8.59 Hz, 2 H) 7.19 (s, 1 H) 7.39 (d, J=1.26 Hz, 1 H) 7.52 (d, J=8.59 Hz, 2 H) 7.58 (dd, J=8.46, 2.15 Hz, 1 H) 7.91 (s, 1 H) 8.10 (d, J=2.15 Hz, 1 H) 8.23 (d, J=8.46 Hz, 1 H) 8.60 (s, 1 H). LCMS m/z 466.0 (M+H)⁺.

Preparation of Intermediate 323a

Ethyl 4-[4-(difluoromethyl)phenoxy]-2-methyl-1-benzofuran-6-carboxylate

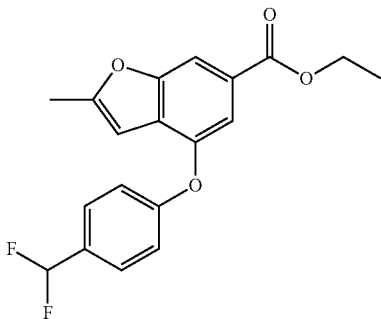

A mixture of ethyl 4-hydroxy-2-methyl-1-benzofuran-6-carboxylate (252c) (1.10 g, 5 mmol), 1-bromo-4-(difluoromethyl)benzene (1.24 g, 6 mmol), Cs$_2$CO$_3$ (2.44 g, 7.5 mmol) and CuI (5 mg, 0.03 mmol) in DMF (5 mL) was heated in a microwave at 160° C. for 60 minutes. Water was then added and the product was extracted with CHCl$_3$ (3×), dried over MgSO$_4$ and concentrated to give an oil residue. The oil was purified via silica gel chromatography using hexanes/EtOAc (100/0 to 70/30) to give the title compound (710 mg, 41%) as a yellow solid. ¹H NMR (300 MHz, CHLOROFORM-D) δ ppm 1.38 (t, J=7.06 Hz, 3 H) 2.44 (s, 3 H) 4.37 (q, J=7.06 Hz, 2 H) 6.22 (d, J=0.94 Hz, 1 H) 6.63 (t, J=56.61 Hz, 1 H) 7.03 (d, J=8.29 Hz, 2 H) 7.46 (d, J=8.29 Hz, 2 H) 7.55 (d, J=1.13 Hz, 1 H) 7.89-8.05 (m, 1 H).

Preparation of Intermediate 323b

Ethyl 2-(bromomethyl)-4-[4-(difluoromethyl)phenoxy]-1-benzofuran-6-carboxylate

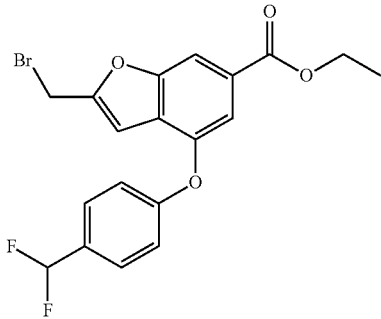

To a solution of ethyl 4-[4-(difluoromethyl)phenoxy]-2-methyl-1-benzofuran-6-carboxylate (710 mg, 2.05 mmol) and NBS (438 mg, 2.46 mmol) in CHCl$_3$ (25 mL) was added benzoyl peroxide (49.7 mg, 0.205 mmol). The mixture was refluxed for 14 hours. The solvent was evaporated, and the product was purified via gradient silica gel chromatography using hexanes/EtOAc (100/0 to 70/30) to give the title compound (440 mg, 51%) as a light-yellow solid. ¹H NMR (300 MHz, CHLOROFORM-D) δ ppm 1.38 (t, J=7.16 Hz, 3 H) 4.38 (q, J=7.16 Hz, 2 H) 4.53 (s, 2 H) 6.39-6.89 (m, 2 H) 7.07 (d, J=8.48 Hz, 2 H) 7.49 (d, J=8.48 Hz, 2 H) 7.54 (d, J=0.94 Hz, 1 H) 8.01 (s, 1 H).

Preparation of Intermediate 323c

Ethyl 4-[4-(difluoromethyl)phenoxy]-2-formyl-1-benzofuran-6-carboxylate

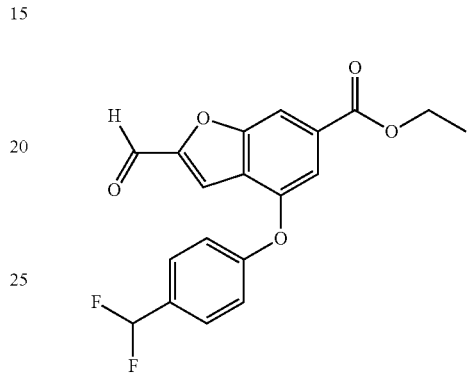

A solution of ethyl 2-(bromomethyl)-4-[4-(difluoromethyl)phenoxy]-1-benzofuran-6-carboxylate (440 mg, 1.03 mmol) and IBX (579 mg, 2.07 mmol) in DMSO (2 mL) was heated at 65° C. for 3 h. The reaction was quenched with water and the product was extracted with CHCl$_3$ (3×). The combined organic layers was washed with water (2×), dried over MgSO$_4$ and concentrated. The product was purified via gradient silica gel chromatography using hexanes/EtOAc (100/0 to 50/50) to give the title compound (300 mg, 81%) as a white solid. ¹H NMR (300 MHz, CHLOROFORM-D) δ ppm 1.39 (t, J=7.16 Hz, 3 H) 4.39 (q, J=7.16 Hz, 2 H) 6.67 (t, J=56.42 Hz, 1 H) 7.11-7.18 (m, J=8.67 Hz, 2 H) 7.48 (d, J=0.94 Hz, 1 H) 7.51 (d, J=0.94 Hz, 1 H) 7.55 (d, J=8.67 Hz, 2 H) 8.08 (d, J=0.94 Hz, 1 H) 9.87 (s, 1 H).

Preparation of Intermediate 323d

4-[4-(Difluoromethyl)phenoxy]-6-(ethoxycarbonyl)-1-benzofuran-2-carboxylic acid

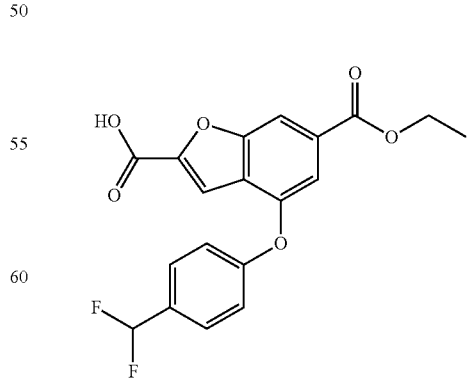

To acetonitrile (10 mL) was added periodic acid (209 mg, 0.916 mmol) and stirred vigorously at room temperature for 15 min. Ethyl 4-[4-(difluoromethyl)phenoxy]-2-formyl-1-benzofuran-6-carboxylate (300 mg, 0.833 mmol) was then added (in ice-bath) followed by addition of pyridium fluorochromate (3.32.mg, 0.02 mmol) in CH$_3$CN (5 mL). The reaction was stirred at 0° C. for 1 hour. The reaction was diluted with ethyl acetate and washed with brine/water (1:1), dried over MgSO$_4$ and concentrated to give the title compound (300 mg, 96%) as an orange solid, which was usedin the next step without further purification. $^1$H NMR (300 MHz, CHLOROFORM-D) δ ppm 1.33 (t, J=7.16 Hz, 3 H) 4.33 (q, J=7.16 Hz, 2 H) 6.61 (t, J=56.52 Hz, 1 H) 7.06 (d, J=8.48 Hz, 2 H) 7.37 (s, 1 H) 7.43-7.54 (m, 3 H) 8.02 (s, 1 H).

Preparation of Intermediate 323e

Ethyl 4-[4-(difluoromethyl)phenoxy]-2-[(dimethylamino)-carbonyl]-1-benzofuran-6-carboxylate

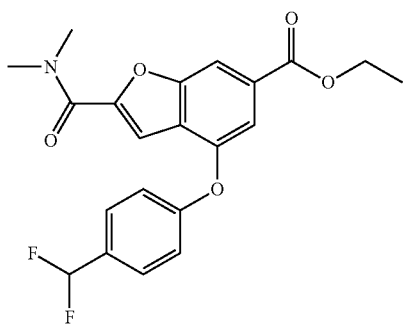

To a solution of 4-[4-(difluoromethyl)phenoxy]-6-(ethoxycarbonyl)-1-benzofuran-2-carboxylic acid (300 mg, 0.80 mmol) in DMF (10 mL) was added HATU (606 mg, 1.59 mmol), DIEA (515 mg, 4.0 mmol) and the solution was stirred at 0° C. for 15 min. Dimethylamine hydrochloride (97.5 mg, 1.20 mmol) was added and the solution was warmed gradually to room temperature and stirred for 14 h. Water was added to the reaction and the product was extracted with CHCl$_3$. The combined organic layers were washed with water twice, dried over MgSO$_4$, and concentrated. The product was purified via gradient silica gel chromatography using CHCl$_3$/MeOH (100/0 to 95/5) to give the title compound (240 mg, 70%) as a light yellow solid. $^1$H NMR (300 MHz, CHLOROFORM-D) δ ppm 1.38 (t, J=7.16 Hz, 3 H) 3.13 (s, 3 H) 3.32 (s, 3 H) 4.38 (q, J=7.16 Hz, 2 H) 6.64 (t, J=56.61 Hz, 1 H) 7.09 (d, J=8.48 Hz, 2 H) 7.16 (s, 1 H) 7.50 (d, J=8.48 Hz, 2 H) 7.55 (s, 1 H) 8.05 (s, 1 H).

Preparation of Intermediate 323f 4-(4-Formylphenoxy)-N$^2$,N$^2$-dimethyl-N$^6$-(5-methylpyridin-2yl)-1-benzofuran-2,6-dicarboxamide

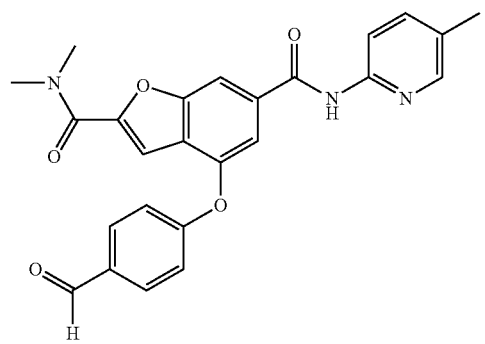

2-Amino-5-methyl pyridine (214 mg, 1.98 mmol) was dissolved in DCE (10 mL) at 0° C., then Al(CH$_3$)$_2$Cl (1.98 mL, 1M in hexanes) was added drop wise. After the addition, the ice-bath was removed, and the mixture was stirred for 30 minutes at room temperature. Ethyl 4-[4-(difluoromethyl)-phenoxy]-2-[(dimethylamino)carbonyl]-1-benzofuran-6-carboxylate (80 mg, 0.2 mmol) was added, and the stirring was continued for an additional 14 h. The reaction was quenched with potassium sodium tartrate tetrahydrate (20% w/w) cautiously. The product was extracted with CHCl$_3$, washed with brine and dried over MgSO$_4$. The product was purified by chromatography on silica gel to give the title compound (40 mg, 45%) as a white solid. $^1$H NMR (300 MHz, CHLOROFORM-D) δ ppm 2.26 (s, 3 H) 3.12 (s, 3 H) 3.31 (s, 3 H) 7.10 (d, J=8.67 Hz, 2 H) 7.15 (s, 1 H) 7.48 (d, J=1.13 Hz, 1 H) 7.54 (dd, J=8.48, 2.17 Hz, 1 H) 7.86 (d, J=8.67 Hz, 2 H) 7.95 (s, 1 H) 8.01 (s, 1 H) 8.22 (d, J=8.48 Hz, 1 H) 8.94 (s, 1 H) 9.92 (s, 1 H).

Example 324

N,N-Dimethyl-3-[(2-methyl-6-{[(5-methylpyridin-2-yl)amino]-carbonyl}-1-benzofuran-4-yl)oxy]azetidine-1-carboxamide

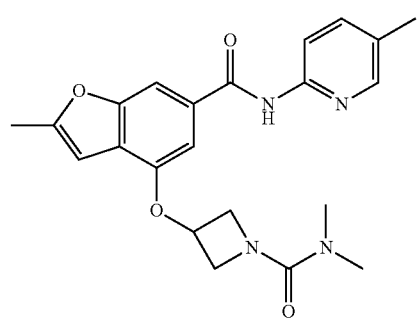

To a solution of 2-amino-5-methyl pyridine (203 mg, 1.88 mmol) in dichloromethane (5 mL) at 0° C. was added Al(CH$_3$)$_2$Cl (1.88 mL, 1M in hexanes) drop wise. After the addition, the ice-bath was removed, and the mixture was stirred for 30 minutes at room temperature. Ethyl 4-({1-[(dimethylamino)carbonyl]azetidin-3-yl}oxy)-2-methyl-1-benzofuran-6-carboxylate (65 mg, 0.19 mmol) was added and the stirring was continued for 14 h. The reaction was quenched with potassium sodium tartrate tetrahydrate (20% w/w) cautiously. The product was extracted with CHCl$_3$, washed with brine and dried over Na$_2$SO$_4$. The product was purified by gradient silica gel chromatography using CHCl$_3$/MeOH (95/5 to 85/15) to give the title compound (70 mg, 90%) as a white solid. $^1$H NMR (400 MHz, DMSO-d6) δ ppm 2.15 (s, 3 H) 2.37 (s, 3 H) 2.78 (s, 6 H) 3.30-3.44 (m, 2 H) 3.44-3.60 (m, 1 H) 3.88 (dd, J=12.13, 6.06 Hz, 1 H) 4.05 (dd, J=11.75, 2.40 Hz, 1 H) 6.70 (s, 1 H) 6.98 (d, J=9.60 Hz, 1 H) 7.71-7.85 (m, 1 H) 7.92 (s, 1 H) 8.17 (d, J=8.34 Hz, 1 H) 8.28-8.44 (m, 2 H); MS (ESI, pos): 409.

Preparation of Intermediate 324a

Ethyl 4-{[1-(diphenylmethyl)azetidin-3-yl]oxy}-2-methyl-1-benzofuran-6-carboxylate

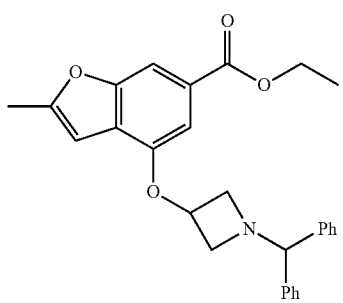

A mixture of ethyl 4-hydroxy-2-methyl-1-benzofuran-6-carboxylate (252c) (1.70 g, 7.72 mmol), 1-(diphenylmethyl)azetidin-3-yl methanesulfonate (193a) (2.95 g, 9.29 mmol) and Cs$_2$CO$_3$ (6.29 g, 19.3 mmol) in DMF (10 mL) was stirred for 4 hours at 100° C. The reaction was cooled to room temperature, diluted with EtOAc and washed with water and brine, dried over MgSO$_4$, and concentrated under reduced pressure. The product was purified via gradient silica gel chromatography using EtOAc/Hexanes (10/90 to 40/60) to give the desired compound (2.15 g, 63%) as a white solid after evaporation of the solvent. $^1$H NMR (300 MHz, CHLOROFORM-d) δ ppm 1.32-1.49 (m, 3 H) 2.42-2.57 (m, 3 H) 3.10-3.29 (m, 2 H) 3.75-3.94 (m, 2 H) 4.27-4.42 (m, 2 H) 4.43-4.52 (m, 1 H) 4.91-5.10 (m, 1 H) 6.50 (s, 1 H) 7.05 (s, 1 H) 7.15-7.25 (m, 2 H) 7.24-7.35 (m, 4 H) 7.39-7.54 (m, 4 H) 7.74 (s, 1 H); MS (ESI, pos): 442.

Preparation of Intermediate 324b

Ethyl 4-(azetidin-3-yloxy)-2-methyl-1-benzofuran-6-carboxylate

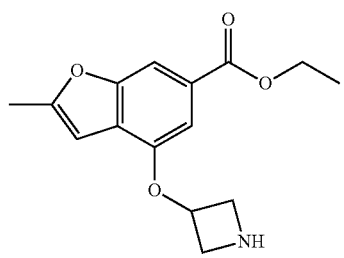

A mixture of ethyl 4-{[1-(diphenylmethyl)azetidin-3-yl]oxy}-2-methyl-1-benzofuran-6-carboxylate (2.1 g, 4.77 mmol) in EtOAc/MeOH (10 mL/20 mL) and Pd/C (0.060 g, 10%, 0.048 mmol) was stirred for 14 hours under a hydrogen atmosphere (balloon). The mixture was filtered through a bed of Celite washing with methanol. The sample was concentrated to give a pale white solid (quantitative yield), which was used without further purification. $^1$H NMR (300 MHz, CHLOROFORM-d) δ ppm 1.35-1.52 (m, 3 H) 2.18 (s, 1 H) 2.47 (s, 3 H) 3.78-3.94 (m, 2 H) 4.00-4.13 (m, J=7.16 Hz, 2 H) 4.29-4.49 (m, 2 H) 5.11-5.27 (m, 1 H) 6.52 (s, 1 H) 7.05 (s, 1 H) 7.78 (s, 1 H); MS (ESI, pos): 276.

Preparation of Intermediate 324c

Ethyl 4-({1-[(dimethylamino)carbonyl]azetidin-3-yl}oxy)-2-methyl-1-benzofuran-6-carboxylate

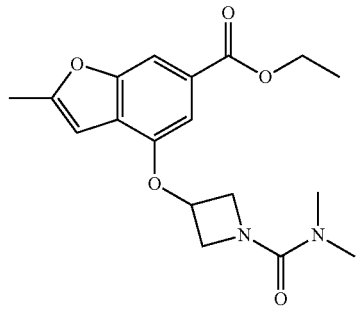

To a solution of ethyl 4-(azetidin-3-yloxy)-2-methyl-1-benzofuran-6-carboxylate (200 mg, 0.73 mmol) in dissolved in DCM with containing TEA (0.4 mL, 2.9 mmol) was added dimethylcarbamic chloride (0.1 mL, 1.09 mmol). The mixture solution was stirred at room temperature for 2 hrs. The reaction was diluted with DCM, washed with NaHCO$_3$, brine, dried over Na$_2$SO$_4$ and concentrated under reduced pressure. The product was purified via gradient silica gel chromatography using EtOAc/Hexanes (20/80 to 60/40) to provide the product (138 mg, 55%) as a colorless oil. $^1$H NMR (300 MHz, CHLOROFORM-d) δ ppm 1.36-1.54 (m, 3

H) 2.49 (s, 3 H) 2.88 (s, 6 H) 4.06-4.20 (m, 2 H) 4.33-4.53 (m, 4 H) 5.04-5.18 (m, 1 H) 6.52 (s, 1 H) 7.01 (s, 1 H) 7.80 (s, 1 H); MS (ESI, pos): 347.

Example 325

2-Methyl-4-{[1-(methylsulfonyl)azetidin-3-yl]oxy}-N-(2-methyl-2H-1,2,3-triazol-4-yl)-1-benzofuran-6-carboxamide

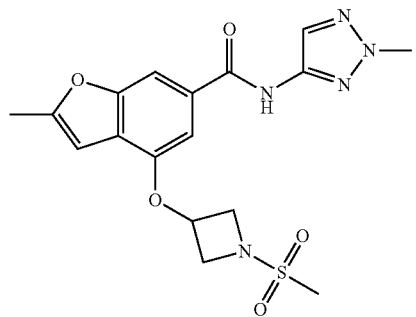

To a solution of 2-methyl-2H-1,2,3-triazol-4-amine (267 mg, 1.98 mmol) in dichloromethane (5 mL) at 0° C. was added Al(CH$_3$)$_2$Cl (1.98 mL, 1.98 mmol, 1M in hexanes) drop-wise. After the addition, the ice-bath was removed, and the mixture was stirred for 30 minutes at room temperature. Ethyl 2-methyl-4-{[1-(methylsulfonyl)azetidin-3-yl]oxy}-1-benzofuran-6-carboxylate (70 mg, 0.198 mmol) was added and the stirring was continued for 14 h. The reaction was quenched with potassium sodium tartrate tetrahydrate (20% w/w) cautiously. The product was extracted with CH$_2$Cl$_2$, washed with brine and dried over Na$_2$SO$_4$. The product was purified by gradient silica gel chromatography using CHCl$_3$/MeOH (95/5 to 85/15) to give the title compound (55 mg, 68%) as a white solid after evaporation of the solvents. $^1$H NMR (400 MHz, CHLOROFORM-d) δ ppm 2.51 (s, 3 H) 2.94 (s, 3 H) 4.06-4.15 (m, 3 H) 4.16 (d, J=4.80 Hz, 2 H) 4.39 (dd, J=9.60, 6.32 Hz, 2 H) 5.05-5.23 (m, 1 H) 6.54 (s, 1 H) 6.97 (s, 1 H) 7.54 (s, 1 H) 8.12 (s, 1 H) 8.46 (s, 1 H); MS (ESI, pos): 406.

Preparation of Intermediate 325a

Ethyl 2-methyl-4-{[1-(methylsulfonyl)azetidin-3-yl]oxy}-1-benzofuran-6-carboxylate

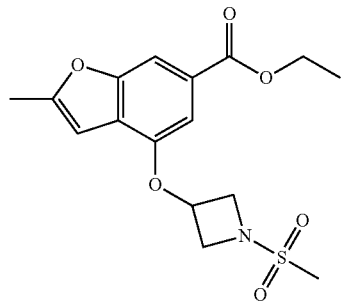

To a solution of ethyl 4-(azetidin-3-yloxy)-2-methyl-1-benzofuran-6-carboxylate (324b) (200 mg, 0.73 mmol) in DCM containing TEA (0.4 mL, 2.9 mmol) was added methanesulfonyl chloride (0.07 mL, 0.87 mmol). The mixture was stirred at room temperature for 2 hrs. The reaction was diluted with DCM, washed with NaHCO$_3$, brine, dried over Na$_2$SO$_4$ and concentrated under reduced pressure. The product was purified via gradient silica gel chromatography using EtOAc/Hexanes (10/90 to 30/70) to provide the product (206 mg, 80%) as a white solid after evaporation of the solvents. $^1$H NMR (300 MHz, CHLOROFORM-d) δ ppm 1.34-1.51 (m, 3 H) 2.49 (s, 3 H) 2.89-3.07 (m, 3 H) 4.06-4.22 (m, J=9.23, 4.33 Hz, 2 H) 4.33-4.54 (m, 4 H) 5.07-5.23 (m, 1 H) 6.52 (s, 1 H) 7.02 (s, 1 H)l MS (ESI, pos): 354.

Example 326 and 327 were prepared in a similar manner as described for Example 325, from Intermediate 325a and the appropriate amino heterocycles.

Example 326

2-Methyl-N-(5-methylpyridin-2-yl)-4-{[1-(methylsulfonyl)-azetidin-3-yl]oxy}-1-benzofuran-6-carboxamide

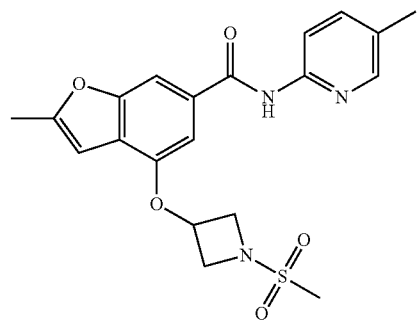

$^1$H NMR (300 MHz, CHLOROFORM-d) δ ppm 2.34 (s, 3 H) 2.51 (s, 3 H) 2.95 (s, 3 H) 4.08-4.23 (m, 2 H) 4.34-4.50 (m, 2 H) 5.10-5.26 (m, 1 H) 6.54 (s, 1 H) 6.98 (s, 1 H) 7.57-7.70 (m, 2 H) 8.14 (s, 1 H) 8.27 (d, J=8.67 Hz, 1 H) 8.57 (s, 1 H); LCMS m/z 416 (M+H)$^+$.

Example 327

2-Methyl-N-(1-methyl-1H-pyrazol-3-yl)-4-{[1-(methylsulfonyl)-azetidin-3-yl]oxy}-1-benzofuran-6-carboxamide

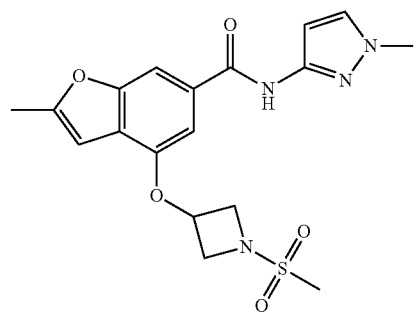

$^1$H NMR (400 MHz, CHLOROFORM-d) δ ppm 2.45-2.69 (m, 3 H) 2.85-3.13 (m, 3 H) 3.64-3.83 (m, 3 H) 4.11 (dd, J=9.09, 4.80 Hz, 2 H) 4.35 (dd, J=8.97, 6.44 Hz, 2 H) 4.95-5.24 (m, 1 H) 6.85 (s, 1 H) 6.95 (s, 1 H) 7.31 (d, J=2.27 Hz, 1 H) 7.56 (s, 1 H) 9.04 (s, 1 H); LCMS m/z 405 (M+H)$^+$.

Example 328

2-Methyl-7-(1-methyl-2-phenylethoxy)-N-(1-methyl-1H-pyrazol-3-yl)-1-benzothiophene-5-carboxamide

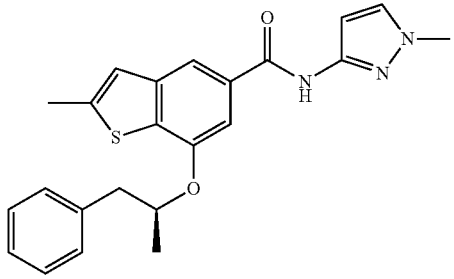

3-Amino-1-methyl pyrazole (649 mg, 6.69 mmol) was dissolved in DCE (10 mL) at 0° C., then Al(CH$_3$)$_2$Cl (6.69 mL, 1M in hexanes) was added drop wise. After the addition, the ice-bath was removed, and the mixture was stirred for 30 min at room temperature. Ethyl 2-methyl-7-[(1S)-1-methyl-2-phenylethoxy]-1-benzothiophene-5-carboxylate (237 mg, 0.669 mmol) was added and the stirring was continued for 14 h. The reaction was quenched with potassium sodium tartrate tetrahydrate (20% w/w) cautiously. The product was extracted with CHCl$_3$, washed with brine and dried over MgSO$_4$. The product was purified by reverse phase HPLC to give the title compound (155 mg, 57%) as a white solid. 1H NMR (300 MHz, CHLOROFORM-D) δ ppm 1.38 (d, J=6.03 Hz, 3 H) 2.59 (s, 3 H) 2.95 (dd, J=13.75, 6.22 Hz, 1 H) 3.16 (dd, J=13.75, 6.03 Hz, 1 H) 3.74 (s, 3 H) 4.78-5.01 (m, 1 H) 6.89 (d, J=2.26H) 7.00 (d, J~1.13 Hz, 1 H) 7.12-7.23 (m, 1 H) 7.26-7.42 (m, 6 H) 7.81 (d, J=1.13 Hz, 1 H) 9.60 (s, 1 H). LCMS m/z 406.0 (M+H)$^+$.

Preparation of Intermediate 328a

5-Methylthiophene-3-carbaldehyde

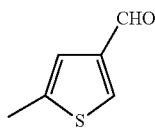

To a solution of N-methylpiperazine (32.5 g, 36 mL, 0.33 mol) in THF (500 mL) at −78° C. was added drop-wise a solution of n-BuLi (1.6 M in hexane, 210 mL). The mixture was stirred for 0.25 h, and 3-thiophenecarbaldehyde (30 g, 0.27 mol) was added drop-wise. The mixture was stirred for 15 min more. TMEDA (81 mL, 63 g, 0.54 mol) and then sec-BuLi (1.3 M in cyclohexane, 250 mL) were added. The mixture was stirred at −78° C. for 2 h. Methyl iodide (153 g, 67 mL, 1.08 mol) was added drop-wise. The mixture was allowed to come to room temperature, stirred overnight, poured into cold water (1 L), and extracted with ether (1 L). The ethereal layer was washed with brine, dried with Na$_2$SO$_4$, and evaporated in vacuum. The crude product was purified on a layer of silica gel (300×150 mm) with hexane/ethyl acetate mixture, (5:1). Fractions with the target product were collected and evaporated in vacuum to give 26 g (0.2 mol, 76%) of a mixture of the desired product and 2-methylthiopene-3-carbaldehyde in 9:1 ratio as a colorless liquid.

Preparation of Intermediate 328b 3-(Ethoxycarbonyl)-4-(5-methyl-3-thienyl)but-3-enoic Acid

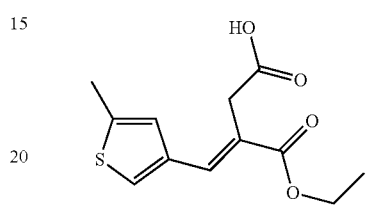

Sodium ethylate (17 g, 0.24 mol) was added under vigorous stirring to a solution of 5-methylthiophene-3-carbaldehyde (26 g 90% purity, 0.20 mol) and diethyl succinate (54 g, 0.31 mol) in ethanol (400 mL). The reaction mixture was refluxed for 3 h and evaporated in vacuum (~20 mmHg) at 50° C. until the solvent distillation ceased. The obtained residue was diluted with 300 mL of 10% HCl and 500 mL of ethyl acetate. The mixture was shaken. The organic layer was separated, diluted with 700 mL of a saturated aqueous solution of NaHCO$_3$, and shaken. The aqueous layer was separated, neutralized by 10% HCl to pH 2, and subjected to extraction by 1 L of ethyl acetate. The organic layer was evaporated in vacuum (~20 mmHg) at 60° C. The residue was chromatographed on a layer of silica gel (200×150 mm) with hexane/ethyl acetate mixture (1:1). Fractions with the target product were collected and evaporated in vacuum to give the desired product 30 g (0.12 mol, 57%) as an oil.

Preparation of Intermediate 328c

Ethyl 7-(Acetyloxy)-2-methyl-1-benzothiophene-5-carboxylate

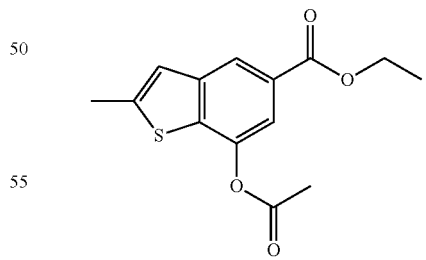

Sodium acetate (30 g, 0.36 mol) was added under vigorous stirring to a solution of 3-(ethoxycarbonyl)-4-(5-methyl-3-thienyl)but-3-enoic acid (30 g, 0.12 mol) in 300 mL of acetic anhydride. The reaction mixture was refluxed for 3 h and evaporated in vacuum (~20 mmHg) at 70° C. until the solvent distillation ceased. The obtained crude product was suspended in 500 mL of dichloromethane. The suspension was filtered. The precipitate was washed by 250 mL of dichloromethane. The combined solutions were washed by 350 mL of a saturated aqueous solution of NaHCO₃ and evaporated in vacuum to dryness. The obtained crude product was chromatographed on a layer of silica gel (250×150 mm) with hexane/ethyl acetate mixture (3:1) to give the desired product 14 g (50 mmol, 42%) as a solid.

Preparation of Intermediate 328d

Ethyl 7-Hydroxy-2-methyl-1-benzothiophene-5-carboxylate

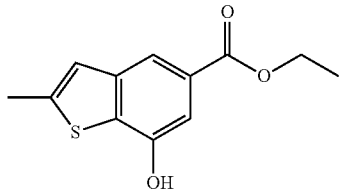

Ethyl 7-(acetyloxy)-2-methyl-1-benzothiophene-5-carboxylate was dissolved in absolute ethanol (500 mL). Potassium carbonate (18 g, 0.13 mol) was added. The reaction mixture was stirred for 3 h at 60° C. and diluted with 200 mL of dichloromethane. The suspension was filtered. The precipitate was washed by 100 mL of dichloromethane. The combined solutions were washed by 200 mL of a 10% aqueous solution of citric acid and evaporated in vacuum to dryness. The residue was crystallized from ether/hexane mixture (1:5) to give the desired product 10 g (42 mmol, 84%) as a cream solid. $^1$H NMR (DMSO-d6): δ ppm 1.30 (t, 3H), 2.50 (s, 3H), 4.30 (qt, 2H), 7.20 (s, 1H), 7.95(s, 1H), 7.85 (s, 1H); MS(APCl, pos): 237.1.

Preparation of Intermediate 328e

Ethyl 2-methyl-7-(1-methyl-2-phenylethoxy)-1-benzothiophene-5-carboxylate

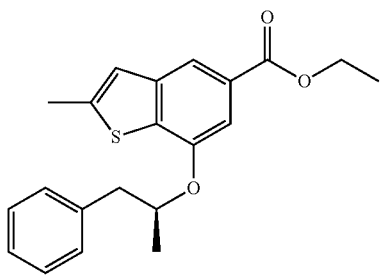

To a solution of ethyl 7-hydroxy-2-methyl-1-benzothiophene-5-carboxylate (500 mg, 2.12 mmol), Ph₃P (1110 mg, 4.23 mmol) and 1-phenyl-2-propane (576 mg, 4.23 mmol) in CH₂Cl₂ (20 mL) was added DIAD (856 mg, 4.23 mmol) drop wise at 0° C. The resulting solution was stirred at room temperature for 4 h. The reaction mixture was concentrated to give an oil residue. The residue was purified by HPLC to give the title compound (500 mg, 67%) as a colorless oil. $^1$H NMR (300 MHz, CHLOROFORM-D) δ ppm 1.36-1.47 (m, 6 H) 2.59 (d, J=1.13 Hz, 3 H) 2.84-3.00 (m, 1 H) 3.10-3.27 (m, 1 H) 4.38 (q, J=7.16 Hz, 2 H) 4.71-4.93 (m, 1 H) 7.01 (d, J=1.13 Hz, 1 H) 7.26-7.33 (m, 5 H) 7.35 (s, 1 H) 7.97 (d, J=1.13 Hz, 1 H).

Examples 329 and 330 were prepared in a similar manner as described for Example 252, via two steps, from Intermediate 328d.

Example 329

2-Methyl-N-(5-methylpyridin-2-yl)-7-[4-(methylsulfonyl)-phenoxy]-1-benzothiophene-5-carboxamide

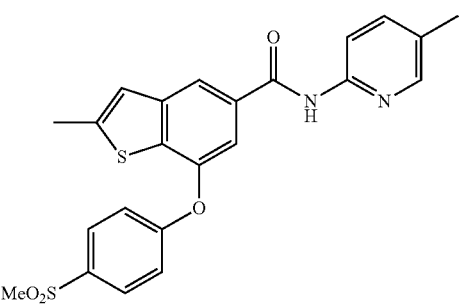

$^1$H NMR (300 MHz, CHLOROFORM-D) δ ppm 2.38 (s, 3 H) 2.61 (s, 3 H) 3.06 (s, 3 H) 7.09-7.23 (m, 3 H) 7.55 (s, 1 H) 7.80 (d, J=8.85 Hz, 1 H) 7.86-7.99 (m, 2 H) 8.08 (s, 1 H) 8.21 (s, 1 H) 8.51 (d, J=8.85 Hz, 1 H) 10.52 (s, 1 H); LCMS m/z 453.0 (M+H)⁺.

Example 330

2-Methyl-N-(1-methyl-1H-pyrazol-3-yl)-7-[4-(methylsulfonyl)-phenoxy]-1-benzothiophene-5-carboxamide

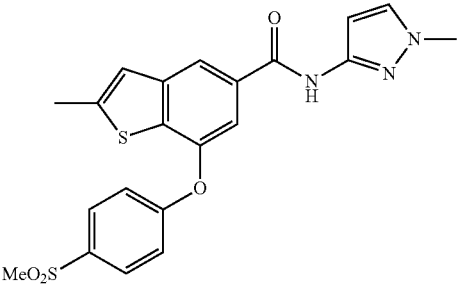

$^1$H NMR (300 MHz, CHLOROFORM-D) δ ppm 2.60 (s, 3 H) 3.06 (s, 3 H) 3.80 (s, 3 H) 6.85 (d, J=2.26 Hz, 1 H) 7.12 (d, J=1.13 Hz, 1 H) 7.14-7.23 (m, 2 H) 7.28 (d, J=2.26 Hz, 1 H)

Example 331

7-{4-[(Dimethylamino)carbonyl]phenoxy}-2-methyl-N-(1-methyl-1H-pyrazol-3-yl)-1-benzothiophene-5-carboxamide

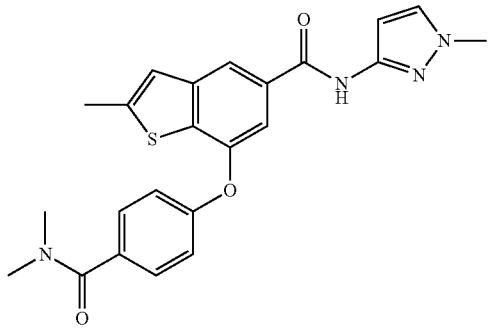

The title compound was prepared in a similar manner as described for Example 276, via three steps from Intermediate 328d. ¹H NMR (300 MHz, CHLOROFORM-D) δ ppm 2.59 (s, 3 H) 3.07 (s, 6 H) 3.75 (s, 3 H) 6.81 (d, J=2.26 Hz, 1 H) 6.97-7.14 (m, 3 H) 7.27 (d, J=2.26 Hz, 1 H) 7.35-7.52 (m, 3 H) 7.99 (d, J−1.13 Hz, 1 H) 9.22 (s, 1 H); LCMS m/z 435.0 (M+H)⁺.

Examples 332 and 333 were prepared in a similar manner as described for Example 252, via two steps from ethyl 7-hydroxybenzofuran-5-carboxylate (332c).

Preparation of Intermediate 332a 3-(Ethoxycarbonyl)-4-(furan-3-yl)but-3-enoic acid

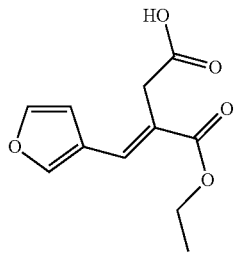

Sodium ethylate (6.5 g, 95 mmol) was added under vigorous stirring to a solution of 2-furaldehyde (10 g, 79 mmol) and diethyl succinate (27.6 g, 158 mmol) in ethanol (300 mL). The reaction mixture was refluxed for 3 h and evaporated in vacuum (~20 mmHg) at 50° C. until the solvent distillation ceased. The obtained residue was diluted with 200 mL of 10% HCl and 300 mL of ethyl acetate. The mixture was shaken. The organic layer was separated, diluted with 200 mL of a saturated aqueous solution of NaHCO₃, and shaken. The aqueous layer was separated, neutralized by 10% HCl to pH 2, and subjected to extraction by 400 mL of ethyl acetate. The organic layer was evaporated in vacuum (~20 mmHg) at 60° C. and chromatographed on a layer of silica gel (200×150 mm) with hexane/ethyl acetate mixture (1:1). Fractions containing the target product were collected and evaporated in vacuum to give the product 9.3 g (38 mmol, 49%) as a light-brown oil.

Preparation of Intermediate 332b

Ethyl 7-(Acetyloxy)-1-benzofuran-5-carboxylate

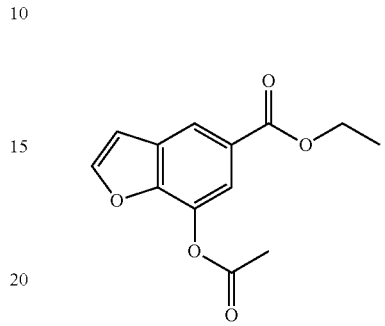

Sodium acetate (10 g, 120 mmol) was added under vigorous stirring to a solution of 3-(ethoxycarbonyl)-4-(furan-3-yl)but-3-enoic acid (12.3 g, 48 mmol) in 100 mL of acetic anhydride. The reaction mixture was refluxed for 3 h and evaporated in vacuum (~20 mmHg) at 70° C. until the solvent distillation ceased. The obtained crude product was suspended in 250 mL of dichloromethane. The suspension was filtered. The precipitate was washed by 100 mL of dichloromethane. The combined solutions were washed by 200 mL of a saturated aqueous solution of NaHCO₃ and evaporated in vacuum to dryness. The obtained crude product was chromatographed on a layer of silica gel (150×100 mm) with hexane/ethyl acetate mixture (3:1) to give the desired product 5.2 g (29 mmol, 61%) as a yellow solid.

Preparation of Intermediate 332c

Ethyl 7-Hydroxy-1-benzofuran-5-carboxylate

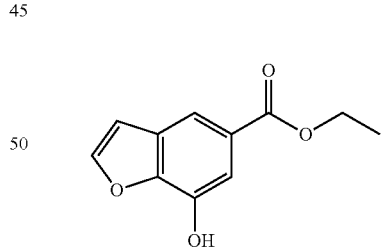

Ethyl 7-(Acetyloxy)-1-benzofuran-5-carboxylate was dissolved in absolute ethanol (200 mL). Potassium carbonate (7 g, 50 mmol) was added. The reaction mixture was stirred for 3 h at 60° C. and diluted with 200 mL of dichloromethane. The suspension was filtered. The precipitate was washed by 100 mL of dichloromethane. The combined solutions were washed by 200 mL of a 10% aqueous solution of citric acid and evaporated in vacuum to dryness. The obtained crude product was chromatographed on a layer of silica gel (150× 100 mm) with hexane/ethyl acetate mixture (2:1) to give the desired product 2.8 g (13 mmol, 38%) as a cream solid. ¹H NMR (DMSO-D6): δ ppm 1.35 (s, 3H), 4.20 (qt, 2H), 7.15 (m, 1H), 7.39 (m, 1H), 7.77 (m, 1H), i8.04 (m, 1H); MS (APCI, pos): 241.1.

Example 332

N-(1-Methyl-1H-pyrazol-3-yl)-7-[4-(methylsulfonyl)phenoxy]-1-benzofuran-5-carboxamide

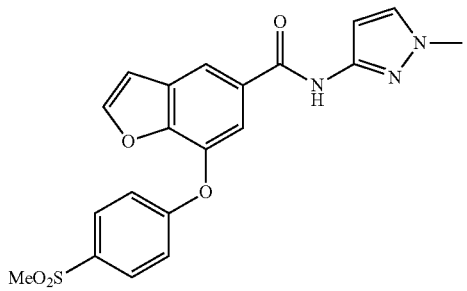

¹H NMR (300 MHz, CHLOROFORM-D) δ ppm 3.06 (s, 3 H) 3.77 (s, 3 H) 6.82 (d, J=2.26 Hz, 1 H) 6.90 (d, J=2.07 Hz, 1 H) 7.05-7.20 (m, 2 H) 7.29 (d, J=2.26 Hz, 1 H) 7.63 (d, J=1.51 Hz, 1 H) 7.67 (d, J=2.07 Hz, 1 H) 7.84-7.97 (m, 2 H) 8.02 (d, J=1.51 Hz, 1 H) 9.02 (s, 1 H); LCMS m/z 412.0 (M+H)⁺.

Example 333

N-(5-methylpyridin-2-yl)-7-[4-(methylsulfonyl)phenoxy]-1-benzofuran-5-carboxamide

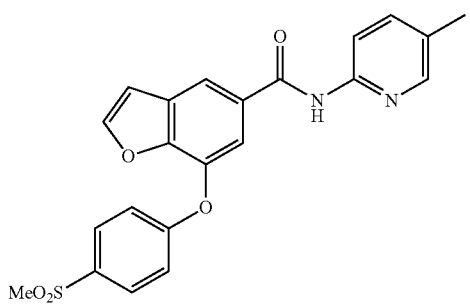

¹H NMR (300 MHz, CHLOROFORM-D) δ ppm 2.42 (s, 3 H) 3.06 (s, 3 H) 6.96 (d, J=2.07 Hz, 1 H) 7.12-7.23 (m, 2 H) 7.69 (d, J=2.07 Hz, 1 H) 7.77 (d, J=1.51 Hz, 1 H) 7.84-8.00 (m, 3 H) 8.06 (s, 1 H) 8.26 (d, J=1.51 Hz, 1 H) 8.64 (d, J=8.85 Hz, 1 H) 11.57 (s, 1 H); LCMS m/z 423.0 (M+H)⁺.

Examples 334 and 335 were prepared in a similar manner as described for Example 276, via three steps, from ethyl 7-hydroxybenzofuran-5-carboxylate (332c).

Example 334

7-{4-[(Dimethylamino)carbonyl]phenoxy}-N-(1-methyl-1H-pyrazol-3-yl)-1-benzofuran-5-carboxamide

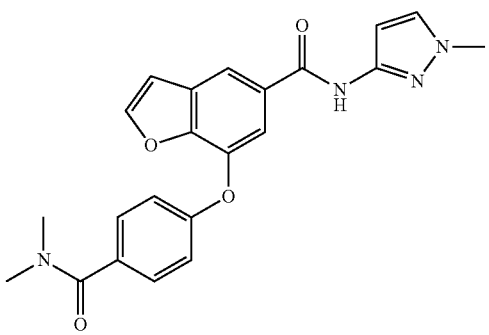

¹H NMR (300 MHz, CHLOROFORM-D) δ ppm 3.06 (d, J=9.04 Hz, 6 H) 3.74 (s, 3 H) 6.80 (d, J=2.07 Hz, 1 H) 6.87 (d, J=2.26 Hz, 1 H) 7.04 (d, J=8.48 Hz, 2 H) 7.27 (d, J=2.26 Hz, 1 H) 7.42 (d, J=8.48 Hz, 2 H) 7.52 (s, 1 H) 7.67 (d, J=2.07 Hz, 1 H) 7.93 (d, J=1.32 Hz, 1 H) 8.89 (s, 1 H); LCMS m/z 405.0 (M+H)⁺.

Example 335

7-{4-[(Dimethylamino)carbonyl]phenoxy}-N-(5-methylpyridin-2-yl)-1-benzofuran-5-carboxamide

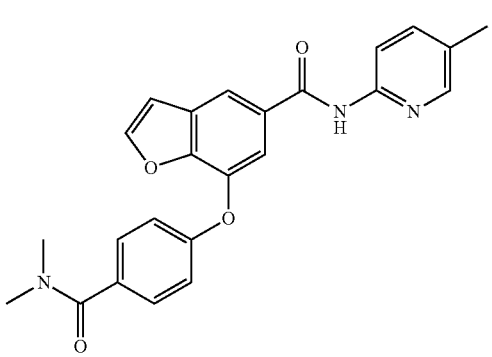

¹H NMR (300 MHz, CHLOROFORM-D) δ ppm 2.31 (s, 3 H) 3.08 (s, 6 H) 6.90 (d, J=2.26 Hz, 1 H) 7.05 (d, J=8.67 Hz, 2 H) 7.38-7.47 (d, J=8.67 Hz, 2 H) 7.57 (s, 1 H) 7.61 (d, J=8.48 Hz, 1 H) 7.69 (d, J=2.26 Hz, 1 H) 8.02 (d, J=1.51 Hz, 1 H) 8.09 (s, 1 H) 8.23 (d, J=8.48 Hz, 1 H) 8.91 (s, 1 H); LCMS m/z 416.0 (M+H)+.

Example 336

7-[(1S)-1-Methyl-2-phenylethoxy]-N-(1-methyl-1H-pyrazol-3-yl)-1-benzofuran-5-carboxamide

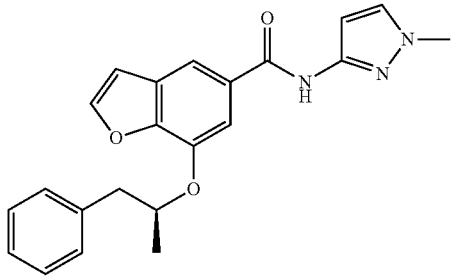

The title compound was prepared in a similar manner as described for Example 328, via two steps, from ethyl 7-hydroxybenzofuran-5-carboxylate (332c). $^1$H NMR (300 MHz, CHLOROFORM-D) δ ppm 1.38 (d, J=6.03 Hz, 3 H) 2.92 (dd, J=13.75, 6.78 Hz, 1 H) 3.22 (dd, J=13.56, 6.03 Hz, 1 H) 3.66 (s, 3 H) 4.85-5.03 (m, 1 H) 6.79 (d, J=2.26 Hz, 1 H) 6.89 (d, J=2.26 Hz, 1 H) 7.12-7.24 (m, 1 H) 7.25-7.36 (m, 5 H) 7.46 (s, 1 H) 7.67 (d, J=2.07 Hz, 1 H) 7.73 (d, J=1.32 Hz, 1 H) 9.71 (s, 1 H); LCMS m/z 376.0 (M+H)+.

Examples 337 and 338 were prepared in a similar manner as described for Example 252, via two steps, from ethyl 7-hydroxy-2-methylbenzofuran-5-carboxylate (337d).

Preparation of Intermediate 337a

5-Methyl-3-furaldehyde

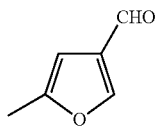

To a solution of N-methylpiperazine (31 g, 35 mL, 0.31 mol) in THF (500 mL) at −78° C. was added drop-wise a solution of n-BuLi (1.6 M in hexane, 200 mL). The mixture was stirred for 0.25 h, and 3-furaldehyde (25 g, 0.26 mol) was added drop-wise. The mixture was stirred for 0.25 h more. TMEDA (77 mL, 60g, 0.52 mol) and then sec-BuLi (1.3 M in cyclohexane, 250 mL) were added, and the mixture was stirred at −78° C. for 2 h. Methyl iodide (148 g, 65 mL, 1.04 mol) was added drop-wise. The mixture was allowed to come to room temperature, stirred overnight, poured into cold water (1 L), and extracted with ether (1L). The ethereal layer was washed with brine, dried with Na$_2$SO$_4$, and evaporated in vacuum. The crude product was purified on a layer of silica gel (300×150 mm) with hexane/ethyl acetate mixture, 5:1 as eluent. Fractions with the target product were collected and evaporated in vacuum to give 21 g (0.19 mol, 74%) of a mixture of the desired product and 2-methyl-3-furaldehyde in 4:1 ratio as a colorless liquid.

Preparation of Intermediate 337b 3-(Ethoxycarbonyl)-4-(5-methyl-3-furyl)but-3-enoic Acid

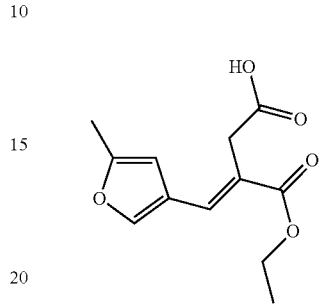

Sodium ethylate (16 g, 0.23 mol) was added under vigorous stirring to a solution of 5-methyl-3-furaldehyde (21 g 80% purity, 0.19 mol) and diethyl succinate (50 g, 0.286 mol) in ethanol (400 mL). The reaction mixture was refluxed for 3 h and evaporated in vacuum (~20 mmHg) at 50° C. until the solvent distillation ceased. The obtained residue was diluted with 300 mL of 10% HCl and 500 mL of ethyl acetate. The mixture was shaken. The organic layer was separated, diluted with 700 mL of a saturated aqueous solution of NaHCO$_3$, and shaken. The aqueous layer was separated, neutralized by 10% HCl to pH 2, and subjected to extraction by 1 L of ethyl acetate. The organic layer was evaporated in vacuum (~20 mmHg) at 60° C. and chromatographed on a layer of silica gel (200×150 mm) with hexane/ethyl acetate mixture (1:1). Fractions with the target product were collected, evaporated in vacuum and crystallized from ether/hexane mixture, 1:3 to give the desired product 14 g (58 mmol, 31%) as yellow crystals.

Preparation of Intermediate 337c

Ethyl 7-(Acetyloxy)-2-methyl-1-benzofuran-5-carboxylate

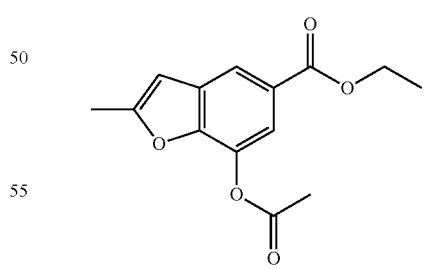

Sodium acetate (15 g, 0.18 mol) was added under vigorous stirring to a solution of 3-(ethoxycarbonyl)-4-(5-methyl-3-furyl)but-3-enoic acid (14 g, 58 mmol) in 150 mL of acetic anhydride. The reaction mixture was refluxed for 3 h and evaporated in vacuum (~20 mmHg) at 70° C. until the solvent distillation ceased. The obtained crude product was suspended in 300 mL of dichloromethane. The suspension was filtered. The precipitate was washed by 250 mL of dichloromethane. The combined solutions were washed by 350 mL of a saturated aqueous solution of NaHCO$_3$ and evaporated in vacuum to dryness. The obtained crude product was chromatographed on a layer of silica gel (250×150 mm) with hexane/ethyl acetate mixture (3:1) as eluent to give the desired product 12.5 g (47 mmol, 81%) as a solid.

Preparation of Intermediate 337d

Ethyl 7-Hydroxy-2-methyl-1-benzofuran-5-carboxylate

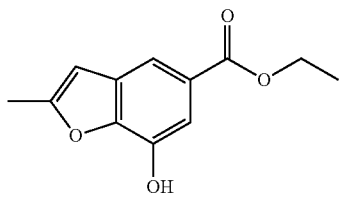

Ethyl 7-(Acetyloxy)-2-methyl-1-benzofuran-5-carboxylate was dissolved in absolute ethanol (200 mL).

Potassium carbonate (18 g, 0.13 mol) was added. The reaction mixture was stirred for 3 h at 60° C. and diluted with 200 mL of dichloromethane. The suspension was filtered. The precipitate was washed by 100 mL of dichloromethane. The combined solutions were washed by 200 mL of a 10% aqueous solution of citric acid and evaporated in vacuum to dryness. The residue was and crystallized from ether/hexane mixture, 1:5 to give the desired product 8.5 g (38 mmol, 81%) as a cream solid. $^1$H NMR (DMSO-D6): δ ppm 1.35 (t, 3H), 2.40 (s, 3H), 4.20 (qt, 2H), 6.65 (s, 1H), 7.32 (s, 1H), 7.65 (s, 1H); MS (APCI, pos): 221.1.

Example 337

2-Methyl-N-(5-methylpyridin-2-yl)-7-[4-(methylsulfonyl)-phenoxy]-1-benzofuran-5-carboxamide

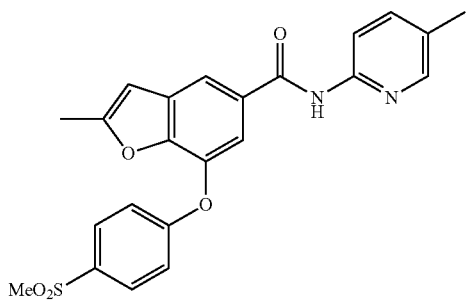

$^1$H NMR (300 MHz, CHLOROFORM-D) δ ppm 2.30 (s, 3 H) 2.45 (s, 3 H) 3.06 (s, 3 H) 6.52 (d, J=0.94 Hz, 1 H) 7.07-7.21 (m, 2 H) 7.47-7.65 (m, 2 H) 7.84-8.00 (m, 3 H) 8.10 (s, 1 H) 8.24 (d, J=8.29 Hz, 1 H) 8.59 (s, 1 H); LCMS m/z 437.0 (M+H)$^+$.

Example 338

2-Methyl-N-(1-methyl-1H-pyrazol-3-yl)-7-[4-(methylsulfonyl)-phenoxy]-1-benzofuran-5-carboxamide

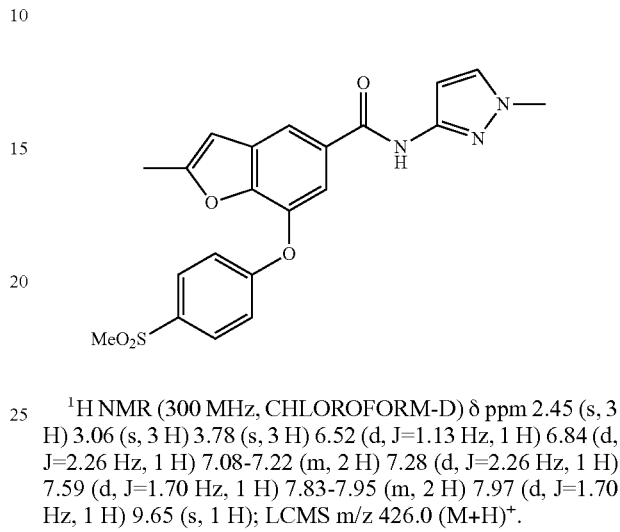

$^1$H NMR (300 MHz, CHLOROFORM-D) δ ppm 2.45 (s, 3 H) 3.06 (s, 3 H) 3.78 (s, 3 H) 6.52 (d, J=1.13 Hz, 1 H) 6.84 (d, J=2.26 Hz, 1 H) 7.08-7.22 (m, 2 H) 7.28 (d, J=2.26 Hz, 1 H) 7.59 (d, J=1.70 Hz, 1 H) 7.83-7.95 (m, 2 H) 7.97 (d, J=1.70 Hz, 1 H) 9.65 (s, 1 H); LCMS m/z 426.0 (M+H)$^+$.

Example 339

7-{4-[(Dimethylamino)carbonyl]phenoxy}-2-methyl-N-(5-methylpyridin-2-yl)-1-benzofuran-5-carboxamide

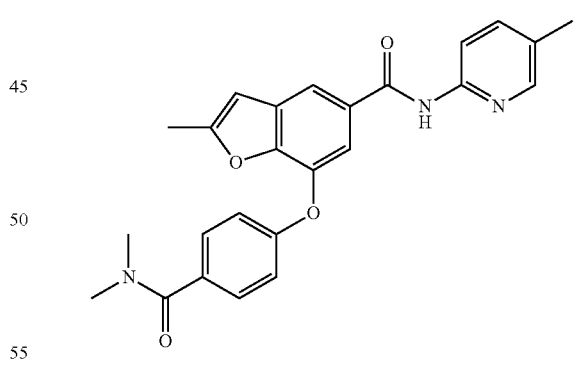

The title compound was prepared in a similar manner as described for Example 276, via three steps, from ethyl 7-hydroxy-2-methylbenzofuran-5-carboxylate (337d). $^1$H NMR (300 MHz, CHLOROFORM-D) δ ppm 2.30 (s, 3 H) 2.46 (s, 3 H) 3.06 (d, J=11.11 Hz, 6 H) 6.51 (s, 1 H) 7.01-7.15 (m, 2 H) 7.38-7.45 (m, 2 H) 7.46 (d, J=1.51 Hz, 1 H) 7.59 (dd, J=8.48, 2.07 Hz, 1 H) 7.88 (d, J=1.51 Hz, 1 H) 8.08 (s, 1 H) 8.23 (d, J=8.48 Hz, 1 H) 8.87 (s, 1 H); LCMS m/z 430.0 (M+H)$^+$.

Example 340

2-Methyl-7-[(1S)-1-methyl-2-phenylethoxy]-N-(1-methyl-1H-pyrazol-3-yl)-1-benzofuran-5-carboxamide

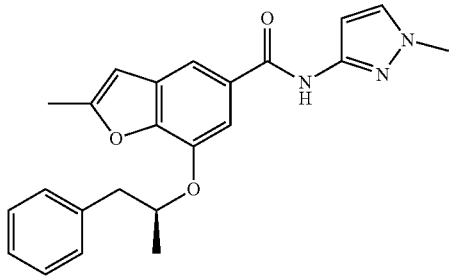

The title compound was prepared in a similar manner as described for Example 328, via two steps, from ethyl 7-hydroxy-2-methylbenzofuran-5-carboxylate (337d). $^1$H NMR (300 MHz, CHLOROFORM-D) δ ppm 1.38 (d, J=6.03 Hz, 3 H) 2.49 (s, 3 H) 2.91 (dd, J=13.56, 6.97 Hz, 1 H) 3.23 (dd, J=13.56, 6.03 Hz, 1 H) 3.72 (s, 3 H) 4.78-4.97 (m, 1 H) 6.39 (d, J=0.94 Hz, 1 H) 6.84 (d, J=2.26 Hz, 1 H) 7.16-7.24 (m, 1 H) 7.26-7.31 (m, 5 H) 7.33 (d, J=1.51 Hz, 1 H) 7.54 (d, J=1.51 Hz, 1 H) 8.98 (s, 1 H); LCMS m/z 390.0 (M+H)$^+$.

Example 341

4-(4-(Dimethylcarbamoyl)-3-fluorophenoxy)-N-(1-methyl-1H-pyrazol-3-yl)benzofuran-6-carboxamide

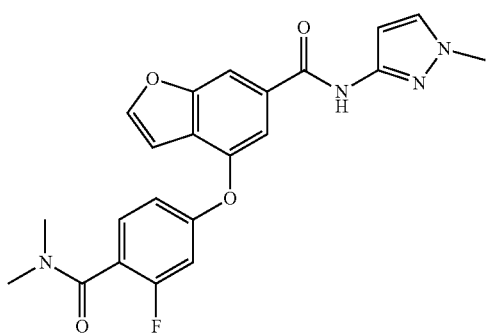

Cs$_2$CO$_3$ (0.806 g, 2.47 mmol) was added to a solution of ethyl 4-hydroxy-benzofuran-6-carboxylate (8a) (0.256 g, 1.24 mmol) and 2,4-difluoro-N,N-dimethylbenzamide (0.287 g, 1.55 mmol) in DMF (5 mL). The mixture was stirred at 150° C. for 8 hours and then cooled to room temperature. 1-Methyl-1H-pyrazol-3-amine (0.21 g, 2.11 mmol) and then HATU (0.71 g, 1.87 mmol) were added. The reaction mixture was stirred at 50° C. for one hour and then filtered. Purification by HPLC gave a solid (200 mg, 39% yield) as the expected product. $^1$H NMR (400 MHz, DMSO-d$_6$) δ 10.95 (s, 1 H) 8.22 (s, 1 H) 8.16 (m, 1 H)) 7.62-7.36 (s, 1 H) 7.60-7.61 (m, 1 H) 7.39-7.43 (m, 1 H) 7.08-7.11 (m, 1 H) 6.95-6.97 (m, 1 H) 6.89 (s, 1 H) 6.59-6.60 (m, 1 H) 3.78 (s, 3 H) 2.99 (s, 3 H) 2.88 (m, 3 H). LCMS for C$_{22}$H$_{19}$FN$_4$O$_4$ m/z 423.10 (M+H)$^+$.

Example 342

4-(4-(Dimethylcarbamoyl)-3-fluorophenoxy)-N-(5-methylpyridin-2-yl)benzofuran-6-carboxamide

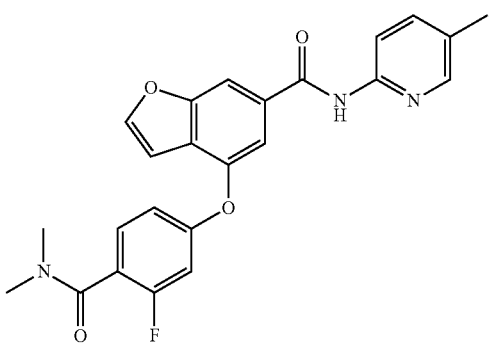

The title compound was prepared in a similar manner as described for Example 341, from ethyl 4-hydroxy-benzofuran-6-carboxylate (8a) (0.26 g, 1.24 mmol), 2,4-difluoro-N,N-dimethylbenzamide (0.287 g, 1.55 mmol), and 2-amino-5-methyl pyridine (0.228 g, 2.11 mmol) (except that amide coupling was carried out at 75° C. for four hours) to give a solid (81 mg, 15% yield) as the expected product. $^1$H NMR (400 MHz, DMSO-d$_6$) δ 10.84 (s, 1 H) 8.27 (s, 1 H) 8.22-8.23 (m, 1 H) 8.18-8.19 (m, 1 H)) 8.06-8.08 (d, 1 H) 7.67 (m, 1 H) 7.64 (m, 1 H) 7.39-7.44 (t, 1 H) 7.09-7.12 (m, 1 H) 6.95-6.97 (m, 1 H) 6.90 (m, 1 H) 3.00 (s, 3 H) 2.88 (m, 3 H) 2.28 (s, 3 H). LCMS for C$_{24}$H$_{20}$FN$_3$O$_4$ m/z 434.10 (M+H)$^+$.

Example 343

4-(4-(Methylsulfonyl)phenoxy)-N-(1-methyl-1H-pyrazol-3-Abenzofuran-6-carboxamide

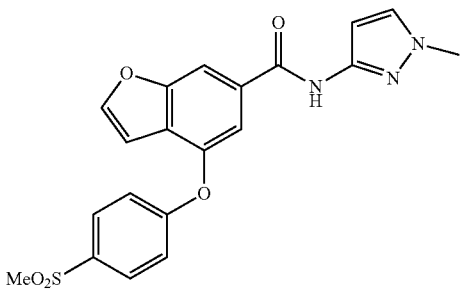

Cs$_2$CO$_3$ (0.806 g, 2.47 mmol) was added to a solution of ethyl 4-hydroxybenzofuran-6-carboxylate (8a) (0.27 g, 1.24 mmol) and 1-fluoro-4-(methylsulfonyl)benzene (0.22 g, 1.26 mmol) in DMF (5 ML). The mixture was stirred at 120° C. for 8 hours and then cooled to room temperature. 1-Methyl-1H-pyrazol-3-amine (0.18 g, 1.85 mmol) and HATU (0.7 g, 1.85 mmol) were added. The reaction mixture was stirred at 50° C. for one hour and then filtered. Purification by HPLC gave a solid (103 mg, 21% yield) as the expected product. $^1$H NMR (400 MHz, DMSO-d$_6$) δ 10.97 (s, 1 H) 8.24-8.26 (m, 1 H) 8.17-8.19 (m, 1 H) 7.92-7.97 (m, 2 H) 7.65-7.67 (m, 1 H) 7.60-7.61 (m, 2 H) 7.25-7.29 (m, 1 H) 6.87-6.88 (m, 1 H) 6.58 (m, 1 H) 3.78 (s, 3 H), 3.21 (s, 3 H), 2.58 (m, 3 H). LCMS for C$_{20}$H$_{17}$N$_3$O$_6$S m/z 412.10 (M+H)$^+$.

Example 344

6-Isopropoxy-N-(5-methylpyridin-2-yl)benzofuran-4-carboxamide

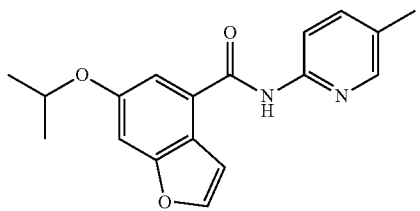

The title compound was prepared in a similar manner as described for Example 1, from 2-amino-5-methyl pyridine and methyl 6-isopropoxybenzofuran-4-carboxylate (344a) to give a white solid (28 mg, 37% yield). $^1$H NMR (400 MHz, CDCl$_3$) δ 8.77 (s, 1 H) 8.29 (d, J=8.56 Hz, 1 H) 8.04 (d, J=2.52 Hz, 1 H) 7.65 (d, J=2.27 Hz, 1 H) 7.58 (dd, J=8.31, 2.27 Hz, 1 H) 7.34 (d, J=2.01 Hz, 1 H) 7.21-7.23 (m, 2 H) 4.55-4.64 (m, 1 H) 2.30 (s, 3 H) 1.37 (d, J=6.04 Hz, 6 H); LCMS for C$_{18}$H$_{18}$N$_2$O$_3$ m/z 311.10 (M+H)$^+$.

Preparation of Intermediate 344a

Methyl 6-isopropoxybenzofuran-4-carboxylate

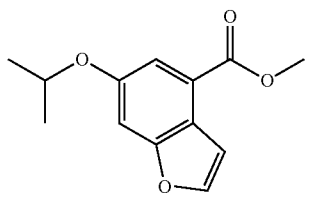

The title compound was prepared in a similar manner as described for Example 6c. $^1$H NMR (400 MHz, CDCl$_3$) δ 7.64 (d, J=2.01 Hz, 1 H) 7.61 (d, J=2.27 Hz, 1 H) 7.26 (d, J=2.27 Hz, 1 H) 7.24 (d, J=2.27 Hz, 1 H) 4.59-4.66 (m, 1 H), 3.98 (s, 3H), 1.38 (d, J=6.04 Hz, 6 H); LCMS for C$_{13}$H$_{14}$O$_4$ m/z 235.10 (M+H$^+$).

Example 345

2-Bromo-6-isopropoxy-N-(5-methylpyridin-2-yl)benzofuran-4-carboxamide

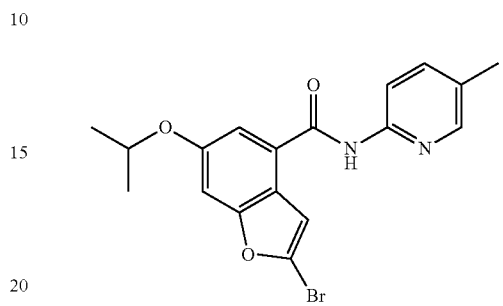

The title compound was prepared in a similar manner as described for Example 1, from 2-amino-5-methyl pyridine and methyl 2-bromo-6-isopropoxybenzofuran-4-carboxylate (345a) to give an off-white solid (1.45 g, 53% yield). $^1$H NMR (400 MHz, CDCl$_3$) δ 8.47 (s, 1 H) 8.27 (d, J=8.31 Hz, 1 H) 8.14 (s, 1 H) 7.60 (dd, J=8.44, 1.89 Hz, 1 H) 7.30 (d, J=2.01 Hz, 1 H) 7.24 (s, 1 H) 7.16 (d, J=1.76 Hz, 1 H) 4.57-4.64 (m, 1 H) 2.34 (s, 3 H) 1.38 (d, J=6.04 Hz, 6 H); LCMS for C$_{18}$H$_{17}$BrN$_2$O$_3$ m/z 389.00 (M+H)$^+$.

Preparation of Intermediate 345a

Methyl 2-bromo-6-isopropoxybenzofuran-4-carboxylate

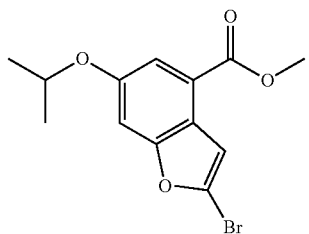

A mixture of methyl 6-isopropoxybenzofuran-4-carboxylate (344a) (2.17 g, 9.25 mmol) and NBS (4.12 g, 23.1 mmol) in 50 mL of CHCl$_3$ was heated at 60° C. for 5 hrs, followed by addition of another batch of NBS (2.50 g, 14.0 mmol). After stirring for an additional 1.2 h, the reaction was concentrated, and the residue was purified with Biotage column chromatography eluting with CHCl$_3$ to give a yellow oil (2.52 g, 87% yield). $^1$H NMR (400 MHz, CDCl$_3$) δ 7.57 (d, J=2.27 Hz, 1 H)

7.22 (s, 1 H) 7.18 (d, J=2.01 Hz, 1 H) 4.56-4.64 (m, 1 H), 3.97 (s, 3H), 1.37 (d, J=6.04 Hz, 6 H); LCMS for $C_{13}H_{13}BrO_4$ m/z 312.0 (M+H)$^+$.

Example 346

6-Isopropoxy-N-(5-methylpyridin-2-yl)-2-(prop-1-en-2-yl)benzofuran-4-carboxamide

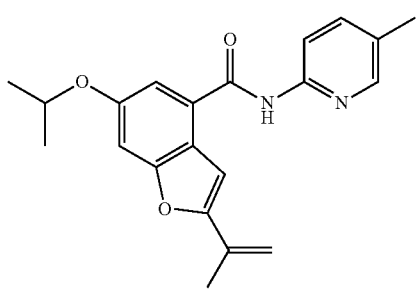

A solution of 2-bromo-6-isopropoxy-N-(5-methylpyridin-2-yl)benzofuran-4-carboxamide (263 mg, 0.68 mmol), isopropenyl boronic acid (58.4 mg, 0.68 mmol), Pd(PPh$_3$)$_2$Cl$_2$ (23.9 mg, 0.034 mmol) and aqueous Na$_2$CO$_3$ (1.0 M in H$_2$O, 1.36 mL) in 1.4 mL of CH$_3$CN was heated in a microwave reactor at 150° C. for 5 min. The solvent was removed in vacuo. The residue was purified with Biotage column chromatography to give a light yellow solid (102 mg, 43% yield). $^1$H NMR (400 MHz, CDCl$_3$) δ 9.07 (s, 1 H) 8.30 (d, J=8.56 Hz, 1 H) 7.96 (d, J=2.01 Hz, 1 H) 7.56 (dd, J=8.56, 2.27 Hz, 1 H) 7.26 (d, J=2.27 Hz, 1 H) 7.14 (d, J=1.51 Hz, 1 H) 7.09 (s, 1 H) 5.76 (s, 1 H) 5.17 (s, 1 H) 4.53-4.59 (m, 1 H) 2.27 (s, 3H) 2.11 (s, 3H) 1.36 (d, J=6.04 Hz, 6 H); LCMS for $C_{21}H_{22}N_2O_3$ m/z 351.10 (M+H)$^+$.

Example 347

6-Isopropoxy-N-(5-methylpyridin-2-yl)-2-phenyl-benzofuran-4-carboxamide

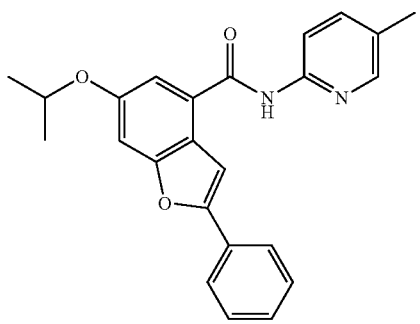

The title compound was prepared in a similar manner as described for Example 346. $^1$H NMR (400 MHz, CDCl$_3$) δ 8.82 (s, 1 H) 8.32 (d, J=8.56 Hz, 1 H) 8.08 (d, J=2.27 Hz, 1 H) 7.85-7.89 (m, 2 H) 7.59 (dd, J=8.56, 2.27 Hz, 1 H) 7.52 (s, 1 H) 7.45 (t, J=7.55 Hz, 2 H) 7.36 (t, J=7.30 Hz, 1 H) 7.32 (d, J=2.01 Hz, 1 H) 7.24 (d, J=1.26 Hz, 1 H) 4.58-4.65 (m, 1 H) 2.31 (s, 3H) 1.39 (d, J=6.04 Hz, 6 H); LCMS for $C_{24}H_{22}N_2O_3$ m/z 387.10 (M+H)$^+$.

Example 348

6-Isopropoxy-2-isopropyl-N-(5-methylpyridin-2-yl)benzofuran-4-carboxamide

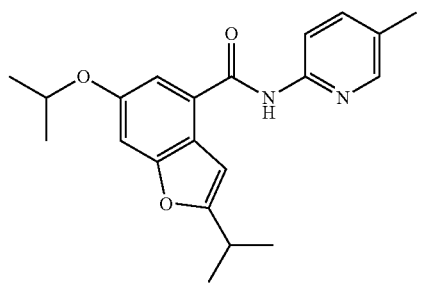

A solution of 6-isopropoxy-N-(5-methylpyridin-2-yl)-2-(prop-1-en-2-yl)benzofuran-4-carboxamide (118 mg, 0.34 mmol) in 10 mL of MeOH was passed through H-cube (10 bar of H$_2$, 15° C., 5% Pd/C cartridge) at a rate of 1.0 mL/min. The collected solution was subsequently concentrated to give a light yellow gum (65 mg, 54%). $^1$H NMR (400 MHz, CDCl$_3$) δ 8.53 (s, 1 H) 8.31 (d, J=8.56 Hz, 1 H) 8.14 (s, 1 H) 7.60 (dd, J=8.44, 2.14 Hz, 1 H) 7.29 (d, J=2.01 Hz, 1 H) 7.16 (d, J=2.01 Hz, 1 H) 6.84 (s, 1 H) 4.56-4.63 (m, 1 H), 3.04-3.13 (m, 1 H), 2.34 (s, 3H), 1.37 (m, 12 H); LCMS for $C_{21}H_{24}N_2O_3$ m/z 353.20 (M+H)$^+$.

Example 349

2-(Azetidine-1-carbonyl)-6-isopropoxy-N-(5-methylpyridin-2-yl)benzofuran-4-carboxamide

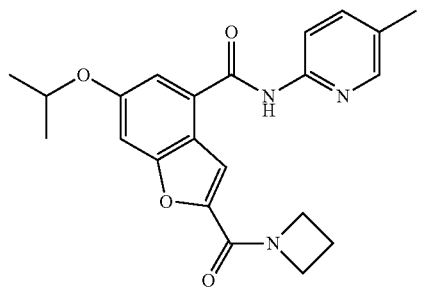

A 0.5-2.0 mL microwave vial was charged with 2-bromo-6-isopropoxy-N-(5-methylpyridin-2-yl)benzofuran-4-carboxamide (156 mg, 0.40 mmol), Herrmann's palladacycle (20 mg, 0.02 mmol), Mo(CO)$_6$ (106 mg, 0.40 mmol), azetidine (80 μL, 1.2 mmol), DBU (180 1.2 mmol) and dry THF (1.0 mL). The vial was immediately sealed and irradiated with microwave to 150° C. for 15 min. After cooling, the reaction was concentrated, and the residue was purified with Biotage column chromatography twice, first eluting with EtOAc and then with 5% MeOH/CHCl$_3$, to give a white solid (62 mg, 39%). $^1$H NMR (400 MHz, CDCl$_3$) δ 8.57 (s, 1 H) 8.26 (d, J=8.31 Hz, 1 H) 8.12 (d, J=2.01 Hz, 1 H) 7.74 (s, 1 H) 7.59 (dd, J=8.31, 2.27 Hz, 1 H) 7.35 (d, J=2.01 Hz, 1 H) 7.19

(d, J=1.26 Hz, 1 H) 4.59-4.67 (m, 3 H), 4.27 (t, J=7.43 Hz, 2 H) 2.39-2.48 (m, 2 H), 2.33 (s, 3H), 1.37 (d, J=6.04 Hz, 6 H); LCMS for $C_{22}H_{23}N_3O_4$ m/z 394.20 (M+H)$^+$.

Examples 350 and 351 were prepared in a similar manner as described for Example 252, via two steps, from ethyl 4-hydroxy-3-methyl-1-benzothiophene-6-carboxylate (350d).

Preparation of Intermediate 350a

4-Methylthiopene-2-carbaldehyde

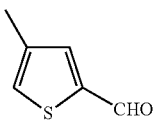

To a solution of 3-methylthiophene (75 g, 0.762 mol) in ether (750 mL) was added drop wise a solution of n-BuLi (1.6 M in hexane, 500 mL). The mixture was stirred for 1.5 h at room temperature. DMF (73 g, 1 mol) was then added. The reaction mixture was let to stir overnight, poured into saturated ammonium chloride (1 L), and extracted with ether (1 L). The ethereal layer was washed with brine, dried with $Na_2SO_4$, and evaporated in vacuum. The crude product was purified on a layer of silica gel (300×150 mm) with hexane/ethyl acetate mixture, 5:1 as eluent. Fractions with the target product were collected and evaporated in vacuum to give 88 g (0.7 mol, 91%) of a mixture of the desired product and 3-methylthiopene-2-carbaldehyde in 4:1 ratio as a colorless liquid.

Preparation of Intermediate 350b 3-(Ethoxycarbonyl)-4-(4-methylthien-2-yl)but-3-enoic Acid

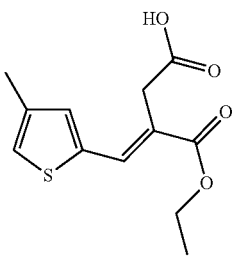

Sodium ethylate (71 g, 1.05 mol) was added under vigorous stirring to a solution of 4-methylthiopene-2-carbaldehyde (88 g, 80% purity, 0.56 mol) and diethyl succinate (183 g, 1.05 mol) in ethanol (1 L). The reaction mixture was refluxed for 3 h and evaporated in vacuum (~20 mmHg) at 50° C. until the solvent distillation ceased. The obtained residue was diluted with 500 mL of 10% HCl and 500 mL of ethyl acetate. The mixture was shaken. The organic layer was separated, diluted with 1 L of a saturated aqueous solution of $NaHCO_3$, and shaken. The aqueous layer was separated, neutralized by 10% HCl to pH 2, and subjected to extraction by 1 L of ethyl acetate. The organic layer was evaporated in vacuum (~20 mmHg) at 60° C. and chromatographed on a layer of silica gel (300×150 mm) with hexane/ethyl acetate mixture, 1:1 as eluent. Fractions with the target product were collected and evaporated in vacuum to give the desired product 61 g (0.24 mol, 43%) as yellow crystals.

Preparation of Intermediate 350c

Ethyl 4-(Acetyloxy)-3-methyl-1-benzothiophene-6-carboxylate

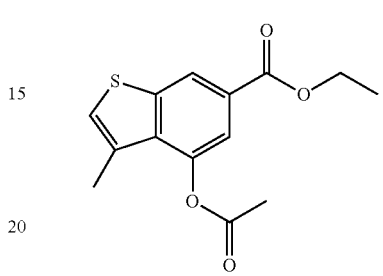

Sodium acetate (90 g, 1.08 mol) was added under vigorous stirring to a solution of 3-(ethoxycarbonyl)-4-(4-methylthien-2-yl)but-3-enoic acid (61 g, 0.24 mol) in 700 mL of acetic anhydride. The reaction mixture was refluxed for 3 h and evaporated in vacuum (~20 mmHg) at 70° C. until the solvent distillation ceased. The obtained crude product was suspended in 500 mL of dichloromethane. The suspension was filtered. The precipitate was washed by 250 mL of dichloromethane. The combined solutions were washed by 350 mL of a saturated aqueous solution of $NaHCO_3$ and evaporated in vacuum to dryness. The obtained crude product was chromatographed on a layer of silica gel (250×150 mm) with hexane/ethyl acetate mixture (3:1) to give the desired product 38.5 g (140 mmol, 58%) as a solid.

Preparation of Intermediate 350d

Ethyl 4-Hydroxy-3-methyl-1-benzothiophene-6-carboxylate

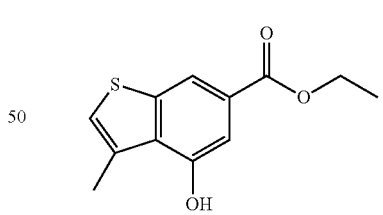

Ethyl 4-(acetyloxy)-3-methyl-1-benzothiophene-6-carboxylate was dissolved in absolute ethanol (500 mL). Potassium carbonate (35 g, 0.25 mol) was added. The reaction mixture was stirred for 3 h at 60° C. and diluted with 200 mL of dichloromethane. The suspension was filtered. The precipitate was washed by 100 mL of dichloromethane. The combined solutions were washed by 200 mL of a 10% aqueous solution of citric acid and evaporated in vacuum to dryness. The obtained crude product was chromatographed on a layer of silica gel (150×100 mm) with hexane/ethyl acetate mixture (2:1) to give the desired product 19.5 g (82 mmol, 60%) as a cream solid. $^1$H NMR (DMSO-D6): δ ppm 1.35

(t,3H), 2.60 (s, 3H), 4.20 (qt, 2H), 7.29 (m, 1H), 7.35 (s, 1H), 7.95 (s, 1H); MS (APCI, pos): 237.1.

Example 350

3-Methyl-N-(5-methylpyridin-2-yl)-4-[4-(methylsulfonyl)-phenoxy]-1-benzothiophene-6-carboxamide

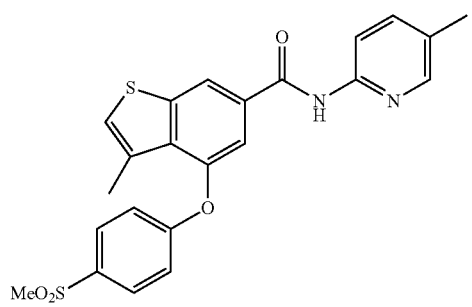

$^{1}$H NMR (300 MHz, CHLOROFORM-D) δ ppm 2.31 (s, 3 H) 2.44 (s, 3 H) 3.06 (s, 3 H) 7.00-7.16 (m, 2 H) 7.21 (d, J=0.94 Hz, 1 H) 7.53 (d, J=1.32 Hz, 1 H) 7.60 (dd, J=8.57, 2.17 Hz, 1 H) 7.85-7.99 (m, 2 H) 8.06 (s, 1 H) 8.29 (d, J=8.48 Hz, 1 H) 8.35 (d, J=1.32 Hz, 1 H) 9.27 (s, 1H); LCMS m/z 453.0 (M+H)$^{+}$.

Example 351

3-Methyl-N-(1-methyl-1H-pyrazol-3-yl)-4-[4-(methylsulfonyl)-phenoxy]-1-benzothiophene-6-carboxamide

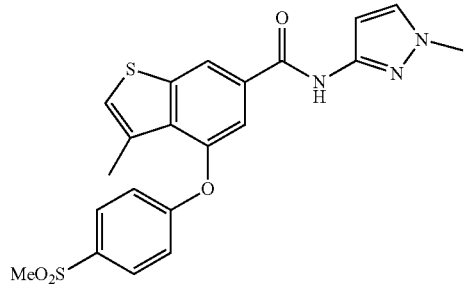

$^{1}$H NMR (300 MHz, CHLOROFORM-D) δ ppm 2.44 (d, J=0.94 Hz, 3 H) 3.05 (s, 3 H) 3.79 (s, 3 H) 6.87 (d, J=2.45 Hz, 1 H) 7.01-7.16 (m, 2 H) 7.19 (d, J=1.13 Hz, 1 H) 7.29 (d, J=2.26 Hz, 1 H) 7.56 (d, J=1.51 Hz, 1 H) 7.80-7.98 (m, 2 H) 8.36 (d, J=1.51 Hz, 1 H) 9.87 (s, 1 H); LCMS m/z 442.0 (M+H)$^{+}$.

Examples 352 and 353 were prepared in a similar manner as described for Example 276, via three steps, from ethyl 4-hydroxy-3-methyl-1-benzothiophene-6-carboxylate (350d).

Example 352

4-{4-[(Dimethylamino)carbonyl]phenoxy}-3-methyl-N-(1-methyl-1H-pyrazol-3-yl)-1-benzothiophene-6-carboxamide

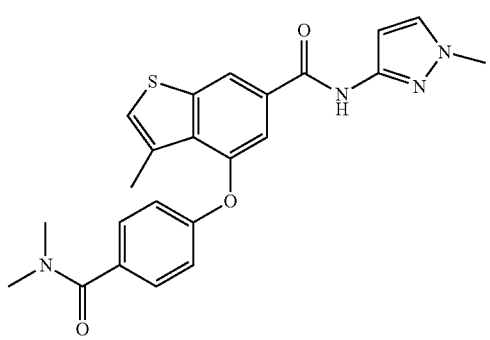

$^{1}$H NMR (300 MHz, CHLOROFORM-D) δ ppm 2.47 (s, 3 H) 3.06 (s, 6 H) 3.70 (s, 3 H) 6.80 (d, J=2.07 Hz, 1 H) 6.94 (d, J=8.67 Hz, 2 H) 7.13 (d, J=1.13 Hz, 1 H) 7.27 (d, J=2.07 Hz, 1 H) 7.34-7.50 (m, 3 H) 8.16 (d, J=1.13 Hz, 1 H) 9.33 (s, 1 H); LCMS m/z 435.0 (M+H)$^{+}$.

Example 353

4-{4-[(Dimethylamino)carbonyl]phenoxy}-3-methyl-N-(5-methylpyridin-2-yl)-1-benzothiophene-6-carboxamide

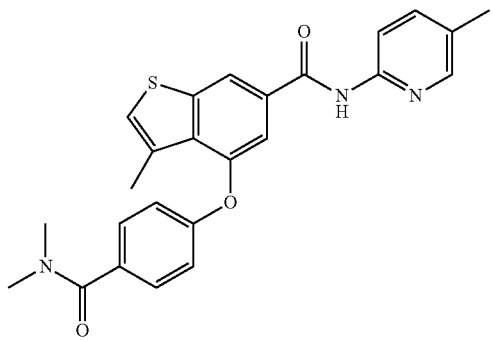

$^{1}$H NMR (300 MHz, CHLOROFORM-D) δ ppm 2.31 (s, 3 H) 2.49 (s, 3 H) 3.08 (br.s, 6 H) 6.93-7.02 (m, 2 H) 7.18 (d, J=1.13 Hz, 1 H) 7.35-7.46 (m, 3 H) 7.62 (dd, J=8.48, 2.26 Hz, 1 H) 8.08 (d, J=2.26 Hz, 1 H) 8.22 (d, J=8.48 Hz, 1 H) 8.26 (d, J=1.13 Hz, 1 H) 9.09 (s, 1 H); LCMS m/z 446.0 (M+H)⁺.

Example 354

3-Methyl-4-[(1S)-1-methyl-2-phenylethoxy]-N-(1-methyl-1H-pyrazol-3-yl)-1-benzothiophene-6-carboxamide

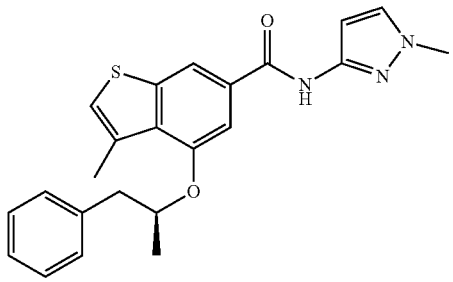

The title compound was prepared in a similar manner as described for Example 328, via two steps, from ethyl 4-hydroxy-3-methyl-1-benzothiophene-6-carboxylate (350d). ¹H NMR (300 MHz, CHLOROFORM-D) δ ppm 1.38 (d, J=6.03 Hz, 3 H) 2.58 (d, J=1.13 Hz, 3 H) 2.96 (dd, J=13.75, 6.22 Hz,1 H) 3.17 (dd, J=13.75, 6.03 Hz, 1 H) 3.77 (s, 3 H) 4.81-5.01 (m, 1 H) 6.86 (d, J=2.26 Hz, 1 H) 7.00 (d, J=1.13 Hz, 1 H) 7.13-7.24 (m, 1 H) 7.25-7.37 (m, 6 H) 7.84 (d, J=1.32 Hz, 1 H) 8.99 (s, 1 H); LCMS m/z 406.0 (M+H)⁺.

Example 355

4-(4-Methanesulfonyl-phenoxy)-benzo[b]thiophene-6-carboxylic acid(5-methyl-pyridin-2-yl)-amide

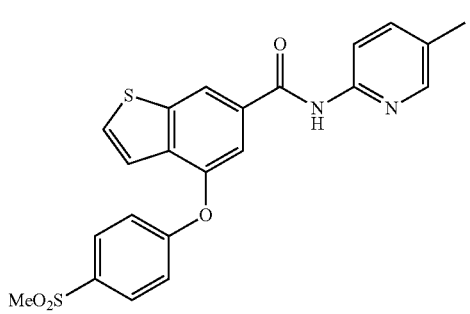

Dimethylaluminum chloride (15.5 mmol, 15.5 ml of 1M in hexanes) was added to a solution of 2-amino-5-picoline (1.67g, 15.5 mmol) in dichloroethane (10 ml) at 0 C. The mixture was allowed to warm to room temperature, held 30 minutes at room temperature, then recooled to 0° C. and treated with 4-(4-methanesulfonyl-phenoxy)-benzo[b]thiophene-6-carboxylic acid ethyl ester (0.58 g, crude product from previous step) in dichloroethane (5 ml). The mixture is allowed to warm to room temperature and held at room temperature for 8 h. The reaction was quenched by the drop wise addition of MeOH (2 mL) at 0 C, followed by 1M aqueous pH6 phosphate buffer (10 ml), then ethyl acetate (50 ml). Separation of the organic layer followed by evaporation yielded crude product (1.1 g). This was purified by silica gel chromatography (0-20% MeOH/CHCl₃) to yield 0.35 g (59%) of 4-(4-methanesulfonyl-phenoxy)-benzo[b]thiophene-6-carboxylic acid (5-methyl-pyridin-2-yl)-amide. ¹H NMR (400 MHz, DMSO-d6) δ ppm 10.85(s, 1H), 8.69 (s, 1H), 8.22(d, J=8.8, 2H), 8.10 (d, J=8.6, 1H), 8.03 (d, J=5.5, 1H), 7.94 (d, J=8.8, 2H), 7.76 (d, J=1.3, 1H), 7.67 (dd, J=9.0, 2.0, 1H), 7.38 (d, J=5.5, 1H), 7.26 (d, J=8.8, 2H), 3.21 (s, 3H0, 2.28 (s, 3H). LRMS for C₂₂H₁₈N₂O₄S₂ m/z 439 (M+H)⁺. Anal. Calcd. for C₂₂H₁₈N₂O₄S₂ C, 60.26;H, 4.14; N, 6.39; Found: C, 60.58; H, 4.23; N, 6.22.

Preparation of Intermediate 355a 3-(Ethoxycarbonyl)-4-thien-2-ylbut-3-enoic acid

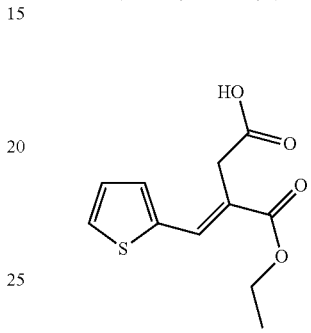

Sodium ethylate (41.4 g, 0.61 mol) was added under vigorous stirring to a solution of thiophene-2-carbaldehyde (57 g, 0.51 mol) and diethyl succinate (176 g, 1.01 mol) in ethanol (1 L). The reaction mixture was refluxed for 3 h and evaporated in vacuum (~20 mmHg) at 50° C. until the solvent distillation ceased. The obtained residue was diluted with 500 mL of 10% HCl and 500 mL of ethyl acetate. The mixture was shaken. The organic layer was separated, diluted with 300 mL of a saturated aqueous solution of NaHCO₃, and shaken. The aqueous layer was separated, neutralized by 10% HCl to pH 2, and subjected to extraction by 1 L of ethyl acetate. The organic layer was evaporated in vacuum (~20 mmHg) at 60° C. and chromatographed on a layer of silica gel (300×150 mm) with hexane/ethyl acetate mixture, 1:1 as eluent. Fractions with the target product were collected and evaporated in vacuum to give 60 g (0.25 mol, 49%) of 3-(ethoxycarbonyl)-4-thien-2-ylbut-3-enoic acid as a light-brown oil.

Preparation of Intermediate 355b 4-(Acetyloxy)-1-benzothiophene-6-carboxylic acid ethyl ester

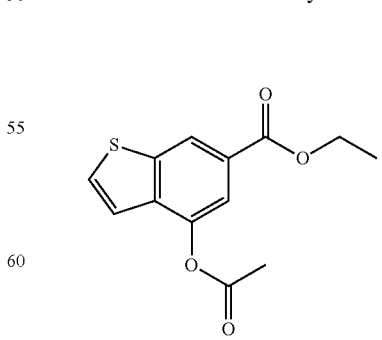

Sodium acetate (30 g, 0.36 mol) was added under vigorous stirring to a solution of 3-(ethoxycarbonyl)-4-thien-2-ylbut-3-enoic acid (60 g, 0.25 mol) in 250 mL of acetic anhydride.

The reaction mixture was refluxed for 3 h and evaporated in vacuum (~20 mmHg) at 70° C. until the solvent distillation ceased. The obtained crude product was suspended in 500 mL of dichloromethane. The suspension was filtered. The precipitate was washed by 250 mL of dichloromethane. The combined solutions were washed by 350 mL of a saturated aqueous solution of NaHCO₃ and evaporated in vacuum to dryness. The obtained crude product was chromatographed on a layer of silica gel (250×150 mm) with hexane/ethyl acetate mixture, 3:1 as eluent to give 21 g (79 mmol, 32%) of compound 4-(acetyloxy)-1-benzothiophene-6-carboxylic acid ethyl ester as a gray solid.

Preparation of Intermediate 355c

4-Hydroxy-1-benzothiophene-6-carboxylic acid ethyl ester

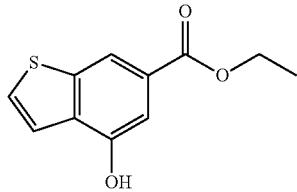

4-(Acetyloxy)-1-benzothiophene-6-carboxylate was dissolved in absolute ethanol (200 mL). Potassium carbonate (14 g, 0.1 mol) was added. The reaction mixture was stirred for 3 h at 60° C. and diluted with 200 mL of dichloromethane. The suspension was filtered. The precipitate was washed by 100 mL of dichloromethane. The combined solutions were washed by 200 mL of a 10% aqueous solution of citric acid and evaporated in vacuum to dryness. The obtained crude product was chromatographed on a layer of silica gel (150× 100 mm) with hexane/ethyl acetate mixture, 2:1 as eluent to give 6.5 g (29 mmol, 37%) of ethyl 4-hydroxy-1-benzothiophene-6-carboxylate as a cream-colored solid.

Preparation of Intermediate 355d 4-(4-Methanesulfonyl-phenoxy)-benzo[b]thiophene-6-carboxylic acid ethyl ester

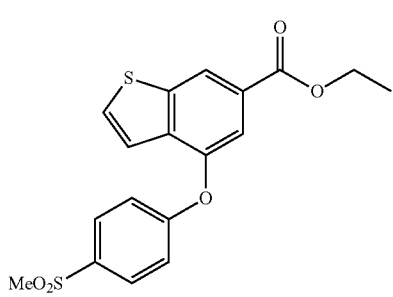

4-Hydroxy-1-benzothiophene-6-carboxylic acid ethyl ester (300 mg, 1.35 mmol) in dimethylacetamide (6.8 ml) was treated with cesium carbonate (0.44 g, 1.35 mmol) and 4-fluorophenyl methane sulfonamide (0.23 g, 1.35 mmol) and heated at 100 C for 3 h. The reaction was diluted with EtOAc (50 ml) and washed with 3×10 saturated aqueous sodium bicarbonate. Evaporation yielded 0.58 g of 4-(4-Methanesulfonyl-phenoxy)-benzo[b]thiophene-6-carboxylic acid ethyl ester. LRMS for $C_{18}H_{17}O_6S_2$ m/z 377 (M+H)⁺.

Example 356

4-(4-(Methylsulfonyl)phenoxy)-N-(1-methyl-1H-pyrazol-3-yl)benzo-[b]-thiophene-6-carboxamide

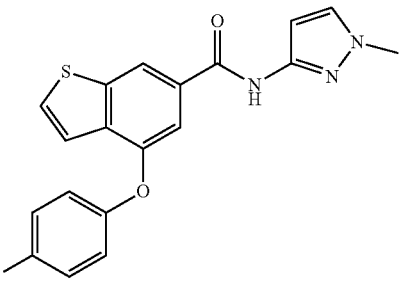

Cs₂CO₃ (0.806 g, 2.47 mmol) was added to a solution of ethyl 4-hydroxybenzo[b]thiophene-6-carboxylate (0.275 g, 1.24 mmol) and 1-fluoro-4-(methylsulfonyl)benzene (0.22 g, 1.26 mmol) in DMF (5 ML). The mixture was stirred at 120° C. for 8 hours and then cooled to room temperature. 1-Methyl-1H-pyrazol-3-amine (0.18 g, 1.85 mmol) and HATU (0.7 g, 1.85 mmol) were added. The reaction mixture was stirred at 50° C. for one hour and then filtered. Purification by HPLC gave a solid (127 mg, 24% yield) as expected product. ¹H NMR (400 MHz, DMSO-d₆) δ 10.97 (s, 1 H) 8.57-8.63 (m, 1 H) 8.01-8.07 (m, 1 H) 7.94-7.96 (m 2 H) 7.73 (m, 1 H) 7.61 (m, 1 H) 7.38-7.41 (m, 1 H) 7.25-7.27 (m, 2 H) 6.60 (m, 1 H) 3.78 (s, 3 H), 3.22 (s, 3 H). LCMS for $C_{20}H_{17}N_3O_4S_2$ m/z 428.10 (M+H)⁺.

Example 357

4-(4-(Dimethylcarbamoyl)-3-fluorophenoxy)-N-(1-methyl-1H-pyrazol-3-yl)benzo[b]thiophene-6-carboxamide

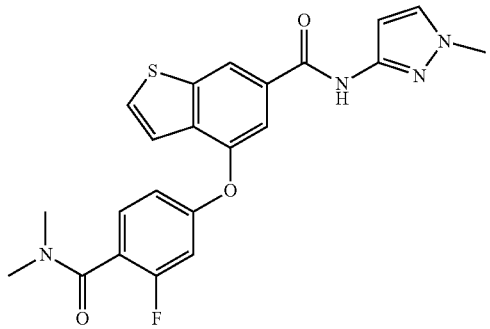

Cs₂CO₃ (0.806 g, 2.47 mmol) was added to a solution of ethyl 4-hydroxybenzo[b]thiophene-6-carboxylate (0.275 g, 1.24 mmol) and 2,4-difluoro-N,N-dimethylbenzamide (0.234 g, 1.26 mmol) in DMF (5 ML). The mixture was stirred at 150° C. for 10 hours and then cooled to room temperature. 1-Methyl-1H-pyrazol-3-amine (0.18 g, 1.85 mmol) and HATU (0.7 g, 1.85 mmol) were added. The reaction mixture was stirred at 50° C. for one hour and then filtered. Purification by HPLC gave a solid (200 mg, 38% yield) as expected product. $^1$H NMR (400 MHz, DMSO-d$_6$) δ 10.96 (s, 1 H) 8.59 (m, 1 H) 8.00 (m, 1 H)) 7.61-7.68 (m, 2 H) 7.39-7.43 (m, 2 H) 7.08-7.11 (m, 1 H) 6.92-6.95 (m, 1 H) 6.60 (s, 1 H) 3.79 (s, 3 H) 3.00 (s, 3 H) 2.88 (m, 3 H). LCMS for C$_{22}$H$_{19}$FN$_4$O$_3$S m/z 439.10 (M+H)$^+$.

Example 358

4-(4-(Dimethylcarbamoyl)-3-fluorophenoxy)-N-(5-methylpyridin-2-yl)benzo[b]thiophene-6-carboxamide

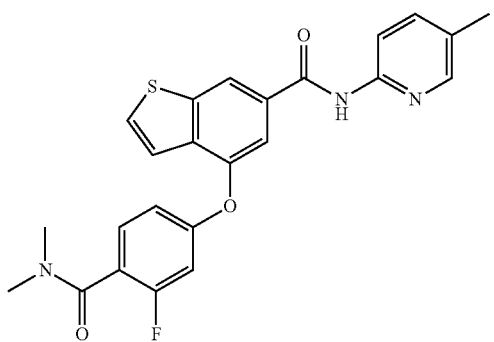

Cs$_2$CO$_3$ (0.806 g, 2.47 mmol) was added to a solution of ethyl 4-hydroxybenzo[b]thiophene-6-carboxylate (0.275 g, 1.24 mmol) and 2,4-difluoro-N,N-dimethylbenzamide (0.286 g, 1.55 mmol) in DMF (5 ML). The mixture was stirred at 150° C. for 8 hours and then cooled to room temperature. 2-Amino-5-methyl pyridine (0.228 g, 2.11 mmol) and then HATU (0.7 g, 1.85 mmol) were added. The reaction mixture was stirred at 75° C. for four hours and then filtered. Purification by HPLC gave a solid (57 mg, 10% yield) as expected product. $^1$H NMR (400 MHz, DMSO-d$_6$) δ 10.84 (s, 1 H) 8.64 (s, 1 H) 8.22 (m, 1 H) 8.07-8.09 (d, 1 H)) 8.01-8.02 (d, 1 H) 7.69 (m, 1 H) 7.65-7.68 (m, 1 H) 7.39-7.43 (m, 2 H) 7.08-7.11 (m, 1 H) 6.93-6.95 (m, 1 H) 2.99 (s, 3 H) 2.87 (m, 3 H) 2.28 (s, 3 H). LCMS for C$_{24}$H$_{20}$FN$_3$O$_3$S m/z 450.10 (M+H)$^+$.

Example 359

4-(4-Methanesulfonyl-phenoxy)-2-methyl-benzo[b]thiophene-6-carboxylic acid (5-methyl-pyridin-2-yl)-amide

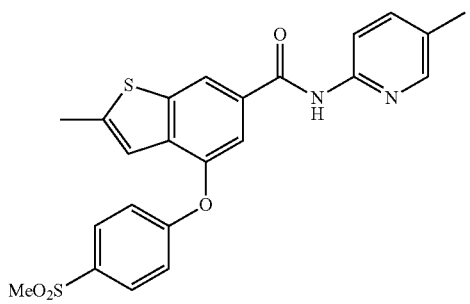

Dimethylaluminum chloride (16.1 mmol, 16.1 ml of 1M in hexanes) is added to a solution of 2-amino-5-picoline (1.74g, 16.1 mmol) in dichloroethane (10 ml) at 0 C. The mixture was allowed to warm to room temperature over a period of 1 h, then recooled to 0 C and treated with 4-(4-methanesulfonyl-phenoxy)-2-methyl-benzo[b]thiophene-6-carboxylic acid ethyl ester (0.63 g, crude product from previous step) in dichloroethane (5 ml) at 0 C. The mixture was allowed to warm to room temperature, and held at room temperature for 8 h. The reaction was quenched by the drop wise addition of MeOH (2 ml) at 0 C, followed by 1M aqueous pH6 phosphate buffer (10 ml), then ethyl acetate was added (50 ml). Separation of the organic layer followed by evaporation yields 0.80 g crude product. Purification by silica gel chromatography (0-20% MeOH-CHCl$_3$) yielded 0.39 g (68%) of product 4-(4-methanesulfonyl-phenoxy)-2-methyl-benzo[b]thiophene-6-carboxylic acid(5-methyl-pyridin-2-yl)-amide. LRMS for C$_{23}$H$_{20}$N$_2$O$_4$S$_2$ m/z 453 (M+H)$^+$. $^1$H NMR (400 MHz, DMSO-d6) δ ppm 10.80 (s, 1H), 8.56 (s, 1H), 8.22 (d, J=2.3, 1H), 8.08 (d, J=8.3, 1H), 7.93 (d, J=8.8, 2H), 7.74 (d, J=1.2, 2H), 7.67 (dd, J=8.6, 2.0, 1H), 7.22 (d, J=8.8, 2H), 7.09 (s, 1H), 3.21 (s, 3H), 2.59 (d, J=1.0, 3H), 2.28 (s, 3H). Anal. Calcd. for C$_{23}$H$_{20}$N$_2$O$_4$S$_2$: C, 61.04; H, 4.45; N, 6.19; Found: C, 61.01; H, 4.47; N, 5.96.

Preparation of Intermediate 359a 3-(Ethoxycarbonyl)-4-(5-methyl-2-thienyl)but-3-enoic acid

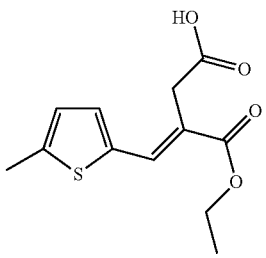

Sodium ethylate (6.5 g, 95 mmol) was added under vigorous stirring to a solution of 5-methylthiophene-2-carbaldehyde (10 g, 79 mmol) and diethyl succinate (27.6 g, 158 mmol) in ethanol (300 mL). The reaction mixture was refluxed for 3 h and evaporated in vacuum (~20 mmHg) at 50° C. until the solvent distillation ceased. The obtained residue was diluted with 200 mL of 10% HCl and 300 mL of ethyl acetate. The mixture was shaken. The organic layer was separated, diluted with 200 mL of a saturated aqueous solution of NaHCO$_3$, and shaken. The aqueous layer was separated, neutralized by 10% HCl to pH 2, and subjected to extraction by 400 mL of ethyl acetate. The organic layer was evaporated in vacuum (~20 mmHg) at 60° C. and chromatographed on a layer of silica gel (200×150 mm) with hexane/ethyl acetate mixture, 1:1 as eluent. Fractions containing the target product were collected and evaporated in vacuum to give 12.3 g (48 mmol, 61%) of 3-(ethoxycarbonyl)-4-(5-methyl-2-thienyl)but-3-enoic acid as a light-brown oil.

Preparation of Intermediate 359b 4-(Acetyloxy)-2-methyl-1-benzothiophene-6-carboxylic acid ethyl ester

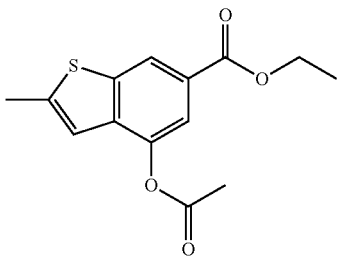

Sodium acetate (10 g, 120 mmol) was added under vigorous stirring to a solution of 3-(ethoxycarbonyl)-4-(5-methyl-2-thienyl)but-3-enoic acid (12.3 g, 48 mmol) in 100 mL of acetic anhydride. The reaction mixture was refluxed for 3 h and evaporated in vacuum (~20 mmHg) at 70° C. until the solvent distillation ceased. The obtained crude product was suspended in 250 mL of dichloromethane. The suspension was filtered. The precipitate was washed by 100 mL of dichloromethane. The combined solutions were washed by 200 mL of a saturated aqueous solution of NaHCO$_3$ and evaporated in vacuum to dryness. The obtained crude product was chromatographed on a layer of silica gel (150×100 mm) with hexane/ethyl acetate mixture, 3:1 as eluent to give 8.2 g (29 mmol, 61%) of 4-(acetyloxy)-2-methyl-1-benzothiophene-6-carboxylic acid ethyl ester as a yellow solid.

Preparation of Intermediate 359c

4-Hydroxy-2-methyl-1-benzothiophene-6-carboxylic acid ethyl ester

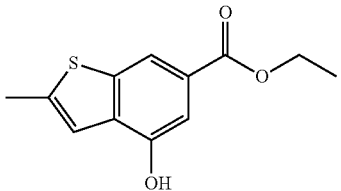

Ethyl 4-(acetyloxy)-2-methyl-1-benzothiophene-6-carboxylate was dissolved in absolute ethanol (200 mL). Potassium carbonate (7 g, 50 mmol) was added. The reaction mixture was stirred for 3 h at 60° C. and diluted with 200 mL of dichloromethane. The suspension was filtered. The precipitate was washed by 100 mL of dichloromethane. The combined solutions were washed by 200 mL of a 10% aqueous solution of citric acid and evaporated in vacuum to dryness. The obtained crude product was chromatographed on a layer of silica gel (150×100 mm) with hexane/ethyl acetate mixture, 2:1 as eluent to give 5.5 g (23 mmol, 79%) of 4-Hydroxy-2-methyl-1-benzothiophene-6-carboxylate ethyl ester as a cream solid.

Preparation of Intermediate 359d 4-(4-Methanesulfonyl-phenoxy)-2-methyl-benzo[b]thiophene-6-carboxylic acid ethyl ester

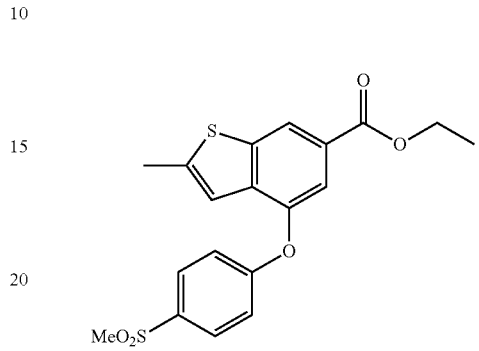

4-Hydroxy-2-methyl-1-benzothiophene-6-carboxylic acid ethyl ester (300 mg, 1.27 mmol) in dimethylacetamide (6.36 ml, 0.2 M) was treated with cesium carbonate (0.41 g, 1.27 mmol) and 4-fluorophenylmethane sulfonamide (0.22 g, 1.27 mmol) and heated at 100 C for 3h. The reaction was then diluted with EtOAc (50 ml), and washed with 3×10 ml of saturated aqueous sodium bicarbonate. Evaporation yields 0.63 g of 4-(4-methanesulfonyl-phenoxy)-2-m3thyl-benzo[b]thiophene-6-carboxylic acid ethyl ester. LRMS for $C_{19}H_{19}O_5S_2$ m/z 391 (M+H)$^+$.

Example 360

4-(4-(Methylsulfonyl)phenoxy)-2-methyl-N-(1-methyl-1H-pyrazol-3-yl)benzo[b]thiophene-6-carboxamide

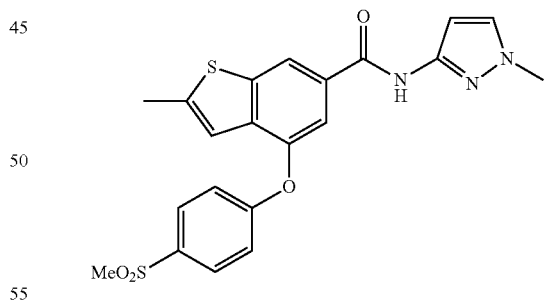

Cs$_2$CO$_3$ (0.806 g, 2.47 mmol) was added to a solution of ethyl 4-hydroxybenzo[b]thiophene-6-carboxylate (0.293 g, 1.24 mmol) and 1-fluoro-4-(methylsulfonyl)benzene (0.22 g, 1.26 mmol) in DMF (5 ML). The mixture was stirred at 120° C. for 8 hours and then cooled to room temperature. 1-Methyl-1H-pyrazol-3-amine (0.18 g, 1.85 mmol) and HATU (0.7 g, 1.85 mmol) were added. The reaction mixture was stirred at 50° C. for one hour and then filtered. Purification by HPLC gave a solid (107 mg, 20% yield) as expected product. $^1$H NMR (400 MHz, DMSO-d$_6$) δ 10.91 (s, 1 H) 8.51 (s, 1 H) 7.92-7.94 (m, 2 H) 7.71 (m, 1 H) 7.60-7.61 (m, 1 H) 7.20-7.23

(m, 2 H) 7.08-7.10 (m, 1 H) 6.58-6.59 (m, 1 H) 3.78 (s, 3 H), 3.21 (s, 3 H), 2.58 (m, 3 H). LCMS for $C_{21}H_{19}N_3O_4S_2$ m/z 442.10 (M+H)$^+$.

Example 361

4-(4-(Dimethylcarbamoyl)-3-fluorophenoxy)-2-methyl-N-(5-methylpyridin-2-yl)benzo[b]thiophene-6-carboxamide

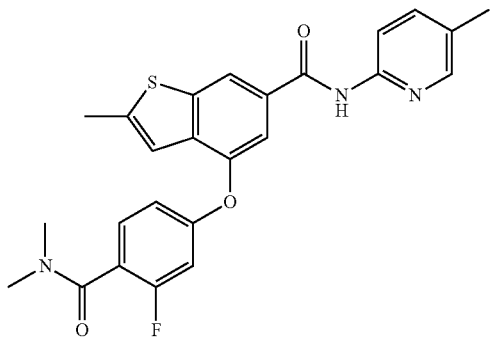

Cs$_2$CO$_3$ (0.806 g, 2.47 mmol) was added to a solution of ethyl 4-hydroxy-2-methylbenzo[b]thiophene-6-carboxylate (0.275 g, 1.16 mmol) and 2,4-difluoro-N,N-dimethylbenzamide (0.269 g, 1.45 mmol) in DMF (5 ML). The mixture was stirred at 150° C. for 8 hours and then cooled to room temperature. 2-Amino-5-methyl pyridine (0.214 g, 2 mmol) and HATU (0.67 g, 1.75 mmol) were added. The reaction mixture was stirred at 75° C. for four hours and then filtered. Purification by HPLC gave a solid (92 mg, 17% yield) as expected product. $^1$H NMR (400 MHz, DMSO-d$_6$) δ 10.79 (s, 1 H) 8.52 (s, 1 H) 8.21 (m, 1 H) 8.06-8.08 (d, 1 H) 7.68 (m, 1 H) 7.64-7.67 (m, 1 H) 7.37-7.41 (t, 1 H) 7.12 (s, 1 H) 7.02-7.06 (m, 1 H) 6.87-6.90 (m, 1 H) 2.99 (s, 3 H) 2.87 (s, 3 H) 2.59-2.60 (m, 3 H) 2.28 (s, 1 H). LCMS for $C_{25}H_{22}FN_3O_3S$ m/z 464.10 (M+H)$^+$.

Example 362

4-(4-(Dimethylcarbamoyl)-3-fluorophenoxy)-2-methyl-N-(1-methyl-1H-pyrazol-3-yl)benzo[b]thiophene-6-carboxamide

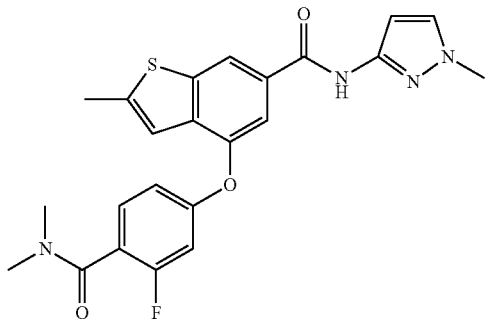

Cs$_2$CO$_3$ (0.806 g, 2.47 mmol) was added to a solution of ethyl 4-hydroxy-2-methylbenzo[b]thiophene-6-carboxylate (0.275 g, 1.16 mmol) and 2,4-difluoro-N,N-dimethylbenzamide (0.269 g, 1.45 mmol) in DMF (5 ML). The mixture was stirred at 150° C. for 8 hours and then cooled to room temperature. 1-Methyl-1H-pyrazol-3-amine (0.19 g, 1.98 mmol) and HATU (0.664 g, 1.75 mmol) were added. The reaction mixture was stirred at 80° C. for one hour and then filtered. Purification by HPLC gave a solid (100 mg, 19% yield) as expected product. $^1$H NMR (400 MHz, CD$_3$OD) δ 8.27 (s, 1 H) 7.54 (m, 1 H) 7.48 (m, 1 H) 7.34-7.38 (t, 1 H) 7.00 (s, 1 H) 6.82-6.89 (m, 2 H) 6.59-6.60 (m, 1 H) 3.81 (s, 3 H) 3.09 (s, 3 H) 2.97 (m, 3 H) 2.58 (m, 3 H). LCMS for $C_{23}H_{21}FN_4O_3S$ m/z 453.10 (M+H)$^+$.

Example 363

7-(4-Methanesulfonyl-phenoxy)-benzo[b]thiophene-5-carboxylic acid(5-methyl-pyridin-2-yl)-amide

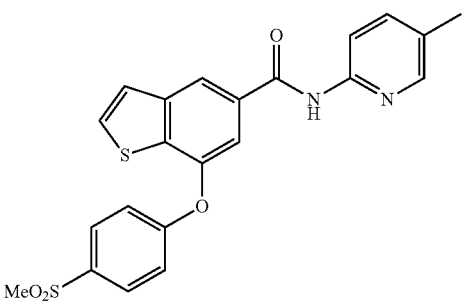

7-Hydroxy-benzo[b]thiophene-5-carboxylic acid ethyl ester (295 mg, 1.33 mmol) in dimethylacetamide (6.5 ml) was treated with cesium carbonate (0.43 g, 1.33 mmol), and 4-fluorophenylmethane sulfonamide (0.23 g, 1.33 mmol), and heated at 100 C for 3 h. The mixture was diluted with EtOAc (50 ml) and washed with saturated aqueous NaHCO$_3$ (3×10 ml). Evaporation yields 0.56 g of 4-(4-methanesulfonyl-phenoxy)-benzo[b]thiophene-6-carboxylic acid ethyl ester (6). LRMS for $C_{18}H_{17}S_2O_5$ m/z 377 (M+H)$^+$. Dimethylaluminum chloride (7.5 mmol, 7.5 ml of 1M in hexanes) was added to a solution of 2-amino-3-picoline (0.81 g, 7.50 mmol) in dichloroethane (10 mL) at 0 C. The mixture was allowed to warm to room temperature, held 30 minutes at room temperature, then recooled to 0 C and treated with 4-(4-methanesulfonyl-phenoxy)-benzo[b]thiophene-6-carboxylic acid ethyl ester (0.56 g, crude material from previous step) in dichloroethane (5 ml). The mixture was allowed to warm to room temperature and held at room temperature for 8 h. The reaction was quenched by the drop wise addition of methanol (2 ml) at 0 C, followed by addition of 1M aqueous pH6 phosphate buffer (10 ml), then ethyl acetate (50 ml). Separation of the organic layer followed by evaporation yields the crude product (0.89 g). This was purified on a silica gel chromatography column using a 0-20% MeOH/CHCl$_3$ gradient to yield 0.26 g (45%) of product 7-(4-Methanesulfonyl-phenoxy)-benzo[b]thiophene-5-carboxylic acid (5-methyl-pyridin-2-yl)-amide (7). $^1$H NMR (400 MHz, DMSO-d6) δ ppm 10.86 (s, 1H), 8.55 (d, J=1.3, 1H), 8.22 (d, J=1.8, 1H), 8.09 (d, J=8.6, 1H), 7.96 (dt, J=8.8, 2.0, 2H), 7.95 (d, J=5.8, 1H), 7.77 (d, J=1.0, 1H), 7.69 (d, J=5.3, 1H), 7.67 (dd, J=8.8, 2.3, 1H), 7.32 (dt, J=8.8, 2.0, 2H), 3.23 (s, 3H), 2.28 (s, 3H). LRMS for $C_{22}H_{18}N_2O_4S_2$ m/z 439 (M+H)$^+$. Anal. Calcd. for $C_{22}H_{18}N_2O_4S_2$ C, 60.26; H, 4.14; N, 6.39; Found: C, 60.13; H, 4.08; N, 6.32.

Preparation of Intermediate 363a 3-(Ethoxycarbonyl)-4-(2-thienyl)but-3-enoic acid

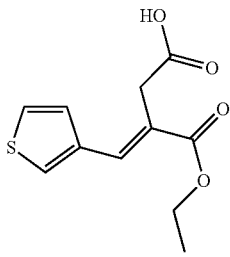

Sodium ethylate (36.3 g, 0.53 mol) was added under vigorous stirring to a solution of 3-thiophenecarboxaldehyde (50 g, 0.44 mol) and diethyl succinate (116 g, 0.66 mol) in ethanol (1 L). The reaction mixture was refluxed for 8 h and evaporated in vacuum (~20 mmHg) at 50° C. until the solvent distillation ceased. The obtained residue was diluted with 500 mL of 10% HCl and 500 mL of ethyl acetate. The mixture was shaken. The organic layer was separated, diluted with 500 mL of a saturated aqueous solution of $NaHCO_3$, and aqueous layer shaken. The was separated, neutralized by 10% HCl to pH 2, and subjected to extraction by 1 L of ethyl acetate. The organic layer was evaporated in vacuum (~20 mmHg) at 60° C. and chromatographed on a layer of silica gel (200×150 mm; hexane/ethyl acetate mixture, 1:1). Fractions with the target product were collected and evaporated in vacuum to give 61 g (0.25 mol, 57%) of 3-(ethoxycarbonyl)-4-(2-thienyl)but-3-enoic acid as a light-brown oil.

Preparation of Intermediate 363b

Ethyl 7-acetoxy-1-benzothiophene-5-carboxylate

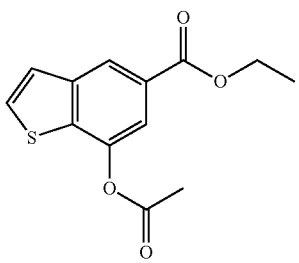

Sodium acetate (40 g, 0.48 mol) was added under vigorous stirring to a solution of 3-(ethoxycarbonyl)-4-(2-thienyl)but-3-enoic acid (61 g, 0.25 mol) in 250 mL of acetic anhydride. The reaction mixture was refluxed for 2 h and evaporated in vacuum (~20 mmHg) at 70° C. until the solvent distillation ceased. The obtained crude product was suspended in 500 mL of dichloromethane. The suspension was filtered. The precipitate was washed by 200 mL of dichloromethane. The combined solutions were washed by 200 mL of a saturated aqueous solution of $NaHCO_3$ and evaporated in vacuum to dryness. The obtained crude product was chromatographed on a layer of silica gel (200×150 mm) with hexane/ethyl acetate mixture, 3:1 as eluent to give 31 g (0.12 mol, 46%) of ethyl 7-acetoxy-1-benzothiophene-5-carboxylate as a yellow solid.

Preparation of Intermediate 363c

Ethyl 7-hydroxy-1-benzothiophene-5-carboxylate

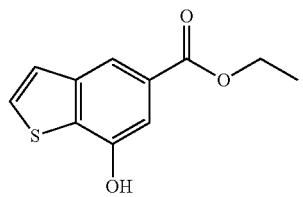

Ethyl 7-acetoxy-1-benzothiophene-5-carboxylate was dissolved in absolute ethanol (500 mL). Potassium carbonate (21 g, 0.15 mol) was added. The reaction mixture was stirred for 3 h at 60° C. and diluted with 500 mL of dichloromethane. The suspension was filtered. The precipitate was washed by 200 mL of dichloromethane. The combined solutions were washed by 200 mL of a 10% aqueous solution of citric acid and evaporated in vacuum to dryness. The obtained crude product was chromatographed on a layer of silica gel (200× 150 mm; hexane/ethyl acetate mixture, 2:1) to give 16.5 g (63 mmol, 63%) of compound ethyl 7-hydroxy-1-benzothiophene-5-carboxylate as a red-brown solid. LRMS for $C_{11}H_{11}SO_3$ m/z 223 (M+H)$^+$.

Example 364

7-(4-(Methylsulfonyl)phenoxy)-N-(1-methyl-1H-pyrazol-3-yl)benzo-[b]-thiophene-5-carboxamide

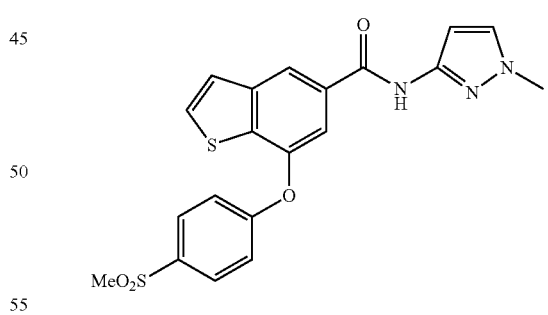

$Cs_2CO_3$ (0.806 g, 2.47 mmol) was added to a solution of ethyl 7-hydroxybenzo[b]thiophene-5-carboxylate (0.275 g, 1.24 mmol) and 1-fluoro-4-(methylsulfonyl)benzene (0.22 g, 1.26 mmol) in DMF (5 ML). The mixture was stirred at 120° C. for 8 hours and then cooled to room temperature. 1-Methyl-1H-pyrazol-3-amine (0.21 g, 2.17 mmol) and then HATU (0.71 g, 1.87 mmol) were added. The reaction mixture was stirred at 50° C. for one hour and then filtered. Purification by HPLC gave a solid (6 mg, 1% yield) as expected product. $^1$H NMR (400 MHz, $CD_3OD$) δ 8.38 (s, 1 H) 7.96-7.99 (m, 2 H) 7.73-7.76 (m, 1 H) 7.58-7.61 (m, 2 H) 7.53 (s, 1 H) 7.23-7.28 (m, 2 H) 6.60 (s, 1 H) 3.84 (s, 3 H) 3.13 (s, 3 H). LCMS for $C_{20}H_{17}N_3O_4S_2$ m/z 428.10 (M+H$^+$).

Example 365

7-(4-(Dimethylcarbamoyl)-3-fluorophenoxy)-N-(5-methylpyridin-2-yl)benzo[b]thiophene-5-carboxamide

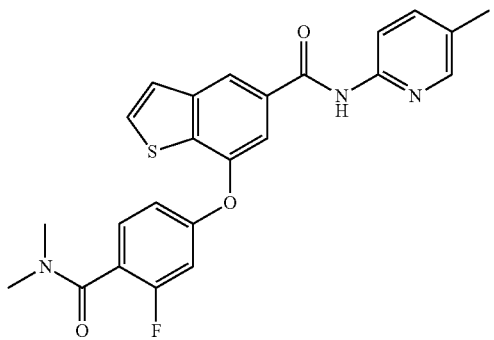

Cs$_2$CO$_3$ (0.806 g, 2.47 mmol) was added to a solution of ethyl 7-hydroxybenzo[b]thiophene-5-carboxylate (0.275 g, 1.24 mmol) and 2,4-difluoro-N,N-dimethylbenzamide (0.286 g, 1.55 mmol) in DMF (5 ML). The mixture was stirred at 150° C. for 8 hours and then cooled to room temperature. 2-Amino-5-methyl pyridine (0.228 g, 2.11 mmol) and then HATU (0.7 g, 1.85 mmol) were added. The reaction mixture was stirred at 75° C. for four hours and then filtered. Purification by HPLC gave a solid (56 mg, 10% yield) as expected product. $^1$H NMR (400 MHz, DMSO-d$_6$) δ 10.90 (s, 1 H) 8.51 (m, 1 H) 8.23 (s, 1 H) 8.07-8.09 (d, 1 H)) 7.93-7.94 (m, 1 H) 7.67-7.70 (m, 3 H) 7.41-7.46 (t, 1 H) 7.15-7.17 (m, 1 H) 7.00-7.03 (m, 1 H) 3.00 (s, 3 H) 2.88 (m, 3 H) 2.29 (s, 3 H). LCMS for $C_{24}H_{20}FN_3O_3S$ m/z 450.10 (M+H)$^+$.

Example 366

7-(4-(Dimethylcarbamoyl)-3-fluorophenoxy)-N-(1-methyl-1H-pyrazol-3-yl)benzo[b]thiophene-5-carboxamide

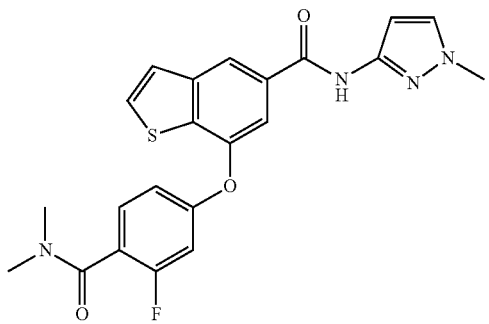

Cs$_2$CO$_3$ (0.806 g, 2.47 mmol) was added to a solution of ethyl 7-hydroxybenzo[b]thiophene-5-carboxylate (0.275 g, 1.24 mmol) and 2,4-difluoro-N,N-dimethylbenzamide (0.286 g, 1.55 mmol) in DMF (5 ML). The mixture was stirred at 150° C. for 8 hours and then cooled to room temperature. 1-Methyl-1H-pyrazol-3-amine (0.21 g, 2.17 mmol) and then HATU (0.71 g, 1.87 mmol) were added. The reaction mixture was stirred at 50° C. for one hour and then filtered. Purification by HPLC gave a solid (100 mg, 19% yield) as expected product. DMSO-d$_6$) δ 10.96 (s, 1 H) 8.46 (m, 1 H) 7.91-7.93 (d, 1 H)) 7.67 (m, 1 H) 7.65-7.66 (m, 1 H) 7.60-7.61 (m, 1 H) 7.41-7.45 (t, 1 H) 7.14-7.17 (m, 1 H) 6.99-7.01 (m, 1 H) 6.59 (m, 1 H) 3.78 (s, 3 H) 3.00 (s, 3 H) 2.88 (m, 3 H).

Example 367

N-(5-methylpyridin-2-yl)-7-[4-(methylsulfonyl)phenoxy]-1,3-benzoxazole-5-carboxamide

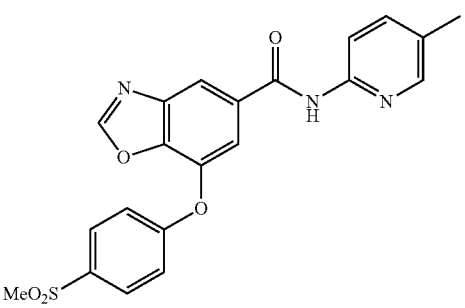

The title compound was prepared in a similar manner as described for Example 252, via two steps, from methyl 7-hydroxybenzo[d]oxazole-5-carboxylate (367e). $^1$H NMR (300 MHz, CHLOROFORM-D) δ ppm 2.30 (s, 3 H) 3.06 (s, 3 H) 7.12-7.22 (m, 2 H) 7.58 (dd, J=8.48, 2.26 Hz, 1 H) 7.80 (d, J=1.32 Hz, 1 H) 7.88-7.98 (m, 2 H) 8.09 (d, J=2.26 Hz, 1 H) 8.17 (s, 1 H) 8.23 (d, J=8.48 Hz, 1 H) 8.26 (d, J=1.32 Hz, 1 H); LCMS m/z 424.40 (M+H)$^+$.

Preparation of Intermediate 367a 3,4-Dihydroxy-5-nitrobenzaldehyde

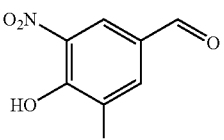

To a vigorously stirred suspension of 4-hydroxy-3-methoxy-5-nitrobenzaldehyde (47.0 g, 238 mmol) in EtOAc (450 mL) at room temperature, anhydrous aluminum chloride (38.1 g, 286 mmol) was added in one portion. Then pyridine (77 mL, 954 mmol) was added drop wise at 45-50° C. for 30 min. The reaction mixture was refluxed for 2 h and allowed to cool down to 60° C. The reaction mixture was carefully poured into ice/concentrated HCl mixture (265 mL). After stirring at 50° C. for 1 h, the reaction mixture was cooled to 0° C. The formed precipitate was separated by filtration, washed Preparation of Intermediate 367b 3,4-Dihydroxy-5-nitrobenzoic Acid

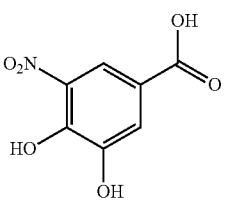

A solution of sodium chlorite (47.6 g, 526 mmol) in water (350 mL) was added drop wise to a solution of 3,4-dihydroxy-5-nitrobenzaldehyde (68.8 g, 376 mmol) and sodium dihydrogen phosphate (45.1 g, 376 mmol) in DMSO/H$_2$O mixture (375 mL/150 mL) at room temperature for 1.5 h. The reaction mixture was stirred at room temperature for 1 h and poured into a separatory funnel containing a 5% solution NaHCO$_3$ (500 mL). The product was extracted with dichloromethane (3×100 mL). The water layer was acidified with concentrated HCl to pH~1 and extracted with ether (3×250 mL). The combined organic layers were washed with brine (200 mL), dried over Na$_2$SO$_4$, and evaporated to afford the desired acid (70.3 g, 353 mmol, 94% yield).

Preparation of Intermediate 367c

Methyl 3,4-Dihydroxy-5-nitrobenzoate

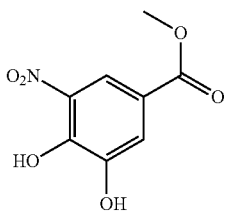

Thionyl chloride (6.07 mL, 83 mmol) was added drop wise to a stirred solution of 3,4-dihydroxy-5-nitrobenzoic acid (14.4 g, 72.3 mmol) in MeOH (70 mL) at room temperature for 1 h. The reaction mixture was refluxed for 3 h and concentrated. The residue was recrystallized from water and vacuum-dried to afford the desired ester (11.0 g, 51.6 mmol, 71.4% yield).

Preparation of Intermediate 367d

Methyl 3-Amino-4,5-dihydroxybenzoate Hydrochloride

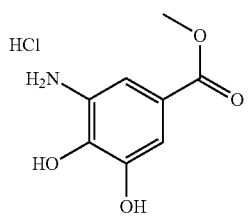

To a stirred solution of methyl 3,4-dihydroxy-5-nitrobenzoate (11.9 g, 55.8 mmol) in EtOH (200 mL), 4M HCl in dioxane (13.96 mL, 55.8 mmol) and 10% palladium on carbon (4.0 g, 3.76 mmol) were added. The reaction mixture was hydrogenated at atmospheric pressure of H$_2$ for 3 h (TLC-monitoring). The resulting mixture was filtered and concentrated. The residue was triturated with ether (100 mL). The precipitate was filtered off and vacuum-dried to afford amine product as the hydrochloride salt (12.0 g, 54.6 mmol, 98% yield).

Preparation of Intermediate 367e: Methyl 7-Hydroxy-1,3-benzoxazole-5-carboxylate

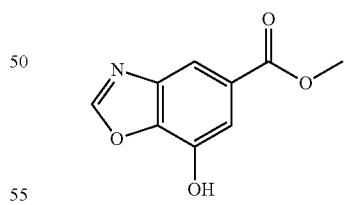

To stirred triethyl orthoformate (35.0 mL, 210 mmol) was added methyl 3-amino-4,5-dihydroxybenzoate hydrochloride (6.30 g, 28.7 mmol). The stirred suspension was refluxed for 20 min (until a clear solution formed), cooled to room temperature, and poured into hexane (200 mL). The formed precipitate was separated by filtration and vacuum-dried to afford the desired benzoxazole (4.26 g, 22.05 mmol, 77% yield). $^1$H NMR (400 MHz, DMSO-d$_6$): δ 10.90 (br. s, 1H), 8.79 (s, 1H), 7.80 (d, J=1.3 Hz, 1H), 7.50 (d, J=1.3 Hz, 1H), 3.86 (s, 3H).

Examples 368 and 369 were prepared in a similar manner as described for Example 252, via two steps, from methyl 7-hydroxy-2-methylbenzo[d]oxazole-5-carboxylate (368e).

Preparation of Intermediate 368a 3,4-Dihydroxy-5-nitrobenzaldehyde

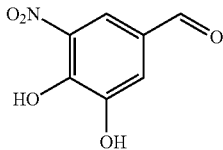

To a vigorously stirred suspension of 4-hydroxy-3-methoxy-5-nitrobenzaldehyde (47.0 g, 238 mmol) in EtOAc (450 mL) at room temperature, anhydrous aluminum chloride (38.1 g, 286 mmol) was added in one portion. Then pyridine (77 mL, 954 mmol) was added drop wise at 45-50° C. for 30 min. The reaction mixture was refluxed for 2 h and allowed to cool down to 60° C. The reaction mixture was carefully poured into ice/concentrated HCl mixture (265 mL). After stirring at 50° C. for 1 h, the reaction mixture was cooled to 0° C. The formed precipitate was separated by filtration, washed with water, and vacuum-dried to afford the desired compound (29.4 g, 161 mmol, 67.3% yield).

Preparation of Intermediate 368b 3,4-Dihydroxy-5-nitrobenzoic Acid

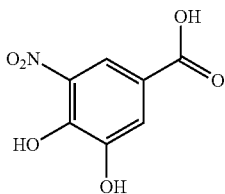

A solution of sodium chlorite (47.6 g, 526 mmol) in water (350 mL) was added drop wise to a solution of 3,4-dihydroxy-5-nitrobenzaldehyde (68.8 g, 376 mmol) and sodium dihydrogen phosphate (45.1 g, 376 mmol) in DMSO/H$_2$O mixture (375 mL/150 mL) at room temperature over 1.5 h. The reaction mixture was stirred at room temperature for 1 h and poured into a separatory funnel containing a 5% solution NaHCO$_3$ (500 mL). The product was extracted with dichloromethane (3×100 mL). The water layer was acidified with concentrated HCl to pH~1 and extracted with ether (3×250 mL). The combined organic layers were washed with brine (200 mL), dried over Na$_2$SO$_4$, and evaporated to afford the desired acid (70.3 g, 353 mmol, 94% yield).

Preparation of Intermediate 368c

Methyl 3,4-Dihydroxy-5-nitrobenzoate

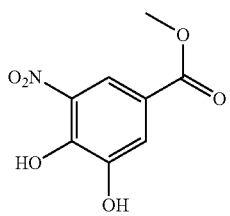

Thionyl chloride (6.07 mL, 83 mmol) was added drop wise to a stirred solution of 3,4-dihydroxy-5-nitrobenzoic acid (14.4 g, 72.3 mmol) in MeOH (70 mL) at room temperature for 1 h. The reaction mixture was refluxed for 3 h and concentrated. The residue was recrystallized from water and vacuum-dried to afford the desired ester (11.0 g, 51.6 mmol, 71.4% yield).

Preparation of Intermediate 368d

Methyl 3-amino-4,5-dihydroxybenzoate hydrochloride

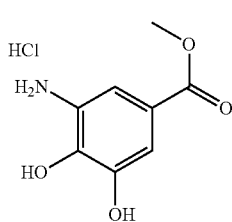

To a stirred solution of methyl 3,4-dihydroxy-5-nitrobenzoate (11.9 g, 55.8 mmol) in EtOH (200 mL) was added 4M HCl in dioxane (13.96 mL, 55.8 mmol) and 10% palladium on carbon (4.0 g, 3.76 mmol). The reaction mixture was hydrogenated at atmospheric pressure of H$_2$ for 3 h (TLC-monitoring). The resulting mixture was filtered and concentrated. The residue was triturated with ether (100 mL). The precipitate was filtered off and vacuum-dried to afford amine product as the hydrochloride salt (12.0 g, 54.6 mmol, 98% yield).

Preparation of Intermediate 368e

Methyl 7-hydroxy-2-methyl-1,3-benzoxazole-5-carboxylate

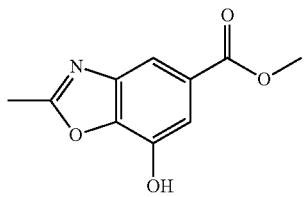

To stirred triethyl orthoacetate (35.0 mL, 190 mmol) was added methyl 3-amino-4,5-dihydroxybenzoate hydrochloride (6.00 g, 27.3 mmol). The stirred suspension was refluxed for 20 min and cooled to room temperature. The reaction mixture was poured into hexane (200 mL). The formed precipitate was separated by filtration and vacuum-dried to afford the desired benzoxazole (4.98 g, 24.04 mmol, 88% yield). $^1$H NMR (400 MHz, DMSO-$d_6$): δ 10.74 (br. s, 1H), 7.66 (d, J=1.4 Hz, 1H), 7.43 (d, J=1.4 Hz, 1H), 3.85 (s, 3H), 2.62 (s, 3H).

Example 368

2-Methyl-N-(1-methyl-1H-pyrazol-3-yl)-7-[4-(methylsulfonyl)-phenoxy]-1,3-benzoxazole-5-carboxamide

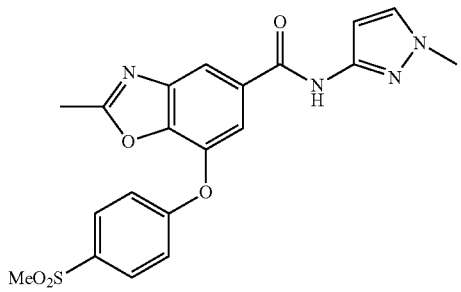

$^1$H NMR (300 MHz, CHLOROFORM-D) δ ppm 2.65 (s, 3 H) 3.07 (s, 3 H) 3.79 (s, 3 H) 6.79 (d, J=2.26 Hz, 1 H) 7.08-7.22 (m, 2 H) 7.29 (d, J=2.26 Hz, 1 H) 7.64 (d, J=1.32 Hz, 1 H) 7.88-7.98 (m, 2 H) 8.01 (d, J=1.32 Hz, 1 H) 8.83 (s, 1 H); LCMS m/z 427.40 (M+H)$^+$.

Example 369

2-Methyl-N-(5-methylpyridin-2-yl)-7-[4-(methylsulfonyl)-phenoxy]-1,3-benzoxazole-5-carboxamide

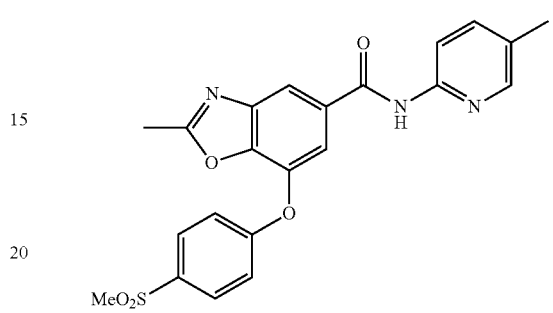

$^1$H NMR (300 MHz, CHLOROFORM-D) δ ppm 2.32 (s, 3 H) 2.66 (s, 3 H) 3.07 (s, 3 H) 7.11-7.22 (m, 2 H) 7.60 (dd, J=8.48, 2.26 Hz, 1 H) 7.70 (d, J=1.51 Hz, 1 H) 7.87-8.01 (m, 2 H) 8.08 (d, J=2.26 Hz, 1 H) 8.12 (d, J=1.51 Hz, 1 H) 8.28 (d, J=8.48 Hz, 1 H) 9.29 (s, 1 H); LCMS m/z 438.40 (M+H)$^+$.

Example 370

7-{4-[(Dimethylamino)carbonyl]phenoxy}-2-methyl-N-(5-methylpyridin-2-yl)-1,3-benzoxazole-5-carboxamide

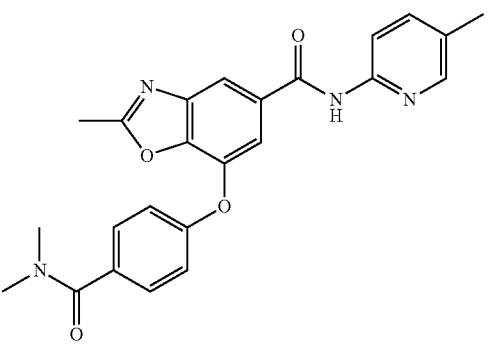

The title compound was prepared in a similar manner as described for Example 276, via three steps, from methyl 7-hydroxy-2-methylbenzo[d]oxazole-5-carboxylate (368e). $^1$H NMR (300 MHz, CHLOROFORM-D) δ ppm 2.33 (s, 3 H) 2.65-2.67 (s, 3 H) 3.03 (s, 3 H) 3.11 (s, 3 H) 7.05 (d, J=8.67 Hz, 2 H) 7.41 (d, J=8.67 Hz, 2 H) 7.53 (d, J=1.32 Hz, 1 H) 7.65

(dd, J=8.57, 2.17 Hz, 1 H) 7.99 (d, J=1.32 Hz, 1 H) 8.12 (d, J=2.17 Hz, 1 H) 8.17 (d, J=8.57 Hz, 1 H) 9.04 (s, 1 H); LCMS m/z 431.40 (M+H)$^+$.

Example 371

N-(5-Methylpyridin-2-yl)-4-[4-(methylsulfonyl)phenoxy]-1,3-benzothiazole-6-carboxamide

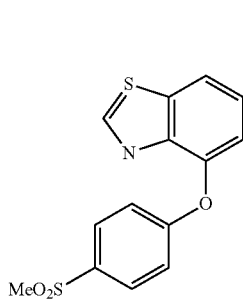

The title compound was prepared in a similar manner as described for Example 252, via two steps, from methyl 4-hydroxybenzo[d]thiazole-6-carboxylate (371e). $^1$H NMR (300 MHz, CHLOROFORM-D) δ ppm 2.32 (s, 3 H) 3.06 (s, 3 H) 7.07-7.22 (m, 2 H) 7.59 (dd, J=8.48, 2.45 Hz, 1 H) 7.73 (d, J=1.51 Hz, 1 H) 7.86-8.01 (m, 2 H) 8.11 (s, 1 H) 8.24 (d, J=8.48 Hz, 1 H) 8.44 (d, J=1.70 Hz, 1 H) 8.70 (s, 1 H) 9.11 (s, 1 H); LCMS m/z 440.20 (M+H)$^+$.

Preparation of Intermediate 371a

Methyl 3-methoxy-4-nitrobenzoate

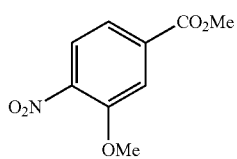

To a mixture of 3-hydroxy-4-nitrobenzoic acid (203 g, 1.109 mol) and K$_2$CO$_3$ (345 g, 2.496 mol) in DMF (3000 mL) was added drop wise CH$_3$I (400 g, 2.817 mol) at ambient temperature. The mixture was stirred at ambient temperature for 13 h. TLC (EtOAc: Petroleum ether 1:4) indicated the reaction was complete. Most of the solvent was removed under reduced pressure and the residue was diluted with water (2 L). Then the mixture was extracted with EtOAc (2 L×3). The combined organic layers were washed with water (1L×3), dried over Na$_2$SO$_4$ and concentrated under reduced pressure to yield the desired ester (172 g, 73.5%) as a yellow solid.

$^1$H NMR (400 MHz, CDCl$_3$): δ 7.848-7.827 (d, 2H), 7.759 (s, 1H), 7.705-7.681 (d, 1H), 4.018 (s, 3H), 3.969 (s, 3H).

Preparation of Intermediate 371b

Methyl 4-amino-3-methoxybenzoate

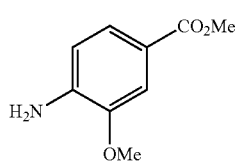

To a solution of methyl 3-methoxy-4-nitrobenzoate (172 g, 0.815 mol) in methanol (2 L) was added Raney Ni (60 g) in one portion. The resulting mixture was stirred at ambient temperature under H$_2$ for 24 h. TLC (EtOAc: Petroleum ether 1:3) indicated the reaction was complete. The reaction mixture was filtered through a pad of Celite and the filter cake was washed with methanol (100 mL×5). The filtrate was concentrated in vacuum to afford the desired amine (128 g, 86.7%) as a yellow solid. $^1$H NMR (400 MHz, CDCl$_3$): δ 7.383-7.349 (dd, 1H), 7.268 (d, 1H), 6.633-6.605 (d, 1H), 5.617 (s, 2H), 3.782 (s, 3H), 3.740 (s, 3H).

Preparation of Intermediate 371c: Methyl 2-amino-4-methoxy-1,3-benzothiazole-6-carboxylate

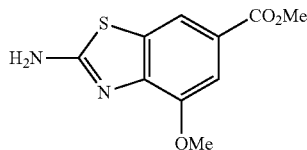

To a solution of methyl 4-amino-3-methoxybenzoate (307 g, 1.696 mol) in anhydrous methanol (4 L) was added an intimated mixture of KSCN (1640 g, 16.9 mol) and anhydrous CuSO$_4$ (1350 g, 8.44 mol) in one portion. The mixture was heated to reflux for 4 h. TLC (EtOAc/Petroleum ether 1:4) showed the reaction was complete. The mixture was filtered and the filtrate was diluted with water. The solution was heated to boiling until a slightly clear solution formed. The mixture was cooled to ambient temperature and left standing for 1 day. A dark yellow solid was formed, which was collected by filtration to afford the desired product (338 g, 84%) as a dark yellow solid. ¹H NMR (400 MHz, CDCl₃): δ 9.000-8.200 (br, 2H), 8.052 (s, 1H), 7.435 (s, 1H), 3.927 (s, 3H), 3.827 (s, 3H).

Preparation of Intermediate 371d: Methyl 4-methoxy-1,3-benzothiazole-6-carboxylate

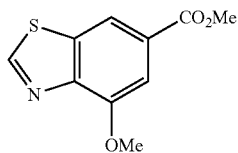

To a stirred solution of methyl 2-amino-4-methoxy-1,3-benzothiazole-6-carboxylate (100 g, 0.42 mol) in DMF (1 L) was added drop wise isoamyl nitrite (108 g, 0.92 mol) at 65° C. Then the resulting mixture was stirred at 65° C. for 20 min. TLC (EtOAc/Petroleum ether 1:4) showed the reaction was complete. After cooling to ambient temperature, the mixture was poured into ice water (1 L). The resulting mixture was extracted with EtOAc (1 L×3). The combined organic layers were washed with water (1 L×2), dried over Na₂SO₄ and concentrated in vacuum. The residue was purified by chromatography (silica gel, EtOAc/Petroleum ether 1:50 to 1:10) to afford the product (22 g, 23%) as a yellow solid. ¹H NMR (400 MHz, CDCl₃): δ 9.050 (s, 1H), 8.285-8.281 (d, 1H), 7.592-7.587 (d, 1H), 4.110 (s, 3H), 3.965 (s, 3H).

Preparation of Intermediate 371e: Methyl 4-hydroxy-1,3-benzothiazole-6-carboxylate

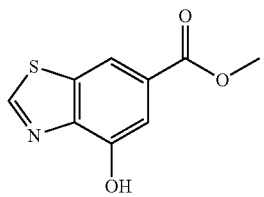

To a stirred solution of methyl 4-methoxy-1,3-benzothiazole-6-carboxylate (20.0 g, 0.0897 mol) in anhydrous CH₂Cl₂ (300 mL) was added drop wise BBr₃ (112.5 g, 0.448 mol) at -78° C. Then the resulting mixture was stirred at -78° C. for 3 hours and allowed to warm to room temperature overnight. TLC (EtOAc/Petroleum ether 1:4) showed the reaction was complete. The reaction mixture was concentrated in vacuum and methanol (100 mL) was added drop wise to the residue. Then the mixture was concentrated again in vacuum. The residue was washed with water and recrystallized from methanol to afford the desired product (12 g, 64%) as a white solid. ¹H NMR (400 MHz, CDCl₃): δ 10.671 (s, 1H), 9.437 (s, 1H), 8.252-8.248 (s, 1H), 7.488-7.484 (s, 1H), 3.898 (s, 3H).

Example 372

4-[4-(Methylsulfonyl)phenoxy]-N-pyridin-2-yl-1,3-benzothiazole-6-carboxamide

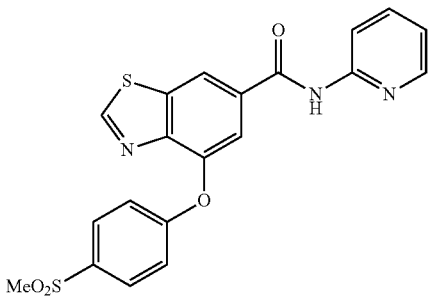

The title compound was prepared in a similar manner as described for Example 252, via two steps, from methyl 4-hydroxybenzo[d]thiazole-6-carboxylate (371e). ¹H NMR (400 MHz, CDCl₃): δ 10.000-9.500 (br, 1H), 9.135 (s, 1H), 8.524-8.490 (m, 2H), 8.299 (br, 1H), 7.979-7.896 (m, 3H), 7.786 (s, 1H), 7.212-7.190 (m, 3H), 3.071 (s, 3H). MS (pos): 426.1.

Example 373

6-Methoxy-2-methyl-1H-benzoimidazole-4-carboxylic acid(5-methyl-pyridin-2-yl)-amide

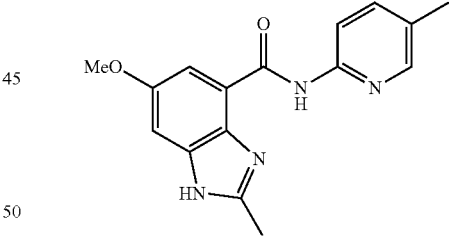

HATU (431 mg, 1.13 mmol) was added to a mixture of 6-methoxy-2-methyl-1H-benzoimidazole-4-carboxylic acid (350 mg, 1.0 mmol), 2-amino-5-picoline (134 mg, 1.24 mmol), and DIEA (0.359mL, 2.06 mmol) in DMF (5 mL) while stirring at room temperature. The resulting mixture was stirred at room temperature under N₂ atmosphere for 16 hours. The mixture was worked up with water and extracted into chloroform; the organic layer was dried over MgSO4, concentrated. The crude product was purified by flash silica-gel chromatography (ISCO) eluting with CHCl₃:MeOH (95:5) to gain 85 mg light brown color solid product in 27% yield. ¹H NMR (400 MHz, DMSO-d6) δ ppm 12.68 (s, 1 H) 12.41 (s, 1 H) 8.27 (d, J=8.56 Hz, 1 H) 8.23 (s, 1 H) 7.68 (dd, J=8.56, 1.76 Hz, 1 H) 7.51 (d, J=2.27 Hz, 1 H) 7.23 (d, J=2.27 Hz, 1

H) 3.85 (s, 3 H) 2.61 (s, 3 H) 2.29 (s, 3 H). LRMS for C$_{16}$H$_{16}$N$_4$O$_2$ m/z 297 (M+H)$^+$.

Preparation of Intermediate 373a 1-(1,1-Diethoxy-ethyl)-6-methoxy-2-methyl-1H-benzoimidazole-4-carbonitrile

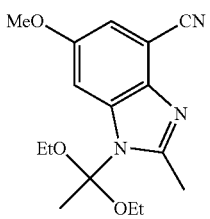

A mixture of 2,3-diamino-5-methoxybenzonitrile (Ref: U.S. Pat. No. 6,387,938 B1) (1.5 g, 8.7 mmol) in triethyl orthoacetate (16.5 mL, 87.3 mmol) was stirred at 120° C. for 2 hours. The mixture was concentrated to dryness to obtain 2.55 g dark colored oil. The product was carried on to the next step without any further purification. LRMS for C$_{16}$H$_{21}$N$_3$O$_3$ m/z 304.2 (M+H)$^+$.

Preparation of Intermediate 373b

6-Methoxy-2-methyl-1H-benzoimidazole-4-carboxylic acid

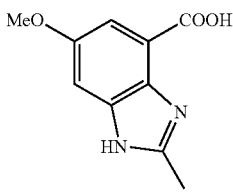

A mixture of 1-(1,1-diethoxy-ethyl)-6-methoxy-2-methyl-1H-benzoimidazole-4-carbonitrile (2.5 g, 8.2 mmol), diethylene glycol (5 mL) and 6 N KOH aqueous solution (2.5 mL) was stirred at 150° C. for 16 hours. The mixture was poured into ice water (15 mL) and washed with ethyl acetate (3×100mL). The water layer was then adjusted to pH 7-6 with 6 N HCl aqueous solution. The resulting mixture was washed with EtOAc and the water layer was concentrated down to a volume of 10 mL. The crude product was purified by preparative HPLC to obtain 350 mg of dark colored sticky gum product. $^1$H NMR (400 MHz, DMSO-d6) δ ppm 13.98 (bs, 1H) 7.55 (d, J=2.5 Hz, 1H) 7.51 (d, J=2.5 Hz, 1H) 4.20 (bs, 1H) 3.9 (s, 3H) 2.77 (s, 3H). LRMS for C$_{16}$H$_{21}$N$_3$O$_3$ m/z 205 (M−H)$^−$.

Example 374

5-(2-Chloro-benzyloxy)-2,2-dimethyl-chroman-7-carboxylic acid(5-methyl-pyridin-2-yl)-amide and Example 375: 7-(2-Chloro-benzyloxy)-2,2-dimethyl-chroman-5-carboxylic acid(5-methyl-pyridin-2-yl)-amide

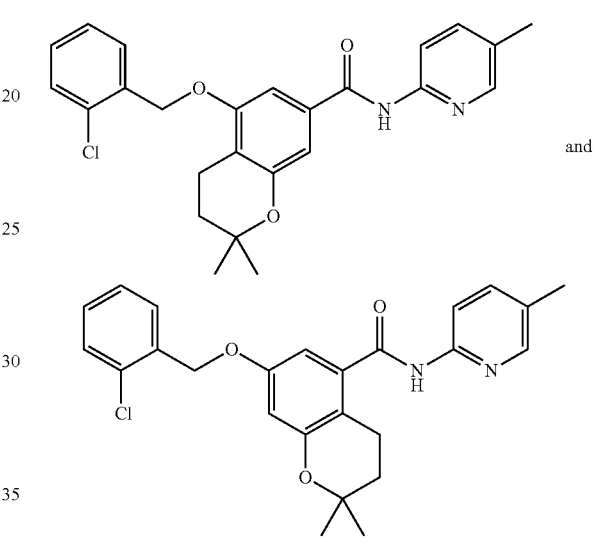

The title compound was prepared in a similar manner as described for Example 1, from dimethylaluminum chloride (1.0 M in hexanes, 2.9 mL, 2.9 mmol), 5-methyl-2-aminopyridine (314 mg, 2.9 mmol), and a mixture of 5-(2-chlorobenzyloxy)-2,2-dimethyl-chroman-7-carboxylic acid methyl ester and 7-(2-chloro-benzyloxy)-2,2-dimethyl-chroman-5-carboxylic acid methyl ester (374c) (crude 104 mg). Purification by reverse phase chromatography gave 5-(2-chlorobenzyloxy)-2,2-dimethyl-chroman-7-carboxylic acid(5-methyl-pyridin-2-yl)-amide (374) (11 mg, 10% yield) and 7-(2-chloro-benzyloxy)-2,2-dimethyl-chroman-5-carboxylic acid(5-methyl-pyridin-2-yl)-amide (375) as a white solid (25 mg, 23% yield).

Example 374: $^1$H NMR (400 MHz, CDCl$_3$) δ 12.26 (br. s., 1 H) 8.81 (d, J=8.84 Hz, 1 H) 7.99-8.08 (m, 2 H) 7.58 (dd, J=6.95, 2.40 Hz, 1 H) 7.38-7.44 (m, 1 H) 7.33 (s, 1 H) 7.28-7.32 (m, 2 H) 7.23 (s, 1 H) 5.30 (s, 2 H) 2.77 (t, J=6.82 Hz, 2 H) 2.44 (s, 3 H) 1.81 (t, J=6.82 Hz, 2 H) 1.34 (s, 6 H); LCMS for C$_{25}$H$_{25}$ClN$_2$O$_3$ m/z 436.90 (M+H)$^+$; Anal. Calcd. for C$_{25}$H$_{25}$ClN$_2$O$_3$.1.29TFA: C, 56.72; H, 4.54; N, 4.89; Found: C, 56.68; H, 4.53; N, 4.89.

Example 375: $^1$H NMR (400 MHz, CDCl$_3$) δ 12.27 (s, 1 H) 8.80 (d, J=8.84 Hz, 1 H) 8.00-8.09 (m, 2 H) 7.57 (dd, J=7.45, 1.64 Hz, 1 H) 7.39 (dd, J=7.58, 1.52 Hz, 1 H) 7.23-7.32 (m, 2 H) 6.95 (d, J=2.53 Hz, 1 H) 6.61 (d, J=2.53 Hz, 1 H) 5.20 (s, 2 H) 2.92 (t, J=6.69 Hz, 2 H) 2.45 (s, 3 H) 1.77 (t, J=6.69 Hz, 2 H) 1.36 (s, 6 H); LCMS for C$_{25}$H$_{25}$ClN$_2$O$_3$ m/z 436.90

(M+H)+; Anal. Calcd. for $C_{25}H_{25}ClN_2O_3 \cdot 1.30TFA$: C, 56.65; H, 4.53; N, 4.79; Found: C, 56.51; H, 4.43; N, 4.89.

Preparation of Intermediate 374a

3-Hydroxy-5-(3-methyl-but-2-enyloxy)-benzoic acid methyl ester

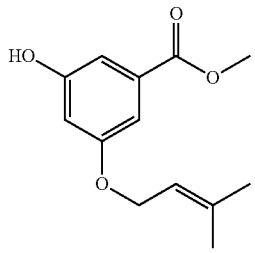

The title compound was prepared in a similar manner as described for Intermediate 1a, from methyl 3,5-dihydroxy-benzoate (11.3 g, 67 mmol), potassium carbonate (18.5 g, 134 mmol), and 1-bromo-3-methyl-but-2-ene (10 g, 67 mmol). Purification by column chromatography eluting with 20% EtOAc in hexane gave a pale yellow solid (3.41 g, 20% yield). $^1$H NMR (400 MHz, CDCl$_3$) δ 7.17-7.20 (m, 1 H) 7.12-7.17 (m, 1 H) 6.63 (t, J=2.27 Hz, 1 H) 5.41-5.51 (m, 1 H) 5.50 (s, 1H) 4.53 (d, J=6.57 Hz, 2 H) 3.91 (m, 3 H) 1.80 (s, 3 H) 1.69 (s, 3 H); LCMS for $C_{13}H_{16}O_4$ m/z 237.10 (M+H)+.

Preparation of Intermediate 374b 3-(2-Chloro-benzyloxy)-5-(3-methyl-but-2-enyloxy)-benzoic acid methyl ester

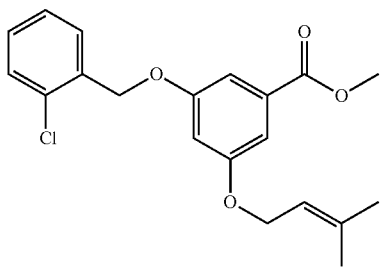

The title compound was prepared in a similar manner as described for Intermediate 1a, from potassium carbonate (1.25 g, 9.06 mmol), 2-chloro benzyl bromide (0.59 mL, 4.53 mmol), and 3-hydroxy-5-(3-methyl-but-2-enyloxy)-benzoic acid methyl ester (374a) (1.07 g, 4.53 mmol). Purification by flash column chromatography eluting with 5% EtOAc in hexanes gave a colorless oil (1.60 g, 100% yield). $^1$H NMR (400 MHz, CDCl$_3$) δ 7.51-7.61 (m, 1 H) 7.37-7.45 (m, 1 H) 7.30 (dd, J=3.92, 2.40 Hz, 2 H) 7.27-7.29 (m, 1 H) 7.24 (dd, J=2.27, 1.26 Hz, 1 H) 6.76 (t, J=2.40 Hz, 1 H) 5.49 (tt, J=6.82, 1.39 Hz, 1 H) 5.15-5.23 (m, 3 H) 4.54 (d, J=6.82 Hz, 2 H) 3.92 (s, 3 H) 1.81 (s, 3 H) 1.73-1.79 (m, 3 H); LCMS for $C_{20}H_{21}ClO_4$ m/z 383.00 (M+Na)+.

Preparation of Intermediate 374c

Mixture of 5-(2-chloro-benzyloxy)-2,2-dimethyl-chroman-7-carboxylic acid methyl ester and 7-(2-chloro-benzyloxy)-2,2-dimethyl-chroman-5-carboxylic acid methyl ester

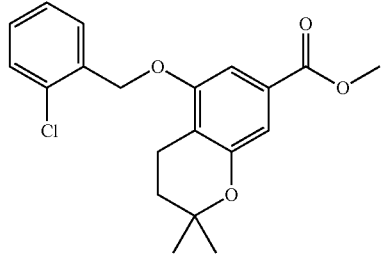

and

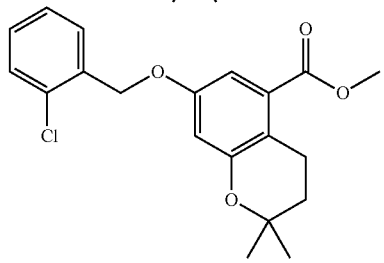

Montarillonite K10 (404 mg) was added to a solution of 3-(2-chloro-benzyloxy)-5-(3-methyl-but-2-enyloxy)-benzoic acid methyl ester (374b) (304 mg, 0.84 mmol) in CCl$_4$ (3 mL). The suspension was stirred at 50° C. overnight. The mixture was filtered and concentrated. The residue was purified by flash column chromatography eluting with 5% EtOAc in hexanes to give a mixture of 5-(2-chloro-benzyloxy)-2,2-dimethyl-chroman-7-carboxylic acid methyl ester and 7-(2-chloro-benzyloxy)-2,2-dimethyl-chroman-5-carboxylic acid methyl ester and starting material as colorless oil (104 mg) which was used as is in the next step. LCMS for $C_{20}H_{21}Cl_4$ m/z 383.00 (M+Na)+.

Example 376

2-Methyl-N-(5-methylpyridin-2-yl)-7-(4-(methylsulfonyl)-phenoxy)-3-oxoisoindoline-5-carboxamide

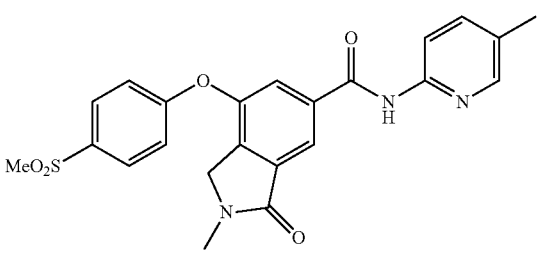

To a solution of 5-methyl-2-aminopyridine (144 mg, 1.33 mmol) in DCE at 0° C. was added Al(CH$_3$)$_2$Cl drop-wise. The reaction was stirred at room temperature for 20 minutes followed by the addition of methyl 2-methyl-7-(4-(methylsulfonyl)phenoxy)-3-oxoisoindoline-5-carboxylate. After stirring the reaction at room temperature for 14 hours, it was diluted with CH$_2$Cl$_2$ and quench with potassium sodium tartrate tetrahydrate (20% w/w) (1 mL) slowly. The solution was washed with brine, dried over Na$_2$SO$_4$, and concentrated. The crude sample was introduced into a silica gel column and eluted with 5-10% MeOH/CHCl$_3$ to provide the product (40 mg, 85% yield) as a white solid. $^1$H NMR (300 MHz, CHLOROFORM-d) δ ppm 2.33 (s, 3 H) 3.10 (s, 3 H) 3.19-3.33 (m, 3 H) 4.40 (s, 2 H) 7.19 (d, J=8.67 Hz, 2 H) 7.53-7.66 (m, 1 H) 7.82 (s, 1 H) 7.97 (d, J=8.67 Hz, 2 H) 8.10-8.17 (m, 1 H) 8.19 (s, 2 H) 8.81 (s, 1 H); LC-MS (ESI)+ m/z=452.00 (M+H)$^+$.

Preparation of Intermediate 376a

Dimethyl 5-(allyloxy)isophthalate

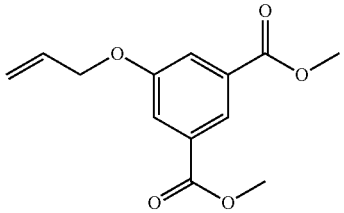

To a mixture of dimethyl 5-hydroxy-isophthalate (10 g, 47.577 mmol), Cs$_2$CO$_3$ (31 g, 95.2mmol) in DMF was added allyl bromide (4.83 mL, 57.1 mmol) drop-wise. After stirring the mixture for 14 hours, the reaction was treated with water, extracted with EtOAc (2×). The combined organic extract was dried over sodium sulfate, filtered and evaporated to provide the desired product as white solid (12 g, 100% yield). The crude product was used without further purification. $^1$H NMR (300 MHz, CHLOROFORM-d) δ ppm 3.94 (s, 6 H) 4.56-4.71 (m, 2 H) 5.33 (dd, J=10.46, 1.41 Hz, 1 H) 5.39-5.53 (m, 1 H) 5.96-6.17 (m, 1 H) 7.76 (d, J=1.32 Hz, 2 H) 8.28 (t, J=1.41 Hz, 1 H); LC-MS: (ESI)+m/z=251.00 (M+1)$^+$.

Preparation of Intermediate 376b

Dimethyl 4-allyl-5-hydroxyisophthalate

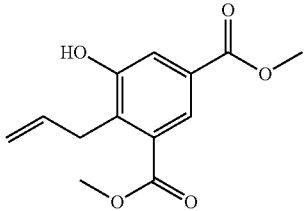

A solution of dimethyl 5-(allyloxy)isophthalate (1.5 g, 5.994 mmol) in N,N-dimethylaniline (15 mL) was heat at 200° C. for 14 hours. After it was cooled to room temperature, the reaction was diluted with EtOAc, washed with 0.5 N HCl, brine, and dried with Na$_2$SO$_4$. The solvent was evaporated under reduced pressure. The desired product was purified via silica gel gradient column chromatography with EtOAc/Hex (10-25%) to afford the title compound (750 mg, yield 70%) as a white solid. $^1$H NMR (300 MHz, CHLOROFORM-d) δ ppm 3.82 (d, J=6.22 Hz, 2 H) 3.92 (d, J=5.84 Hz, 6 H) 5.02-5.11 (m, 1 H) 5.10-5.17 (m, 1 H) 5.81 (s, 1 H) 5.90-6.13 (m, 1 H) 7.70 (d, J=1.70 Hz, 1 H) 8.11 (d, J=1.51 Hz, 1 H); LC-MS(ESI)+ m/z=251.00 (M+H)$^+$.

Preparation of Intermediate 376c

Dimethyl 4-allyl-5-(4-(methylsulfonyl)phenoxy)isophthalate

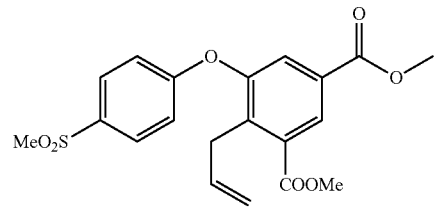

A mixture of dimethyl 4-allyl-5-hydroxyisophthalate (2.0 g, 7.99 mmol), 4-fluorophenyl methyl sulfone (2.1 g, 12 mmol), Cs$_2$CO$_3$ (5.2 g, 16 mmol) and CuI (400 mg, 2.1 mmol) in DMF (20 mL) was heated to for 4 hours. The solvent was removed under reduced pressure. The residue was poured into water (20 mL) and extracted with EtOAc (50 mL×2). The combined organic layer was washed with brine (20 mL×2), dried over Na$_2$SO$_4$ and concentrated. The product was purified via silica gel gradient chromatography eluted with EtOAc in hexanes (10/90 to 30/90) to afford the title compound (2.5 g, 78%) as a white solid. $^1$H NMR (300 MHz, CHLOROFORM-d) δ ppm 1.83 (dd, J=6.69, 1.60 Hz, 2 H) 3.03-3.16 (m, 3 H) 3.93 (d, 6 H) 6.14-6.34 (m, 1 H) 6.63 (dd, J=16.11, 1.60 Hz, 1 H) 6.88-6.98 (m, 1 H) 6.97-7.09 (m, 2 H) 7.79 (d, J=1.70 Hz, 1 H) 7.87-8.01 (m, 2 H) 8.29 (d, J=1.70 Hz, 1 H); LC-MS (ESI)+m/z =405.00 (M+H)$^+$.

Preparation of Intermediate 376d

Dimethyl 5-(4-(methylsulfonyl)phenoxy)-4-(prop-1-enyl)isophthalate

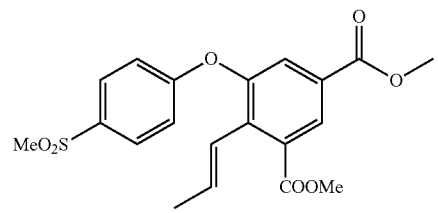

To a solution of dimethyl 4-allyl-5-(4-(methylsulfonyl)phenoxy)isophthalate (3.0 g, 8.814 mmol) in CH$_2$Cl$_2$ (25 mL) was added bis(acetonitrile-palladium(II) chloride (229 mg, 0.881 mmol). The mixture was refluxed under N$_2$ for 14 hours. After removal of the solvent, the crude material was introduced into a silica gel column and eluted with EtOAc in hexanes (10/90 to 30/70) to afford the title compound (2.65 g, 88%) as a white solid. $^1$H NMR (300 MHz, CHLOROFORM-d) δ ppm 1.82 (dd, J=6.69, 1.79 Hz, 3 H) 3.04-3.18 (m, 3 H) 3.93 (d, 6 H) 6.00 (none, 1 H) 6.22 (dd, J=16.01, 6.78 Hz, 1 H) 6.62 (dd, J=16.01, 1.70 Hz, 1 H) 6.94-7.09 (m, 2 H) 7.77 (d, J=1.70 Hz, 1 H) 7.85-8.00 (m, 2 H) 8.28 (d, J=1.70 Hz, 1 H); LC-MS(ESI)+ m/z=405.00 (M+H)+.

Preparation of Intermediate 376e

Dimethyl 4-formyl-5-(4-(methylsulfonyl)-phenoxy)-isophthalate

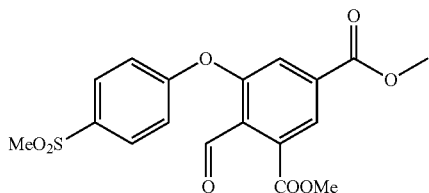

A solution of dimethyl 5-(4-(methylsulfonyl)phenoxy)-4-(prop-1-enyl)isophthalate (2.6 g, 7.8 mmol) in CH$_2$Cl$_2$ and methanol was cooled to −78° C. and treated with ozone until the solution appeared blue (20 min). Nitrogen was bubbled through the solution until the blue color dissipated. Dimethylsulfide (1.0 mL) was added and the cold-bath was removed allowing the reaction mixture to warm to room temperature overnight. Concentration of the solution under vacuum provided an oil, which was introduced into a silica gel column and eluted with 10-30% EtOAc in hexanes to afford the title compound (2.5 g, 98%) as a white solid. $^1$H NMR (300 MHz, CHLOROFORM-d) δ ppm 3.08 (q, 3 H) 3.95 (dd, 6 H) 7.08-7.16 (m, 2 H) 7.98 (q, J=2.07 Hz, 2 H) 7.99-8.03 (m, 1 H) 8.33-8.39 (m, 1 H) 10.46 (s, 1 H); LC-MS (ERS)+ m/z=393.00 (M+H)+.

Preparation of Intermediate 376f

Methyl 2-methyl-7-(4-(methylsulfonyl)phenoxy)-3-oxoisoindoline-5-carboxylate

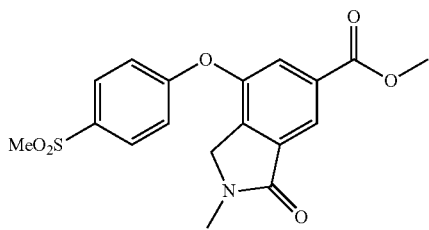

A sealed tube was charged with a solution of dimethyl 4-formyl-5-(4-(methylsulfonyl)phenoxy)-isophthalate (210 mg, 0.535 mmol) in MeOH and aminomethane hydrochloride (72.3 mg, 1.07 mmol). After stirring the reaction at room temperature for 2 hours, NaCNBH$_3$ (84.1 mg, 1.34 mmol) was added. The mixture was then stirred at 65° C. for 14 hours. The solvent was evaporated and replaced with ethyl acetate. The organic layer was then washed with brine (3×), dried over MgSO$_4$, and concentrated. The crude sample was introduced into a silica gel column chromatography and eluted with 5-10% MeOH/CHCl3 to provide the desired product (100 mg, 50% yield) as white solid. $^1$H NMR (300 MHz, CHLOROFORM-d) δ ppm 3.09 (s, 3 H) 3.21 (s, 3 H) 3.94 (s, 3 H) 4.36 (s, 2 H) 7.07-7.21 (m, 2 H) 7.84 (d, J=1.13 Hz, 1 H) 7.90-8.03 (m, 2 H) 8.37 (d, J=1.13 Hz, 1 H); LC-MS (ESI)+ m/z=376.00 (M+H)+.

Examples 377-388 were prepared in a similar manner as described for Example 376, from the appropriate amino heterocycles and primary amines. For Examples 377 and 378, benzyl bromide was used instead of fluorophenyl sulfone.

Example 377

7-(Benzyloxy)-2-cyclopropyl-N-(1-methyl-1H-pyrazol-3-yl)-3-oxoisoindoline-5-carboxamide

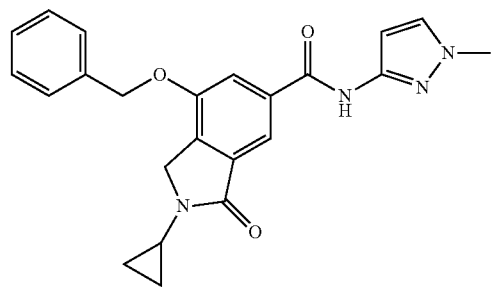

Example 378

7-(Benzyloxy)-2-cyclopropyl-N-(5-methylpyridin-2-yl)-3-oxoisoindoline-5-carboxamide

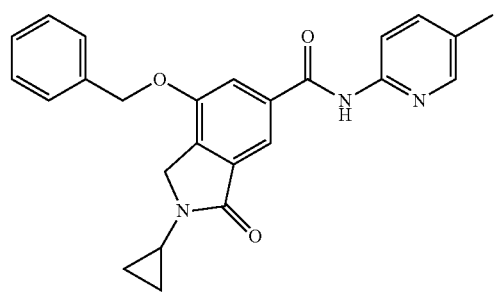

Example 379

2-Ethyl-N-(5-methylpyridin-2-yl)-7-(4-(methylsulfonyl)-phenoxy)-3-oxoisoindoline-5-carboxamide

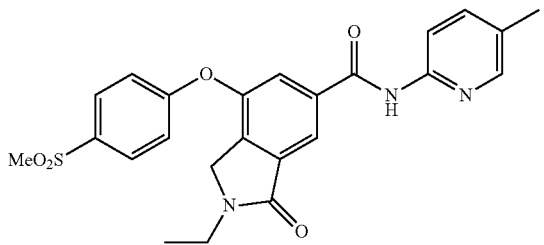

Example 380

2-Ethyl-N-(1-methyl-1H-pyrazol-3-yl)-7-(4-(methyl-sulfonyl)-phenoxy)-3-oxoisoindoline-5-carboxamide

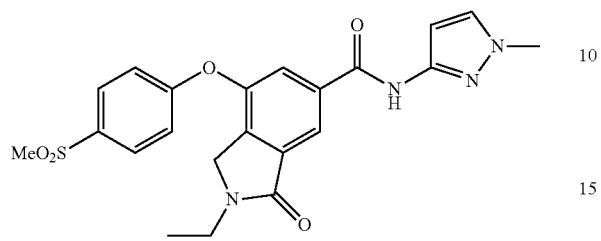

Example 381

2-Isobutyl-N-(5-methylpyridin-2-yl)-7-(4-(methyl-sulfonyl)-phenoxy)-3-oxoisoindoline-5-carboxamide

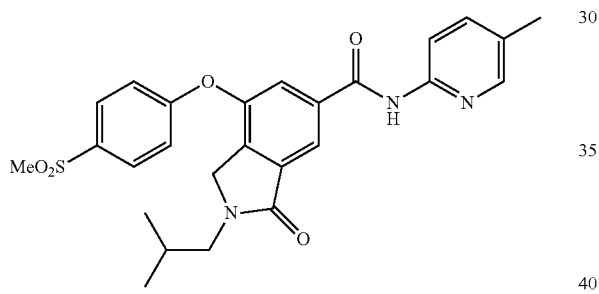

Example 382

2-Isobutyl-N-(1-methyl-1H-pyrazol-3-yl)-7-(4-(methylsulfonyl)-phenoxy)-3-oxoisoindoline-5-carboxamide

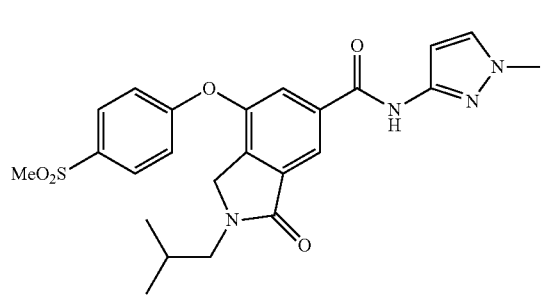

Example 383

2-Isopropyl-N-(5-methylpyridin-2-yl)-7-(4-(methyl-sulfonyl)-phenoxy)-3-oxoisoindoline-5-carboxamide

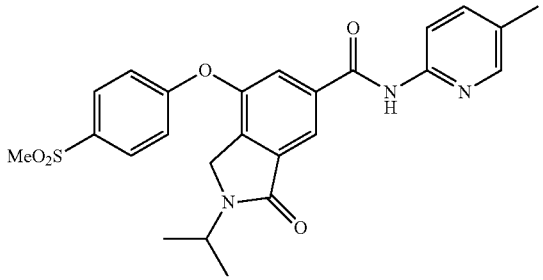

Example 384

2-Isopropyl-N-(1-methyl-1H-pyrazol-3-yl)-7-(4-(methylsulfonyl)-phenoxy)-3-oxoisoindoline-5-carboxamide

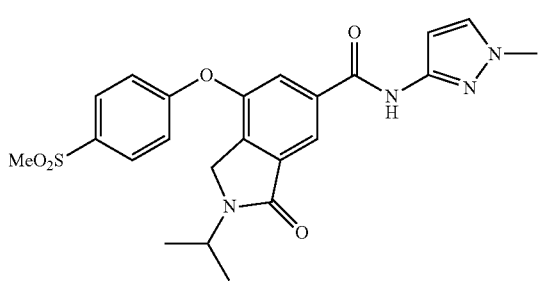

Example 385

2-Cyclopropyl-N-(5-methylpyridin-2-yl)-7-(4-(methylsulfonyl)-phenoxy)-3-oxoisoindoline-5-carboxamide

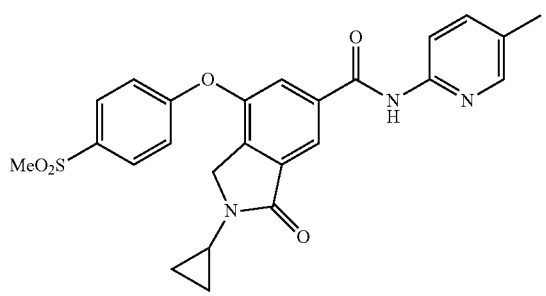

Example 387

2-(2-Methoxyethyl)-N-(5-methylpyridin-2-yl)-7-(4-(methylsulfonyl)-phenoxy)-3-oxoisoindoline-5-carboxamide

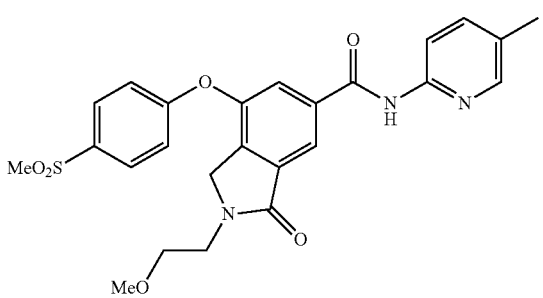

Example 386

2-Cyclopropyl-N-(1-methyl-1H-pyrazol-3-yl)-7-(4-(methylsulfonyl)-phenoxy)-3-oxoisoindoline-5-carboxamide

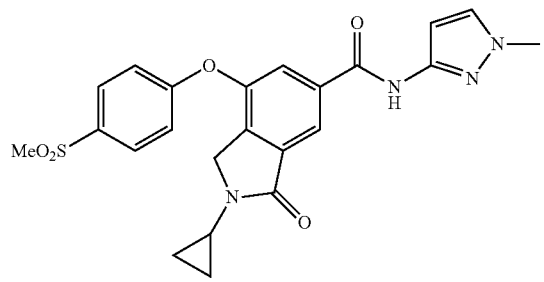

Example 388

2-(2-Methoxyethyl)-N-(1-methyl-1H-pyrazol-3-yl)-7-(4-(methylsulfonyl)-phenoxy)-3-oxoisoindoline-5-carboxamide

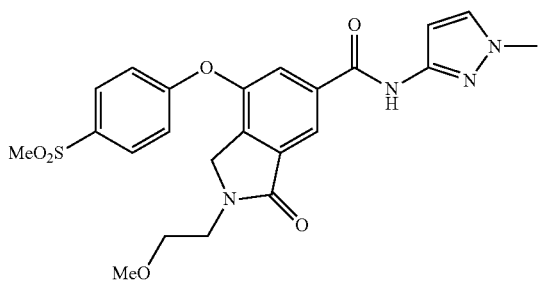

| Example | MW | MF | NMR | m/z |
|---|---|---|---|---|
| 377 | 402.5 | C23H22N4O3 | 1H NMR (300 MHz, CHLOROFORM-d) d ppm 0.78-1.05 (m, 4 H) 2.88-3.04 (m, J = 3.96 Hz, 1 H) 3.82 (s, 3 H) 4.33 (s, 2 H) 5.21 (s, 2 H) 6.79 (d, J = 2.26 Hz, 1 H) 7.30 (d, J = 2.26 Hz, 1 H) 7.35-7.50 (m, 5 H) 7.79 (s, 1 H) 7.83 (d, J = 0.94 Hz, 1 H) 8.78 (s, 1 H) | 403.00 |
| 378 | 413.5 | C25H23N3O3 | 1H NMR (300 MHz, CHLOROFORM-d) d ppm 0.79-1.03 (m, 4 H) 2.33 (s, 3 H) 2.87-3.09 (m, 1 H) 4.35 (s, 2 H) 5.23 (s, 2 H) 7.34-7.50 (m, 5 H) 7.58 (dd, J = 8.38, 1.98 Hz, 1 H) 7.78 (d, J = 1.13 Hz, 1 H) 7.90 (d, J = 0.94 Hz, 1 H) 8.15 (s, 1 H) 8.24 (d, J = 8.48 Hz, 1 H) 8.71 (s, 1 H) | 414.00 |
| 379 | 465.5 | C24H23N3O5S | 1H NMR (300 MHz, CHLOROFORM-d) d ppm 1.29 (t, 3 H) 2.32 (s, 3 H) 3.10 (s, 3 H) 3.72 (q, 2 H) 4.41 (s, 2 H) 7.20 (dd, 2 H) 7.59 (dd, 1 H) 7.80 (s, 1 H) 7.97 (d, J = 9.04 Hz, 2 H) 8.09-8.29 (m, 3 H) 8.68 (s, 1 H) | 466.00 |
| 380 | 454.5 | C22H22N4O5S | 1H NMR (300 MHz, CHLOROFORM-d) d ppm 1.29 (t, J = 7.25 Hz, 3 H) 3.10 (s, 3 H) 3.71 (q, 2 H) 3.83 (s, 3 H) 4.41 (s, 2 H) 6.75 (s, 1 H) 7.19 (d, J = 8.67 Hz, 2 H) 7.29 (s, 1 H) 7.79 (s, 1 H) 7.97 (d, J = 8.67 Hz, 2 H) 8.10 (s, 1 H) 8.61 (s, 1 H) | 455.00 |
| 381 | 493.6 | C26H27N3O5S | 1H NMR (300 MHz, CHLOROFORM-d) d ppm 0.97 (d, J = 6.59 Hz, 6 H) 2.00-2.15 (m, 1 H) 2.32 (s, 3 H) 3.10 (s, 3 H) 3.45 (d, J = 7.35 Hz, 2 H) 4.41 (s, 2 H) 7.12-7.25 (m, 2 H) 7.57 (dd, J = 8.38, 2.17 Hz, 1 H) 7.81 (d, J = 1.32 Hz, 1 H) 7.92-8.06 (m, 2 H) 8.14 (s, 1 H) 8.20 (t, J = 4.14 Hz, 2 H) 8.85 (s, 1 H) | 494.00 |
| 382 | 482.6 | C24H26N4O5S | 1H NMR (300 MHz, CHLOROFORM-d) d ppm 0.95 (d, J = 6.59 Hz, 6 H) 1.77-1.99 (m, 2 H) 1.99-2.16 (m, 1 H) 3.10 (s, 3 H) 3.45 (d, J = 7.54 Hz, 2 H) 3.83 (s, 3 H) 4.40 (s, 2 H) 6.76 (d, J = 1.70 Hz, 1 H) | 483.00 |

-continued

| Example | MW | MF | NMR | m/z |
|---|---|---|---|---|
| 383 | 479.6 | C25H25N3O5S | 7.19 (d, J = 8.67 Hz, 2 H) 7.30 (d, J = 1.88 Hz, 1 H) 7.81 (s, 1 H) 7.97 (d, J = 8.67 Hz, 2 H) 8.16 (s, 1 H) 8.98 (s, 1 H)<br>1H NMR (300 MHz, CHLOROFORM-d) d ppm 1.32 (d, J = 6.78 Hz, 6 H) 2.32 (s, 3 H) 3.10 (s, 3 H) 4.39 (s, 2 H) 4.62-4.82 (m, J = 6.59 Hz, 1 H) 7.20 (d, J = 8.85 Hz, 2 H) 7.52-7.65 (m, 1 H) 7.79 (s, 1 H) 7.98 (d, J = 8.67 Hz, 2 H) 8.25 (s, 3 H) 8.72 (s, 1 H) | 480.00 |
| 384 | 468.5 | C23H24N4O5S | 1H NMR (300 MHz, CHLOROFORM-d) d ppm 1.31 (d, J = 6.78 Hz, 6 H) 3.10 (s, 3 H) 3.83 (s, 3 H) 4.39 (s, 2 H) 4.62-4.80 (m, 1 H) 6.75 (d, J = 2.26 Hz, 1 H) 7.16-7.25 (m, 2 H) 7.30 (d, J = 2.26 Hz, 1 H) 7.78 (d, J = 1.32 Hz, 1 H) 7.93-8.04 (m, 2 H) 8.12 (d, J = 1.13 Hz, 1 H) 8.74 (s, 1 H) | 469.00 |
| 385 | 477.5 | C25H23N3O5S | 1H NMR (300 MHz, CHLOROFORM-d) d ppm 0.82-1.04 (m, 4 H) 2.35 (s, 3 H) 2.87-3.01 (m, 1 H) 3.10 (s, 3 H) 4.35 (s, 2 H) 7.13-7.23 (m, 2 H) 7.68 (d, 1 H) 7.86 (d, J = 1.13 Hz, 1 H) 7.92-8.03 (m, 2 H) 8.09 (s, 1 H) 8.23 (d, J = 1.13 Hz, 1 H) 8.34 (d, 1 H) 9.64 (s, 1 H) | 478.00 |
| 386 | 466.5 | C23H22N4O5S | 1H NMR (300 MHz, CHLOROFORM-d) d ppm 0.83-1.02 (m, 4 H) 2.88-3.03 (m, 1 H) 3.10 (s, 3 H) 3.83 (s, 3 H) 4.35 (s, 2 H) 6.76 (d, J = 2.07 Hz, 1 H) 7.11-7.22 (m, 2 H) 7.30 (d, J = 2.26 Hz, 1 H) 7.79 (s, 1 H) 7.97 (d, J = 8.85 Hz, 2 H) 8.11 (s, 1 H) 8.84 (s, 1 H) | 467.00 |
| 387 | 495.6 | C25H25N3O6S | 1H NMR (300 MHz, CHLOROFORM-d) d ppm 2.33 (s, 3 H) 3.10 (s, 3 H) 3.36 (s, 3 H) 3.61-3.71 (m, 2 H) 3.82 (t, J = 4.90 Hz, 2 H) 4.56 (s, 2 H) 7.11-7.25 (m, 2 H) 7.59 (dd, J = 8.48, 2.26 Hz, 1 H) 7.81 (d, J = 1.32 Hz, 1 H) 7.92-8.04 (m, 2 H) 8.15 (s, 1 H) 8.17-8.28 (m, 2 H) 8.69 (s, 1 H) | 496.00 |
| 388 | 484.5 | C23H24N4O6S | 1H NMR (300 MHz, CHLOROFORM-d) d ppm 3.10 (s, 3 H) 3.35 (s, 3 H) 3.57-3.71 (m, 2 H) 3.78-3.92 (m, 5 H) 4.55 (s, 2 H) 6.77 (d, J = 2.07 Hz, 1 H) 7.14-7.24 (m, 2 H) 7.30 (d, J = 2.07 Hz, 1 H) 7.80 (d, J = 1.13 Hz, 1 H) 7.92-8.04 (m, 2 H) 8.15 (s, 1 H) 8.79 (s, 1 H) | 485.00 |

Example 389

2-Isobutyl-N-(1-methyl-1H-pyrazol-3-yl)-5-[4-(methylsulfonyl)-phenoxy]-1-oxo-1,2,3,4-tetrahydroisoquinoline-7-carboxamide

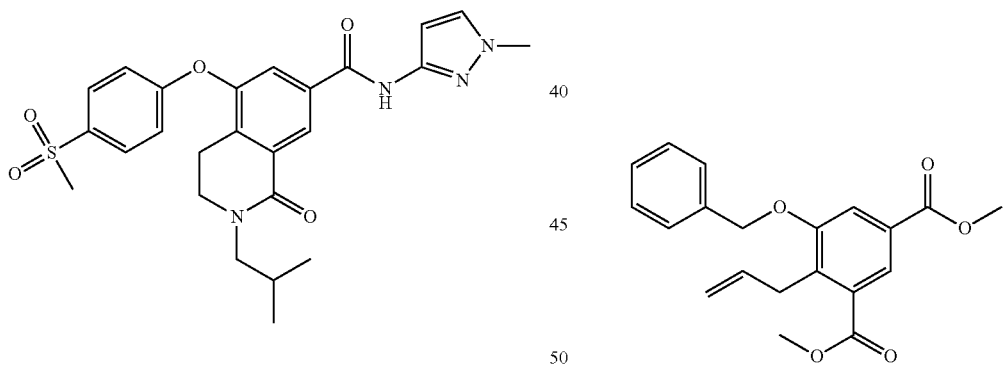

To a solution of amino methyl pyrazole (338 mg, 3.48 mmol) in DCE at 0° C. was added drop wise Al(CH$_3$)$_2$Cl (4.0 mL, 1.0M). After the addition the ice bath was removed and the reaction was stirred for 20 min at room temperature. Methyl 2-isobutyl-5-[4-(methylsulfonyl)phenoxy]-1-oxo-1,2,3,4-tetrahydroisoquinoline-7-carboxylate was added and the reaction was stirred at room temperature overnight. The sample was diluted with CH$_2$Cl$_2$, quenched by the slow addition of with potassium sodium tartrate tetrahydrate (20% w/w) (1 mL) slowly. The sample was washed with brine, dried over Na$_2$SO$_4$ and concentrated. The product was purified via silica gel gradient chromatography using MeOH/CHCl$_3$ (5/95 to 10/90) to provide the desired product (105 mg, 85% yield) as white solid. $^1$H NMR (300 MHz, CHLOROFORM-d) δ ppm 0.98 (d, J=6.59 Hz, 6 H) 1.97-2.21 (m, 1 H) 2.98 (t, J=6.50 Hz, 2 H) 3.08 (s, 3 H) 3.42 (d, J=7.54 Hz, 2 H) 3.57 (t, J=6.50 Hz, 2 H) 3.83 (s, 3 H) 6.76 (d, J=2.07 Hz, 1 H) 7.08 (d, J=8.85 Hz, 2 H) 7.29 (d, J=2.26 Hz, 1 H) 7.82 (s, 1 H) 7.93 (d, J=8.85 Hz, 2 H) 8.45 (s, 1 H) 8.94 (s, 1 H); MS (ESI, pos): 497.

Preparation of Intermediate 389a

Dimethyl 4-allyl-5-(benzyloxy)isophthalate

To a mixture of dimethyl 4-allyl-5-hydroxyisophthalate (376b) (5.05 g, 20.18 mmol) and Cs$_2$CO$_3$ (13 g, 40.1 mmol) in CH$_3$CN (30 mL) was added benzyl bromide (3.6 mL, 30.27 mmol). The mixture was stirred at room temperature for 14 hours. The solution was treated with water, and extracted with EtOAc (2×). The organic layer was dried over sodium sulfate, filtered and evaporated to provide the desired product as white solid (6.5 g, 98% yield). The crude product was used without purification. $^1$H NMR (300 MHz, CHLOROFORM-d) δ ppm 3.85 (t, J=6.78 Hz, 2 H) 3.89-3.93 (m, 3 H) 3.93 (s, 3 H) 4.93-4.99 (m, 1 H) 4.99-5.07 (m, 1 H) 5.16 (s, 2 H) 5.87-6.11

(m, 1 H) 7.30-7.38 (m, 1 H) 7.39-7.55 (m, 4 H) 7.74 (d, J=1.51 Hz, 1 H) 8.12 (d, J=1.70 Hz, 1 H); MS (ESI, pos):341.

Preparation of Intermediate 389b

Dimethyl 5-(benzyloxy)-4-(2-oxoethyl)isophthalate

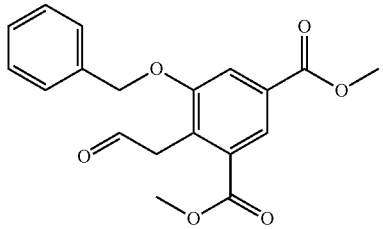

A solution of dimethyl 4-allyl-5-(benzyloxy)isophthalate (3.5 g, 10.28 mmol) in $CH_2Cl_2$ and methanol was cooled to −78° C. and treated with ozone until the solution appeared blue (20 min). Nitrogen was bubbled through the solution until the blue color dissipated. Dimethylsulfide (1.0 mL) was added and the cold-bath was removed allowing the reaction mixture to warm to room temperature overnight. Concentration of the solution under vacuum provided an oil which was purified by column chromatography on silica gel eluted with 10-30% EtOAc in hexanes to afford the aldehyde (3.0g, 98%) as a white solid. $^1$H NMR (300 MHz, CHLOROFORM-d) δ ppm 3.90 (s, 3 H) 3.95 (s, 3 H) 4.29 (s, 2 H) 5.14 (s, 2 H) 7.31-7.56 (m, 5 H) 7.81 (d, J=1.32 Hz, 1 H) 8.29 (d, J=1.51 Hz, 1 H) 9.75 (s, 1 H); MS (ESI, pos): 343.

Preparation of Intermediate 389c

Methyl 5-(benzyloxy)-2-isobutyl-1-oxo-1,2,3,4-tetrahydroisoquinoline-7-carboxylate

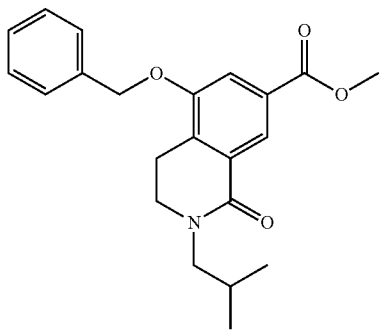

To a solution of dimethyl 5-(benzyloxy)-4-(2-oxoethyl)isophthalate (1.5 g, 4.38 mmol) in MeOH was added isobutylamine (385 mg, 0.522 mL, 5.26 mmol). The reaction was stirred at room temperature for 2 hrs, then $NaCNBH_3$ (84.1 mg, 1.34 mmol) was added. The mixture was stirred at 75° C. overnight. The solvents were removed under reduced pressure, diluted with ethyl acetate and washed with brine (3×). The product was purified via gradient silica gel chromatography using $MeOH/CHCl_3$ (5/95 to 10/90) to provide the product (1.1 g, 50% yield) as a film $^1$H NMR (300 MHz, CHLOROFORM-d) δ ppm 0.96 (dd, 6 H) 1.96-2.16 (m, 1 H) 3.05 (t, J=6.69 Hz, 2 H) 3.36-3.46 (m, J=7.63, 7.63 Hz, 2 H) 3.49-3.62 (m, 2 H) 3.88-4.02 (m, 3 H) 5.16 (s, 2 H) 7.32-7.56 (m, 5 H) 7.74 (d, J=1.32 Hz, 1 H) 8.42 (d, J=1.32 Hz, 1 H); MS (ESI, pos): 368.

Preparation of Intermediate 389d

Methyl 5-hydroxy-2-isobutyl-1-oxo-1,2,3,4-tetrahydroisoquinoline-7-carboxylate

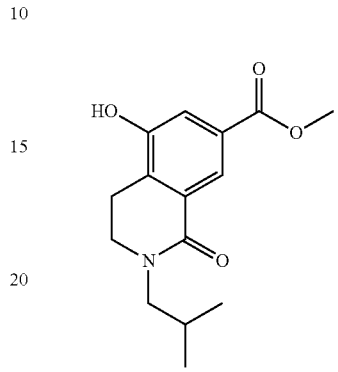

To a solution of methyl 5-(benzyloxy)-2-isobutyl-1-oxo-1,2,3,4-tetrahydroisoquinoline-7-carboxylate (1 g, 2.72 mmol) in MeOH (10 mL) was added catalyst amount of 10% Pd on C. This mixture was stirred under $H_2$ balloon at room temperature for 3 hr. The solids were filtered through a bed of Celite. Removal of the solvent gave the product (750 mg, 98%) as light yellow solid. $^1$H NMR (300 MHz, CHLOROFORM-d) δ ppm 0.97 (d, 6 H) 1.98-2.16 (m, 1 H) 3.05 (t, J=6.59 Hz, 2 H) 3.38-3.50 (m, 2 H) 3.57 (t, J=6.69 Hz, 2 H) 3.82-3.93 (m, 3 H) 7.50 (s, 1 H) 7.74 (d, J=1.51 Hz, 1 H) 8.30 (d, J=1.32 Hz, 1 H); MS (ESI, pos): 278.

Preparation of Intermediate 389e

Methyl 2-isobutyl-5-[4-(methylsulfonyl)phenoxy]-1-oxo-1,2,3,4-tetrahydroisoquinoline-7-carboxylate

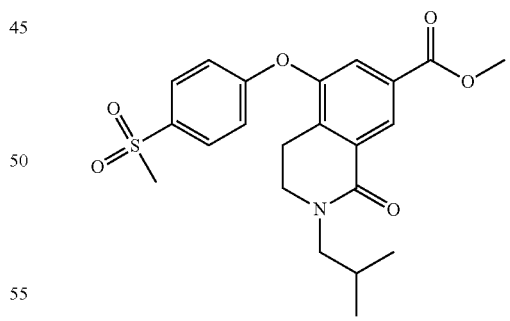

A mixture of methyl 5-hydroxy-2-isobutyl-1-oxo-1,2,3,4-tetrahydroisoquinoline-7-carboxylate (250 mg, 0.90 mmol), 4-fluorophenyl methyl sulfone (236 mg, 1.35 mmol), $Cs_2CO_3$ (441 mg, 1.35 mmol) and CuI (100 mg, 1 mmol) in DMF (20 mL) was heated to 100° C. for 4 hours. The solvent was removed under reduced pressure. The residue was poured into water (20 mL) and extracted with EtOAc (50 mL×2). The combined organic layers was washed with brine (20 mL×2), dried over $Na_2SO_4$ and concentrated. The product was purified via column chromatography on silica gel eluted with 10-30% EtOAc in hexanes to afford the ether (312 mg, 78%) as a white solid. $^1$H NMR (300 MHz, CHLOROFORM-d) δ ppm 0.97 (d, J=6.78 Hz, 6 H) 1.94-2.16 (m, 1 H) 2.94 (t, J=6.59 Hz, 2 H) 3.04-3.16 (m, 3 H) 3.41 (d, J=7.54 Hz, 2 H) 3.55 (t, J=6.59 Hz, 2 H) 3.87-4.01 (m, 3 H) 7.00-7.11 (m, 2 H) 7.80 (d, J=1.70 Hz, 1 H) 7.88-8.00 (m, 2 H) 8.66 (d, J=1.51 Hz, 1 H); MS (ESI, pos): 432.

Examples 390-393 were prepared in a similar manner as described for Example 376, from the appropriate amino heterocycles, primary amines, and fluorophenyl intermediates. Example 394 was isolated as a minor side product during the preparation of Example 390, from methyl 5-(benzyloxy)-2-methyl-1-oxo-1,2,3,4-tetrahydroisoquinoline-7-carboxylate (hydrogenation of methyl 5-(benzyloxy)-2-methyl-1-oxo-1,2,3,4-tetrahydroisoquinoline-7-carboxylate gave methyl 5-hydroxy-2-methyl-1-oxo-1,2-dihydroisoquinoline-7-carboxylate as the side product).

Example 390

2-Methyl-N-(5-methylpyridin-2-yl)-5-(4-(methylsulfonyl)-phenoxy)-1-oxo-1,2,3,4-tetrahydroisoquinoline-7-carboxamide

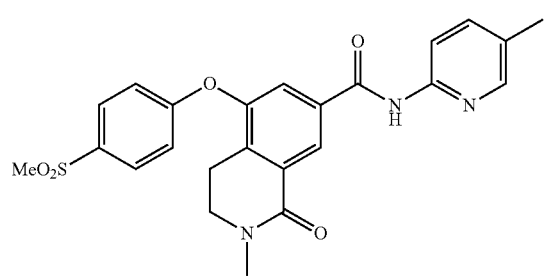

Example 391

2-Isobutyl-N-(5-methylpyridin-2-yl)-5-(4-(methylsulfonyl)-phenoxy)-1-oxo-1,2,3,4-tetrahydroisoquinoline-7-carboxamide

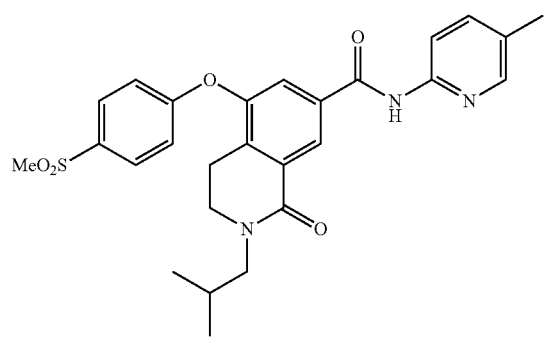

Example 392

5-(4-(Dimethylcarbamoyl)-3-fluorophenoxy)-2-isobutyl-N-(1-methyl-1H-pyrazol-3-yl)-1-oxo-1,2,3,4-tetrahydroisoquinoline-7-carboxamide

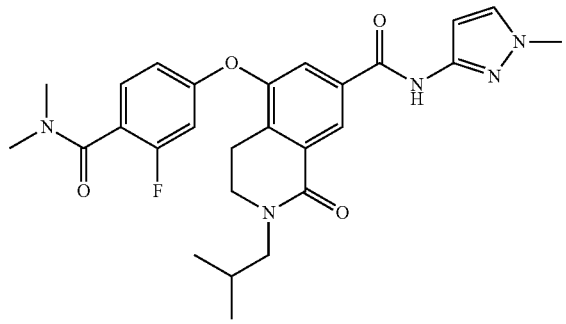

Example 393

5-(4-(Dimethylcarbamoyl)-3-fluorophenoxy)-2-isobutyl-N-(5-methylpyridin-2-yl)-1-oxo-1,2,3,4-tetrahydroisoquinoline-7-carboxamide

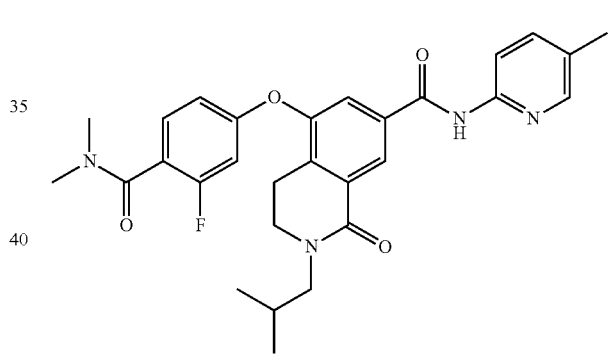

Example 394

2-Methyl-N-(5-methylpyridin-2-yl)-5-(4-(methylsulfonyl)-phenoxy)-1-oxo-1,2-dihydroisoquinoline-7-carboxamide

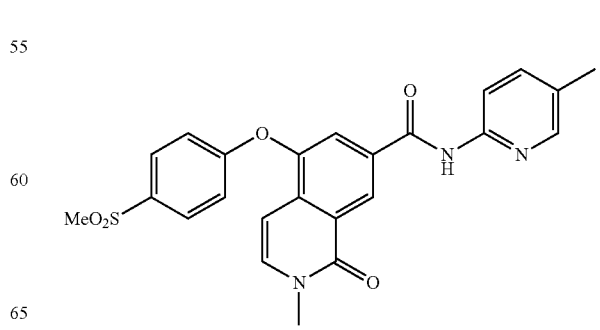

| Example | MW | MF | NMR | m/z |
|---|---|---|---|---|
| 390 | 465.5 | C24H23N3O5S | 1H NMR (300 MHz, CHLOROFORM-d) d ppm 2.36 (s, 3 H) 3.01 (t, J = 6.69 Hz, 2 H) 3.08 (s, 3 H) 3.20 (s, 3 H) 3.60 (t, J = 6.69 Hz, 2 H) 7.09 (d, J = 8.85 Hz, 2 H) 7.69 (dd, J = 8.67, 1.70 Hz, 1 H) 7.85-7.98 (m, 3 H) 8.11 (d, J = 0.94 Hz, 1 H) 8.37 (d, J = 8.67 Hz, 1 H) 8.57 (d, J = 1.51 Hz, 1 H) 9.67 (s, 1 H) | 466.10 |
| 391 | 507.6 | C27H29N3O5S | 1H NMR (300 MHz, CHLOROFORM-d) d ppm 0.99 (d, J = 6.59 Hz, 6 H) 1.98-2.15 (m, 1 H) 2.32 (s, 3 H) 2.98 (t, J = 6.59 Hz, 2 H) 3.08 (s, 3 H) 3.43 (d, J = 7.54 Hz, 2 H) 3.58 (t, J = 6.50 Hz, 2 H) 7.08 (d, J = 8.85 Hz, 2 H) 7.58 (d, 1 H) 7.82 (s, 1 H) 7.93 (d, J = 8.85 Hz, 2 H) 8.11-8.30 (m, 2 H) 8.49 (s, 1 H) 8.71 (s, 1 H) | 508.00 |
| 392 | 507.6 | C27H30FN5O4 | 1H NMR (300 MHz, CHLOROFORM-d) d ppm 0.98 (d, J = 6.59 Hz, 6 H) 1.98-2.17 (m, 1 H) 2.86-3.06 (m, 5 H) 3.12 (s, 3 H) 3.42 (d, J = 7.35 Hz, 2 H) 3.56 (t, 2 H) 3.83 (s, 3 H) 6.58-6.70 (m, 1 H) 6.71-6.86 (m, 2 H) 7.28-7.32 (m, 1 H) 7.33-7.45 (m, 1 H) 7.82 (s, 1 H) 8.40 (s, 1 H) 8.68 (s, 1 H) | 508.00 |
| 393 | 518.6 | C29H31FN4O4 | 1H NMR (300 MHz, CHLOROFORM-d) d ppm 0.92 (d, J = 6.59 Hz, 6 H) 1.90-2.09 (m, 1 H) 2.48 (s, 3 H) 2.97 (s, 3 H) 2.99-3.08 (m, 2 H) 3.16 (s, 3 H) 3.33-3.44 (m, 2 H) 3.52-3.65 (m, 2 H) 6.54-6.78 (m, 2 H) 7.18 (d, 1 H) 7.58 (s, 1 H) 7.97 (d, 1 H) 8.14 (d, 1 H) 8.26 (s, 1 H) 8.50 (s, 1 H) 12.05 (s, 1 H) | 519.00 |
| 394 | 463.5 | C24H21N3O5S | 1H NMR (300 MHz, CHLOROFORM-d) d ppm 2.33 (s, 3 H) 3.08 (s, 3 H) 3.66 (s, 3 H) 6.67 (d, J = 7.54 Hz, 1 H) 7.07-7.17 (m, 2 H) 7.21 (d, J = 7.54 Hz, 1 H) 7.51-7.66 (m, 1 H) 7.86-7.99 (m, 3 H) 8.15 (s, 1 H) 8.23 (d, 1 H) 8.82 (s, 1 H) 8.90 (br. s., 1 H) | 464.10 |

Example 395

7-Methoxy-2,2-dimethyl-N-(1-methyl-1H-pyrazol-3-yl)-2,3-dihydrobenzofuran-5-carboxamide

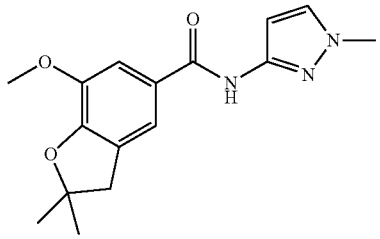

To a solution of 7-methoxy-2,2-dimethyl-2,3-dihydrobenzofuran-5-carboxylic acid (24 g, 0.11 mol) in CH$_2$Cl$_2$ (500 mL) were added EDCI (31.6 g, 1.08 mol), NMM (54.5 g, 0.54 mol), HOBt (22 g, 0.16 mol) and 1-methyl-1H-pyrazol-3-ylamine (11 g, 0.11 mol) sequentially. The mixture was stirred at room temperature overnight. TLC (EtOAc/petroleum ether=1/1) showed the reaction was complete. The mixture was washed with water (250 mL), sat. aq. citric acid (250 mL×2), sat. NaHCO$_3$ (250 mL) and brine (250 mL) sequentially. The organic phase was dried over Na$_2$SO$_4$ and concentrated to give a white solid. The crude solid was purified by column chromatography (EtOAc/petroleum ether=1/10~1/1) to give the title compound (9.6 g, 30%) as a white solid. $^1$H NMR (400 MHz, DMSO): δ 10.49 (s, 1H), 7.49 (s, 1H), 7.44 (s, 2H), 6.48 (s, 1H), 3.74 (s, 3H), 3.69 (s, 3H), 2.96 (s, 2H), 1.35 (s, 6H).

Preparation of Intermediate 395a

Methyl 3-methoxy-4-(2-methylallyloxy)benzoate

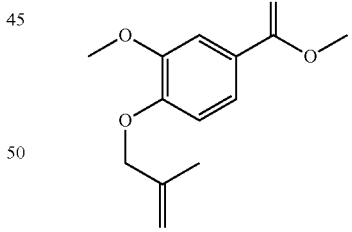

To a suspension of methyl 4-hydroxy-3-methoxybenzoate (100 g, 0.55 mol) and K$_2$CO$_3$ (92 g, 0.66 mol) in DMF (800 ml) was added drop wise 3-chloro-2-methyl-propene (55 g, 0.60 mol). The mixture was stirred at 60° C. overnight. TLC (EtOAc/petroleum ether=1/3) showed no starting material was present. The reaction mixture was filtered and the filtrate was added water (400 ml). The mixture was extracted with EtOAc (400 ml×3). The combined organic phase was washed with brine (400 mL), dried (Na$_2$SO$_4$) and concentrated to give the product (130 g, 100%) as yellow oil. The oil was used directly to the next step without further purification. $^1$H NMR (400 MHz, CDCl$_3$): δ 7.54 (d, 1H), 7.19 (s, 1H), 6.80 (d, 1H), 5.00(d, 2H), 4.50 (s, 2H), 3.83 (d, 6H), 1.76 (s, 3H).

Preparation of Intermediate 395b

Methyl 4-hydroxy-3-methoxy-5-(2-methylallyl)benzoate

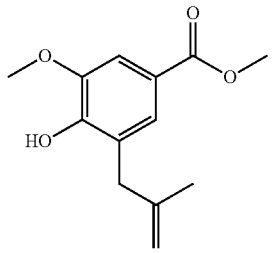

A solution of methyl 3-methoxy-4-(2-methylallyloxy)benzoate (130 g, 0.55 mol) in NMP (500 mL) was heated to reflux for 6 h. TLC (EtOAc/petroleum ether=1/5) showed the reaction was complete. The mixture was washed with 1 N aq. HCl and extracted with EtOAc (250 mL×3). The combined organic phases were washed with brine (400 mL), dried over Na$_2$SO$_4$ and concentrated to give the product (150 g, 100%) as a brown oil. The oil was used directly to the next step without further purification.

Preparation of Intermediate 395c

Methyl 7-methoxy-2,2-dimethyl-2,3-dihydrobenzofuran-5-carboxylate

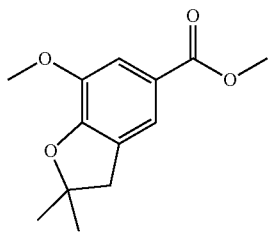

A solution of methyl 4-hydroxy-3-methoxy-5-(2-methylallyl)benzoate (150 g, 0.63 mol) in conc. HCl (300 mL) and MeOH (300 mL) was heated to reflux for 2 h. TLC (EtOAc/petroleum ether=1/5) showed the reaction was complete. The solution was evaporated, and the residue was extracted with EtOAc (200 mL×3). The combined organic phases were washed with brine (200 mL), dried over Na$_2$SO$_4$ and concentrated to give a brown oil. The crude oil was purified by column chromatography (EtOAc/petroleum ether=1/30) to give the title compound (80 g, 53%) as a white solid. $^1$H NMR (400 MHz, CDCl$_3$): δ 7.51 (s, 1H), 7.46 (s, 1H), 3.91 (s, 3H), 3.87 (s, 3H), 3.05 (s, 2H), 1.53 (s, 6H).

Preparation of Intermediate 395d

7-Methoxy-2,2-dimethyl-2,3-dihydrobenzofuran-5-carboxylic acid

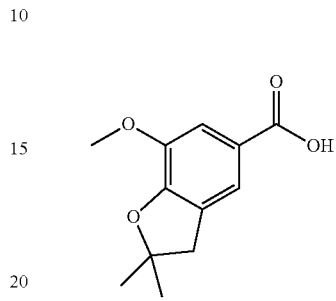

To a solution of methyl 7-methoxy-2,2-dimethyl-2,3-dihydrobenzofuran-5-carboxylate (40 g, 0.17 mol) in MeOH (200 mL) was added NaOH (34 g, 0.85 mol) in one portion. The mixture was stirred at room temperature for 24 h. TLC (EtOAc/petroleum ether=1/1) showed the reaction was complete. Then MeOH was removed under vacuum. The residue was dissolved in water (100 mL), and the solution was acidified with conc. HCl. The solid was filtered and the filter cake was dried in vacuo to give the title compound (25 g, 68%) as a white solid. $^1$H NMR (400 MHz, CDCl$_3$): δ 7.62 (s, 1H), 7.54 (s, 1H), 3.94 (s, 3H), 3.00 (s, 2H), 1.50 (s, 6H).

Example 396

4-[5-(Azetidine-1-carbonyl)-pyrazin-2-yloxy]-2,2-dimethyl-2,3-dihydro-benzofuran-6-carboxylic acid (1-methyl-1H-pyrazol-3-yl)-amide

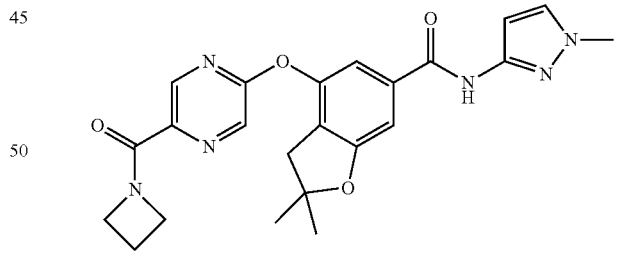

The title compound was prepared in a similar manner as described for Example 1, from 5-[2,2-dimethyl-6-(1-methyl-1H-pyrazol-3-ylcarbamoyl)-2,3-dihydro-benzofuran-4-yloxy]-pyrazine-2-carboxylic acid methyl ester (396a) and azetidine. $^1$H NMR (400 MHz, CDCl$_3$) δ 8.86 (d, J=1.26 Hz, 1 H) 8.35 (d, J=1.26 Hz, 1 H) 8.30 (s, 1 H) 7.23-7.32 (m, 1 H) 7.18 (d, J=1.26 Hz, 1 H) 7.12 (d, J=1.26 Hz, 1 H) 6.79 (d, J=2.27 Hz, 1 H) 4.70 (t, J=7.83 Hz, 2 H) 4.27 (t, J=7.83 Hz, 2 H) 3.81 (s, 3 H) 2.85 (s, 2 H) 2.31-2.46 (m, 2 H) 1.49 (s, 6 H);

LCMS for $C_{23}H_{24}N_6O_4$ m/z 449.20 (M+H⁺); Anal. Calcd. for $C_{23}H_{24}N_6O_4$.0.18 AcOH: C, 61.09; H, 5.43; N, 18.30; Found: C, 61.21; H, 5.64; N, 18.31.

Preparation of Intermediate 396a

5-[2,2-Dimethyl-6-(1-methyl-1H-pyrazol-3-ylcarbamoyl)-2,3-dihydro-benzofuran-4-yloxy]-pyrazine-2-carboxylic acid methyl ester

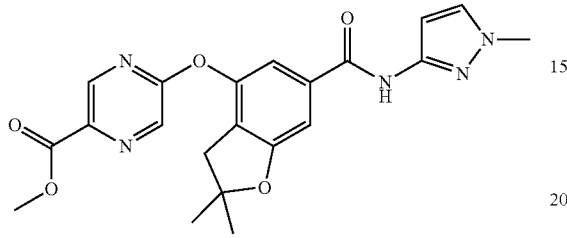

A mixture of methyl 5-chloropyrazine-2-carboxylate (60.1 mg, 0.348 mmol), 4-hydroxy-2,2-dimethyl-2,3-dihydro-benzofuran-6-carboxylic acid (1-methyl-1H-pyrazol-3-yl)-amide (31a) (100 mg, 0.348 mmol) and $Cs_2CO_3$ (227 mg, 0.696 mmol) in DMF was heated to 160° C. in a microwave for 30 min, cooled to room temperature, quenched with $H_2O$ and extracted with 3×EtOAc. The combined organic layer was washed with 2×$H_2O$, dried over $Na_2SO_4$ and concentrated. The residue was purified by column chromatography eluting with 45% to 70% EtOAc in hexanes to give a colorless thick oil (71 mg, 48% yield). ¹H NMR (400 MHz, CDCl₃) δ 8.94 (s, 1 H) 8.85 (d, J=1.01 Hz, 1 H) 8.52 (d, J=1.26 Hz, 1 H) 7.27 (d, J=2.27 Hz, 1 H) 7.21 (s, 1 H) 7.15 (s, 1 H) 6.80 (d, J=2.02 Hz, 1 H) 4.03 (s, 3 H) 3.74 (s, 3 H) 2.86 (s, 2 H) 1.49 (s, 6 H); LCMS for $C_{21}H_{21}N_5O_5$ m/z 424.20 (M+H⁺).

Examples 397-399 were prepared in a similar manner as described for Example 176, from 5-[2,2-dimethyl-6-(1-methyl-1H-pyrazol-3-ylcarbamoyl)-2,3-dihydro-benzofuran-4-yloxy]-pyridine-2-carboxylic acid (180) and the appropriate amines.

Example 397

4-[6-(3-Fluoro-azetidine-1-carbonyl)-pyridin-3-yloxy]-2,2-dimethyl-2,3-dihydro-benzofuran-6-carboxylic acid(1-methyl-1H-pyrazol-3-yl)-amide

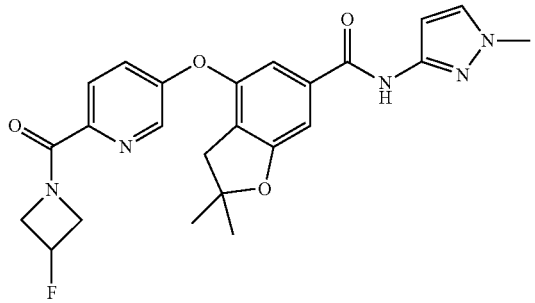

¹H NMR (400 MHz, CDCl₃) δ 9.75 (s, 1 H) 8.33 (d, J=2.78 Hz, 1 H) 8.13 (d, J=8.84 Hz, 1 H) 7.37 (dd, J=8.72, 2.91 Hz, 1 H) 7.24-7.30 (m, 1 H) 7.21 (s, 1 H) 7.16 (d, J=1.26 Hz, 1 H) 6.85 (d, J=2.27 Hz, 1 H) 5.22-5.50 (m, 1 H) 4.90-5.07 (m, 1 H) 4.71-4.88 (m, 1 H) 4.41-4.61 (m, 1 H) 4.24-4.39 (m, 1 H) 3.79 (s, 3 H) 2.91 (s, 2 H) 1.50 (s, 6 H); LCMS for $C_{24}H_{24}FN_5O_4$ m/z 466.20 (M+H⁺); Anal. Calcd. for $C_{24}H_{24}FN_5O_4$.0.30 AcOH.0.35$H_2O$: C, 60.32; H, 5.33; N, 14.30; Found: C, 60.25; H, 5.32; N, 14.37.

Example 398

2,2-Dimethyl-4-[6-(pyrrolidine-1-carbonyl)-pyridin-3-yloxy]-2,3-dihydro-benzofuran-6-carboxylic acid (1-methyl-1H-pyrazol-3-yl)-amide

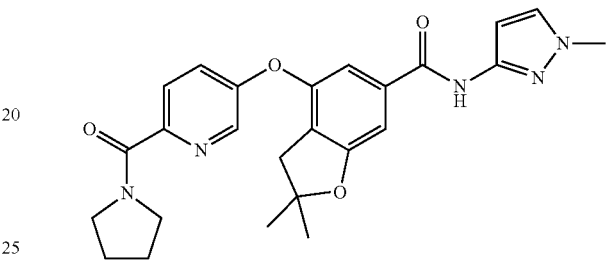

¹H NMR (400 MHz, CDCl₃) δ 8.71 (s, 1 H) 8.33 (br, s, 1 H) 7.90 (br, s, 1 H) 7.34 (dd, J=8.59, 2.53 Hz, 1 H) 7.24-7.28 (m, 1 H) 7.07 (d, J=8.34 Hz, 2 H) 6.79 (d, J=2.02 Hz, 1 H) 3.76-3.89 (m, 5 H) 3.69 (t, J=6.69 Hz, 2 H), 2.92 (s, 2 H) 1.94 (t, J=6.69 Hz, 4 H), 1.50 (s, 6 H); LCMS for $C_{25}H_{27}N_5O_4$ m/z 462.20 (M+H⁺); Anal. Calcd. for $C_{25}H_{27}N_5O_4$.0.30 AcOH.0.20 $H_2O$: C, 63.64; H, 5.97; N, 14.50; Found: C, 63.63; H, 5.99; N, 14.53.

Example 399

5-[2,2-Dimethyl-6-(1-methyl-1H-pyrazol-3-ylcarbamoyl)-2,3-dihydro-benzofuran-4-yloxy]-pyridine-2-carboxylic acid cyanomethyl-methyl-amide

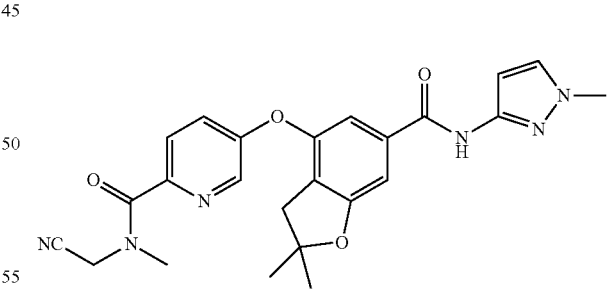

¹H NMR (400 MHz, CDCl₃) δ 8.71 (br. s., 1 H) 8.34 (d, J=2.78 Hz, 1 H) 7.73-8.07 (m, 1 H) 7.37 (d, J=3.03 Hz, 1 H) 7.25-7.30 (m, 1 H) 7.09 (d, J=5.81 Hz, 2 H) 6.79 (d, J=2.27 Hz, 1 H) 4.88 (s, 1 H) 4.50 (s, 1 H) 3.79 (s, 3 H) 3.39 (s, 3 H) 2.92 (s, 2 H) 1.50 (s, 6 H); LCMS for $C_{24}H_{24}N_6O_4$ m/z 461.20 (M+H⁺); Anal. Calcd. for $C_{24}H_{24}N_6O_4$.0.25 AcOH.0.75$H_2O$: C, 60.18; H, 5.46; N, 17.19; Found: C, 59.82; H, 5.25; N, 17.31.

Example 400

4-(3,5-Difluoro-4-methylcarbamoyl-phenoxy)-2,2-dimethyl-2,3-dihydro-benzofuran-6-carboxylic acid (1-methyl-1H-pyrazol-3-yl)-amide

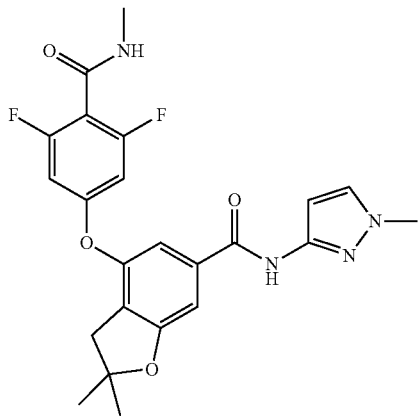

The title compound was prepared in a similar manner as described for Example 112. $^1$H NMR (400 MHz, CDCl$_3$) δ 9.33 (s, 1 H) 7.10 (d, J=1.01 Hz, 1 H) 6.95 (d, J=1.26 Hz, 1 H) 6.73 (d, J=2.27 Hz, 2 H) 6.47 (d, J=8.59 Hz, 2 H) 3.71 (s, 3 H) 3.02 (d, J=5.05 Hz, 3 H) 2.93 (s, 2 H) 1.51 (s, 6 H); LCMS for C$_{23}$H$_{22}$F$_2$N$_4$O$_4$ m/z 457.20 (M+H)$^+$; Anal. Calcd. for C$_{23}$H$_{22}$F$_2$N$_4$O$_4$.0.36H$_2$O: C, 59.67; H, 4.95; N, 12.10; Found: C, 59.68; H, 4.94; N, 12.09.

Example 401

(+)-4-(4-Cyclopropanesulfonyl-3-fluoro-phenoxy)-2-hydroxymethyl-2-methyl-2,3-dihydro-benzofuran-6-carboxylic acid(5-methyl-pyridin-2-yl)-amide and Example 402: (−)-4-(4-Cyclopropanesulfonyl-3-fluoro-phenoxy)-2-hydroxymethyl-2-methyl-2,3-dihydro-benzofuran-6-carboxylic acid(5-methyl-pyridin-2-yl)-amide

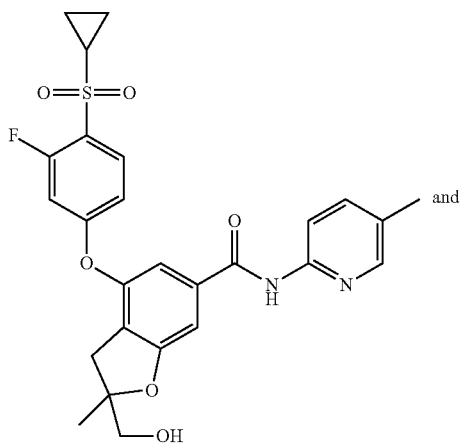

and

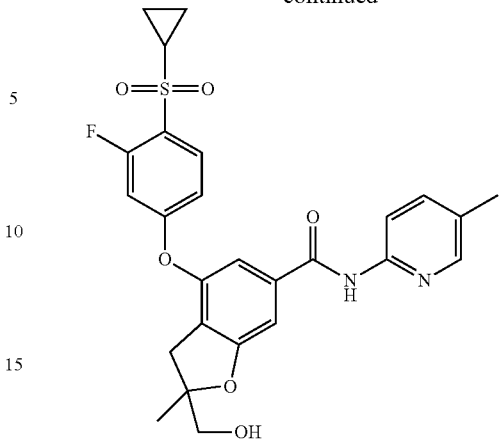

The title compound was prepared in a similar manner as described for Example 245, followed by chiral separation by SFC column chromatography.

Example 401: [α]$_D$=+15.15, 100% ee; $^1$H NMR (400 MHz, CDCl$_3$) δ 8.47 (s, 1 H) 8.23 (d, J=8.34 Hz, 1 H) 8.12 (s, 1 H) 7.99 (dd, J=8.84, 6.06 Hz, 1 H) 7.58 (dd, J=8.46, 1.89 Hz, 1 H) 7.16-7.24 (m, 2 H) 6.94 (ddd, J=8.84, 7.58, 2.27 Hz, 1 H) 6.62 (dd, J=9.60, 2.27 Hz, 1 H) 3.74 (dd, J=12.13, 5.31 Hz, 1 H) 3.62 (d, J=6.82 Hz, 1 H) 3.15-3.25 (m, 1 H) 2.92-3.00 (m, 1 H) 2.85 (d, J=16.67 Hz, 1 H) 2.32 (s, 3 H) 1.46 (s, 3 H) 1.33-1.43 (m, 2 H) 1.04-1.14 (m, 2 H); LCMS for C$_{26}$H$_{25}$FN$_2$O$_6$S m/z 513.20 (M+H)$^+$; Anal. Calcd. for C$_{26}$H$_{25}$FN$_2$O$_6$S.0.12H$_2$O: C, 60.67; H, 4.94; N, 5.44; Found: C, 60.66; H, 4.93; N, 5.19.

Example 402: [α]$_D$=−21.76, 97.2% ee; $^1$H NMR (400 MHz, CDCl$_3$) δ 8.49 (s, 1 H) 8.23 (d, J=8.34 Hz, 1 H) 8.12 (s, 1 H) 7.99 (dd, J=8.72, 6.44 Hz, 1 H) 7.58 (dd, J=8.21, 2.15 Hz, 1 H) 7.18-7.24 (m, 2 H) 6.90-7.00 (m, 1 H) 6.62 (dd, J=9.60, 2.27 Hz, 1 H) 3.75 (d, J=12.13 Hz, 1 H) 3.57-3.68 (m, 1 H) 3.20 (d, J=16.67 Hz, 1 H) 2.90-3.01 (m, 1 H) 2.85 (d, J=16.67 Hz, 1 H) 2.32 (s, 3 H) 1.46 (s, 3 H) 1.32-1.42 (m, 3 H) 1.09 (d, J=7.83 Hz, 2 H); LCMS for C$_{26}$H$_{25}$FN$_2$O$_6$S m/z 513.20 (M+H)$^+$; Anal. Calcd. for C$_{26}$H$_{25}$FN$_2$O$_6$S.0.10H$_2$O: C, 60.71; H, 4.94; N, 5.45; Found: C, 60.82; H, 4.91; N, 5.20.

Preparation of sulfonamide intermediate: 4-fluoro-N,N-dimethylbenzenesulfonamide

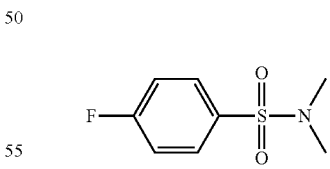

To a solution of dimethylamine (27.7 g, 342.2 mmol) in THF (172 mL) was added CH$_2$Cl$_2$ (300 mL) at 0° C., then DIPEA (127.8 mL, 773.2 mmol) was added, followed by a solution of 4-fluorobenzene-1-sulfonyl chloride (60 g, 309.2 mmol) in CH$_2$Cl$_2$ (200 mL). The resulting mixture was allowed to warm to room temperature and stirred overnight. TLC (Petroleum ether:EtOAc=5:1) indicated the reaction was complete. Water (200 mL) and 1 N HCl (380 mL) were added. The organic layer was separated and evaporated under reduced pressure to afford the crude product. The crude product was washed with petroleum ether to give the title compound (52.5 g) as a white solid. Yield: 83.7%.

Preparation of sulfonamide intermediate:
1-(4-fluorophenylsulfonyl)azetidine

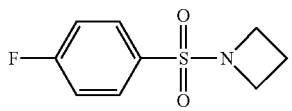

To a solution of KHMDS (62.0 g, 311.5 mmol) in THF (400 mL) was added drop wise azetidine (16.9 g, 296.5 mmol) at 0° C. under nitrogen atmosphere, and the reaction mixture was stirred for 10 minutes. A solution of 4-fluorobenzene-1-sulfonyl chloride (57.5 g, 296.5 mmol) in THF (200 mL) was added drop wise subsequently and the reaction mixture was allowed to warm to ambient temperature overnight. TLC (Petroleum ether:EtOAc=5:1) indicated the reaction was complete. The reaction mixture was concentrated under reduced pressure. The residue was partitioned between ethyl acetate (200 mL×3) and water (100 mL). The organic layer was separated and dried over $Na_2SO_4$, filtered and concentrated to give the title compound (38.5 g) as a pale yellow solid. Yield: 60.4%.

In analogous fashion, the following sulfonamide intermediates were prepared.

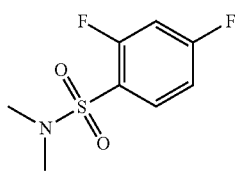

$^1$H NMR (400 MHz, $CDCl_3$) δ 7.86-7.93 (m, J=8.34, 8.34, 6.32 Hz, 1 H) 6.95-7.05 (m, 2 H) 2.84 (s, 3 H) 2.84 (s, 3 H); LCMS for $C_8H_9F_2NO_2S$ m/z 222.00 (M+H)$^+$.

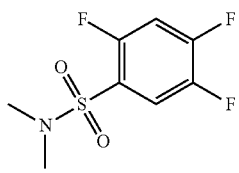

$^1$H NMR (400 MHz, $CDCl_3$) δ 7.74 (td, J=8.84, 6.06 Hz, 1 H) 7.11 (td, J=9.22, 6.06 Hz, 1 H) 2.87 (s, 3 H) 2.86 (s, 3 H).

Preparation of sulfone intermediate:
1,2-difluoro-4-(methylsulfonyl)benzene

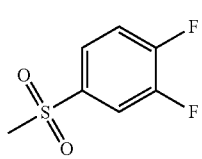

Iodomethane (15 mL, 0.22 mol) was added to a stirred mixture of 3,4-difluorobenzenethiol (30 g, 0.21 mol) and potassium carbonate (32.6 g, 0.24 mol) in DMF (250 mL), and left overnight. The reaction mixture was diluted with water (100 mL) and extracted with ethyl ether (100 mL×3), the organic phases were dried over $Na_2SO_4$ and evaporated under reduced pressure to give (3,4-difluorophenyl)(methyl)sulfane as a yellow liquid. Yield: 30 g, 89.3%. 3-Chloroperoxybenzoic acid (85% in purity, 62.5 g, 0.305 mol) was added in portions to a solution of (3,4-difluorophenyl)(methyl)sulfane (25 g, 0.155 mol) in dichloromethane (650 mL), and the mixture was stirred at room temperature for 2 h. The mixture was washed with saturated aqueous sodium sulfite solution (200 mL). The organic phases were sequentially washed with aqueous sodium bicarbonate solution (100 mL×2) and water (100 mL), dried over $Na_2SO_4$ and evaporated under reduced pressure to give the title compound as a white solid. Yield: 18 g, 60%.

Preparation of sulfone intermediate:
2-chloro-1-fluoro-4-(methylsulfonyl)benzene

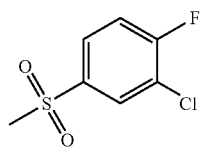

To a stirred mixture of 3-chloro-4-fluorobenzenethiol (65 g, 0.403 mol) and potassium carbonate (54 g, 0.39 mol) in DMF (450 mL) was added drop wise $CH_3I$ (24.96 mL, 0.442 mol) at room temperature, and the mixture was stirred overnight. The reaction mixture was diluted with water (200 mL) and extracted with ethyl ether (150 mL×3), the combined organic phases were dried over $Na_2SO_4$ and evaporated under reduced pressure to give (3-chloro-4-fluorophenyl)(methyl)sulfane (70 g, 98%) as a yellow liquid. To a solution of (3-chloro-4-fluorophenyl)(methyl)sulfane (66 g, 0.37 mol) in dichloromethane (1600 mL) was added 3-chloroperoxybenzoic acid (85% purity, 157 g, 0.77 mol) in portions, and the mixture was stirred at room temperature for 2 h. Then the mixture was washed with saturated aqueous sodium sulfite (600 mL). The organic phases were separated and sequentially washed with saturated aqueous sodium bicarbonate (250 mL×2) and water (250 mL), dried over $Na_2SO_4$ and evaporated under reduced pressure to give a yellow solid. The crude product was re-crystallized from ether (200 mL) to give the title compound (39.45 g, 51%) as a white solid.

Preparation of sulfone intermediate:
2-chloro-4-fluoro-1-(methylsulfonyl)benzene

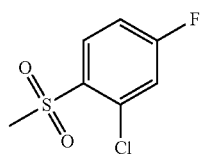

To a stirred mixture of 2-chloro-4-fluorobenzenethiol (65 g, 0.403 mol) and potassium carbonate (54 g, 0.39 mol) in DMF (450 mL) was added drop wise $CH_3I$ (24.96 mL, 0.442 mol) at room temperature and the mixture was stirred overnight. The reaction mixture was diluted with water (200 mL) and extracted with ethyl ether (150 mL×3), the combined organic phases were dried over $Na_2SO_4$ and evaporated under reduced pressure to give (2-chloro-4-fluorophenyl)(methyl) sulfane (70 g, 98%) as a yellow liquid. To a solution of (2-chloro-4-fluorophenyl)(methyl)sulfane (66 g, 0.37 mol) in dichloromethane (1600 mL) was added 3-chloroperoxybenzoic acid (85% purity, 157 g, 0.77 mol) in portions, and the mixture was stirred at room temperature for 2 h. The mixture was washed with aq. saturated sodium sulfite solution (600 mL). The organic phase was separated and sequentially washed with aq. sodium bicarbonate solution (250 mL×2) and water (250 mL), dried over $Na_2SO_4$ and evaporated under reduced pressure to give a yellow solid. The crude product was re-crystallized from ether (200 mL) to give the title compound (33.1 g, 43%) as a white solid.

Preparation of sulfone intermediate:
1-(ethylsulfonyl)-4-fluorobenzene

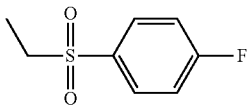

To a stirred solution of 4-fluorobenzenethiol (80 g, 0.625 mol) and bromoethane (71.88 g, 0.666 mol) in DMF (1.25 L) under nitrogen atmosphere, $Cs_2CO_3$ (213.75 g, 0.666 mol) was added. The reaction mixture was stirred at 25° C. overnight. TLC (petroleum ether) indicated the reaction was complete. The mixture was diluted with water (800 mL), extracted with ethyl acetate (600 mL×3). The combined organic layers were washed with water (500 mL×2) and brine (500 mL), dried over $Na_2SO_4$ and concentrated in vacuum to give ethyl (4-fluorophenyl)sulfane (60 g, 61.5%) as a colorless oil. A mixture of ethyl(4-fluorophenyl)sulfane (60 g, 0.38 mol), acetic acid (1 L) and 30% $H_2O_2$ (180 mL) was stirred at reflux under $N_2$ overnight. TLC (petroleum ether:ethyl acetate=4:1) indicated the reaction was complete. After cooled to room temperature, the reaction mixture was poured into water (500 mL). Then $NaHSO_3$ (200 g) was add. The mixture was extracted with ethyl acetate (500 mL×3), dried over $Na_2SO_4$ and concentrated in vacuum to remove the remaining acetic acid. Then the residue was poured into saturated aq. NaOH (800 mL) and extracted with ethyl acetate (500 mL×3) again. The organic layer was dried over $Na_2SO_4$ and concentrated in vacuum to give the title compound (66 g, 92.4%) as a colorless liquid.

Preparation of sulfone intermediate:
1-(cyclopropylsulfonyl)-4-fluorobenzene

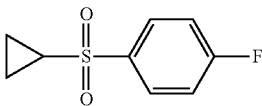

To a stirred solution of 4-fluorobenzenethiol (134 g, 1.05 mol) in DMSO (3 L) under nitrogen atmosphere were added cyclopropyl bromide (140 g, 1.15 mol) and t-BuONa (138.7 g, 1.44 mol). Then the reaction mixture was heated to 80° C. and stirred for 2 days. TLC (petroleum ether) indicated the reaction was complete. After cooled to room temperature, the mixture was poured into water (2 L), extracted with diethyl ether (1.5 L×3). The combined organic phases were washed with water (1 L), then brine (1 L), dried over $Na_2SO_4$ and concentrated in vacuum to give cyclopropyl(4-fluorophenyl) sulfane (129 g, 73.1%) as a colorless oil. To a mixture of cyclopropyl(4-fluorophenyl)sulfane (129 g, 0.77 mol) and acetic acid (1.9 L) was added 30% $H_2O_2$ (1.2 L), and the mixture was heated to reflux and stirred overnight. TLC (petroleum ether:ethyl acetate=4:1) indicated the reaction was complete. After cooled to room temperature, the mixture was poured into water (1 L), then $Na_2S_2O_3$ (200 g) was added to consume excess $H_2O_2$, then $Na_2CO_3$ was added to adjust pH =7. The mixture was extracted with ethyl acetate (1.5 L×2). The combined organic layers were washed with water (1 L), dried over $Na_2SO_4$ and concentrated in vacuum to give 69 g of crude product, which was purified by column chromatography (25% ethyl acetate in petroleum ether) to give the title compound (42 g, 27.3%) as a white solid.

Preparation of sulfone intermediate:
1-(cyclobutylsulfonyl)-4-fluorobenzene

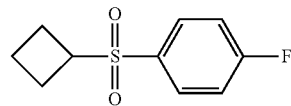

A suspension of 4-fluorobenzenethiol (80 g, 0.625 mol), cyclobutylbromide (45 g, 0.33 mol) and $Cs_2CO_3$ (108 g, 0.33 mol) in DMSO (1.5 L) was heated to 70° C. and stirred overnight. TLC (petroleum ether) indicated the reaction was complete. After cooled to room temperature, the reaction mixture was filtered to remove inorganic salts, and the filtrate was partitioned between diethyl ether (1.5 L) and water (1 L). The aqueous layer was extracted with diethyl ether (700 mL×3). The combined organic phases were washed sequentially with water (1 L×2), then brine (1 L), dried over $MgSO_4$ and concentrated in vacuum to give cyclobutyl(4-fluorophenyl)sulfane (64.8 g, 84.8%) as a pale yellow oil. Cyclobutyl (4-fluorophenyl)sulfane (61.8 g, 0.34 mol) was dissolved in $CH_2Cl_2$ (2 L) and cooled to −15° C., m-CPBA (150.4 g, 0.742 mol) was added portion wise while keeping the temperature between −15° C. and −10° C. After the addition, the reaction mixture was allowed to warm to room temperature and stirred for 3-4 h. TLC (petroleum ether:ethyl acetate=4:1) indicated the reaction was complete. The reaction mixture was partitioned between $CH_2Cl_2$ (2 L) and water (1 L). The organic layer was washed with saturated $NaHCO_3$ solution (1 L) and brine (1 L), dried over $MgSO_4$, filtrated and concentrated in vacuum to give the title compound (59 g, 81.1%) as a white solid.

In analogous fashion, the following sulfone intermediates were prepared.

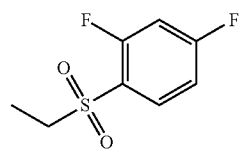

¹H NMR (400 MHz, CDCl₃) δ 7.98 (td, J=8.34, 6.06 Hz, 1 H) 7.05-7.11 (m, 1 H) 7.01 (ddd, J=10.04, 8.15, 2.27 Hz, 1 H) 3.32 (q, J=7.75 Hz, 2 H) 1.32 (t, J=7.33 Hz, 3 H).

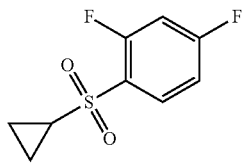

¹H NMR (400 MHz, CDCl₃) δ 7.93 (td, J=8.27, 6.44 Hz, 1 H) 6.98-7.09 (m, 2 H) 2.69-2.78 (m, 1 H) 1.34-1.44 (m, 2 H) 1.06-1.16 (m, 2 H).

Methods for Chiral Separation by SFC:

Preparative enantio separation methods were developed using supercritical fluid chromatography (SFC) technology, with supercritical carbon dioxide providing the bulk of the mobile phase. The separation and isolation of enantiomers was carried out on a Berger SFC MultiGram™ Purification System (Mettler Toledo AutoChem, Inc). Since the preparative chromatography conditions used to separate the enantiomers may vary in the type of chiral stationary phase used, the composition of the mobile phase modifier, or even the pressure and flow rates, all methods are described below following the compounds that were separated by those conditions:

Example A: Chiralcel OJ-H (Cellulose tris-(4-methylbenzoate coated on silica)), 250×21 mm, 5μ semi-preparative column was used as the chiral stationary phase (Chiral Technologies, Inc.). Column temperature was maintained at 35° C. The mobile phase used was supercritical $CO_2$ with methanol as the modifier (range from 20% to 40% depending on the enantiomers to be separated), maintained isocratically at a flow rate of 50-55 mL/min and a constant pressure of 120-140 bar. UV detection at 260 nm was achieved.

Example B: Chiralpak AS-H (amylose tris-(3,5-dimethylphenylcarbamate) 250×21 mm, 5μ semi-preparative column was used as the chiral stationary phase (Chiral Technologies, Inc.). Column temperature was maintained at 35° C. The mobile phase used was supercritical $CO_2$ with 40% methanol as the modifier, maintained isocratically at a flow rate of 55 mL/min and a constant pressure of 140 bar. UV detection at 260 nm was achieved.

Example C: Chiralcel OD-H (Cellulose tris-(3,5-dimethylphenylcarbamate coated on silica)), 250×21 mm, 5μ semi-preparative column was used as the chiral stationary phase (Chiral Technologies, Inc.). Column temperature was maintained at 35° C. The mobile phase used was supercritical $CO_2$ with 25% methanol with 0.1% diethylamine as the modifier, maintained isocratically at a flow rate of 55 mL/min and a constant pressure of 140 bar. UV detection at 260 nm was achieved.

Example 403

4-(5-fluoro-6-(3-fluoroazetidine-1-carbonyl)pyridin-3-yloxy)-2,2-dimethyl-N-(1-methyl-1H-pyrazol-3-yl)-2,3-dihydrobenzofuran-6-carboxamide

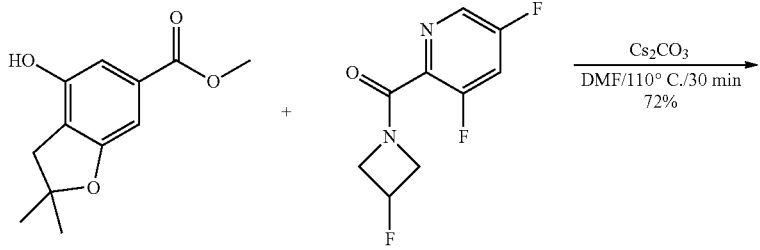

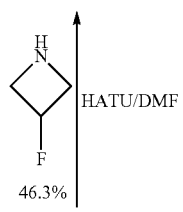

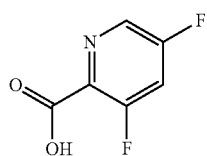

-continued

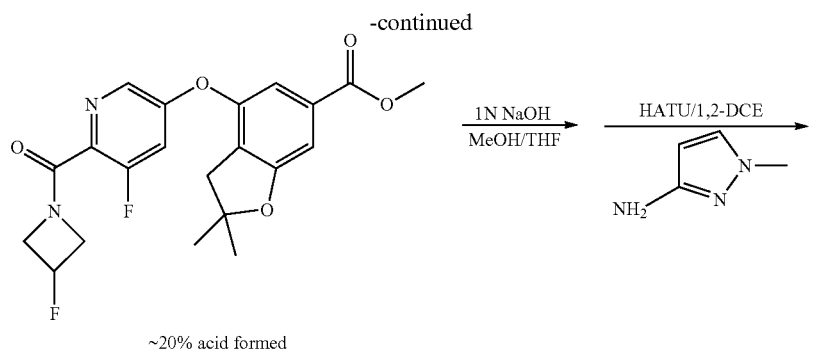

~20% acid formed

+

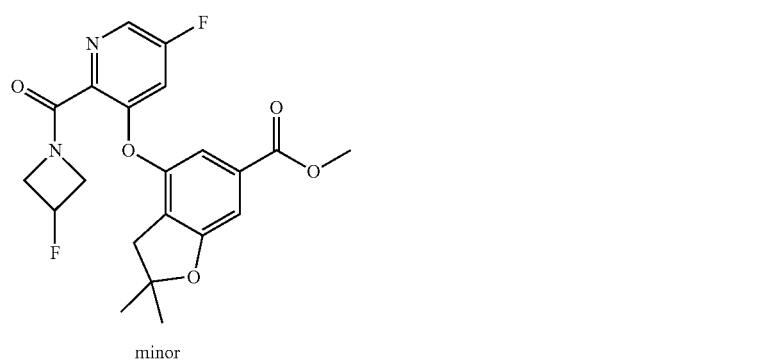

minor

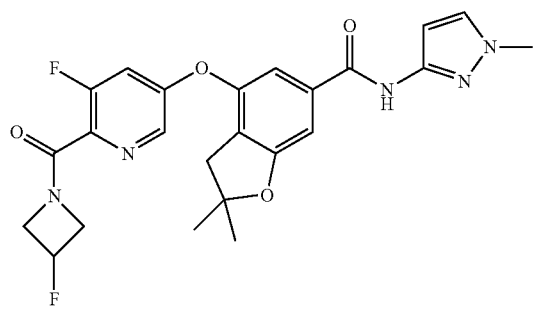

2 steps 65%

To a solution of 4-(5-fluoro-6-(3-fluoroazetidine-1-carbonyl)pyridin-3-yloxy)-2,2-dimethyl-2,3-dihydrobenzofuran-6-carboxylic acid (1.360 g, 3.363 mmol), 3-amino-1-methyl-pyrazole (653 mg, 6.730 mmol), and triethylamine (0.94 ml, 6.730 mmol) in 20 mL of DCE was added HATU (2.56 g, 6.730 mmol). The mixture was stirred at 60° C. for 2 hr, quenched with water, and extracted with 3×CHCl$_3$. The combined organic layer was washed with 2×H$_2$O, dried with Na$_2$SO$_4$, and concentrated to provide an oil that was purified by SFC to give a white solid (874 mg, 54% yield). $^1$H NMR (400 MHz, CDCl$_3$) δ 9.30 (s, 1 H) 8.20 (d, J=2.02 Hz, 1 H) 7.24-7.33 (m, 2 H) 7.15-7.22 (m, 1 H) 7.09 (dd, J=10.86, 2.27 Hz, 1 H) 6.82 (d, J=2.27 Hz, 1 H) 5.37 (d, J=56.84 Hz, 1 H) 4.62-4.79 (m, 1 H) 4.53 (dd, J=12.13, 1.77 Hz, 2 H) 4.27-4.42

(m, 1 H) 3.80 (s, 3 H) 2.92 (s, 2 H) 1.50 (s, 6 H); LCMS for $C_{24}H_{23}F_2N_5O_4$ m/z 484.20 (M+H)$^+$.

Preparation for Intermediate 3a

3-Hydroxy-5-(2-methyl-allyloxy)-benzoic acid methyl ester

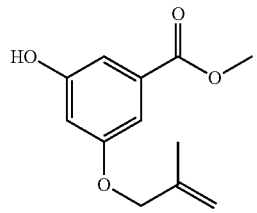

The title compound was prepared in a similar manner as described for Intermediate 1a, from methyl 3,5-dihydroxy-benzoate (15.0 g, 89.2 mmol), potassium carbonate (24.7 g, 178.4 mmol) and 3-bromo-2-methyl-propene (9.0 mL, 89.2 mmol). Purification by column chromatography eluting with 15% EtOAc in hexanes gave a pale yellow solid (7.80 g, 39% yield). $^1$H NMR (400 MHz, CDCl$_3$) δ 7.13-7.22 (m, 2 H) 6.66 (t, J=2.27 Hz, 1 H) 5.81 (s, 1 H) 5.06-5.16 (m, 1 H) 4.93-5.04 (m, 1 H) 4.44 (s, 2 H) 3.91 (s, 3 H) 1.68-1.94 (m, 3 H); LCMS for $C_{12}H_{14}O_4$ m/z 223.10 (M+H)$^+$.

Preparation of Intermediate 3b

3-Methoxy-5-(2-methyl-allyloxy)-benzoic acid methyl ester

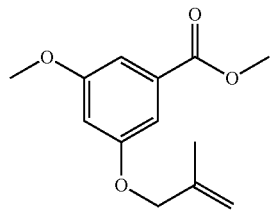

The title compound was prepared in a similar manner as described for Intermediate 1b, from 3-methoxy-5-(2-methyl-allyloxy)-benzoic acid methyl ester (3a) (7.80 g, 35.0 mmol), methyl iodide (2.60 mL, 42.0 mmol) and K$_2$CO$_3$ (9.67 g, 70.0 mmol). Purification by column chromatography eluting with 10% EtOAc in hexanes gave a colorless oil (7.54 g, 91% yield). $^1$H NMR (400 MHz, CDCl$_3$) δ 7.20-7.22 (m, 1 H) 7.18-7.20 (m, 1 H) 6.68 (t, J=2.27 Hz, 1 H) 5.11 (s, 1 H) 5.01 (s, 1 H) 4.46 (s, 2 H) 3.91 (s, 3 H) 3.83 (s, 3 H) 1.84 (s, 3 H); LCMS for $C_{13}H_{16}O_4$ m/z 237.10 (M+H)$^+$.

Preparation of Intermediate 3c

Mixture of 3-hydroxy-5-methoxy-2-(2-methyl-allyl)-benzoic acid methyl ester and 3-hydroxy-5-methoxy-4-(2-methyl-allyl)-benzoic acid methyl ester

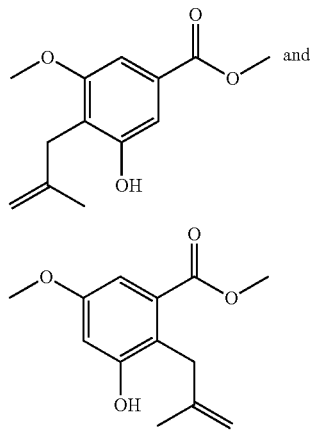

The title compound was prepared in a similar manner as described for Intermediate 1c, from 3-methoxy-5-(2-methyl-allyloxy)-benzoic acid methyl ester (3b) (7.54 g, 32.0 mmol). Purification by column chromatography eluting with 5-20% EtOAc in hexanes gave a mixture of 3-hydroxy-5-methoxy-2-(2-methyl-allyl)-benzoic acid methyl ester and 3-hydroxy-5-methoxy-4-(2-methyl-allyl)-benzoic acid methyl ester as a colorless oil (4.80 g, 64% yield). $^1$H NMR (400 MHz, CDCl$_3$) δ 7.11-7.24 (m) 7.02 (d, J=2.27 Hz) 6.68 (t, J=2.40 Hz) 6.51 (d, J=2.27 Hz) 5.10 (s) 5.00 (s) 3.91 (s) 3.88 (s) 3.83 (s) 3.80 (s) 3.26 (s) 1.83 (s) 1.47 (s); LCMS for $C_{13}H_{16}O_4$ m/z 237.10 (M+H)$^+$.

Preparation of Intermediate 3d

Mixture of 4-methoxy-2,2-dimethyl-2,3-dihydrobenzofuran-6-carboxylic acid methyl ester and 6-methoxy-2,2-dimethyl-2,3-dihydrobenzofuran-4-carboxylic acid methyl ester

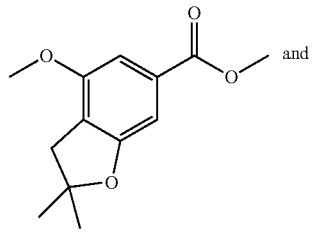

-continued

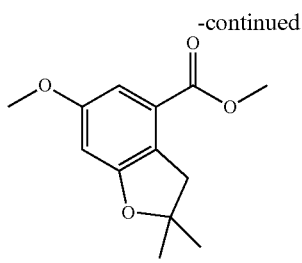

The title compound was prepared in a similar manner as described for Intermediate 1d, from zirconium(IV) chloride (3.03 g, 11.0 mmol) and a mixture of methyl 2-ally-3-hydroxy-5-methoxy-benzoate and methyl 2-ally-3-hydroxy-5-methoxybenzoate (3c) (2.5 g, 13.0 mmol). Purification by column chromatography eluting with 5-10% EtOAc in hexanes gave a mixture of 4-methoxy-2,2-dimethyl-2,3-dihydrobenzofuran-6-carboxylic acid methyl ester and 6-methoxy-2,2-dimethyl-2,3-dihydrobenzofuran-4-carboxylic acid methyl ester (2:1) as a colorless oil (1.74 g, 70% yield). $^1$H NMR (400 MHz, CDCl$_3$) δ 7.12 (s) 7.07 (s) 7.03 (d, J=2.27 Hz) 6.52 (d, J=2.27 Hz) 3.90 (s) 3.87 (s) 3.81 (s) 3.27 (s) 2.97 (s) 1.49 (s) 1.48 (s); LCMS for C$_{13}$H$_{16}$O$_4$ m/z 237.10 (M+H)$^+$.

Preparation of Intermediate 3e

4-Hydroxy-2,2-dimethyl-2,3-dihydrobenzofuran-6-carboxy-lic acid methyl ester

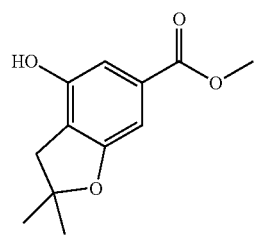

To the mixture of 4-methoxy-2,2-dimethyl-2,3-dihydrobenzofuran-6-carboxylic acid methyl ester and 6-methoxy-2,2-dimethyl-2,3-dihydro-benzofuran-4-carboxylic acid methyl ester (3d) (1.74 g, 7.36 mmol) in CH$_2$Cl$_2$ (10 mL) at 0° C. was added BBr$_3$ (22.0 mL, 22 mmol, 1.0 M solution in CH$_2$Cl$_2$). The reaction mixture was stirred at 0° C. for 6 hr, quenched with H$_2$O (100 mL), extracted with CH$_2$Cl$_2$ (2×100 mL), dried over MgSO$_4$, and concentrated in vacuo. The residue was purified by flash column chromatography eluting with 10% EtOAc in hexanes to give a pale yellow solid (171 mg, 10% yield). $^1$H NMR (400 MHz, CDCl$_3$) δ 7.15 (s, 1 H) 6.99 (s, 1 H) 5.87 (s, 1 H) 3.89 (s, 3 H) 3.00 (s, 2 H) 1.50 (s, 6 H); LCMS for C$_{12}$H$_{14}$O$_4$ m/z 223.0 (M+H)$^+$.

Preparation of Intermediate: (3,5-difluoropyridin-2-yl)(3-fluoroazetidin-1-yl)methanone

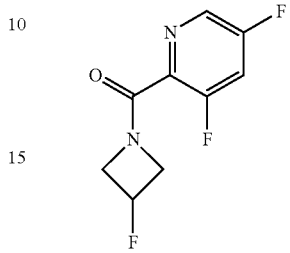

To a solution of 3,5-difluoropicolinic acid (16.40 g, 103.1 mmol), 3-fluoroazetidine (8.59 g, 114 mmol) and triethylamine (27.70 ml, 199.0 mmol) in 100 mL of DMF was added HATU (45.40 g, 119.0 mmol). The mixture was stirred at room temperature for 3 hr, quenched with water, extracted with 3× EtOAc. The combined organic layer was washed with 2×H$_2$O, dried with Na$_2$SO$_4$, and concentrated to provide an oil that was purified by Biotage eluting with 25-40% EtOAc in hexanes to give a yellow solid (11.49 g, 46.3% yield). $^1$H NMR (400 MHz, CDCl$_3$) δ 8.34 (d, J=2.53 Hz, 1 H) 7.31-7.46 (m, 1 H) 5.27-5.52 (m, 1 H) 4.62-4.79 (m, 1 H) 4.42-4.59 (m, 2 H) 4.22-4.38 (m, 1 H); MS for C$_9$H$_7$F$_3$N$_2$O m/z 217.00 (M+H)$^+$ Preparation of Intermediate: methyl 4-(5-fluoro-6-(3-fluoroazetidine-1-carbonyl)pyridin-3-yloxy)-2,2-dimethyl-2,3-dihydrobenzofuran-6-carboxylate

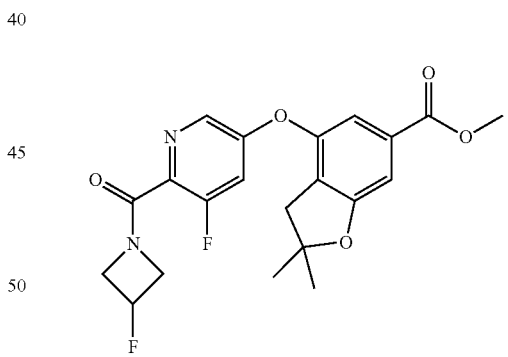

A mixture of (3,5-difluoropyridin-2-yl)(3-fluoroazetidin-1-yl)methanone (7.49 g, 34.60 mmol), methyl 4-hydroxy-2,2-dimethyl-2,3-dihydrobenzofuran-6-carboxylate (7.69 g, 34.60 mmol) and Cs$_2$CO$_3$ (16.90 g, 52.0 mmol) in DMF was heated to 110° C. for 30 min, cooled to room temperature, quenched with H$_2$O and extracted with 3×EtOAc. The combined organic layer was washed with 2×H$_2$O, dried over Na$_2$SO$_4$ and concentrated. The residue was purified by Biotage eluting with 25-40% EtOAc in hexanes to give a white foam with ~20% impurity (10.49 g, 72% yield). $^1$H NMR (400 MHz, CDCl$_3$) δ 8.18 (d, J=2.27 Hz, 1 H) 7.21-7.30 (m, 2 H) 6.98-7.06 (m, 1 H) 5.26-5.49 (m, 1 H) 4.64-4.77 (m, 1 H) 4.46-4.60 (m, 1 H) 4.28-4.42 (m, 1 H) 4.07-4.23 (m, 1 H)

3.88 (s, 3 H) 2.91 (s, 2 H) 1.49 (s, 6 H); LCMS for $C_{21}H_{20}F_2N_2O_5$ m/z 419.20 (M+H)$^+$.

Preparation of Intermediate: 4-(5-fluoro-6-(3-fluoro-azetidine-1-carbonyl)pyridin-3-yloxy)-2,2-dimethyl-2,3-dihydrobenzofuran-6-carboxylic acid

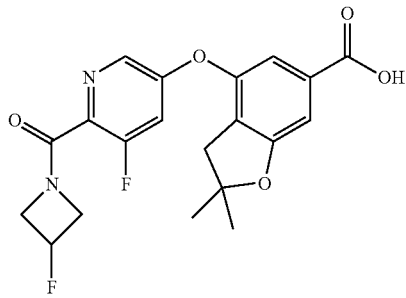

To a solution of methyl 4-(5-fluoro-6-(3-fluoroazetidine-1-carbonyl)pyridin-3-yloxy)-2,2-dimethyl-2,3-dihydrobenzofuran-6-carboxylate (1.520 g, 3.633 mmol), in 10 mL THF and 10 mL MeOH was added 4.25 mL of 1N aqueous NaOH. The resulting solution was stirred at room temperature for 2 hr. The solvent was removed in vacuo. Water was added, and the mixture was washed with EtOAc. The aqueous layer was acidified with 1N HCl until pH ~1, and extracted with 3×EtOAc. The combined organic layer was dried over $Na_2SO_4$ and concentrated to give a white foam (1.32 g, 90% yield), which contains ~15% impurity. LCMS for $C_{20}H_{18}F_2N_2O_5$ m/z 405.20 (M+H)$^+$.

Biochemical Assay

Full-length glucokinase (beta cell isoform) was His-tagged at N-terminus and purified by a Ni column followed by size exclusion chromatography. Glucose was obtained from Calbiochem, and other reagents were from Sigma.

All assays were performed in a Corning 96-well plate using Spectramax PLUS spectrophotometer (Molecular Devices) at room temperature. The final assay volume was 100 uL. The buffer conditions used in this assay were as follows: 50 mM HEPES, 5 mM glucose, 1 mM ATP, 2 mM $MgCl_2$, 0.7mM NADH, 2 mM DTT, 1 Unit/mL PK/LDH, 0.2 mM phosphoenolpyruvate, 25 mM KCl. Tested compound in DMSO solution was added to the buffer and mixed well by a plate shaker for 1 minute. The final concentration of DMSO introduced into the assay was 1%.

Glucokinase was added to the buffer mixture to initiate the reaction in the presence and absence of compound. Reaction was monitored by absorbance at 340nm due to the depletion of NADH. The initial reaction velocity was measured by the slope of a linear time course of 200-900 sec.

The percentage of activation was calculated by the following equation:

% Activation=$(Va/Vo-1) \times 100$;

wherein each of Va and Vo is defined as the initial reaction velocity in the presence and absence of the tested compound, respectively.

To determine the $EC_{50}$ and % max activation, compounds were serially diluted in DMSO by 3 fold. The GK activities were measured as a function of compound concentrations. The data were fitted to the equation below to obtain the $EC_{50}$ and % max activation values:

$Va/Vo=1+$(% max activation/100)/(1+$EC_{50}$/compound concentration)

The percentage activation, $EC_{50}$, and percentage max activation, for the compounds exemplified in the present application are tabulated below. Compounds of the invention generally have GK activating activity with an $EC_{50}$ of less than 10 μM, preferably less than about 1 μM, more preferably less than about 0.1 μM.

| Example | MW | % Activation at 10 uM | EC50 (uM) | % Max Activation |
| --- | --- | --- | --- | --- |
| 1 | 424.48 | 101 | 8.7 | 144 |
| 2 | 438.5 | 113 | 5.3 | 152 |
| 3 | 452.53 | 145 | 0.348 | 140 |
| 4 | 425.46 | 14.6 | ND | ND |
| 5 | 422.46 | −6.3 | ND | ND |
| 6 | 424.48 | 87.6 | 9.6 | 123 |
| 7 | 422.46 | 99.7 | 3.7 | 129 |
| 8 | 424.48 | 127 | 2.8 | 100 |
| 9 | 422.46 | 72.7 | 3.08 | 94.7 |
| 10 | 438.5 | 98.7 | 1.1 | 122 |
| 11 | 427.48 | 158 | 2 | 177 |
| 12 | 427.48 | 162 | 3 | 195 |
| 13 | 427.48 | 182 | 1.8 | 196 |
| 14 | 384.43 | 167 | 1.3 | 115 |
| 15 | 481.53 | 4.3 | ND | ND |
| 16 | 441.51 | 213 | 0.506 | 192 |
| 17 | 439.49 | 161 | 0.51 | 165 |
| 18 | 468.53 | 105 | 0.95 | 114 |
| 19 | 438.5 | 139 | 0.37 | 156 |
| 20 | 442.49 | 230 | 0.314 | 231 |
| 21 | 453.52 | 97.9 | 3.9 | 127 |
| 22 | 468.53 | 118 | 0.29 | 117 |
| 23 | 452.53 | 46.1 | 1.4 | 70 |
| 24 | 459.55 | 121 | 1.49 | 140 |
| 25 | 442.49 | 102 | 1.3 | 116 |
| 26 | 428.46 | 197 | 0.4 | 200 |
| 27 | 473.57 | 112 | 1.1 | 112 |
| 28 | 485.58 | 123 | 2 | 158 |
| 29 | 456.52 | 284 | 0.25 | 255 |
| 30 | 489.57 | 144 | 4.2 | 183 |
| 31 | 406.42 | 135 | 2.1 | 153 |
| 32 | 464.49 | 164 | 0.21 | 177 |
| 33 | 464.49 | 170 | 0.0661 | 171 |
| 34 | 464.49 | 75.1 | >10.0 | ND |
| 35 | 446.5 | 145 | 0.105 | 145 |
| 36 | 441.51 | 130 | 1.1 | 149 |
| 37 | 446.5 | 107 | 0.89 | 143 |
| 38 | 413.42 | 109 | 2.4 | 149 |
| 39 | 438.5 | 105 | 2 | 133 |
| 40 | 411.43 | 109 | 3.6 | 150 |
| 41 | 494.52 | 138 | 1.4 | 141 |
| 42 | 507.56 | 128 | 2.3 | 139 |
| 43 | 500.48 | 164 | 0.73 | 174 |
| 44 | 507.56 | 137 | 0.58 | 146 |
| 45 | 480.49 | 150 | 0.57 | 146 |
| 46 | 452.48 | 118 | 0.31 | 138 |
| 47 | 476.53 | 140 | 1.05 | 156 |
| 48 | 460.53 | 130 | 0.142 | 114 |
| 49 | 489.57 | 133 | 0.455 | 147 |
| 50 | 482.49 | 146 | 0.564 | 149 |
| 51 | 494.52 | 129 | 0.25 | 130 |
| 52 | 500.48 | 136 | 0.28 | 151 |
| 53 | 507.56 | 125 | 0.65 | 135 |
| 54 | 452.48 | 83.3 | 0.0807 | 101 |
| 55 | 480.49 | 143 | 0.68 | 129 |
| 56 | 478.52 | 107 | 0.0507 | 108 |
| 57 | 507.56 | 131 | 0.643 | 148 |
| 58 | 496.51 | 55.3 | 0.075 | 88 |
| 59 | 508.55 | 172 | 0.25 | 168 |
| 60 | 508.55 | 172 | 0.27 | 167 |
| 61 | 492.55 | 109 | 0.1 | 107 |
| 62 | 494.52 | 153 | 0.7 | 165 |
| 63 | 496.51 | 170 | 0.23 | 158 |
| 64 | 496.54 | 172 | 0.27 | 158 |
| 65 | 504.52 | 147 | 0.24 | 141 |
| 66 | 482.51 | 149 | 0.41 | 168 |
| 67 | 477.49 | 131 | 0.066 | 130 |
| 68 | 482.51 | 146 | 0.66 | 175 |

407
-continued

| Example | MW | % Activation at 10 uM | EC50 (uM) | % Max Activation |
|---|---|---|---|---|
| 69 | 438.46 | 122 | 0.37 | 129 |
| 70 | 452.48 | 132 | 0.15 | 118 |
| 71 | 466.51 | 181 | 0.41 | 167 |
| 72 | 468.48 | 182 | 0.95 | 161 |
| 73 | 464.49 | 254 | 0.39 | 232 |
| 74 | 478.52 | 285 | 0.54 | 258 |
| 75 | 470.47 | 193 | 0.26 | 189 |
| 76 | 488.46 | 203 | 0.47 | 206 |
| 77 | 418.45 | 64.4 | 0.15 | 66 |
| 78 | 405.5 | 139 | 1.47 | 149 |
| 79 | 435.52 | 148 | 2.1 | 171 |
| 80 | 377.44 | 111 | 5.9 | 176 |
| 81 | 392.46 | 112 | 5.3 | 148 |
| 82 | 393.45 | 110 | 5.1 | 135 |
| 83 | 407.47 | 78.3 | 8.2 | 148 |
| 84 | 359.42 | 58.4 | >10.0 | ND |
| 85 | 414.5 | 12 | ND | ND |
| 86 | 393.45 | 124 | 4.8 | 159 |
| 87 | 406.48 | 73.6 | 8.6 | 136 |
| 88 | 473.49 | 38.2 | ND | ND |
| 89 | 341.41 | 139 | 3.9 | 157 |
| 90 | 398.49 | 112 | 5.6 | 138 |
| 91 | 425.49 | 150 | 3.5 | 150 |
| 92 | 315.37 | 87 | 9.5 | 164 |
| 93 | 354.41 | 95.2 | 9.7 | 136 |
| 94 | 383.41 | 116 | 4.4 | 140 |
| 95 | 435.48 | 143 | 0.625 | 145 |
| 96 | 383.41 | 107 | 7.3 | 148 |
| 97 | 435.48 | 131 | 3.4 | 123 |
| 98 | 446.47 | 154 | 1.6 | 165 |
| 99 | 412.51 | 112 | 4.3 | 136 |
| 100 | 411.46 | 171 | 1.6 | 156 |
| 101 | 373.45 | 94.7 | 6 | 125 |
| 102 | 359.42 | 92.6 | 8.8 | 137 |
| 103 | 420.47 | 78.9 | 4.7 | 94 |
| 104 | 423.47 | 149 | 1.8 | 134 |
| 105 | 409.44 | 70.1 | 9.4 | 102 |
| 106 | 392.46 | 143 | 2.4 | 141 |
| 107 | 468.94 | 173 | 0.097 | 163 |
| 108 | 468.94 | 82.2 | 0.076 | 107 |
| 109 | 470.47 | 86.9 | 0.28 | 83 |
| 110 | 482.49 | 139 | 0.072 | 131 |
| 111 | 470.47 | 85.2 | 0.045 | 115 |
| 112 | 470.47 | 130 | 0.044 | 153 |
| 113 | 399.4 | 239 | 2.6 | 265 |
| 114 | 459.5 | 156 | 0.203 | 164 |
| 115 | 459.5 | 79.7 | 8.8 | 141 |
| 116 | 470.52 | 110 | 0.073 | 112 |
| 117 | 460.48 | 325 | 0.15 | 283 |
| 118 | 476.94 | 244 | 0.32 | 251 |
| 119 | 476.94 | 242 | 0.43 | 223 |
| 120 | 470.52 | 80.5 | 0.2 | 79 |
| 121 | 459.5 | 124 | 0.5 | 152 |
| 122 | 470.55 | 184 | 0.1 | 159 |
| 123 | 481.57 | 189 | 0.055 | 150 |
| 124 | 493.58 | 156 | 0.038 | 113 |
| 125 | 482.56 | 181 | 0.046 | 162 |
| 126 | 466.56 | 137 | 0.037 | 118 |
| 127 | 455.53 | 193 | 0.066 | 165 |
| 128 | 481.57 | 135 | 0.038 | 112 |
| 129 | 467.54 | 185 | 0.089 | 160 |
| 130 | 488.54 | 211 | 0.14 | 236 |
| 131 | 468.53 | 292 | 0.21 | 272 |
| 132 | 489.53 | 288 | 0.17 | 280 |
| 133 | 456.52 | 308 | 0.12 | 293 |
| 134 | 471.54 | 300 | 0.19 | 271 |
| 135 | 474.51 | 239 | 0.097 | 257 |
| 136 | 473.52 | 237 | 0.12 | 236 |
| 137 | 475.95 | 212 | 0.27 | 218 |
| 138 | 507.52 | 218 | 0.34 | 224 |
| 139 | 475.95 | 242 | 0.55 | 254 |
| 140 | 486.52 | 196 | 0.17 | 236 |
| 141 | 485.53 | 173 | 0.11 | 216 |
| 142 | 453.47 | 145 | 0.0528 | 130 |
| 143 | 453.47 | 47.8 | 0.179 | 50 |
| 144 | 439.44 | 103 | 0.269 | 100 |
| 145 | 479.51 | 47.2 | 0.0727 | 46.5 |

408
-continued

| Example | MW | % Activation at 10 uM | EC50 (uM) | % Max Activation |
|---|---|---|---|---|
| 146 | 492.51 | 25.1 | ND | ND |
| 147 | 518.59 | 35 | ND | ND |
| 148 | 463.51 | 49.5 | 0.0428 | 53 |
| 149 | 434.49 | 105 | 0.12 | 104 |
| 150 | 445.52 | 39.1 | 0.11 | 55 |
| 151 | 432.48 | 98.1 | 0.47 | 97 |
| 152 | 420.47 | 90.7 | 0.85 | 98 |
| 153 | 435.48 | 168 | 0.15 | 161 |
| 154 | 435.48 | 36.3 | 4 | 54 |
| 155 | 461.52 | 38.4 | 0.09 | 43 |
| 156 | 432.48 | 52 | 0.46 | 49 |
| 157 | 431.49 | 69.2 | 0.19 | 71 |
| 158 | 421.45 | 115 | 0.47 | 106 |
| 159 | 465.48 | 243 | 0.15 | 260 |
| 160 | 447.49 | 298 | 0.13 | 250 |
| 161 | 435.48 | 191 | 0.175 | 143 |
| 162 | 435.48 | 105 | 1.6 | 135 |
| 163 | 487.52 | 118 | 0.44 | 137 |
| 164 | 436.47 | 112 | 0.25 | 102 |
| 165 | 446.5 | 76.8 | 0.038 | 57 |
| 166 | 421.46 | 203 | 0.41 | 212 |
| 167 | 447.49 | 148 | 0.0553 | 146 |
| 168 | 435.48 | 172 | 0.199 | 184 |
| 169 | 448.48 | 125 | 0.056 | 141 |
| 170 | 422.44 | 264 | 0.3 | 255 |
| 171 | 422.44 | 171 | 3.6 | 213 |
| 172 | 448.48 | 186 | 0.48 | 169 |
| 173 | 465.48 | 159 | 0.068 | 148 |
| 174 | 436.47 | 238 | 0.84 | 258 |
| 175 | 478.55 | 233 | 0.77 | 251 |
| 176 | 439.45 | 194 | 0.45 | 203 |
| 177 | 453.47 | 204 | 0.35 | 189 |
| 178 | 453.47 | 198 | 0.09 | 147 |
| 179 | 422.43 | ND | ND | ND |
| 180 | 408.41 | 66.5 | >10.0 | ND |
| 181 | 389.41 | 171 | 1.1 | 182 |
| 182 | 432.44 | 244 | 0.29 | 237 |
| 183 | 406.42 | 237 | 1.9 | 236 |
| 184 | 407.4 | 250 | 3.2 | 251 |
| 185 | 449.44 | 248 | 0.104 | 227 |
| 186 | 450.43 | 135 | 0.16 | 234 |
| 187 | 431.45 | 178 | >10.0 | ND |
| 188 | 432.44 | 198 | 0.62 | 230 |
| 189 | 465.9 | 219 | 0.87 | 245 |
| 190 | 459.5 | 83.9 | 7.3 | 138 |
| 191 | 464.49 | 91.2 | 1.7 | 119 |
| 192 | 459.5 | 249 | 2.1 | 285 |
| 193 | 420.49 | 116 | 8.8 | 237 |
| 194 | 421.48 | 146 | 5 | 263 |
| 195 | 385.42 | 98.9 | >10.0 | ND |
| 196 | 384.43 | 62 | >10.0 | ND |
| 197 | 464.49 | 77.6 | >10.0 | ND |
| 198 | 442.49 | 51.4 | >10.0 | ND |
| 199 | 441.51 | 40.3 | >10.0 | ND |
| 200 | 443.48 | 113 | 2.9 | 147 |
| 201 | 457.51 | 107 | 2.8 | 137 |
| 202 | 466.47 | 121 | 0.36 | 108 |
| 203 | 477.49 | 82.6 | 0.81 | 91 |
| 204 | 480.49 | 73.9 | 2 | 94 |
| 205 | 468.48 | 90.8 | 0.42 | 94.5 |
| 206 | 468.48 | 91.3 | 0.27 | 102 |
| 207 | 468.48 | 127 | 0.95 | 142 |
| 208 | 462.5 | 83.9 | 0.71 | 98 |
| 209 | 462.5 | 87 | 0.38 | 96 |
| 210 | 462.5 | 130 | 0.85 | 143 |
| 211 | 450.49 | 83.5 | 1.3 | 90 |
| 212 | 450.49 | 111 | 2.6 | 144 |
| 213 | 450.49 | 83.1 | 0.89 | 113 |
| 214 | 407.47 | 12 | ND | ND |
| 215 | 331.37 | 16.7 | ND | ND |
| 216 | 345.4 | 13 | ND | ND |
| 217 | 359.42 | 5.3 | ND | ND |
| 218 | 358.44 | 43.1 | >10.0 | ND |
| 219 | 370.45 | 8 | ND | ND |
| 220 | 388.47 | 13.8 | ND | ND |
| 221 | 391.47 | 8.4 | ND | ND |
| 222 | 399.4 | 61.1 | >10.0 | ND |

-continued

| Example | MW | % Activation at 10 uM | EC50 (uM) | % Max Activation |
|---|---|---|---|---|
| 223 | 504.44 | 112 | 0.68 | 127 |
| 224 | 445.47 | 142 | 2.3 | 160 |
| 225 | 463.46 | 103 | 2.93 | 242 |
| 226 | 468.46 | 112 | 0.64 | 137 |
| 227 | 457.51 | 165 | 0.69 | 184 |
| 228 | 471.53 | 151 | 0.5 | 156 |
| 229 | 468.48 | 101 | 0.12 | 97 |
| 230 | 468.53 | 91.8 | 0.33 | 95 |
| 231 | 482.55 | 118 | 0.1 | 106 |
| 232 | 475.5 | 188 | 0.39 | 184 |
| 233 | 486.52 | 201 | 0.064 | 165 |
| 234 | 482.51 | 121 | 0.075 | 112 |
| 235 | 475.5 | 69.2 | >10.0 | ND |
| 236 | 486.52 | 55.6 | 2.7 | 66 |
| 237 | 489.52 | 189 | 0.098 | 157 |
| 238 | 489.52 | 89.8 | >10.0 | ND |
| 239 | 479.51 | 32.1 | 0.02 | 42 |
| 240 | 491.52 | 83 | 0.021 | 94 |
| 241 | 480.49 | 127 | 0.058 | 135 |
| 242 | 494.52 | 140 | 0.063 | 144 |
| 243 | 494.52 | 275 | 0.041 | 218 |
| 244 | 494.52 | 287 | 0.21 | 234 |
| 245 | 483.54 | 196 | 0.13 | 236 |
| 246 | 484.53 | 222 | 0.16 | 261 |
| 247 | 497.57 | 252 | 0.083 | 254 |
| 248 | 497.57 | 222 | 0.49 | 225 |
| 249 | 498.56 | 276 | 0.086 | 262 |
| 250 | 498.56 | 227 | 0.42 | 246 |
| 251 | 459.5 | 141 | 0.43 | 169 |
| 252 | 436.49 | 108 | 0.778 | 107 |
| 253 | 490.46 | 32.1 | ND | ND |
| 254 | 462.52 | 53.3 | 3.4 | 71 |
| 255 | 426.45 | 18.8 | ND | ND |
| 256 | 440.45 | 89.2 | 4.5 | 126 |
| 257 | 422.46 | 111 | 1.4 | 119 |
| 258 | 412.42 | 99.7 | 5.8 | 142 |
| 259 | 452.49 | 63.6 | 1 | 60 |
| 260 | 456.9 | 53.1 | 2.9 | 69 |
| 261 | 447.47 | 58.8 | 7.9 | 81 |
| 262 | 466.52 | 151 | 0.78 | 137 |
| 263 | 453.47 | 157 | 0.84 | 146 |
| 264 | 480.5 | 80.5 | 1.3 | 79 |
| 265 | 450.51 | 94.2 | 1.7 | 74 |
| 266 | 452.49 | 81.4 | 1 | 91 |
| 267 | 426.45 | 145 | 1.7 | 165 |
| 268 | 452.49 | 6.4 | >10.0 | ND |
| 269 | 466.51 | 34.8 | 7 | 59 |
| 270 | 466.51 | 98.2 | 7.1 | 139 |
| 271 | 425.46 | 148 | 1.3 | 184 |
| 272 | 436.44 | 49.6 | 0.31 | 51 |
| 273 | 447.46 | 12.7 | ND | ND |
| 274 | 450.51 | 131 | 2.4 | 121 |
| 275 | 439.49 | 211 | 2.6 | 210 |
| 276 | 443.5 | 20 | ND | ND |
| 277 | 430.46 | 34.2 | ND | ND |
| 278 | 420.43 | 131 | 0.47 | 123 |
| 279 | 447.45 | 84.3 | 0.43 | 105 |
| 280 | 467.5 | 130 | 2.4 | 148 |
| 281 | 437.47 | 92.7 | 2.1 | 87 |
| 282 | 427.44 | 140 | >10.0 | ND |
| 283 | 426.45 | 132 | >10.0 | ND |
| 284 | 454.46 | 86.1 | 5.5 | 218 |
| 285 | 493.54 | 121 | 0.547 | 118 |
| 286 | 482.52 | 178 | 2.6 | 224 |
| 287 | 510.53 | 80.3 | 0.562 | 169 |
| 288 | 483.5 | 161 | 1.7 | 188 |
| 289 | 509.54 | 73.8 | 7.8 | 133 |
| 290 | 505.55 | 12.8 | ND | ND |
| 291 | 494.53 | 12.7 | ND | ND |
| 292 | 495.51 | 16.7 | ND | ND |
| 293 | 499.52 | 46.9 | 0.59 | 50 |
| 294 | 466.52 | 122 | 0.2 | 132 |
| 295 | 493.54 | 46.9 | 0.36 | 50 |
| 296 | 463.51 | 70 | 0.2 | 77 |
| 297 | 477.54 | 61.9 | 0.13 | 68 |
| 298 | 467.5 | 113 | 0.21 | 132 |
| 299 | 507.57 | 106 | 0.18 | 107 |
| 300 | 497.96 | 53.4 | 0.71 | 56 |
| 301 | 493.54 | 168 | 0.15 | 137 |
| 302 | 507.57 | 123 | 1.3 | 110 |
| 303 | 494.53 | 195 | 0.65 | 179 |
| 304 | 483.52 | 94.6 | 0.24 | 89 |
| 305 | 472.5 | 166 | 0.14 | 168 |
| 306 | 473.48 | 185 | 0.33 | 186 |
| 307 | 500.51 | 153 | 0.4 | 156 |
| 308 | 513.55 | 141 | 0.11 | 131 |
| 309 | 466.51 | 72.3 | 0.23 | 81 |
| 310 | 455.49 | 118 | 0.73 | 137 |
| 311 | 496.54 | 106 | 0.38 | 114 |
| 312 | 483.5 | 112 | 0.49 | 121 |
| 313 | 456.48 | 131 | 0.92 | 155 |
| 314 | 482.51 | 47.3 | 0.33 | 46 |
| 315 | 456.47 | 11.9 | ND | ND |
| 316 | 452.49 | 73.7 | 0.41 | 78 |
| 317 | 441.46 | 186 | 1.7 | 228 |
| 318 | 508.55 | 91.3 | >10.0 | ND |
| 319 | 479.55 | 59.7 | 5 | 90 |
| 320 | 516.58 | 39.2 | 2.5 | 41 |
| 321 | 472.47 | 100 | 4.3 | 132 |
| 322 | 461.44 | 161 | 6.3 | 235 |
| 323 | 465.45 | 78 | 3.7 | 83 |
| 324 | 408.46 | 18.2 | ND | ND |
| 325 | 405.43 | 137 | >10.0 | ND |
| 326 | 415.47 | 76.9 | 2.1 | 90 |
| 327 | 404.45 | 108 | >10.0 | ND |
| 328 | 405.52 | 41.3 | >10.0 | ND |
| 329 | 452.55 | 86.8 | 1.6 | 113 |
| 330 | 441.53 | 125 | 1.7 | 162 |
| 331 | 434.52 | 47.4 | 0.32 | 56 |
| 332 | 411.44 | 57.5 | >10.0 | ND |
| 333 | 422.46 | 52.8 | 8.6 | 106 |
| 334 | 404.42 | 35 | ND | ND |
| 335 | 415.45 | 26 | ND | ND |
| 336 | 375.43 | 8.4 | ND | ND |
| 337 | 436.49 | 42.6 | 3 | 89 |
| 338 | 425.46 | 84.5 | 4.3 | 147 |
| 339 | 429.47 | −0.7 | ND | ND |
| 340 | 389.45 | 41.2 | >10.0 | ND |
| 341 | 422.41 | 59 | 1.7 | 69 |
| 342 | 433.44 | 15 | ND | ND |
| 343 | 411.44 | 82.5 | >10.0 | ND |
| 344 | 310.35 | 89.5 | 1.4 | 106 |
| 345 | 389.25 | 75.6 | 4 | 116 |
| 346 | 350.42 | 69.2 | 1.5 | 89 |
| 347 | 386.45 | 113 | 0.16 | 158 |
| 348 | 352.43 | 16.6 | ND | ND |
| 349 | 393.44 | −32.1 | ND | ND |
| 350 | 452.55 | 11.2 | ND | ND |
| 351 | 441.53 | 0.9 | ND | ND |
| 352 | 434.52 | 12.3 | ND | ND |
| 353 | 445.54 | 3.4 | ND | ND |
| 354 | 405.52 | 3.5 | ND | ND |
| 355 | 438.53 | 114 | 0.52 | 110 |
| 356 | 427.5 | 77.4 | >10.0 | ND |
| 357 | 438.48 | 32.7 | ND | ND |
| 358 | 449.5 | 50.4 | 0.33 | 56 |
| 359 | 452.55 | 69.9 | 0.19 | 70 |
| 360 | 441.53 | 129 | 0.62 | 142 |
| 361 | 463.53 | 4.2 | ND | ND |
| 362 | 452.51 | 25.9 | ND | ND |
| 363 | 438.53 | 52.3 | 7.65 | 99 |
| 364 | 427.5 | 45.8 | >10.0 | ND |
| 365 | 449.5 | 4 | ND | ND |
| 366 | 438.48 | 6.4 | ND | ND |
| 367 | 423.45 | 47 | 5.8 | 59 |
| 368 | 426.45 | 48.2 | >10.0 | ND |
| 369 | 437.47 | 66.1 | 3.7 | 66 |
| 370 | 430.46 | 14.9 | 0.17 | 3.5 |
| 371 | 439.51 | 35.5 | ND | ND |
| 372 | 425.49 | 29.3 | ND | ND |
| 373 | 296.33 | −1.1 | ND | ND |
| 374 | 436.94 | 17.7 | ND | ND |
| 375 | 436.94 | 5.6 | ND | ND |
| 376 | 451.5 | 73.1 | 6.4 | 90 |

-continued

| Example | MW | % Activation at 10 uM | EC50 (uM) | % Max Activation |
|---|---|---|---|---|
| 377 | 402.45 | 25.6 | ND | ND |
| 378 | 413.48 | −1.85 | ND | ND |
| 379 | 465.53 | 74.1 | 4.5 | 98 |
| 380 | 454.51 | 67.9 | >10.0 | ND |
| 381 | 493.58 | 81 | 3 | 132 |
| 382 | 482.56 | 82 | 9.3 | 156 |
| 383 | 479.55 | 32.6 | ND | ND |
| 384 | 468.53 | 33.2 | ND | ND |
| 385 | 477.54 | 93.2 | 4.5 | 107 |
| 386 | 466.52 | 78.8 | >10.0 | ND |
| 387 | 495.55 | 42.9 | >10.0 | ND |
| 388 | 484.53 | 39.7 | ND | ND |
| 389 | 496.59 | 32.9 | ND | ND |
| 390 | 465.53 | 28.9 | ND | ND |
| 391 | 507.61 | 45.2 | >10.0 | ND |
| 392 | 507.56 | 48.6 | >10.0 | ND |
| 394 | 463.51 | 32 | ND | ND |
| 395 | 301.34 | ND | ND | ND |
| 396 | 448.48 | 204 | 0.36 | 212 |
| 397 | 465.48 | 213 | 0.083 | 202 |
| 398 | 461.52 | 128 | 0.056 | 114 |
| 399 | 460.49 | 212 | 0.61 | 231 |
| 400 | 456.45 | 192 | 0.14 | 177 |
| 401 | 512.56 | 131 | 0.29 | 139 |
| 402 | 512.56 | 19.9 | ND | ND |
| 403 | 484.20 | 196 | 0.121 | 191 |

ND: no data was taken.

Various embodiments of the present invention have been described above but a person skilled in the art realizes further minor alterations that would fall into the scope of the present invention. The breadth and scope of the present invention should not be limited by any of the above-described exemplary embodiments, but should be defined only in accordance with the following claims and their equivalents.

We claim:

1. The compound of the formula

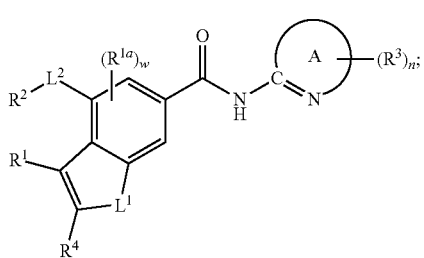

(VIa)

or a pharmaceutically acceptable salt thereof;
wherein $L^1$ is —O—, —$NR^5$—, or —S—;
Ring A is (4-12)-membered heterocyclyl;
each of $R^1$, $R^{1a}$, and $R^4$ are independently selected from H, halo, cyano, nitro, —$CF_3$, —$CHF_2$, —$CH_2F$, trifluoromethoxy, azido, hydroxy, ($C_1$-$C_6$)alkoxy, ($C_1$-$C_6$)alkyl, ($C_2$-$C_6$)alkenyl, ($C_2$-$C_6$)alkynyl, —(C=O)—$R^5$, —(C=O)—O—$R^5$, —O—(C=O)—$R^5$, —$NR^5$(C=O)—$R^7$, —(C=O)—$NR^5R^6$, —$NR^5R^6$, —$NR^5OR^6$, —S(O)$_k$$NR^5R^6$, —S(O)$_j$($C_1$-$C_6$)alkyl, —O—$SO_2$—$R^5$, —$NR^5$—S(O)$_k$, —($CR^5R^6$)$_v$(3-10)-membered cycloalkyl, —($CR^5R^6$)$_v$($C_6$-$C_{10}$aryl), —($CR^5R^6$)$_v$(4-10)-membered heterocyclyl, —($CR^5R^6$)$_q$ (C=)($CR^5R^6$)$_v$($C_6$-$C_{10}$)aryl, —($CR^5R^6$)$_q$ (C=O)($CR^5R^6$)$_v$(4-10)-membered heterocyclyl, —($CR^5R^6$)$_v$O($CR^5R^6$)$_q$($C_6$-$C_{10}$)aryl, —($CR^5R^6$)$_v$O($CR^5R^6$)$_q$(4-10)-membered heterocyclyl, —($CR^5R^6$)$_q$S(O)$_j$($CR^5R^6$)$_v$($C_6$-$C_{10}$)aryl, and —($CR^5R^6$)$_q$S(O)$_j$($CR^5R^6$)$_v$(4-10-membered heterocyclyl;

$L^2$ is >C=O, >C=O—O—, —O—C=O—, —O—C=O—O, —O—C=O—$NR^5$—, —$NR^5$—(C=O)—, —$NR^5$—(C=O)—O—, —$NR^5$—(C=O)—$NR^6$, —(C=O)—$NR^5$—, —O—, —$NR^5$—, —S(O)$_j$—, —$NR^5SO_2$—, —$SO_2NR^5$—, —(C=O)$NR^5SO_2$—, —$SO_2NR^5$(C=O)—, or —$CR^5R^6$;

$R^2$ is H, ($C_1$-$C_6$)alkyl, —($CR^5R^6$)$_v$(3-10)-membered cycloalkyl, —($CR^5R^6$)$_v$($C_6$-$C_{10}$aryl), or —($CR^5R^6$)$_v$(4-12)-membered heterocyclyl;

$R^3$ is H, halo, cyano, nitro, —$CF_3$, —$CHF_2$, —$CH_2F$, trifluoromethoxy, azido, hydroxy, ($C_1$-$C_6$)alkoxy, ($C_1$-$C_6$)alkyl, ($C_2$-$C_6$)alkenyl, ($C_2$-$C_6$)alkynyl, —(C=O)—$R^5$, —(C=O)—O—$R^5$, —O—(C=O)—$R^5$, —$NR^5$(C=O)—$R^7$, —(C=O)—$NR^5R^6$, —$NR^5R^6$, —$NR^5OR^6$, —S(O)$_k$$NR^5R^6$, —S(O)$_j$($C_1$-$C_6$)alkyl, —O—$SO_2$—$R^5$, —$NR^5$—S(O)$_k$, —($CR^5R^6$)$_v$(3-10)-membered cycloalkyl, —($CR^5R^6$)$_v$($C_6$-$C_{10}$aryl), —($CR^5R^6$)$_v$(4-10)-membered heterocyclyl, —($CR^5R^6$)$_q$ (C=O)($CR^5R^6$)$_v$($C_6$-$C_{10}$)aryl, —($CR^5R^6$)$_q$ (C=O)($CR^5R^6$)$_v$(4-10)-membered heterocyclyl, —($CR^5R^6$)$_v$O($CR^5R^6$)$_q$($C_6$-$C_{10}$)aryl, —($CR^5R^6$)$_v$O($CR^5R^6$)$_q$(4-10 membered heterocyclyl, —($CR^5R^6$)$_q$S(O)$_j$($CR^5R^6$)$_v$($C_6$-$C_{10}$)aryl, or —($CR^5R^6$)$_q$ S(O)$_j$($CR^5R^6$)$_v$(4-10)-membered heterocyclyl;

each of $R^5$, $R^6$ and $R^7$ are independently selected from H, ($C_1$-$C_6$)alkyl, —($CR^8R^9$)$_v$(3-10)-membered cycloalkyl, —($CR^8R^9$)$_p$($C_8$-$C_{10}$)aryl, and —($CR^8R^9$)$_p$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R^1$, $R^2$, $R^3$, $R^4$, $R^5$, $R^6$ and $R^7$ are independently optionally substituted with 1 to 3 $R^{11}$ substituents each independently selected from halo, cyano, nitro, —$CF_3$, —$CHF_2$, —$CH_2F$, trifluoromethoxy, azido, hydroxy, —O—$R^{12}$, ($C_1$-$C_6$)alkoxy, ($C_1$-$C_6$)alkyl, ($C_2$-$C_6$)alkenyl, ($C_2$-$C_6$)alkynyl, —(C=O)—$R^8$, —(C=O)—$R^{12}$, —(C=O)—O—$R^8$, —(C=O)—O—$R^{12}$, —O—(C=O)—$R^8$, —O—(C=O)—$R^{12}$, —$NR^8$(C=O)—$R^{10}$, —(C=O)—, —(C=O)—$NR^8R^9$, —(C=O)—$NR^8R^{12}$, —$NR^8R^9$, —$NR^8R^{12}$, —$NR^8OR^9$, —$NR^8OR^{12}$, —S(O)$_k$$NR^8R^9$, —S(O)$_k$$NR^8R^{12}$, —S(O)$_j$($C_1$-$C_6$)alkyl, —S(O)$_j$$R^{12}$, —O—$SO_2$—$R^8$, —O—$SO_2$—$R^{12}$, —$NR^8$—S(O)$_k$, —$NR^{12}$—S(O)$_k$, —($CR^8R^9$)$_v$(3-10)-membered cycloalkyl, —($CR^8R^9$)$_v$($C_6$-$C_{10}$aryl), —($CR^8R^9$)$_v$(4-10)-membered heterocyclyl, —($CR^8R^9$)$_q$(C=O) ($CR^8R^9$)$_v$($C_6$-$C_{10}$)aryl, —($CR^8R^9$)$_q$(C=O)($CR^8R^9$)$_v$(4-10)-membered heterocyclyl, —($CR^8R^9$)$_q$O($CR^8R^9$)$_q$ ($C_6$-$C_{10}$)aryl, —($CR^8R^9$)$_q$O($CR^8R^9$)$_q$(4-10)-membered heterocyclyl, —($CR^8R^9$)$_q$S(O)$_j$ ($CR^8R^9$)$_v$($C_6$-$C_{10}$)aryl, and —($CR^8R^9$)$_q$S(O)$_j$($CR^8R^9$)$_v$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R^{11}$ are independently optionally substituted with 1 to 3 $R^{13}$ substituents each independently selected from halo, cyano, nitro, —$CF_3$, —$CHF_2$, —$CH_2F$, trifluoromethoxy, azido, ($CH_2$)$_v$OH, ($C_1$-$C_6$)alkoxy, ($C_1$-$C_6$)alkyl, ($C_2$-$C_6$)alkenyl, ($C_2$-$C_6$)alkynyl, —(C=O)—$R^8$, —(C=O)—$R^{12}$, —(C=O)—O—$R^8$, —(C=O)—O—$R^{12}$, —O—(C=O)—$R^8$, —O—(C=O)—$R^{12}$, —$NR^8$(C=O)—$R^{10}$, —(C=O)—$NR^8R^9$, —$NR^8R^9$, and —$NR^8R^{12}$;

any nitrogen atoms of the (4-10)-membered heterocyclyl of the foregoing $R^1$, $R^2$, $R^3$, $R^4$, $R^5$, $R^6$, $R^7$, $R^{11}$ and $R^{12}$ are independently optionally substituted with $(C_1-C_6)$alkyl, $(C_2-C_6)$alkenyl, $(C_2-C_6)$alkynyl, —(C=O)—$R^8$, —(C=O)—O—$R^8$, —(C=O)—$NR^8R^9$, —$(CR^8R^9)_v$(3-10)-membered cycloalkyl, —$(CR^8R^9)_v(C_6-C_{10}$aryl), —$(CR^8R^9)_v$(4-10)-membered heterocyclyl, —$(CR^8R^9)_q$(C=O)$(CR^8R^9)_v(C_6-C_{10})$aryl, or —$(CR'R^9)_q$(C=O)$(CR^8R^9)_v$(4-10)-membered heterocyclyl;

each $R^8$, $R^9$, and $R^{10}$ are independently H or $(C_1-C_6)$alkyl;

$R^{12}$ is —$(CR^8R^9)_v$(3-10)-membered cycloalkyl, —$(CR^8R^9)_v(C_6-C_{10}$aryl), or —$(CR^8R^9)_v$(4-10)-membered heterocyclyl;

p, q, and v are each independently 0, 1, 2, 3, 4, or 5;

w, n and j are each independently 0, 1, or 2;

k is 1 or 2; and t and z are each independently 1, 2, 3, or 4;

with the proviso that when

Ring A is pyridin-2-yl or thiazol-2-yl;

$L^1$ is —O—;

$L^2$ is —O—; and $R^2$ is $(C_1-C_6)$alkyl, —$(CR^5R^6)_v$(3-10)-membered cycloalkyl, —$(CR^5R^6)_v(C_6-C_{10}$aryl), or —$(CR^5R^6)_v$(4-12)-membered heterocyclyl; then $R^2$ is further substituted by $R^{11}$ substituents each independently selected from —$SO_2$—$(C_1-C_6)$alkyl, —$S(O)_j$$R^{12}$, —$S(O)_kNR^8R^9$, —$S(O)_kNR^8R^{12}$, —(C=O)—$R^{12}$, —(C=O)—$NR^8R^9$, or —(C=O)—$NR^8R^{12}$.

2. The compound of claim 1 or a pharmaceutically acceptable salt thereof wherein said Ring A is selected from the group consisting of oxadiazolyl, triazolyl, pyrrolyl, oxazolyl, imidazolyl, imidazolinyl, pyrazolyl, pyrazolinyl, isoxazolyl, isothiazolyl, thiadiazolyl, pyrimidinyl, pyridazinyl, pyrazinyl, triazinyl, benzimidazolyl, benzothiazolyl, quinolinyl, quinazolinyl, quinoxalinyl, pyridinylcyclohexyl, and naphthyridinyl.

3. The compound of claim 2 or a pharmaceutically acceptable salt thereof wherein Ring A is pyrazinyl;

$R^3$ is $(C_1-C_6)$alkyl and n is 1.

4. The compound of claim 3 or a pharmaceutically acceptable salt thereof wherein $R^1$ is H and $R^4$ is $(C_1-C_4)$alkyl.

5. The compound of claim 4 or a pharmaceutically acceptable salt thereof wherein $L^1$ is —O—; and $L^2$ is —O—.

6. The compound of claim 5 or a pharmaceutically acceptable salt thereof wherein $R^2$ is pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl and wherein $R^2$ is substituted with a —(C=O)—$NR^8R^9$.

7. A pharmaceutical composition comprising an effective amount of a compound according to claim 1, or a pharmaceutically acceptable salt thereof, and a pharmaceutically acceptable carrier.

* * * * *